US011541044B2

(12) United States Patent
McCormick et al.

(10) Patent No.: US 11,541,044 B2
(45) Date of Patent: Jan. 3, 2023

(54) K-RAS MODULATORS

(71) Applicants: The Regents of the University of California, Oakland, CA (US); Leidos Biomedical Research, Inc., Frederick, MD (US)

(72) Inventors: Frank McCormick, San Francisco, CA (US); Adam R. Renslo, Oakland, CA (US); David Turner, Frederick, MD (US); Stephan Gysin, Basel (CH); Anna E. Maciag, Frederick, MD (US); Oleg Chertov, Frederick, MD (US)

(73) Assignees: The Regents of the University of California, Oakland, CA (US); Leidos Biomedical Research, Inc., Fredrick, MD (US)

( * ) Notice: Subject to any disclaimer, the term of this patent is extended or adjusted under 35 U.S.C. 154(b) by 0 days.

(21) Appl. No.: 17/082,125

(22) Filed: Oct. 28, 2020

(65) Prior Publication Data

US 2021/0196695 A1 Jul. 1, 2021

Related U.S. Application Data

(62) Division of application No. 15/571,475, filed as application No. PCT/US2016/031344 on May 6, 2016, now Pat. No. 10,857,140.

(60) Provisional application No. 62/158,356, filed on May 7, 2015, provisional application No. 62/157,915, filed on May 6, 2015.

(51) Int. Cl.
| | | |
|---|---|---|
| C07D 209/30 | (2006.01) | |
| C07D 211/60 | (2006.01) | |
| A61K 31/445 | (2006.01) | |
| A61P 35/00 | (2006.01) | |
| A61K 47/54 | (2017.01) | |
| C07D 207/16 | (2006.01) | |
| C07D 211/28 | (2006.01) | |

(52) U.S. Cl.
CPC .......... *A61K 31/445* (2013.01); *A61K 47/545* (2017.08); *A61P 35/00* (2018.01); *C07D 207/16* (2013.01); *C07D 211/28* (2013.01); *C07D 211/60* (2013.01)

(58) Field of Classification Search
CPC .......................... C07D 209/30; C07D 211/60
See application file for complete search history.

(56) References Cited

U.S. PATENT DOCUMENTS

| | | | |
|---|---|---|---|
| 4,924,004 A | 5/1990 | Ohlendorf et al. | |
| 5,436,244 A | 7/1995 | Clemence et al. | |
| 5,475,109 A | 12/1995 | Selnick et al. | |
| 6,916,817 B1 | 7/2005 | Tucker | |
| 8,324,239 B2 | 12/2012 | Barnes et al. | |
| 8,383,659 B2 | 2/2013 | Nanchen et al. | |
| 10,857,140 B2 | 12/2020 | McCormick et al. | |
| 2007/0112000 A1 | 5/2007 | Barton et al. | |
| 2014/0288045 A1 | 9/2014 | Ren et al. | |
| 2015/0087628 A1 | 3/2015 | Ostrem et al. | |
| 2020/0247762 A1 | 8/2020 | McCormick et al. | |

FOREIGN PATENT DOCUMENTS

| | | |
|---|---|---|
| CN | 1901910 A | 1/2007 |
| EP | 2836482 B1 | 12/2019 |
| JP | S61227567 A | 10/1986 |
| JP | H07242641 A | 9/1995 |
| JP | 2006506451 A | 2/2006 |
| JP | 2006519827 A | 8/2006 |
| JP | 2009526807 A | 7/2009 |
| WO | 1996006078 | 2/1996 |
| WO | 1996040146 | 12/1996 |
| WO | 2001012189 | 2/2001 |
| WO | 2003004474 | 1/2003 |
| WO | WO-2004/014380 | 2/2004 |
| WO | WO-2004/076449 | 9/2004 |
| WO | WO-2005/032472 | 4/2005 |
| WO | WO-2005/047286 | 5/2005 |
| WO | 2005058883 | 6/2005 |
| WO | WO-2005/073198 | 8/2005 |
| WO | 2007109154 | 9/2007 |
| WO | WO-2009/015237 | 1/2009 |
| WO | WO-2009/018505 | 2/2009 |
| WO | WO-2010/138758 | 12/2010 |
| WO | WO-2013/155223 | 10/2013 |
| WO | WO-2014/027053 | 2/2014 |
| WO | WO-2014/093230 | 6/2014 |
| WO | 2014152588 A | 9/2014 |
| WO | WO-2014/152588 | 9/2014 |
| WO | WO-2015/048570 | 4/2015 |
| WO | WO-2016/161361 | 10/2016 |
| WO | WO-2016/179558 | 11/2016 |
| WO | WO-2017/181177 | 10/2017 |

OTHER PUBLICATIONS

Burlingame et al., "Simple one-pot synthesis of disulfide fragments for use in disulfide-exchange screening," ACS Comb. Sci. 13:205-208 (2011).
Burlingame et al., "Simple one-pot synthesis of disulfide fragments for use in disulfide-exchange screening," ACS Comb. Sci. 13:205-208, supplemental information part 1, 3 total pages (2011).
Burlingame et al., "Simple one-pot synthesis of disulfide fragments for use in disulfide-exchange screening," ACS Comb. Sci. 13:205-208, supplemental information part 2, 78 total pages (2011).
CAS RN 120014-29-1, STN entry Date Apr. 7, 1989 for compound named 1-benzoyl-4-piperidinecarboxaldehyde. DPSIN: Open Parser for Systematic IUPAC nomenclature.
Colombano et al., "A novel potent nicotinamide phosphoribosyltransferase inhibitor synthesized via click chemistry," Journal of Medicinal Chemistry, Jan. 1, 2010, pp. 616-623, vol. 53, No. 2.

(Continued)

*Primary Examiner* — Brian E McDowell
(74) *Attorney, Agent, or Firm* — Mintz, Levin, Cohn, Ferris, Glovsky and Popeo, P.C.

(57) ABSTRACT

Provided herein, inter alia, are methods and compounds for inhibiting K-Ras and for treating cancer.

19 Claims, 56 Drawing Sheets

Specification includes a Sequence Listing.

(56) References Cited

OTHER PUBLICATIONS

De Costa et al., "Synthesis and Biological Evaluation of Conformationally Restricted 2-(1-Pyrrolidinyl)-N-[2-(3, 4lichloropheny)ethyll-N-met hylethylenediamines as a c Receptor Ligands. 1. Pyrrolidine, Piperidine, Homopiperidine, and Tetrahydroisoquinoline Classes," J. Med. Chem, Jan. 1, 1992, pp. 4334-4343.

Durust et al., "Synthesis of novel triazoles bearing 1,2,4-oxadiazole and phenylsulfonyl groups by 1,3-dipolar aycloaddition of some organic azides and their biological activities," Turkish Journal of Chemistry, 38(5) 2014, 739-755.

Extended European Search Report for EP Application No. 16790206.3 dated Dec. 5, 2018.

Gentile et al., "Ras Binder Induces a Modified Switch-II Pocket in GTP and GDP States," Cell Chemical Biology 24(12):1455-1466 (Dec. 21, 2017, e-published Oct. 12, 2017).

Harkala et al., "Synthesis and biological evaluation of benzimidazole-linked 1,2,3-triazole congeners as agents," Drganic and Medicinal Chemistry Letters, vol. 4, No. 14, 2014, pp. 1-4.

Iddon et al., "Azoles. Part 13. Synthesis and bromine .fwdarw. lithium exchange reactions of some 1-substituted 4, 5libromo-1 H-1,2,3-triazoles and 2-substitute 4,5-dibromo-2H1,2,3-triazoles," Journal of the Chemical Society, Perkin Transactions 1: Organic and Bio-Organic Chemistry, (12), 1996, 1341-1347.

Imase et al., "A New Route to Tricyclic 2-Pyridone Frameworks via Formation of Bicyclic N-Alkenyl Alkynylamides followed by Gold-catalyzed Cycloisomerization," Chemistry Letter, 2009, Vo. 38, No. 12, pp. 1152-1153.

International Search Report for PCT Application No. PCT/US2018/028593, dated Oct. 29, 2018.

International Search Report dated Aug. 19, 2016, for PCT Application No. PCT/US2016/031344, filed May 6, 2016, 4 pages.

Liu et al., "Developing irreversible inhibitors of the protein kinase cysteinome," Chem. & Biol. Rev. 20:146-159 (Feb. 21, 2013).

Madsen et al., "Synthesis of Rhodamine 6G-Based Compounds for the ATRP Synthesis f Flourescently Labeled Diocompatible Polymers," BioMacromolecules, 2011, vol. 12, pp. 2225-2234.

Pasha et al., "Design and synthesis of imidazo [2,1-b] thiazole linked triazole conjugates: Microtubule-lestabilizing agents," European Journal of Medicinal Chemistry, Editions Scientifique Elsevier, Paris, FR, vol. 126 Sep. 20, 2016, pp. 36-51.

Pruet et al., "Optimized 5-membered Heterocycle-Linked Pterins for the Inhibition of Ricin Toxin A," ACS Medicinal Chemistry Letters, vol. 3, No. 7, 2012.

PUBCHEM 110091647, created Feb. 25, 2011, located at https://pubchem.ncbi.nlm.nih.gov/substance/110091647, 6 pages.

PUBCHEM 223343680, created Nov. 10, 2014, located at https://pubchem.ncbi.nlm.nih.gov/substance/223343680, 5 pages.

PUBCHEM 74797094, created Jun. 11, 2009, located at https://pubchem.ncbi.nlm.nih.gov/substance/74797094, 5 pages.

PubChem-CID-11750091, 4-RE)-2-(Benzenesulfony)ethenyl]-1-(4-methylphenypsulfonylpiperidine, Create Date: Oct. 26, 2006, p. 2 Fig.

PubChem-CID-56178526, (Z)-2-Cyano-N-l[11(4-methoxyphenyl)methylpiperidin-4-yllmethyl]-3-[1-(1-methoxypropan-2-il)-2,5-dimethylpyrrol-3-yl]prop-2-enamide, Create Date: Jan. 25, 2012, p. 2, Fig.

PubChem-CID-56217953, (Z)-N-l[1-(Benzenesulfonyppiperidin-4-yl]methy]-2-cyano-3-(2,5-dimethyl-1-propylpyrrol-3-yl] pro-2-enamide, Create Date: Jan. 25, 2012, p. 2, Fig.

PubChem-CID-56314596, (Z)-2-Cyano-[11(4-methoxyphenyl)-2,5-dimethylpyrrol-3-ylkNI1(1-propan-2-ylpyrrolidin-3-yl) nethyl]prop-2-enamide, Create Date: Jan. 25, 2012, p. 2, Fig.

PubChem-CID-77141576, 1-Methyl-3/44-(2-methylsulfonylethenyp-piperidin-1-yl]-2-oxoquinoline-3-carbonitrile, Create Date: Sep. 10, 2014, p. 2, Fig.

Registry (STN) No. 1046208-96-1, Sep. 4, 2008.
Registry (STN) No. 1060988-53-5, Oct. 14, 2008.
Registry (STN) No. 1099889-61-8, Feb. 3, 2009.
Registry (STN) No. 1235685-68-3, Aug. 10, 2010.
Registry (STN) No. 1276209-51-8, Apr. 7, 2011.
Registry (STN) No. 1276217-66-3, Apr. 7, 2011.
Registry (STN) No. 1276225-82-1, Apr. 7, 2011.
Registry (STN) No. 1276249-08-1, Apr. 7, 2011.
Registry (STN) No. 1302884-07-6, May 30, 2011.
Registry (STN) No. 1302915-05-4, May 30, 2011.
Registry (STN) No. 1302950-32-8, May 30, 2011.
Registry (STN) No. 1302979-50-5, May 30, 2011.
Registry (STN) No. 1303073-87-1, May 31, 2011.
Registry (STN) No. 1303187-17-8, May 31, 2011.
Registry (STN) No. 1303228-57-0, May 31, 2011.
Registry (STN) No. 1303251-45-7, May 31, 2011.
Registry (STN) No. 1303294-15-6, May 31, 2011.
Registry (STN) No. 1303982-77-9, May 30, 2011.
Registry (STN) No. 1322620-59-6, Aug. 24, 2011.
Registry (STN) No. 1322804-03-4, Aug. 24, 2011.
Registry (STN) No. 1322808-30-9, Aug. 24, 2011.
Registry (STN) No. 1322872-96-7, Aug. 24, 2011.
Registry (STN) No. 1322930-26-6, Aug. 25, 2011.
Registry (STN) No. 1335283-57-2, Oct. 14, 2011.
Registry (STN) No. 1335636-92-4, Oct. 16, 2011.
Registry (STN) No. 1420450-66-3, Feb. 13, 2013.
Registry (STN) No. 1420531-71-0, Feb. 13, 2013.
Registry (STN) No. 838705-56-3, Jun. 28, 2007.
Registry (STN) No. 927551-13-1, Mar. 20, 2007.
Registry (STN) No. 927581-98-4, Mar. 20, 2007.
Registry (STN) No. 938827-79-3, Jun. 25, 2007.
Registry (STN) No. 939705-56-3, Jun. 28, 2007.

Shi et al., "Amino(methyl)pyrrolidines as novel scaffolds for factor Xa inhibitors," Bioorganic & Medicinal Chemistry Letters 17(21): 5952-5958 (Nov. 1, 2007, e-published Aug. 21, 2007).

Stratmann et al., "Welwitindolinones, Unusual Alkaloids from the Blue-Green Algae Hapalosiphon welwitschii and Westiella intricata. Relationship to Fischerindoles and Hapalinodoles," J. Am. Chem. Soc. 116(22):9935-9942 (1994).

Tome, "Product class 13: 1,2,3-triazoles," Science of Synthesis, 13, 2004, 415-601.

Turner et al., "Simple plate-based, parallel synthesis of disulfide fragments using the CuAAC click reaction," ACS Comb. Sci. 16:661-664, supplemental information, 49 total pages (2014).

Turner et al., "Simple plate-based, parallel synthesis of disulfide fragments using the CuAAC click reaction," ACS Comb. Sci. 16(12):661-664 (Dec. 8, 2014, e-published Nov. 12, 2014).

Wang et al., "Targeting Mutant KRAS for anticancer Therapeutics: A Review of Novel Small Molecule Modulators," Journal of Medicinal Chemistry, Apr. 23, 2013, pp. 5219-5230, vol. 56, No. 13.

Winter et al., "Structure-Activity Rltionships of Chromone Derivatiaves toward the Mechanism of Interaction with and Inhibition of Breast Cancer Resistance Protein ABCG2," Journal of Medicinal Chemistry, vol. 56, No. 24, 2013, pp. M49-M9860.

Written Opinion dated Aug. 19, 2016, for PCT Application No. PCT/US2016/031344, filed May 6, 2016, 6 pages.

XP002792949, Nov. 4, 2008, retrieved from STN Database accession No. 1070668-79-7.
XP002792950, Nov. 2, 2008, retrieved from STN Database accession No. 1069483-13-t.
XP002792951, May 27, 2004, retrieved from STN Database accession No. 686272-37-7.
XP002792952, Nov. 3, 2008, retrieved from STN Database accession No. 1069948-57-7.
XP002792953, Aug. 10, 2010, retrieved from STN Database accession No. 11235624-64-2.

Registry (STN) No. 1839919-81-1, Jan. 1, 2006.
Registry (STN) No. 1484135-82-1, Dec. 1, 2013.
Registry (STN) No. 1285326-06-8, Apr. 19, 2021.
Registry (STN) No. 1535205-78-7, Apr. 19, 2021.
Registry (STN) No. 1372050-86-6, May 1, 2012.
Registry (STN) No. 1783181-50-9, Jun. 18, 2015.
Registry (STN) No. 1783236-10-1, Jun. 18, 2015.
Registry (STN) No. 925605-78-3, Mar. 8, 2007.
Registry (STN) No. 1197616-23-1, Dec. 16, 2009.
Registry (STN) No. 1370924-59-6, Apr. 29, 2012.

(56) References Cited

OTHER PUBLICATIONS

Registry (STN) No. 791079-49-7, Dec. 1, 2004.
Registry (STN) No. 959240-11-0, Dec. 21, 2007.
Registry (STN) No. 1090732-25-1, Dec. 28, 2008.
European Examination Report from corresponding application No. 18723515.2 dated Jan. 7, 2022 (8 pages).
Registry (STN) No. 1384596-49-9, Jul. 27, 2012 (1 page).
Registry (STN) No. 916030-58-5, entered date Dec. 20, 2006 (1 page).
Database Registry Chemical Abstract Service, Columbus, Ohio, US; Jan. 31, 2014, XP055875576, Database accession No. 1535205-78-7.
Database Registry Chemical Abstracts Service, Columbus, Ohio, US; Dec. 1, 2004, XP055875595, Database accession No. 791079-49-7.
Database Registry Chemical Abstracts Service, Columbus, Ohio, US; Dec. 1, 2013, XP055875540, Database accession No. 1484135-82-1.
Database Registry Chemical Abstracts Service, Columbus, Ohio, US; Jan. 1, 2006, XP055875535, Database accession No. 1839919-81-1.
Database Registry Chemical Abstracts Service, Columbus, Ohio, US; May 1, 2012, XP055875585, Database accession No. 1372050-86-6.
Database Registry Chemical Abstracts Service, Columbus, Ohio, US; Dec. 16, 2009, XP055875592, Database accession No. 1197616-23-1.
Database Registry Chemical Abstracts Service, Columbus, Ohio, US; Jun. 18, 2015, XP055875586, Database accession No. 1783181-50-9.
Database Registry Chemical Abstracts Service, Columbus, Ohio, US; Jun. 18, 2015, XP055875590, Database accession No. 1783236-10-1.
Database Registry Chemical Abstracts Service, Columbus, Ohio, US; Dec. 21, 2007, XP055875597, Database accession No. 959240-11-0.
Database Registry Chemical Abstracts Service, Columbus, Ohio, US; Apr. 25, 2011, XP055875566, Database accession No. 1285326-06-8.
Database Registry Chemical Abstracts Service, Columbus, Ohio, US; Dec. 28, 2008, XP055875600, Database accession No. 1090732-25-4.
Database Registry Chemical Abstracts Service, Columbus, Ohio, US; Apr. 29, 2012, XP055875593, Database accession No. 1370924-59-6.
Database Registry Chemical Abstracts Service, Columbus, Ohio, US; Mar. 8, 2007, XP055875591, Database accession No. 925605-78-3.
Database Registry, Chemical Abstracts Service, Columbus, Ohio, US; Aug. 23, 2006, XP055875515, Database accession No. 903676-36-8.
Geske et al., "Evaluation of a focused library of N-aryl L-homoserine lactones reveals a new set of potent quorum sensing modulators", Bioorganic & Medicinal Chemistry Letters, 2008, 18, 5978-5981.
Registry (STN) No. 903676-36-8, Nov. 1, 2021.

SMDC 917069 (also known as 3G4)

SMDC 963109

SMDC 963108

SMDC 963107

'95'

Molecular Weight: 408.88
SMDC 973195

'96'

Molecular Weight: 394.85
SMDC 973196

'14'

Molecular Weight: 322.79
SMDC 973214

'553'

Molecular Weight: 358.84
SMDC 973553

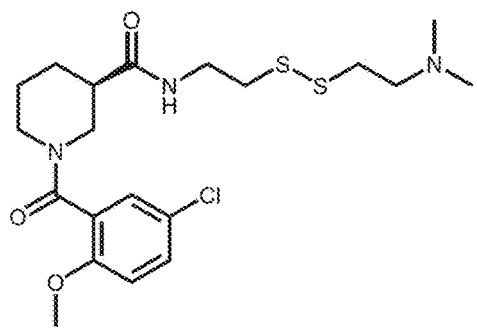
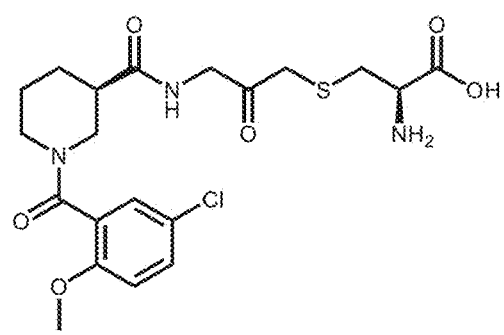
6B9 : Tethering Compound (FB9)  
6B9 - bound to Cys after electrophilic reaction
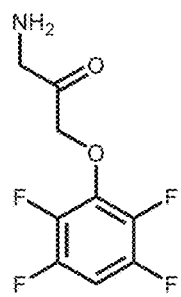
Electrophilic modification
FIG. 6B
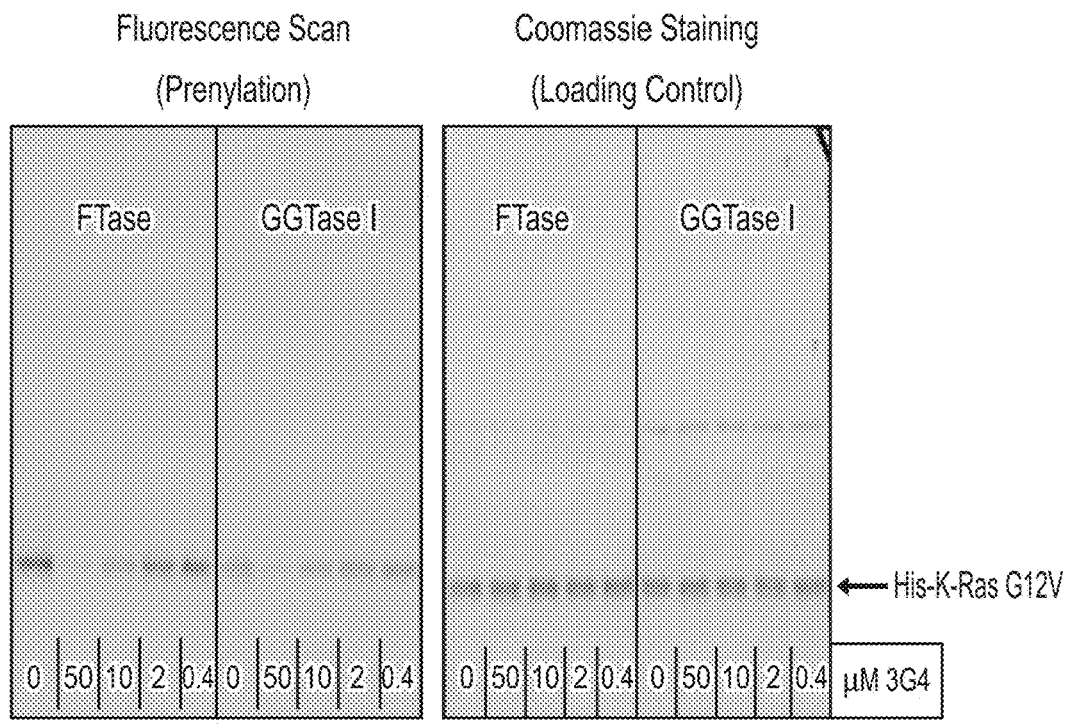
FIG. 7A

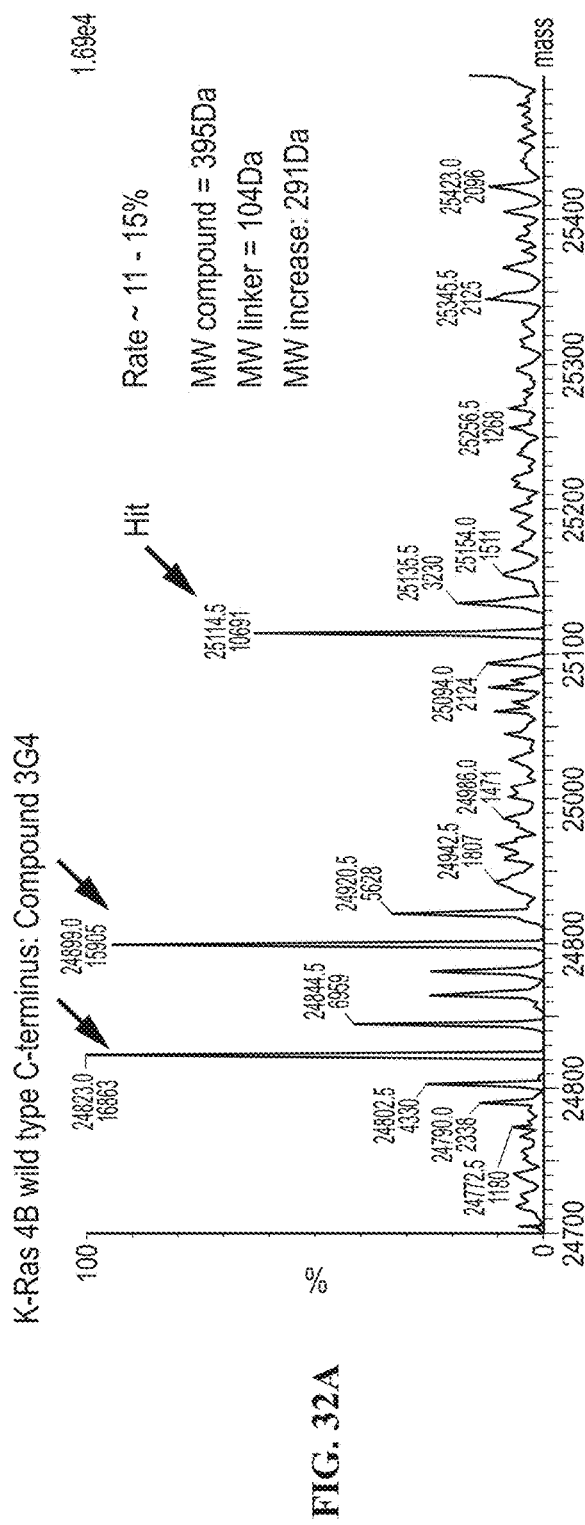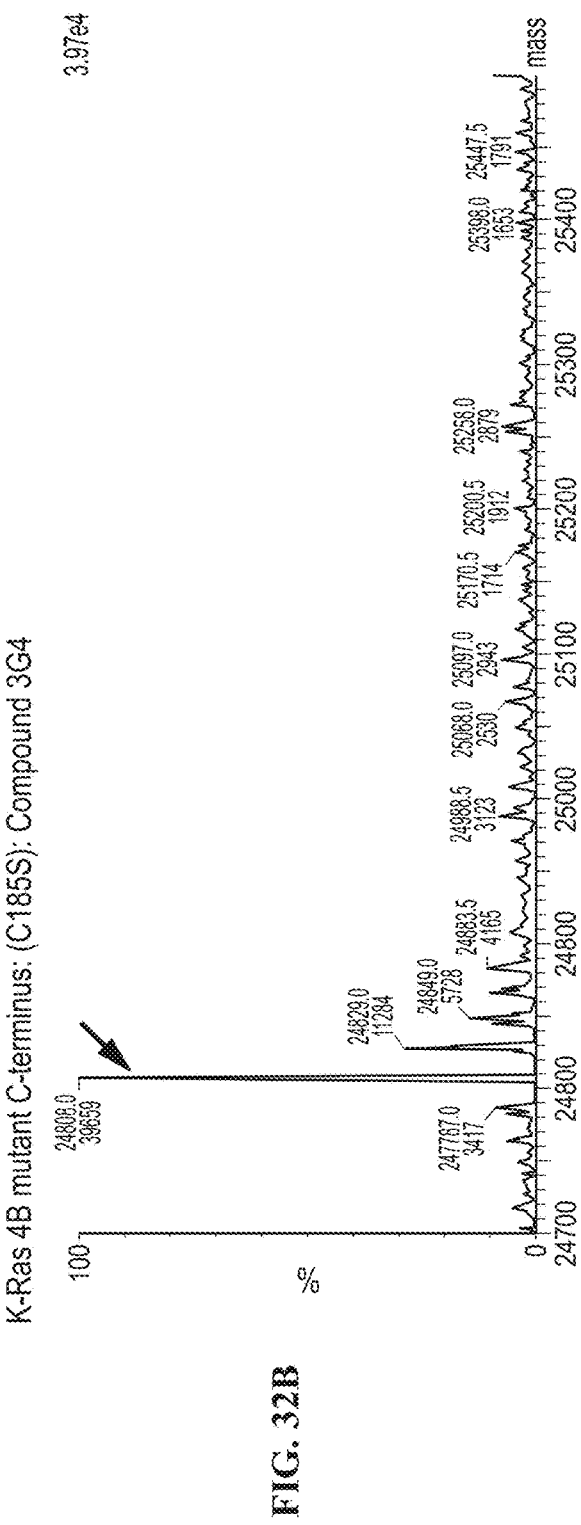
FIG. 32A
FIG. 32B

Full-size KRAS (G-Hs.KRAS4b, 1-188); RPX150917.19; RP115091714O242
Average [M+H]+ 21482.5940

GMTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHHYREQIKRVKDSEDVPMVLVGNKCDLPSRTVDTK
QAQDLARSYGIPFIETSAKTRQGVDDAFYTLVREIRKHKEKMSKDGKKKKKSKTKCVIM

```
        10         20         30         40         50         60
GMTEYKLVVV GAGGVGKSAL TIQLIQNHFV DEYDPTIEDS YRKQVVIDGE TCLLDILDTA
        70         80         90        100        110        120
GQEEYSAMRD QYMRTGEGFL CVFAINNTKS FEDIHHYREQ IKRVKDSEDV PMVLVGNKCD
       130        140        150        160        170        180
LPSRTVDTKQ AQDLARSYGI PFIETSAKTR QGVDDAFYTL VREIRKHKEK MSKDGKKKKK

KSKTKCVIM
```

FIG. 42

Farnesylated carboxylmethylated KRAS4b GG-HsKRAS-4b,
RP1151105092454 Average [M+H]+ 21283.35

GGTEYKLVVVGAGGVGKSALTIQLIQNHFVDEYDPTIEDSYRKQVVIDGET
CLLDILDTAGQEEYSAMRDQYMRTGEGFLCVFAINNTKSFEDIHHYREQIK
RVKDSEDVPMVLVGNKCDLPSRTVDTKQAQDLARSYGIPFIETSAKTRQG
VDDAFYTLVREIRKHKEKMSKDGKKKKKKSKTKC-famMe

SEQUENCE LISTING

```
<160> NUMBER OF SEQ ID NOS: 12

<210> SEQ ID NO 1
<211> LENGTH: 189
<212> TYPE: PRT
<213> ORGANISM: Artificial Sequence
<220> FEATURE:
<223> OTHER INFORMATION: Synthetic polypeptide

<400> SEQUENCE: 1

Gly Met Thr Glu Tyr Lys Leu Val Val Val Gly Ala Gly Gly Val Gly
1               5                   10                  15

Lys Ser Ala Leu Thr Ile Gln Leu Ile Gln Asn His Phe Val Asp Glu
            20                  25                  30

Tyr Asp Pro Thr Ile Glu Asp Ser Tyr Arg Lys Gln Val Ile Asp
        35                  40                  45

Gly Glu Thr Cys Leu Leu Asp Ile Leu Asp Thr Ala Gly Gln Glu Glu
    50                  55                  60

Tyr Ser Ala Met Arg Asp Gln Tyr Met Arg Thr Gly Glu Gly Phe Leu
65                  70                  75                  80

Cys Val Phe Ala Ile Asn Asn Thr Lys Ser Phe Glu Asp Ile His His
                85                  90                  95

Tyr Arg Glu Gln Ile Lys Arg Val Lys Asp Ser Glu Asp Val Pro Met
            100                 105                 110

Val Leu Val Gly Asn Lys Cys Asp Leu Pro Ser Arg Thr Val Asp Thr
        115                 120                 125

Lys Gln Ala Gln Asp Leu Ala Arg Ser Tyr Gly Ile Pro Phe Ile Glu
    130                 135                 140

Thr Ser Ala Lys Thr Arg Gln Gly Val Asp Asp Ala Phe Tyr Thr Leu
145                 150                 155                 160

Val Arg Glu Ile Arg Lys His Lys Glu Lys Met Ser Lys Asp Gly Lys
                165                 170                 175

Lys Lys Lys Lys Lys Ser Lys Thr Lys Cys Val Ile Met
            180                 185

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2
```

```
Asp Ile His His Tyr Arg Glu
1               5

<210> SEQ ID NO 3
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 3

Gly Lys Lys Lys Lys Lys Ser Lys Thr Lys Cys Val Ile Met
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 4

Lys Met Ser Lys Asp Gly Lys Lys Lys Lys Lys Ser Lys Thr Lys
1               5                   10                  15

Cys Val Ile Met
            20

<210> SEQ ID NO 5
<211> LENGTH: 186
<212> TYPE: PRT
<213> ORGANISM: Artificial Sequence
<220> FEATURE:
<223> OTHER INFORMATION: Synthetic polypeptide

<400> SEQUENCE: 5

Gly Gly Thr Glu Tyr Lys Leu Val Val Val Gly Ala Gly Gly Val Gly
1               5                   10                  15

Lys Ser Ala Leu Thr Ile Gln Leu Ile Gln Asn His Phe Val Asp Glu
            20                  25                  30

Tyr Asp Pro Thr Ile Glu Asp Ser Tyr Arg Lys Gln Val Val Ile Asp
        35                  40                  45

Gly Glu Thr Cys Leu Leu Asp Ile Leu Asp Thr Ala Gly Gln Glu Glu
    50                  55                  60

Tyr Ser Ala Met Arg Asp Gln Tyr Met Arg Thr Gly Glu Gly Phe Leu
65                  70                  75                  80

Cys Val Phe Ala Ile Asn Asn Thr Lys Ser Phe Glu Asp Ile His His
                85                  90                  95

Tyr Arg Glu Gln Ile Lys Arg Val Lys Asp Ser Glu Asp Val Pro Met
            100                 105                 110

Val Leu Val Gly Asn Lys Cys Asp Leu Pro Ser Arg Thr Val Asp Thr
        115                 120                 125

Lys Gln Ala Gln Asp Leu Ala Arg Ser Tyr Gly Ile Pro Phe Ile Glu
    130                 135                 140

Thr Ser Ala Lys Thr Arg Gln Gly Val Asp Asp Ala Phe Tyr Thr Leu
145                 150                 155                 160

Val Arg Glu Ile Arg Lys His Lys Glu Lys Met Ser Lys Asp Gly Lys
                165                 170                 175

Lys Lys Lys Lys Lys Ser Lys Thr Lys Cys
            180                 185
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Ser Phe Glu Asp Ile His His Tyr Arg
1               5

<210> SEQ ID NO 7
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 7

Ser Phe Glu Asp Ile His His Tyr Arg Glu Gln Ile Lys Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 8

Ser Phe Glu Asp Ile His His Tyr Arg Glu Gln Ile Lys
1               5                   10

<210> SEQ ID NO 9
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 9

Asp Ser Glu Asp Val Pro Met Val Leu Val Gly Asn Lys Cys Asp Leu
1               5                   10                  15

Pro Ser Arg

<210> SEQ ID NO 10
<211> LENGTH: 189
<212> TYPE: PRT
<213> ORGANISM: Homo sapiens

<400> SEQUENCE: 10

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95
```

```
Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
        130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 11
<211> LENGTH: 189
<212> TYPE: PRT
<213> ORGANISM: Homo sapiens
<220> FEATURE:
<221> NAME/KEY: MOD_RES
<222> LOCATION: (186)..(186)
<223> OTHER INFORMATION: Residue may be farnesylated

<400> SEQUENCE: 11

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 12
<211> LENGTH: 188
<212> TYPE: PRT
<213> ORGANISM: Homo sapiens
<220> FEATURE:
<221> NAME/KEY: MOD_RES
<222> LOCATION: (185)..(185)
<223> OTHER INFORMATION: Residue may be farnesylated

<400> SEQUENCE: 12

Met Thr Glu Tyr Lys Leu Val Val Val Gly Ala Gly Gly Val Gly Lys
```

```
1               5                    10                   15
Ser Ala Leu Thr Ile Gln Leu Ile Gln Asn His Phe Val Asp Glu Tyr
            20                  25                30

Asp Pro Thr Ile Glu Asp Ser Tyr Arg Lys Gln Val Val Ile Asp Gly
        35              40                  45

Glu Thr Cys Leu Leu Asp Ile Leu Asp Thr Ala Gly Gln Glu Glu Tyr
        50                  55              60

Ser Ala Met Arg Asp Gln Tyr Met Arg Thr Gly Glu Gly Phe Leu Cys
65              70              75                          80

Val Phe Ala Ile Asn Asn Thr Lys Ser Phe Glu Asp Ile His His Tyr
                85              90                      95

Arg Glu Gln Ile Lys Arg Val Lys Asp Ser Glu Asp Val Pro Met Val
            100             105             110

Leu Val Gly Asn Lys Cys Asp Leu Pro Ser Arg Thr Val Asp Thr Lys
            115             120             125

Gln Ala Gln Asp Leu Ala Arg Ser Tyr Gly Ile Pro Phe Ile Glu Thr
        130             135             140

Ser Ala Lys Thr Arg Gln Gly Val Asp Asp Ala Phe Tyr Thr Leu Val
145             150             155                         160

Arg Glu Ile Arg Lys His Lys Glu Lys Met Ser Lys Asp Gly Lys Lys
                165             170             175

Lys Lys Lys Lys Ser Lys Thr Lys Cys Val Ile Met
            180             185
```

K-RAS MODULATORS

CROSS-REFERENCES TO RELATED APPLICATIONS

This application is a divisional of U.S. patent application Ser. No. 15/571,475, filed May 1, 2018, now U.S. Pat. No. 10,857,140, which is the national stage filing under 35 USC 371 of international application PCT/US2016/031344, filed May 6, 2016, which claims the benefit of U.S. Provisional Application No. 62/157,915, filed May 6, 2015, and U.S. Provisional Application No. 62/158,356, filed May 7, 2015 each of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under Contract No. HHSN261200800001E awarded by the National Cancer Institute. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-569N01US_ST25.txt, created Nov. 2, 2017, 10,778 bytes, machine format IBM-PC, MS Windows operating system, is hereby incorporated by reference.

BACKGROUND OF THE INVENTION

K-Ras is the most frequently mutated oncogene in human cancer. Past attempts to directly modulate the activity of this enzyme have been unsuccessful. Ras proteins are small guanine nucleotide-binding proteins that act as molecular switches by cycling between active GTP-bound and inactive GDP-bound conformations. The Ras proteins play a critical role in the regulation of cell proliferation, differentiation, and survival. Dysregulation of the Ras signaling pathway is almost invariably associated with disease. Hyper-activating somatic mutations in Ras are among the most common lesions found in human cancer. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. Similarly, H-Ras mutations are common in cancers such as papillary thyroid cancer, lung cancers and skin cancers. Finally, N-Ras mutations occur frequently in hepatocellular carcinoma. There is a need in the art for effective Ras inhibitors and anticancer compounds. Disclosed herein are solutions to these and other problems in the art.

BRIEF SUMMARY OF THE INVENTION

Described herein, inter alia, is the use of covalent (e.g. reversible or irreversible) modulators to target a Ras (e.g., K-Ras) protein, including but not limited to oncogenic mutants.

In an aspect is provided a compound having the formula:

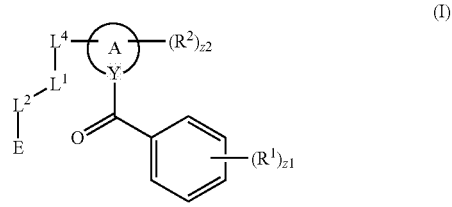

(I)

wherein, Y is N or CH; Ring A is a $C_3$-$C_7$ cycloalkyl or 3 to 7 membered heterocycloalkyl; $R^1$ is independently halogen, $CX^1_3$, —$CHX^1_2$, —$CH_2X^1$, —CN, —$SO_2Cl$, —$SO_{n1}R^{10}$, —$SO_{v1}NR^7R^8$, —$NHNR^7R^8$, —$ONR^7R^8$, —NHC=(O)$NHNR^7R^8$, —$NHC(O)NR^7R^8$, —$N(O)_{m1}$, —$NR^7R^8$, —$C(O)R^9$, —C(O)—$OR^9$, —$C(O)NR^7R^8$, —$OR^{10}$, —$NR^7SO_2R^{10}$, —$NR^7C(O)R^9$, —$NR^7C(O)OR^9$, —$NR^7OR^9$, —$OCX^1_3$, —$OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $L^2$ is a bond, —O—, —C(O)—, —S—, —SO—, —S(O)$_2$—, —$NR^{7B}$—, —$NR^{7B}C(O)$—, —C(O)$NR^{7B}$—, —$SO_2NR^{7B}$—, —$NR^{7B}SO_2$—, —$OC(O)NR^{7B}$—, —$NR^{7B}C(O)O$—, —$CR^{9B}$=NO—, —ON=$CR^{9B}$—, —$NR^{8B}C(O)NR^{7B}$—, —$NR^{8B}C(=NR^{10B})NR^{7B}$—, —$NR^{8B}C(=NR^{10B})$—, —C(=$NR^{10B}$)$NR^{7B}$—, —OC(=$NR^{10B}$)—, —C(=$NR^{10B}$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $L^4$ is a bond, —O—, —C(O)—, —S—, —SO—, —S(O)$_2$—, —$NR^4$—, —$NR^4C(O)$—, —$C(O)NR^4$—, —$SO_2NR^4$—, —$NR^4SO_2$—, —$NR^4SO_2$—, —$OC(O)NR^4$—, —$NR^4C(O)$O—, substituted or unsubstituted $C_1$-$C_3$ alkylene, substituted or unsubstituted 2 to 3 membered heteroalkylene; E is an electrophilic moiety; $R^2$ is independently oxo, halogen, $CX^2_3$, —$CHX^2_2$, —$CH_2X^2$, —CN, —$SO_2Cl$, —$SO_{n2}R^{14}$, —$SO_{v2}NR^{11}R^{12}$, —$NHNR^{11}R^{12}$, —$ONR^{11}R^{12}$, —NHC= (O)$NHNR^{11}R^{12}$, —$NHC(O)NR^{11}R^{12}$, —$N(O)_{m2}$, —$NR^{11}R^{12}$, —$C(O)R^{14}$, —C(O)—$OR^{14}$, —$C(O)NR^{11}R^{12}$, —$OR^{15}$, —$NR^{11}SO_2R^{15}$, —$NR^{11}C(O)R^{14}$, —$NR^{11}C(O)$ $OR^{14}$, —$NR^{11}OR^{14}$, —$OCX^2_3$, —$OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents or two $R^2$ substituents bonded to the same atom may optionally be joined to form a substituted or unsubstituted cycloalkyl or substituted or unsubstituted heterocycloalkyl; $R^4$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^7$, $R^8$, $R^9$, $R^{10}$, $R^{7B}$, $R^{8B}$, $R^{9B}$, $R^{10B}$, $R^{11}$, $R^{12}$, $R^{14}$, and $R^{15}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl; each X, X$^1$, and X$^2$ is independently —F, —Cl, —Br, or —I; n1, n2, v1, and v2 are independently an integer from 0 to 4; m1 and m2 are independently an integer from 1 to 2; z1 is independently an integer from 0 to 5; and z2 is independently an integer from 0 to 10.

In another aspect is provided a pharmaceutical composition including a compound described herein and a pharmaceutically acceptable excipient.

In another aspect, a method of treating a disease in a patient in need of such treatment is provided. In embodiments, the disease is cancer.

In another aspect is provided a method of reducing the level of activity of a K-Ras protein (e.g., human K-Ras 4B), the method including contacting the K-Ras protein with a compound described herein (including in embodiments, examples, figures, and tables).

In another aspect, a method of modulating a K-Ras protein is provided. The method including contacting the K-Ras protein with an effective amount of a compound described herein (including in embodiments, examples, figures, and tables).

In another aspect is provided, a K-Ras protein covalently (e.g., reversibly or irreversibly) bonded to a compound, for example a compound as described herein (including modulators, inhibitors, or in embodiments, examples, and tables).

BRIEF DESCRIPTION OF THE DRAWINGS

FIG. 2A depicts the structure of SMDC 917069, also referred to herein as 3G4. FIG. 2B depicts the structure of SMDC 963109. FIG. 2C depicts the structure of SMDC 963108. FIG. 2D depicts the structure of SMDC 963107.

FIGS. 6A-6B. Compound FB9; electrophile is the tetra fluorophenoxy-group which is also the leaving group after the thioether linkage between the cysteine thiol and the rest of FB9, depicted in FIG. 6B.

FIG. 7A-7B. In Vitro Prenylation Assays with Purified K-Ras and FTase or GGTase. A fluorescent substrate for farnesyl transferase, 3,7-dimethyl-8-(7-nitro-benzo[1,2,5] oxadiazol-4-ylamino)-octa-2,6-diene-1-pyrophosphate (NBD-GPP), has similar kinetics as the natural substrate for farnesyl pyrophosphate. FIG. 7A is with concentrations of 3G4. FIG. 7B is with concentrations of 6B9.

FIG. 13B and FIG. 13D were performed after 5 hours. FIG. 13C and FIG. 13E were performed at 23 hours.

FIG. 17B depicts the extent of the KRas labeling relative to compound TC-1.

FIGS. 32A-32B. FIG. 32A: K-ras 4B wile type C-terminus: Compound 3G4. FIG. 32B: K-ras 4B mutant C-terminus (C185S): compound 3G4.

FIG. 38A: Vinyl sulfonamide analogue of FB9, compound 994566, decreased Kras protein expression in mouse embryonic fibroblasts (MEF) expressing Kras4B G12D. Cells were serum-starved overnight, followed by treatment with 994566 and EGF (30 ng/ml). Medium was changed to complete (10% FBS) after 8 h, then compound was added again. Cell lysates were collected after 96 h in culture. FIG. 38B: Structures of vinyl acrylamide (left) and vinyl sulfonamide (right) analogues of FB9.

FIG. 42. Sequence of KRAS4b used in MALDI-TOF experiments (SEQ ID NO: 1)
GMTEYKLVVVGAGGVGKSALTIQLIQNHFVDEYDPTIEDSYRKQVVIDGE

TCLLDILDTAGQEEYSAMRDQYMRTGEGFLCVFAINNTKSFEDIHHYREQ

IKRVKDSEDVPMVLVGNKCDLPSRTVDTKQAQDLARSYGIPFIETSAKTR

QGVDDAFYTLVREIRKHKEKMSKDGKKKKKKSKTKCVIM.

Figure 43:
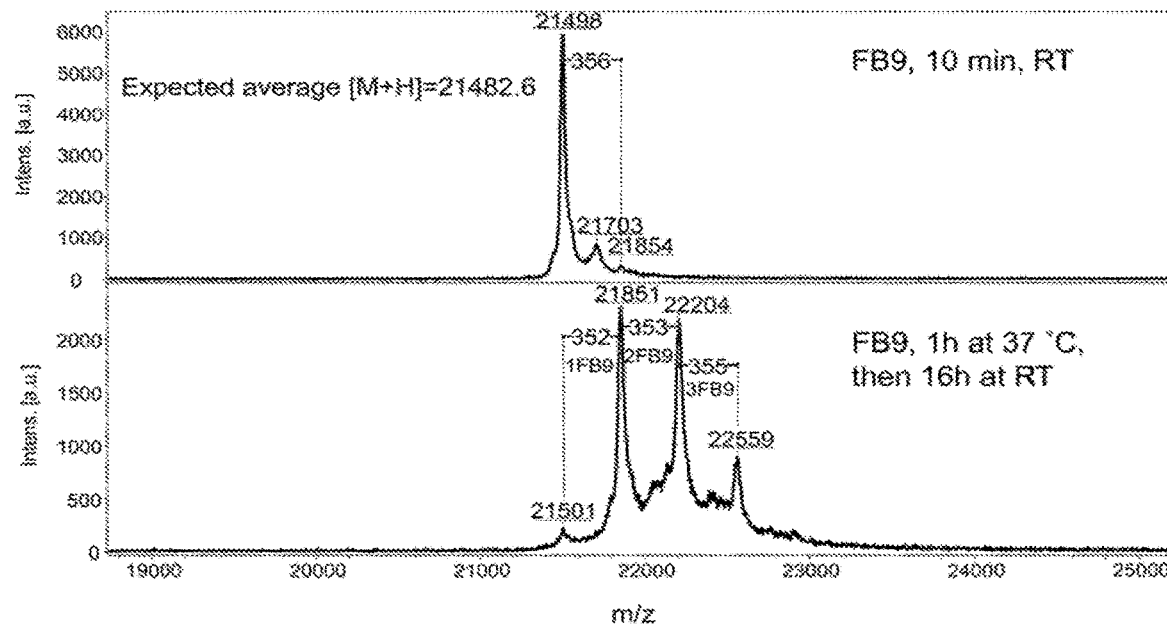

FIG. 43. MALDI-TOF spectra of KRAS4B (SEQ ID NO: 1) modified by FB9.

Figure 44:
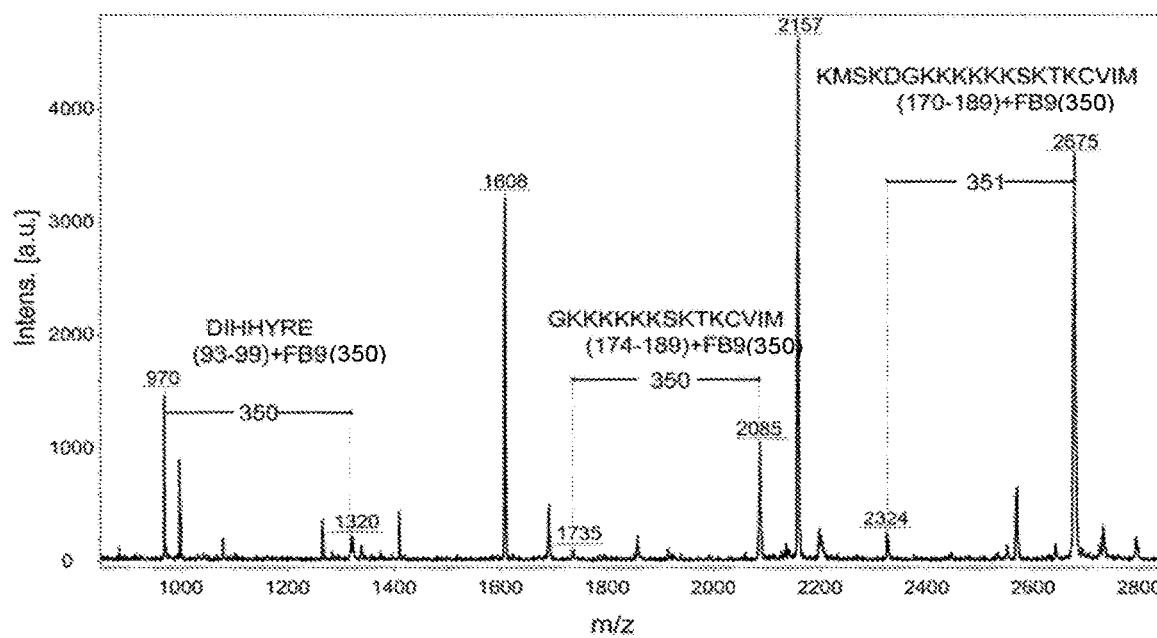

FIG. 44. MALDI-TOF MS (linear mode) of the Glu-C digest (overnight, RT) of FB9-modified full-size (1-188) KRAS4b. The sequences listed within FIG. 44 are DIHHYRE (SEQ ID NO:2), GKKKKKKSKTKCVIM (SEQ ID NOG), and KMSKDGKKKKKKSKTKCVIM (SEQ ID NO:4).

Figure 45A:
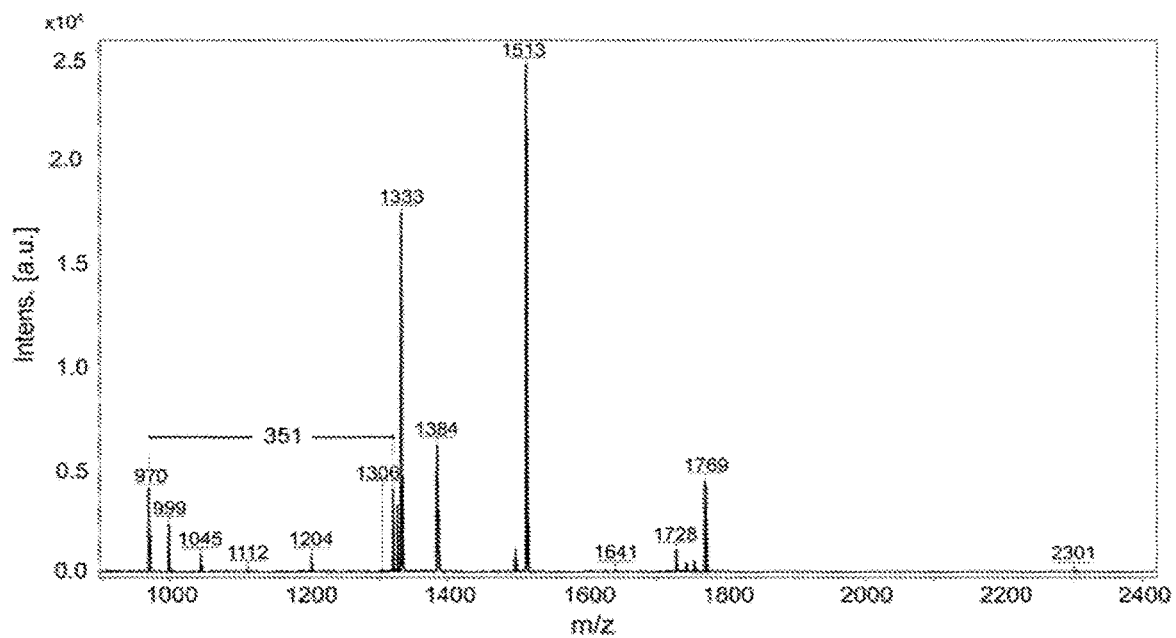
Figure 45B:
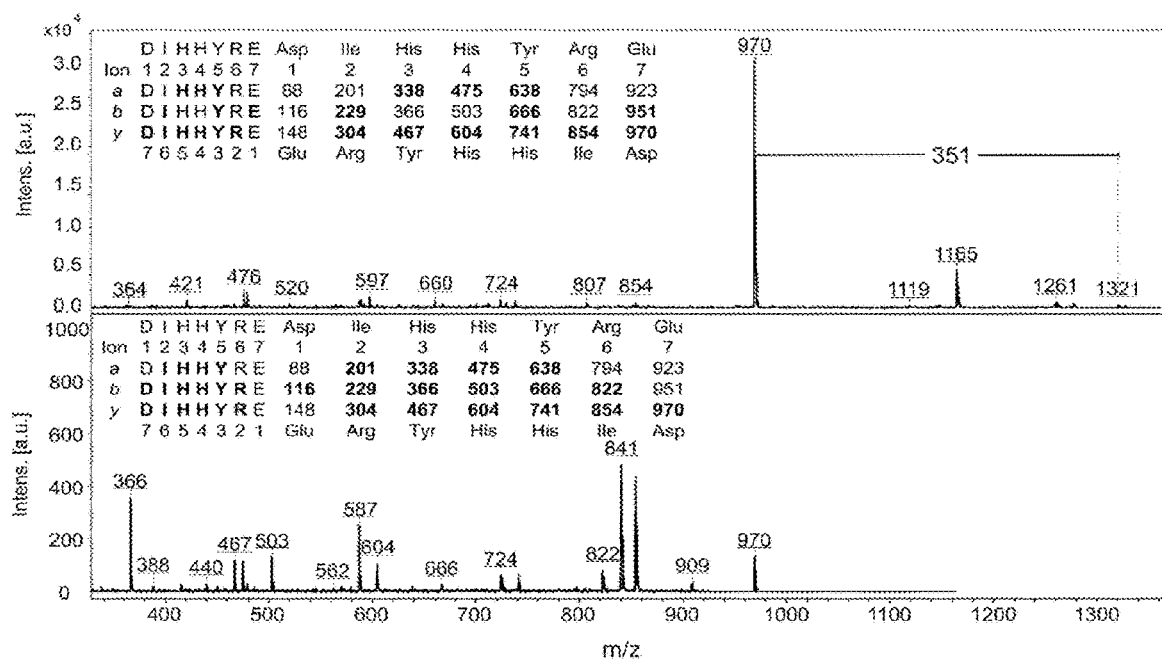

FIGS. 45A-45B. Identification of residues modified by FB9 on KRAS 4b. FIG. 45A: Peptides obtained after digestion by Glu-C were further digested by trypsin. FIG. 45B: Common fragments and a comparison of fragmentation spectra of peptides 969.485 and 1320.614.

Figures 46A, 46B:
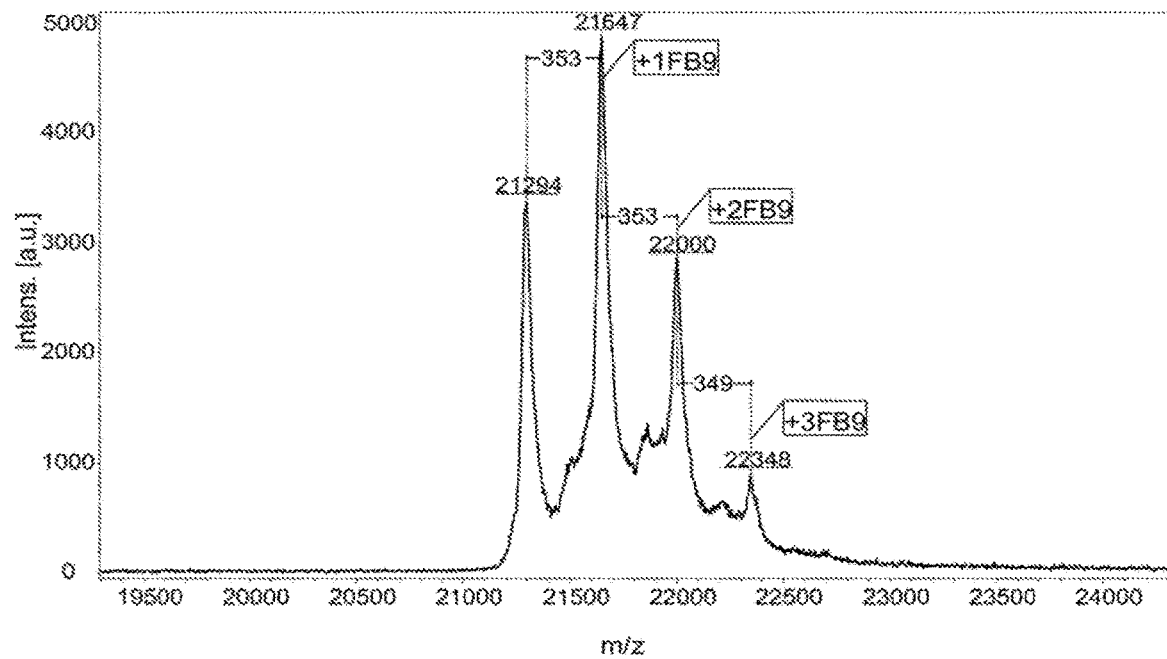

FIGS. 46A-46B. FIG. 46A: The sequence of the protein used for experiment, specifically GGTEYKL-VVVGAGGVGKSALTIQLIQNHFVDEYDPTIEDSYR-KQVVIDGETC LLDILDTAGQEEYSAMRDQYMRT-GEGFLCVFAINNTKSFEDIHHYREQIKRVKDSEDVP MVLVGNKCDLPSRTVDTKQAQDLARSYGIPFIET-SAKTRQGVDDAFYTLVREIRKHKEK MSKDGKKK-KKKSKTKC (SEQ ID NOG). FIG. 46B: MALDI-TOF spectrum of the FME-Kras4b protein modified by FB9.

Figure 47:
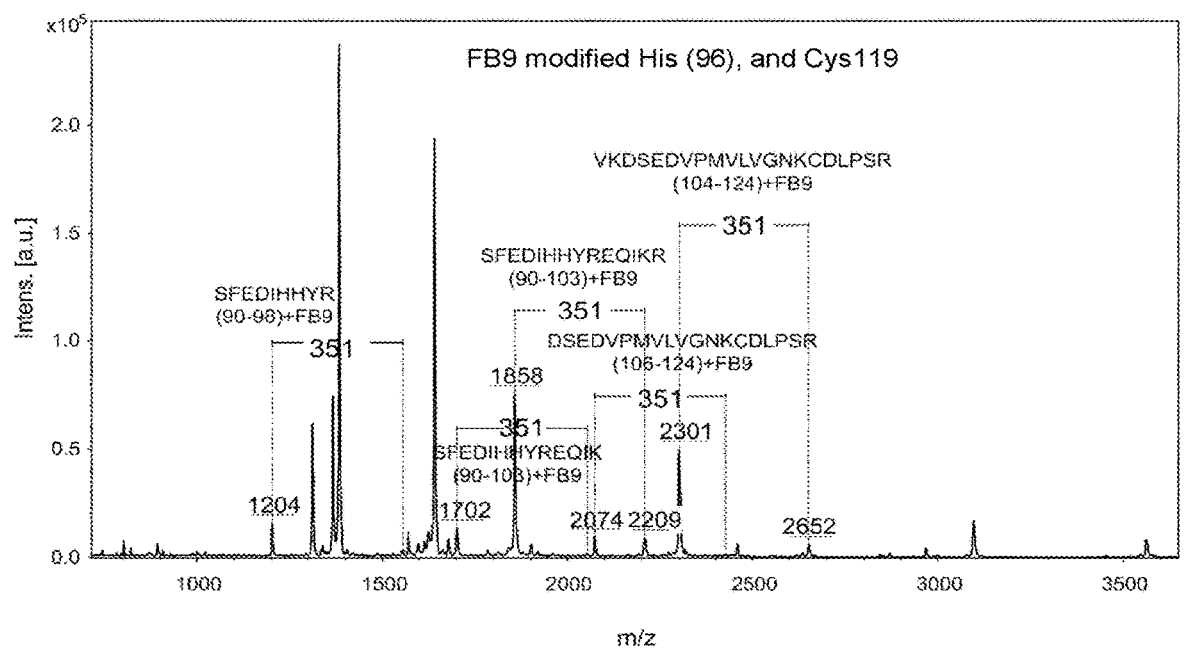

FIG. 47. MALDI-TOF analysis of peptides modified by FB9 in Kras4b. The sequences listed within FIG. 47 are SFEDIHHYR (SEQ ID NO:6), SFEDIHHYREQIKR (SEQ ID NOG), SFEDIHHYREQIK (SEQ ID NO:8), and DSEDVPMVLVGNKCDLPSR (SEQ ID NO:9).

I. DEFINITIONS

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., selected from the group consisting of O, N, P, Si, and S, and wherein the nitrogen and sulfur atoms may optionally be oxidized, and the nitrogen heteroatom may optionally be quaternized). The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O) NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocyclic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

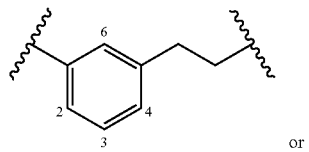

or

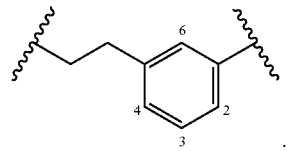

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —NH$_2$, —COOH, —CONH$_2$, —NO$_2$, —SH, —SO$_2$CH$_3$—SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$CH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R'")$_d$—, where s and d are independently integers of from 0 to 3, and X' is —O—, —NR'—, —S—, —S(O)—, —S(O)$_2$—, or —S(O)₂NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorous (P), and silicon (Si).

A "substituent group," as used herein, means a group selected from the following moieties:
(A) oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC= (O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
  (i) oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
   (a) oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC=(O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl, and
   (b) alkyl, heteroalkyl, cycloalkyl, heterocycloalkyl, aryl, heteroaryl, substituted with at least one substituent selected from: oxo, halogen, —CF₃, —CN, —OH, —NH₂, —COOH, —CONH₂, —NO₂, —SH, —SO₃H, —SO₄H, —SO₂NH₂, —NHNH₂, —ONH₂, —NHC= (O)NHNH₂, —NHC=(O) NH₂, —NHSO₂H, —NHC=(O)H, —NHC(O)—OH, —NHOH, —OCF₃, —OCHF₂, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C4-C20 alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_3$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol or additional number may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable moiety" as used herein refers to a moiety that can be covalently or noncovalently attached to a compound or biomolecule that can be detected for instance, using techniques known in the art. In embodiments, the detectable moiety is covalently attached. The detectable moiety may provide for imaging of the attached compound or biomolecule. The detectable moiety may indicate the contacting between two compounds. Exemplary detectable moieties are fluorophores, antibodies, reactive dies, radiolabeled moieties, magnetic contrast agents, and quantum dots. Exemplary fluorophores include fluorescein, rhodamine, GFP, coumarin, FITC, Alexa fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex. vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. In some embodiments of the compositions or methods described herein, treating cancer includes slowing the rate of growth or spread of cancer cells, reducing metastasis, or reducing the growth of metastatic tumors. The term "treating" and conjugations thereof, include prevention of an injury, pathology, condition, or disease.

An "effective amount" is an amount sufficient for a compound to accomplish a stated purpose relative to the absence of the compound (e.g. achieve the effect for which it is administered, treat a disease, reduce enzyme activity, increase enzyme activity, reduce signaling pathway, reduce one or more symptoms of a disease or condition (e.g. reduce signaling pathway stimulated by GTP bound Ras (e.g. K-Ras), reduce the signaling pathway activity of Ras, reduce the signaling pathway activity of K-Ras, reduce the signaling pathway activity of K-Ras4A, reduce the signaling pathway activity of K-Ras4B, reduce the signaling pathway activity of H-Ras, reduce the signaling pathway activity of N-Ras, reduce the signaling pathway activity of a mutant K-Ras, inhibit the binding of K-Ras to SOS, inhibit the binding of K-Ras to a GEF, reduce the localization of K-Ras to a membrane, reduce the prenylation of K-Ras, inhibit the localization of K-Ras to a membrane, inhibit the prenylation of K-Ras). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist (e.g. disrupt the protein-protein interaction between K-Ras and a signaling pathway binding protein such as PI3K, disrupt the interaction of K-Ras and GEF, disrupt the interaction of K-Ras and SOS, disrupt the interaction of K-Ras with Raf, disrupt the localization of K-Ras to a membrane, disrupt the prenylation of K-Ras). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity (e.g. signaling pathway) of a protein (e.g. Ras, K-Ras, mutant K-Ras, K-Ras G12C, K-Ras G12D, K-Ras G13C, K-Ras G13D, K-Ras G12V, K-Ras G12S) in the absence of a compound as described herein (including embodiments, examples, figures, or Tables).

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme (e.g. Ras, K-Ras, H-Ras, N-Ras, K-Ras4A, K-Ras4B, mutant Ras, mutant K-Ras, K-Ras G12C, K-Ras G13C, K-Ras G12D, K-Ras G13D, K-Ras G12V, K-Ras G12S). In some embodiments, the protein may be K-Ras. In some embodiments, the protein may be a mutant K-Ras (e.g. K-Ras G12C, K-Ras G13C, K-Ras G12D, K-Ras G13D, K-Ras G12V, K-Ras G12S). In some embodiments, the protein may be K-Ras4A. In some embodiments, the protein may be K-Ras4B. In some embodiments contacting includes allowing a compound described herein to interact with a protein or enzyme that is involved in a signaling pathway.

As defined herein, the term "inhibition", "inhibit", "inhibiting" and the like in reference to a protein-inhibitor interaction means negatively affecting (e.g. decreasing) the activity or function of the protein (e.g. decreasing the signaling pathway stimulated by GTP bound Ras (e.g. K-Ras, K-Ras G12C, K-Ras G13C, K-Ras G12D, K-Ras G13D, K-Ras G12V, K-Ras G12S), nucleotide exchange, effector protein binding, effector protein activation, guanine exchange factor (GEF) binding, SOS binding, GEF-facilitated nucleotide exchange, phosphate release, nucleotide release, nucleotide binding, membrane localization, prenylation of the protein) relative to the activity or function of the protein in the absence of the inhibitor. In some embodiments inhibition refers to reduction of a disease or symptoms of disease. In some embodiments, inhibition refers to a reduction in the activity of a signal transduction pathway or signaling pathway (e.g. reduction of a pathway involving GTP bound Ras (e.g. K-Ras, K-Ras G12C, K-Ras G13C, K-Ras G12D, K-Ras G13D, K-Ras G12V, K-Ras G12S), reduction of a pathway involving mutant K-Ras (e.g. K-Ras G12C, K-Ras G13C, K-Ras G12D, K-Ras G13D, K-Ras G12V, K-Ras G12S)). Thus, inhibition includes, at least in part, partially or totally blocking stimulation, decreasing, preventing, or delaying activation, or inactivating, desensitizing, or down-regulating the signaling pathway or enzymatic activity or the amount of a protein (e.g. K-Ras, K-Ras G12C, K-Ras G13C, K-Ras G12D, K-Ras G13D, K-Ras G12V, K-Ras G12S). In some embodiments, inhibition refers to inhibition of interactions of Ras (K-Ras, K-Ras G12C, K-Ras G13C, K-Ras G12D, K-Ras G13D, K-Ras G12V, K-Ras G12S) with signaling pathway binding partners (e.g. PI3K, SOS, Raf). In some embodiments, inhibition refers to inhibition of interactions of Ras with a GEF (e.g. SOS). In some embodiments, inhibition refers to inhibition of Ras prenylation. In some embodiments, inhibition refers to inhibition of Ras localization. In some embodiments, inhibition refers to inhibition of Ras membrane localization.

The term "modulator" refers to a composition that increases or decreases the level of a target molecule or the function (e.g., effector protein binding, effector protein activation, guanine exchange factor (GEF) binding, SOS binding, prenylation, localization) of a target molecule or the physical state (e.g. Ras subcellular localization, Ras post-translational processing, Ras post-translational modifications (prenylation)) of the target of the molecule (e.g. a target may be K-Ras and the function may be to hydrolyze GTP or activate a signaling pathway that is activated by GTP bound K-Ras, interaction of K-Ras with protein binding partners (e.g. PI3K, SOS, Raf)) relative to the absence of the composition. In some embodiments, a K-Ras disease modulator is a compound that reduces the severity of one or more symptoms of a disease associated with K-Ras (e.g. cancer, metastatic cancer) relative to the absence of the compound. A K-Ras modulator is a compound that increases or decreases the activity or function or level of activity or level of function of K-Ras or level of K-Ras or level of K-Ras in a particular physical state relative to the absence of the compound. A mutant K-Ras modulator is a compound that that increases or decreases the activity or function or level of activity or level of function of mutant K-Ras or level of mutant K-Ras or level of mutant K-Ras in a particular physical state relative to the absence of the compound. A K-Ras G12C modulator, K-Ras G12D modulator, K-Ras G13C modulator, K-Ras G12V modulator, K-Ras G12S modulator, or K-Ras G13D modulator is a compound that increases or decreases the activity or function or level of activity or level of function of that particular mutant K-Ras or level of that particular mutant K-Ras or level of that particular mutant K-Ras in a particular physical state relative to the absence of the compound. A K-Ras inhibitor is a compound that decreases the activity or function or level of activity or level of function of K-Ras or level of K-Ras or level of K-Ras in a particular physical state relative to the absence of the compound. A mutant K-Ras inhibitor is a compound that that decreases the activity or function or level of activity or level of function of mutant K-Ras or level of mutant K-Ras or level of mutant K-Ras in a particular physical state relative to the absence of the compound. A K-Ras G12C inhibitor, K-Ras G12D inhibitor, K-Ras G13C inhibitor, K-Ras G12V inhibitor, K-Ras G12S inhibitor, or K-Ras G13D inhibitor is a compound that decreases the activity or function or level of activity or level of function of that particular mutant K-Ras or level of that particular mutant K-Ras or level of that particular mutant K-Ras in a particular physical state relative to the absence of the compound.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. In some embodiments, the disease is a disease related to (e.g. caused by) a Ras. In some embodiments, the disease is a disease related to (e.g. caused by) a K-Ras (e.g. K-Ras G12C, G13C, G12D, G12V, G12S, or G13D) or aberrant K-Ras signaling pathway activity (e.g. lung cancer, breast cancer, colon cancer, colorectal cancer, pancreatic cancer, leukemia). Examples of diseases, disorders, or conditions include, but are not limited to cancer. Examples of diseases, disorders, or conditions include, but are not limited to MYH-associated polyposis. In some instances, "disease" or "condition" refers to cancer. In some instances, "disease" or "condition" refers to MYH-associated polyposis. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, vermcous carcinoma, or carcinoma villosum.

"Ras associated cancer" (also referred to herein as "Ras related cancer") refers to a cancer caused by aberrant Ras activity or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of Ras, K-Ras, H-Ras, N-Ras, mutant K-Ras (including K-Ras G12C, K-Ras G13C, K-Ras G12D, K-Ras G12V, K-Ras G12S, K-Ras G13D mutants), mutant N-Ras, and mutant H-Ras are well known in the art and determining such cancers are within the skill of a person of skill in the art.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a Ras inhibitor" means administering a compound that inhibits the activity or level (e.g. amount) or level of a signaling pathway of one or more Ras proteins (e.g. a Ras inhibitor, K-Ras inhibitor, N-Ras inhibitor, H-Ras inhibitor, mutant K-Ras inhibitor, K-Ras G12C inhibitor, K-Ras G12V inhibitor, K-Ras G12S inhibitor, K-Ras G13C inhibitor, K-Ras G12D inhibitor, K-Ras G13D inhibitor) to a subject. Administration may include, without being limited by mechanism, allowing sufficient time for the Ras inhibitor to reduce the activity of one or more Ras proteins or for the Ras inhibitor to reduce one or more symptoms of a disease (e.g. cancer, wherein the Ras inhibitor may arrest the cell cycle, slow the cell cycle, reduce DNA replication, reduce cell replication, reduce cell growth, reduce metastasis, or cause cell death). The term "administer (or administering) a K-Ras inhibitor" means administering a compound that inhibits the activity or level (e.g. amount) or level of a signaling pathway of one or more K-Ras proteins (K-Ras, mutant K-Ras, K-Ras G12C, K-Ras G12V, K-Ras G12S, K-Ras G12D, K-Ras G13C, K-Ras G13D).

The compounds described herein can be used in combination with one another, with other active agents known to be useful in treating a disease associated with cells expressing a particular Ras, K-Ras, mutant K-Ras (e.g. cancer), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As a non-limiting example, the compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin, etc.), and the like.

The compounds described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the compounds described herein can be co-administered with conventional immunotherapeutic agents including, but not limited to, immunostimulants (e.g., *Bacillus* Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), and radioimmunotherapy (e.g., anti-CD20 monoclonal antibody conjugated to $^{111}$In, $^{90}$Y, or $^{131}$I, etc.).

In a further embodiment, the compounds described herein can be co-administered with conventional radiotherapeutic agents including, but not limited to, radionuclides such as $^{47}$Sc, $^{H}$Cu, $^{67}$Cu, $^{89}$Sr, $^{86}$Y, $^{87}$Y, $^{90}$Y, $^{105}$Rh, $^{m}$Ag, $^{m}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In therapeutic use for the treatment of cancer, compound utilized in the pharmaceutical compositions of the present invention may be administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The compounds described herein can be used in combination with one another, with other active agents known to be useful in treating cancer or with adjunctive agents that may not be effective alone, but may contribute to the efficacy of the active agent.

The term "associated" or "associated with" in the context of a substance or substance activity or function associated with a disease (e.g. a protein associated disease, a cancer associated with aberrant Ras activity, K-Ras associated cancer, mutant K-Ras associated cancer, activated K-Ras associated cancer, K-Ras G12C associated cancer, K-Ras G12V associated cancer, K-Ras G12S associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or in part) the substance or substance activity or function. For example, a cancer associated with aberrant Ras activity or function may be a cancer that results (entirely or partially) from aberrant Ras activity or function (e.g. enzyme activity, protein-protein interaction, signaling pathway) or a cancer wherein a particular symptom of the disease is caused (entirely or partially) by aberrant Ras activity or function. As used herein, what is described as being associated with a disease, if a causative agent, could be a target for treatment of the disease. For example, a cancer associated with aberrant Ras activity or function or a Ras associated cancer, may be treated with a Ras modulator or Ras inhibitor, in the instance where increased Ras activity or function (e.g. signaling pathway activity) causes the cancer. For example, a cancer associated with K-Ras G12V may be a cancer that a subject with K-Ras G12V is at higher risk of developing as compared to a subject without K-Ras G12V.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechlorethamine, cyclophosphamide, chlorambucil, melphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epimbicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), ilavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; etlomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+ estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perllubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycinD; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurprin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin, aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esombicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride;

puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxy epothilone D (i.e. Desoxyepothilone F and dEpoF), 26-fluoroepothilone, steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., *Bacillus* Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*Pseudomonas* exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, Ras inhibitors, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "Electrophilic" as used herein refers to a chemical group that is capable of accepting electron density. An "electrophilic substituent", "electrophilic chemical moiety", or "electrophic moiety" refers to an electron-poor chemical group, substitutent, or moiety (monovalent chemical group), which may react with an electron-donating group, such as a nucleophile, by accepting an electron pair or electron density to form a bond. In some embodiments, the electrophilic substituent of the compound is capable of reacting with a cysteine residue. In some embodiments, the electrophilic substituent is capable of forming a covalent bond with a cysteine residue (e.g., K-ras cysteine residue, residue corresponding to C185 of human K-Ras 4B) and may be referred to as a "covalent cysteine modifier moiety" or "covalent cysteine modifier substituent". The covalent bond formed between the electrophilic substituent and the sulfhydryl group of the cysteine may be a reversible or irreversible bond. In some embodiments, the electrophilic substituent is capable of forming a covalent bond with a histidine residue (e.g., K-ras histidine residue, residue corresponding to H95 of human K-Ras 4B) and may be referred to as a "covalent histidine modifier moiety" or "covalent histidine modifier substituent". The covalent bond formed between the electrophilic substituent and the histidine may be a reversible or irreversible bond.

"Nucleophilic" as used herein refers to a chemical group that is capable of donating electron density.

The term "Ras" refers to one or more of the family of human Ras GTPase proteins (e.g. K-Ras, H-Ras, N-Ras). The term "K-Ras" refers to the nucleotide sequences or proteins of human K-Ras (e.g. human K-Ras4A (NP_203524.1), human K-Ras4B (NP_004976.2), or both K-Ras4A and K-Ras4B). The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a G in wildtype protein but a C in the K-Ras G12C mutant protein). In some embodiments K-Ras refers to K-Ras4A and K-Ras4B. In some embodiments, K-Ras refers to K-Ras4A. In some embodiments, K-Ras refers to K-Ras4B. In embodiments K-Ras refers to a protein having an amino acid sequence described herein.

The term "Ras inhibitor test compound" as used herein refers to a compound that is being characterized in an assay for the ability to inhibit an activity, function, or level (e.g. amount) of a Ras protein. The term "K-Ras inhibitor test compound" as used herein refers to a compound that is being characterized in an assay for the ability to inhibit an activity, function, or level (e.g. amount) of K-Ras protein.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components. For example, binding of a K-Ras with a compound as described herein may result in a change in one or more protein-protein interactions of the K-Ras or interactions between the K-Ras and a membrane, resulting in changes in cell growth, proliferation, or survival.

An amino acid residue in a protein "corresponds" to a given residue when it occupies the same essential structural position within the protein as the given residue. For example, a selected residue in a selected protein corresponds to Gly 12 of Human K-Ras4A or Fluman K-Ras 4B or both when the selected residue occupies the same essential spatial or other structural relationship as Gly 12 in Human K-Ras4A or Human K-Ras 4B or both. In some embodiments, where a selected protein is aligned for maximum homology with the Human K-Ras4A or Human K-Ras 4B protein, the position in the aligned selected protein aligning with Gly 12 is said to correspond to Gly 12. Instead of a primary sequence alignment, a three dimensional structural alignment can also be used, e.g., where the structure of the selected protein is aligned for maximum correspondence with the Human K-Ras4A or Human K-Ras 4B protein and the overall structures compared. In this case, an amino acid that occupies the same essential position as Gly 12 in the structural model is said to correspond to the Gly 12 residue. Another example is wherein a selected residue in a selected protein corresponds to C185 of Human K-Ras 4B when the selected residue (e.g., cysteine residue) occupies essential the same sequence, spatial, or other structural position within the protein as C185 in Human K-Ras 4B.

The terms "unsubstituted vinyl sulfone moiety", "unsubstituted vinyl sulfonamide moiety", "unsubstituted fluoro ($C_1$-$C_4$)alkylketone moiety", "unsubstituted chloro($C_1$-$C_4$) alkylketone moiety", "unsubstituted acrylamide moiety", "unsubstituted disulfide moiety", "unsubstituted thiol moiety", "unsubstituted phosphonate moiety", "unsubstituted aldehyde moiety", "unsubstituted enone moiety", "unsubstituted diazomethylketone moiety", "unsubstituted diazomethylamide moiety", "unsubstituted cyanocyclopropyl carboxamide moiety", "unsubstituted epoxide moiety", "unsubstituted epoxyketone moiety", "unsubstituted epoxyamide moiety", "unsubstituted aryl aldehyde moiety", "unsubstituted aryl dialdehyde moiety", "unsubstituted dialdehyde moiety", "unsubstituted nitrogen mustard moiety", "unsubstituted propargyl moiety", or "unsubstituted propargylamide moiety" are used according to their plain ordinary chemical meaning and refer to those monovalent chemical groups named having the lowest molecular weight for each such group while obeying the rules of chemical valency. A substituted form of one of the named groups may be substituted with one or more of any of the substituent groups described herein while obeying the rules of chemical valency.

H-Ras WT Human
(SEQ ID NO: 10)
MTEYKLVVVG AGGVGKSALT IQLIQNHFVD EYDPTIEDSY

RKQVVIDGET CLLDILDTAG QEEYSAMRDQ YMRTGEGFLC

VFAINNTKSF EDIHQYREQI KRVKDSDDVP MVLVGNKCDL

AARTVESRQA QDLARSYGIP YIETSAKTRQ GVEDAFYTLV

REIRQHKLRK LNPPDESGPG CMSCKCVLS

K-Ras 4A WT Human
(SEQ ID NO: 11)
mteyklvvvg aggvgksalt iqliqnhfvd eydptiedsy rkqvvidget clldildtag qeeysamrdq ymrtgegflc -continued vfainntksf edihhyreqi krvkdsedvp mvlvgnkcdl psrtvdtkqa qdlarsygip fietsaktrq rvedafytiv reirqyrlkk iskeektpgc vkikkciim K-Ras 4B WT Human
(SEQ ID NO: 12)
mteyklvvvg aggvgksalt iqliqnhfvd eydptiedsy rkqvvidget clldildtag qeeysamrdq ymrtgegflc vfainntksf edihhyreqi krvkdsedvp mvlvgnkcdl psrtvdtkqa qdlarsygip fietsaktrq gvddafytlv reirkhkekm skdgkkkkkk sktkcvim

II. COMPOUNDS

In an aspect is provided a compound having the formula:

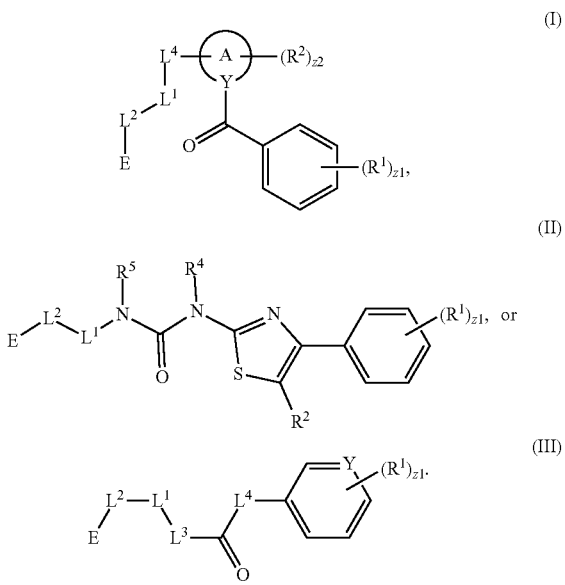

A is a $C_3$-$C_7$ cycloalkyl or 3 to 7 membered heterocycloalkyl. Y is N or CH or C. $R^1$ is independently halogen, $CX^1_3$, —$CHX^1_2$, —$CH_2X^1$, —CN, —$SO_2Cl$, —$SO_{n1}R^{10}$, —$SO_{v1}NR^7R^8$, —$NHNR^7R^8$, —$ONR^7R^8$, —NHC(=O) $NHNR^7R^8$, —$NHC(O)NR^7R^8$, —$N(O)_{m1}$, —$NR^7R^8$, —$C(O)R^9$, —C(O)—$OR^9$, —$C(O)NR^7R^8$, —$OR^{10}$, —$NR^7SO_2R^{10}$, —$NR^7C(O)R^9$, —$NR^7C(O)OR^9$, —$NR^7OR^9$, —$OCX^1_3$, —$OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $L^1$ is a bond, —O—, —C(O)—, —S—, —SO—, —$S(O)_2$—, —$NR^{74}$—, —$NR^{74}C(O)$—, —$C(O)NR^{74}$—, —$SO_2NR^{74}$—, —$NR^{74}SO_2$—, —$OC(O)NR^{74}$—, —$NR^{74}C(O)O$—, —$CR^{9A}$=NO—, —ON=$CR^{9A}$—, —$NR^{8A}C(O)NR^{74}$—, —$NR^{8A}C$(=$NR^{10A}$)$NR^{74}$—, —$NR^{8A}C$(=$NR^{10A}$)—, —C(=NR$^{10A}$)NR$^{7A}$—, —OC(=NR$^{10A}$)—, —C(=NR$^{10A}$) O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. L$^2$ is a bond, —O—, —C(O)—, —S—, —SO—, —S(O)$_2$—, —NR$^{7B}$—, —NR$^{7B}$C(O)—, —C(O)NR$^{7B}$—, —SO$_2$NR$^{7B}$—, —NR$^{7B}$SO$_2$—, —OC(O)NR$^{7B}$—, —NR$^{7B}$C(O)O—, —CR$^{9B}$=NO—, —ON=CR$^{9B}$—, —NR$^{8B}$C(O)NR$^{7B}$—, —NR$^{8B}$C(=NR$^{10B}$)NR$^{7B}$—, —NR$^{8B}$C(=NR$^{10B}$)—, —C(=NR$^{10B}$)NR$^{7B}$—, —OC(=NR$^{10B}$)—, —C(=NR$^{10B}$) O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. L$^3$ is a bond, —O—, —C(O)—, —S—, —SO—, —S(O)$_2$—, —NR$^5$—, —NR$^5$C (O)—, —C(O)NR$^5$—, —SO$_2$NR$^5$—, —NR$^5$SO$_2$—, —OC (O)NR$^5$—, —NR$^5$C(O)O—, substituted or unsubstituted C$_1$-C$_6$ alkylene, substituted or unsubstituted 2 to 6 membered heteroalkylene. L$^4$ is a bond, —O—, —C(O)—, —S—, —SO—, —S(O)$_2$—, —NR$^4$—, —NR$^4$C(O)—, —C(O)NR$^4$—, —SO$_2$NR$^4$—, —NR$^4$SO$_2$—, —NR$^4$SO$_2$—, —OC(O)NR$^4$—, —NR$^4$C(O)O—, substituted or unsubstituted C$_1$-C$_3$ alkylene, substituted or unsubstituted 2 to 3 membered heteroalkylene. E is an electrophilic moiety. R$^2$ is independently hydrogen, oxo, halogen, CX$^2_3$, —CHX$^2_2$, —CH$_2$X$^2$, —CN, —SO$_2$Cl, —SO$_{n2}$R$^{14}$, —SO$_{v2}$NR$^{11}$R$^{12}$, —NHNR$^{11}$R$^{12}$, —ONR$^{11}$R$^{12}$, —NHC=(O)NHNR$^{11}$R$^{12}$, —NHC(O)NR$^{11}$R$^{12}$, —N(O)$_{m2}$, —NR$^{11}$R$^{12}$, —C(O)R$^{14}$, —C(O)—OR$^{14}$, —C(O)NR$^{11}$R$^{12}$, —OR$^{15}$, —NR$^{11}$SO$_2$R$^{15}$, —NR$^{11}$C(O)R$^{14}$, —NR$^{11}$C(O)OR$^{14}$, —NR$^{11}$OR$^{14}$, —OCX$^2_3$, —OCHX$^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^2$ substituents or two R$^2$ substituents bonded to the same atom may optionally be joined to form a substituted or unsubstituted cycloalkyl, substituted or unsubstituted heterocycloalkyl, substituted or unsubstituted aryl, or substituted or unsubstituted heteroaryl. R$^4$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. R$^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. R$^7$, R$^8$, R$^9$, R$^{10}$, R$^{7A}$, R$^{8A}$, R$^{9A}$, R$^{10A}$, R$^{7B}$, R$^{8B}$, R$^{9B}$, R$^{10B}$, R$^{11}$, R$^{12}$, R$^{14}$, and R$^{15}$ are independently hydrogen, halogen, —CX$_3$, —CN, —OH, —NH$_2$, —COOH, —CONH$_2$, —NO$_2$, —SH, —SO$_2$Cd, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl. Each X, X$^1$, and X$^2$ is independently —F, —Cl, —Br, or —I. The symbols n1, n2, v1, and v2 are independently an integer from 0 to 4. The symbols m1 and m2 are independently an integer from 1 to 2. The symbol z1 is independently an integer from 0 to 5. The symbol z2 is independently an integer from 0 to 10.

In embodiments, the compound has the formula:

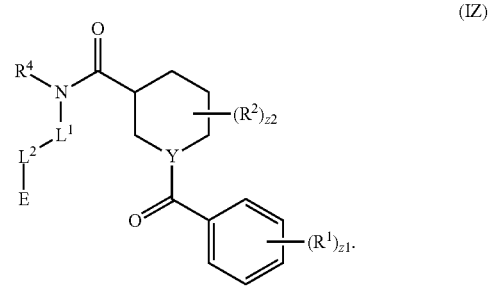

(IZ)

R$^1$, R$^2$, R$^4$, L$^1$, L$^2$, E, Y z1 and z2 are as described herein.

In embodiments, the compound has the formula:

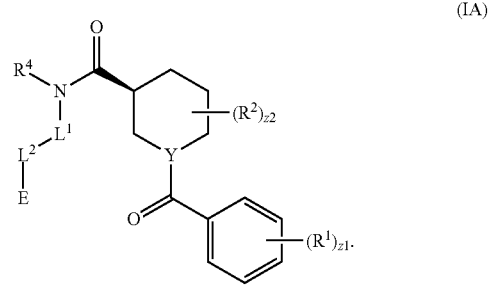

(IA)

R$^1$, R$^2$, R$^4$, L$^1$, L$^2$, E, Y z1 and z2 are as described herein.

In embodiments, the compound has the formula:

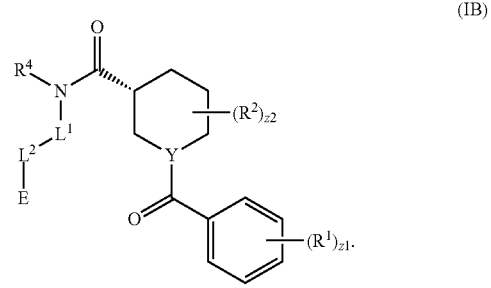

(IB)

R$^1$, R$^2$, R$^4$, L$^1$, L$^2$, E, Y z1 and z2 are as described herein.

In embodiments, the compound has the formula:

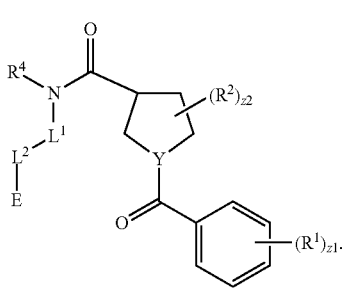
(IC)

$R^1$, $R^2$, $R^4$, $L^1$, $L^2$, E, Y z1 and z2 are as described herein.

In embodiments, the compound has the Formula:

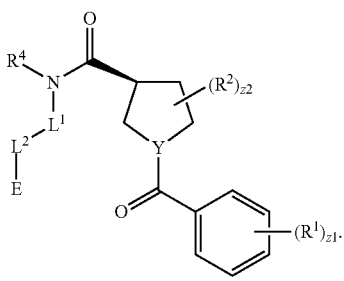
(ID)

$R^1$, $R^2$, $R^4$, $L^1$, $L^2$, E, Y z1 and z2 are as described herein.

In embodiments, the compound has the formula:

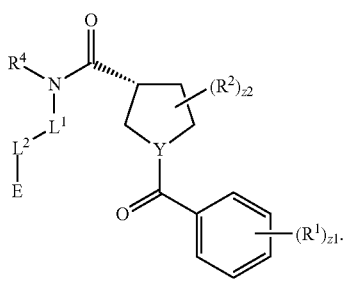
(IE)

$R^1$, $R^2$, $R^4$, $L^1$, $L^2$, E, Y z1 and z2 are as described herein.

In embodiments, the compound has the formula:

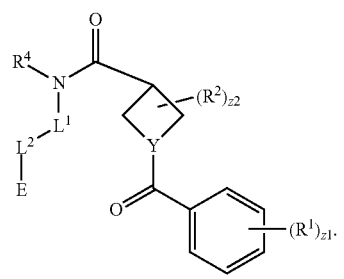
(IF)

$R^1$, $R^2$, $R^4$, $L^1$, $L^2$, E, Y z1 and z2 are as described herein.

In embodiments, the compound has the formula:

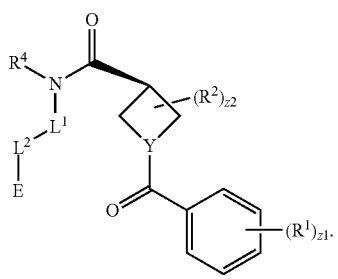
(IG)

$R^1$, $R^2$, $R^4$, $L^1$, $L^2$, E, Y z1 and z2 are as described herein.

In embodiments, the compound has the formula:

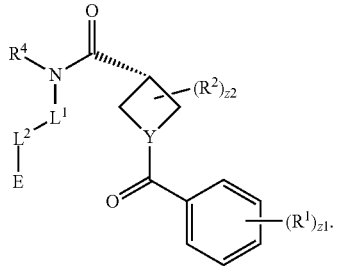
(IH)

$R^1$, $R^2$, $R^4$, $L^1$, $L^2$, E, Y z1 and z2 are as described herein.

In embodiments, the compound has the formula:

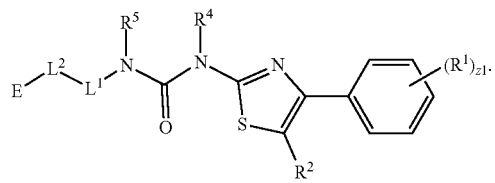
(II)

$R^1$, $R^2$, $R^4$, $R^5$, $L^1$, $L^2$, E, and z1 are as described herein.

In embodiments of the compound of formula II, $R^2$, $R^4$, and $R^5$ are hydrogen. In embodiments, the compound has the formula:

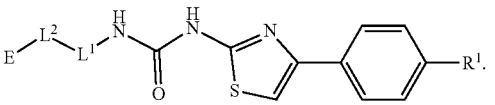
(IIA)

$R^1$, $L^1$, $L^2$, and E, are as described herein.

In embodiments, the compound has the formula:

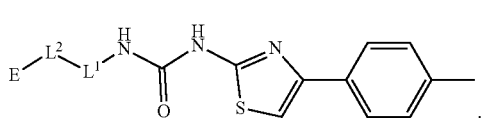
(IIB)

$L^1$, $L^2$, and E are as described herein (e.g., for formulae I, II, III, VI, and embodiments thereof or in examples, figures, tables, or claims).

In embodiments, the compound has the formula:

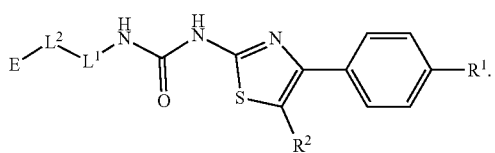
(IIC)

$R^1$, $R^2$, $L^1$, $L^2$, and E are as described herein (e.g., for formulae I, II, III, VI, and embodiments thereof or in examples, figures, tables, or claims).

In embodiments, the compound has the formula:

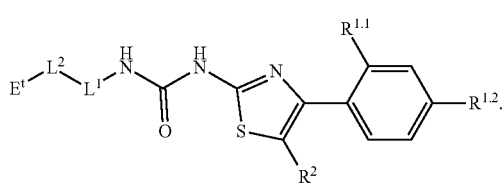
(IID)

$R^1$, $R^2$, $L^1$, $L^2$, and E are as described herein (e.g., for formulae I, II, III, VI, VI, and embodiments thereof or in examples, figures, tables, or claims). $R^{1.1}$ and $R^{1.2}$ have the values of $R^1$. $R^{1.1}$ and $R^{1.2}$ may be optionally different halogens (e.g., F and/or Cl). $R^1$ may be halogen (e.g., F or Cl). $R^2$ may be unsubstituted methyl.

In embodiments, the compound has the formula:

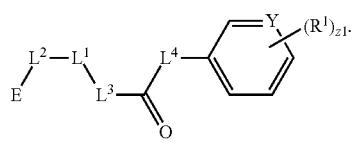
(III)

$R^1$, $L^1$, $L^2$, $L^3$, $L^4$, E, Y, and z1 are as described herein.

In embodiments, the compound has the formula:

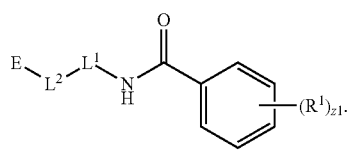
(IIIA)

$R^1$, $L^1$, $L^2$, E, and z1 are as described herein.

In embodiments, $L^3$ is a bond, —O—, —C(O)—, —S—, —SO—, —S(O)$_2$—, —NH—, —NHCH(CH$_3$)C(O)NH—, or unsubstituted $C_1$-$C_3$ alkylene. In embodiments, $L^4$ is a bond, —CH$_2$O—, —C(O)—, —NH—, or —O—. In embodiments, $L^3$ is a bond, —O—, —C(O)—, —S—, —SO—, —S(O)$_2$—, —NH—, —NHCH(CH$_3$)C(O)NH—, or unsubstituted $C_1$-$C_3$ alkylene and $L^4$ is a bond, —CH$_2$O—, —C(O)—, —NH—, or —O—. In embodiments, $L^3$ is a bond. In embodiments, $L^3$ is a bond. In embodiments, $L^3$ is —O—. In embodiments, $L^3$ is —C(O)—. In embodiments, $L^3$ is —S—. In embodiments, $L^3$ is —SO—. In embodiments, $L^3$ is —S(O)$_2$—. In embodiments, $L^3$ is —NR$^5$—. In embodiments, $L^3$ is —NH—. In embodiments, $L^3$ is —NR$^5$C(O)—. In embodiments, $L^3$ is —NHC(O)—. In embodiments, $L^3$ is —C(O)NR$^5$—. In embodiments, $L^3$ is —C(O)NH—. In embodiments, $L^3$ is —SO$_2$NR$^5$—. In embodiments, $L^3$ is —SO$_2$NH—. In embodiments, $L^3$ is —NR$^5$SO$_2$—. In embodiments, $L^3$ is —NHSO$_2$—. In embodiments, $L^3$ is —OC(O)NR$^5$—. In embodiments, $L^3$ is —OC(O)NH—. In embodiments, $L^3$ is —NR$^5$C(O)O—. In embodiments, $L^3$ is —NHC(O)O—. In embodiments, $L^3$ is substituted or unsubstituted $C_1$-$C_6$ alkylene. In embodiments, $L^3$ is substituted or unsubstituted 2 to 6 membered heteroalkylene. In embodiments, $L^3$ is unsubstituted methylene. In embodiments, $L^3$ is a bond.

In embodiments, $L^4$ is a bond. In embodiments, $L^4$ is —O—. In embodiments, $L^4$ is —C(O)—. In embodiments, $L^4$ is —S—. In embodiments, $L^4$ is —SO—. In embodiments, $L^4$ is —S(O)$_2$—. In embodiments, $L^4$ is —NR$^4$—. In embodiments, $L^4$ is —NR$^4$C(O)—. In embodiments, $L^4$ is —C(O)NR$^4$—. In embodiments, $L^4$ is —SO$_2$NR$^4$—. In embodiments, $L^4$ is —NR$^4$SO$_2$—. In embodiments, $L^4$ is —OC(O)NR$^4$—. In embodiments, $L^4$ is —NR$^4$C(O)O—. In embodiments, $L^4$ is substituted or unsubstituted $C_1$-$C_3$ alkylene. In embodiments, $L^4$ is substituted or unsubstituted 2 to 3 membered heteroalkylene. In embodiments, $L^4$ is —NH—. In embodiments, $L^4$ is —NHC(O)—. In embodiments, $L^4$ is —C(O)NH—. In embodiments, $L^4$ is —SO$_2$NH—. In embodiments, $L^4$ is —NHSO$_2$—. In embodiments, $L^4$ is —OC(O)NH—. In embodiments, $L^4$ is —NHC(O)O—. In embodiments, $L^4$ is unsubstituted $C_1$-$C_3$ alkylene. In embodiments, $L^4$ is unsubstituted 2 to 3 membered heteroalkylene. In embodiments, $L^4$ is —CH$_2$NH—. In embodiments, $L^4$ is an unsubstituted methylene.

In embodiments, Ring A is a $C_3$-$C_7$ cycloalkyl. In embodiments, Ring A is a 3 to 7 membered heterocycloalkyl. In embodiments, Ring A is a $C_5$-$C_7$ cycloalkyl. In embodiments, Ring A is a 5 to 7 membered heterocycloalkyl. In embodiments, Ring A is a $C_3$ cycloalkyl. In embodiments, Ring A is a $C_4$ cycloalkyl. In embodiments, Ring A is a $C_5$ cycloalkyl. In embodiments, Ring A is a $C_6$ cycloalkyl. In embodiments, Ring A is a $C_7$ cycloalkyl. In embodiments, Ring A is a saturated $C_3$ cycloalkyl. In embodiments, Ring A is a saturated $C_4$ cycloalkyl. In embodiments, Ring A is a saturated $C_5$ cycloalkyl. In embodiments, Ring A is a saturated $C_6$ cycloalkyl. In embodiments, Ring A is a saturated $C_7$ cycloalkyl. In embodiments, Ring A is an unsaturated $C_3$ cycloalkyl. In embodiments, Ring A is an unsaturated $C_4$ cycloalkyl. In embodiments, Ring A is an unsaturated $C_5$ cycloalkyl. In embodiments, Ring A is an unsaturated $C_6$ cycloalkyl. In embodiments, Ring A is an unsaturated $C_7$ cycloalkyl. In embodiments, Ring A is a 3 membered heterocycloalkyl. In embodiments, Ring A is a 4 membered heterocycloalkyl. In embodiments, Ring A is a 5 membered heterocycloalkyl. In embodiments, Ring A is a 6 membered heterocycloalkyl. In embodiments, Ring A is a 7 membered heterocycloalkyl. In embodiments, Ring A is a saturated 3 membered heterocycloalkyl. In embodiments, Ring A is a saturated 4 membered heterocycloalkyl. In embodiments, Ring A is a saturated 5 membered heterocycloalkyl. In embodiments, Ring A is a saturated 6 membered heterocycloalkyl. In embodiments, Ring A is a saturated 7 membered heterocycloalkyl. In embodiments, Ring A is an unsaturated 3 membered heterocycloalkyl. In embodiments, Ring A is an unsaturated 4 membered heterocycloalkyl. In embodiments, Ring A is an unsaturated 5 membered heterocycloalkyl. In embodiments, Ring A is an unsaturated 6 membered heterocycloalkyl. In embodiments, Ring A is an unsaturated 7 membered heterocycloalkyl. In embodiments, Ring A is an aziridinyl. In embodiments, Ring A is an azirinyl. In embodiments, Ring A is a diaziridinyl. In embodiments, Ring A is a diazirinyl. In embodiments, Ring A is an azetidinyl. In embodiments, Ring A is an azetyl. In embodiments, Ring A is a diazetidinyl. In embodiments, Ring A is a diazetyl. In embodiments, Ring A is a piperidinyl. In embodiments, Ring A is pyrrolidinyl. In embodiments, Ring A is azepanyl. In embodiments, Ring A is a N-piperidinyl. In embodiments, Ring A is N-pyrrolidinyl. In embodiments, Ring A is N-azepanyl. In embodiments, Ring A is a 1-piperidinyl. In embodiments, Ring A is 1-pyrrolidinyl. In embodiments, Ring A is 1-azepanyl. In embodiments, Ring A is piperazinyl. In embodiments, Ring A is imidazolidinyl. In embodiments, Ring A is pyrazolidinyl. In embodiments, Ring A is oxazolidinyl. In embodiments, Ring A is isoxazolidinyl. In embodiments, Ring A is thiazolidinyl. In embodiments, Ring A is isothiazolidinyl. In embodiments, Ring A is pyridinyl. In embodiments, Ring A is pyranyl. In embodiments, Ring A is thiopyranyl. In embodiments, Ring A is oxanyl. In embodiments, Ring A is thianyl. In embodiments, Ring A is morpholinyl. In embodiments, Ring A is thiomorpholinyl. In embodiments, Ring A is dioxanyl. In embodiments, Ring A is dithianyl. In embodiments, Ring A is diazinyl. In embodiments, Ring A is oxazinyl. In embodiments, Ring A is thiazinyl. In embodiments, Ring A is dioxinyl. In embodiments, Ring A is dithiinyl.

In embodiments, Y is CH. In embodiments, Y is N. In embodiments, Y is C.

In embodiments, $R^1$ is independently halogen, $-CX^1_3$, $-CHX^1_2$, $-CH_2X^1$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^1$ is independently halogen, $-CX^1_3$, $-CHX^1_2$, $-CH_2X^1$, $-OH$, $-SH$, $-COOH$, $-OCX^1_3$, $-OCHX^1_2$, $-CH_3$, $-CH_2CH_3$, $-OCH_3$, $-OCH_2CH_3$, $-SCH_3$, or $-SCH_2CH_3$. In embodiments, $R^1$ is independently halogen or $-OCH_3$. In embodiments, $R^1$ is substituted or unsubstituted $C_1$-$C_6$ alkyl. In embodiments, $R^1$ is substituted or unsubstituted 2 to 6 membered heteroalkyl. In embodiments, $R^1$ is substituted or unsubstituted $C_3$-$C_8$ cycloalkyl. In embodiments, $R^1$ is substituted or unsubstituted 3 to 8 membered heterocycloalkyl. In embodiments, $R^1$ is substituted or unsubstituted $C_6$ aryl. In embodiments, $R^1$ is substituted or unsubstituted 5 to 6 membered heteroaryl. In embodiments, $R^1$ is independently halogen. In embodiments, $R^1$ is independently $-CX^1_3$. In embodiments, $R^1$ is independently $-CHX^1_2$. In embodiments, $R^1$ is independently $-CH_2X^1$. In embodiments, $R^1$ is independently $-OH$. In embodiments, $R^1$ is independently $-SH$. In embodiments, $R^1$ is independently $-COOH$. In embodiments, $R^1$ is independently $-OCX^1_3$. In embodiments, $R^1$ is independently $-OCHX^1_2$. In embodiments, $R^1$ is independently $-CH_3$. In embodiments, $R^1$ is independently $-CH_2CH_3$. In embodiments, $R^1$ is independently $-OCH_3$. In embodiments, $R^1$ is independently $-OCH_2CH_3$. In embodiments, $R^1$ is independently $-SCH_3$. In embodiments, $R^1$ is independently $-SCH_2CH_3$. In embodiments, $R^1$ is independently $-Cl$ or $-OCH_3$. In embodiments, $R^1$ is independently halogen, $-CX^1_3$, $-CN$, $-OH$, $-NH_2$, $-COOH$, $-CONH_2$, $-NO_2$, $-SH$, $-OCX^1_3$, $-OCHX^1_2$, $-CHX^1_2$, $-CH_2X^1$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently halogen, $-CX^1_3$, $-CN$, unsubstituted $C_1$-$C_4$ alkyl, or unsubstituted 2 to 4 membered heteroalkyl. In embodiments, $R^1$ is independently unsubstituted methyl, unsubstituted ethyl, unsubstituted isopropyl, or unsubstituted tert-butyl. In embodiments, $R^1$ is independently unsubstituted methyl. In embodiments, $R^1$ is independently unsubstituted ethyl. In embodiments, $R^1$ is independently unsubstituted propyl. In embodiments, $R^1$ is independently unsubstituted n-propyl. In embodiments, $R^1$ is independently unsubstituted isopropyl. In embodiments, $R^1$ is independently unsubstituted butyl. In embodiments, $R^1$ is independently unsubstituted n-butyl. In embodiments, $R^1$ is independently unsubstituted isobutyl. In embodiments, $R^1$ is independently unsubstituted tert-butyl. In embodiments, $R^1$ is independently unsubstituted pentyl. In embodiments, $R^1$ is independently unsubstituted hexyl. In embodiments, $R^1$ is independently unsubstituted heptyl. In embodiments, $R^1$ is independently unsubstituted octyl. In embodiments, $R^1$ is independently $-F$. In embodiments, $R^1$ is independently $-Cl$. In embodiments, $R^1$ is independently $-Br$. In embodiments, $R^1$ is independently $-I$. In embodiments, $R^1$ is independently unsubstituted methoxy. In embodiments, $R^1$ is independently unsubstituted ethoxy. In embodiments, $R^1$ is independently $-CF_3$. In embodiments, $R^1$ is independently $-CCl_3$. In embodiments, $R^1$ is an unsubstituted isopropyl. In embodiments, $R^1$ is an unsubstituted phenyl. In embodiments, $R^1$ is an unsubstituted pyridyl. In embodiments, $R^1$ is independently halogen. In embodiments, $R^1$ is independently $-CX^1_3$. In embodiments, $R^1$ is independently $-CHX^1_2$. In embodiments, $R^1$ is independently $-CH_2X'$. In embodiments, $R^1$ is independently $-CN$. In embodiments, $R^1$ is independently $-OH$. In embodiments, $R^1$ is independently $-NH_2$. In embodiments, $R^1$ is independently $-COOH$. In embodiments, $R^1$ is independently $-CONH_2$. In embodiments, $R^1$ is independently $-NO_2$. In embodiments, $R^1$ is independently $-SH$. In embodiments, $R^1$ is independently $-SO_2Cl$. In embodiments, $R^1$ is independently $-SO_3H$. In embodiments, $R^1$ is independently $-SO_4H$. In embodiments, $R^1$ is independently $-SO_2NH_2$. In embodiments, $R^1$ is independently $-NHNH_2$. In embodiments, $R^1$ is independently $-ONH_2$. In embodiments, $R^1$ is independently $-NHC(O)NHNH_2$. In embodiments, $R^1$ is independently $-NHC(O)NH_2$. In embodiments, $R^1$ is independently $-NHSO_2H$. In embodiments, $R^1$ is independently $-NHC(O)H$. In embodiments, $R^1$ is independently $-NHC(O)OH$. In embodiments, $R^1$ is independently $-NHOH$. In embodiments, $R^1$ is independently $-OCX^1_3$. In embodiments, $R^1$ is independently $-OCHX_2$. In embodiments, $R^1$ is independently substituted or unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently substituted or unsubstituted heteroaryl. In embodiments, $R^1$ is independently substituted alkyl. In embodiments, $R^1$ is independently substituted heteroalkyl. In embodiments, $R^1$ is independently substituted cycloalkyl. In embodiments, $R^1$ is independently substituted heterocycloalkyl. In embodiments, $R^1$ is independently substituted aryl. In embodiments, $R^1$ is independently substituted heteroaryl. In embodiments, $R^1$ is independently unsubstituted alkyl. In embodiments, $R^1$ is independently unsubstituted heteroalkyl. In embodiments, $R^1$ is independently unsubstituted cycloalkyl. In embodiments, $R^1$ is independently unsubstituted heterocycloalkyl. In embodiments, $R^1$ is independently unsubstituted aryl. In embodiments, $R^1$ is independently unsubstituted heteroaryl. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently unsubstituted $C_3$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl. In embodiments, $R^1$ is independently substituted $C_1$-$C_4$ alkyl. In embodiments, $R^1$ is independently substituted 2 to 4 membered heteroalkyl. In embodiments, $R^1$ is independently substituted $C_3$-$C_6$ cycloalkyl. In embodiments, $R^1$ is independently substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted C4-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl.

In embodiments, $R^{1.1}$ is independently halogen, $—CX^1_3$, $—CHX^1_2$, $—CH_2X^1$, $—CN$, $—OH$, $—NH_2$, $—COOH$, $—CONH_2$, $—NO_2$, $—SH$, $—SO_2Cl$, $—SO_3H$, $—SO_4H$, $—SO_2NH_2$, $—NHNH_2$, $—ONH_2$, $—NHC(O)NHNH_2$, $—NHC(O)NH_2$, $—NHSO_2H$, $—NHC(O)H$, $—NHC(O)OH$, $—NHOH$, $—OCX^1_3$, $—OCHX^1_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^{1.1}$ is independently halogen, $—CX^1_3$, $—CHX^1_2$, $—CH_2X^1$, $—OH$, $—SH$, $—COOH$, $—OCX^1_3$, $—OCHX^1_2$, $—CH_3$, $—CH_2CH_3$, $—OCH_3$, $—OCH_2CH_3$, $—SCH_3$, or $—SCH_2CH_3$. In embodiments, $R^{1.1}$ is independently halogen or $—OCH_3$. In embodiments, $R^{1.1}$ is substituted or unsubstituted $C_1$-$C_6$ alkyl. In embodiments, $R^{1.1}$ is substituted or unsubstituted 2 to 6 membered heteroalkyl. In embodiments, $R^{1.1}$ is substituted or unsubstituted $C_3$-$C_8$ cycloalkyl. In embodiments, $R^{1.1}$ is substituted or unsubstituted 3 to 8 membered heterocycloalkyl. In embodiments, $R^{1.1}$ is substituted or unsubstituted $C_6$ aryl. In embodiments, $R^{1.1}$ is substituted or unsubstituted 5 to 6 membered heteroaryl. In embodiments, $R^{1.1}$ is independently halogen. In embodiments, $R^{1.1}$ is independently $—CX^1_3$. In embodiments, $R^{1.1}$ is independently $—CHX^1_2$. In embodiments, $R^{1.1}$ is independently $—CH_2X^1$. In embodiments, $R^{1.1}$ is independently $—OH$. In embodiments, $R^{1.1}$ is independently $—SH$. In embodiments, $R^{1.1}$ is independently $—COOH$. In embodiments, $R^{1.1}$ is independently $—OCX^1_3$. In embodiments, $R^{1.1}$ is independently $—OCHX^1_2$. In embodiments, $R^{1.1}$ is independently $—CH_3$. In embodiments, $R^{1.1}$ is independently $—CH_2CH_3$. In embodiments, $R^{1.1}$ is independently $—OCH_3$. In embodiments, $R^{1.1}$ is independently $—OCH_2CH_3$. In embodiments, $R^{1.1}$ is independently $—SCH_3$. In embodiments, $R^{1.1}$ is independently $—SCH_2CH_3$. In embodiments, $R^{1.1}$ is independently $—Cl$ or $—OCH_3$. In embodiments, $R^{1.1}$ is independently halogen, $—CX^1_3$, $—CN$, $—OH$, $—NH_2$, $—COOH$, $—CONH_2$, $—NO_2$, $—SH$, $—OCX^1_3$, $—OCHX^1_2$, $—CHX^1_2$, $—CH_2X^1$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{1.1}$ is independently halogen, $—CX^1_3$, $—CN$, unsubstituted $C_1$-$C_4$ alkyl, or unsubstituted 2 to 4 membered heteroalkyl. In embodiments, $R^{1.1}$ is independently unsubstituted methyl, unsubstituted ethyl, unsubstituted isopropyl, or unsubstituted tert-butyl. In embodiments, $R^{1.1}$ is independently unsubstituted methyl. In embodiments, $R^{1.1}$ is independently unsubstituted ethyl. In embodiments, $R^{1.1}$ is independently unsubstituted propyl. In embodiments, $R^{1.1}$ is independently unsubstituted n-propyl. In embodiments, $R^{1.1}$ is independently unsubstituted isopropyl. In embodiments, $R^{1.1}$ is independently unsubstituted butyl. In embodiments, $R^{1.1}$ is independently unsubstituted n-butyl. In embodiments, $R^{1.1}$ is independently unsubstituted isobutyl. In embodiments, $R^{1.1}$ is independently unsubstituted tert-butyl. In embodiments, $R^{1.1}$ is independently unsubstituted pentyl. In embodiments, $R^{1.1}$ is independently unsubstituted hexyl. In embodiments, $R^{1.1}$ is independently unsubstituted heptyl. In embodiments, $R^{1.1}$ is independently unsubstituted octyl. In embodiments, $R^{1.1}$ is independently $—F$. In embodiments, $R^{1.1}$ is independently $—Cl$. In embodiments, $R^{1.1}$ is independently $—Br$. In embodiments, $R^{1.1}$ is independently $—I$. In embodiments, $R^{1.1}$ is independently unsubstituted methoxy. In embodiments, $R^{1.1}$ is independently unsubstituted ethoxy. In embodiments, $R^{1.1}$ is independently $—CF_3$. In embodiments, $R^{1.1}$ is independently $—CCl_3$. In embodiments, $R^{1.1}$ is an unsubstituted isopropyl. In embodiments, $R^{1.1}$ is an unsubstituted phenyl. In embodiments, $R^{1.1}$ is an unsubstituted pyridyl. In embodiments, $R^{1.1}$ is independently halogen. In embodiments, $R^{1.1}$ is independently —$CX^1_3$. In embodiments, $R^{1.1}$ is independently —$CHX^1_2$. In embodiments, $R^{1.1}$ is independently —$CH_2X^1$. In embodiments, $R^{1.1}$ is independently —CN. In embodiments, $R^{1.1}$ is independently —OH. In embodiments, $R^{1.1}$ is independently —$NH_2$. In embodiments, $R^{1.1}$ is independently —COOH. In embodiments, $R^{1.1}$ is independently —$CONH_2$. In embodiments, $R^{1.1}$ is independently —$NO_2$. In embodiments, $R^{1.1}$ is independently —SH. In embodiments, $R^{1.1}$ is independently —$SO_2Cl$. In embodiments, $R^{1.1}$ is independently —$SO_3H$. In embodiments, $R^{1.1}$ is independently —$SO_4H$. In embodiments, $R^{1.1}$ is independently —$SO_2NH_2$. In embodiments, $R^{1.1}$ is independently —$NHNH_2$. In embodiments, $R^{1.1}$ is independently —$ONH_2$. In embodiments, $R^{1.1}$ is independently —$NHC(O)NHNH_2$. In embodiments, $R^{1.1}$ is independently —$NHC(O)NH_2$. In embodiments, $R^{1.1}$ is independently —$NHSO_2H$. In embodiments, $R^{1.1}$ is independently —NHC(O)H. In embodiments, $R^{1.1}$ is independently —NHC(O)OH. In embodiments, $R^{1.1}$ is independently —NHOH. In embodiments, $R^{1.1}$ is independently —$OCX^1_3$. In embodiments, $R^{1.1}$ is independently —$OCHX^1_2$. In embodiments, $R^{1.1}$ is independently substituted or unsubstituted alkyl. In embodiments, $R^{1.1}$ is independently substituted or unsubstituted heteroalkyl. In embodiments, $R^{1.1}$ is independently substituted or unsubstituted cycloalkyl. In embodiments, $R^{1.1}$ is independently substituted or unsubstituted heterocycloalkyl. In embodiments, $R^{1.1}$ is independently substituted or unsubstituted aryl. In embodiments, $R^{1.1}$ is independently substituted or unsubstituted heteroaryl. In embodiments, $R^{1.1}$ is independently substituted alkyl. In embodiments, $R^{1.1}$ is independently substituted heteroalkyl. In embodiments, $R^{1.1}$ is independently substituted cycloalkyl. In embodiments, $R^{1.1}$ is independently substituted heterocycloalkyl. In embodiments, $R^{1.1}$ is independently substituted aryl. In embodiments, $R^{1.1}$ is independently substituted heteroaryl. In embodiments, $R^{1.1}$ is independently unsubstituted alkyl. In embodiments, $R^{1.1}$ is independently unsubstituted heteroalkyl. In embodiments, $R^{1.1}$ is independently unsubstituted cycloalkyl. In embodiments, $R^{1.1}$ is independently unsubstituted heterocycloalkyl. In embodiments, $R^{1.1}$ is independently unsubstituted aryl. In embodiments, $R^{1.1}$ is independently unsubstituted heteroaryl. In embodiments, $R^{1.1}$ is independently substituted or unsubstituted $C_1$-$C_8$ alkyl. In embodiments, $R^{1.1}$ is independently substituted or unsubstituted 2 to 8 membered heteroalkyl. In embodiments, $R^{1.1}$ is independently substituted or unsubstituted $C_3$-$C_8$ cycloalkyl. In embodiments, $R^{1.1}$ is independently substituted or unsubstituted 3 to 8 membered heterocycloalkyl. In embodiments, $R^{1.1}$ is independently substituted or unsubstituted $C_6$-$C_{10}$ aryl. In embodiments, $R^{1.1}$ is independently substituted or unsubstituted 5 to 10 membered heteroaryl. In embodiments, $R^{1.1}$ is independently substituted $C_1$-$C_8$ alkyl. In embodiments, $R^{1.1}$ is independently substituted 2 to 8 membered heteroalkyl. In embodiments, $R^{1.1}$ is independently substituted $C_3$-$C_5$ cycloalkyl. In embodiments, $R^{1.1}$ is independently substituted 3 to 8 membered heterocycloalkyl. In embodiments, $R^{1.1}$ is independently substituted $C_6$-$C_{10}$ aryl. In embodiments, $R^{1.1}$ is independently substituted 5 to 10 membered heteroaryl. In embodiments, $R^{1.1}$ is independently unsubstituted $C_1$-$C_8$ alkyl. In embodiments, $R^{1.1}$ is independently unsubstituted 2 to 8 membered heteroalkyl. In embodiments, $R^{1.1}$ is independently unsubstituted $C_3$-$C_8$ cycloalkyl. In embodiments, $R^{1.1}$ is independently unsubstituted 3 to 8 membered heterocycloalkyl. In embodiments, $R^{1.1}$ is independently unsubstituted $C_6$-$C_{10}$ aryl. In embodiments, $R^{1.1}$ is independently unsubstituted 5 to 10 membered heteroaryl. In embodiments, $R^{1.1}$ is independently substituted or unsubstituted $C_1$-$C_4$ alkyl. In embodiments, $R^{1.1}$ is independently substituted or unsubstituted 2 to 4 membered heteroalkyl. In embodiments, $R^{1.1}$ is independently substituted or unsubstituted $C_3$-$C_6$ cycloalkyl. In embodiments, $R^{1.1}$ is independently substituted or unsubstituted 3 to 6 membered heterocycloalkyl. In embodiments, $R^{1.1}$ is independently substituted or unsubstituted phenyl. In embodiments, $R^{1.1}$ is independently substituted or unsubstituted 5 to 6 membered heteroaryl. In embodiments, $R^{1.1}$ is independently substituted $C_1$-$C_4$ alkyl. In embodiments, $R^{1.1}$ is independently substituted 2 to 4 membered heteroalkyl. In embodiments, $R^{1.1}$ is independently substituted $C_3$-$C_6$ cycloalkyl. In embodiments, $R^{1.1}$ is independently substituted 3 to 6 membered heterocycloalkyl. In embodiments, $R^{1.1}$ is independently substituted phenyl. In embodiments, $R^{1.1}$ is independently substituted 5 to 6 membered heteroaryl. In embodiments, $R^{1.1}$ is independently unsubstituted $C_1$-$C_4$ alkyl. In embodiments, $R^{1.1}$ is independently unsubstituted 2 to 4 membered heteroalkyl. In embodiments, $R^{1.1}$ is independently unsubstituted $C_3$-$C_6$ cycloalkyl. In embodiments, $R^{1.1}$ is independently unsubstituted 3 to 6 membered heterocycloalkyl. In embodiments, $R^{1.1}$ is independently unsubstituted phenyl. In embodiments, $R^{1.1}$ is independently unsubstituted 5 to 6 membered heteroaryl. In embodiments, $R^{1.1}$ is independently hydrogen.

In embodiments, $R^{1.2}$ is independently halogen, —$CX^1_3$, —$CHX^1_2$, —$CH_2X^1$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^1_3$, —$OCHX^1_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^{1.2}$ is independently halogen, —$CX^1_3$, —$CHX^1_2$, —$CH_2X^1$, —OH, —SH, —COOH, —$OCX^1_3$, —$OCHX^1_2$, —$CH_3$, —$CH_2CH_3$, —$OCH_3$, —$OCH_2CH_3$, —$SCH_3$, or —$SCH_2CH_3$. In embodiments, $R^{1.2}$ is independently halogen or —$OCH_3$. In embodiments, $R^{1.2}$ is substituted or unsubstituted $C_1$-$C_6$ alkyl. In embodiments, $R^{1.2}$ is substituted or unsubstituted 2 to 6 membered heteroalkyl. In embodiments, $R^{1.2}$ is substituted or unsubstituted $C_3$-$C_8$ cycloalkyl. In embodiments, $R^{1.2}$ is substituted or unsubstituted 3 to 8 membered heterocycloalkyl. In embodiments, $R^{1.2}$ is substituted or unsubstituted $C_6$ aryl. In embodiments, $R^{1.2}$ is substituted or unsubstituted 5 to 6 membered heteroaryl. In embodiments, $R^{1.2}$ is independently halogen. In embodiments, $R^{1.2}$ is independently —$CX^1_3$. In embodiments, $R^{1.2}$ is independently —$CHX^1_2$. In embodiments, $R^{1.2}$ is independently —$CH_2X^1$. In embodiments, $R^{1.2}$ is independently —OH. In embodiments, $R^{1.2}$ is independently —SH. In embodiments, $R^{1.2}$ is independently —COOH. In embodiments, $R^{1.2}$ is independently —$OCX^1_3$. In embodiments, $R^{1.2}$ is independently —$OCHX^1_2$. In embodiments, $R^{1.2}$ is independently —$CH_3$. In embodiments, $R^{1.2}$ is independently —$CH_2CH_3$. In embodiments, $R^{1.2}$ is independently —$OCH_3$. In embodiments, $R^{1.2}$ is independently —$OCH_2CH_3$. In embodiments, $R^{1.2}$ is independently —$SCH_3$. In embodiments, $R^{1.2}$ is independently —$SCH_2CH_3$. In embodiments, $R^{1.2}$ is independently —Cl or —$OCH_3$. In embodiments, $R^{1.2}$ is independently halogen, —$CX^1_3$, —CN, —OH, —$NH_2$, —COOH, —$CONH_2$, —$NO_2$, —SH, —$OCX^1_3$, —$OCHX^1_2$, —$CHX^1_2$, —$CH_2X^1$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{1.2}$ is independently halogen, —$CX^1_3$, —CN, unsubstituted $C_1$-$C_4$ alkyl, or unsubstituted 2 to 4 membered heteroalkyl. In embodiments, $R^{1.2}$ is independently unsubstituted methyl, unsubstituted ethyl, unsubstituted isopropyl, or unsubstituted tert-butyl. In embodiments, $R^{1.2}$ is independently unsubstituted methyl. In embodiments, $R^{1.2}$ is independently unsubstituted ethyl. In embodiments, $R^{1.2}$ is independently unsubstituted propyl. In embodiments, $R^{1.2}$ is independently unsubstituted n-propyl. In embodiments, $R^{1.2}$ is independently unsubstituted isopropyl. In embodiments, $R^{1.2}$ is independently unsubstituted butyl. In embodiments, $R^{1.2}$ is independently unsubstituted n-butyl. In embodiments, $R^{1.2}$ is independently unsubstituted isobutyl. In embodiments, $R^{1.2}$ is independently unsubstituted tert-butyl. In embodiments, $R^{1.2}$ is independently unsubstituted pentyl. In embodiments, $R^{1.2}$ is independently unsubstituted hexyl. In embodiments, $R^{1.2}$ is independently unsubstituted heptyl. In embodiments, $R^{1.2}$ is independently unsubstituted octyl. In embodiments, $R^{1.2}$ is independently —F. In embodiments, $R^{1.2}$ is independently —Cl. In embodiments, $R^{1.2}$ is independently —Br. In embodiments, $R^{1.2}$ is independently —I. In embodiments, $R^{1.2}$ is independently unsubstituted methoxy. In embodiments, $R^{1.2}$ is independently unsubstituted ethoxy. In embodiments, $R^{1.2}$ is independently —$CF_3$. In embodiments, $R^{1.2}$ is independently —$CCl_3$. In embodiments, $R^{1.2}$ is an unsubstituted isopropyl. In embodiments, $R^{1.2}$ is an unsubstituted phenyl. In embodiments, $R^{1.2}$ is an unsubstituted pyridyl. In embodiments, $R^{1.2}$ is independently halogen. In embodiments, $R^{1.2}$ is independently —$CX^1$ In embodiments, $R^{1.2}$ is independently —$CHX_2$. In embodiments, $R^{1.2}$ is independently —$CH_2X^1$. In embodiments, $R^{1.2}$ is independently —CN. In embodiments, $R^{1.2}$ is independently —OH. In embodiments, $R^{1.2}$ is independently —$NH_2$. In embodiments, $R^{1.2}$ is independently —COOH. In embodiments, $R^{1.2}$ is independently —$CONH_2$. In embodiments, $R^{1.2}$ is independently —$NO_2$. In embodiments, $R^{1.2}$ is independently —SH. In embodiments, $R^{1.2}$ is independently —$SO_2Cl$. In embodiments, $R^{1.2}$ is independently —$SO_3H$. In embodiments, $R^{1.2}$ is independently —$SO_4H$. In embodiments, $R^{1.2}$ is independently —$SO_2NH_2$. In embodiments, $R^{1.2}$ is independently —$NHNH_2$. In embodiments, $R^{1.2}$ is independently —$ONH_2$. In embodiments, $R^{1.2}$ is independently —$NHC(O)NHNH_2$. In embodiments, $R^{1.2}$ is independently —$NHC(O)NH_2$. In embodiments, $R^{1.2}$ is independently —$NHSO_2H$. In embodiments, $R^{1.2}$ is independently —$NHC(O)H$. In embodiments, $R^{1.2}$ is independently —$NHC(O)OH$. In embodiments, $R^{1.2}$ is independently —NHOH. In embodiments, $R^{1.2}$ is independently —$OCX^1_3$. In embodiments, $R^{1.2}$ is independently —$OCHX^1_2$. In embodiments, $R^{1.2}$ is independently substituted or unsubstituted alkyl. In embodiments, $R^{1.2}$ is independently substituted or unsubstituted heteroalkyl. In embodiments, $R^{1.2}$ is independently substituted or unsubstituted cycloalkyl. In embodiments, $R^{1.2}$ is independently substituted or unsubstituted heterocycloalkyl. In embodiments, $R^{1.2}$ is independently substituted or unsubstituted aryl. In embodiments, $R^{1.2}$ is independently substituted or unsubstituted heteroaryl. In embodiments, $R^{1.2}$ is independently substituted alkyl. In embodiments, $R^{1.2}$ is independently substituted heteroalkyl. In embodiments, $R^{1.2}$ is independently substituted cycloalkyl. In embodiments, $R^{1.2}$ is independently substituted heterocycloalkyl. In embodiments, $R^{1.2}$ is independently substituted aryl. In embodiments, $R^{1.2}$ is independently substituted heteroaryl. In embodiments, $R^{1.2}$ is independently unsubstituted alkyl. In embodiments, $R^{1.2}$ is independently unsubstituted heteroalkyl. In embodiments, $R^{1.2}$ is independently unsubstituted cycloalkyl. In embodiments, $R^{1.2}$ is independently unsubstituted heterocycloalkyl. In embodiments, $R^{1.2}$ is independently unsubstituted aryl. In embodiments, $R^{1.2}$ is independently unsubstituted heteroaryl. In embodiments, $R^{1.2}$ is independently substituted or unsubstituted $C_1$-$C_8$ alkyl. In embodiments, $R^{1.2}$ is independently substituted or unsubstituted 2 to 8 membered heteroalkyl. In embodiments, $R^{1.2}$ is independently substituted or unsubstituted $C_3$-$C_5$ cycloalkyl. In embodiments, $R^{1.2}$ is independently substituted or unsubstituted 3 to 8 membered heterocycloalkyl. In embodiments, $R^{1.2}$ is independently substituted or unsubstituted $C_6$-$C_{10}$ aryl. In embodiments, $R^{1.2}$ is independently substituted or unsubstituted 5 to 10 membered heteroaryl. In embodiments, $R^{1.2}$ is independently substituted $C_1$-$C_8$ alkyl. In embodiments, $R^{1.2}$ is independently substituted 2 to 8 membered heteroalkyl. In embodiments, $R^{1.2}$ is independently substituted $C_3$-$C_8$ cycloalkyl. In embodiments, $R^{1.2}$ is independently substituted 3 to 8 membered heterocycloalkyl. In embodiments, $R^{1.2}$ is independently substituted $C_6$-$C_{10}$ aryl. In embodiments, $R^{1.2}$ is independently substituted 5 to 10 membered heteroaryl. In embodiments, $R^{1.2}$ is independently unsubstituted $C_1$-$C_8$ alkyl. In embodiments, $R^{1.2}$ is independently unsubstituted 2 to 8 membered heteroalkyl. In embodiments, $R^{1.2}$ is independently unsubstituted $C_3$-$C_8$ cycloalkyl. In embodiments, $R^{1.2}$ is independently unsubstituted 3 to 8 membered heterocycloalkyl. In embodiments, $R^{1.2}$ is independently unsubstituted $C_6$-$C_{10}$ aryl. In embodiments, $R^{1.2}$ is independently unsubstituted 5 to 10 membered heteroaryl. In embodiments, $R^{1.2}$ is independently substituted or unsubstituted $C_1$-$C_4$ alkyl. In embodiments, $R^{1.2}$ is independently substituted or unsubstituted 2 to 4 membered heteroalkyl. In embodiments, $R^{1.2}$ is independently substituted or unsubstituted $C_3$-$C_6$ cycloalkyl. In embodiments, $R^{1.2}$ is independently substituted or unsubstituted 3 to 6 membered heterocycloalkyl. In embodiments, $R^{1.2}$ is independently substituted or unsubstituted phenyl. In embodiments, $R^{1.2}$ is independently substituted or unsubstituted 5 to 6 membered heteroaryl. In embodiments, $R^{1.2}$ is independently substituted $C_1$-$C_4$ alkyl. In embodiments, $R^{1.2}$ is independently substituted 2 to 4 membered heteroalkyl. In embodiments, $R^{1.2}$ is independently substituted $C_3$-$C_6$ cycloalkyl. In embodiments, $R^{1.2}$ is independently substituted 3 to 6 membered heterocycloalkyl. In embodiments, $R^{1.2}$ is independently substituted phenyl. In embodiments, $R^{1.2}$ is independently substituted 5 to 6 membered heteroaryl. In embodiments, $R^{1.2}$ is independently unsubstituted $C_1$-$C_4$ alkyl. In embodiments, $R^{1.2}$ is independently unsubstituted 2 to 4 membered heteroalkyl. In embodiments, $R^{1.2}$ is independently unsubstituted $C_3$-$C_6$ cycloalkyl. In embodiments, $R^{1.2}$ is independently unsubstituted 3 to 6 membered heterocycloalkyl. In embodiments, $R^{1.2}$ is independently unsubstituted phenyl. In embodiments, $R^{1.2}$ is independently unsubstituted 5 to 6 membered heteroaryl. In embodiments, $R^{1.2}$ is independently hydrogen.

In embodiments, z1 is 2. In embodiments, z1 is 3. In embodiments, z1 is 0. In embodiments, z1 is 1. In embodiments, z1 is 4. In embodiments, z1 is 5.

In embodiments, $R^2$ is independently hydrogen, oxo, halogen, $CX^2_3$, —$CHX^2_2$, —$CH_2X^2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^2$ is independently oxo, halogen, $CX^2_3$, —$CHX^2_2$, —$CH_2X^2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^2$ is independently hydrogen, halogen, $CX^2_3$, —$CHX^2_2$, —$CH_2X^2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^2$ is independently oxo, halogen, —$CX^2_3$, —$CHX^2_2$, —$CH_2X^2$, —OH, —SH, —$OCX^2_3$, —$OCHX^2_2$, —$CH_3$, —$CH_2CH_3$, —$OCH_3$, —$OCH_2CH_3$, —$SCH_3$, or —$SCH_2CH_3$. In embodiments, $R^2$ is independently hydrogen, halogen, —$CX^2_3$, —$CHX^2_2$, —$CH_2X^2$, —OH, —SH, —$OCX^2_3$, —$OCHX^2_2$, —$CH_3$, —$CH_2CH_3$, —$OCH_3$, —$OCH_2CH_3$, —$SCH_3$, or —$SCH_2CH_3$. In embodiments, $R^2$ is independently hydrogen. In embodiments, $R^2$ is independently halogen. In embodiments, $R^2$ is independently unsubstituted methyl. In embodiments, two adjacent $R^2$ substituents or two $R^2$ substituents bonded to the same atom may optionally be joined to form a substituted or unsubstituted cycloalkyl or substituted or unsubstituted heterocycloalkyl. In embodiments, two adjacent $R^2$ substituents may optionally be joined to form a substituted or unsubstituted cycloalkyl or substituted or unsubstituted heterocycloalkyl or substituted or unsubstituted aryl or substituted or unsubstituted heteroaryl. In embodiments, $R^2$ is independently halogen, —$CX^2_3$, —$CHX^2_2$, —$CH_2X^2$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^2_3$, —$OCHX^2_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^2$ is independently halogen, —$CX^2_3$, —$CHX^2_2$, —$CH_2X^2$, —OH, —SH, —COOH, —$OCX^2_3$, —$OCHX^2_2$, —$CH_3$, —$CH_2CH_3$, —$OCH_3$, —$OCH_2CH_3$, —$SCH_3$, or —$SCH_2CH_3$. In embodiments, $R^2$ is independently halogen or —$OCH_3$. In embodiments, $R^2$ is substituted or unsubstituted $C_1$-$C_6$ alkyl. In embodiments, $R^2$ is substituted or unsubstituted 2 to 6 membered heteroalkyl. In embodiments, $R^2$ is substituted or unsubstituted $C_3$-$C_5$ cycloalkyl. In embodiments, $R^2$ is substituted or unsubstituted 3 to 8 membered heterocycloalkyl. In embodiments, $R^2$ is substituted or unsubstituted $C_6$ aryl. In embodiments, $R^2$ is substituted or unsubstituted 5 to 6 membered heteroaryl. In embodiments, $R^2$ is independently halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —OH. In embodiments, $R^2$ is independently —SH. In embodiments, $R^2$ is independently —COOH. In embodiments, $R^2$ is independently —$OCX^2_3$. In embodiments, $R^2$ is independently —$OCHX^2_2$. In embodiments, $R^2$ is independently —$CH_3$. In embodiments, $R^2$ is independently —$CH_2CH_3$. In embodiments, $R^2$ is independently —$OCH_3$. In embodiments, $R^2$ is independently —$OCH_2CH_3$. In embodiments, $R^2$ is independently —$SCH_3$. In embodiments, $R^2$ is independently —$SCH_2CH_3$. In embodiments, $R^2$ is independently —Cl or —$OCH_3$. In embodiments, $R^2$ is independently halogen, —$CX^2_3$, —CN, —OH, —$NH_2$, —COOH, —$CONH_2$, —$NO_2$, —SH, —$OCX^2_3$, —$OCHX^2_2$, —$CHX^2_2$, —$CH_2X^2$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^2$ is independently halogen, —$CX^2_3$, —CN, unsubstituted $C_1$-$C_4$ alkyl, or unsubstituted 2 to 4 membered heteroalkyl. In embodiments, $R^2$ is independently unsubstituted methyl, unsubstituted ethyl, unsubstituted isopropyl, or unsubstituted tert-butyl. In embodiments, $R^2$ is independently unsubstituted methyl. In embodiments, $R^2$ is independently unsubstituted ethyl. In embodiments, $R^2$ is independently unsubstituted propyl. In embodiments, $R^2$ is independently unsubstituted n-propyl. In embodiments, $R^2$ is independently unsubstituted isopropyl. In embodiments, $R^2$ is independently unsubstituted butyl. In embodiments, $R^2$ is independently unsubstituted n-butyl. In embodiments, $R^2$ is independently unsubstituted isobutyl. In embodiments, $R^2$ is independently unsubstituted tert-butyl. In embodiments, $R^2$ is independently unsubstituted pentyl. In embodiments, $R^2$ is independently unsubstituted hexyl. In embodiments, $R^2$ is independently unsubstituted heptyl. In embodiments, $R^2$ is independently unsubstituted octyl. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently unsubstituted methoxy. In embodiments, $R^2$ is independently unsubstituted ethoxy. In embodiments, $R^2$ is independently —$CF_3$. In embodiments, $R^2$ is independently —$CCl_3$. In embodiments, $R^2$ is an unsubstituted isopropyl. In embodiments, $R^2$ is an unsubstituted phenyl. In embodiments, $R^2$ is an unsubstituted pyridyl. In embodiments, $R^2$ is independently halogen. In embodiments, $R^2$ is independently —$CX^2_3$. In embodiments, $R^2$ is independently —$CHX^2_2$. In embodiments, $R^2$ is independently —$CH_2X^2$. In embodiments, $R^2$ is independently —CN. In embodiments, $R^2$ is independently —OH. In embodiments, $R^2$ is independently —$NH_2$. In embodiments, $R^2$ is independently —COOH. In embodiments, $R^2$ is independently —$CONH_2$. In embodiments, $R^2$ is independently —$NO_2$. In embodiments, $R^2$ is independently —SH. In embodiments, $R^2$ is independently —$SO_2Cl$. In embodiments, $R^2$ is independently —$SO_3H$. In embodiments, $R^2$ is independently —$SO_4H$. In embodiments, $R^2$ is independently —$SO_2NH_2$. In embodiments, $R^2$ is independently —$NHNH_2$. In embodiments, $R^2$ is independently —$ONH_2$. In embodiments, $R^2$ is independently —NHC(O)$NHNH_2$. In embodiments, $R^2$ is independently —NHC(O)$NH_2$. In embodiments, $R^2$ is independently —$NHSO_2H$. In embodiments, $R^2$ is independently —NHC(O)H. In embodiments, $R^2$ is independently —NHC(O)OH. In embodiments, $R^2$ is independently —NHOH. In embodiments, $R^2$ is independently —OCX$^2_3$. In embodiments, $R^2$ is independently —OCHX$^2_2$. In embodiments, $R^2$ is independently substituted or unsubstituted alkyl. In embodiments, $R^2$ is independently substituted or unsubstituted heteroalkyl. In embodiments, $R^2$ is independently substituted or unsubstituted cycloalkyl. In embodiments, $R^2$ is independently substituted or unsubstituted heterocycloalkyl. In embodiments, $R^2$ is independently substituted or unsubstituted aryl. In embodiments, $R^2$ is independently substituted or unsubstituted heteroaryl. In embodiments, $R^2$ is independently substituted alkyl. In embodiments, $R^2$ is independently substituted heteroalkyl. In embodiments, $R^2$ is independently substituted cycloalkyl. In embodiments, $R^2$ is independently substituted heterocycloalkyl. In embodiments, $R^2$ is independently substituted aryl. In embodiments, $R^2$ is independently substituted heteroaryl. In embodiments, $R^2$ is independently unsubstituted alkyl. In embodiments, $R^2$ is independently unsubstituted heteroalkyl. In embodiments, $R^2$ is independently unsubstituted cycloalkyl. In embodiments, $R^2$ is independently unsubstituted heterocycloalkyl. In embodiments, $R^2$ is independently unsubstituted aryl. In embodiments, $R^2$ is independently unsubstituted heteroaryl. In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_8$ cycloalkyl. In embodiments, $R^2$ is independently substituted or unsubstituted 3 to 8 membered heterocycloalkyl. In embodiments, $R^2$ is independently substituted or unsubstituted $C_6$-$C_{10}$ aryl. In embodiments, $R^2$ is independently substituted or unsubstituted 5 to 10 membered heteroaryl. In embodiments, $R^2$ is independently substituted $C_1$-$C_8$ alkyl. In embodiments, $R^2$ is independently substituted 2 to 8 membered heteroalkyl. In embodiments, $R^2$ is independently substituted $C_3$-$C_8$ cycloalkyl. In embodiments, $R^2$ is independently substituted 3 to 8 membered heterocycloalkyl. In embodiments, $R^2$ is independently substituted $C_6$-$C_{10}$ aryl. In embodiments, $R^2$ is independently substituted 5 to 10 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_8$ cycloalkyl. In embodiments, $R^2$ is independently unsubstituted 3 to 8 membered heterocycloalkyl. In embodiments, $R^2$ is independently unsubstituted $C_6$-$C_{10}$ aryl. In embodiments, $R^2$ is independently unsubstituted 5 to 10 membered heteroaryl. In embodiments, $R^2$ is independently substituted or unsubstituted $C_1$-$C_4$ alkyl. In embodiments, $R^2$ is independently substituted or unsubstituted 2 to 4 membered heteroalkyl. In embodiments, $R^2$ is independently substituted or unsubstituted $C_3$-$C_6$ cycloalkyl. In embodiments, $R^2$ is independently substituted or unsubstituted 3 to 6 membered heterocycloalkyl. In embodiments, $R^2$ is independently substituted or unsubstituted phenyl. In embodiments, $R^2$ is independently substituted or unsubstituted 5 to 6 membered heteroaryl. In embodiments, $R^2$ is independently substituted $C_1$-$C_4$ alkyl. In embodiments, $R^2$ is independently substituted 2 to 4 membered heteroalkyl. In embodiments, $R^2$ is independently substituted $C_3$-$C_6$ cycloalkyl. In embodiments, $R^2$ is independently substituted 3 to 6 membered heterocycloalkyl. In embodiments, $R^2$ is independently substituted phenyl. In embodiments, $R^2$ is independently substituted 5 to 6 membered heteroaryl. In embodiments, $R^2$ is independently unsubstituted $C_1$-$C_4$ alkyl. In embodiments, $R^2$ is independently unsubstituted 2 to 4 membered heteroalkyl. In embodiments, $R^2$ is independently unsubstituted $C_3$-$C_6$ cycloalkyl. In embodiments, $R^2$ is independently unsubstituted 3 to 6 membered heterocycloalkyl. In embodiments, $R^2$ is independently unsubstituted phenyl. In embodiments, $R^2$ is independently unsubstituted 5 to 6 membered heteroaryl.

In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z2 is 7. In embodiments, z2 is 8. In embodiments, z2 is 9. In embodiments, z2 is 10.

In embodiments, $R^4$ is hydrogen. In embodiments, $R^5$ is hydrogen. In embodiments, $R^4$ is unsubstituted methyl. In embodiments, $R^4$ is unsubstituted ethyl. In embodiments, $R^4$ is unsubstituted propyl. In embodiments, $R^4$ is unsubstituted butyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted butyl. In embodiments, $R^4$ is substituted or unsubstituted alkyl. In embodiments, $R^4$ is substituted or unsubstituted heteroalkyl. In embodiments, $R^4$ is substituted or unsubstituted cycloalkyl. In embodiments, $R^4$ is substituted or unsubstituted heterocycloalkyl. In embodiments, $R^4$ is substituted or unsubstituted aryl. In embodiments, $R^4$ is substituted or unsubstituted heteroaryl. In embodiments, $R^5$ is substituted or unsubstituted alkyl. In embodiments, $R^5$ is substituted or unsubstituted heteroalkyl. In embodiments, $R^5$ is substituted or unsubstituted cycloalkyl. In embodiments, $R^1$ is substituted or unsubstituted heterocycloalkyl. In embodiments, is substituted or unsubstituted aryl. In embodiments, $R^5$ is substituted or unsubstituted heteroaryl.

In embodiments, $L^1$ is a bond, —O—, —C(O)—, —S—, —SO—, —S(O)$_2$—, —NR$^{7A}$—, —NR$^{7A}$C(O)—, —C(O)NR$^{7A}$—, —SO$_2$NR$^{7A}$—, —NR$^{7A}$SO$_2$—, —OC(O)NR$^{7A}$—, —NR$^{7A}$C(O)O—, —CR$^{9A}$=NO—, —ON=CR$^{9A}$—, —NR$^{8A}$C(O)NR$^{7A}$—, —NR$^{8A}$C(=NR$^{10A}$)NR$^{7A}$—, —NR$^{8A}$C(=NR$^{10A}$)—, —C(=NR$^{mA}$)NR$^{7A}$—, —OC(=NR$^{10A}$)—, —C(=NR$^{10A}$)O—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^1$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, substituted or unsubstituted alkylene (e.g., $C_1$-$C_8$, $C_1$-$C_6$, or $C_1$-$C_4$), substituted or unsubstituted heteroalkylene (e.g., 2 to 8 membered, 2 to 6 membered, or 2 to 4 membered), substituted or unsubstituted cycloalkylene (e.g., $C_3$-$C_8$, $C_3$-$C_6$, or $C_5$-$C_6$), substituted or unsubstituted heterocycloalkylene (e.g., 3 to 8 membered, 3 to 6 membered, or 5 to 6 membered), substituted or unsubstituted arylene (e.g., $C_6$-$C_{10}$, $C_{10}$, or phenylene), or substituted or unsubstituted heteroarylene (e.g., 5 to 10 membered, 5 to 9 membered, or 5 to 6 membered).

In embodiments, $L^1$ is a bond, substituted or unsubstituted alkylene, or substituted or unsubstituted heteroalkylene. In embodiments, $L^1$ is a bond, unsubstituted $C_1$-$C_4$ alkylene, or unsubstituted 2 to 4 membered heteroalkylene. In embodiments, $L^1$ is a bond. In embodiments, $L^1$ is a bond, —O—, —C(O)—, —S—, —SO—, —S(O)$_2$—, —NH—, —NHC (O)—, —C(O)NH—, —SO$_2$NH—, —NHSO$_2$—, —OC(O) NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. In embodiments, L$^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. In embodiments, L$^1$ is a bond. In embodiments, L$^1$ is a bond, —O—, —C(O)—, —S—, —NH—, —NHC(O)—, —C(O)NH—, unsubstituted C$_1$-C$_4$ alkylene, or unsubstituted 2 to 4 membered heteroalkylene. In embodiments, L$^1$ is —NH—. In embodiments, L$^1$ is —CH(CH$_2$Cl)CH$_2$—. In embodiments, L$^1$ is —C(O)CH(CH$_2$Cl)CH$_2$—. In embodiments, L$^1$ is —NHC(O)CH(CH$_2$Cl)CH$_2$—. In embodiments, L$^1$ is halo-substituted C$_1$-C$_4$ alkylene. In embodiments, L$^1$ is halo-substituted C$_2$-C$_4$ alkylene. In embodiments, L$^1$ is halo-substituted C$_3$-C$_4$ alkylene. In embodiments, L$^1$ is halo-substituted C$_3$ alkylene. In embodiments, L$^1$ is a bond. In embodiments, L$^1$ is —O—. In embodiments, L$^1$ is —C(O)—. In embodiments, L$^1$ is —S—. In embodiments, L$^1$ is —SO—. In embodiments, L$^1$ is —S(O)$_2$—. In embodiments, L$^1$ is —NH—. In embodiments, L$^1$ is —NHC(O)—. In embodiments, L$^1$ is —C(O)NH—. In embodiments, L$^1$ is —SO$_2$NH—. In embodiments, L$^1$ is —NHSO$_2$—. In embodiments, L$^1$ is —OC(O)NH—. In embodiments, L$^1$ is —NHC(O)O—. In embodiments, L$^1$ is —CH=NO—. In embodiments, L$^1$ is —ON=CH—. In embodiments, L$^1$ is —NHC(O)NH—. In embodiments, L$^1$ is —NHC(=NH)NH—. In embodiments, L$^1$ is —NHC(=NH)—. In embodiments, L$^1$ is —C(=NH)NH—. In embodiments, L$^1$ is —OC(=NH)—. In embodiments, L$^1$ is —C(=NH)O—.

In embodiments, L$^1$ is a bond, —O—, —C(O)—, —S—, —SO—, —S(O)$_2$—, —NR$^{7A}$—, —NR$^{7A}$C(O)—, —C(O)NR$^{7A}$—, —SO$_2$NR$^{7A}$—, —NR$^{7A}$SO$_2$—, —OC(O)NR$^{7A}$—, —NR$^{7A}$C(O)O—, —CR$^{9A}$=NO—, —ON=CR$^{9A}$—, —NR$^{8A}$C(O)NR$^{7A}$—, —NR$^{8A}$C(=NR$^{10A}$)NR$^{7A}$—, —NR$^{8A}$C(=NR$^{10A}$)—, —C(=NR$^{10A}$)NR$^{7A}$—, —OC(=NR$^{10A}$)—, —C(=NR$^{10A}$)O—, R$^{7A}$-substituted or unsubstituted alkylene (e.g., C$_3$-C$_3$, C$_1$-C$_6$, or C$_1$-C$_4$), R$^{7A}$-substituted or unsubstituted heteroalkylene (e.g., 2 to 8 membered, 2 to 6 membered, or 2 to 4 membered), R$^{7A}$-substituted or unsubstituted cycloalkylene (e.g., C$_3$-C$_8$, C$_3$-C$_6$, or C$_5$-C$_6$), R$^{7A}$-substituted or unsubstituted heterocycloalkylene (e.g., 3 to 8 membered, 3 to 6 membered, or 5 to 6 membered), R$^{7A}$-substituted or unsubstituted arylene (e.g., C$_6$-C$_{10}$, C$_{10}$, or phenylene), or R$^{7A}$-substituted or unsubstituted heteroarylene (e.g., 5 to 10 membered, 5 to 9 membered, or 5 to 6 membered).

In embodiments, L$^1$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, R$^{7A}$-substituted or unsubstituted alkylene (e.g., C$_1$-C$_8$, C$_1$-C$_6$, or C$_1$-C$_4$), R$^{7A}$-substituted or unsubstituted heteroalkylene (e.g., 2 to 8 membered, 2 to 6 membered, or 2 to 4 membered), R$^{7A}$-substituted or unsubstituted cycloalkylene (e.g., C$_3$-C$_8$, C$_3$-C$_6$, or C$_5$-C$_6$), R$^{7A}$-substituted or unsubstituted heterocycloalkylene (e.g., 3 to 8 membered, 3 to 6 membered, or 5 to 6 membered), R$^{7A}$-substituted or unsubstituted arylene (e.g., C$_6$-C$_{10}$, C$_{10}$, or phenylene), or R$^{7A}$-substituted or unsubstituted heteroarylene (e.g., 5 to 10 membered, 5 to 9 membered, or 5 to 6 membered).

In embodiments, L$^2$ is a bond, —O—, —C(O)—, —S—, —SO—, —S(O)$_2$—, —NR$^{7B}$—, —NR$^{7B}$C(O)—, —C(O)NR$^{7B}$—, —SO$_2$NR$^{7B}$—, —NR$^{7B}$SO$_2$—, —OC(O)NR$^{7B}$—, —NR$^{7B}$C(O)O—, —CR$^{9B}$=NO—, —ON=CR$^{9B}$—, —NR$^{8B}$C(O)NR$^{7B}$—, —NR$^{8B}$C(=NR$^{10B}$)NR$^{7B}$—, —NR$^{8B}$C(=NR$^{10B}$)—, —C(=NR$^{10B}$)NR$^{7B}$—, —OC(=NR$^{10B}$)—, —C(=NR$^{10B}$)O—, substituted or unsubstituted alkylene (e.g., C$_3$-C$_8$, C$_1$-C$_6$, or C$_1$-C$_4$), substituted or unsubstituted heteroalkylene (e.g., 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8 membered, 3 to 6 membered, or 5 to 6 membered), substituted or unsubstituted arylene (e.g., C$_6$-C$_{10}$, C$_{10}$, or phenylene), or substituted or unsubstituted heteroarylene (e.g., 5 to 10 membered, 5 to 9 membered, or 5 to 6 membered).

In embodiments, L$^2$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, substituted or unsubstituted alkylene (e.g., C$_3$-C$_8$, C$_1$-C$_6$, or C$_1$-C$_4$), substituted or unsubstituted heteroalkylene (e.g., 2 to 8 membered, 2 to 6 membered, or 2 to 4 membered), substituted or unsubstituted cycloalkylene (e.g., C$_3$-C$_8$, C$_3$-C$_6$, or C$_5$-C$_6$), substituted or unsubstituted heterocycloalkylene (e.g., 3 to 8 membered, 3 to 6 membered, or 5 to 6 membered), substituted or unsubstituted arylene (e.g., C$_6$-C$_{10}$, C$_{10}$, or phenylene), or substituted or unsubstituted heteroarylene (e.g., 5 to 10 membered, 5 to 9 membered, or 5 to 6 membered).

In embodiments, L$^2$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. In embodiments, L$^2$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene. In embodiments, L$^2$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —NHC(O)NH—, substituted or unsubstituted alkylene, or substituted or unsubstituted heteroalkylene. In embodiments, L$^2$ is a bond, —O—, —C(O)—, —S—, —NH—, —NHC(O)—, —C(O)NH—, unsubstituted C$_1$-C$_4$ alkylene, or unsubstituted 2 to 4 membered heteroalkylene. In embodiments, L$^2$ is a bond. In embodiments, L$^2$ is —NH—. In embodiments, L$^2$ is —CH(CH$_2$Cl)CH$_2$—. In embodiments, L$^2$ is —C(O)CH(CH$_2$Cl)CH$_2$—. In embodiments, L$^2$ is —NHC(O)CH(CH$_2$Cl)CH$_2$—. In embodiments, L$^2$ is —NHC(O)—. In embodiments, L$^2$ is —NH—. In embodiments, L$^2$ is halo-substituted C$_1$-C$_4$ alkylene. In embodiments, L$^2$ is halo-substituted $C_2$-$C_4$ alkylene. In embodiments, $L^2$ is halo-substituted $C_3$-$C_4$ alkylene. In embodiments, $L^2$ is halo-substituted $C_3$ alkylene.

In embodiments, $L^2$ is a bond, —O—, —C(O)—, —S—, —SO—, —S(O)$_2$—, —NR$^{7B}$—, —NR$^{7B}$C(O)—, —C(O)NR$^{7B}$—, —SO$_2$NR$^{7B}$—, —NR$^{7B}$SO$_2$—, —OC(O)NR$^{7B}$—, —NR$^{7B}$C(O)O—, —CR$^{9B}$=NO—, —ON=CR$^{9B}$—, —NR$^{8B}$C(O)NR$^{7B}$—, —NR$^{8B}$C(=NR$^{10B}$)NR$^{7B}$—, —NR$^{8B}$C(=NR$^{10B}$)—, —C(=NR$^{10B}$)NR$^{7B}$—, —OC(=NR$^{10B}$)—, —C(=NR$^{10B}$)O—, $R^{7B}$-substituted or unsubstituted alkylene (e.g., $C_1$-$C_8$, $C_1$-$C_6$, or $C_1$-$C_4$), $R^{7B}$-substituted or unsubstituted heteroalkylene (e.g., 2 to 8 membered, 2 to 6 membered, or 2 to 4 membered), $R^{7B}$-substituted or unsubstituted cycloalkylene (e.g., $C_3$-$C_8$, $C_3$-$C_6$, or $C_5$-$C_6$), $R^{7B}$-substituted or unsubstituted heterocycloalkylene (e.g., 3 to 8 membered, 3 to 6 membered, or 5 to 6 membered), $R^{7B}$-substituted or unsubstituted arylene (e.g., $C_6$-$C_{10}$, $C_{10}$, or phenylene), or $R^{7B}$-substituted or unsubstituted heteroarylene (e.g., 5 to 10 membered, 5 to 9 membered, or 5 to 6 membered). In embodiments, $L^2$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —CH=NO—, —ON=CH—, —NHC(O)NH—, —NHC(=NH)NH—, —NHC(=NH)—, —C(=NH)NH—, —OC(=NH)—, —C(=NH)O—, $R^{7B}$-substituted or unsubstituted alkylene (e.g., $C_1$-$C_8$, $C_1$-$C_6$, or $C_3$-$C_4$), $R^{7B}$-substituted or unsubstituted heteroalkylene (e.g., 2 to 8 membered, 2 to 6 membered, or 2 to 4 membered), $R^{7B}$-substituted or unsubstituted cycloalkylene (e.g., $C_3$-$C_5$, $C_3$-$C_6$, or $C_5$-$C_6$), $R^{7B}$-substituted or unsubstituted heterocycloalkylene (e.g., 3 to 8 membered, 3 to 6 membered, or 5 to 6 membered), $R^{7B}$-substituted or unsubstituted arylene (e.g., $C_6$-$C_{10}$, $C_{10}$, or phenylene), or $R^{7B}$-substituted or unsubstituted heteroarylene (e.g., 5 to 10 membered, 5 to 9 membered, or 5 to 6 membered).

In embodiments, $L^2$ is

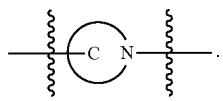

Ring C is a substituted or unsubstituted heterocycloalkylene or substituted or unsubstituted heteroarylene. In embodiments, Ring C is a substituted or unsubstituted 5 to 6 membered heterocycloalkylene or substituted or unsubstituted 5 to 6 membered heteroarylene. In embodiments, Ring C is an $R^{7B}$-substituted or unsubstituted heterocycloalkylene or $R^{7B}$-substituted or unsubstituted heteroarylene. In embodiments, Ring C is a $R^{7B}$-substituted or unsubstituted 5 to 6 membered heterocycloalkylene or $R^{7B}$-substituted or unsubstituted 5 to 6 membered heteroarylene.

In embodiments, E is a covalent cysteine modifier moiety. In embodiments, E is a covalent histidine modifier moiety. In embodiments, E is

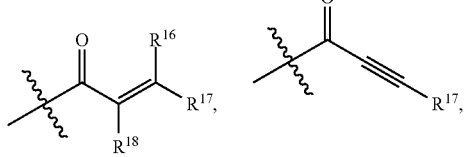

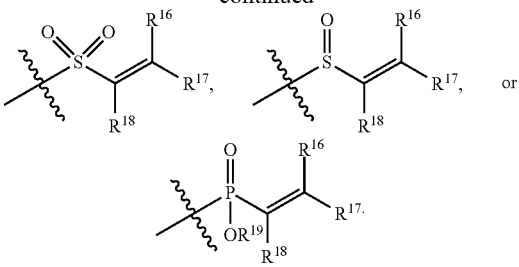

In embodiments, E is

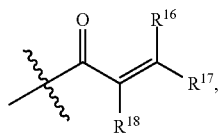

In embodiments, E is

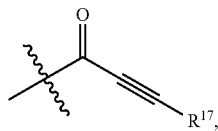

In embodiments, E is

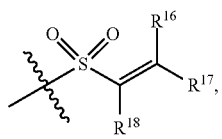

In embodiments, E is

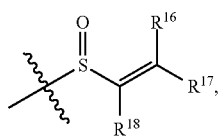

In embodiments, E is

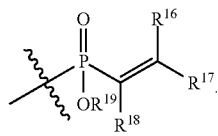

$R^{16}$ is independently hydrogen, halogen, $CX^{16}_3$, —CHX$^{16}_2$, —CH$_2$X$^{16}$, —CN, —SO$_2$Cl, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{17}$ is independently hydrogen, halogen, $CX^{17}{}_3$, —$CHX^{17}{}_2$, —$CH_2X^{17}$, —CN, —$SO_2Cl$, —$SO_{n17}R^{17D}$, —$SO_{v17}NR^{17A}R^{17B}$, —$NHNR^{17A}R^{17B}$, —$ONR^{17A}R^{17B}$, —NHC=(O)NHNR$^{17A}R^{17B}$, —NHC(O)NR$^{17A}R^{17B}$, —N(O)$_{m17}$, —NR$^{17A}R^{17B}$, —C(O)R$^{17C}$, —C(O)—OR$^{17C}$, —C(O)NR$^{17A}R^{17B}$, —OR$^{17D}$, —NR$^{17A}SO_2R^{17D}$, —NR$^{17A}C(O)R^{17C}$, —NR$^{17A}C(O)OR^{17C}$, —NR$^{17A}OR^{17C}$, —OCX$^{17}{}_3$, —OCHX$^{17}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{18}$ is independently hydrogen, halogen, $CX^{18}{}_3$, —$CHX^{18}{}_2$, —$CH_2X^{18}$, —CN, —$SO_2Cl$, —$SO_{n18}R^{18D}$, —$SO_{v18}NR^{18A}R^{18B}$, —$NHNR^{18A}R^{18B}$, —$ONR^{18A}R^{18B}$, —NHC=(O)NHNR$^{18A}R^{18B}$, —NHC(O)NR$^{18A}R^{18B}$, —N(O)$_{m18}$, —NR$^{18A}R^{18B}$, —C(O)R$^{18C}$, —C(O)—OR$^{18C}$, —C(O)NR$^{18A}R^{18B}$, —OR$^{18D}$, —NR$^{18A}SO_2R^{18D}$, —NR$^{18A}C(O)R^{18C}$, —NR$^{18A}C(O)OR^{18C}$, —NR$^{18A}OR^{18C}$, —OCX$^{18}{}_3$, —OCHX$^{18}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{19}$ is independently hydrogen, halogen, $CX^{19}{}_3$, —$CHX^{19}{}_2$, —$CH_2X^{19}$, —CN, —$SO_2Cl$, —$SO_{n19}R^{19D}$, —$SO_{v19}NR^{19A}R^{19B}$, —$NHNR^{19A}R^{19B}$, —$ONR^{19A}R^{19B}$, —NHC=(O)NHNR$^{19A}R^{19B}$, —NHC(O)NR$^{19A}R^{19B}$, —N(O)$_{m19}$, —NR$^{19A}R^{19B}$, —C(O)R$^{19C}$, —C(O)—OR$^{19C}$, —C(O)NR$^{19A}R^{19B}$, —OR$^{19D}$, —NR$^{19A}SO_2R^{19D}$, —NR$^{19A}C(O)R^{19C}$, —NR$^{19A}C(O)OR^{19C}$, —NR$^{19A}OR^{19C}$, —OCX$^{19}{}_3$, —OCHX$^{19}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$, $R^{19D}$, are independently hydrogen, halogen, —$CX_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl. Each X, $X^{16}$, $X^{17}$, $X^{18}$ and $X^{19}$ is independently —F, —Cl, —Br, or —I. The symbols n16, n17, n18, n19, v16, v17, v18, and v19 are independently an integer from 0 to 4. The symbols m16, m17, m18, and m19 are independently an integer from 1 to 2. In embodiments, $R^{18}$ is —CN. In embodiments, $R^{16}$ is unsubstituted methyl. In embodiments, $R^{17}$ is unsubstituted methyl. In embodiments, $R^{19}$ is unsubstituted methyl. In embodiments, $R^{18}$ is hydrogen. In embodiments, $R^{16}$ is hydrogen. In embodiments, $R^{17}$ is hydrogen. In embodiments, $R^{19}$ is hydrogen.

X may independently be —F. X may independently be —Cl. X may independently be —Br. X may independently be —I. $X^{16}$ may independently be —F. $X^{16}$ may independently be —Cl. $X^{16}$ may independently be —Br. $X^{16}$ may independently be —I. $X^{17}$ may independently be —F. $X^{17}$ may independently be —Cl. $X^{17}$ may independently be —Br. $X^{17}$ may independently be —I. $X^{18}$ may independently be —F. $X^{18}$ may independently be —Cl. $X^{18}$ may independently be —Br. $X^{18}$ may independently be —I. $X^{19}$ may independently be —F. $X^{19}$ may independently be —Cl. $X^{19}$ may independently be —Br. $X^{19}$ may independently be —I.

n16 may independently be 0. n16 may independently be 1. n16 may independently be 2. n16 may independently be 3. n16 may independently be 4. n17 may independently be 0. n17 may independently be 1. n17 may independently be 2. n17 may independently be 3. n17 may independently be 4. n18 may independently be 0. n18 may independently be 1. n18 may independently be 2. n18 may independently be 3. n18 may independently be 4. n19 may independently be 0. n19 may independently be 1. n19 may independently be 2. n19 may independently be 3. n19 may independently be 4.

v16 may independently be 0. v16 may independently be 1. v16 may independently be 2. v16 may independently be 3. v16 may independently be 4. v17 may independently be 0. v17 may independently be 1. v17 may independently be 2. v17 may independently be 3. v17 may independently be 4. v18 may independently be 0. v18 may independently be 1. v18 may independently be 2. v18 may independently be 3. v18 may independently be 4. v19 may independently be 0. v19 may independently be 1. v19 may independently be 2. v19 may independently be 3. v19 may independently be 4.

m16 may independently be 1. m16 may independently be 2. m17 may independently be 1. m17 may independently be 2. m18 may independently be 1. m18 may independently be 2. m19 may independently be 1. m19 may independently be 2.

In embodiments, $R^{16}$ is hydrogen. In embodiments, $R^{16}$ is halogen. In embodiments, $R^{16}$ is $CX^{16}{}_3$. In embodiments, $R^{16}$ is —$CHX^{16}{}_2$. In embodiments, $R^{16}$ is —$CH_2X^{16}$. In embodiments, $R^{16}$ is —CN. In embodiments, $R^{16}$ is —$SO_{n16}R^{16D}$. In embodiments, $R^{16}$ is —$SO_{v16}NR^{16A}R^{16B}$. In embodiments, $R^{16}$ is —NHNR$^{16A}R^{16B}$. In embodiments, $R^{16}$ is —ONR$^{16A}R^{16B}$. In embodiments, $R^{16}$ is —NHC=(O)NHNR$^{16A}R^{16B}$. In embodiments, $R^{16}$ is —NHC(O)NR$^{16A}R^{16B}$. In embodiments, $R^{16}$ is —N(O)$_{m16}$. In embodiments, $R^{16}$ is —NR$^{16A}R^{16B}$. In embodiments, $R^{16}$ is —C(O)R$^{16C}$. In embodiments, $R^{16}$ is —C(O)—OR$^{16C}$. In embodiments, $R^{16}$ is —C(O)NR$^{16A}R^{16B}$. In embodiments, $R^{16}$ is —OR$^{16D}$. In embodiments, $R^{16}$ is —NR$^{16A}SO_2R^{16D}$. In embodiments, $R^{16}$ is —NR$^{16A}C(O)R^{16C}$. In embodiments, $R^{16}$ is —NR$^{16A}C(O)OR^{16C}$. In embodiments, $R^{16}$ is —NR$^{16A}OR^{16C}$. In embodiments, $R^{16}$ is —OCX$^{16}{}_3$. In embodiments, $R^{16}$ is —OCHX$^{16}{}_2$. In embodiments, $R^{16}$ is substituted or unsubstituted alkyl. In embodiments, $R^{16}$ is substituted or unsubstituted heteroalkyl. In embodiments, $R^{16}$ is substituted or unsubstituted cycloalkyl. In embodiments, $R^{16}$ is substituted or unsubstituted heterocycloalkyl. In embodiments, $R^{16}$ is substituted or unsubstituted aryl. In embodiments, $R^{16}$ is substituted or unsubstituted heteroaryl.

In embodiments, $R^{16}$ is substituted alkyl. In embodiments, $R^{16}$ is substituted heteroalkyl. In embodiments, $R^{16}$ is substituted cycloalkyl. In embodiments, $R^{16}$ is substituted heterocycloalkyl. In embodiments, $R^{16}$ is substituted aryl. In embodiments, $R^{16}$ is substituted heteroaryl. In embodiments, $R^{16}$ is unsubstituted alkyl. In embodiments, $R^{16}$ is unsubstituted heteroalkyl. In embodiments, $R^{16}$ is unsubstituted cycloalkyl. In embodiments, $R^{16}$ is unsubstituted heterocycloalkyl. In embodiments, $R^{16}$ is unsubstituted aryl. In embodiments, $R^{16}$ is unsubstituted heteroaryl. In embodiments, $R^{16}$ is unsubstituted methyl. In embodiments, $R^{16}$ is unsubstituted ethyl. In embodiments, $R^{16}$ is unsubstituted propyl. In embodiments, $R^{16}$ is unsubstituted isopropyl. In embodiments, $R^{16}$ is unsubstituted butyl. In embodiments, $R^{16}$ is unsubstituted tert-butyl. In embodiments, $R^{16}$ is —CH$_2$Ph. In embodiments, $R^{16}$ is independently halogen, —CX$^{16}_3$, —CHX$^{16}_2$, —CH$_2$X$^{16}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{16}_3$, —OCHX$^{16}_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl. In embodiments, $R^{16}$ is independently halogen, —CX$^{16}_3$, —CHX$^{16}_2$, —CH$_2$X$^{16}$, —OH, —SH, —COOH, —OCX$^{16}_3$, —OCHX$^{16}_2$, —CH$_3$, —CH$_2$CH$_3$, —OCH$_3$, —OCH$_2$CH$_3$, —SCH$_3$, or —SCH$_2$CH$_3$. In embodiments, $R^{16}$ is independently halogen or —OCH$_3$. In embodiments, $R^{16}$ is substituted or unsubstituted $C_3$-$C_6$ alkyl. In embodiments, $R^{16}$ is substituted or unsubstituted 2 to 6 membered heteroalkyl. In embodiments, $R^{16}$ is substituted or unsubstituted $C_3$-$C_8$ cycloalkyl. In embodiments, $R^{16}$ is substituted or unsubstituted 3 to 8 membered heterocycloalkyl. In embodiments, $R^{16}$ is substituted or unsubstituted $C_6$ aryl. In embodiments, $R^{16}$ is substituted or unsubstituted 5 to 6 membered heteroaryl. In embodiments, $R^{16}$ is independently halogen. In embodiments, $R^{16}$ is independently —CX$^{16}_3$. In embodiments, $R^{16}$ is independently —CHX$^{16}_2$. In embodiments, $R^{16}$ is independently —CH$_2$X$^{16}$. In embodiments, $R^{16}$ is independently —OH. In embodiments, $R^{16}$ is independently —SH. In embodiments, $R^{16}$ is independently —COOH. In embodiments, $R^{16}$ is independently —OCX$^{16}_3$. In embodiments, $R^{16}$ is independently —OCHX$^{16}_2$. In embodiments, $R^{16}$ is independently —CH$_3$. In embodiments, $R^{16}$ is independently —CH$_2$CH$_3$. In embodiments, $R^{16}$ is independently —OCH$_3$. In embodiments, $R^{16}$ is independently —OCH$_2$CH$_3$. In embodiments, $R^{16}$ is independently —SCH$_3$. In embodiments, $R^{16}$ is independently —SCH$_2$CH$_3$. In embodiments, $R^{16}$ is independently —Cl or —OCH$_3$. In embodiments, $R^{16}$ is independently halogen, —CX$^{16}_3$, —CN, —OH, —NH$_2$, —COOH, —CONH$_2$, —NO$_2$, —SH, —OCX$^{16}_3$, —OCHX$^{16}_2$, —CHX$^{16}_2$, —CH$_2$X$^{16}$, substituted or unsubstituted $C_1$-$C_8$ alkyl, or substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^{16}$ is independently halogen, —CX$^{16}_3$, —CN, unsubstituted $C_1$-$C_4$ alkyl, or unsubstituted 2 to 4 membered heteroalkyl. In embodiments, $R^{16}$ is independently unsubstituted methyl, unsubstituted ethyl, unsubstituted isopropyl, or unsubstituted tert-butyl. In embodiments, $R^{16}$ is independently unsubstituted methyl. In embodiments, $R^{16}$ is independently unsubstituted ethyl. In embodiments, $R^{16}$ is independently unsubstituted propyl. In embodiments, $R^{16}$ is independently unsubstituted n-propyl. In embodiments, $R^{16}$ is independently unsubstituted isopropyl. In embodiments, $R^{16}$ is independently unsubstituted butyl. In embodiments, $R^{16}$ is independently unsubstituted n-butyl. In embodiments, $R^{16}$ is independently unsubstituted isobutyl. In embodiments, $R^{16}$ is independently unsubstituted tert-butyl. In embodiments, $R^{16}$ is independently unsubstituted pentyl. In embodiments, $R^{16}$ is independently unsubstituted hexyl. In embodiments, $R^{16}$ is independently unsubstituted heptyl. In embodiments, $R^{16}$ is independently unsubstituted octyl. In embodiments, $R^{16}$ is independently —F. In embodiments, $R^{16}$ is independently —Cl. In embodiments, $R^{16}$ is independently —Br. In embodiments, $R^{16}$ is independently —I. In embodiments, $R^{16}$ is independently unsubstituted methoxy. In embodiments, $R^{16}$ is independently unsubstituted ethoxy. In embodiments, $R^{16}$ is independently —CF$_3$. In embodiments, $R^{16}$ is independently —CCl$_3$. In embodiments, $R^{16}$ is an unsubstituted isopropyl. In embodiments, $R^{16}$ is an unsubstituted phenyl. In embodiments, $R^{16}$ is an unsubstituted pyridyl. In embodiments, $R^{16}$ is independently halogen. In embodiments, $R^{16}$ is independently —CX$^{16}_3$. In embodiments, $R^{16}$ is independently —CHX$^{16}_2$. In embodiments, $R^{16}$ is independently —CH$_2$X$^{16}$. In embodiments, $R^{16}$ is independently —CN. In embodiments, $R^{16}$ is independently —OH. In embodiments, $R^{16}$ is independently —NH$_2$. In embodiments, $R^{16}$ is independently —COOH. In embodiments, $R^{16}$ is independently —CONH$_2$. In embodiments, $R^{16}$ is independently —NO$_2$. In embodiments, $R^{16}$ is independently —SH. In embodiments, $R^{16}$ is independently —SO$_2$Cl. In embodiments, $R^{16}$ is independently —SO$_3$H. In embodiments, $R^{16}$ is independently —SO$_4$H. In embodiments, $R^{16}$ is independently —SO$_2$NH$_2$. In embodiments, $R^{16}$ is independently —NHNH$_2$. In embodiments, $R^{16}$ is independently —ONH$_2$. In embodiments, $R^{16}$ is independently —NHC(O)NHNH$_2$. In embodiments, $R^{16}$ is independently —NHC(O)NH$_2$. In embodiments, $R^{16}$ is independently —NHSO$_2$H. In embodiments, $R^{16}$ is independently —NHC(O)H. In embodiments, $R^{16}$ is independently —NHC(O)OH. In embodiments, $R^{16}$ is independently —NHOH. In embodiments, $R^{16}$ is independently —OCX$^{16}_3$. In embodiments, $R^{16}$ is independently —OCHX$^{16}_2$. In embodiments, $R^{16}$ is independently substituted or unsubstituted alkyl. In embodiments, $R^{16}$ is independently substituted or unsubstituted heteroalkyl. In embodiments, $R^{16}$ is independently substituted or unsubstituted cycloalkyl. In embodiments, $R^{16}$ is independently substituted or unsubstituted heterocycloalkyl. In embodiments, $R^{16}$ is independently substituted or unsubstituted aryl. In embodiments, $R^{16}$ is independently substituted or unsubstituted heteroaryl. In embodiments, $R^{16}$ is independently substituted alkyl. In embodiments, $R^{16}$ is independently substituted heteroalkyl. In embodiments, $R^{16}$ is independently substituted cycloalkyl. In embodiments, $R^{16}$ is independently substituted heterocycloalkyl. In embodiments, $R^{16}$ is independently substituted aryl. In embodiments, $R^{16}$ is independently substituted heteroaryl. In embodiments, $R^{16}$ is independently unsubstituted alkyl. In embodiments, $R^{16}$ is independently unsubstituted heteroalkyl. In embodiments, $R^{16}$ is independently unsubstituted cycloalkyl. In embodiments, $R^{16}$ is independently unsubstituted heterocycloalkyl. In embodiments, $R^{16}$ is independently unsubstituted aryl. In embodiments, $R^{16}$ is independently unsubstituted heteroaryl. In embodiments, $R^{16}$ is independently substituted or unsubstituted $C_1$-$C_8$ alkyl. In embodiments, $R^{16}$ is independently substituted or unsubstituted 2 to 8 membered heteroalkyl. In embodiments, $R^{16}$ is independently substituted or unsubstituted $C_3$-$C_8$ cycloalkyl. In embodiments, $R^{16}$ is independently substituted or unsubstituted 3 to 8 membered heterocycloalkyl. In embodiments, $R^{16}$ is independently substituted or unsubstituted $C_6$-$C_{10}$ aryl. In embodiments, $R^{16}$ is independently substituted or unsubstituted 5 to 10 membered heteroaryl. In embodiments, $R^{16}$ is independently substituted $C_1$-$C_5$ alkyl. In embodiments, $R^{16}$ is independently substituted 2 to 8 membered heteroalkyl. In embodiments, $R^{16}$ is independently substituted $C_3$-$C_8$ cycloalkyl. In embodiments, $R^{16}$ is independently substituted 3 to 8 membered heterocycloalkyl. In embodiments, $R^{16}$ is independently substituted $C_6$-$C_{10}$ aryl. In embodiments, $R^{16}$ is independently substituted 5 to 10 membered heteroaryl. In embodiments, $R^{16}$ is independently unsubstituted $C_1$-$C_8$ alkyl. In embodiments, $R^{16}$ is independently unsubstituted 2 to 8 membered heteroalkyl. In embodiments, $R^{16}$ is independently unsubstituted $C_3$-$C_8$ cycloalkyl. In embodiments, $R^{16}$ is independently unsubstituted 3 to 8 membered heterocycloalkyl. In embodiments, $R^{16}$ is independently unsubstituted $C_6$-$C_{10}$ aryl. In embodiments, $R^{16}$ is independently unsubstituted 5 to 10 membered heteroaryl. In embodiments, $R^{16}$ is independently substituted or unsubstituted $C_1$-$C_4$ alkyl. In embodiments, $R^{16}$ is independently substituted or unsubstituted 2 to 4 membered heteroalkyl. In embodiments, $R^{16}$ is independently substituted or unsubstituted $C_3$-$C_6$ cycloalkyl. In embodiments, $R^{16}$ is independently substituted or unsubstituted 3 to 6 membered heterocycloalkyl. In embodiments, $R^{16}$ is independently substituted or unsubstituted phenyl. In embodiments, $R^{16}$ is independently substituted or unsubstituted 5 to 6 membered heteroaryl. In embodiments, $R^{16}$ is independently substituted $C_1$-$C_4$ alkyl. In embodiments, $R^{16}$ is independently substituted 2 to 4 membered heteroalkyl. In embodiments, $R^{16}$ is independently substituted $C_3$-$C_6$ cycloalkyl. In embodiments, $R^{16}$ is independently substituted 3 to 6 membered heterocycloalkyl. In embodiments, $R^{16}$ is independently substituted phenyl. In embodiments, $R^{16}$ is independently substituted 5 to 6 membered heteroaryl. In embodiments, $R^{16}$ is independently unsubstituted CV $C_4$ alkyl. In embodiments, $R^{16}$ is independently unsubstituted 2 to 4 membered heteroalkyl. In embodiments, $R^{16}$ is independently unsubstituted $C_3$-$C_6$ cycloalkyl. In embodiments, $R^{16}$ is independently unsubstituted 3 to 6 membered heterocycloalkyl. In embodiments, $R^{16}$ is independently unsubstituted phenyl. In embodiments, $R^{16}$ is independently unsubstituted 5 to 6 membered heteroaryl.

In embodiments, $R^{16A}$ is hydrogen. In embodiments, $R^{16A}$ is —$CX_3$. In embodiments, $R^{16A}$ is —CN. In embodiments, $R^{16A}$ is —COOH. In embodiments, $R^{16A}$ is —$CONH_2$. In embodiments, $R^{16A}$ is —$CHX_2$. In embodiments, $R^{16A}$ is —$CH_2X$. In embodiments, $R^{16A}$ is unsubstituted methyl. In embodiments, $R^{16A}$ is unsubstituted ethyl. In embodiments, $R^{16A}$ is unsubstituted propyl. In embodiments, $R^{16A}$ is unsubstituted isopropyl. In embodiments, $R^{16A}$ is unsubstituted butyl. In embodiments, $R^{16A}$ is unsubstituted tert-butyl.

In embodiments, $R^{16B}$ is hydrogen. In embodiments, $R^{16D}$ is —$CX_3$. In embodiments, $R^{16B}$ is —CN. In embodiments, $R^{16B}$ is —COOH. In embodiments, $R^{16B}$ is —$CONH_2$. In embodiments, $R^{16B}$ is —$CHX_2$. In embodiments, $R^{16B}$ is —$CH_2X$. In embodiments, $R^{16B}$ is unsubstituted methyl. In embodiments, $R^{16B}$ is unsubstituted ethyl. In embodiments, $R^{16B}$ is unsubstituted propyl. In embodiments, $R^{16B}$ is unsubstituted isopropyl. In embodiments, $R^{16B}$ is unsubstituted butyl. In embodiments, $R^{16B}$ is unsubstituted tert-butyl.

In embodiments, $R^{16C}$ is hydrogen. In embodiments, $R^{16C}$ is —$CX_3$. In embodiments, $R^{16C}$ is —CN. In embodiments, $R^{16C}$ is —COOH. In embodiments, $R^{16C}$ is —$CONH_2$. In embodiments, $R^{16C}$ is —$CHX_2$. In embodiments, $R^{16C}$ is —$CH_2X$. In embodiments, $R^{16C}$ is unsubstituted methyl. In embodiments, $R^{16C}$ is unsubstituted ethyl. In embodiments, $R^{16C}$ is unsubstituted propyl. In embodiments, $R^{16C}$ is unsubstituted isopropyl. In embodiments, $R^{16C}$ is unsubstituted butyl. In embodiments, $R^{16C}$ is unsubstituted tert-butyl.

In embodiments, $R^{16D}$ is hydrogen. In embodiments, $R^{16D}$ is —$CX_3$. In embodiments, $R^{16D}$ is —CN. In embodiments, $R^{16D}$ is —COOH. In embodiments, $R^{16D}$ is —$CONH_2$. In embodiments, $R^{16D}$ is —$CHX_2$. In embodiments, $R^{16D}$ is —$CH_2X$. In embodiments, $R^{16D}$ is unsubstituted methyl. In embodiments, $R^{16D}$ is unsubstituted ethyl. In embodiments, $R^{16D}$ is unsubstituted propyl. In embodiments, $R^{16D}$ is unsubstituted isopropyl. In embodiments, $R^{16D}$ is unsubstituted butyl. In embodiments, $R^{16D}$ is unsubstituted tert-butyl.

In embodiments, $R^{17}$ is hydrogen. In embodiments, $R^{17}$ is halogen. In embodiments, $R^{17}$ is $CX^{17}_3$. In embodiments, $R^{17}$ is —$CHX^{17}_2$. In embodiments, $R^{17}$ is —$CH_2X^{17}$. In embodiments, $R^{17}$ is —CN. In embodiments, $R^{17}$ is —$SO_{n17}R^{17D}$. In embodiments, $R^{17}$ is —$SO_{v17}NR^{17A}R^{17B}$. In embodiments, $R^{17}$ is —$NHNR^{17A}R^{17B}$. In embodiments, $R^{17}$ is —$ONR^{17A}R^{17B}$. In embodiments, $R^{17}$ is —NHC=(O)$NHNR^{17A}R^{17B}$. In embodiments, $R^{17}$ is —NHC(O)$NR^{17A}R^{17B}$. In embodiments, $R^{17}$ is —$N(O)_{m17}$. In embodiments, $R^{17}$ is —$NR^{17A}R^{17B}$. In embodiments, $R^{17}$ is —C(O)$R^{17C}$. In embodiments, $R^{17}$ is —C(O)—$OR^{17C}$. In embodiments, $R^{17}$ is —C(O)$NR^{17A}R^{17B}$. In embodiments, $R^{17}$ is —$OR^{17D}$. In embodiments, $R^{17}$ is —$NR^{17A}SO_2R^{17D}$. In embodiments, $R^{17}$ is —$NR^{17A}C(O)R^{17C}$. In embodiments, $R^{17}$ is —$NR^{17A}C(O)OR^{17C}$. In embodiments, $R^{17}$ is —$NR^{17A}OR^{17C}$. In embodiments, $R^{17}$ is —$OCX^{17}_3$. In embodiments, $R^{17}$ is —$OCHX^{17}_2$. In embodiments, $R^{17}$ is substituted or unsubstituted alkyl. In embodiments, $R^{17}$ is substituted or unsubstituted heteroalkyl. In embodiments, $R^{17}$ is substituted or unsubstituted cycloalkyl. In embodiments, $R^{17}$ is substituted or unsubstituted heterocycloalkyl. In embodiments, $R^{17}$ is substituted or unsubstituted aryl. In embodiments, $R^{17}$ is substituted or unsubstituted heteroaryl. In embodiments, $R^{17}$ is substituted alkyl. In embodiments, $R^{17}$ is substituted heteroalkyl. In embodiments, $R^{17}$ is substituted cycloalkyl. In embodiments, $R^{17}$ is substituted heterocycloalkyl. In embodiments, $R^{17}$ is substituted aryl. In embodiments, $R^{17}$ is substituted heteroaryl. In embodiments, $R^{17}$ is unsubstituted alkyl. In embodiments, $R^{17}$ is unsubstituted heteroalkyl. In embodiments, $R^{17}$ is unsubstituted cycloalkyl. In embodiments, $R^{17}$ is unsubstituted heterocycloalkyl. In embodiments, $R^{17}$ is unsubstituted aryl. In embodiments, $R^{17}$ is unsubstituted heteroaryl. In embodiments, $R^{17}$ is unsubstituted methyl. In embodiments, $R^{17}$ is unsubstituted ethyl. In embodiments, $R^{17}$ is unsubstituted propyl. In embodiments, $R^{17}$ is unsubstituted isopropyl. In embodiments, $R^{17}$ is unsubstituted butyl. In embodiments, $R^{17}$ is unsubstituted tert-butyl. In embodiments, $R^{17}$ is —$CH_2Ph$.

In embodiments, $R^{17A}$ is hydrogen. In embodiments, $R^{17A}$ is —$CX_3$. In embodiments, $R^{17A}$ is —CN. In embodiments, $R^{17A}$ is —COOH. In embodiments, $R^{17A}$ is —$CONH_2$. In embodiments, $R^{17A}$ is —$CHX_2$. In embodiments, $R^{17A}$ is —$CH_2X$. In embodiments, $R^{17A}$ is unsubstituted methyl. In embodiments, $R^{17A}$ is unsubstituted ethyl. In embodiments, $R^{17A}$ is unsubstituted propyl. In embodiments, $R^{17A}$ is unsubstituted isopropyl. In embodiments, $R^{17A}$ is unsubstituted butyl. In embodiments, $R^{17A}$ is unsubstituted tert-butyl.

In embodiments, $R^{17B}$ is hydrogen. In embodiments, $R^{17B}$ is —$CX_3$. In embodiments, $R^{17B}$ is —CN. In embodiments, $R^{17B}$ is —COOH. In embodiments, $R^{17B}$ is —$CONH_2$. In embodiments, $R^{17B}$ is —$CHX_2$. In embodiments, $R^{17B}$ is —$CH_2X$. In embodiments, $R^{17B}$ is unsubstituted methyl. In embodiments, $R^{17B}$ is unsubstituted ethyl. In embodiments, $R^{17B}$ is unsubstituted propyl. In embodiments, $R^{17B}$ is unsubstituted isopropyl. In embodiments, $R^{17B}$ is unsubstituted butyl. In embodiments, $R^{17B}$ is unsubstituted tert-butyl.

In embodiments, $R^{17C}$ is hydrogen. In embodiments, $R^{17C}$ is —$CX_3$. In embodiments, $R^{17C}$ is —CN. In embodiments, $R^{17C}$ is —COOH. In embodiments, $R^{17C}$ is —$CONH_2$. In embodiments, $R^{17C}$ is —$CHX_2$. In embodiments, $R^{17C}$ is —$CH_2X$. In embodiments, $R^{17C}$ is unsubstituted methyl. In embodiments, $R^{17C}$ is unsubstituted ethyl. In embodiments, $R^{17C}$ is unsubstituted propyl. In embodiments, $R^{17C}$ is unsubstituted isopropyl. In embodiments, $R^{17C}$ is unsubstituted butyl. In embodiments, $R^{17C}$ is unsubstituted tert-butyl.

In embodiments, $R^{17D}$ is hydrogen. In embodiments, $R^{17D}$ is —$CX_3$. In embodiments, $R^{17D}$ is —CN. In embodiments, $R^{17D}$ is —COOH. In embodiments, $R^{17D}$ is —$CONH_2$. In embodiments, $R^{17D}$ is —$CHX_2$. In embodiments, $R^{17D}$ is —$CH_2X$. In embodiments, $R^{17D}$ is unsubstituted methyl. In embodiments, $R^{17D}$ is unsubstituted ethyl. In embodiments, $R^{17D}$ is unsubstituted propyl. In embodiments, $R^{17D}$ is unsubstituted isopropyl. In embodiments, $R^{17D}$ is unsubstituted butyl. In embodiments, $R^{17D}$ is unsubstituted tert-butyl.

In embodiments, $R^{18}$ is hydrogen. In embodiments, $R^{18}$ is halogen. In embodiments, $R^{18}$ is $CX^{18}_3$. In embodiments, $R^{18}$ is —$CHX^{18}_2$. In embodiments, $R^{18}$ is —$CH_2X^{18}$. In embodiments, $R^{18}$ is —CN. In embodiments, $R^{18}$ is —$SO_{n18}R^{18D}$. In embodiments, $R^{18}$ is —$SO_{v18}NR^{18A}R^{18B}$. In embodiments, $R^{18}$ is —$NHNR^{18A}R^{18B}$. In embodiments, $R^{18}$ is —$ONR^{18A}R^{18B}$. In embodiments, $R^{18}$ is —NHC=(O)$NHNR^{18A}R^{18B}$. In embodiments, $R^{18}$ is —NHC(O)$NR^{18A}R^{18B}$. In embodiments, $R^{18}$ is —$N(O)_{m18}$. In embodiments, $R^{18}$ is —$NR^{18A}R^{18B}$. In embodiments, $R^{18}$ is —C(O)$R^{18C}$. In embodiments, $R^{18}$ is —C(O)—$OR^{18C}$. In embodiments, $R^{18}$ is —C(O)$NR^{18A}R^{18B}$. In embodiments, $R^{18}$ is —$OR^{18D}$. In embodiments, $R^{18}$ is —$NR^{18A}SO_2R^{18D}$. In embodiments, $R^{18}$ is —$NR^{18A}C(O)R^{18C}$. In embodiments, $R^{18}$ is —$NR^{18A}C(O)OR^{18C}$. In embodiments, $R^{18}$ is —$NR^{18A}OR^{18C}$. In embodiments, $R^{18}$ is —$OCX^{18}_3$. In embodiments, $R^{18}$ is —$OCHX^{18}_2$. In embodiments, $R^{18}$ is substituted or unsubstituted alkyl. In embodiments, $R^{18}$ is substituted or unsubstituted heteroalkyl. In embodiments, $R^{18}$ is substituted or unsubstituted cycloalkyl. In embodiments, $R^{18}$ is substituted or unsubstituted heterocycloalkyl. In embodiments, $R^{18}$ is substituted or unsubstituted aryl. In embodiments, $R^{18}$ is substituted or unsubstituted heteroaryl. In embodiments, $R^{18}$ is substituted alkyl. In embodiments, $R^{18}$ is substituted heteroalkyl. In embodiments, $R^{18}$ is substituted cycloalkyl. In embodiments, $R^{18}$ is substituted heterocycloalkyl. In embodiments, $R^{18}$ is substituted aryl. In embodiments, $R^{18}$ is substituted heteroaryl. In embodiments, $R^{18}$ is unsubstituted alkyl. In embodiments, $R^{18}$ is unsubstituted heteroalkyl. In embodiments, $R^{18}$ is unsubstituted cycloalkyl. In embodiments, $R^{18}$ is unsubstituted heterocycloalkyl. In embodiments, $R^{18}$ is unsubstituted aryl. In embodiments, $R^{18}$ is unsubstituted heteroaryl. In embodiments, $R^{18}$ is unsubstituted methyl. In embodiments, $R^{18}$ is unsubstituted ethyl. In embodiments, $R^{18}$ is unsubstituted propyl. In embodiments, $R^{18}$ is unsubstituted isopropyl. In embodiments, $R^{18}$ is unsubstituted butyl. In embodiments, $R^{18}$ is unsubstituted tert-butyl. In embodiments, $R^{18}$ is —$CH_2Ph$.

In embodiments, $R^{18A}$ is hydrogen. In embodiments, $R^{18A}$ is —$CX_3$. In embodiments, $R^{18A}$ is —CN. In embodiments, $R^{18A}$ is —COOH. In embodiments, $R^{18A}$ is —$CONH_2$. In embodiments, $R^{18A}$ is —$CHX_2$. In embodiments, $R^{18A}$ is —$CH_2X$. In embodiments, $R^{18A}$ is unsubstituted methyl. In embodiments, $R^{18A}$ is unsubstituted ethyl. In embodiments, $R^{18A}$ is unsubstituted propyl. In embodiments, $R^{18A}$ is unsubstituted isopropyl. In embodiments, $R^{18A}$ is unsubstituted butyl. In embodiments, $R^{18A}$ is unsubstituted tert-butyl.

In embodiments, $R^{18B}$ is hydrogen. In embodiments, $R^{18B}$ is —$CX_3$. In embodiments, $R^{18B}$ is —CN. In embodiments, $R^{18B}$ is —COOH. In embodiments, $R^{18B}$ is —$CONH_2$. In embodiments, $R^{18B}$ is —$CHX_2$. In embodiments, $R^{18B}$ is —$CH_2X$. In embodiments, $R^{18B}$ is unsubstituted methyl. In embodiments, $R^{18B}$ is unsubstituted ethyl. In embodiments, $R^{18B}$ is unsubstituted propyl. In embodiments, $R^{18B}$ is unsubstituted isopropyl. In embodiments, $R^{18B}$ is unsubstituted butyl. In embodiments, $R^{18B}$ is unsubstituted tert-butyl.

In embodiments, $R^{18C}$ is hydrogen. In embodiments, $R^{18C}$ is —$CX_3$. In embodiments, $R^{18C}$ is —CN. In embodiments, $R^{18C}$ is —COOH. In embodiments, $R^{18C}$ is —$CONH_2$. In embodiments, $R^{18C}$ is —$CHX_2$. In embodiments, $R^{18C}$ is —$CH_2X$. In embodiments, $R^{18C}$ is unsubstituted methyl. In embodiments, $R^{18C}$ is unsubstituted ethyl. In embodiments, $R^{18C}$ is unsubstituted propyl. In embodiments, $R^{18C}$ is unsubstituted isopropyl. In embodiments, $R^{18C}$ is unsubstituted butyl. In embodiments, $R^{18C}$ is unsubstituted tert-butyl.

In embodiments, $R^{18D}$ is hydrogen. In embodiments, $R^{18D}$ is —$CX_3$. In embodiments, $R^{18D}$ is —CN. In embodiments, $R^{18D}$ is —COOH. In embodiments, $R^{18D}$ is —$CONH_2$. In embodiments, $R^{18D}$ is —$CHX_2$. In embodiments, $R^{18D}$ is —$CH_2X$. In embodiments, $R^{18D}$ is unsubstituted methyl. In embodiments, $R^{18D}$ is unsubstituted ethyl. In embodiments, $R^{18D}$ is unsubstituted propyl. In embodiments, $R^{18D}$ is unsubstituted isopropyl. In embodiments, $R^{18D}$ is unsubstituted butyl. In embodiments, $R^{18D}$ is unsubstituted tert-butyl.

In embodiments, $R^{19}$ is hydrogen. In embodiments, $R^{19}$ is halogen. In embodiments, $R^{19}$ is $CX^{19}_3$. In embodiments, $R^{19}$ is —$CHX^{19}_2$. In embodiments, $R^{19}$ is —$CH_2X^{19}$. In embodiments, $R^{19}$ is —CN. In embodiments, $R^{19}$ is —$SO_{n19}R^{19D}$. In embodiments, $R^{19}$ is —$SO_{v19}NR^{19A}R^{19B}$. In embodiments, $R^{19}$ is —$NHNR^{19A}R^{19B}$. In embodiments, $R^{19}$ is —$ONR^{19A}R^{19B}$. In embodiments, $R^{19}$ is —NHC=(O)$NHNR^{19A}R^{19B}$. In embodiments, $R^{19}$ is —NHC(O)$NR^{19A}R^{19B}$. In embodiments, $R^{19}$ is —$N(O)_{m19}$. In embodiments, $R^{19}$ is —$NR^{19A}R^{19B}$. In embodiments, $R^{19}$ is —C(O)$R^{19C}$. In embodiments, $R^{19}$ is —C(O)—$OR^{19C}$. In embodiments, $R^{19}$ is —C(O)$NR^{19A}R^{19B}$. In embodiments, $R^{19}$ is —$OR^{19D}$. In embodiments, $R^{19}$ is —$NR^{19A}SO_2R^{19D}$. In embodiments, $R^{19}$ is —$NR^{19A}C(O)R^{19C}$. In embodiments, $R^{19}$ is —$NR^{19A}C(O)OR^{19C}$. In embodiments, $R^{19}$ is —$NR^{19A}OR^{19C}$. In embodiments, $R^{19}$ is —$OCX^{19}_3$. In embodiments, $R^{19}$ is —$OCHX^{19}_2$. In embodiments, $R^{19}$ is substituted or unsubstituted alkyl. In embodiments, $R^{19}$ is substituted or unsubstituted heteroalkyl. In embodiments, $R^{19}$ is substituted or unsubstituted cycloalkyl. In embodiments, $R^{19}$ is substituted or unsubstituted heterocycloalkyl. In embodiments, $R^{19}$ is substituted or unsubstituted aryl. In embodiments, $R^{19}$ is substituted or unsubstituted heteroaryl. In embodiments, $R^{19}$ is substituted alkyl. In embodiments, $R^{19}$ is substituted heteroalkyl. In embodiments, $R^{19}$ is substituted cycloalkyl. In embodiments, $R^{19}$ is substituted heterocycloalkyl. In embodiments, $R^{19}$ is substituted aryl. In embodiments, $R^{19}$ is substituted heteroaryl. In embodiments, $R^{19}$ is unsubstituted alkyl. In embodiments, $R^{19}$ is unsubstituted heteroalkyl. In embodiments, $R^{19}$ is unsubstituted cycloalkyl. In embodiments, $R^{19}$ is unsubstituted heterocycloalkyl. In embodiments, $R^{19}$ is unsubstituted aryl. In embodiments, $R^{19}$ is unsubstituted heteroaryl. In embodiments, $R^{19}$ is unsubstituted methyl. In embodiments, $R^{19}$ is unsubstituted ethyl. In embodiments, $R^{19}$ is unsubstituted propyl. In embodiments, $R^{19}$ is unsubstituted isopropyl. In embodiments, $R^{19}$ is unsubstituted butyl. In embodiments, $R^{19}$ is unsubstituted tert-butyl. In embodiments, $R^{19}$ is —$CH_2Ph$.

In embodiments, $R^{19A}$ is hydrogen. In embodiments, $R^{19A}$ is —$CX_3$. In embodiments, $R^{19A}$ is —CN. In embodiments, $R^{19A}$ is —COOH. In embodiments, $R^{19A}$ is —$CONH_2$. In embodiments, $R^{19A}$ is —$CHX_2$. In embodiments, $R^{19A}$ is —$CH_2X$. In embodiments, $R^{19A}$ is unsubstituted methyl. In embodiments, $R^{19A}$ is unsubstituted ethyl. In embodiments, $R^{19A}$ is unsubstituted propyl. In embodiments, $R^{19A}$ is unsubstituted isopropyl. In embodiments, $R^{19A}$ is unsubstituted butyl. In embodiments, $R^{19A}$ is unsubstituted tert-butyl.

In embodiments, $R^{19B}$ is hydrogen. In embodiments, $R^{19B}$ is —$CX_3$. In embodiments, $R^{19B}$ is —CN. In embodiments, $R^{19B}$ is —COOH. In embodiments, $R^{19B}$ is —$CONH_2$. In embodiments, $R^{19B}$ is —$CHX_2$. In embodiments, $R^{19B}$ is —$CH_2X$. In embodiments, $R^{19B}$ is unsubstituted methyl. In embodiments, $R^{19B}$ is unsubstituted ethyl. In embodiments, $R^{19B}$ is unsubstituted propyl. In embodiments, $R^{19B}$ is unsubstituted isopropyl. In embodiments, $R^{19B}$ is unsubstituted butyl. In embodiments, $R^{19B}$ is unsubstituted tert-butyl.

In embodiments, $R^{19C}$ is hydrogen. In embodiments, $R^{19C}$ is —$CX_3$. In embodiments, $R^{19C}$ is —CN. In embodiments, $R^{19C}$ is —COOH. In embodiments, $R^{19C}$ is —$CONH_2$. In embodiments, $R^{19C}$ is —$CHX_2$. In embodiments, $R^{19C}$ is —$CH_2X$. In embodiments, $R^{19C}$ is unsubstituted methyl. In embodiments, $R^{19C}$ is unsubstituted ethyl. In embodiments, $R^{19C}$ is unsubstituted propyl. In embodiments, $R^{19C}$ is unsubstituted isopropyl. In embodiments, $R^{19C}$ is unsubstituted butyl. In embodiments, $R^{19C}$ is unsubstituted tert-butyl.

In embodiments, $R^{19D}$ is hydrogen. In embodiments, $R^{19D}$ is —$CX_3$. In embodiments, $R^{19D}$ is —CN. In embodiments, $R^{19D}$ is —COOH. In embodiments, $R^{19D}$ is —$CONH_2$. In embodiments, $R^{19D}$ is —$CHX_2$. In embodiments, $R^{19D}$ is —$CH_2X$. In embodiments, $R^{19D}$ is unsubstituted methyl. In embodiments, $R^{19D}$ is unsubstituted ethyl. In embodiments, $R^{19D}$ is unsubstituted propyl. In embodiments, $R^{19D}$ is unsubstituted isopropyl. In embodiments, $R^{19D}$ is unsubstituted butyl. In embodiments, $R^{19D}$ is unsubstituted tert-butyl.

In embodiments, E is

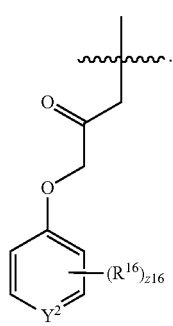

In embodiments, E is

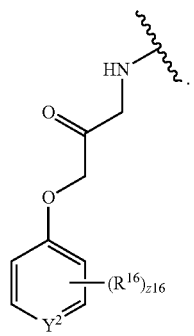

In embodiments, E is

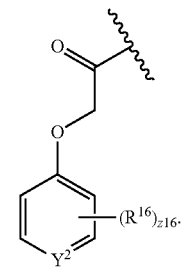

In embodiments, E is

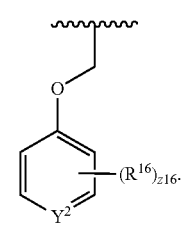

In embodiments, E is

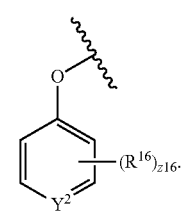

In embodiments, -$L^2$-$L^1$-$L^4$

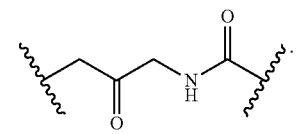 [SMILES: *CC(=O)CNC(*)=O]

In embodiments, -L²-L¹-L⁴- is

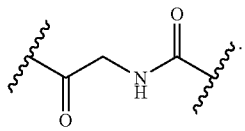 [SMILES: *C(=O)CNC(*)=O]

In embodiments, -L²-L¹-L⁴- is —CH₂NHC(O)—.

In embodiments, $R^{16}$ is independently halogen, $CX^{16}_3$, —CHX$^{16}_2$, —CH₂X$^{16}$, —CN, —OH, —NH₂, —COOH, —CONH₂, —NO₂, —SH, —SO₂Cl, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^{16}$ is independently halogen. In embodiments, $R^{16}$ is independently —F.

$Y^2$ is N or CH. In embodiments, $Y^2$ is CH. In embodiments, $Y^2$ is N.

The symbol z16 is an integer from 0 to 4. Each $X^{16}$ is independently —F, —Cl, —Br, or —I.

In embodiments, z16 is 4. In embodiments, z16 is 2. In embodiments, z16 is 1. In embodiments, z16 is 0. In embodiments, z16 is 3.

In embodiments, E is

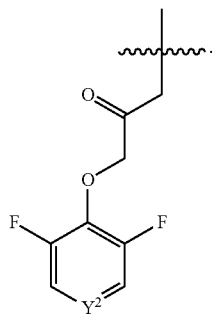

In embodiments, E is

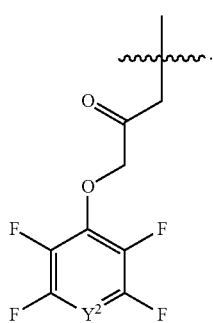

In embodiments, E is

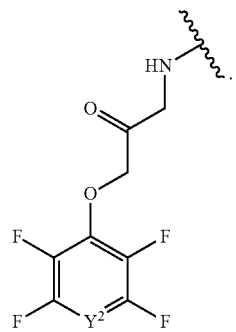

In embodiments, E is

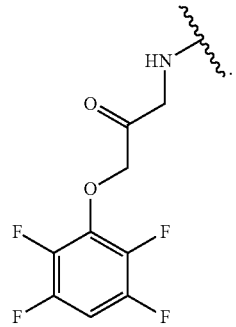 [SMILES: *NCC(=O)COc1c(F)c(F)cc(F)c1F]

In embodiments, E comprises a substituted or unsubstituted vinyl sulfone moiety, substituted or unsubstituted vinyl sulfonamide moiety, substituted or unsubstituted fluoro(C₁-C₄)alkylketone moiety, substituted or unsubstituted chloro (C₁-C₄)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety,

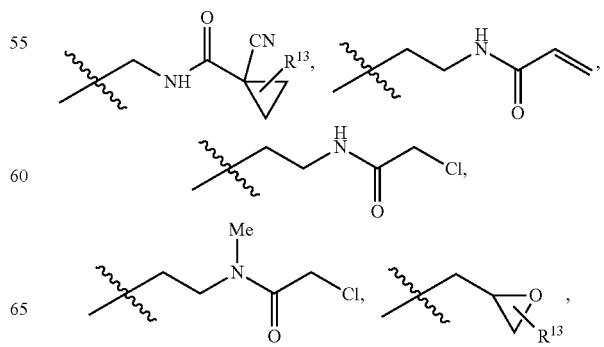

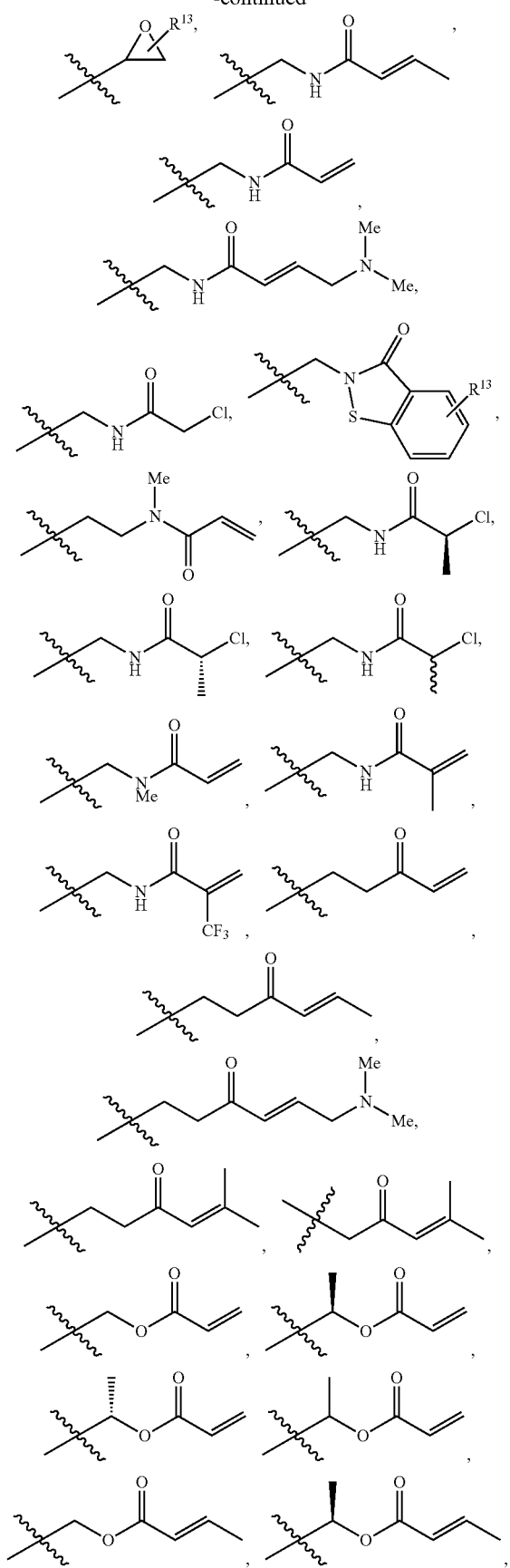
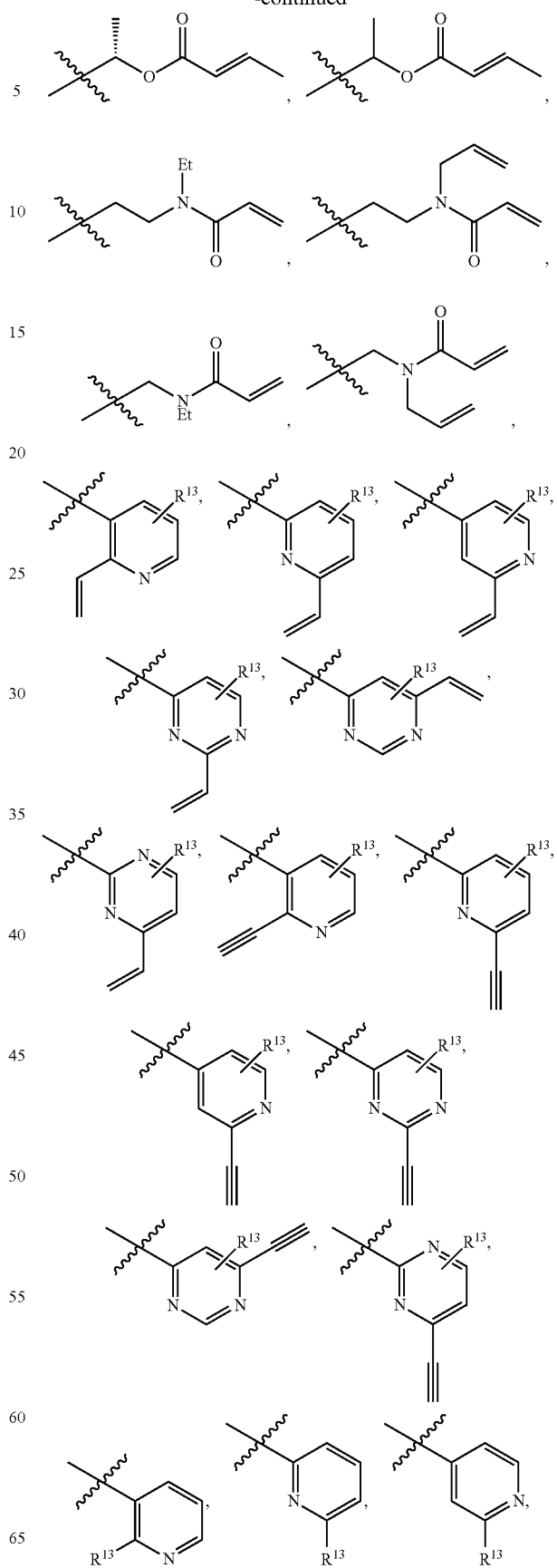

71
-continued
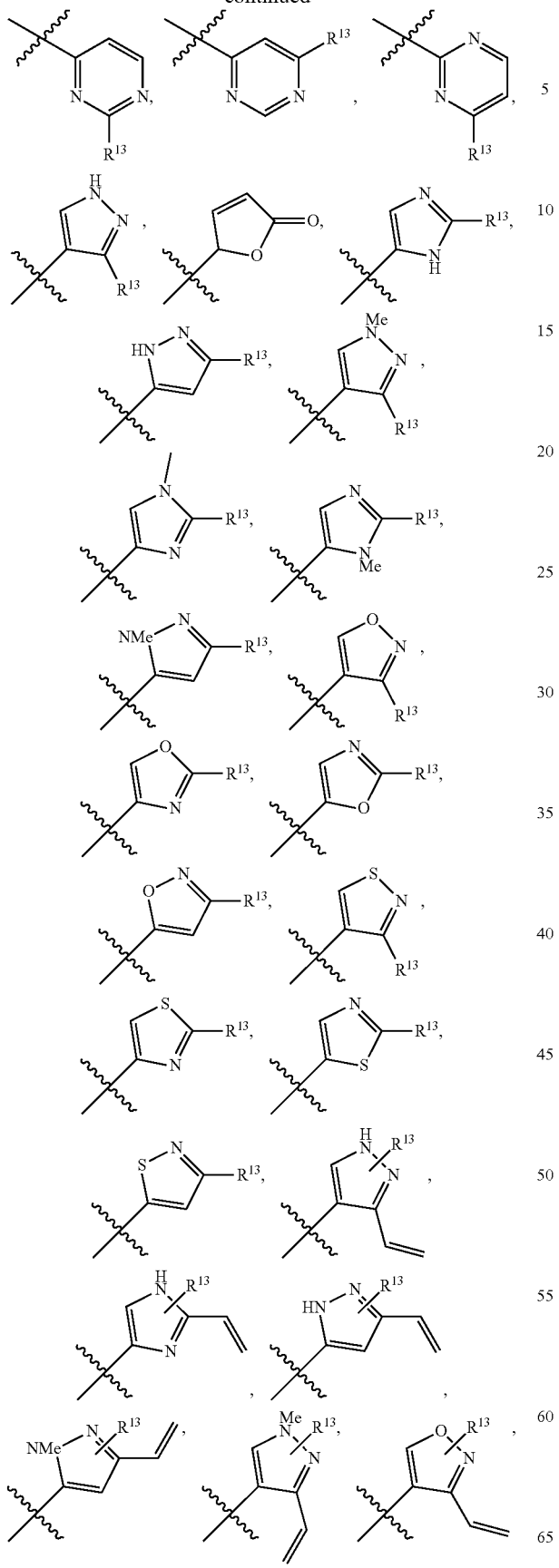
72
-continued
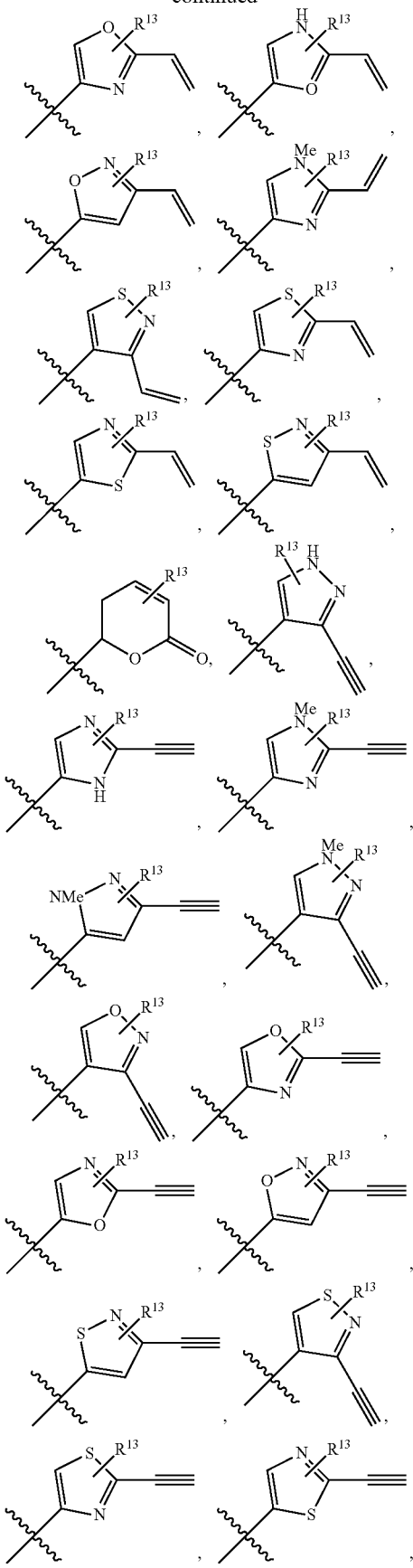

-continued
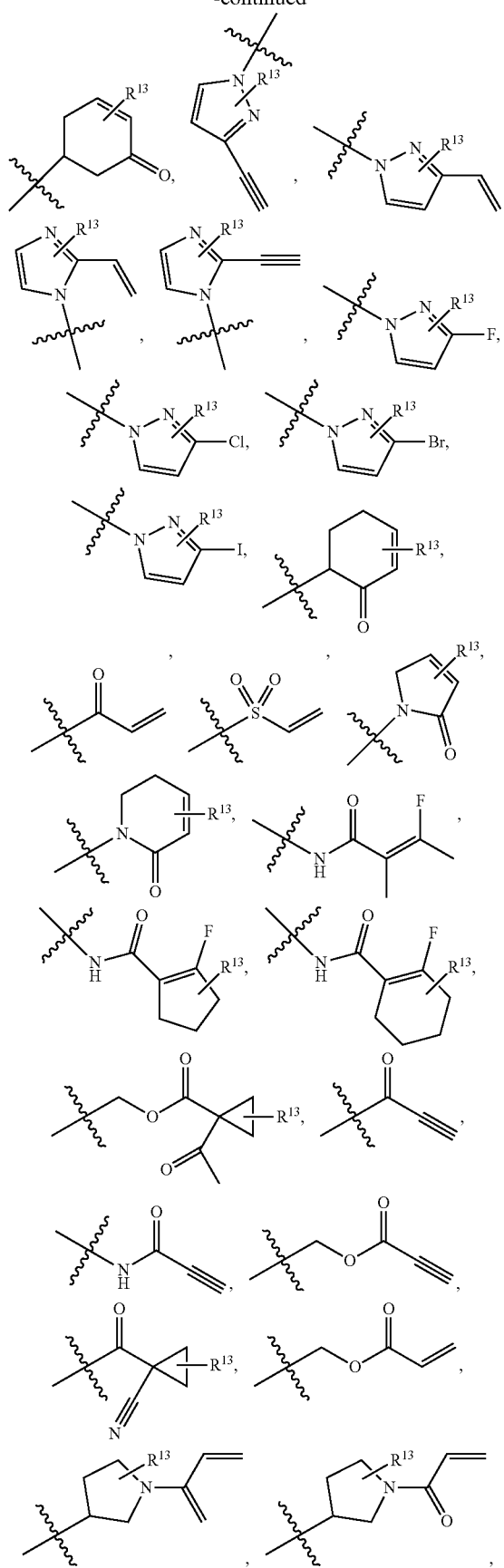
-continued
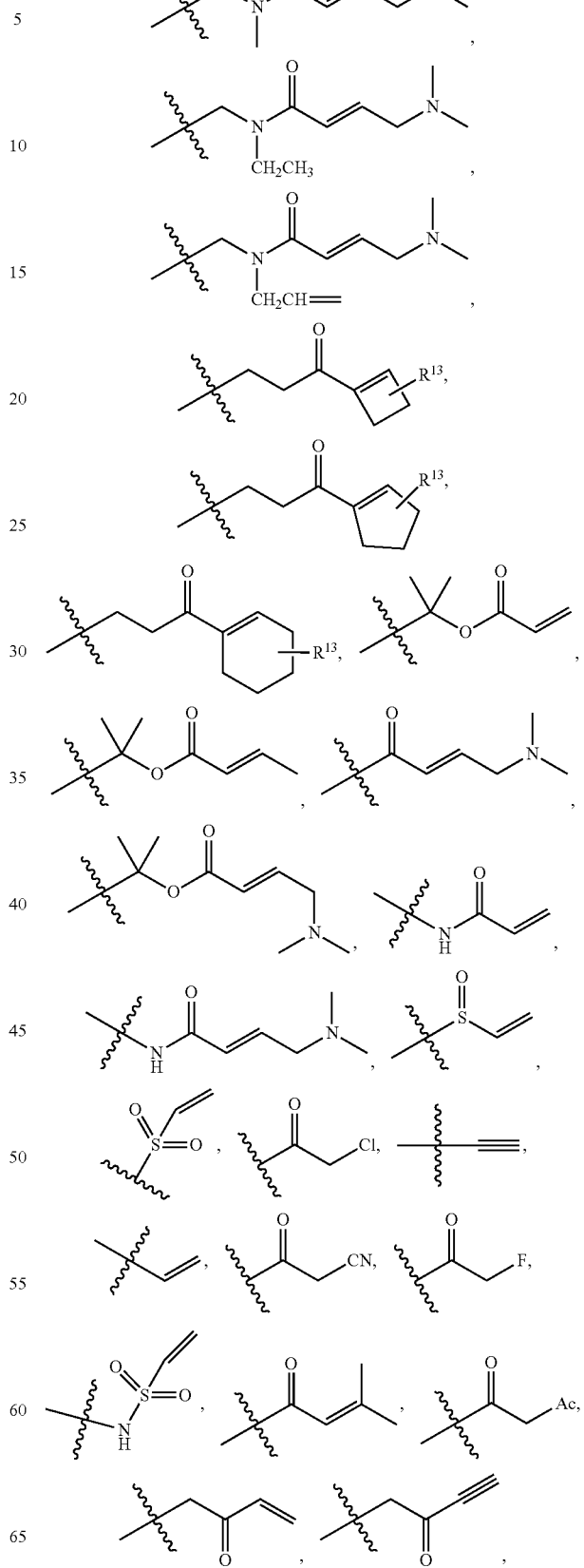

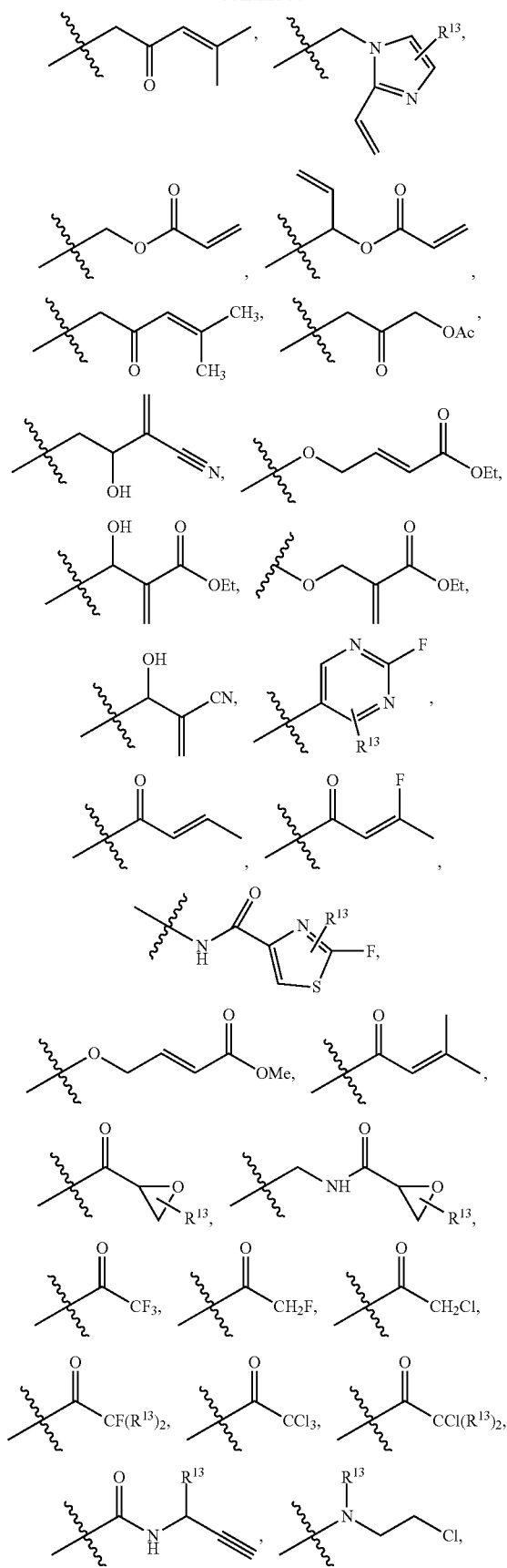
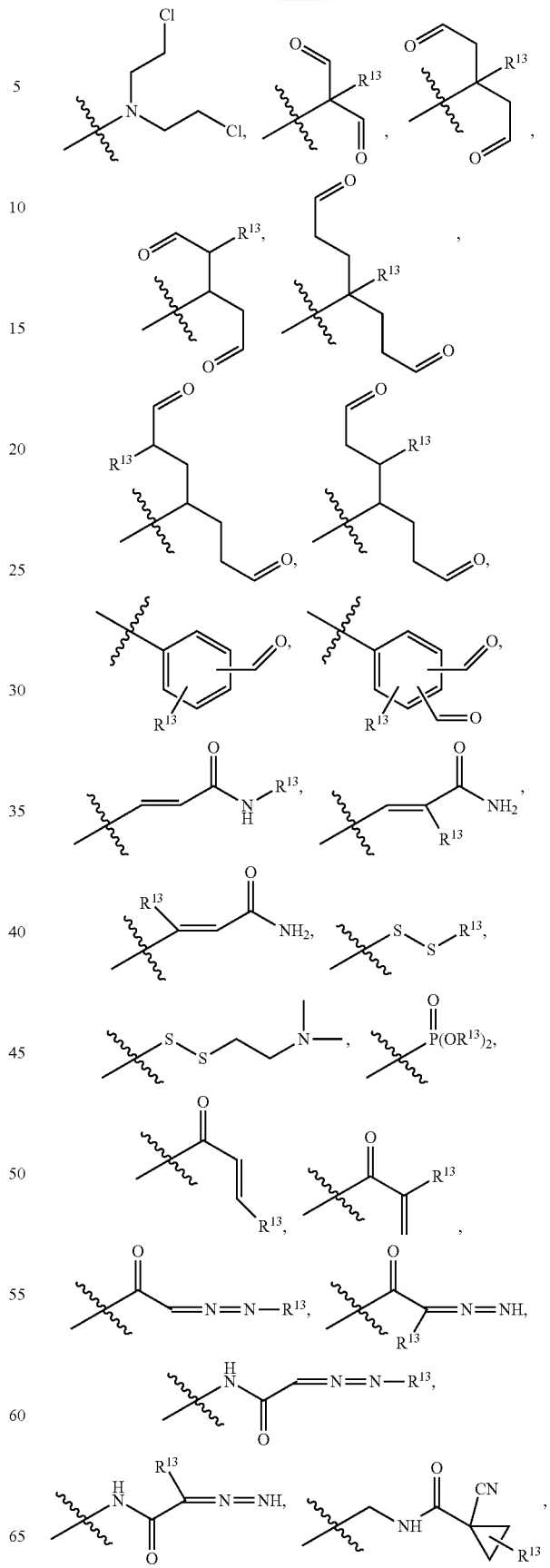

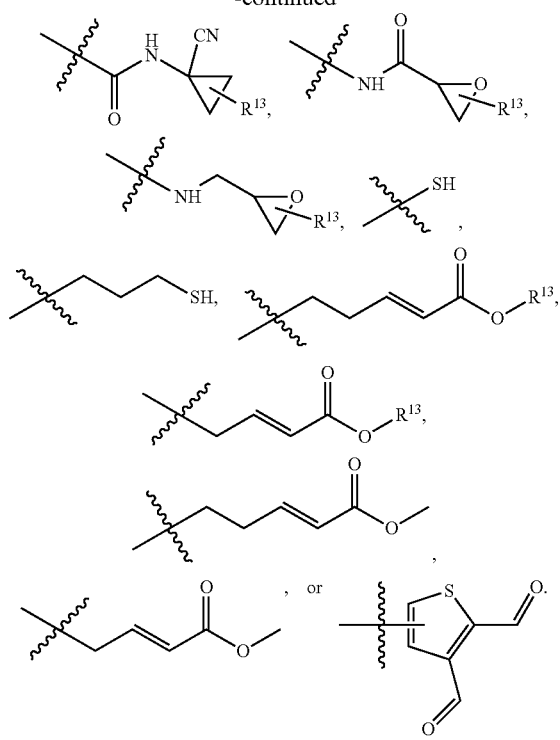

In embodiments, E is a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety,

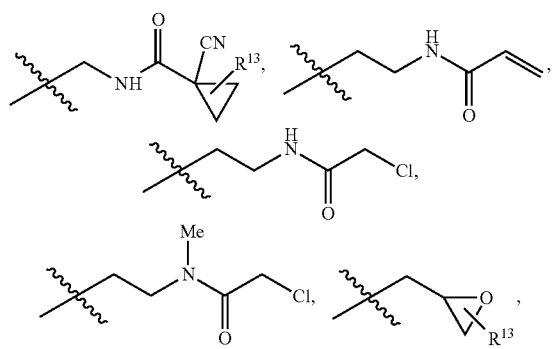

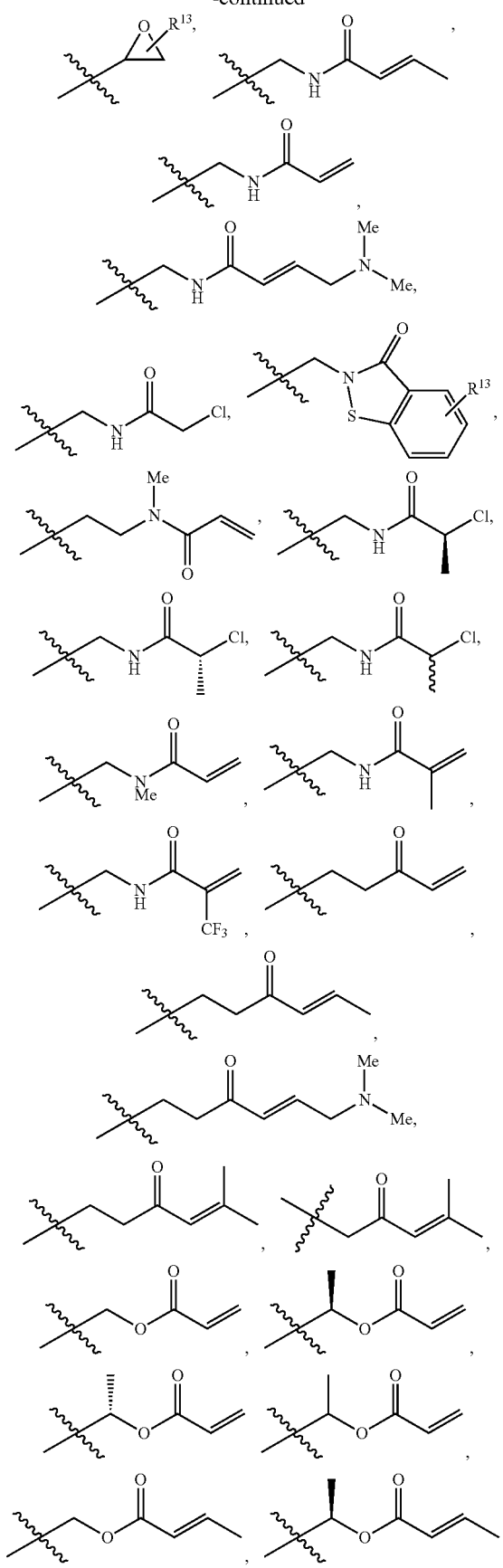

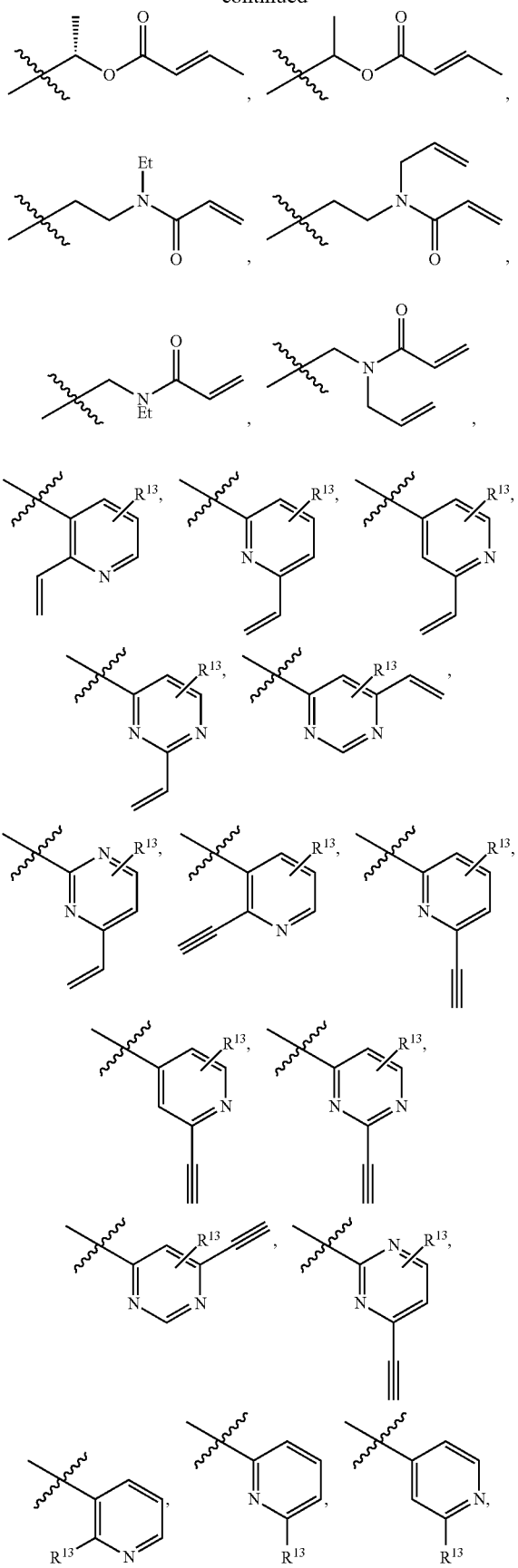
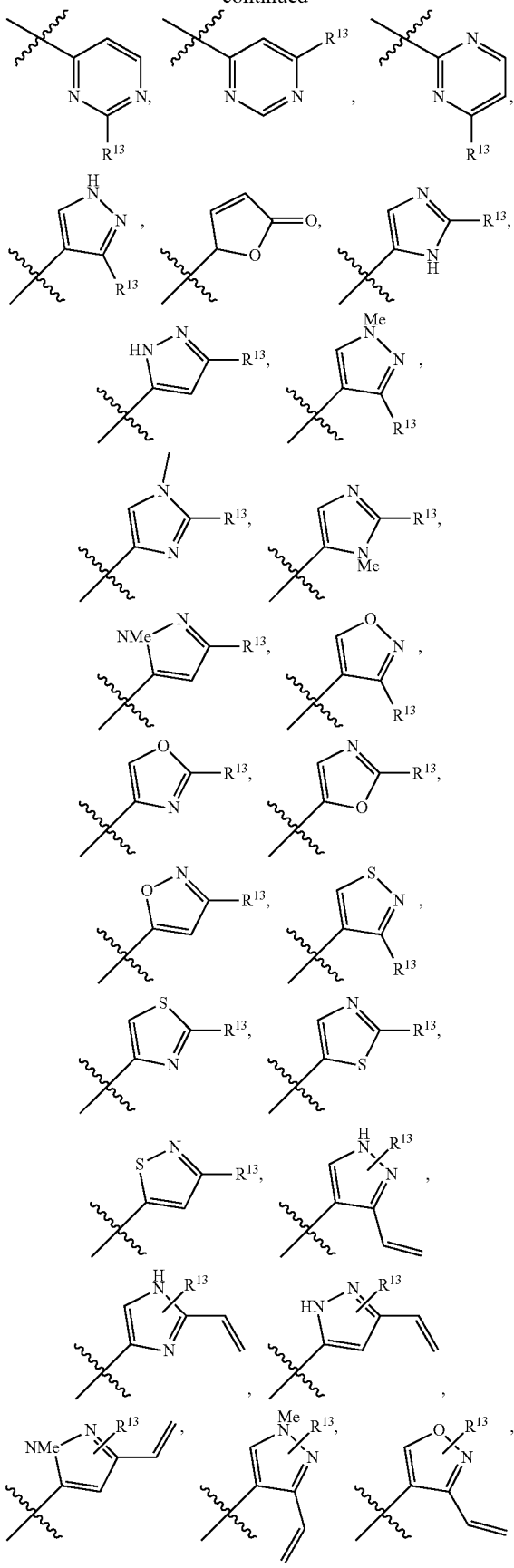

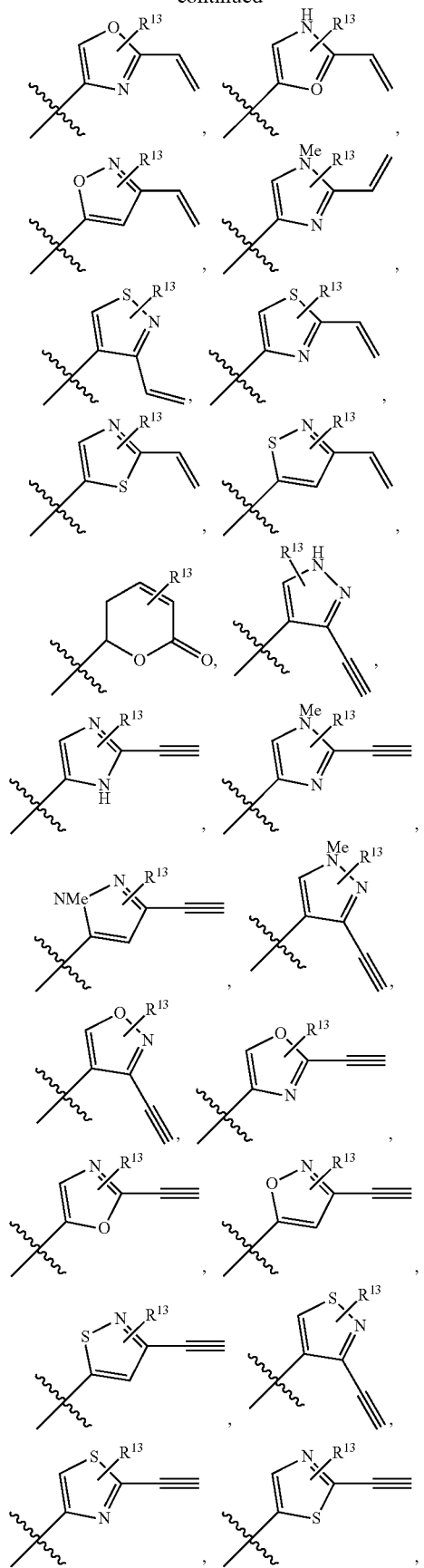
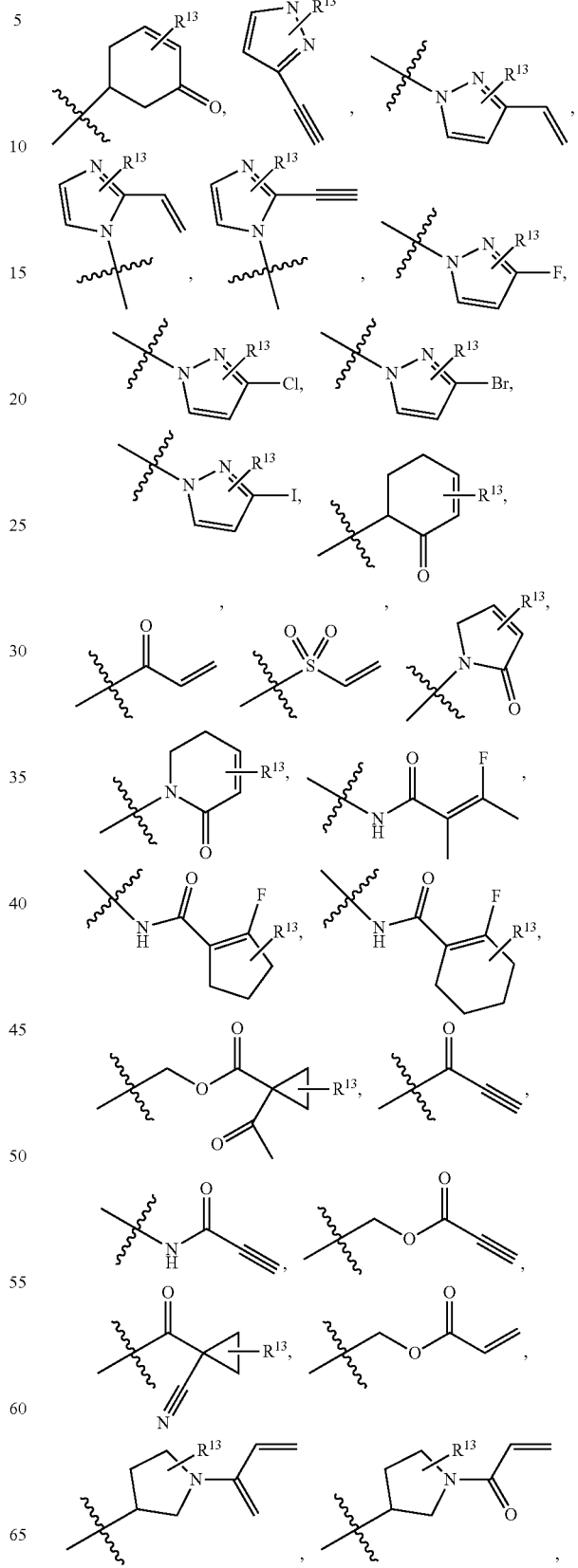

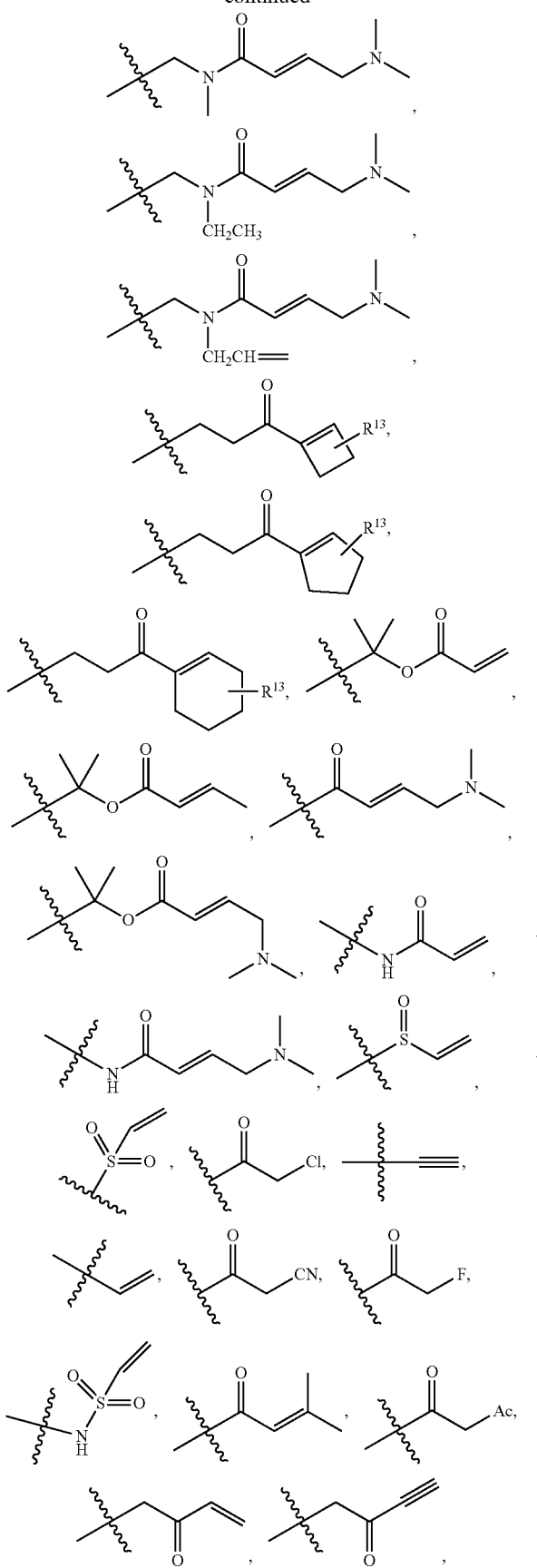
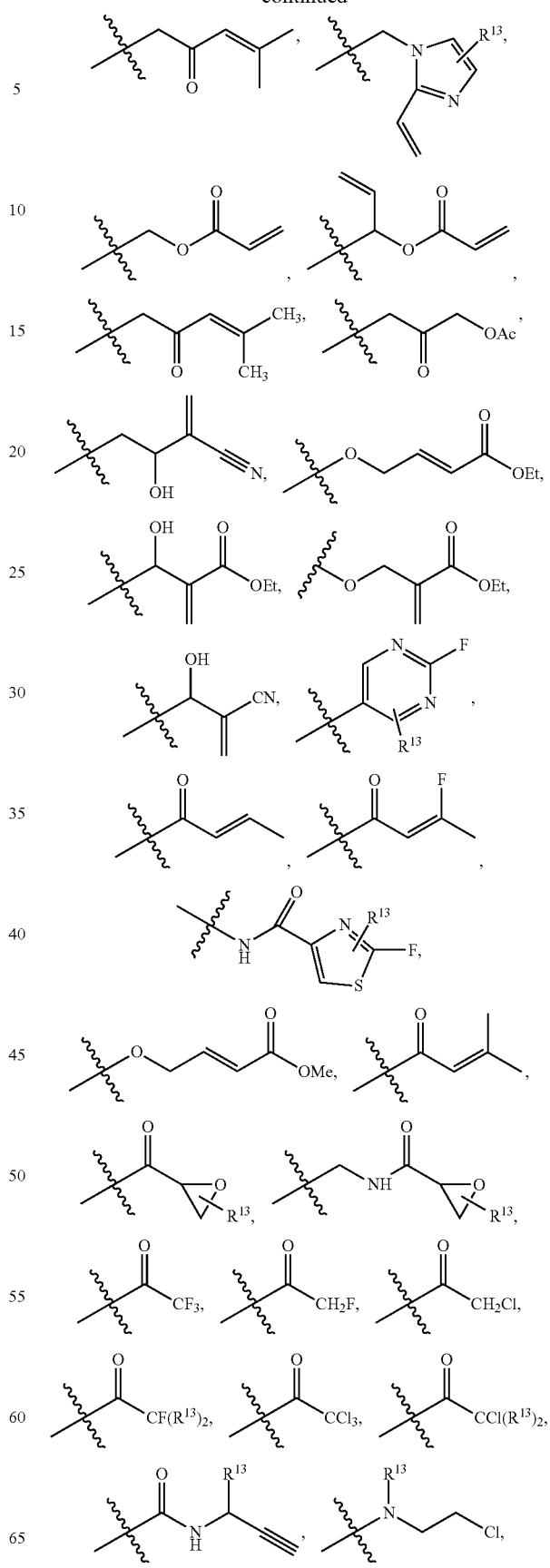

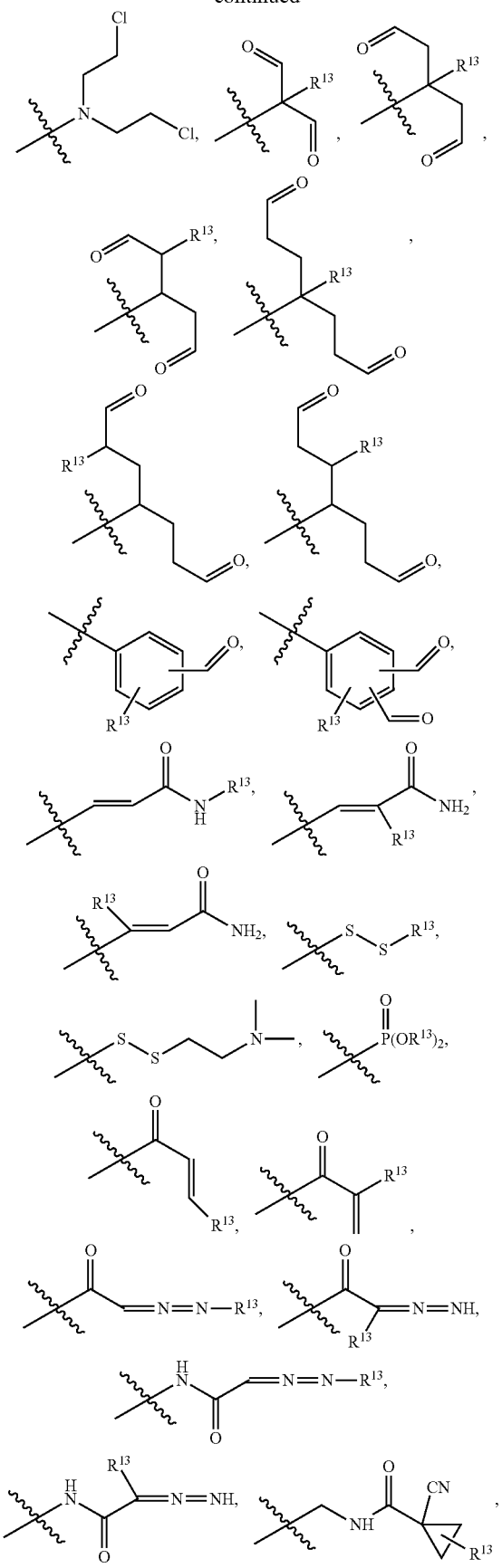
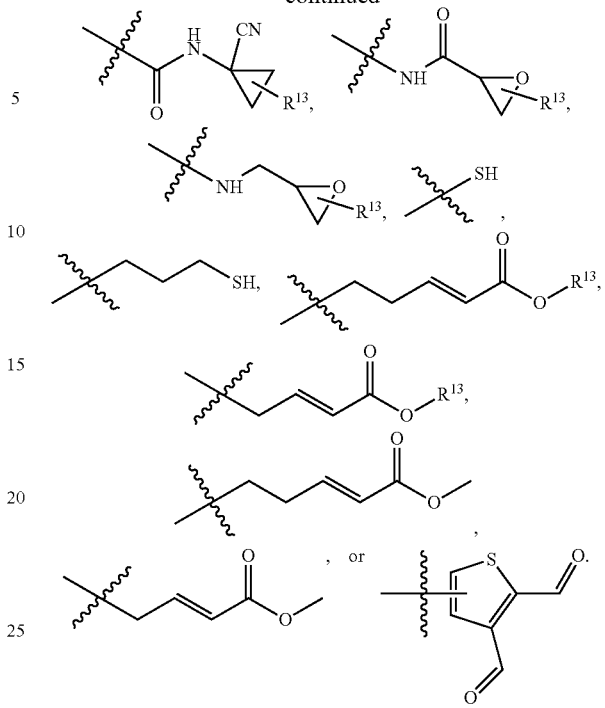

In embodiments, E is an unsubstituted vinyl sulfone moiety, unsubstituted vinyl sulfonamide moiety, unsubstituted fluoro($C_1$-$C_4$)alkylketone moiety, unsubstituted chloro ($C_1$-$C_4$)alkylketone moiety, unsubstituted acrylamide moiety, unsubstituted disulfide moiety, unsubstituted thiol moiety, unsubstituted phosphonate moiety, unsubstituted aldehyde moiety, unsubstituted enone moiety, unsubstituted diazomethylketone moiety, unsubstituted diazomethylamide moiety, unsubstituted cyanocyclopropyl carboxamide moiety, unsubstituted epoxide moiety, unsubstituted epoxyketone moiety, unsubstituted epoxyamide moiety, unsubstituted aryl aldehyde moiety, unsubstituted aryl dialdehyde moiety, unsubstituted dialdehyde moiety, unsubstituted nitrogen mustard moiety, unsubstituted propargyl moiety, or unsubstituted propargylamide moiety.

$R^{13}$ is independently hydrogen, oxo, halogen, $CX^{13}{}_3$, —$CHX^{13}{}_2$, —$CH_2X^{13}$, —CN, —$SO_{n13}R^{22}$, —$SO_{v13}NR^{2U}R^{21}$, —$NHNR^{2U}R^{21}$, —$ONR^{2U}R^{21}$, —NHC=(O)NHNR$^{20}$R$^{21}$, —NHC(O)NR$^{20}$R$^{21}$, —N(O)$_{m13}$, —NR$^{2U}$R$^{21}$, —C(O)R$^{22}$, —C(O)—OR$^{22}$, —C(O)NR$^{20}$R$^{21}$, —OR$^{23}$, —NR$^{20}$SO$_2$R$^{23}$, —NR$^{20}$C(O)R$^{22}$, —NR$^{20}$C(O)OR$^{22}$, —NR$^{20}$OR$^{22}$, —OCX$^{13}{}_3$, —OCHX$^{13}{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; an $R^{20}$ and $R^{21}$ substituent bonded to the same atom may optionally be joined to form a substituted or unsubstituted heterocycloalkyl or substituted or unsubstituted heteroaryl. In embodiments, $R^{13}$ is independently hydrogen. In embodiments, $R^{13}$ is independently substituted or unsubstituted alkyl. In embodiments, $R^{13}$ is independently oxo, halogen, $CX^{13}{}_3$, —$CHX^{13}{}_2$, —$CH_2X^{13}$, —CN, —$SO_{n13}R^{22}$, —$SO_{v13}NR^{20}R^{21}$, —NHNR$^{20}$R$^{21}$, —ONR$^{20}$R$^{21}$, —NHC=(O)NHNR$^{20}$R$^{21}$, —NHC(O)NR$^{20}$R$^{21}$, —N(O)$_{m13}$, —NR$^{20}$R$^{21}$, —C(O)R$^{22}$, —C(O)—OR$^{22}$, —C(O)NR$^{20}$R$^{21}$, —OR$^{23}$, —NR$^{20}$SO$_2$R$^2$—NR$^{20}$C(O)R$^{22}$, —NR$^{20}$C(O)OR$^{22}$, —NR$^{20}$OR$^{22}$, —OCX$^{13}{}_3$, —OCHX$^{13}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, R$^{13}$ is independently substituted or unsubstituted heteroalkyl. In embodiments, R$^{13}$ is independently substituted or unsubstituted cycloalkyl. In embodiments, R$^{13}$ is independently substituted or unsubstituted heterocycloalkyl. In embodiments, R$^{13}$ is independently substituted or unsubstituted aryl. In embodiments, R$^{13}$ is independently substituted or unsubstituted heteroaryl. In embodiments, R$^{13}$ is independently halogen, —CX$^{13}_3$, —CHX$^{13}_2$, —CH$_2$X$^{13}$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^{13}_3$, —OCHX$^{13}_2$, substituted or unsubstituted C$_1$-C$_6$ alkyl, substituted or unsubstituted 2 to 6 membered heteroalkyl, substituted or unsubstituted C$_3$-C$_8$ cycloalkyl, substituted or unsubstituted 3 to 8 membered heterocycloalkyl, substituted or unsubstituted C$_6$ aryl, or substituted or unsubstituted 5 to 6 membered heteroaryl. In embodiments, R$^{13}$ is independently halogen, —CX$^{13}_3$, —CHX$^{13}_2$, —CH$_2$X$^{13}$, —OH, —SH, —COOH, —OCX$^{13}_3$, —OCHX$^{13}_2$, —CH$_3$, —CH$_2$CH$_3$, —OCH$_3$, —OCH$_2$CH$_3$, —SCH$_3$, or —SCH$_2$CH$_3$. In embodiments, R$^{13}$ is independently halogen or —OCH$_3$. In embodiments, R$^{13}$ is substituted or unsubstituted C$_3$-C$_6$ alkyl. In embodiments, R$^{13}$ is substituted or unsubstituted 2 to 6 membered heteroalkyl. In embodiments, R$^{13}$ is substituted or unsubstituted C$_3$-C$_8$ cycloalkyl. In embodiments, R$^{13}$ is substituted or unsubstituted 3 to 8 membered heterocycloalkyl. In embodiments, R$^{13}$ is substituted or unsubstituted C$_6$ aryl. In embodiments, R$^{13}$ is substituted or unsubstituted 5 to 6 membered heteroaryl. In embodiments, R$^{13}$ is independently halogen. In embodiments, R$^{13}$ is independently —CX$^{13}_3$. In embodiments, R$^{13}$ is independently —CHX$^{13}_2$. In embodiments, R$^{13}$ is independently —CH$_2$X$^{13}$. In embodiments, R$^{13}$ is independently —OH. In embodiments, R$^{13}$ is independently —SH. In embodiments, R$^{13}$ is independently —COOH. In embodiments, R$^{13}$ is independently —OCX$^{13}_3$. In embodiments, R$^{13}$ is independently —OCHX$^{13}_2$. In embodiments, R$^{13}$ is independently —CH$_3$. In embodiments, R$^{13}$ is independently —CH$_2$CH$_3$. In embodiments, R$^{13}$ is independently —OCH$_3$. In embodiments, R$^{13}$ is independently —OCH$_2$CH$_3$. In embodiments, R$^{13}$ is independently —SCH$_3$. In embodiments, R$^{13}$ is independently —SCH$_2$CH$_3$. In embodiments, R$^{13}$ is independently —Cl or —OCH$_3$. In embodiments, R$^{13}$ is independently halogen, —CX$^{13}_3$, —CN, —OH, —NH$_2$, —COOH, —CONH$_2$, —NO$_2$, —SH, —OCX$^{13}_3$, —OCHX$^{13}_2$, —CHX$^{13}_2$, —CH$_2$X$^{13}$, substituted or unsubstituted C$_1$-C$_8$ alkyl, or substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted phenyl, or substituted or unsubstituted 5 to 6 membered heteroaryl. In embodiments, R$^{13}$ is independently halogen, —CX$^{13}_3$, —CN, unsubstituted C$_1$-C$_4$ alkyl, or unsubstituted 2 to 4 membered heteroalkyl. In embodiments, R$^{13}$ is independently unsubstituted methyl, unsubstituted ethyl, unsubstituted isopropyl, or unsubstituted tert-butyl. In embodiments, R$^{13}$ is independently unsubstituted methyl. In embodiments, R$^{13}$ is independently unsubstituted ethyl. In embodiments, R$^{13}$ is independently unsubstituted propyl. In embodiments, R$^{13}$ is independently unsubstituted n-propyl. In embodiments, R$^{13}$ is independently unsubstituted isopropyl. In embodiments, R$^{13}$ is independently unsubstituted butyl. In embodiments, R$^{13}$ is independently unsubstituted n-butyl. In embodiments, R$^{13}$ is independently unsubstituted isobutyl. In embodiments, R$^{13}$ is independently unsubstituted tert-butyl. In embodiments, R$^{13}$ is independently unsubstituted pentyl. In embodiments, R$^{13}$ is independently unsubstituted hexyl. In embodiments, R$^{13}$ is independently unsubstituted heptyl. In embodiments, R$^{13}$ is independently unsubstituted octyl. In embodiments, R$^{13}$ is independently —F. In embodiments, R$^{13}$ is independently —Cl. In embodiments, R$^{13}$ is independently —Br. In embodiments, R$^{13}$ is independently —I. In embodiments, R$^{13}$ is independently unsubstituted methoxy. In embodiments, R$^{13}$ is independently unsubstituted ethoxy. In embodiments, R$^{13}$ is independently —CF$_3$. In embodiments, R$^{13}$ is independently —CCl$_3$. In embodiments, R$^{13}$ is an unsubstituted isopropyl. In embodiments, R$^{13}$ is an unsubstituted phenyl. In embodiments, R$^{13}$ is an unsubstituted pyridyl. In embodiments, R$^{13}$ is independently halogen. In embodiments, R$^{13}$ is independently —CX$^{13}_3$. In embodiments, R$^{13}$ is independently —CHX$_2$. In embodiments, R$^{13}$ is independently —CH$_2$X$^{13}$. In embodiments, R$^{13}$ is independently —CN. In embodiments, R$^{13}$ is independently —OH. In embodiments, R$^{13}$ is independently —NH$_2$. In embodiments, R$^{13}$ is independently —COOH. In embodiments, R$^{13}$ is independently —CONH$_2$. In embodiments, R$^{13}$ is independently —NO$_2$. In embodiments, R$^{13}$ is independently —SH. In embodiments, R$^{13}$ is independently —SO$_2$Cl. In embodiments, R$^{13}$ is independently —SO$_3$H. In embodiments, R$^{13}$ is independently —SO$_4$H. In embodiments, R$^{13}$ is independently —SO$_2$NH$_2$. In embodiments, R$^{13}$ is independently —NHNH$_2$. In embodiments, R$^{13}$ is independently —ONH$_2$. In embodiments, R$^{13}$ is independently —NHC(O)NHNH$_2$. In embodiments, R$^{13}$ is independently —NHC(O)NH$_2$. In embodiments, R$^{13}$ is independently —NHSO$_2$H. In embodiments, R$^{13}$ is independently —NHC(O)H. In embodiments, R$^{13}$ is independently —NHC(O)OH. In embodiments, R$^{13}$ is independently —NHOH. In embodiments, R$^{13}$ is independently —OCX$^{13}_3$. In embodiments, R$^{13}$ is independently —OCHX$^{13}_2$. In embodiments, R$^{13}$ is independently substituted or unsubstituted alkyl. In embodiments, R$^{13}$ is independently substituted or unsubstituted heteroalkyl. In embodiments, R$^{13}$ is independently substituted or unsubstituted cycloalkyl. In embodiments, R$^{13}$ is independently substituted or unsubstituted heterocycloalkyl. In embodiments, R$^{13}$ is independently substituted or unsubstituted aryl. In embodiments, R$^{13}$ is independently substituted or unsubstituted heteroaryl. In embodiments, R$^{13}$ is independently substituted alkyl. In embodiments, R$^{13}$ is independently substituted heteroalkyl. In embodiments, R$^{13}$ is independently substituted cycloalkyl. In embodiments, R$^{13}$ is independently substituted heterocycloalkyl. In embodiments, R$^{13}$ is independently substituted aryl. In embodiments, R$^{13}$ is independently substituted heteroaryl. In embodiments, R$^{13}$ is independently unsubstituted alkyl. In embodiments, R$^{13}$ is independently unsubstituted heteroalkyl. In embodiments, R$^{13}$ is independently unsubstituted cycloalkyl. In embodiments, R$^{13}$ is independently unsubstituted heterocycloalkyl. In embodiments, R$^{13}$ is independently unsubstituted aryl. In embodiments, R$^{13}$ is independently unsubstituted heteroaryl. In embodiments, R$^{13}$ is independently substituted or unsubstituted C$_1$-C$_8$ alkyl. In embodiments, R$^{13}$ is independently substituted or unsubstituted 2 to 8 membered heteroalkyl. In embodiments, R$^{13}$ is independently substituted or unsubstituted C$_3$-C$_8$ cycloalkyl. In embodiments, R$^{13}$ is independently substituted or unsubstituted 3 to 8 membered heterocycloalkyl. In embodiments, R$^{13}$ is independently substituted or unsubstituted $C_6$-$C_{10}$ aryl. In embodiments, $R^{13}$ is independently substituted or unsubstituted 5 to 10 membered heteroaryl. In embodiments, $R^{13}$ is independently substituted $C_1$-$C_8$ alkyl. In embodiments, $R^{13}$ is independently substituted 2 to 8 membered heteroalkyl. In embodiments, $R^{13}$ is independently substituted $C_3$-$C_8$ cycloalkyl. In embodiments, $R^{13}$ is independently substituted 3 to 8 membered heterocycloalkyl. In embodiments, $R^{13}$ is independently substituted $C_6$-$C_{10}$ aryl. In embodiments, $R^{13}$ is independently substituted 5 to 10 membered heteroaryl. In embodiments, $R^{13}$ is independently unsubstituted $C_1$-$C_8$ alkyl. In embodiments, $R^{13}$ is independently unsubstituted 2 to 8 membered heteroalkyl. In embodiments, $R^{13}$ is independently unsubstituted $C_3$-$C_8$ cycloalkyl. In embodiments, $R^{13}$ is independently unsubstituted 3 to 8 membered heterocycloalkyl. In embodiments, $R^{13}$ is independently unsubstituted $C_6$-$C_{10}$ aryl. In embodiments, $R^{13}$ is independently unsubstituted 5 to 10 membered heteroaryl. In embodiments, $R^{13}$ is independently substituted or unsubstituted $C_1$-$C_4$ alkyl. In embodiments, $R^{13}$ is independently substituted or unsubstituted 2 to 4 membered heteroalkyl. In embodiments, $R^{13}$ is independently substituted or unsubstituted $C_3$-$C_6$ cycloalkyl. In embodiments, $R^{13}$ is independently substituted or unsubstituted 3 to 6 membered heterocycloalkyl. In embodiments, $R^{13}$ is independently substituted or unsubstituted phenyl. In embodiments, $R^{13}$ is independently substituted or unsubstituted 5 to 6 membered heteroaryl. In embodiments, $R^{13}$ is independently substituted $C_1$-$C_4$ alkyl. In embodiments, $R^{13}$ is independently substituted 2 to 4 membered heteroalkyl. In embodiments, $R^{13}$ is independently substituted $C_3$-$C_6$ cycloalkyl. In embodiments, $R^{13}$ is independently substituted 3 to 6 membered heterocycloalkyl. In embodiments, $R^{13}$ is independently substituted phenyl. In embodiments, $R^{13}$ is independently substituted 5 to 6 membered heteroaryl. In embodiments, $R^{13}$ is independently unsubstituted $C_1$-$C_4$ alkyl. In embodiments, $R^{13}$ is independently unsubstituted 2 to 4 membered heteroalkyl. In embodiments, $R^{13}$ is independently unsubstituted $C_3$-$C_6$ cycloalkyl. In embodiments, $R^{13}$ is independently unsubstituted 3 to 6 membered heterocycloalkyl. In embodiments, $R^{13}$ is independently unsubstituted phenyl. In embodiments, $R^{13}$ is independently unsubstituted 5 to 6 membered heteroaryl.

$R^{20}$, $R^{21}$, $R^{22}$, and $R^{23}$ are independently hydrogen, halogen, —$CX^A_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^A_3$, —$OCHX^A_2$, —$CHX^A_2$, —$CH_2X^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{20}$ and $R^{21}$ substituents bonded to the same nitrogen atom may optionally be joined to form a substituted or unsubstituted heterocycloalkyl or substituted or unsubstituted heteroaryl.

Each $X^A$ and $X^{13}$ is independently —F, —Cl, —Br, or —I. The symbols n13 and v13 are independently an integer from 0 to 4. The symbol m13 is independently an integer from 1 to 2.

In embodiments, the compound has the formula:

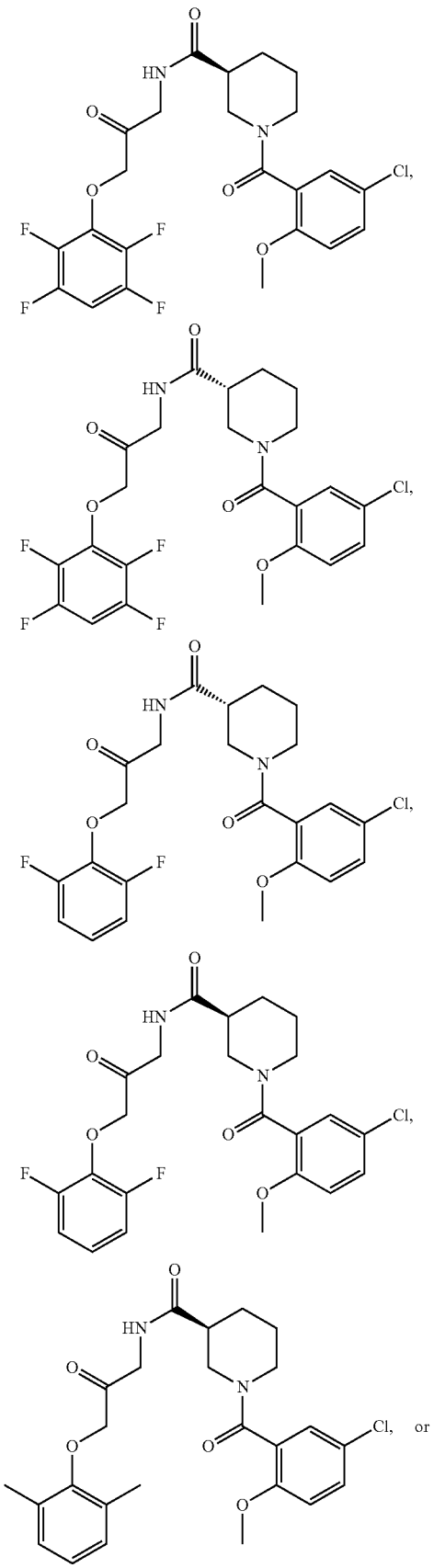

or

-continued

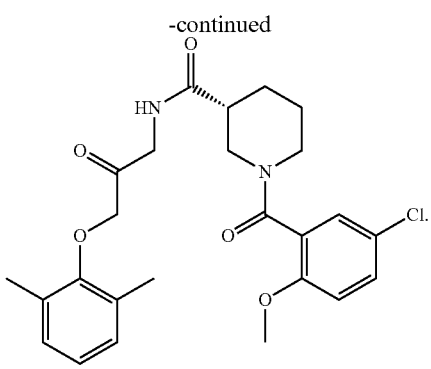

In embodiments, the compound has the formula:

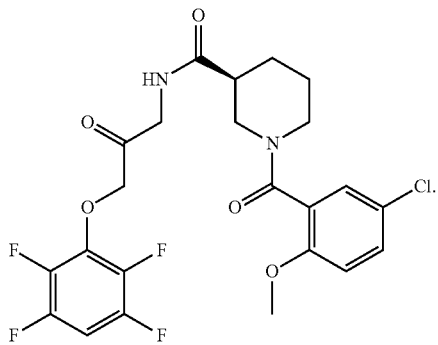 [SMILES: COc1ccc(Cl)cc1C(=O)N1CCC[C@H](C(=O)NCC(=O)COc2c(F)c(F)cc(F)c2F)C1]

In embodiments, the compound has the formula:

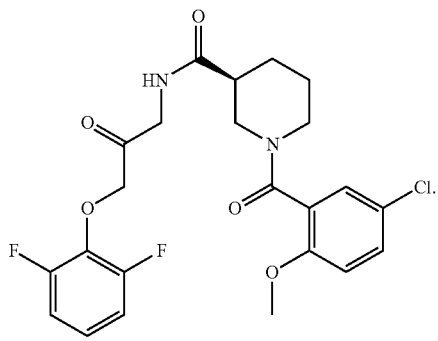 [SMILES: COc1ccc(Cl)cc1C(=O)N1CCC[C@H](C(=O)NCC(=O)COc2c(F)cccc2F)C1]

In embodiments, the compound has the formula:

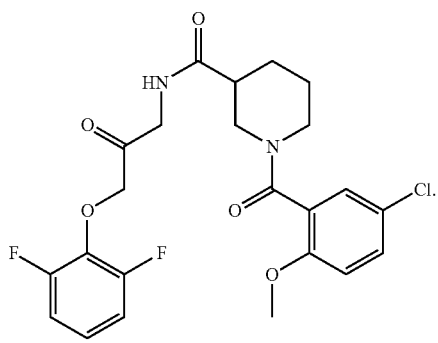 [SMILES: COc1ccc(Cl)cc1C(=O)N1CCCC(C(=O)NCC(=O)COc2c(F)cccc2F)C1]

In embodiments, the compound has the formula:

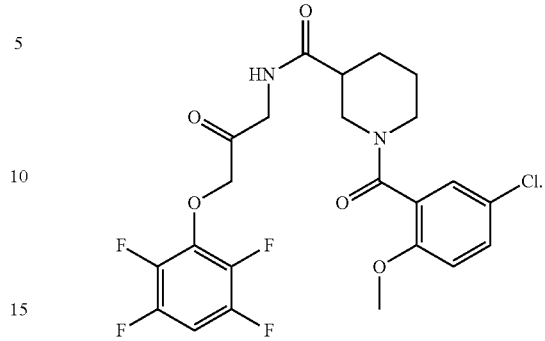

In embodiments, the compound has the formula:

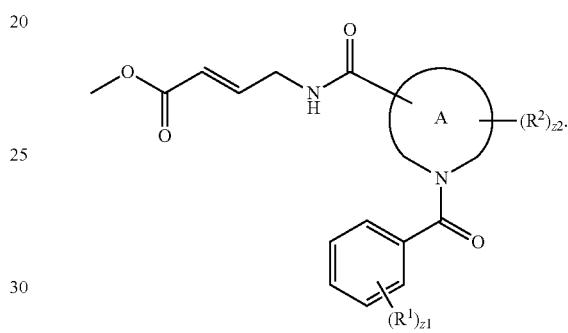

Ring A, $R^1$, z1, $R^2$, and z2 are as described herein.
In embodiments, the compound has the formula:

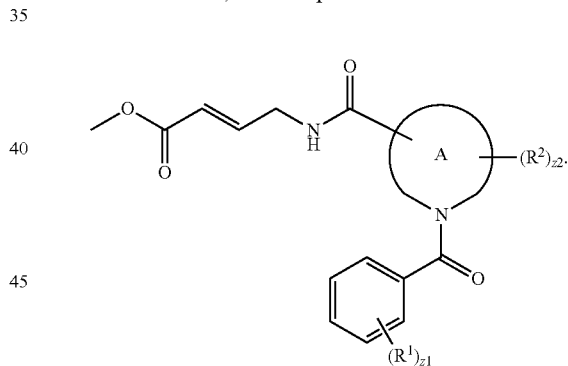

Ring A, $R^1$, z1, $R^2$, and z2 are as described herein.
In embodiments, the compound has the formula:

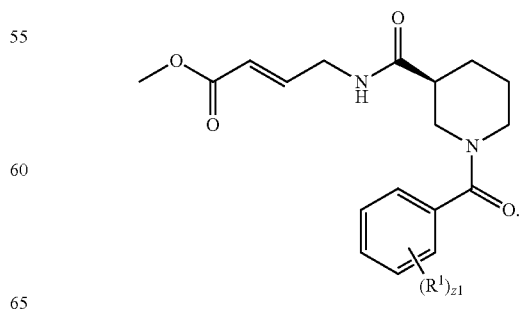

and z1 are as described herein.

In embodiments, the compound has the formula:

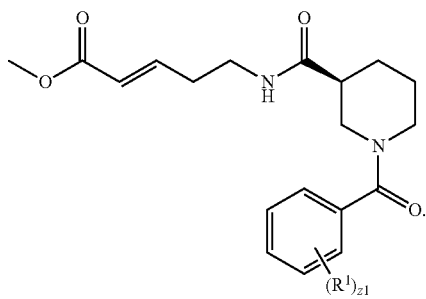

R¹ and z1 are as described herein.

In embodiments, the compound has the formula:

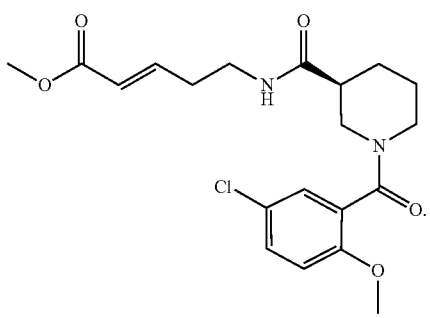 [SMILES: COC(=O)/C=C/CCNC(=O)[C@H]1CCCN(C(=O)c2cc(Cl)ccc2OC)C1]

In embodiments, the compound has the formula:

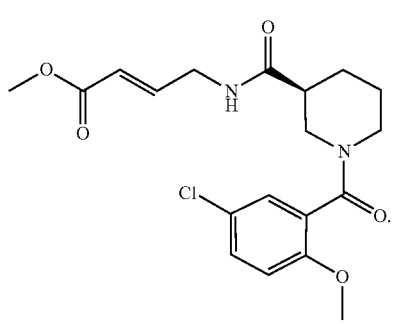 [SMILES: COC(=O)/C=C/CNC(=O)[C@H]1CCCN(C(=O)c2cc(Cl)ccc2OC)C1]

In embodiments, the compound has the formula:

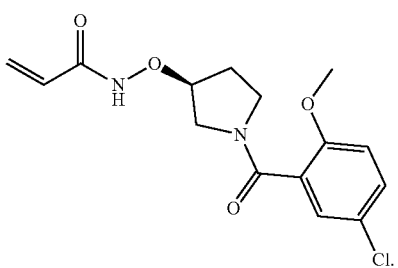 [SMILES: C=CC(=O)NO[C@H]1CCN(C(=O)c2cc(Cl)ccc2OC)C1]

In embodiments, the compound has the formula:

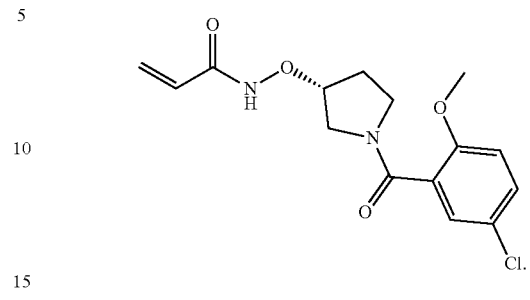

In embodiments, the compound has the formula:

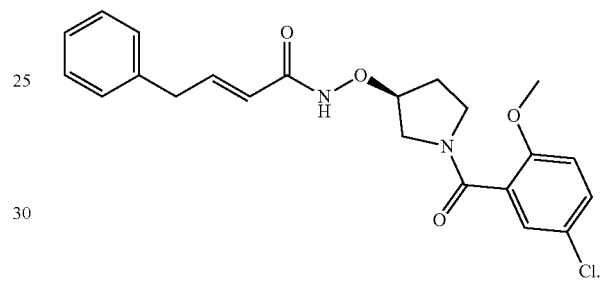

In embodiments, the compound has the formula:

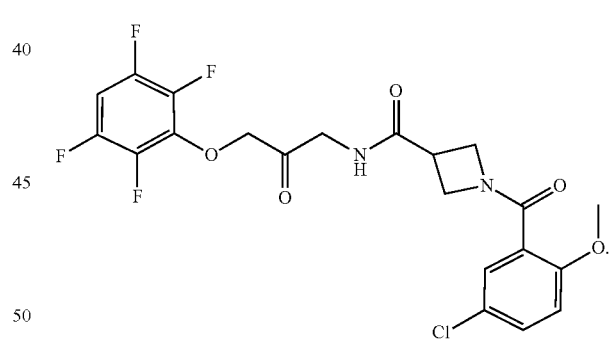

In embodiments, the compound has the formula:

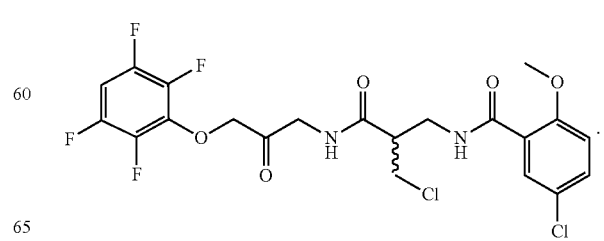

In embodiments, the compound has the formula:

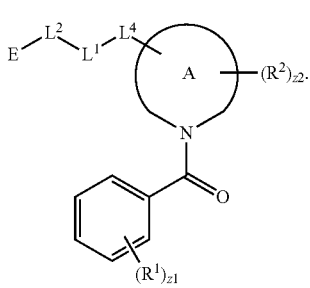

Ring A, $R^1$, z1, $R^2$, z2, $L^1$, $L^2$, $L^4$, and E are as described herein.

In embodiments, the compound has the formula:

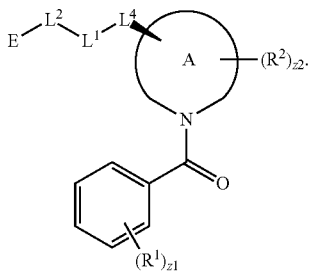

A, $R^1$, z1, $R^2$, z2, $L^1$, $L^2$, $L^4$, and E are as described herein.

In embodiments, Ring A is a 5 to 7 membered heterocycloalkyl. In embodiments, Ring A is a 3 to 5 membered heterocycloalkyl. In embodiments, Ring A is pyrrolidinyl. In embodiments, Ring A is piperidinyl. In embodiments, Ring A is azetidinyl. In embodiments, Y is N.

In embodiments, $R^1$ is independently halogen, $CX^1_3$, —$CHX^1_2$, —$CH_2X^1$, —CN, —$SO_2NH_2$, —$NHNH_2$, —$ONH_2$, —NHC=(O)$NHNH_2$, —NHC(O)$NH_2$, —N(O)$_2$, —$NH_2$, —C(O)H, —C(O)OH, —C(O)$NH_2$, —OH, —$NHSO_2H$, —NHC(O)H, —NHC(O)OH, —NHOH, —$OCX^1_3$, —$OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^1$ is independently halogen, —$CF_3$, —$NH_2$, —C(O)H, —C(O)OH, —C(O)$NH_2$, —OH, substituted or unsubstituted $C_1$-$C_4$ alkyl, or substituted or unsubstituted 2 to 4 membered heteroalkyl. In embodiments, $R^1$ is independently halogen, —$CF_3$, —$NH_2$, —C(O)H, —C(O)OH, —C(O)$NH_2$, —OH, unsubstituted $C_1$-$C_4$ alkyl, or unsubstituted 2 to 4 membered heteroalkyl.

In embodiments, $L^1$ is a bond. In embodiments, $L^1$ is —NH—.

In embodiments, $L^2$ is a bond. In embodiments, $L^2$ is —NH—.

In embodiments, $L^4$ is a bond. In embodiments, $L^4$ is substituted or unsubstituted $C_1$-$C_3$ alkylene. In embodiments, $L^4$ is unsubstituted methylene.

In embodiments, E is

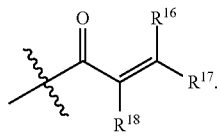

In embodiments, E is

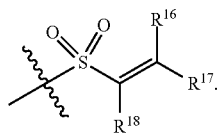

In embodiments, $R^{16}$ is unsubstituted methyl. In embodiments, $R^{17}$ is unsubstituted methyl. In embodiments, $R^{18}$ is unsubstituted methyl. In embodiments, $R^{18}$ is hydrogen. In embodiments, $R^{16}$ is hydrogen. In embodiments, $R^{17}$ is hydrogen. In embodiments, $R^{16}$ is —$CH_2N(CH_3)_2$. In embodiments, $R^{17}$ is —$CH_2N(CH_3)_2$. In embodiments, $R^{18}$ is —$CH_2N(CH_3)_2$. In embodiments, $R^{16}$ is —$CH_2CH_2N(CH_3)_2$. In embodiments, $R^{17}$ is —$CH_2CH_2N(CH_3)_2$. In embodiments, $R^{17}$ is —$CH_2Ph$. In embodiments, $R^{18}$ is —$CH_2CH_2N(CH_3)_2$.

In embodiments, $R^2$ is independently halogen, $CX^2_3$, —$CHX^2_2$, —$CH_2X^2$, —CN, —$SO_3H$, —$SO_4H$, —$SO_2NH_2$, —$NHNH_2$, —$ONH_2$, —NHC=(O)$NHNH_2$, —NHC(O)$NH_2$, —N(O)$_2$, —$NH_2$, —C(O)H, —C(O)OH, —C(O)$NH_2$, —OH, —$NHSO_2H$, —NHC(O)H, —NHC(O)OH, —NHOH, —$OCX^2_3$, —$OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^2$ is independently halogen, —$CF_3$, —$NH_2$, —C(O)H, —C(O)OH, —C(O)$NH_2$, —OH, substituted or unsubstituted $C_1$-$C_4$ alkyl, or substituted or unsubstituted 2 to 4 membered heteroalkyl. In embodiments, $R^2$ is independently halogen, —$CF_3$, —$NH_2$, —C(O)H, —C(O)OH, —C(O)$NH_2$, —OH, unsubstituted $C_1$-$C_4$ alkyl, or unsubstituted 2 to 4 membered heteroalkyl. In embodiments, $R^2$ is independently —Cl. In embodiments, $R^2$ is independently —F. In embodiments, $R^2$ is independently —Br. In embodiments, $R^2$ is independently —I. In embodiments, $R^2$ is independently —$OCH_3$. In embodiments, $R^2$ is independently —$OCH_2CH_3$.

In embodiments, z1 is 2. In embodiments, z2 is 0.

In embodiments, the compound has the formula:

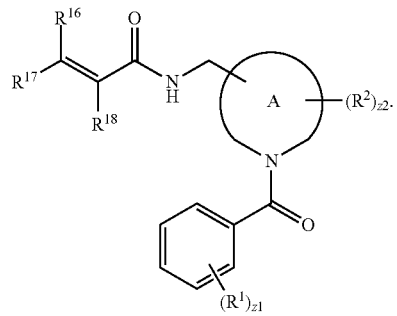

Ring A, $R^1$, z1, $R^2$, z2, $R^{16}$, $R^{17}$, and $R^{18}$ are as described herein. In embodiments, $R^{16}$, $R^{17}$, and $R^{18}$ are hydrogen.

In embodiments, the compound has the formula:

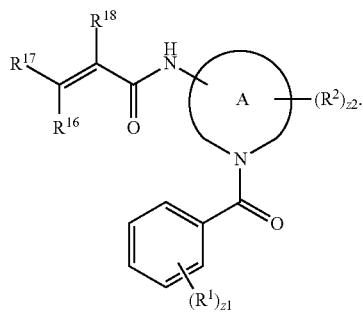

Ring A, $R^1$, z1, $R^2$, z2, $R^{16}$, $R^{17}$, and $R^{18}$ are as described herein. In embodiments, $R^{16}$, $R^{17}$, and $R^{18}$ are hydrogen.

In embodiments, the compound has the formula:

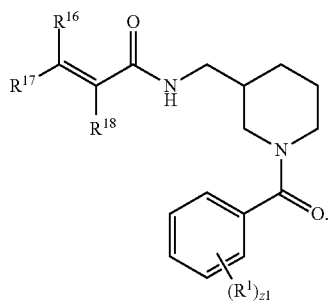

$R^1$, z1, $R^{16}$, $R^{17}$, and $R^{18}$ are as described herein. In embodiments, $R^{16}$, $R^{17}$, and $R^{18}$ are hydrogen.

In embodiments, the compound has the formula:

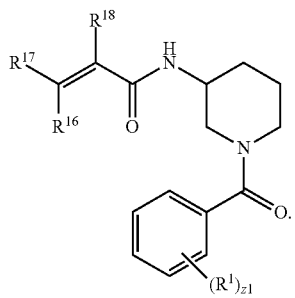

$R^1$, z1, $R^{16}$, $R^{17}$, and $R^{18}$ are as described herein. In embodiments, $R^{16}$, $R^{17}$, and $R^{18}$ are hydrogen.

In embodiments, the compound has the formula:

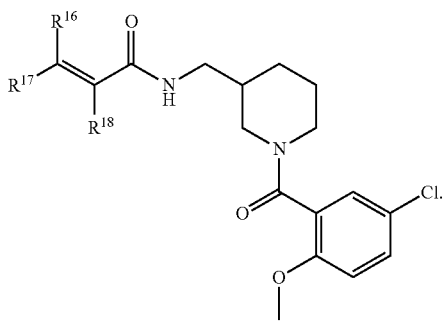

$R^{16}$, $R^{17}$, and $R^{18}$ are as described herein. In embodiments, $R^{16}$, $R^{17}$, and $R^{18}$ are hydrogen.

In embodiments, the compound has the formula:

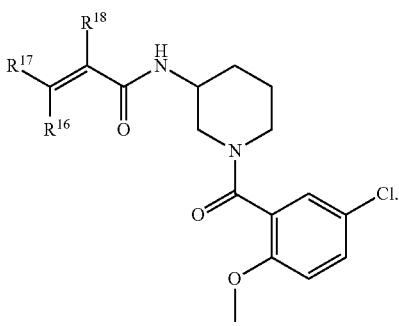

$R^{16}$, $R^{17}$, and $R^{18}$ are as described herein. In embodiments, $R^{16}$, $R^{17}$, and $R^{18}$ are hydrogen.

In embodiments, the compound has the formula:

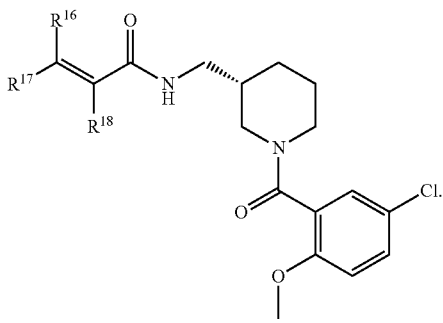

$R^{16}$, $R^{17}$, and $R^{18}$ are as described herein. In embodiments, $R^{16}$, $R^{17}$, and $R^{18}$ are hydrogen.

In embodiments, the compound has the formula:

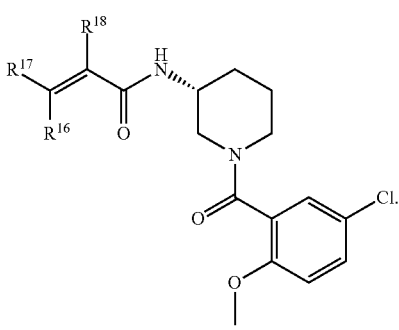

$R^{17}$, and $R^{18}$ are as described herein. In embodiments, $R^{16}$, $R^{17}$, and $R^{18}$ are hydrogen.

In embodiments, the compound has the formula:

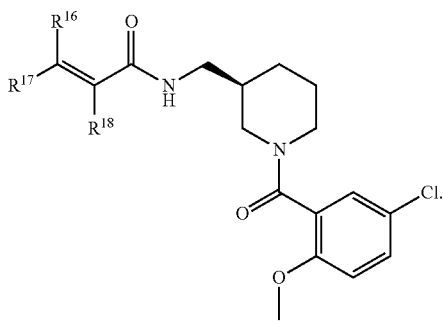

$R^{16}$, $R^{17}$, and $R^{18}$ are as described herein. In embodiments, $R^{16}$, $R^{17}$, and $R^{18}$ are hydrogen.

In embodiments, the compound has the formula:

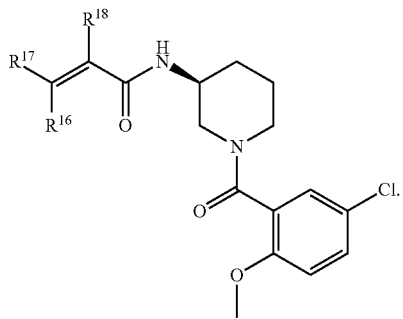

$R^{16}$, $R^{17}$, and $R^{18}$ are as described herein. In embodiments, $R^{16}$, $R^{17}$, and $R^{18}$ are hydrogen.

In embodiments, the compound has the formula:

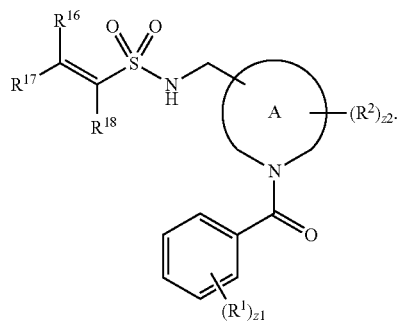

Ring A, $R^1$, z1, $R^2$, z2, $R^{16}$, $R^{17}$, and $R^{18}$ are as described herein. In embodiments, $R^{16}$, $R^{17}$, and $R^{18}$ are hydrogen. In embodiments, the compound has the formula:

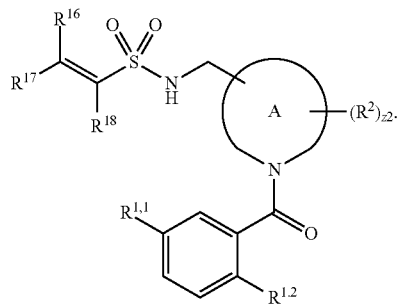

Ring A, $R^2$, z2, $R^{16}$, $R^{17}$, and $R^{18}$ are as described herein. In embodiments, $R^{16}$, $R^{17}$, and $R^{18}$ are hydrogen. $R^{1.1}$ and $R^{1.2}$ have the values of $R^1$. $R^{1.1}$ may be halogen. $R^{1.1}$ may be hydrogen. $R^{1.1}$ may be —Cl. $R^{1.2}$ may be hydrogen. $R^{1.2}$ may be unsubstituted 2 to 4 membered heteroalkyl. $R^{1.2}$ may be unsubstituted 2 to 3 membered heteroalkyl. $R^{1.2}$ may be unsubstituted methoxy. $R^{1.2}$ may be unsubstituted ethoxy. $R^{1.2}$ may be unsubstituted propoxy.

In embodiments, the compound has the formula:

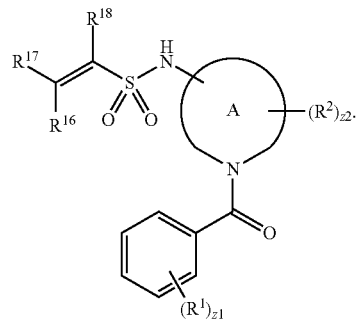

Ring A, $R^1$, z1, $R^2$, z2, $R^{16}$, $R^{17}$, and $R^{18}$ are as described herein. In embodiments, $R^{16}$, $R^{17}$, $R^{18}$ are hydrogen.

In embodiments, the compound has the formula:

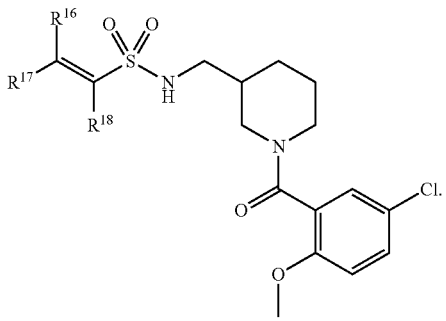

$R^{16}$, $R^{17}$, and $R^{18}$ are as described herein. In embodiments, $R^{16}$, $R^{17}$, and $R^{18}$ are hydrogen. In embodiments, the compound has the formula:

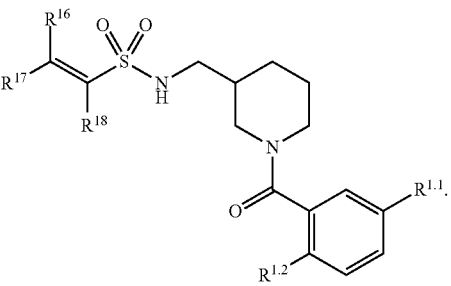

$R^{16}$, $R^{17}$, and $R^{18}$ are as described herein. In embodiments, $R^{16}$, $R^{17}$, and $R^{18}$ are hydrogen. $R^{1.1}$ and $R^{1.2}$ have the values of $R^1$. $R^{1.1}$ may be halogen. $R^{1.1}$ may be hydrogen. $R^{1.1}$ may be —Cl. $R^{1.2}$ may be hydrogen. $R^{1.2}$ may be unsubstituted 2 to 4 membered heteroalkyl. $R^{1.2}$ may be unsubstituted 2 to 3 membered heteroalkyl. $R^{1.2}$ may be unsubstituted methoxy. $R^{1.2}$ may be unsubstituted ethoxy. $R^{1.2}$ may be unsubstituted propoxy.

In embodiments, the compound has the formula:

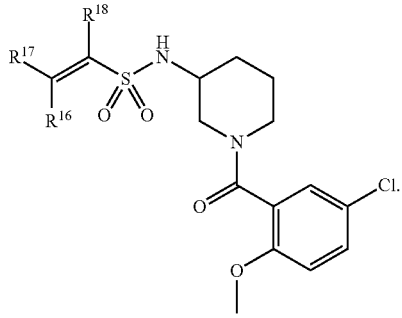

$R^{16}$, $R^{17}$, and $R^{18}$ are as described herein. In embodiments, $R^{16}$, $R^{17}$, and $R^{18}$ are hydrogen.

In embodiments, the compound has the formula:

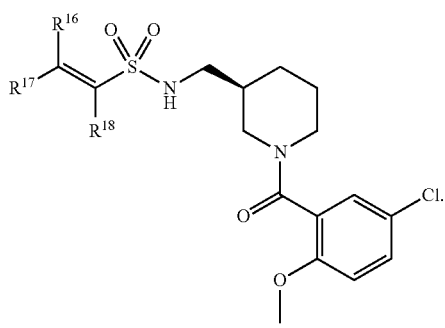

$R^{16}$, $R^{17}$, and $R^{18}$ are as described herein. In embodiments, $R^{16}$, $R^{17}$, and $R^{18}$ are hydrogen. In embodiments, the compound has the formula:

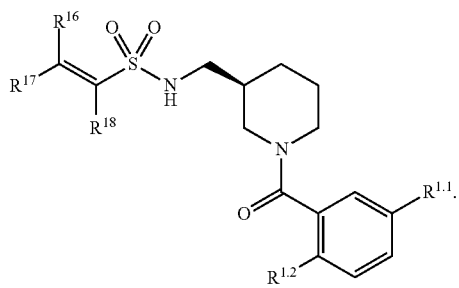

$R^{16}$, $R^{17}$, and $R^{18}$ are as described herein. In embodiments, $R^{16}$, $R^{17}$, and $R^{18}$ are hydrogen. $R^{1.1}$ and $R^{1.2}$ have the values of $R^{1}$. $R^{1.1}$ may be halogen. $R^{1.1}$ may be hydrogen. $R^{1.1}$ may be —Cl. $R^{1.2}$ may be hydrogen. $R^{1.2}$ may be unsubstituted 2 to 4 membered heteroalkyl. $R^{1.2}$ may be unsubstituted 2 to 3 membered heteroalkyl. $R^{1.2}$ may be unsubstituted methoxy. $R^{1.2}$ may be unsubstituted ethoxy. $R^{1.2}$ may be unsubstituted propoxy.

In embodiments, the compound has the formula:

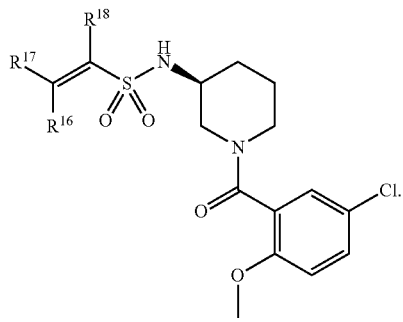

$R^{16}$, $R^{17}$, and $R^{18}$ are as described herein. In embodiments, $R^{16}$, $R^{17}$, and $R^{18}$ are hydrogen.

In embodiments, the compound has the formula:

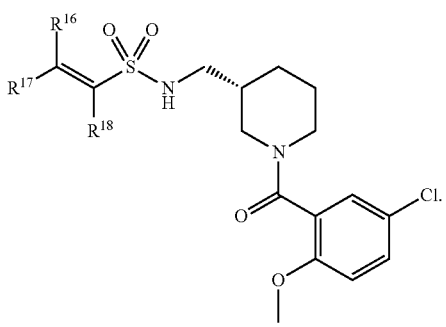

$R^{16}$, $R^{17}$, and $R^{18}$ are as described herein. In embodiments, $R^{16}$, $R^{17}$, and $R^{18}$ are hydrogen.

In embodiments, the compound has the formula:

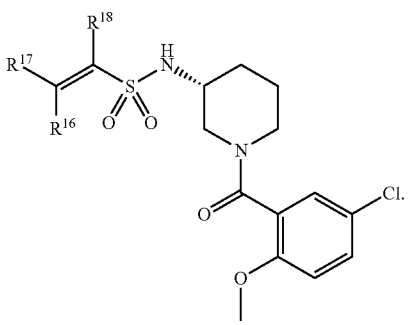

$R^{16}$, $R^{17}$, and $R^{18}$ are as described herein. In embodiments, $R^{16}$, $R^{17}$, and $R^{18}$ are hydrogen.

In embodiments, the compound has the formula:

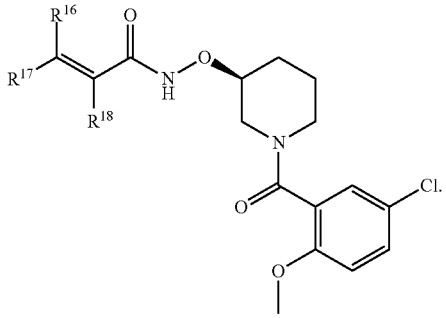

$R^{16}$, $R^{17}$, and $R^{18}$ are as described herein. In embodiments, $R^{16}$, $R^{17}$, and $R^{18}$ are hydrogen.

In embodiments, the compound has the formula:

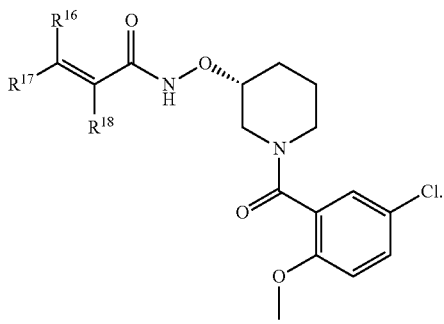

$R^{16}$, $R^{17}$, and $R^{18}$ are as described herein. In embodiments, $R^{16}$, $R^{17}$, and $R^{18}$ are hydrogen.

In embodiments, the compound has the formula:

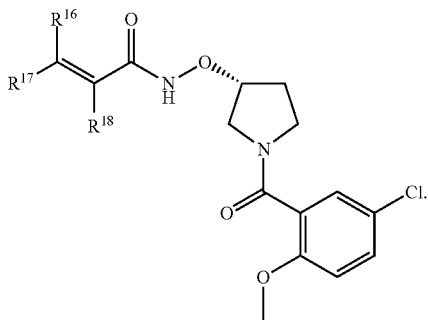

$R^{16}$, $R^{17}$, and $R^{18}$ are as described herein. In embodiments, $R^{16}$, $R^{17}$, and $R^{18}$ are hydrogen.

In embodiments, the compound has the formula:

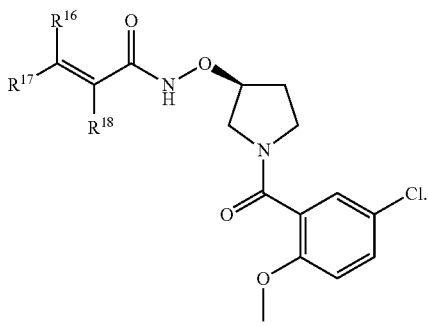

$R^{16}$, $R^{17}$, and $R^{18}$ are as described herein. In embodiments, $R^{16}$, $R^{17}$, and $R^{18}$ are hydrogen. In embodiments, $R^{16}$ and $R^{18}$ are hydrogen and $R^{17}$ is —CH$_2$Ph.

In embodiments, the compound has the formula:

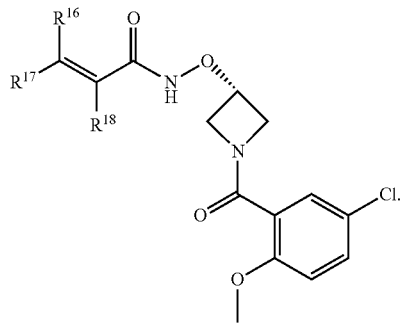

$R^{16}$, $R^{17}$, and $R^{18}$ are as described herein. In embodiments, $R^{16}$, $R^{17}$, and $R^{18}$ are hydrogen.

In embodiments, the compound has the formula:

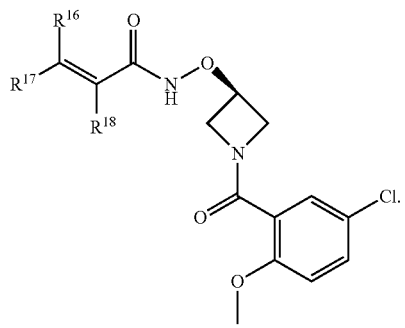

$R^{16}$, $R^{17}$, and $R^{18}$ are as described herein. In embodiments, $R^{16}$, $R^{17}$, and $R^{18}$ are hydrogen.

In embodiments, the compound has the formula:

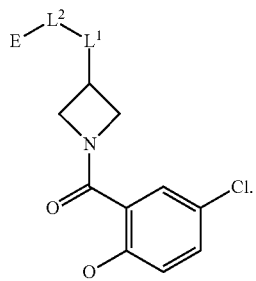

$L^1$, $L^2$, and E are as described herein. In embodiments, the compound has the formula:

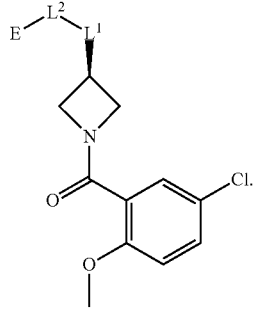

$L^1$, $L^2$, and E are as described herein. In embodiments, the compound has the formula:

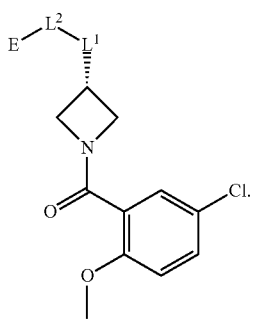

$L^1$, $L^2$, and E are as described herein. In embodiments, $R^{16}$, $R^{17}$, and $R^{18}$ are hydrogen. In embodiments, E is:

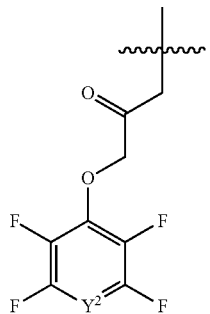

and $Y^2$ is as described herein. In embodiments, E is:

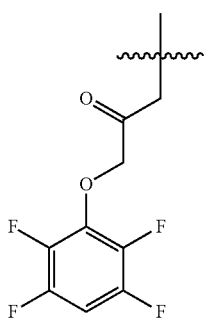

in embodiments, E is:

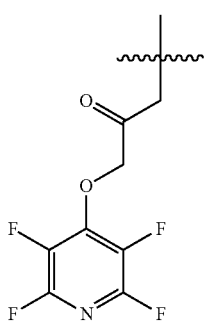

In embodiments, $L^1$ is —C(O)—. In embodiments, $L^2$ is —NH—.

In embodiments, the compound has the formula:

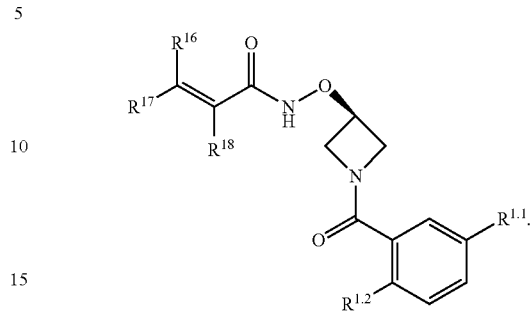

$R^{16}$, $R^{17}$, and $R^{18}$ are as described herein. In embodiments, $R^{16}$, $R^{17}$, and $R^{18}$ are hydrogen. $R^{1.1}$ and $R^{1.2}$ have the values of $R^1$. $R^{1.1}$ may be halogen. $R^{1.1}$ may be hydrogen. $R^{1.1}$ may be —Cl. $R^{1.2}$ may be hydrogen. $R^{1.2}$ may be unsubstituted 2 to 4 membered heteroalkyl. $R^{1.2}$ may be unsubstituted 2 to 3 membered heteroalkyl. $R^{1.2}$ may be unsubstituted methoxy. $R^{1.2}$ may be unsubstituted ethoxy. $R^{1.2}$ may be unsubstituted propoxy.

In embodiments, the compound has the formula:

(IIIB)

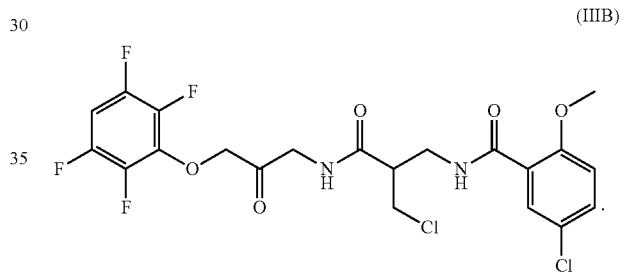

In embodiments, the compound has the formula:

(IIIB)

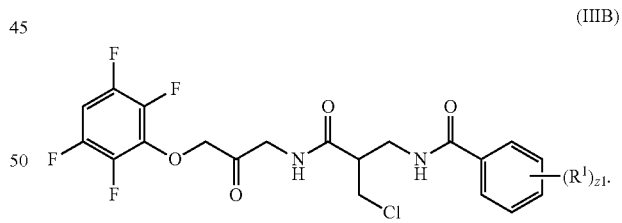

$R^1$ and z1 are as described herein.

In embodiments, the compound has the formula:

$R^1$, $L^1$, $L^2$, $L^4$, E, and z1 are as described herein. In embodiments, the compound has the formula:

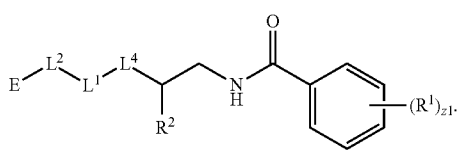

$R^1$, $R^2$, $L^1$, $L^2$, $L^4$, E, and z1 are as described herein.

In embodiments, the compound includes

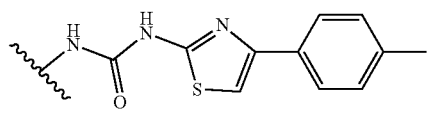

In embodiments, the compound includes

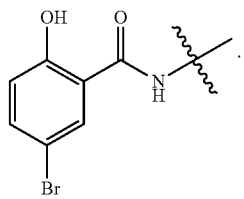 [SMILES: *NC(=O)c1cc(Br)ccc1O]

In embodiments, the compound includes

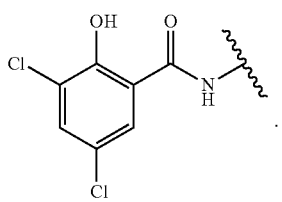 [SMILES: *NC(=O)c1cc(Cl)cc(Cl)c1O]

In embodiments, the compound includes

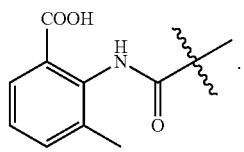 [SMILES: *C(=O)Nc1c(C)cccc1C(=O)O]

In embodiments, the compound includes

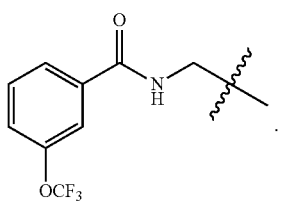 [SMILES: *CNC(=O)c1cccc(OC(F)(F)F)c1]

In embodiments, the compound includes

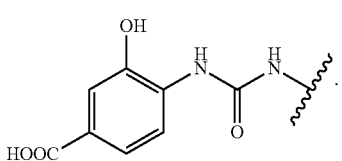 [SMILES: *NC(=O)Nc1ccc(C(=O)O)cc1O]

In embodiments, the compound includes

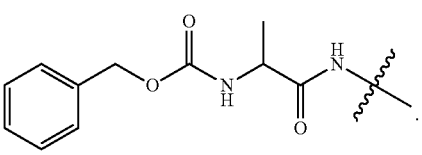 [SMILES: *NC(=O)C(C)NC(=O)OCc1ccccc1]

In embodiments, the compound includes

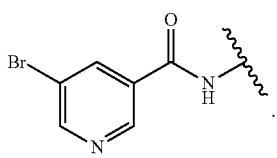 [SMILES: *NC(=O)c1cncc(Br)c1]

in embodiments, the compound includes

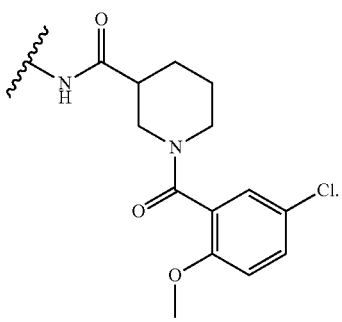 [SMILES: *NC(=O)C1CCCN(C(=O)c2cc(Cl)ccc2OC)C1]

In embodiments, the compound includes

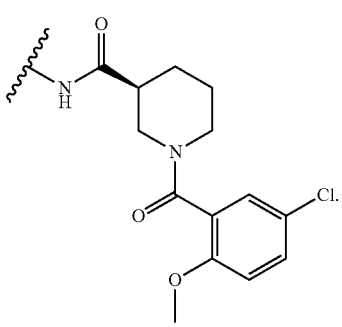 [SMILES: *NC(=O)[C@H]1CCCN(C(=O)c2cc(Cl)ccc2OC)C1]

In embodiments, the compound is a compound described herein, including in an example, figures, or table.

In embodiments, the compound includes

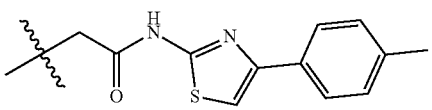

In embodiments, the compound includes

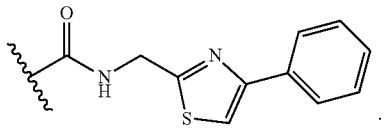 [SMILES: *C(=O)NCc1nc(-c2ccccc2)cs1]

In embodiments, the compound includes

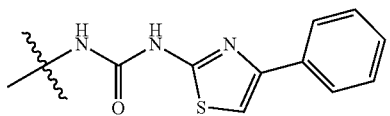

In embodiments, the compound includes

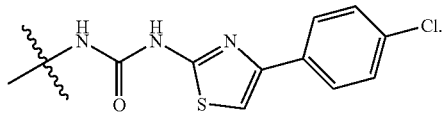 [SMILES: *NC(=O)Nc1nc(-c2ccc(Cl)cc2)cs1]

In embodiments, the compound includes

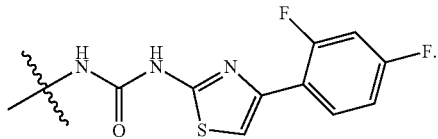 [SMILES: *NC(=O)Nc1nc(-c2ccc(F)cc2F)cs1]

In embodiments, the compound includes

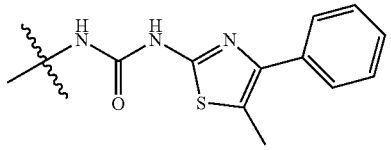

In embodiments, the compound includes

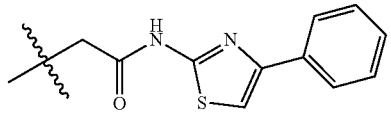 [SMILES: *CC(=O)Nc1nc(-c2ccccc2)cs1]

In embodiments, the compound includes

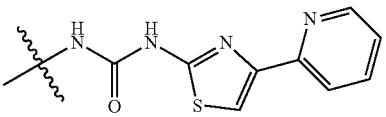

In embodiments, the compound includes

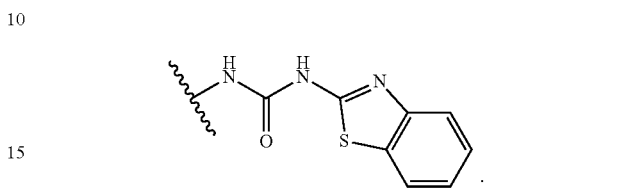

In an aspect is provided a compound having the formula:

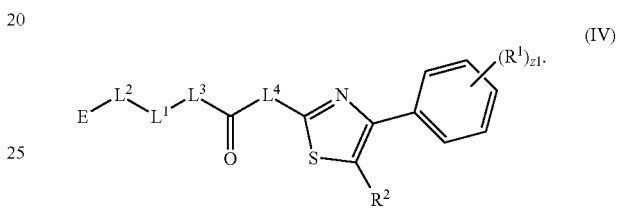

(IV)

$R^1$, $R^2$, $R^4$, $R^5$, $L^1$, $L^2$, $L^3$, $L^4$, E, and z1 are as described herein (e.g., for formulae I, II, III, and embodiments thereof or in examples, figures, tables, or claims). $L^4$ may be —N($R^4$)—. $L^4$ may be —CH$_2$N($R^4$)—. $L^3$ may be —N($R^5$)—. $L^3$ may be a bond. $L^4$ may be a bond. $R^4$ and $R^3$ may be hydrogen. $L^3$ may be unsubstituted methylene. $L^3$ may be unsubstituted ethylene. $L^3$ may be unsubstituted n-propylene. $L^3$ may be unsubstituted n-butylene. $R^2$ may be unsubstituted methyl. $R^2$ may be hydrogen.

In an aspect is provided a compound having the formula:

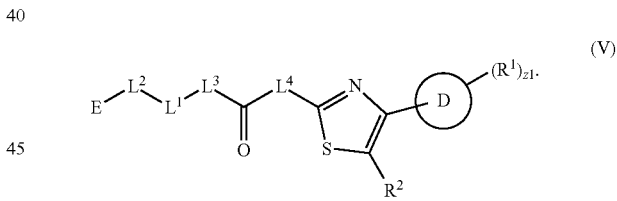

(V)

$R^1$, $R^2$, $R^4$, $R^5$, $L^1$, $L^2$, $L^3$, $L^4$, E, and z1 are as described herein (e.g., for formulae I, II, III, VI, and embodiments thereof or in examples, figures, tables, or claims). $L^4$ may be —N($R^4$)—. $L^4$ may be —N(H)—. $L^4$ may be —CH$_2$N($R^4$)—. $L^3$ may be —N($R^5$)—. $L^3$ may be —N(H)—. $L^3$ may be a bond. $L^4$ may be a bond. $R^4$ and $R^5$ may be hydrogen. $L^3$ may be unsubstituted methylene. $L^3$ may be unsubstituted ethylene. $L^3$ may be unsubstituted n-propylene. $L^3$ may be unsubstituted n-butylene. $R^2$ may be unsubstituted methyl. $R^2$ may be hydrogen. Ring D is cycloalkyl, heterocycloalkyl, aryl, or heteroaryl. In embodiments, Ring D is $C_3$-$C_8$ cycloalkyl, 3 to 8 membered heterocycloalkyl, $C_6$-$C_{10}$ aryl, or 5 to 10 membered heteroaryl. In embodiments, Ring D is $C_3$-$C_8$ cycloalkyl. In embodiments, Ring D is 3 to 8 membered heterocycloalkyl. In embodiments, Ring D is $C_6$-$C_{10}$ aryl. In embodiments, Ring D is 5 to 10 membered heteroaryl. In embodiments, Ring D is phenyl. In embodiments, Ring D is 5 to 9 membered heteroaryl. In embodiments, Ring D is 5 to 6 membered heteroaryl. In embodiments, Ring D is 5 membered heteroaryl. In embodiments, Ring D is 6 membered heteroaryl. In embodiments, Ring D is pyridyl. In embodiments, the compound is

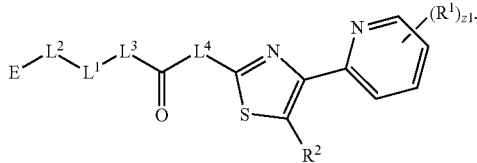

$R^1$, $R^2$, $R^4$, $R^5$, $L^1$, $L^2$, $L^3$, $L^4$, E, and z1 are as described herein (e.g., for formulae I, II, III, VI, and embodiments thereof or in examples, figures, tables, or claims). In embodiments, z1 is 0. In embodiments, the compound is

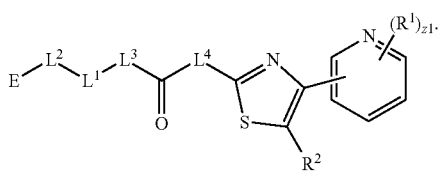

$R^1$, $R^2$, $R^4$, $R^5$, $L^1$, $L^2$, $L^3$, $L^4$, E, and z1 are as described herein (e.g., for formulae I, II, III, VI, and embodiments thereof or in examples, figures, tables, or claims).

In an aspect is provided a compound having the formula:

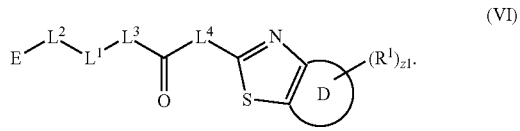

(VI)

$R^1$, $R^2$, $R^4$, $R^5$, $L^1$, $L^2$, $L^3$, $L^4$, E, and z1 are as described herein (e.g., for formulae I, II, III, IV, V, and embodiments thereof or in examples, figures, tables, or claims). $L^4$ may be —N($R^4$)—. $L^4$ may be —N(H)—. $L^4$ may be —CH$_2$N($R^4$)—. $L^3$ may be —N($R^5$)—. $L^3$ may be —N(H)—. $L^3$ may be a bond. $L^4$ may be a bond. $R^4$ and $R^5$ may be hydrogen. $L^3$ may be unsubstituted methylene. $L^3$ may be unsubstituted ethylene. $L^3$ may be unsubstituted n-propylene. $L^3$ may be unsubstituted n-butylene. $R^2$ may be unsubstituted methyl. $R^2$ may be hydrogen. Ring D is cycloalkyl, heterocycloalkyl, aryl, or heteroaryl. In embodiments, Ring D is $C_3$-$C_8$ cycloalkyl, 3 to 8 membered heterocycloalkyl, $C_6$-$C_{10}$ aryl, or 5 to 10 membered heteroaryl. In embodiments, Ring D is $C_3$-$C_8$ cycloalkyl. In embodiments, Ring D is 3 to 8 membered heterocycloalkyl. In embodiments, Ring D is $C_6$-$C_{10}$ aryl. In embodiments, Ring D is 5 to 10 membered heteroaryl. In embodiments, Ring D is phenyl. In embodiments, Ring D is 5 to 9 membered heteroaryl. In embodiments, Ring D is 5 to 6 membered heteroaryl. In embodiments, Ring D is 5 membered heteroaryl. In embodiments, Ring D is 6 membered heteroaryl. In embodiments, Ring D is pyridyl.

In embodiments, $R^1$ is independently hydrogen, oxo, halogen, —CX$^1_3$, —CHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^1_3$, —OCHX$^1_2$, $R^{30}$-substituted or unsubstituted alkyl (e.g., $C_1$-$C_8$, $C_1$-$C_6$, or $C_1$-$C_4$), $R^{30}$-substituted or unsubstituted heteroalkyl (e.g., 2 to 8 membered, 2 to 6 membered, or 2 to 4 membered), $R^{30}$-substituted or unsubstituted cycloalkyl (e.g., $C_3$-$C_5$, $C_3$-$C_6$, or $C_5$-$C_6$), $R^{30}$-substituted or unsubstituted heterocycloalkyl (e.g., 3 to 8 membered, 3 to 6 membered, or 5 to 6 membered), $R^{30}$-substituted or unsubstituted aryl (e.g., $C_6$-$C_{10}$, $C_{10}$, or phenyl), or $R^{30}$-substituted or unsubstituted heteroaryl (e.g., 5 to 10 membered, 5 to 9 membered, or 5 to 6 membered). In embodiments, $R^1$ is independently oxo, halogen, —CX$^1_3$, —CHX$^1_2$, —OCH$_2$X$^1$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^1_3$, —OCHX$^1_2$, $R^{30}$-substituted or unsubstituted alkyl (e.g., $C_1$-$C_8$, $C_1$-$C_6$, or $C_1$-$C_4$), $R^{30}$-substituted or unsubstituted heteroalkyl (e.g., 2 to 8 membered, 2 to 6 membered, or 2 to 4 membered), $R^{30}$-substituted or unsubstituted cycloalkyl (e.g., $C_3$-$C_5$, $C_3$-$C_6$, or $C_5$-$C_6$), $R^{30}$-substituted or unsubstituted heterocycloalkyl (e.g., 3 to 8 membered, 3 to 6 membered, or 5 to 6 membered), $R^{30}$-substituted or unsubstituted aryl (e.g., $C_6$-$C_{10}$, $C_{10}$, or phenyl), or $R^{30}$-substituted or unsubstituted heteroaryl (e.g., 5 to 10 membered, 5 to 9 membered, or 5 to 6 membered). $X^1$ is halogen. In embodiments, $X^1$ is F.

$R^{30}$ is independently oxo, halogen, —CX$^{30}_3$, —CHX$^{30}_2$, —OCH$_2$X$^{30}$, —OCHX$^{30}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{30}_3$, —OCHX$^{30}_2$, $R^{31}$-substituted or unsubstituted alkyl (e.g., $C_1$-$C_8$, $C_1$-$C_6$, or $C_1$-$C_4$), $R^{31}$-substituted or unsubstituted heteroalkyl (e.g., 2 to 8 membered, 2 to 6 membered, or 2 to 4 membered), $R^{31}$-substituted or unsubstituted cycloalkyl (e.g., $C_3$-$C_8$, $C_3$-$C_6$, or $C_5$-$C_6$), $R^{31}$-substituted or unsubstituted heterocycloalkyl (e.g., 3 to 8 membered, 3 to 6 membered, or 5 to 6 membered), $R^{31}$-substituted or unsubstituted aryl (e.g., $C_6$-$C_{10}$, $C_{10}$, or phenyl), or $R^{31}$-substituted or unsubstituted heteroaryl (e.g., 5 to 10 membered, 5 to 9 membered, or 5 to 6 membered). $X^{30}$ is halogen. In embodiments, $X^{30}$ is F.

$R^{31}$ is independently oxo, halogen, —CX$^{31}_3$, —CHX$^{31}_2$, —OCH$_2$X$^{31}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{31}_3$, —OCHX$^{31}_2$, $R^{32}$-substituted or unsubstituted alkyl (e.g., $C_1$-$C_5$, $C_1$-$C_6$, or $C_1$-$C_4$), $R^{32}$-substituted or unsubstituted heteroalkyl (e.g., 2 to 8 membered, 2 to 6 membered, or 2 to 4 membered), $R^{32}$-substituted or unsubstituted cycloalkyl (e.g., $C_3$-$C_8$, $C_3$-$C_6$, or $C_5$-$C_6$), $R^{32}$-substituted or unsubstituted heterocycloalkyl (e.g., 3 to 8 membered, 3 to 6 membered, or 5 to 6 membered), $R^{32}$-substituted or unsubstituted aryl (e.g., $C_6$-$C_{10}$, $C_{10}$, or phenyl), or $R^{32}$-substituted or unsubstituted heteroaryl (e.g., 5 to 10 membered, 5 to 9 membered, or 5 to 6 membered). $X^{31}$ is halogen. In embodiments, $X^{31}$ is F.

In embodiments, $R^2$ is independently hydrogen, oxo, halogen, —CX$^2_3$, —CHX$^2_2$, —OCH$_2$X$^2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^2_3$, —OCHX$^2_2$, $R^{33}$-substituted or unsubstituted alkyl (e.g., $C_1$-$C_8$, $C_1$-$C_6$, or $C_1$-$C_4$), $R^{33}$-substituted or unsubstituted heteroalkyl (e.g., 2 to 8 membered, 2 to 6 membered, or 2 to 4 membered), $R^{33}$-substituted or unsubstituted cycloalkyl (e.g., $C_3$-$C_8$, $C_3$-$C_6$, or $C_5$-$C_6$), $R^{33}$-substituted or unsubstituted heterocycloalkyl (e.g., 3 to 8 membered, 3 to 6 membered, or 5 to 6 membered), $R^{33}$-substituted or unsubstituted aryl (e.g., $C_6$-$C_{10}$, $C_{10}$, or phenyl), or $R^{33}$-substituted or unsubstituted heteroaryl (e.g., 5 to 10 membered, 5 to 9 membered, or 5 to 6 membered). In embodiments, $R^2$ is independently oxo, halogen, —$CX^2{}_3$, —$CHX^2{}_2$, —$OCH_2X^2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^2{}_3$, —$OCHX^2{}_2$, $R^{33}$-substituted or unsubstituted alkyl (e.g., $C_1$-$C_8$, $C_1$-$C_6$, or $C_1$-$C_4$), $R^{33}$-substituted or unsubstituted heteroalkyl (e.g., 2 to 8 membered, 2 to 6 membered, or 2 to 4 membered), $R^{33}$-substituted or unsubstituted cycloalkyl (e.g., $C_3$-$C_8$, $C_3$-$C_6$, or $C_5$-$C_6$), $R^{33}$-substituted or unsubstituted heterocycloalkyl (e.g., 3 to 8 membered, 3 to 6 membered, or 5 to 6 membered), $R^{33}$-substituted or unsubstituted aryl (e.g., $C_6$-$C_{10}$, Cm, or phenyl), or $R^{33}$-substituted or unsubstituted heteroaryl (e.g., 5 to 10 membered, 5 to 9 membered, or 5 to 6 membered). $X^2$ is halogen. In embodiments, $X^2$ is F.

$R^{33}$ is independently oxo, halogen, —$CX^{33}{}_3$, —$CHX^{33}{}_2$, —$OCH_2X^{33}$, —$OCHX^{33}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{33}{}_3$, —$OCHX^{33}{}_2$, $R^{34}$-substituted or unsubstituted alkyl (e.g., $C_1$-$C_8$, $C_1$-$C_6$, or $C_1$-$C_4$), $R^{34}$-substituted or unsubstituted heteroalkyl (e.g., 2 to 8 membered, 2 to 6 membered, or 2 to 4 membered), $R^{34}$-substituted or unsubstituted cycloalkyl (e.g., $C_3$-$C_8$, $C_3$-$C_6$, or $C_5$-$C_6$), $R^{34}$-substituted or unsubstituted heterocycloalkyl (e.g., 3 to 8 membered, 3 to 6 membered, or 5 to 6 membered), $R^{34}$-substituted or unsubstituted aryl (e.g., $C_6$-$C_{10}$, $C_{10}$, or phenyl), or $R^{34}$-substituted or unsubstituted heteroaryl (e.g., 5 to 10 membered, 5 to 9 membered, or 5 to 6 membered). $X^{33}$ is halogen. In embodiments, $X^{33}$ is F.

$R^{34}$ is independently oxo, halogen, —$CX^{34}{}_3$, —$CHX^{34}{}_2$, —$OCH_2X^{34}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{34}{}_3$, —$OCHX^{34}{}_2$, $R^{35}$-substituted or unsubstituted alkyl (e.g., $C_1$-$C_8$, $C_1$-$C_6$, or $C_1$-$C_4$), $R^{35}$-substituted or unsubstituted heteroalkyl (e.g., 2 to 8 membered, 2 to 6 membered, or 2 to 4 membered), $R^{35}$-substituted or unsubstituted cycloalkyl (e.g., $C_3$-$C_5$, $C_3$-$C_6$, or $C_5$-$C_6$), $R^{35}$-substituted or unsubstituted heterocycloalkyl (e.g., 3 to 8 membered, 3 to 6 membered, or 5 to 6 membered), $R^{35}$-substituted or unsubstituted aryl (e.g., $C_6$-$C_{10}$, $C_{10}$, or phenyl), or $R^{35}$-substituted or unsubstituted heteroaryl (e.g., 5 to 10 membered, 5 to 9 membered, or 5 to 6 membered). $X^{34}$ is halogen. In embodiments, $X^{34}$ is F.

In embodiments, $R^3$ is independently hydrogen, oxo, halogen, —$CX^3{}_3$, —$CHX^3{}_2$, —$OCH_2X^3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^3{}_3$, —$OCHX^3{}_2$, $R^{36}$-substituted or unsubstituted alkyl (e.g., $C_1$-$C_8$, $C_1$-$C_6$, or $C_1$-$C_4$), $R^{36}$-substituted or unsubstituted heteroalkyl (e.g., 2 to 8 membered, 2 to 6 membered, or 2 to 4 membered), $R^{36}$-substituted or unsubstituted cycloalkyl (e.g., $C_3$-$C_5$, $C_3$-$C_6$, or $C_5$-$C_6$), $R^{36}$-substituted or unsubstituted heterocycloalkyl (e.g., 3 to 8 membered, 3 to 6 membered, or 5 to 6 membered), $R^{36}$-substituted or unsubstituted aryl (e.g., $C_6$-$C_{10}$, $C_{10}$, or phenyl), or $R^{36}$-substituted or unsubstituted heteroaryl (e.g., 5 to 10 membered, 5 to 9 membered, or 5 to 6 membered). $X^3$ is halogen. In embodiments, $X^3$ is F.

$R^{36}$ is independently oxo, halogen, —$CX^{36}{}_3$, —$CHX^{36}{}_2$, —$OCH_2X^{36}$, —$OCHX^{36}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{36}{}_3$, —$OCHX^{36}{}_2$, $R^{37}$-substituted or unsubstituted alkyl (e.g., $C_1$-$C_8$, $C_1$-$C_6$, or $C_1$-$C_4$), $R^{37}$-substituted or unsubstituted heteroalkyl (e.g., 2 to 8 membered, 2 to 6 membered, or 2 to 4 membered), $R^{37}$-substituted or unsubstituted cycloalkyl (e.g., $C_3$-$C_8$, $C_3$-$C_6$, or $C_5$-$C_6$), $R^{37}$-substituted or unsubstituted heterocycloalkyl (e.g., 3 to 8 membered, 3 to 6 membered, or 5 to 6 membered), $R^{37}$-substituted or unsubstituted aryl (e.g., $C_6$-$C_{10}$, $C_{10}$, or phenyl), or $R^{37}$-substituted or unsubstituted heteroaryl (e.g., 5 to 10 membered, 5 to 9 membered, or 5 to 6 membered). $X^{36}$ is halogen. In embodiments, $X^{36}$ is F.

$R^{37}$ is independently oxo, halogen, —$CX^{37}{}_3$, —$CHX^{37}{}_2$, —$OCH_2X^{37}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{37}{}_3$, —$OCHX^{37}{}_2$, $R^{38}$-substituted or unsubstituted alkyl (e.g., $C_1$-$C_8$, $C_1$-$C_6$, or $C_1$-$C_4$), $R^{38}$-substituted or unsubstituted heteroalkyl (e.g., 2 to 8 membered, 2 to 6 membered, or 2 to 4 membered), $R^{38}$-substituted or unsubstituted cycloalkyl (e.g., $C_3$-$C_5$, $C_3$-$C_6$, or $C_5$-$C_6$), $R^{38}$-substituted or unsubstituted heterocycloalkyl (e.g., 3 to 8 membered, 3 to 6 membered, or 5 to 6 membered), $R^{38}$-substituted or unsubstituted aryl (e.g., $C_6$-$C_{10}$, $C_{10}$, or phenyl), or $R^{38}$-substituted or unsubstituted heteroaryl (e.g., 5 to 10 membered, 5 to 9 membered, or 5 to 6 membered). $X^{37}$ is halogen. In embodiments, $X^{37}$ is F.

In embodiments, $R^4$ is independently hydrogen, oxo, halogen, —$CX^1{}_3$, —$CHX^1{}_2$, —$OCH_2X^4$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^1{}_3$, —$OCHX^1{}_2$, $R^{39}$-substituted or unsubstituted alkyl (e.g., $C_1$-$C_8$, $C_1$-$C_6$, or $C_1$-$C_4$), $R^{39}$-substituted or unsubstituted heteroalkyl (e.g., 2 to 8 membered, 2 to 6 membered, or 2 to 4 membered), $R^{39}$-substituted or unsubstituted cycloalkyl (e.g., $C_3$-$C_5$, $C_3$-$C_6$, or $C_5$-$C_6$), $R^{39}$-substituted or unsubstituted heterocycloalkyl (e.g., 3 to 8 membered, 3 to 6 membered, or 5 to 6 membered), $R^{39}$-substituted or unsubstituted aryl (e.g., $C_6$-$C_{10}$, $C_{10}$, or phenyl), or $R^{39}$-substituted or unsubstituted heteroaryl (e.g., 5 to 10 membered, 5 to 9 membered, or 5 to 6 membered). $X^4$ is halogen. In embodiments, $X^4$ is F.

$R^{39}$ is independently oxo, halogen, —$CX^{39}{}_3$, —$CHX^{39}{}_2$, —$OCH_2X^{39}$, —$OCHX^{39}{}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{39}{}_3$, —$OCHX^{39}{}_2$, $R^{40}$-substituted or unsubstituted alkyl (e.g., $C_1$-$C_8$, $C_1$-$C_6$, or $C_1$-$C_4$), $R^{40}$-substituted or unsubstituted heteroalkyl (e.g., 2 to 8 membered, 2 to 6 membered, or 2 to 4 membered), $R^{40}$-substituted or unsubstituted cycloalkyl (e.g., $C_3$-$C_8$, $C_3$-$C_6$, or $C_5$-$C_6$), $R^{40}$-substituted or unsubstituted heterocycloalkyl (e.g., 3 to 8 membered, 3 to 6 membered, or 5 to 6 membered), $R^{40}$-substituted or unsubstituted aryl (e.g., $C_6$-$C_{10}$, $C_{10}$, or phenyl), or $R^{4U}$-substituted or unsubstituted heteroaryl (e.g., 5 to 10 membered, 5 to 9 membered, or 5 to 6 membered). $X^{39}$ is halogen. In embodiments, $X^{39}$ is F.

$R^{40}$ is independently oxo, halogen, $-CX^{40}_3$, $-CHX^{40}_2$, $-OCH_2X^{40}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{40}_3$, $-OCHX^{40}_2$, $R^{41}$-substituted or unsubstituted alkyl (e.g., $C_1$-$C_8$, $C_3$-$C_6$, or $C_1$-$C_4$), $R^{41}$-substituted or unsubstituted heteroalkyl (e.g., 2 to 8 membered, 2 to 6 membered, or 2 to 4 membered), $R^{41}$-substituted or unsubstituted cycloalkyl (e.g., $C_3$-$C_8$, $C_3$-$C_6$, or $C_5$-$C_6$), $R^{41}$-substituted or unsubstituted heterocycloalkyl (e.g., 3 to 8 membered, 3 to 6 membered, or 5 to 6 membered), $R^{41}$-substituted or unsubstituted aryl (e.g., $C_6$-$C_{10}$, $C_{10}$, or phenyl), or $R^{41}$-substituted or unsubstituted heteroaryl (e.g., 5 to 10 membered, 5 to 9 membered, or 5 to 6 membered). $X^{40}$ is halogen. In embodiments, $X^{40}$ is F.

In embodiments, $R^5$ is independently hydrogen, oxo, halogen, $-CX^5_3$, $-CHX^5_2$, $-OCH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^5_3$, $-OCHX^5_2$, $R^{42}$-substituted or unsubstituted alkyl (e.g., $C_1$-$C_8$, $C_1$-$C_6$, or $C_1$-$C_4$), $R^{42}$-substituted or unsubstituted heteroalkyl (e.g., 2 to 8 membered, 2 to 6 membered, or 2 to 4 membered), $R^{42}$-substituted or unsubstituted cycloalkyl (e.g., $C_3$-$C_8$, $C_3$-$C_6$, or $C_5$-$C_6$), $R^{42}$-substituted or unsubstituted heterocycloalkyl (e.g., 3 to 8 membered, 3 to 6 membered, or 5 to 6 membered), $R^{42}$-substituted or unsubstituted aryl (e.g., $C_6$-$C_{10}$, $C_{10}$, or phenyl), or $R^{42}$-substituted or unsubstituted heteroaryl (e.g., 5 to 10 membered, 5 to 9 membered, or 5 to 6 membered). $X^5$ is halogen. In embodiments, $X^5$ is F.

$R^{42}$ is independently oxo, halogen, $-CX^{42}_3$, $-CHX^{42}_2$, $-OCH_2X^{42}$, $-OCHX^{42}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{42}_3$, $-OCHX^{42}_2$, $R^{43}$-substituted or unsubstituted alkyl (e.g., $C_1$-$C_8$, $C_1$-$C_6$, or $C_1$-$C_4$), $R^{43}$-substituted or unsubstituted heteroalkyl (e.g., 2 to 8 membered, 2 to 6 membered, or 2 to 4 membered), $R^{43}$-substituted or unsubstituted cycloalkyl (e.g., $C_3$-$C_8$, $C_3$-$C_6$, or $C_5$-$C_6$), $R^{43}$-substituted or unsubstituted heterocycloalkyl (e.g., 3 to 8 membered, 3 to 6 membered, or 5 to 6 membered), $R^{43}$-substituted or unsubstituted aryl (e.g., $C_6$-$C_{10}$, $C_{10}$, or phenyl), or $R^{43}$-substituted or unsubstituted heteroaryl (e.g., 5 to 10 membered, 5 to 9 membered, or 5 to 6 membered). $X^{42}$ is halogen. In embodiments, $X^{42}$ is F.

$R^{43}$ is independently oxo, halogen, $-CX^{43}_3$, $-CHX^{43}_2$, $-OCH_2X^{43}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{43}_3$, $-OCHX^{43}_2$, $R^{44}$-substituted or unsubstituted alkyl (e.g., $C_1$-$C_8$, $C_1$-$C_6$, or $C_1$-$C_4$), $R^{44}$-substituted or unsubstituted heteroalkyl (e.g., 2 to 8 membered, 2 to 6 membered, or 2 to 4 membered), $R^{44}$-substituted or unsubstituted cycloalkyl (e.g., $C_3$-$C_8$, $C_3$-$C_6$, or $C_5$-$C_6$), $R^{44}$-substituted or unsubstituted heterocycloalkyl (e.g., 3 to 8 membered, 3 to 6 membered, or 5 to 6 membered), $R^{44}$-substituted or unsubstituted aryl (e.g., $C_6$-$C_{10}$, $C_{10}$, or phenyl), or $R^{44}$-substituted or unsubstituted heteroaryl (e.g., 5 to 10 membered, 5 to 9 membered, or 5 to 6 membered). $X^{43}$ is halogen. In embodiments, $X^{43}$ is F.

In embodiments, $R^6$ is independently hydrogen, oxo, halogen, $-CX^6_3$, $-CHX^6_2$, $-OCH_2X^6$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^6_3$, $-OCHX^6_2$, $R^{45}$-substituted or unsubstituted alkyl (e.g., $C_1$-$C_8$, $C_3$-$C_6$, or $C_1$-$C_4$), $R^{45}$-substituted or unsubstituted heteroalkyl (e.g., 2 to 8 membered, 2 to 6 membered, or 2 to 4 membered), $R^{45}$-substituted or unsubstituted cycloalkyl (e.g., $C_3$-$C_8$, $C_3$-$C_6$, or $C_5$-$C_6$), $R^{45}$-substituted or unsubstituted heterocycloalkyl (e.g., 3 to 8 membered, 3 to 6 membered, or 5 to 6 membered), $R^{45}$-substituted or unsubstituted aryl (e.g., $C_6$-$C_{10}$, $C_{10}$, or phenyl), or $R^{45}$-substituted or unsubstituted heteroaryl (e.g., 5 to 10 membered, 5 to 9 membered, or 5 to 6 membered). $X^6$ is halogen. In embodiments, $X^6$ is F.

$R^{45}$ is independently oxo, halogen, $-CX^{45}_3$, $-CHX^{45}_2$, $-OCH_2X^{45}$, $-OCHX^{45}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{45}_3$, $-OCHX^{45}_2$, $R^{46}$-substituted or unsubstituted alkyl (e.g., $C_1$-$C_8$, $C_1$-$C_6$, or $C_1$-$C_4$), $R^{46}$-substituted or unsubstituted heteroalkyl (e.g., 2 to 8 membered, 2 to 6 membered, or 2 to 4 membered), $R^{46}$-substituted or unsubstituted cycloalkyl (e.g., $C_3$-$C_8$, $C_3$-$C_6$, or $C_5$-$C_6$), $R^{46}$-substituted or unsubstituted heterocycloalkyl (e.g., 3 to 8 membered, 3 to 6 membered, or 5 to 6 membered), $R^{46}$-substituted or unsubstituted aryl (e.g., $C_6$-$C_{10}$, $C_{10}$, or phenyl), or $R^{46}$-substituted or unsubstituted heteroaryl (e.g., 5 to 10 membered, 5 to 9 membered, or 5 to 6 membered). $X^{45}$ is halogen. In embodiments, $X^{45}$ is F.

$R^{46}$ is independently oxo, halogen, $-CX^{46}_3$, $-CHX^{46}_2$, $-OCH_2X^{46}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{46}_3$, $-OCHX^{46}_2$, $R^{47}$-substituted or unsubstituted alkyl (e.g., $C_1$-$C_5$, $C_1$-$C_6$, or $C_1$-$C_4$), $R^{47}$-substituted or unsubstituted heteroalkyl (e.g., 2 to 8 membered, 2 to 6 membered, or 2 to 4 membered), $R^{47}$-substituted or unsubstituted cycloalkyl (e.g., $C_3$-$C_8$, $C_3$-$C_6$, or $C_5$-$C_6$), $R^{47}$-substituted or unsubstituted heterocycloalkyl (e.g., 3 to 8 membered, 3 to 6 membered, or 5 to 6 membered), $R^{47}$-substituted or unsubstituted aryl (e.g., $C_6$-$C_{10}$, $C_{10}$, or phenyl), or $R^{47}$-substituted or unsubstituted heteroaryl (e.g., 5 to 10 membered, 5 to 9 membered, or 5 to 6 membered). $X^{46}$ is halogen. In embodiments, $X^{46}$ is F.

In embodiments, $R^7$ is independently hydrogen, oxo, halogen, $-CX^7_3$, $-CHX^7_2$, $-OCH_2X^7$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^7_3$, $-OCHX^7_2$, $R^{48}$-substituted or unsubstituted alkyl (e.g., $C_1$-$C_8$, $C_1$-$C_6$, or $C_1$-$C_4$), $R^{48}$-substituted or unsubstituted heteroalkyl (e.g., 2 to 8 membered, 2 to 6 membered, or 2 to 4 membered), $R^{48}$-substituted or unsubstituted cycloalkyl (e.g., $C_3$-$C_5$, $C_3$-$C_6$, or $C_5$-$C_6$), $R^{48}$-substituted or unsubstituted heterocycloalkyl (e.g., 3 to 8 membered, 3 to 6 membered, or 5 to 6 membered), $R^{48}$-substituted or unsubstituted aryl (e.g., $C_6$-$C_{10}$, $C_{10}$, or phenyl), or $R^{48}$-substituted or unsubstituted heteroaryl (e.g., 5 to 10 membered, 5 to 9 membered, or 5 to 6 membered). $X^7$ is halogen. In embodiments, $X^7$ is F.

$R^{48}$ is independently oxo, halogen, $-CX^{48}_3$, $-CHX^{48}_2$, $-OCH_2X^{48}$, $-OCHX^{48}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{48}_3$, $-OCHX^{48}_2$, $R^{49}$-substituted or unsubstituted alkyl (e.g., $C_1$-$C_8$, $C_1$-$C_6$, or $C_1$-$C_4$), $R^{49}$-substituted or unsubstituted heteroalkyl (e.g., 2 to 8 membered, 2 to 6 membered, or 2 to 4 membered), $R^{49}$-substituted or unsubstituted cycloalkyl (e.g., $C_3$-$C_8$, $C_3$-$C_6$, or $C_5$-$C_6$), $R^{49}$-substituted or unsubstituted heterocycloalkyl (e.g., 3 to 8 membered, 3 to 6 membered, or 5 to 6 membered), $R^{49}$-substituted or unsubstituted aryl (e.g., $C_6$-$C_{10}$, $C_{10}$, or phenyl), or $R^{49}$-substituted or unsubstituted heteroaryl (e.g., 5 to 10 membered, 5 to 9 membered, or 5 to 6 membered). $X^{48}$ is halogen. In embodiments, $X^{48}$ is F.

$R^{49}$ is independently oxo, halogen, —$CX^{49}_3$, —$CHX^{49}_2$, —$OCH_2X^{49}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{49}_3$, —$OCHX^{49}_2$, $R^{50}$-substituted or unsubstituted alkyl (e.g., $C_1$-$C_5$, $C_1$-$C_6$, or $C_1$-$C_4$), $R^{50}$-substituted or unsubstituted heteroalkyl (e.g., 2 to 8 membered, 2 to 6 membered, or 2 to 4 membered), $R^{50}$-substituted or unsubstituted cycloalkyl (e.g., $C_3$-$C_8$, $C_3$-$C_6$, or $C_5$-$C_6$), $R^{50}$-substituted or unsubstituted heterocycloalkyl (e.g., 3 to 8 membered, 3 to 6 membered, or 5 to 6 membered), $R^{50}$-substituted or unsubstituted aryl (e.g., $C_6$-$C_{10}$, $C_{10}$, or phenyl), or $R^{50}$-substituted or unsubstituted heteroaryl (e.g., 5 to 10 membered, 5 to 9 membered, or 5 to 6 membered). $X^{49}$ is halogen. In embodiments, $X^{49}$ is F.

In embodiments, $R^8$ is independently hydrogen, oxo, halogen, —$CX^8_3$, —$CHX^8_2$, —$OCH_2X^8$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^8_3$, —$OCHX^8_2$, $R^{51}$-substituted or unsubstituted alkyl (e.g., $C_1$-$C_8$, $C_1$-$C_6$, or $C_1$-$C_4$), $R^{51}$-substituted or unsubstituted heteroalkyl (e.g., 2 to 8 membered, 2 to 6 membered, or 2 to 4 membered), $R^{71}$-substituted or unsubstituted cycloalkyl (e.g., $C_3$-$C_8$, $C_3$-$C_6$, or $C_5$-$C_6$), $R^{51}$-substituted or unsubstituted heterocycloalkyl (e.g., 3 to 8 membered, 3 to 6 membered, or 5 to 6 membered), $R^{51}$-substituted or unsubstituted aryl (e.g., $C_6$-$C_{10}$, $C_{10}$, or phenyl), or $R^{51}$-substituted or unsubstituted heteroaryl (e.g., 5 to 10 membered, 5 to 9 membered, or 5 to 6 membered). $X^8$ is halogen. In embodiments, $X^8$ is F.

$R^{51}$ is independently oxo, halogen, —$CX^{51}_3$, —$CHX^{51}_2$, —$OCH_2X^{51}$, —$OCHX^{51}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{51}_3$, —$OCHX^{51}_2$, $R^{52}$-substituted or unsubstituted alkyl (e.g., $C_3$-$C_8$, $C_1$-$C_6$, or $C_1$-$C_4$), $R^{52}$-substituted or unsubstituted heteroalkyl (e.g., 2 to 8 membered, 2 to 6 membered, or 2 to 4 membered), $R^{52}$-substituted or unsubstituted cycloalkyl (e.g., $C_3$-$C_8$, $C_3$-$C_6$, or $C_5$-$C_6$), $R^{52}$-substituted or unsubstituted heterocycloalkyl (e.g., 3 to 8 membered, 3 to 6 membered, or 5 to 6 membered), $R^{52}$-substituted or unsubstituted aryl (e.g., $C_6$-$C_{10}$, $C_{10}$, or phenyl), or $R^{52}$-substituted or unsubstituted heteroaryl (e.g., 5 to 10 membered, 5 to 9 membered, or 5 to 6 membered). $X^{51}$ is halogen. In embodiments, $X^{51}$ is F.

$R^{52}$ is independently oxo, halogen, —$CX^{52}_3$, —$CHX^{52}_2$, —$OCH_2X^{52}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{52}_3$, —$OCHX^{52}_2$, $R^{53}$-substituted or unsubstituted alkyl (e.g., $C_1$-$C_5$, $C_1$-$C_6$, or $C_1$-$C_4$), $R^{53}$-substituted or unsubstituted heteroalkyl (e.g., 2 to 8 membered, 2 to 6 membered, or 2 to 4 membered), $R^{53}$-substituted or unsubstituted cycloalkyl (e.g., $C_3$-$C_8$, $C_3$-$C_6$, or $C_5$-$C_6$), $R^{53}$-substituted or unsubstituted heterocycloalkyl (e.g., 3 to 8 membered, 3 to 6 membered, or 5 to 6 membered), $R^{53}$-substituted or unsubstituted aryl (e.g., $C_6$-$C_{10}$, $C_{10}$, or phenyl), or $R^{53}$-substituted or unsubstituted heteroaryl (e.g., 5 to 10 membered, 5 to 9 membered, or 5 to 6 membered). $X^{52}$ is halogen. In embodiments, $X^{52}$ is F.

In embodiments, $R^9$ is independently hydrogen, oxo, halogen, —$CX^9_3$, —$CHX^9_2$, —$OCH_2X^9$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^9_3$, —$OCHX^9_2$, $R^{54}$-substituted or unsubstituted alkyl (e.g., $C_1$-$C_8$, $C_1$-$C_6$, or $C_1$-$C_4$), $R^{54}$-substituted or unsubstituted heteroalkyl (e.g., 2 to 8 membered, 2 to 6 membered, or 2 to 4 membered), $R^{54}$-substituted or unsubstituted cycloalkyl (e.g., $C_3$-$C_8$, $C_3$-$C_6$, or $C_5$-$C_6$), $R^{54}$-substituted or unsubstituted heterocycloalkyl (e.g., 3 to 8 membered, 3 to 6 membered, or 5 to 6 membered), $R^{54}$-substituted or unsubstituted aryl (e.g., $C_6$-$C_{10}$, $C_{10}$, or phenyl), or $R^{54}$-substituted or unsubstituted heteroaryl (e.g., 5 to 10 membered, 5 to 9 membered, or 5 to 6 membered). $X^9$ is halogen. In embodiments, $X^9$ is F.

$R^{54}$ is independently oxo, halogen, —$CX^{54}_3$, —$CHX^{54}_2$, —$OCH_2X^{54}$, —$OCHX^{54}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{54}_3$, —$OCHX^{54}_2$, $R^{55}$-substituted or unsubstituted alkyl (e.g., $C_1$-$C_8$, $C_1$-$C_6$, or $C_1$-$C_4$), $R^{55}$-substituted or unsubstituted heteroalkyl (e.g., 2 to 8 membered, 2 to 6 membered, or 2 to 4 membered), $R^{55}$-substituted or unsubstituted cycloalkyl (e.g., $C_3$-$C_8$, $C_3$-$C_6$, or $C_5$-$C_6$), $R^{55}$-substituted or unsubstituted heterocycloalkyl (e.g., 3 to 8 membered, 3 to 6 membered, or 5 to 6 membered), $R^{55}$-substituted or unsubstituted aryl (e.g., $C_6$-$C_{10}$, $C_{10}$, or phenyl), or $R^{55}$-substituted or unsubstituted heteroaryl (e.g., 5 to 10 membered, 5 to 9 membered, or 5 to 6 membered). $X^{54}$ is halogen. In embodiments, $X^{54}$ is F.

$R^{55}$ is independently oxo, halogen, —$CX^{55}_3$, —$CHX^{55}_2$, —$OCH_2X^{55}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{55}_3$, —$OCHX^{55}_2$, $R^{56}$-substituted or unsubstituted alkyl (e.g., $C_1$-$C_8$, $C_1$-$C_6$, or $C_1$-$C_4$), $R^{56}$-substituted or unsubstituted heteroalkyl (e.g., 2 to 8 membered, 2 to 6 membered, or 2 to 4 membered), $R^{56}$-substituted or unsubstituted cycloalkyl (e.g., $C_3$-$C_8$, $C_3$-$C_6$, or $C_5$-$C_6$), $R^{56}$-substituted or unsubstituted heterocycloalkyl (e.g., 3 to 8 membered, 3 to 6 membered, or 5 to 6 membered), $R^{56}$-substituted or unsubstituted aryl (e.g., $C_6$-$C_{10}$, $C_{10}$, or phenyl), or $R^{56}$-substituted or unsubstituted heteroaryl (e.g., 5 to 10 membered, 5 to 9 membered, or 5 to 6 membered). $X^{55}$ is halogen. In embodiments, $X^{55}$ is F.

In embodiments, $R^{10}$ is independently hydrogen, oxo, halogen, —$CX^{10}_m$, —$CHX^{10}_2$, —$OCH_2X^{10}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{10}_3$, —$OCHX^{10}_2$, $R^{57}$-substituted or unsubstituted alkyl (e.g., $C_1$-$C_5$, $C_1$-$C_6$, or $C_1$-$C_4$), $R^{57}$-substituted or unsubstituted heteroalkyl (e.g., 2 to 8 membered, 2 to 6 membered, or 2 to 4 membered), $R^{57}$-substituted or unsubstituted cycloalkyl (e.g., $C_3$-$C_8$, $C_3$-$C_6$, or $C_5$-$C_6$), $R^{57}$-substituted or unsubstituted heterocycloalkyl (e.g., 3 to 8 membered, 3 to 6 membered, or 5 to 6 membered), $R^{57}$-substituted or unsubstituted aryl (e.g., $C_6$-$C_{10}$, $C_{10}$, or phenyl), or $R^{57}$-substituted or unsubstituted heteroaryl (e.g., 5 to 10 membered, 5 to 9 membered, or 5 to 6 membered). $X^{10}$ is halogen. In embodiments, $X^{10}$ is F.

$R^{57}$ is independently oxo, halogen, —$CX^{57}_3$, —$CHX^{57}_2$, —$OCH_2X^{57}$, —$OCHX^{57}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{57}_3$, —$OCHX^{57}_2$, $R^{58}$-substituted or unsubstituted alkyl (e.g., $C_1$-$C_8$, $C_1$-$C_6$, or $C_1$-$C_4$), $R^{58}$-substituted or unsubstituted heteroalkyl (e.g., 2 to 8 membered, 2 to 6 membered, or 2 to 4 membered), $R^{58}$-substituted or unsubstituted cycloalkyl (e.g., $C_3$-$C_8$, $C_3$-$C_6$, or $C_5$-$C_6$), $R^{58}$-substituted or unsubstituted heterocycloalkyl (e.g., 3 to 8 membered, 3 to 6 membered, or 5 to 6 membered), $R^{58}$-substituted or unsubstituted aryl (e.g., $C_6$-$C_{10}$, $C_{10}$, or phenyl), or $R^{58}$-substituted or unsubstituted heteroaryl (e.g., 5 to 10 membered, 5 to 9 membered, or 5 to 6 membered). $X^{57}$ is halogen. In embodiments, $X^{57}$ is F.

$R^{58}$ is independently oxo, halogen, —$CX^{58}_3$, —$CHX^{58}_2$, —$OCH_2X^{58}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{58}_3$, —$OCHX^{58}_2$, $R^{59}$-substituted or unsubstituted alkyl (e.g., $C_1$-$C_8$, $C_1$-$C_6$, or $C_1$-$C_4$), $R^{59}$-substituted or unsubstituted heteroalkyl (e.g., 2 to 8 membered, 2 to 6 membered, or 2 to 4 membered), $R^{59}$-substituted or unsubstituted cycloalkyl (e.g., $C_3$-$C_5$, $C_3$-$C_6$, or $C_5$-$C_6$), $R^{59}$-substituted or unsubstituted heterocycloalkyl (e.g., 3 to 8 membered, 3 to 6 membered, or 5 to 6 membered), $R^{59}$-substituted or unsubstituted aryl (e.g., $C_6$-$C_{10}$, $C_{10}$, or phenyl), or $R^{59}$-substituted or unsubstituted heteroaryl (e.g., 5 to 10 membered, 5 to 9 membered, or 5 to 6 membered). $X^{58}$ is halogen. In embodiments, $X^{58}$ is F.

In embodiments, $R^{7A}$ is independently hydrogen, oxo, halogen, —$CX^{7A}_3$, —$CHX^{7A}_2$, —$OCH_2X^{7A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{7A}_3$, —$OCHX^{7A}_2$, $R^{48A}$-substituted or unsubstituted alkyl (e.g., $C_1$-$C_8$, $C_1$-$C_6$, or $C_1$-$C_4$), $R^{48A}$-substituted or unsubstituted heteroalkyl (e.g., 2 to 8 membered, 2 to 6 membered, or 2 to 4 membered), $R^{48A}$-substituted or unsubstituted cycloalkyl (e.g., $C_3$-$C_8$, $C_3$-$C_6$, or $C_5$-$C_6$), $R^{48A}$-substituted or unsubstituted heterocycloalkyl (e.g., 3 to 8 membered, 3 to 6 membered, or 5 to 6 membered), $R^{48A}$-substituted or unsubstituted aryl (e.g., $C_6$-$C_{10}$, $C_{10}$, or phenyl), or $R^{48A}$-substituted or unsubstituted heteroaryl (e.g., 5 to 9 membered, or 5 to 6 membered). In embodiments, $R^{7A}$ is independently oxo, halogen, —$CX^{7A}_3$, —$CHX^{7A}_2$, —$OCH_2X^{7A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{7A}_3$, —$OCHX^{7A}_2$, $R^{48A}$-substituted or unsubstituted alkyl (e.g., $C_1$-$C_8$, $C_1$-$C_6$, or $C_1$-$C_4$), $R^{48A}$-substituted or unsubstituted heteroalkyl (e.g., 2 to 8 membered, 2 to 6 membered, or 2 to 4 membered), $R^{48A}$-substituted or unsubstituted cycloalkyl (e.g., $C_3$-$C_8$, $C_3$-$C_6$, or $C_5$-$C_6$), $R^{48A}$-substituted or unsubstituted heterocycloalkyl (e.g., 3 to 8 membered, 3 to 6 membered, or 5 to 6 membered), $R^{48A}$-substituted or unsubstituted aryl (e.g., $C_6$-$C_{10}$, $C_{10}$, or phenyl), or $R^{48A}$-substituted or unsubstituted heteroaryl (e.g., 5 to 10 membered, 5 to 9 membered, or 5 to 6 membered). $X^{7A}$ is halogen. In embodiments, $X^{7A}$ is F.

$R^{48A}$ is independently oxo, halogen, —$CX^{48A}_3$, —$CHX^{48A}_2$, —$OCH_2X^{48A}$, —$OCHX^{48A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{48A}_3$, —$OCHX^{48A}_2$, $R^{49A}$-substituted or unsubstituted alkyl (e.g., $C_1$-$C_8$, $C_1$-$C_6$, or $C_1$-$C_4$), $R^{49A}$-substituted or unsubstituted heteroalkyl (e.g., 2 to 8 membered, 2 to 6 membered, or 2 to 4 membered), $R^{49A}$-substituted or unsubstituted cycloalkyl (e.g., $C_3$-$C_8$, $C_3$-$C_6$, or $C_5$-$C_6$), $R^{49A}$-substituted or unsubstituted heterocycloalkyl (e.g., 3 to 8 membered, 3 to 6 membered, or 5 to 6 membered), $R^{49A}$-substituted or unsubstituted aryl (e.g., $C_6$-$C_{10}$, $C_{10}$, or phenyl), or $R^{49A}$-substituted or unsubstituted heteroaryl (e.g., 5 to 10 membered, 5 to 9 membered, or 5 to 6 membered). $X^{48A}$ is halogen. In embodiments, $X^{48A}$ is F.

$R^{49A}$ is independently oxo, halogen, —$CX^{49A}_3$, —$CHX^{49A}_2$, —$OCH_2X^{49A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{49A}_3$, —$OCHX^{49A}_2$, $R^{50A}$-substituted or unsubstituted alkyl (e.g., $C_1$-$C_8$, $C_1$-$C_6$, or $C_1$-$C_4$), $R^{50A}$-substituted or unsubstituted heteroalkyl (e.g., 2 to 8 membered, 2 to 6 membered, or 2 to 4 membered), $R^{50A}$-substituted or unsubstituted cycloalkyl (e.g., $C_3$-$C_8$, $C_3$-$C_6$, or $C_5$-$C_6$), $R^{50A}$-substituted or unsubstituted heterocycloalkyl (e.g., 3 to 8 membered, 3 to 6 membered, or 5 to 6 membered), $R^{50A}$-substituted or unsubstituted aryl (e.g., $C_6$-$C_{10}$, $C_{10}$, or phenyl), or $R^{50A}$-substituted or unsubstituted heteroaryl (e.g., 5 to 10 membered, 5 to 9 membered, or 5 to 6 membered). $X^{49A}$ is halogen. In embodiments, $X^{49A}$ is F.

In embodiments, $R^{8A}$ is independently hydrogen, oxo, halogen, —$CX^{8A}_3$, —$CHX^{8A}_2$, —$OCH_2X^{8A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{8A}_3$, —$OCHX^{8A}_2$, $R^{51A}$-substituted or unsubstituted alkyl (e.g., $C_1$-$C_8$, $C_1$-$C_6$, or $C_1$-$C_4$), $R^{51A}$-substituted or unsubstituted heteroalkyl (e.g., 2 to 8 membered, 2 to 6 membered, or 2 to 4 membered), $R^{51A}$-substituted or unsubstituted cycloalkyl (e.g., $C_3$-$C_8$, $C_3$-$C_6$, or $C_5$-$C_6$), $R^{71A}$-substituted or unsubstituted heterocycloalkyl (e.g., 3 to 8 membered, 3 to 6 membered, or 5 to 6 membered), $R^{51A}$-substituted or unsubstituted aryl (e.g., $C_6$-$C_{10}$, $C_{10}$, or phenyl), or $R^{51A}$-substituted or unsubstituted heteroaryl (e.g., 5 to 10 membered, 5 to 9 membered, or 5 to 6 membered). $X^{8A}$ is halogen. In embodiments, $X^{8A}$ is F.

$R^{51A}$ is independently oxo, halogen, —$CX^{51A}_3$, —$CHX^{51A}_2$, —$OCH_2X^{51A}$, —$OCHX^{51A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{51A}_3$, —$OCHX^{51A}_2$, $R^{52A}$-substituted or unsubstituted alkyl (e.g., $C_1$-$C_8$, $C_1$-$C_6$, or $C_1$-$C_4$), $R^{52A}$-substituted or unsubstituted heteroalkyl (e.g., 2 to 8 membered, 2 to 6 membered, or 2 to 4 membered), $R^{52A}$-substituted or unsubstituted cycloalkyl (e.g., $C_3$-$C_8$, $C_3$-$C_6$, or $C_5$-$C_6$), $R^{52A}$-substituted or unsubstituted heterocycloalkyl (e.g., 3 to 8 membered, 3 to 6 membered, or 5 to 6 membered), $R^{52A}$-substituted or unsubstituted aryl (e.g., $C_6$-$C_{10}$, $C_{10}$, or phenyl), or $R^{52A}$-substituted or unsubstituted heteroaryl (e.g., 5 to 10 membered, 5 to 9 membered, or 5 to 6 membered). $X^{51A}$ is halogen. In embodiments, $X^{51A}$ is F.

$R^{52A}$ is independently oxo, halogen, $-CX^{52A}_3$, $-CHX^{52A}_2$, $-OCH_2X^{52A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{52A}_3$, $-OCHX^{52A}_2$, $R^{53A}$-substituted or unsubstituted alkyl (e.g., $C_1$-$C_8$, $C_1$-$C_6$, or $C_1$-$C_4$), $R^{53A}$-substituted or unsubstituted heteroalkyl (e.g., 2 to 8 membered, 2 to 6 membered, or 2 to 4 membered), $R^{53A}$-substituted or unsubstituted cycloalkyl (e.g., $C_3$-$C_8$, $C_3$-$C_6$, or $C_5$-$C_6$), $R^{53A}$-substituted or unsubstituted heterocycloalkyl (e.g., 3 to 8 membered, 3 to 6 membered, or 5 to 6 membered), $R^{53A}$-substituted or unsubstituted aryl (e.g., $C_6$-$C_{10}$, $C_{10}$, or phenyl), or $R^{53A}$-substituted or unsubstituted heteroaryl (e.g., 5 to 10 membered, 5 to 9 membered, or 5 to 6 membered). $X^{52A}$ is halogen. In embodiments, $X^{52A}$ is F.

In embodiments, $R^{9A}$ is independently hydrogen, oxo, halogen, $-CX^{9A}_3$, $-CHX^{9A}_2$, $-OCH_2X^{9A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{9A}_3$, $-OCHX^{9A}_2$, $R^{54A}$-substituted or unsubstituted alkyl (e.g., $C_1$-$C_8$, $C_1$-$C_6$, or $C_1$-$C_4$), $R^{54A}$-substituted or unsubstituted heteroalkyl (e.g., 2 to 8 membered, 2 to 6 membered, or 2 to 4 membered), $R^{54A}$-substituted or unsubstituted cycloalkyl (e.g., $C_3$-$C_8$, $C_3$-$C_6$, or $C_5$-$C_6$), $R^{54A}$-substituted or unsubstituted heterocycloalkyl (e.g., 3 to 8 membered, 3 to 6 membered, or 5 to 6 membered), $R^{54A}$-substituted or unsubstituted aryl (e.g., $C_6$-$C_{10}$, $C_{10}$, or phenyl), or $R^{54A}$-substituted or unsubstituted heteroaryl (e.g., 5 to 10 membered, 5 to 9 membered, or 5 to 6 membered). $X^{9A}$ is halogen. In embodiments, $X^{9A}$ is F.

$R^{54A}$ is independently oxo, halogen, $-CX^{54A}_3$, $-CHX^{54A}_2$, $-OCH_2X^{54A}$, $-OCHX^{54A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{54A}_3$, $-OCHX^{54A}_2$, $R^{55A}$-substituted or unsubstituted alkyl (e.g., $C_3$-$C_3$, $C_1$-$C_6$, or $C_1$-$C_4$), $R^{55A}$-substituted or unsubstituted heteroalkyl (e.g., 2 to 8 membered, 2 to 6 membered, or 2 to 4 membered), $R^{55A}$-substituted or unsubstituted cycloalkyl (e.g., $C_3$-$C_8$, $C_3$-$C_6$, or $C_5$-$C_6$), $R^{55A}$-substituted or unsubstituted heterocycloalkyl (e.g., 3 to 8 membered, 3 to 6 membered, or 5 to 6 membered), $R^{55A}$-substituted or unsubstituted aryl (e.g., $C_6$-$C_{10}$, $C_{10}$, or phenyl), or $R^{55A}$-substituted or unsubstituted heteroaryl (e.g., 5 to 10 membered, 5 to 9 membered, or 5 to 6 membered). $X^{54A}$ is halogen. In embodiments, $X^{54A}$ is F.

$R^{55A}$ is independently oxo, halogen, $-CX^{55A}_3$, $-CHX^{55A}_2$, $-OCH_2X^{55A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{55A}_3$, $-OCHX^{55A}_2$, $R^{56A}$-substituted or unsubstituted alkyl (e.g., $C_1$-$C_8$, $C_1$-$C_6$, or $C_1$-$C_4$), $R^{56A}$-substituted or unsubstituted heteroalkyl (e.g., 2 to 8 membered, 2 to 6 membered, or 2 to 4 membered), $R^{56A}$-substituted or unsubstituted cycloalkyl (e.g., $C_3$-$C_5$, $C_3$-$C_6$, or $C_5$-$C_6$), $R^{56A}$-substituted or unsubstituted heterocycloalkyl (e.g., 3 to 8 membered, 3 to 6 membered, or 5 to 6 membered), $R^{56A}$-substituted or unsubstituted aryl (e.g., $C_6$-$C_{10}$, $C_{10}$, or phenyl), or $R^{56A}$-substituted or unsubstituted heteroaryl (e.g., 5 to 10 membered, 5 to 9 membered, or 5 to 6 membered). $X^{55A}$ is halogen. In embodiments, $X^{55A}$ is F.

In embodiments, $R^{10A}$ is independently hydrogen, oxo, halogen, $-CX^{10A}_3$, $-CHX^{10A}_2$, $-OCH_2X^{10A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{10A}_3$, $-OCHX^{10A}_2$, $R^{57A}$-substituted or unsubstituted alkyl (e.g., $C_1$-$C_8$, $C_1$-$C_6$, or $C_1$-$C_4$), $R^{57A}$-substituted or unsubstituted heteroalkyl (e.g., 2 to 8 membered, 2 to 6 membered, or 2 to 4 membered), $R^{57A}$-substituted or unsubstituted cycloalkyl (e.g., $C_3$-$C_8$, $C_3$-$C_6$, or $C_5$-$C_6$), $R^{57A}$-substituted or unsubstituted heterocycloalkyl (e.g., 3 to 8 membered, 3 to 6 membered, or 5 to 6 membered), $R^{57A}$-substituted or unsubstituted aryl (e.g., $C_6$-$C_{10}$, $C_{10}$, or phenyl), or $R^{57A}$-substituted or unsubstituted heteroaryl (e.g., 5 to 10 membered, 5 to 9 membered, or 5 to 6 membered). $X^{10A}$ is halogen. In embodiments, $X^{10A}$ is F.

$R^{57A}$ is independently oxo, halogen, $-CX^{57A}_3$, $-CHX^{57A}_2$, $-OCH_2X^{57A}$, $-OCHX^{57A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{57A}_3$, $-OCHX^{57A}_2$, $R^{58A}$-substituted or unsubstituted alkyl (e.g., $C_1$-$C_8$, $C_1$-$C_6$, or $C_1$-$C_4$), $R^{58A}$-substituted or unsubstituted heteroalkyl (e.g., 2 to 8 membered, 2 to 6 membered, or 2 to 4 membered), $R^{58A}$-substituted or unsubstituted cycloalkyl (e.g., $C_3$-$C_8$, $C_3$-$C_6$, or $C_5$-$C_6$), $R^{58A}$-substituted or unsubstituted heterocycloalkyl (e.g., 3 to 8 membered, 3 to 6 membered, or 5 to 6 membered), $R^{58A}$-substituted or unsubstituted aryl (e.g., $C_6$-$C_{10}$, $C_{10}$, or phenyl), or $R^{58A}$-substituted or unsubstituted heteroaryl (e.g., 5 to 10 membered, 5 to 9 membered, or 5 to 6 membered). $X^{57A}$ is halogen. In embodiments, $X^{57A}$ is F.

$R^{58A}$ is independently oxo, halogen, $-CX^{58A}_3$, $-CHX^{58A}_2$, $-OCH_2X^{58A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{58A}_3$, $-OCHX^{58A}_2$, $R^{59A}$-substituted or unsubstituted alkyl (e.g., $C_1$-$C_8$, $C_1$-$C_6$, or $C_1$-$C_4$), $R^{59A}$-substituted or unsubstituted heteroalkyl (e.g., 2 to 8 membered, 2 to 6 membered, or 2 to 4 membered), $R^{59A}$-substituted or unsubstituted cycloalkyl (e.g., $C_3$-$C_5$, $C_3$-$C_6$, or $C_5$-$C_6$), $R^{59A}$-substituted or unsubstituted heterocycloalkyl (e.g., 3 to 8 membered, 3 to 6 membered, or 5 to 6 membered), $R^{59A}$-substituted or unsubstituted aryl (e.g., $C_6$-$C_{10}$, $C_{10}$, or phenyl), or $R^{59A}$-substituted or unsubstituted heteroaryl (e.g., 5 to 10 membered, 5 to 9 membered, or 5 to 6 membered). $X^{58A}$ is halogen. In embodiments, $X^{58A}$ is F.

In embodiments, $R^{7B}$ is independently hydrogen, oxo, halogen, $-CX^{7B}_3$, $-CHX^{7B}_2$, $-OCH_2X^{7B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{7B}_3$, $-OCHX^{7B}_2$, $R^{48B}$-substituted or unsubstituted alkyl (e.g., $C_1$-$C_8$, $C_1$-$C_6$, or $C_1$-$C_4$), $R^{48B}$-substituted or unsubstituted heteroalkyl (e.g., 2 to 8 membered, 2 to 6 membered, or 2 to 4 membered), $R^{48B}$-substituted or unsubstituted cycloalkyl (e.g., $C_3$-$C_5$, $C_3$-$C_6$, or $C_5$-$C_6$), $R^{48B}$-substituted or unsubstituted heterocycloalkyl (e.g., 3 to 8 membered, 3 to 6 membered, or 5 to 6 membered), $R^{48B}$-substituted or unsubstituted aryl (e.g., $C_6$-$C_{10}$, $C_{10}$, or phenyl), or $R^{48B}$-substituted or unsubstituted heteroaryl (e.g., 5 to 10 membered, 5 to 9 membered, or 5 to 6 membered). In embodiments, $R^{7B}$ is independently oxo, halogen, $-CX^{7B}_3$, $-CHX^{7B}_2$, $-OCH_2X^{7B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^7-OCHX^{7B}_2$, $R^{48B}$-substituted or unsubstituted alkyl (e.g., $C_1$-$C_8$, $C_1$-$C_6$, or $C_1$-$C_4$), $R^{48B}$-substituted or unsubstituted heteroalkyl (e.g., 2 to 8 membered, 2 to 6 membered, or 2 to 4 membered), $R^{48B}$-substituted or unsubstituted cycloalkyl (e.g., $C_3$-$C_5$, $C_3$-$C_6$, or $C_5$-$C_6$), $R^{48B}$-substituted or unsubstituted heterocycloalkyl (e.g., 3 to 8 membered, 3 to 6 membered, or 5 to 6 membered), $R^{48B}$-substituted or unsubstituted aryl (e.g., $C_6$-$C_{10}$, $C_{10}$, or phenyl), or $R^{48B}$-substituted or unsubstituted heteroaryl (e.g., 5 to 10 membered, 5 to 9 membered, or 5 to 6 membered). $X^{7B}$ is halogen. In embodiments, $X^{7B}$ is F.

$R^{48B}$ is independently oxo, halogen, $-CX^{48B}_3$, $-CHX^{48B}_2$, $-OCH_2X^{48B}$, $-OCHX^{48B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{48B}_3$, $-OCHX^{48B}_2$, $R^{49B}$-substituted or unsubstituted alkyl (e.g., $C_1$-$C_8$, $C_1$-$C_6$, or $C_1$-$C_4$), $R^{48B}$-substituted or unsubstituted heteroalkyl (e.g., 2 to 8 membered, 2 to 6 membered, or 2 to 4 membered), $R^{49B}$-substituted or unsubstituted cycloalkyl (e.g., $C_3$-$C_8$, $C_3$-$C_6$, or $C_5$-$C_6$), $R^{49B}$-substituted or unsubstituted heterocycloalkyl (e.g., 3 to 8 membered, 3 to 6 membered, or 5 to 6 membered), $R^{49B}$-substituted or unsubstituted aryl (e.g., $C_6$-$C_{10}$, $C_{10}$, or phenyl), or $R^{49B}$-substituted or unsubstituted heteroaryl (e.g., 5 to 10 membered, 5 to 9 membered, or 5 to 6 membered). $X^{48B}$ is halogen. In embodiments, $X^{48B}$ is F.

$R^{49B}$ is independently oxo, halogen, $-CX^{49B}_3$, $-CHX^{49B}_2$, $-OCH_2X^{49B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{49B}_3$, $-OCHX^{49B}_2$, $R^{50B}$-substituted or unsubstituted alkyl (e.g., $C_1$-$C_8$, $C_1$-$C_6$, or $C_1$-$C_4$), $R^{50B}$-substituted or unsubstituted heteroalkyl (e.g., 2 to 8 membered, 2 to 6 membered, or 2 to 4 membered), $R^{49B}$-substituted or unsubstituted cycloalkyl (e.g., $C_3$-$C_8$, $C_3$-$C_6$, or $C_5$-$C_6$), $R^{50B}$-substituted or unsubstituted heterocycloalkyl (e.g., 3 to 8 membered, 3 to 6 membered, or 5 to 6 membered), $R^{50B}$-substituted or unsubstituted aryl (e.g., $C_6$-$C_{10}$, $C_{10}$, or phenyl), or $R^{50B}$-substituted or unsubstituted heteroaryl (e.g., 5 to 10 membered, 5 to 9 membered, or 5 to 6 membered). $X^{49B}$ is halogen. In embodiments, $X^{49B}$ is F.

In embodiments, $R^{8B}$ is independently hydrogen, oxo, halogen, $-CX^{8B}_3$, $-CHX^{8B}_2$, $-OCH_2X^{8B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{8B}_3$, $-OCHX^{8B}_2$, $R^{51B}$-substituted or unsubstituted alkyl (e.g., $C_1$-$C_8$, $C_1$-$C_6$, or $C_1$-$C_4$), $R^{51B}$-substituted or unsubstituted heteroalkyl (e.g., 2 to 8 membered, 2 to 6 membered, or 2 to 4 membered), $R^{51B}$-substituted or unsubstituted cycloalkyl (e.g., $C_3$-$C_8$, $C_3$-$C_6$, or $C_5$-$C_6$), $R^{51B}$-substituted or unsubstituted heterocycloalkyl (e.g., 3 to 8 membered, 3 to 6 membered, or 5 to 6 membered), $R^{51B}$-substituted or unsubstituted aryl (e.g., $C_6$-$C_{10}$, $C_{10}$, or phenyl), or $R^{51B}$-substituted or unsubstituted heteroaryl (e.g., 5 to 10 membered, 5 to 9 membered, or 5 to 6 membered). $X^{8B}$ is halogen. In embodiments, $X^{8B}$ is F.

$R^{51B}$ is independently oxo, halogen, $-CX^{51B}_3$, $-CHX^{51B}_2$, $-OCH_2X^{51B}$, $-OCHX^{51B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{51B}_3$, $-OCHX^{51B}_2$, $R^{52B}$-substituted or unsubstituted alkyl (e.g., $C_1$-$C_8$, $C_1$-$C_6$, or $C_1$-$C_4$), $R^{52B}$-substituted or unsubstituted heteroalkyl (e.g., 2 to 8 membered, 2 to 6 membered, or 2 to 4 membered), $R^{52B}$-substituted or unsubstituted cycloalkyl (e.g., $C_3$-$C_8$, $C_3$-$C_6$, or $C_5$-$C_6$), $R^{52B}$-substituted or unsubstituted heterocycloalkyl (e.g., 3 to 8 membered, 3 to 6 membered, or 5 to 6 membered), $R^{52B}$-substituted or unsubstituted aryl (e.g., $C_6$-$C_{10}$, $C_{10}$, or phenyl), or $R^{52B}$-substituted or unsubstituted heteroaryl (e.g., 5 to 10 membered, 5 to 9 membered, or 5 to 6 membered). $X^{51B}$ is halogen. In embodiments, $X^{51B}$ is F.

$R^{52B}$ is independently oxo, halogen, $-CX^{52B}_3$, $-CHX^{52B}_2$, $-OCH_2X^{52B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{52B}_3$, $-OCHX^{52B}_2$, $R^{53B}$-substituted or unsubstituted alkyl (e.g., $C_1$-$C_8$, $C_1$-$C_6$, or $C_1$-$C_4$), $R^{53B}$-substituted or unsubstituted heteroalkyl (e.g., 2 to 8 membered, 2 to 6 membered, or 2 to 4 membered), $R^{53B}$-substituted or unsubstituted cycloalkyl (e.g., $C_3$-$C_5$, $C_3$-$C_6$, or $C_5$-$C_6$), $R^{53B}$-substituted or unsubstituted heterocycloalkyl (e.g., 3 to 8 membered, 3 to 6 membered, or 5 to 6 membered), $R^{53B}$-substituted or unsubstituted aryl (e.g., $C_6$-$C_{10}$, $C_{10}$, or phenyl), or $R^{53B}$-substituted or unsubstituted heteroaryl (e.g., 5 to 10 membered, 5 to 9 membered, or 5 to 6 membered). $X^{52B}$ is halogen. In embodiments, $X^{52B}$ is F.

In embodiments, $R^{9B}$ is independently hydrogen, oxo, halogen, $-CX^{9B}_3$, $-CHX^{9B}_2$, $-OCH_2X^{9B}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^9-OCHX^{9B}_2$, $R^{54B}$-substituted or unsubstituted alkyl (e.g., $C_1$-$C_8$, $C_1$-$C_6$, or $C_1$-$C_4$), $R^{54B}$-substituted or unsubstituted heteroalkyl (e.g., 2 to 8 membered, 2 to 6 membered, or 2 to 4 membered), $R^{54B}$-substituted or unsubstituted cycloalkyl (e.g., $C_3$-$C_8$, $C_3$-$C_6$, or $C_5$-$C_6$), $R^{54B}$-substituted or unsubstituted heterocycloalkyl (e.g., 3 to 8 membered, 3 to 6 membered, or 5 to 6 membered), $R^{54B}$-substituted or unsubstituted aryl (e.g., $C_6$-$C_{10}$, $C_{10}$, or phenyl), or $R^{54B}$-substituted or unsubstituted heteroaryl (e.g., 5 to 10 membered, 5 to 9 membered, or 5 to 6 membered). $X^{9B}$ is halogen. In embodiments, $X^{9B}$ is F.

$R^{54B}$ is independently oxo, halogen, $-CX^{54B}_3$, $-CHX^{54B}_2$, $-OCH_2X^{54B}$, $-OCHX^{54B}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{54B}_3$, $-OCHX^{54B}_2$, $R^{55B}$-substituted or unsubstituted alkyl (e.g., $C_1$-$C_8$, $C_1$-$C_6$, or $C_1$-$C_4$), $R^{55B}$-substituted or unsubstituted heteroalkyl (e.g., 2 to 8 membered, 2 to 6 membered, or 2 to 4 membered), $R^{55B}$-substituted or unsubstituted cycloalkyl (e.g., $C_3$-$C_8$, $C_3$-$C_6$, or $C_5$-$C_6$), $R^{55B}$-substituted or unsubstituted heterocycloalkyl (e.g., 3 to 8 membered, 3 to 6 membered, or 5 to 6 membered), $R^{55B}$-substituted or unsubstituted aryl (e.g., $C_6$-$C_{10}$, $C_{10}$, or phenyl), or $R^{55B}$-substituted or unsubstituted heteroaryl (e.g., 5 to 10 membered, 5 to 9 membered, or 5 to 6 membered). $X^{54B}$ is halogen. In embodiments, $X^{54B}$ is F.

$R^{55B}$ is independently oxo, halogen, —$CX^{55B}_3$, —$CHX^{55B}_2$, —$OCH_2X^{55B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{55B}_3$, —$OCHX^{55B}_2$, $R^{56B}$-substituted or unsubstituted alkyl (e.g., $C_1$-$C_8$, $C_1$-$C_6$, or $C_1$-$C_4$), $R^{56B}$-substituted or unsubstituted heteroalkyl (e.g., 2 to 8 membered, 2 to 6 membered, or 2 to 4 membered), $R^{56B}$-substituted or unsubstituted cycloalkyl (e.g., $C_3$-$C_5$, $C_3$-$C_6$, or $C_5$-$C_6$), $R^{56B}$-substituted or unsubstituted heterocycloalkyl (e.g., 3 to 8 membered, 3 to 6 membered, or 5 to 6 membered), $R^{56B}$-substituted or unsubstituted aryl (e.g., $C_6$-$C_{10}$, $C_{10}$, or phenyl), or $R^{56B}$-substituted or unsubstituted heteroaryl (e.g., 5 to 10 membered, 5 to 9 membered, or 5 to 6 membered). $X^{55B}$ is halogen. In embodiments, $X^{55B}$ is F.

In embodiments, $R^{10B}$ is independently hydrogen, oxo, halogen, —$CX^{10B}_3$, —$CHX^{10B}_2$, —$OCH_2X^{10B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{10B}_3$, —$OCHX^{10B}_2$, $R^{57B}$-substituted or unsubstituted alkyl (e.g., $C_1$-$C_8$, $C_1$-$C_6$, or $C_1$-$C_4$), $R^{57B}$-substituted or unsubstituted heteroalkyl (e.g., 2 to 8 membered, 2 to 6 membered, or 2 to 4 membered), $R^{57B}$-substituted or unsubstituted cycloalkyl (e.g., $C_3$-$C_5$, $C_3$-$C_6$, or $C_5$-$C_6$), $R^{57B}$-substituted or unsubstituted heterocycloalkyl (e.g., 3 to 8 membered, 3 to 6 membered, or 5 to 6 membered), $R^{57B}$-substituted or unsubstituted aryl (e.g., $C_6$-$C_{10}$, $C_{10}$, or phenyl), or $R^{57B}$-substituted or unsubstituted heteroaryl (e.g., 5 to 10 membered, 5 to 9 membered, or 5 to 6 membered). $X^{10B}$ is halogen. In embodiments, $X^{10B}$ is F.

$R^{57B}$ is independently oxo, halogen, —$CX^{57B}_3$, —$CHX^{57B}_2$, —$OCH_2X^{57B}$, —$OCHX^{57B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{57B}_3$, —$OCHX^{57B}_2$, $R^{58B}$-substituted or unsubstituted alkyl (e.g., $C_1$-$C_8$, $C_1$-$C_6$, or $C_1$-$C_4$), $R^{58B}$-substituted or unsubstituted heteroalkyl (e.g., 2 to 8 membered, 2 to 6 membered, or 2 to 4 membered), $R^{10B}$-substituted or unsubstituted cycloalkyl (e.g., $C_3$-$C_8$, $C_3$-$C_6$, or $C_5$-$C_6$), $R^{58B}$-substituted or unsubstituted heterocycloalkyl (e.g., 3 to 8 membered, 3 to 6 membered, or 5 to 6 membered), $R^{58D}$-substituted or unsubstituted aryl (e.g., $C_6$-$C_{10}$, $C_{10}$, or phenyl), or $R^{58B}$-substituted or unsubstituted heteroaryl (e.g., 5 to 10 membered, 5 to 9 membered, or 5 to 6 membered). $X^{57B}$ is halogen. In embodiments, $X^{57B}$ is F.

$R^{58B}$ is independently oxo, halogen, —$CX^{58B}_3$, —$CHX^{58B}_2$, —$OCH_2X^{58B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{58B}_3$, —$OCHX^{58B}_2$, $R^{59B}$-substituted or unsubstituted alkyl (e.g., $C_1$-$C_8$, $C_1$-$C_6$, or $C_1$-$C_4$), $R^{59B}$-substituted or unsubstituted heteroalkyl (e.g., 2 to 8 membered, 2 to 6 membered, or 2 to 4 membered), $R^{59B}$-substituted or unsubstituted cycloalkyl (e.g., $C_3$-$C_8$, $C_3$-$C_6$, or $C_5$-$C_6$), $R^{59B}$-substituted or unsubstituted heterocycloalkyl (e.g., 3 to 8 membered, 3 to 6 membered, or 5 to 6 membered), $R^{59B}$-substituted or unsubstituted aryl (e.g., $C_6$-$C_{10}$, $C_{10}$, or phenyl), or $R^{58B}$-substituted or unsubstituted heteroaryl (e.g., 5 to 10 membered, 5 to 9 membered, or 5 to 6 membered). $X^{58B}$ is halogen. In embodiments, $X^{58B}$ is F.

In embodiments, $R^{11}$ is independently hydrogen, oxo, halogen, —$CX^{11}_3$, —$CHX^{11}_2$, —$OCH_2X^{11}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{11}_3$, —$OCHX^{11}_2$, $R^{60}$-substituted or unsubstituted alkyl (e.g., $C_1$-$C_8$, $C_1$-$C_6$, or $C_1$-$C_4$), $R^{60}$-substituted or unsubstituted heteroalkyl (e.g., 2 to 8 membered, 2 to 6 membered, or 2 to 4 membered), $R^{6U}$-substituted or unsubstituted cycloalkyl (e.g., $C_3$-$C_8$, $C_3$-$C_6$, or $C_5$-$C_6$), $R^{60}$-substituted or unsubstituted heterocycloalkyl (e.g., 3 to 8 membered, 3 to 6 membered, or 5 to 6 membered), $R^{60}$-substituted or unsubstituted aryl (e.g., $C_6$-$C_{10}$, $C_{10}$, or phenyl), or $R^{60}$-substituted or unsubstituted heteroaryl (e.g., 5 to 10 membered, 5 to 9 membered, or 5 to 6 membered). $X^{11}$ is halogen. In embodiments, $X^{11}$ is F.

$R^{60}$ is independently oxo, halogen, —$CX^{60}_3$, —$CHX^{60}_2$, —$OCH_2X^{60}$, —$OCHX^{60}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{60}_3$, —$OCHX^{60}_2$, $R^{61}$-substituted or unsubstituted alkyl (e.g., $C_1$-$C_8$, $C_1$-$C_6$, or $C_1$-$C_4$), $R^{61}$-substituted or unsubstituted heteroalkyl (e.g., 2 to 8 membered, 2 to 6 membered, or 2 to 4 membered), $R^{61}$-substituted or unsubstituted cycloalkyl (e.g., $C_3$-$C_8$, $C_3$-$C_6$, or $C_5$-$C_6$), $R^{61}$-substituted or unsubstituted heterocycloalkyl (e.g., 3 to 8 membered, 3 to 6 membered, or 5 to 6 membered), $R^{61}$-substituted or unsubstituted aryl (e.g., $C_6$-$C_{10}$, $C_{10}$, or phenyl), or $R^{61}$-substituted or unsubstituted heteroaryl (e.g., 5 to 10 membered, 5 to 9 membered, or 5 to 6 membered). $X^{60}$ is halogen. In embodiments, $X^{60}$ is F.

$R^{61}$ is independently oxo, halogen, —$CX^{61}_3$, —$CHX^{61}_2$, —$OCH_2X^{61}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{61}_3$, —$OCHX^{61}_2$, $R^{62}$-substituted or unsubstituted alkyl (e.g., $C_1$-$C_8$, $C_1$-$C_6$, or $C_1$-$C_4$), $R^{62}$-substituted or unsubstituted heteroalkyl (e.g., 2 to 8 membered, 2 to 6 membered, or 2 to 4 membered), $R^{62}$-substituted or unsubstituted cycloalkyl (e.g., $C_3$-$C_8$, $C_3$-$C_6$, or $C_5$-$C_6$), $R^{62}$-substituted or unsubstituted heterocycloalkyl (e.g., 3 to 8 membered, 3 to 6 membered, or 5 to 6 membered), $R^{62}$-substituted or unsubstituted aryl (e.g., $C_6$-$C_{10}$, $C_{10}$, or phenyl), or $R^{62}$-substituted or unsubstituted heteroaryl (e.g., 5 to 10 membered, 5 to 9 membered, or 5 to 6 membered). $X^{61}$ is halogen. In embodiments, $X^{61}$ is F.

In embodiments, $R^{1.2}$ is independently hydrogen, oxo, halogen, —$CX^{12}_3$, —$CHX^{12}_2$, —$OCH_2X^{12}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{12}_3$, —$OCHX^{12}_2$, $R^{63}$-substituted or unsubstituted alkyl (e.g., $C_1$-$C_8$, $C_1$-$C_6$, or $C_1$-$C_4$), $R^{63}$-substituted or unsubstituted heteroalkyl (e.g., 2 to 8 membered, 2 to 6 membered, or 2 to 4 membered), $R^{63}$-substituted or unsubstituted cycloalkyl (e.g., $C_3$-$C_5$, $C_3$-$C_6$, or $C_5$-$C_6$), $R^{63}$-substituted or unsubstituted heterocycloalkyl (e.g., 3 to 8 membered, 3 to 6 membered, or 5 to 6 membered), $R^{63}$-substituted or unsubstituted aryl (e.g., $C_6$-$C_{10}$, $C_{10}$, or phenyl), or $R^{63}$-substituted or unsubstituted heteroaryl (e.g., 5 to 10 membered, 5 to 9 membered, or 5 to 6 membered). $X^{12}$ is halogen. In embodiments, $X^{12}$ is F.

$R^{63}$ is independently oxo, halogen, $-CX^{63}_3$, $-CHX^{63}_2$, $-OCH_2X^{63}$, $-OCHX^{63}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{63}_3$, $-OCHX^{63}_2$, $R^{64}$-substituted or unsubstituted alkyl (e.g., $C_1$-$C_8$, $C_1$-$C_6$, or $C_1$-$C_4$), $R^{64}$-substituted or unsubstituted heteroalkyl (e.g., 2 to 8 membered, 2 to 6 membered, or 2 to 4 membered), $R^{64}$-substituted or unsubstituted cycloalkyl (e.g., $C_3$-$C_8$, $C_3$-$C_6$, or $C_5$-$C_6$), $R^{64}$-substituted or unsubstituted heterocycloalkyl (e.g., 3 to 8 membered, 3 to 6 membered, or 5 to 6 membered), $R^{64}$-substituted or unsubstituted aryl (e.g., $C_6$-$C_{10}$, $C_{10}$, or phenyl), or $R^{64}$-substituted or unsubstituted heteroaryl (e.g., 5 to 10 membered, 5 to 9 membered, or 5 to 6 membered). $X^{63}$ is halogen. In embodiments, $X^{63}$ is F.

$R^{64}$ is independently oxo, halogen, $-CX^{64}_3$, $-CHX^{64}_2$, $-OCH_2X^{64}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{64}_3$, $-OCHX^{64}_2$, $R^{65}$-substituted or unsubstituted alkyl (e.g., $C_1$-$C_8$, $C_1$-$C_6$, or $C_1$-$C_4$), $R^{65}$-substituted or unsubstituted heteroalkyl (e.g., 2 to 8 membered, 2 to 6 membered, or 2 to 4 membered), $R^{65}$-substituted or unsubstituted cycloalkyl (e.g., $C_3$-$C_8$, $C_3$-$C_6$, or $C_5$-$C_6$), $R^{65}$-substituted or unsubstituted heterocycloalkyl (e.g., 3 to 8 membered, 3 to 6 membered, or 5 to 6 membered), $R^{65}$-substituted or unsubstituted aryl (e.g., $C_6$-$C_{10}$, $C_{10}$, or phenyl), or $R^{65}$-substituted or unsubstituted heteroaryl (e.g., 5 to 10 membered, 5 to 9 membered, or 5 to 6 membered). $X^{64}$ is halogen. In embodiments, $X^{64}$ is F.

In embodiments, $R^{13}$ is independently hydrogen, oxo, halogen, $-CX^{13}_3$, $-CHX^{13}_2$, $-OCH_2X^{13}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{13}_3$, $-OCHX^{13}_2$, $R^{66}$-substituted or unsubstituted alkyl (e.g., $C_1$-$C_8$, $C_1$-$C_6$, or $C_1$-$C_4$), $R^{66}$-substituted or unsubstituted heteroalkyl (e.g., 2 to 8 membered, 2 to 6 membered, or 2 to 4 membered), $R^{66}$-substituted or unsubstituted cycloalkyl (e.g., $C_3$-$C_5$, $C_3$-$C_6$, or $C_5$-$C_6$), $R^{66}$-substituted or unsubstituted heterocycloalkyl (e.g., 3 to 8 membered, 3 to 6 membered, or 5 to 6 membered), $R^{66}$-substituted or unsubstituted aryl (e.g., $C_6$-$C_{10}$, $C_{10}$, or phenyl), or $R^{66}$-substituted or unsubstituted heteroaryl (e.g., 5 to 10 membered, 5 to 9 membered, or 5 to 6 membered). $X^{13}$ is halogen. In embodiments, $X^{13}$ is F.

$R^{66}$ is independently oxo, halogen, $-CX^{66}_3$, $-CHX^{66}_2$, $-OCH_2X^{66}$, $-OCHX^{66}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{66}_3$, $-OCHX^{66}_2$, $R^{67}$-substituted or unsubstituted alkyl (e.g., $C_1$-$C_8$, $C_1$-$C_6$, or $C_1$-$C_4$), $R^{67}$-substituted or unsubstituted heteroalkyl (e.g., 2 to 8 membered, 2 to 6 membered, or 2 to 4 membered), $R^{67}$-substituted or unsubstituted cycloalkyl (e.g., $C_3$-$C_8$, $C_3$-$C_6$, or $C_5$-$C_6$), $R^{67}$-substituted or unsubstituted heterocycloalkyl (e.g., 3 to 8 membered, 3 to 6 membered, or 5 to 6 membered), $R^{67}$-substituted or unsubstituted aryl (e.g., $C_6$-$C_{10}$, $C_{10}$, or phenyl), or $R^{67}$-substituted or unsubstituted heteroaryl (e.g., 5 to 10 membered, 5 to 9 membered, or 5 to 6 membered). $X^{66}$ is halogen. In embodiments, $X^{66}$ is F.

$R^{67}$ is independently oxo, halogen, $-CX^{67}_3$, $-CHX^{67}_2$, $-OCH_2X^{67}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{67}_3$, $-OCHX^{67}_2$, $R^{68}$-substituted or unsubstituted alkyl (e.g., $C_1$-$C_8$, $C_1$-$C_6$, or $C_1$-$C_4$), $R^{68}$-substituted or unsubstituted heteroalkyl (e.g., 2 to 8 membered, 2 to 6 membered, or 2 to 4 membered), $R^{68}$-substituted or unsubstituted cycloalkyl (e.g., $C_3$-$C_5$, $C_3$-$C_6$, or $C_5$-$C_6$), $R^{68}$-substituted or unsubstituted heterocycloalkyl (e.g., 3 to 8 membered, 3 to 6 membered, or 5 to 6 membered), $R^{68}$-substituted or unsubstituted aryl (e.g., $C_6$-$C_{10}$, $C_{10}$, or phenyl), or $R^{68}$-substituted or unsubstituted heteroaryl (e.g., 5 to 10 membered, 5 to 9 membered, or 5 to 6 membered). $X^{67}$ is halogen. In embodiments, $X^{67}$ is F.

In embodiments, $R^{14}$ is independently hydrogen, oxo, halogen, $-CX^{14}_3$, $-CHX^{14}_2$, $-OCH_2X^{14}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{14}_3$, $-OCHX^{14}_2$, $R^{69}$-substituted or unsubstituted alkyl (e.g., $C_1$-$C_8$, $C_1$-$C_6$, or $C_1$-$C_4$), $R^{69}$-substituted or unsubstituted heteroalkyl (e.g., 2 to 8 membered, 2 to 6 membered, or 2 to 4 membered), $R^{69}$-substituted or unsubstituted cycloalkyl (e.g., $C_3$-$C_5$, $C_3$-$C_6$, or $C_5$-$C_6$), $R^{69}$-substituted or unsubstituted heterocycloalkyl (e.g., 3 to 8 membered, 3 to 6 membered, or 5 to 6 membered), $R^{69}$-substituted or unsubstituted aryl (e.g., $C_6$-$C_{10}$, $C_{10}$, or phenyl), or $R^{69}$-substituted or unsubstituted heteroaryl (e.g., 5 to 10 membered, 5 to 9 membered, or 5 to 6 membered). $X^{14}$ is halogen. In embodiments, $X^{14}$ is F.

$R^{69}$ is independently oxo, halogen, $-CX®_3$, $-CHX^{69}_2$, $-OCH_2X^{69}$, $-OCHX^{69}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{69}_3$, $-OCHX^{69}_2$, $R^{70}$-substituted or unsubstituted alkyl (e.g., $C_1$-$C_8$, $C_1$-$C_6$, or $C_1$-$C_4$), $R^{70}$-substituted or unsubstituted heteroalkyl (e.g., 2 to 8 membered, 2 to 6 membered, or 2 to 4 membered), $R^{70}$-substituted or unsubstituted cycloalkyl (e.g., $C_3$-$C_8$, $C_3$-$C_6$, or $C_5$-$C_6$), $R^{7U}$-substituted or unsubstituted heterocycloalkyl (e.g., 3 to 8 membered, 3 to 6 membered, or 5 to 6 membered), $R^{70}$-substituted or unsubstituted aryl (e.g., $C_6$-$C_{10}$, $C_{10}$, or phenyl), or $R^{70}$-substituted or unsubstituted heteroaryl (e.g., 5 to 10 membered, 5 to 9 membered, or 5 to 6 membered). $X^{69}$ is halogen. In embodiments, $X^{69}$ is F.

$R^{70}$ is independently oxo, halogen, $-CX^{70}_3$, $-CHX^{70}_2$, $-OCH_2X^{70}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{70}_3$, $-OCHX^{70}_2$, $R^{71}$-substituted or unsubstituted alkyl (e.g., $C_1$-$C_8$, $C_1$-$C_6$, or $C_1$-$C_4$), $R^{71}$-substituted or unsubstituted heteroalkyl (e.g., 2 to 8 membered, 2 to 6 membered, or 2 to 4 membered), $R^{71}$-substituted or unsubstituted cycloalkyl (e.g., $C_3$-$C_8$, $C_3$-$C_6$, or $C_5$-$C_6$), $R^{71}$-substituted or unsubstituted heterocycloalkyl (e.g., 3 to 8 membered, 3 to 6 membered, or 5 to 6 membered), $R^{71}$-substituted or unsubstituted aryl (e.g., $C_6$-$C_{10}$, $C_{10}$, or phenyl), or $R^{71}$-substituted or unsubstituted heteroaryl (e.g., 5 to 10 membered, 5 to 9 membered, or 5 to 6 membered). $X^{70}$ is halogen. In embodiments, $X^{70}$ is F.

In embodiments, $R^{15}$ is independently hydrogen, oxo, halogen, $-CX^{15}_3$, $-CHX^{15}_2$, $-OCH_2X^{15}$, $-CN$, $-OH$, $-NH_2$, $-COOH$, $-CONH_2$, $-NO_2$, $-SH$, $-SO_3H$, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{15}_3$, —OCHX$^{15}_2$, R$^{72}$-substituted or unsubstituted alkyl (e.g., C$_1$-C$_8$, C$_1$-C$_6$, or C$_1$-C$_4$), R$^{72}$-substituted or unsubstituted heteroalkyl (e.g., 2 to 8 membered, 2 to 6 membered, or 2 to 4 membered), R$^{72}$-substituted or unsubstituted cycloalkyl (e.g., C$_3$-C$_8$, C$_3$-C$_6$, or C$_5$-C$_6$), R$^{72}$-substituted or unsubstituted heterocycloalkyl (e.g., 3 to 8 membered, 3 to 6 membered, or 5 to 6 membered), R$^{72}$-substituted or unsubstituted aryl (e.g., C$_6$-C$_{10}$, C$_{10}$, or phenyl), or R$^{72}$-substituted or unsubstituted heteroaryl (e.g., 5 to 10 membered, 5 to 9 membered, or 5 to 6 membered). X$^{15}$ is halogen. In embodiments, X$^{15}$ is F.

R$^{72}$ is independently oxo, halogen, —CX$^{72}_3$, —CHX$^{72}_2$, —OCH$_2$X$^{72}$, —OCHX$^{72}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{72}_3$, —OCHX$^{72}_2$, R$^{73}$-substituted or unsubstituted alkyl (e.g., C$_1$-C$_8$, C$_1$-C$_6$, or C$_1$-C$_4$), R$^{73}$-substituted or unsubstituted heteroalkyl (e.g., 2 to 8 membered, 2 to 6 membered, or 2 to 4 membered), R$^{73}$-substituted or unsubstituted cycloalkyl (e.g., C$_3$-C$_8$, C$_3$-C$_6$, or C$_5$-C$_6$), R$^{73}$-substituted or unsubstituted heterocycloalkyl (e.g., 3 to 8 membered, 3 to 6 membered, or 5 to 6 membered), R$^{73}$-substituted or unsubstituted aryl (e.g., C$_6$-C$_{10}$, C$_{10}$, or phenyl), or R$^{73}$-substituted or unsubstituted heteroaryl (e.g., 5 to 10 membered, 5 to 9 membered, or 5 to 6 membered). X$^{72}$ is halogen. In embodiments, X$^{72}$ is F.

R$^{73}$ is independently oxo, halogen, —CX$^{73}_3$, —CHX$^{73}_2$, —OCH$_2$X$^{73}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{73}_3$, —OCHX$^{73}_2$, R$^{74}$-substituted or unsubstituted alkyl (e.g., C$_1$-C$_8$, C$_1$-C$_6$, or C$_1$-C$_4$), R$^{74}$-substituted or unsubstituted heteroalkyl (e.g., 2 to 8 membered, 2 to 6 membered, or 2 to 4 membered), R$^{74}$-substituted or unsubstituted cycloalkyl (e.g., C$_3$-C$_8$, C$_3$-C$_6$, or C$_5$-C$_6$), R$^{74}$-substituted or unsubstituted heterocycloalkyl (e.g., 3 to 8 membered, 3 to 6 membered, or 5 to 6 membered), R$^{74}$-substituted or unsubstituted aryl (e.g., C$_6$-C$_{10}$, C$_{10}$, or phenyl), or R$^{74}$-substituted or unsubstituted heteroaryl (e.g., 5 to 10 membered, 5 to 9 membered, or 5 to 6 membered). X$^{73}$ is halogen. In embodiments, X$^{73}$ is F.

In embodiments, R$^{16}$ is independently hydrogen, oxo, halogen, —CX$^{16}_3$, —CHX$^{16}_2$, —OCH$_2$X$^{16}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{16}_3$, —OCHX$^{16}_2$, R$^{75}$-substituted or unsubstituted alkyl (e.g., C$_1$-C$_8$, C$_1$-C$_6$, or C$_1$-C$_4$), R$^{75}$-substituted or unsubstituted heteroalkyl (e.g., 2 to 8 membered, 2 to 6 membered, or 2 to 4 membered), R$^{75}$-substituted or unsubstituted cycloalkyl (e.g., C$_3$-C$_8$, C$_3$-C$_6$, or C$_5$-C$_6$), R$^{75}$-substituted or unsubstituted heterocycloalkyl (e.g., 3 to 8 membered, 3 to 6 membered, or 5 to 6 membered), R$^{75}$-substituted or unsubstituted aryl (e.g., C$_6$-C$_{10}$, C$_{10}$, or phenyl), or R$^{75}$-substituted or unsubstituted heteroaryl (e.g., 5 to 10 membered, 5 to 9 membered, or 5 to 6 membered). X$^{16}$ is halogen. In embodiments, X$^{16}$ is F.

R$^{75}$ is independently oxo, halogen, —CX$^{75}_3$, —CHX$^{75}_2$, —OCH$_2$X$^{75}$, —OCHX$^{75}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{75}_3$, —OCHX$^{75}_2$, R$^{76}$-substituted or unsubstituted alkyl (e.g., C$_1$-C$_8$, C$_1$-C$_6$, or C$_1$-C$_4$), R$^{76}$-substituted or unsubstituted heteroalkyl (e.g., 2 to 8 membered, 2 to 6 membered, or 2 to 4 membered), R$^{76}$-substituted or unsubstituted cycloalkyl (e.g., C$_3$-C$_8$, C$_3$-C$_6$, or C$_5$-C$_6$), R$^{76}$-substituted or unsubstituted heterocycloalkyl (e.g., 3 to 8 membered, 3 to 6 membered, or 5 to 6 membered), R$^{76}$-substituted or unsubstituted aryl (e.g., C$_6$-C$_{10}$, C$_{10}$, or phenyl), or R$^{76}$-substituted or unsubstituted heteroaryl (e.g., 5 to 10 membered, 5 to 9 membered, or 5 to 6 membered). X$^{75}$ is halogen. In embodiments, X$^{75}$ is F.

R$^{76}$ is independently oxo, halogen, —CX$^{76}_3$, —CHX$^{76}_2$, —OCH$_2$X$^{76}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{76}_3$, —OCHX$^{76}_2$, R$^{77}$-substituted or unsubstituted alkyl (e.g., C$_1$-C$_8$, C$_1$-C$_6$, or C$_1$-C$_4$), R$^{77}$-substituted or unsubstituted heteroalkyl (e.g., 2 to 8 membered, 2 to 6 membered, or 2 to 4 membered), R$^{77}$-substituted or unsubstituted cycloalkyl (e.g., C$_3$-C$_8$, C$_3$-C$_6$, or C$_5$-C$_6$), R$^{77}$-substituted or unsubstituted heterocycloalkyl (e.g., 3 to 8 membered, 3 to 6 membered, or 5 to 6 membered), R$^{77}$-substituted or unsubstituted aryl (e.g., C$_6$-C$_{10}$, C$_{10}$, or phenyl), or R$^{77}$-substituted or unsubstituted heteroaryl (e.g., 5 to 10 membered, 5 to 9 membered, or 5 to 6 membered). X$^{76}$ is halogen. In embodiments, X$^{76}$ is F.

In embodiments, R$^{17}$ is independently hydrogen, oxo, halogen, —CX$^{17}_3$, —CHX$^{17}_2$, —OCH$_2$X$^{17}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{17}_3$, —OCHX$^{17}_2$, R$^{78}$-substituted or unsubstituted alkyl (e.g., C$_1$-C$_8$, C$_3$-C$_6$, or C$_1$-C$_4$), R$^{78}$-substituted or unsubstituted heteroalkyl (e.g., 2 to 8 membered, 2 to 6 membered, or 2 to 4 membered), R$^{78}$-substituted or unsubstituted cycloalkyl (e.g., C$_3$-C$_8$, C$_3$-C$_6$, or C$_5$-C$_6$), R$^{78}$-substituted or unsubstituted heterocycloalkyl (e.g., 3 to 8 membered, 3 to 6 membered, or 5 to 6 membered), R$^{78}$-substituted or unsubstituted aryl (e.g., C$_6$-C$_{10}$, C$_{10}$, or phenyl), or R$^{78}$-substituted or unsubstituted heteroaryl (e.g., 5 to 10 membered, 5 to 9 membered, or 5 to 6 membered). X$^{17}$ is halogen. In embodiments, X$^{17}$ is F.

R$^{78}$ is independently oxo, halogen, —CX$^{78}_3$, —CHX$^{78}_2$, —OCH$_2$X$^{78}$, —OCHX$^{78}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{78}_3$, —OCHX$^{78}_2$, R$^{79}$-substituted or unsubstituted alkyl (e.g., C$_1$-C$_8$, C$_1$-C$_6$, or C$_1$-C$_4$), R$^{79}$-substituted or unsubstituted heteroalkyl (e.g., 2 to 8 membered, 2 to 6 membered, or 2 to 4 membered), R$^{79}$-substituted or unsubstituted cycloalkyl (e.g., C$_3$-C$_8$, C$_3$-C$_6$, or C$_5$-C$_6$), R$^{79}$-substituted or unsubstituted heterocycloalkyl (e.g., 3 to 8 membered, 3 to 6 membered, or 5 to 6 membered), R$^{79}$-substituted or unsubstituted aryl (e.g., C$_6$-C$_{10}$, C$_{10}$, or phenyl), or R$^{79}$-substituted or unsubstituted heteroaryl (e.g., 5 to 10 membered, 5 to 9 membered, or 5 to 6 membered). X$^{78}$ is halogen. In embodiments, X$^{78}$ is F.

R$^{79}$ is independently oxo, halogen, —CX$^{79}_3$, —CHX$^{79}_2$, —OCH$_2$X$^{79}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{79}_3$, —OCHX$^{79}_2$, R$^{80}$-substituted or unsubstituted alkyl (e.g., C$_1$-C$_5$, C$_1$-C$_6$, or C$_1$-C$_4$), R$^{80}$-substituted or unsubstituted heteroalkyl (e.g., 2 to 8 membered, 2 to 6 membered, or 2 to 4 membered), R$^{80}$-substituted or unsubstituted cycloalkyl (e.g., $C_3$-$C_8$, $C_3$-$C_6$, or $C_5$-$C_6$), $R^{80}$-substituted or unsubstituted heterocycloalkyl (e.g., 3 to 8 membered, 3 to 6 membered, or 5 to 6 membered), $R^{80}$-substituted or unsubstituted aryl (e.g., $C_6$-$C_{10}$, $C_{10}$, or phenyl), or $R^{80}$-substituted or unsubstituted heteroaryl (e.g., 5 to 10 membered, 5 to 9 membered, or 5 to 6 membered). $X^{79}$ is halogen. In embodiments, $X^{79}$ is F.

In embodiments, $R^{18}$ is independently hydrogen, oxo, halogen, —$CX^{18}_3$, —$CHX^{18}_2$, —$OCH_2X^{18}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{18}_3$, —$OCHX^{18}_2$, $R^{81}$-substituted or unsubstituted alkyl (e.g., $C_1$-$C_8$, $C_1$-$C_6$, or $C_1$-$C_4$), $R^{81}$-substituted or unsubstituted heteroalkyl (e.g., 2 to 8 membered, 2 to 6 membered, or 2 to 4 membered), $R^{81}$-substituted or unsubstituted cycloalkyl (e.g., $C_3$-$C_5$, $C_3$-$C_6$, or $C_5$-$C_6$), $R^{81}$-substituted or unsubstituted heterocycloalkyl (e.g., 3 to 8 membered, 3 to 6 membered, or 5 to 6 membered), $R^{81}$-substituted or unsubstituted aryl (e.g., $C_6$-$C_{10}$, $C_{10}$, or phenyl), or $R^{81}$-substituted or unsubstituted heteroaryl (e.g., 5 to 10 membered, 5 to 9 membered, or 5 to 6 membered). $X^{18}$ is halogen. In embodiments, $X^{18}$ is F.

$R^{81}$ is independently oxo, halogen, —$CX^{81}_3$, —$CHX^{81}_2$, —$OCH_2X^{81}$, —$OCHX^{81}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{81}_3$, —$OCHX^{81}_2$, $R^{82}$-substituted or unsubstituted alkyl (e.g., $C_1$-$C_8$, $C_1$-$C_6$, or $C_1$-$C_4$), $R^{82}$-substituted or unsubstituted heteroalkyl (e.g., 2 to 8 membered, 2 to 6 membered, or 2 to 4 membered), $R^{82}$-substituted or unsubstituted cycloalkyl (e.g., $C_3$-$C_8$, $C_3$-$C_6$, or $C_5$-$C_6$), $R^{82}$-substituted or unsubstituted heterocycloalkyl (e.g., 3 to 8 membered, 3 to 6 membered, or 5 to 6 membered), $R^{82}$-substituted or unsubstituted aryl (e.g., $C_6$-$C_{10}$, $C_{10}$, or phenyl), or $R^{82}$-substituted or unsubstituted heteroaryl (e.g., 5 to 10 membered, 5 to 9 membered, or 5 to 6 membered). $X^{81}$ is halogen. In embodiments, $X^{81}$ is F.

$R^{82}$ is independently oxo, halogen, —$CX^{82}_3$, —$CHX^{82}_2$, —$OCH_2X^{82}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{82}_3$, —$OCHX^{82}_2$, $R^{83}$-substituted or unsubstituted alkyl (e.g., $C_1$-$C_5$, $C_1$-$C_6$, or $C_1$-$C_4$), $R^{83}$-substituted or unsubstituted heteroalkyl (e.g., 2 to 8 membered, 2 to 6 membered, or 2 to 4 membered), $R^{83}$-substituted or unsubstituted cycloalkyl (e.g., $C_3$-$C_8$, $C_3$-$C_6$, or $C_5$-$C_6$), $R^{83}$-substituted or unsubstituted heterocycloalkyl (e.g., 3 to 8 membered, 3 to 6 membered, or 5 to 6 membered), $R^{83}$-substituted or unsubstituted aryl (e.g., $C_6$-$C_{10}$, $C_{10}$, or phenyl), or $R^{83}$-substituted or unsubstituted heteroaryl (e.g., 5 to 10 membered, 5 to 9 membered, or 5 to 6 membered). $X^{82}$ is halogen. In embodiments, $X^{82}$ is F.

In embodiments, $R^{19}$ is independently hydrogen, oxo, halogen, —$CX^{19}_3$, —$CHX^{19}_2$, —$OCH_2X^{19}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{19}_3$, —$OCHX^{19}_2$, $R^{84}$-substituted or unsubstituted alkyl (e.g., $C_1$-$C_8$, $C_1$-$C_6$, or $C_1$-$C_4$), $R^{84}$-substituted or unsubstituted heteroalkyl (e.g., 2 to 8 membered, 2 to 6 membered, or 2 to 4 membered), $R^{84}$-substituted or unsubstituted cycloalkyl (e.g., $C_3$-$C_8$, $C_3$-$C_6$, or $C_5$-$C_6$), $R^{84}$-substituted or unsubstituted heterocycloalkyl (e.g., 3 to 8 membered, 3 to 6 membered, or 5 to 6 membered), $R^{84}$-substituted or unsubstituted aryl (e.g., $C_6$-$C_{10}$, $C_{10}$, or phenyl), or $R^{84}$-substituted or unsubstituted heteroaryl (e.g., 5 to 10 membered, 5 to 9 membered, or 5 to 6 membered). $X^{19}$ is halogen. In embodiments, $X^{19}$ is F.

$R^{84}$ is independently oxo, halogen, —$CX^{84}_3$, —$CHX^{84}_2$, —$OCH_2X^{84}$, —$OCHX^{84}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{84}_3$, —$OCHX^{84}_2$, $R^{85}$-substituted or unsubstituted alkyl (e.g., $C_3$-$C_8$, $C_1$-$C_6$, or $C_1$-$C_4$), $R^{85}$-substituted or unsubstituted heteroalkyl (e.g., 2 to 8 membered, 2 to 6 membered, or 2 to 4 membered), $R^{85}$-substituted or unsubstituted cycloalkyl (e.g., $C_3$-$C_8$, $C_3$-$C_6$, or $C_5$-$C_6$), $R^{85}$-substituted or unsubstituted heterocycloalkyl (e.g., 3 to 8 membered, 3 to 6 membered, or 5 to 6 membered), $R^{85}$-substituted or unsubstituted aryl (e.g., $C_6$-$C_{10}$, $C_{10}$, or phenyl), or $R^{85}$-substituted or unsubstituted heteroaryl (e.g., 5 to 10 membered, 5 to 9 membered, or 5 to 6 membered). $X^{84}$ is halogen. In embodiments, $X^{84}$ is F.

$R^{85}$ is independently oxo, halogen, —$CX^{85}_3$, —$CHX^{85}_2$, —$OCH_2X^{85}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{85}_3$, —$OCHX^{85}_2$, $R^{86}$-substituted or unsubstituted alkyl (e.g., $C_1$-$C_5$, $C_1$-$C_6$, or $C_1$-$C_4$), $R^{86}$-substituted or unsubstituted heteroalkyl (e.g., 2 to 8 membered, 2 to 6 membered, or 2 to 4 membered), $R^{86}$-substituted or unsubstituted cycloalkyl (e.g., $C_3$-$C_8$, $C_3$-$C_6$, or $C_5$-$C_6$), $R^{86}$-substituted or unsubstituted heterocycloalkyl (e.g., 3 to 8 membered, 3 to 6 membered, or 5 to 6 membered), $R^{86}$-substituted or unsubstituted aryl (e.g., $C_6$-$C_{10}$, $C_{10}$, or phenyl), or $R^{86}$-substituted or unsubstituted heteroaryl (e.g., 5 to 10 membered, 5 to 9 membered, or 5 to 6 membered). $X^{85}$ is halogen. In embodiments, $X^{85}$ is F.

In embodiments, $R^{16A}$ is independently hydrogen, oxo, halogen, —$CX^{16A}_3$, —$CHX^{16A}_2$, —$OCH_2X^{16A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16A}_3$, —$OCHX^{16A}_2$, $R^{75A}$-substituted or unsubstituted alkyl (e.g., $C_r$$C_8$, $C_1$-$C_6$, or $C_1$-$C_4$), $R^{75A}$-substituted or unsubstituted heteroalkyl (e.g., 2 to 8 membered, 2 to 6 membered, or 2 to 4 membered), $R^{75A}$-substituted or unsubstituted cycloalkyl (e.g., $C_3$-$C_8$, $C_3$-$C_6$, or $C_5$-$C_6$), $R^{75A}$-substituted or unsubstituted heterocycloalkyl (e.g., 3 to 8 membered, 3 to 6 membered, or 5 to 6 membered), $R^{75A}$-substituted or unsubstituted aryl (e.g., $C_6$-$C_{10}$, $C_{10}$, or phenyl), or $R^{75A}$-substituted or unsubstituted heteroaryl (e.g., 5 to 10 membered, 5 to 9 membered, or 5 to 6 membered). $X^{16A}$ is halogen. In embodiments, $X^{16A}$ is F.

$R^{75A}$ is independently oxo, halogen, —$CX^{75A}_3$, —$CHX^{75A}_2$, —$OCH_2X^{75A}$, —$OCHX^{75A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{75A}_3$, —$OCHX^{75A}_2$, $R^{76A}$-substituted or unsubstituted alkyl (e.g., $C_1$-$C_8$, $C_1$-$C_6$, or $C_1$-$C_4$), $R^{76A}$-substituted or unsubstituted heteroalkyl (e.g., 2 to 8 membered, 2 to 6 membered, or 2 to 4 membered), $R^{76A}$-substituted or unsubstituted cycloalkyl (e.g., $C_3$-$C_8$, $C_3$-$C_6$, or $C_5$-$C_6$), $R^{76A}$-substituted or unsubstituted heterocycloalkyl (e.g., 3 to 8 membered, 3 to 6 membered, or 5 to 6 membered), $R^{76A}$-substituted or unsubstituted aryl (e.g., $C_6$-$C_{10}$, $C_{10}$, or phenyl), or $R^{76A}$-substituted or unsubstituted heteroaryl (e.g., 5 to 10 membered, 5 to 9 membered, or 5 to 6 membered). $X^{75A}$ is halogen. In embodiments, $X^{75A}$ is F.

$R^{76A}$ is independently oxo, halogen, $-CX^{76A}_3$, $-CHX^{76A}_2$, $-OCH_2X^{76A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{76A}_3$, $-OCHX^{76A}_2$, $R^{77A}$-substituted or unsubstituted alkyl (e.g., $C_1$-$C_8$, $C_1$-$C_6$, or $C_1$-$C_4$), $R^{77A}$-substituted or unsubstituted heteroalkyl (e.g., 2 to 8 membered, 2 to 6 membered, or 2 to 4 membered), $R^{77A}$-substituted or unsubstituted cycloalkyl (e.g., $C_3$-$C_8$, $C_3$-$C_6$, or $C_5$-$C_6$), $R^{77A}$-substituted or unsubstituted heterocycloalkyl (e.g., 3 to 8 membered, 3 to 6 membered, or 5 to 6 membered), $R^{77A}$-substituted or unsubstituted aryl (e.g., $C_6$-$C_{10}$, $C_{10}$, or phenyl), or $R^{77A}$-substituted or unsubstituted heteroaryl (e.g., 5 to 10 membered, 5 to 9 membered, or 5 to 6 membered). $X^{76A}$ is halogen. In embodiments, $X^{76A}$ is F.

In embodiments, $R^{17A}$ is independently hydrogen, oxo, halogen, $-CX^{17A}_3$, $-CHX^{17A}_2$, $-OCH_2X^{17A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{17A}_3$, $-OCHX^{17A}_2$, $R^{78A}$-substituted or unsubstituted alkyl (e.g., $C_1$-$C_8$, $C_1$-$C_6$, or $C_1$-$C_4$), $R^{78A}$-substituted or unsubstituted heteroalkyl (e.g., 2 to 8 membered, 2 to 6 membered, or 2 to 4 membered), $R^{78A}$-substituted or unsubstituted cycloalkyl (e.g., $C_3$-$C_8$, $C_3$-$C_6$, or $C_5$-$C_6$), $R^{78A}$-substituted or unsubstituted heterocycloalkyl (e.g., 3 to 8 membered, 3 to 6 membered, or 5 to 6 membered), $R^{78A}$-substituted or unsubstituted aryl (e.g., $C_6$-$C_{10}$, $C_{10}$, or phenyl), or $R^{78A}$-substituted or unsubstituted heteroaryl (e.g., 5 to 10 membered, 5 to 9 membered, or 5 to 6 membered). $X^{17A}$ is halogen. In embodiments, $X^{17A}$ is F.

$R^{78A}$ is independently oxo, halogen, $-CX^{78A}_3$, $-CHX^{78A}_2$, $-OCH_2X^{78A}$, $-OCHX^{78A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{78A}_3$, $-OCHX^{78A}_2$, $R^{79A}$-substituted or unsubstituted alkyl (e.g., $C_3$-$C_3$, $C_1$-$C_6$, or $C_1$-$C_4$), $R^{79A}$-substituted or unsubstituted heteroalkyl (e.g., 2 to 8 membered, 2 to 6 membered, or 2 to 4 membered), $R^{79A}$-substituted or unsubstituted cycloalkyl (e.g., $C_3$-$C_8$, $C_3$-$C_6$, or $C_5$-$C_6$), $R^{79A}$-substituted or unsubstituted heterocycloalkyl (e.g., 3 to 8 membered, 3 to 6 membered, or 5 to 6 membered), $R^{79A}$-substituted or unsubstituted aryl (e.g., $C_6$-$C_{10}$, $C_{10}$, or phenyl), or $R^{79A}$-substituted or unsubstituted heteroaryl (e.g., 5 to 10 membered, 5 to 9 membered, or 5 to 6 membered). $X^{78A}$ is halogen. In embodiments, $X^{78A}$ is F.

$R^{79A}$ is independently oxo, halogen, $-CX^{79A}_3$, $-CHX^{79A}_2$, $-OCH_2X^{79A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{79A}_3$, $-OCHX^{79A}_2$, $R^{80A}$-substituted or unsubstituted alkyl (e.g., $C_1$-$C_8$, $C_1$-$C_6$, or $C_1$-$C_4$), $R^{80A}$-substituted or unsubstituted heteroalkyl (e.g., 2 to 8 membered, 2 to 6 membered, or 2 to 4 membered), $R^{80A}$-substituted or unsubstituted cycloalkyl (e.g., $C_3$-$C_5$, $C_3$-$C_6$, or $C_5$-$C_6$), $R^{80A}$-substituted or unsubstituted heterocycloalkyl (e.g., 3 to 8 membered, 3 to 6 membered, or 5 to 6 membered), $R^{80A}$-substituted or unsubstituted aryl (e.g., $C_6$-$C_{10}$, $C_{10}$, or phenyl), or $R^{80A}$-substituted or unsubstituted heteroaryl (e.g., 5 to 10 membered, 5 to 9 membered, or 5 to 6 membered). $X^{79A}$ is halogen. In embodiments, $X^{79A}$ is F.

In embodiments, $R^{18A}$ is independently hydrogen, oxo, halogen, $-CX^{18A}_3$, $-CHX^{18A}_2$, $-OCH_2X^{18A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{18A}_3$, $-OCHX^{18A}_2$, $R^{81A}$-substituted or unsubstituted alkyl (e.g., $C_1$-$C_8$, $C_1$-$C_6$, or $C_1$-$C_4$), $R^{81A}$-substituted or unsubstituted heteroalkyl (e.g., 2 to 8 membered, 2 to 6 membered, or 2 to 4 membered), $R^{81A}$-substituted or unsubstituted cycloalkyl (e.g., $C_3$-$C_8$, $C_3$-$C_6$, or $C_5$-$C_6$), $R^{81A}$-substituted or unsubstituted heterocycloalkyl (e.g., 3 to 8 membered, 3 to 6 membered, or 5 to 6 membered), $R^{81A}$-substituted or unsubstituted aryl (e.g., $C_6$-$C_{10}$, $C_{10}$, or phenyl), or $R^{81A}$-substituted or unsubstituted heteroaryl (e.g., 5 to 10 membered, 5 to 9 membered, or 5 to 6 membered). $X^{18A}$ is halogen. In embodiments, $X^{18A}$ is F.

$R^{81A}$ is independently oxo, halogen, $-CX^{81A}_3$, $-CHX^{81A}_2$, $-OCH_2X^{81A}$, $-OCHX^{81A}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{81A}_3$, $-OCHX^{81A}_2$, $R^{82A}$-substituted or unsubstituted alkyl (e.g., $C_1$-$C_8$, $C_1$-$C_6$, or $C_1$-$C_4$), $R^{82A}$-substituted or unsubstituted heteroalkyl (e.g., 2 to 8 membered, 2 to 6 membered, or 2 to 4 membered), $R^{82A}$-substituted or unsubstituted cycloalkyl (e.g., $C_3$-$C_8$, $C_3$-$C_6$, or $C_5$-$C_6$), $R^{82A}$-substituted or unsubstituted heterocycloalkyl (e.g., 3 to 8 membered, 3 to 6 membered, or 5 to 6 membered), $R^{82A}$-substituted or unsubstituted aryl (e.g., $C_6$-$C_{10}$, $C_{10}$, or phenyl), or $R^{82A}$-substituted or unsubstituted heteroaryl (e.g., 5 to 10 membered, 5 to 9 membered, or 5 to 6 membered). $X^{81A}$ is halogen. In embodiments, $X^{81A}$ is F.

$R^{82A}$ is independently oxo, halogen, $-CX^{82A}_3$, $-CHX^{82A}_2$, $-OCH_2X^{82A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{82A}_3$, $-OCHX^{82A}_2$, $R^{83A}$-substituted or unsubstituted alkyl (e.g., $C_1$-$C_8$, $C_1$-$C_6$, or $C_1$-$C_4$), $R^{83A}$-substituted or unsubstituted heteroalkyl (e.g., 2 to 8 membered, 2 to 6 membered, or 2 to 4 membered), $R^{83A}$-substituted or unsubstituted cycloalkyl (e.g., $C_3$-$C_5$, $C_3$-$C_6$, or $C_5$-$C_6$), $R^{83A}$-substituted or unsubstituted heterocycloalkyl (e.g., 3 to 8 membered, 3 to 6 membered, or 5 to 6 membered), $R^{83A}$-substituted or unsubstituted aryl (e.g., $C_6$-$C_{10}$, $C_{10}$, or phenyl), or $R^{83A}$-substituted or unsubstituted heteroaryl (e.g., 5 to 10 membered, 5 to 9 membered, or 5 to 6 membered). $X^{82A}$ is halogen. In embodiments, $X^{82A}$ is F.

In embodiments, $R^{19A}$ is independently hydrogen, oxo, halogen, $-CX^{19A}_3$, $-CHX^{19A}_2$, $-OCH_2X^{19A}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^{19A}_3$, $-OCHX^{19A}_2$, $R^{84A}$-substituted or unsubstituted alkyl (e.g., $C_1$-$C_8$, $C_1$-$C_6$, or $C_1$-$C_4$), $R^{84A}$-substituted or unsubstituted heteroalkyl (e.g., 2 to 8 membered, 2 to 6 membered, or 2 to 4 membered), $R^{84A}$-substituted or unsubstituted cycloalkyl (e.g., $C_3$-$C_5$, $C_3$-$C_6$, or $C_5$-$C_6$), $R^{84A}$-substituted or unsubstituted heterocycloalkyl (e.g., 3 to 8 membered, 3 to 6 membered, or 5 to 6 membered), $R^{84A}$-substituted or unsubstituted aryl (e.g., $C_6$-$C_{10}$, $C_{10}$, or phenyl), or $R^{84A}$-substituted or unsubstituted heteroaryl (e.g., 5 to 10 membered, 5 to 9 membered, or 5 to 6 membered). $X^{19A}$ is halogen. In embodiments, $X^{19A}$ is F.

$R^{84A}$ is independently oxo, halogen, —$CX^{84A}_3$, —$CHX^{84A}_2$, —$OCH_2X^{84A}$, —$OCHX^{84A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{84A}_3$, —$OCHX^{84A}_2$, $R^{85A}$-substituted or unsubstituted alkyl (e.g., $C_1$-$C_8$, $C_1$-$C_6$, or $C_1$-$C_4$), $R^{85A}$-substituted or unsubstituted heteroalkyl (e.g., 2 to 8 membered, 2 to 6 membered, or 2 to 4 membered), $R^{85A}$-substituted or unsubstituted cycloalkyl (e.g., $C_3$-$C_8$, $C_3$-$C_6$, or $C_5$-$C_6$), $R^{85A}$-substituted or unsubstituted heterocycloalkyl (e.g., 3 to 8 membered, 3 to 6 membered, or 5 to 6 membered), $R^{85A}$-substituted or unsubstituted aryl (e.g., $C_6$-$C_{10}$, $C_{10}$, or phenyl), or $R^{85A}$-substituted or unsubstituted heteroaryl (e.g., 5 to 10 membered, 5 to 9 membered, or 5 to 6 membered). $X^{84A}$ is halogen. In embodiments, $X^{84A}$ is F.

$R^{85A}$ is independently oxo, halogen, —$CX^{85A}_3$, —$CHX^{85A}_2$, —$OCH_2X^{85A}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{85A}_3$, —$OCHX^{85A}_2$, $R^{86A}$-substituted or unsubstituted alkyl (e.g., $C_1$-$C_8$, $C_1$-$C_6$, or $C_1$-$C_4$), $R^{86A}$-substituted or unsubstituted heteroalkyl (e.g., 2 to 8 membered, 2 to 6 membered, or 2 to 4 membered), $R^{86A}$-substituted or unsubstituted cycloalkyl (e.g., $C_3$-$C_8$, $C_3$-$C_6$, or $C_5$-$C_6$), $R^{86A}$-substituted or unsubstituted heterocycloalkyl (e.g., 3 to 8 membered, 3 to 6 membered, or 5 to 6 membered), $R^{86A}$-substituted or unsubstituted aryl (e.g., $C_6$-$C_{10}$, $C_{10}$, or phenyl), or $R^{86A}$-substituted or unsubstituted heteroaryl (e.g., 5 to 10 membered, 5 to 9 membered, or 5 to 6 membered). $X^{85A}$ is halogen. In embodiments, $X^{85A}$ is F.

In embodiments, $R^{16B}$ is independently hydrogen, oxo, halogen, —$CX^{16B}_3$, —$CHX^{16B}_2$, —$OCH_2X^{16B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{16B}_3$, —$OCHX^{16B}_2$, $R^{75B}$-substituted or unsubstituted alkyl (e.g., $C_1$-$C_8$, $C_1$-$C_6$, or $C_1$-$C_4$), $R^{75B}$-substituted or unsubstituted heteroalkyl (e.g., 2 to 8 membered, 2 to 6 membered, or 2 to 4 membered), $R^{75B}$-substituted or unsubstituted cycloalkyl (e.g., $C_3$-$C_8$, $C_3$-$C_6$, or $C_5$-$C_6$), $R^{75B}$-substituted or unsubstituted heterocycloalkyl (e.g., 3 to 8 membered, 3 to 6 membered, or 5 to 6 membered), $R^{75B}$-substituted or unsubstituted aryl (e.g., $C_6$-$C_{10}$, $C_{10}$, or phenyl), or $R^{75B}$-substituted or unsubstituted heteroaryl (e.g., 5 to 10 membered, 5 to 9 membered, or 5 to 6 membered). $X^{16B}$ is halogen. In embodiments, $X^{16B}$ is F.

$R^{75B}$ is independently oxo, halogen, —$CX^{75B}_3$, —$CHX^{75B}_2$, —$OCH_2X^{75B}$, —$OCHX^{75B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{75B}_3$, —$OCHX^{75B}_2$, $R^{76B}$-substituted or unsubstituted alkyl (e.g., $C_1$-$C_8$, $C_1$-$C_6$, or $C_1$-$C_4$), $R^{76B}$-substituted or unsubstituted heteroalkyl (e.g., 2 to 8 membered, 2 to 6 membered, or 2 to 4 membered), $R^{76B}$-substituted or unsubstituted cycloalkyl (e.g., $C_3$-$C_8$, $C_3$-$C_6$, or $C_5$-$C_6$), $R^{76B}$-substituted or unsubstituted heterocycloalkyl (e.g., 3 to 8 membered, 3 to 6 membered, or 5 to 6 membered), $R^{76B}$-substituted or unsubstituted aryl (e.g., $C_6$-$C_{10}$, $C_{10}$, or phenyl), or $R^{76B}$-substituted or unsubstituted heteroaryl (e.g., 5 to 10 membered, 5 to 9 membered, or 5 to 6 membered). $X^{75B}$ is halogen. In embodiments, $X^{75B}$ is F.

$R^{76B}$ is independently oxo, halogen, —$CX^{76B}_3$, —$CHX^{76B}_2$, —$OCH_2X^{76B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{76B}_3$, —$OCHX^{76B}_2$, $R^{77B}$-substituted or unsubstituted alkyl (e.g., $C_1$-$C_8$, $C_1$-$C_6$, or $C_1$-$C_4$), $R^{77B}$-substituted or unsubstituted heteroalkyl (e.g., 2 to 8 membered, 2 to 6 membered, or 2 to 4 membered), $R^{77B}$-substituted or unsubstituted cycloalkyl (e.g., $C_3$-$C_8$, $C_3$-$C_6$, or $C_5$-$C_6$), $R^{77B}$-substituted or unsubstituted heterocycloalkyl (e.g., 3 to 8 membered, 3 to 6 membered, or 5 to 6 membered), $R^{77B}$-substituted or unsubstituted aryl (e.g., $C_6$-$C_{10}$, Cm, or phenyl), or $R^{77B}$-substituted or unsubstituted heteroaryl (e.g., 5 to 10 membered, 5 to 9 membered, or 5 to 6 membered). $X^{76B}$ is halogen. In embodiments, $X^{76B}$ is F.

In embodiments, $R^{17B}$ is independently hydrogen, oxo, halogen, —$CX^{17B}_3$, —$CHX^{17B}_2$, —$OCH_2X^{17B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{17B}_3$, —$OCHX^{17B}_2$, $R^{78B}$-substituted or unsubstituted alkyl (e.g., $C_1$-$C_8$, $C_1$-$C_6$, or $C_1$-$C_4$), $R^{78B}$-substituted or unsubstituted heteroalkyl (e.g., 2 to 8 membered, 2 to 6 membered, or 2 to 4 membered), $R^{78B}$-substituted or unsubstituted cycloalkyl (e.g., $C_3$-$C_5$, $C_3$-$C_6$, or $C_5$-$C_6$), $R^{78B}$-substituted or unsubstituted heterocycloalkyl (e.g., 3 to 8 membered, 3 to 6 membered, or 5 to 6 membered), $R^{78B}$-substituted or unsubstituted aryl (e.g., $C_6$-$C_{10}$, $C_{10}$, or phenyl), or $R^{78B}$-substituted or unsubstituted heteroaryl (e.g., 5 to 10 membered, 5 to 9 membered, or 5 to 6 membered). $X^{17B}$ is halogen. In embodiments, $X^{17B}$ is F.

$R^{78B}$ is independently oxo, halogen, —$CX^{78B}_3$, —$CHX^{78B}_2$, —$OCH_2X^{78B}$, —$OCHX^{78B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{78B}_3$, —$OCHX^{78B}_2$, $R^{79B}$-substituted or unsubstituted alkyl (e.g., $C_1$-$C_8$, $C_1$-$C_6$, or $C_1$-$C_4$), $R^{79B}$-substituted or unsubstituted heteroalkyl (e.g., 2 to 8 membered, 2 to 6 membered, or 2 to 4 membered), $R^{79B}$-substituted or unsubstituted cycloalkyl (e.g., $C_3$-$C_8$, $C_3$-$C_6$, or $C_5$-$C_6$), $R^{79B}$-substituted or unsubstituted heterocycloalkyl (e.g., 3 to 8 membered, 3 to 6 membered, or 5 to 6 membered), $R^{79B}$-substituted or unsubstituted aryl (e.g., $C_6$-$C_{10}$, $C_{10}$, or phenyl), or $R^{79B}$-substituted or unsubstituted heteroaryl (e.g., 5 to 10 membered, 5 to 9 membered, or 5 to 6 membered). $X^{78B}$ is halogen. In embodiments, $X^{78B}$ is F.

$R^{79B}$ is independently oxo, halogen, —$CX^{79B}_3$, —$CHX^{79B}_2$, —$OCH_2X^{79B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, —$OCX^{79B}_3$, —$OCHX^{79B}_2$, $R^{80B}$-substituted or unsubstituted alkyl (e.g., $C_1$-$C_8$, $C_1$-$C_6$, or $C_1$-$C_4$), $R^{80B}$-substituted or unsubstituted heteroalkyl (e.g., 2 to 8 membered, 2 to 6 membered, or 2 to 4 membered), $R^{80B}$-substituted or unsubstituted cycloalkyl (e.g., $C_3$-$C_8$, $C_3$-$C_6$, or $C_5$-$C_6$), $R^{80B}$-substituted or unsubstituted heterocycloalkyl (e.g., 3 to 8 membered, 3 to 6 membered, or 5 to 6 membered), $R^{80B}$-substituted or unsubstituted aryl (e.g., $C_6$-$C_{10}$, $C_{10}$, or phenyl), or $R^{80B}$-substituted or unsubstituted heteroaryl (e.g., 5 to 10 membered, 5 to 9 membered, or 5 to 6 membered). $X^{79B}$ is halogen. In embodiments, $X^{79B}$ is F.

In embodiments, $R^{18B}$ is independently hydrogen, oxo, halogen, —$CX^{18B}_3$, —$CHX^{18B}_2$, —$OCH_2X^{18B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{18B}_3$, —$OCHX^{18B}_2$, $R^{81B}$-substituted or unsubstituted alkyl (e.g., $C_1$-$C_8$, $C_1$-$C_6$, or $C_1$-$C_4$), $R^{81B}$-substituted or unsubstituted heteroalkyl (e.g., 2 to 8 membered, 2 to 6 membered, or 2 to 4 membered), $R^{81B}$-substituted or unsubstituted cycloalkyl (e.g., $C_3$-$C_5$, $C_3$-$C_6$, or $C_5$-$C_6$), $R^{81B}$-substituted or unsubstituted heterocycloalkyl (e.g., 3 to 8 membered, 3 to 6 membered, or 5 to 6 membered), $R^{81B}$-substituted or unsubstituted aryl (e.g., $C_6$-$C_{10}$, $C_{10}$, or phenyl), or $R^{81B}$-substituted or unsubstituted heteroaryl (e.g., 5 to 10 membered, 5 to 9 membered, or 5 to 6 membered). $X^{18B}$ is halogen. In embodiments, $X^{18B}$ is F.

$R^{81B}$ is independently oxo, halogen, —$CX^{81B}_3$, —$CHX^{81B}_2$, —$OCH_2X^{81B}$, —$OCHX^{81B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{81B}_3$, —$OCHX^{81B}_2$, $R^{82B}$-substituted or unsubstituted alkyl (e.g., $C_1$-$C_8$, $C_1$-$C_6$, or $C_1$-$C_4$), $R^{82B}$-substituted or unsubstituted heteroalkyl (e.g., 2 to 8 membered, 2 to 6 membered, or 2 to 4 membered), $R^{82B}$-substituted or unsubstituted cycloalkyl (e.g., $C_3$-$C_8$, $C_3$-$C_6$, or $C_5$-$C_6$), $R^{82B}$-substituted or unsubstituted heterocycloalkyl (e.g., 3 to 8 membered, 3 to 6 membered, or 5 to 6 membered), $R^{82B}$-substituted or unsubstituted aryl (e.g., $C_6$-$C_{10}$, $C_{10}$, or phenyl), or $R^{82B}$-substituted or unsubstituted heteroaryl (e.g., 5 to 10 membered, 5 to 9 membered, or 5 to 6 membered). $X^{81B}$ is halogen. In embodiments, $X^{81B}$ is F.

$R^{82B}$ is independently oxo, halogen, —$CX^{82B}_3$, —$CHX^{82B}_2$, —$OCH_2X^{82B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{82B}_3$, —$OCHX^{82B}_2$, $R^{83B}$-substituted or unsubstituted alkyl (e.g., $C_1$-$C_8$, $C_1$-$C_6$, or $C_1$-$C_4$), $R^{83B}$-substituted or unsubstituted heteroalkyl (e.g., 2 to 8 membered, 2 to 6 membered, or 2 to 4 membered), $R^{83B}$-substituted or unsubstituted cycloalkyl (e.g., $C_3$-$C_5$, $C_3$-$C_6$, or $C_5$-$C_6$), $R^{83B}$-substituted or unsubstituted heterocycloalkyl (e.g., 3 to 8 membered, 3 to 6 membered, or 5 to 6 membered), $R^{83B}$-substituted or unsubstituted aryl (e.g., $C_6$-$C_{10}$, $C_{10}$, or phenyl), or $R^{83B}$-substituted or unsubstituted heteroaryl (e.g., 5 to 10 membered, 5 to 9 membered, or 5 to 6 membered). $X^{82B}$ is halogen. In embodiments, $X^{82B}$ is F.

In embodiments, $R^{19B}$ is independently hydrogen, oxo, halogen, —$CX^{19B}_3$, —$CHX^{19B}_2$, —$OCH_2X^{19B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{19B}_3$, —$OCHX^{19B}_2$, $R^{84B}$-substituted or unsubstituted alkyl (e.g., $C_1$-$C_8$, $C_1$-$C_6$, or $C_1$-$C_4$), $R^{84B}$-substituted or unsubstituted heteroalkyl (e.g., 2 to 8 membered, 2 to 6 membered, or 2 to 4 membered), $R^{84B}$-substituted or unsubstituted cycloalkyl (e.g., $C_3$-$C_5$, $C_3$-$C_6$, or $C_5$-$C_6$), $R^{84B}$-substituted or unsubstituted heterocycloalkyl (e.g., 3 to 8 membered, 3 to 6 membered, or 5 to 6 membered), $R^{84B}$-substituted or unsubstituted aryl (e.g., $C_6$-$C_{10}$, $C_{10}$, or phenyl), or $R^{84B}$-substituted or unsubstituted heteroaryl (e.g., 5 to 10 membered, 5 to 9 membered, or 5 to 6 membered). $X^{19B}$ is halogen. In embodiments, $X^{19B}$ is F.

$R^{84B}$ is independently oxo, halogen, —$CX^{84B}_3$, —$CHX^{84B}_2$, —$OCH_2X^{84B}$, —$OCHX^{84B}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{84B}_3$, —$OCHX^{84B}_2$, $R^{85B}$-substituted or unsubstituted alkyl (e.g., $C_1$-$C_8$, $C_1$-$C_6$, or $C_1$-$C_4$), $R^{85B}$-substituted or unsubstituted heteroalkyl (e.g., 2 to 8 membered, 2 to 6 membered, or 2 to 4 membered), $R^{85B}$-substituted or unsubstituted cycloalkyl (e.g., $C_3$-$C_8$, $C_3$-$C_6$, or $C_5$-$C_6$), $R^{85B}$-substituted or unsubstituted heterocycloalkyl (e.g., 3 to 8 membered, 3 to 6 membered, or 5 to 6 membered), $R^{85B}$-substituted or unsubstituted aryl (e.g., $C_6$-$C_{10}$, $C_{10}$, or phenyl), or $R^{85B}$-substituted or unsubstituted heteroaryl (e.g., 5 to 10 membered, 5 to 9 membered, or 5 to 6 membered). $X^{84B}$ is halogen. In embodiments, $X^{84B}$ is F.

$R^{85B}$ is independently OXO, halogen, —$CX^{85B}_3$, —$CHX^{85B}_2$, —$OCH_2X^{85B}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{85B}_3$, —$OCHX^{85B}_2$, $R^{86B}$-substituted or unsubstituted alkyl (e.g., $C_1$-$C_8$, $C_1$-$C_6$, or $C_1$-$C_4$), $R^{86B}$-substituted or unsubstituted heteroalkyl (e.g., 2 to 8 membered, 2 to 6 membered, or 2 to 4 membered), $R^{86B}$-substituted or unsubstituted cycloalkyl (e.g., $C_3$-$C_8$, $C_3$-$C_6$, or $C_5$-$C_6$), $R^{86B}$-substituted or unsubstituted heterocycloalkyl (e.g., 3 to 8 membered, 3 to 6 membered, or 5 to 6 membered), $R^{86B}$-substituted or unsubstituted aryl (e.g., $C_6$-$C_{10}$, $C_{10}$, or phenyl), or $R^{86B}$-substituted or unsubstituted heteroaryl (e.g., 5 to 10 membered, 5 to 9 membered, or 5 to 6 membered). $X^{85B}$ is halogen. In embodiments, $X^{85B}$ is F.

In embodiments, $R^{16C}$ is independently hydrogen, oxo, halogen, —$CX^{16C}_3$, —$CHX^{16C}_2$, —$OCH_2X^{16C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{16C}_3$, —$OCHX^{16C}_2$, $R^{75C}$-substituted or unsubstituted alkyl (e.g., $C_1$-$C_8$, $C_1$-$C_6$, or $C_1$-$C_4$), $R^{75C}$-substituted or unsubstituted heteroalkyl (e.g., 2 to 8 membered, 2 to 6 membered, or 2 to 4 membered), $R^{75C}$-substituted or unsubstituted cycloalkyl (e.g., $C_3$-$C_8$, $C_3$-$C_6$, or $C_5$-$C_6$), $R^{75C}$-substituted or unsubstituted heterocycloalkyl (e.g., 3 to 8 membered, 3 to 6 membered, or 5 to 6 membered), $R^{75C}$-substituted or unsubstituted aryl (e.g., $C_6$-$C_{10}$, $C_{10}$, or phenyl), or $R^{75C}$-substituted or unsubstituted heteroaryl (e.g., 5 to 10 membered, 5 to 9 membered, or 5 to 6 membered). $X^{16C}$ is halogen. In embodiments, $X^{16C}$ is F.

$R^{75C}$ is independently oxo, halogen, —$CX^{75C}_3$, —$CHX^{75C}_2$, —$OCH_2X^{75C}$, —$OCHX^{75C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{75C}_3$, —$OCHX^{75C}_2$, $R^{76C}$-substituted or unsubstituted alkyl (e.g., $C_1$-$C_8$, $C_1$-$C_6$, or $C_1$-$C_4$), $R^{76C}$-substituted or unsubstituted heteroalkyl (e.g., 2 to 8 membered, 2 to 6 membered, or 2 to 4 membered), $R^{76C}$-substituted or unsubstituted cycloalkyl (e.g., $C_3$-$C_8$, $C_3$-$C_6$, or $C_5$-$C_6$), $R^{76C}$-substituted or unsubstituted heterocycloalkyl (e.g., 3 to 8 membered, 3 to 6 membered, or 5 to 6 membered), $R^{76C}$-substituted or unsubstituted aryl (e.g., $C_6$-$C_{10}$, $C_{10}$, or phenyl), or $R^{76C}$-substituted or unsubstituted heteroaryl (e.g., 5 to 10 membered, 5 to 9 membered, or 5 to 6 membered). $X^{75C}$ is halogen. In embodiments, $X^{75C}$ is F.

$R^{76C}$ is independently oxo, halogen, —$CX^{76C}_3$, —$CHX^{76C}_2$, —$OCH_2X^{76C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{76C}_3$, —$OCHX^{76C}_2$, $R^{77C}$-substituted or unsubstituted alkyl (e.g., $C_1$-$C_8$, $C_1$-$C_6$, or $C_1$-$C_4$), $R^{77C}$-substituted or unsubstituted heteroalkyl (e.g., 2 to 8 membered, 2 to 6 membered, or 2 to 4 membered), $R^{77C}$-substituted or unsubstituted cycloalkyl (e.g., $C_3$-$C_8$, $C_3$-$C_6$, or $C_5$-$C_6$), $R^{77C}$-substituted or unsubstituted heterocycloalkyl (e.g., 3 to 8 membered, 3 to 6 membered, or 5 to 6 membered), $R^{77C}$-substituted or unsubstituted aryl (e.g., $C_6$-$C_{10}$, $C_{10}$, or phenyl), or $R^{77C}$-substituted or unsubstituted heteroaryl (e.g., 5 to 10 membered, 5 to 9 membered, or 5 to 6 membered). $X^{76C}$ is halogen. In embodiments, $X^{76C}$ is F.

In embodiments, $R^{17C}$ is independently hydrogen, oxo, halogen, —$CX^{17C}_3$, —$CHX^{17C}_2$, —$OCH_2X^{17C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{17C}_3$, —$OCHX^{17C}_2$, $R^{78C}$-substituted or unsubstituted alkyl (e.g., $C_1$-$C_8$, $C_1$-$C_6$, or $C_1$-$C_4$), $R^{78C}$-substituted or unsubstituted heteroalkyl (e.g., 2 to 8 membered, 2 to 6 membered, or 2 to 4 membered), $R^{78C}$-substituted or unsubstituted cycloalkyl (e.g., $C_3$-$C_8$, $C_3$-$C_6$, or $C_5$-$C_6$), $R^{78C}$-substituted or unsubstituted heterocycloalkyl (e.g., 3 to 8 membered, 3 to 6 membered, or 5 to 6 membered), $R^{78C}$-substituted or unsubstituted aryl (e.g., $C_6$-$C_{10}$, $C_{10}$, or phenyl), or $R^{78C}$-substituted or unsubstituted heteroaryl (e.g., 5 to 10 membered, 5 to 9 membered, or 5 to 6 membered). $X^{17C}$ is halogen. In embodiments, $X^{17C}$ is F.

$R^{78C}$ is independently oxo, halogen, —$CX^{78C}_3$, —$CHX^{78C}_2$, —$OCH_2X^{78C}$, —$OCHX^{78C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{78C}_3$, —$OCHX^{78C}_2$, $R^{79C}$-substituted or unsubstituted alkyl (e.g., $C_1$-$C_8$, $C_1$-$C_6$, or $C_1$-$C_4$), $R^{79C}$-substituted or unsubstituted heteroalkyl (e.g., 2 to 8 membered, 2 to 6 membered, or 2 to 4 membered), $R^{79C}$-substituted or unsubstituted cycloalkyl (e.g., $C_3$-$C_8$, $C_3$-$C_6$, or $C_5$-$C_6$), $R^{79C}$-substituted or unsubstituted heterocycloalkyl (e.g., 3 to 8 membered, 3 to 6 membered, or 5 to 6 membered), $R^{79C}$-substituted or unsubstituted aryl (e.g., $C_6$-$C_{10}$, $C_{10}$, or phenyl), or $R^{79C}$-substituted or unsubstituted heteroaryl (e.g., 5 to 10 membered, 5 to 9 membered, or 5 to 6 membered). $X^{78C}$ is halogen. In embodiments, $X^{78C}$ is F.

$R^{79C}$ is independently oxo, halogen, —$CX^{79C}_3$, —$CHX^{79C}_2$, —$OCH_2X^{79C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{79C}_3$, —$OCHX^{79C}_2$, $R^{80C}$-substituted or unsubstituted alkyl (e.g., $C_1$-$C_8$, $C_1$-$C_6$, or $C_1$-$C_4$), $R^{80C}$-substituted or unsubstituted heteroalkyl (e.g., 2 to 8 membered, 2 to 6 membered, or 2 to 4 membered), $R^{80C}$-substituted or unsubstituted cycloalkyl (e.g., $C_3$-$C_8$, $C_3$-$C_6$, or $C_5$-$C_6$), $R^{80C}$-substituted or unsubstituted heterocycloalkyl (e.g., 3 to 8 membered, 3 to 6 membered, or 5 to 6 membered), $R^{80C}$-substituted or unsubstituted aryl (e.g., $C_6$-$C_{10}$, $C_{10}$, or phenyl), or $R^{80C}$-substituted or unsubstituted heteroaryl (e.g., 5 to 10 membered, 5 to 9 membered, or 5 to 6 membered). $X^{79C}$ is halogen. In embodiments, $X^{79C}$ is F.

In embodiments, $R^{18C}$ is independently hydrogen, oxo, halogen, —$CX^{18C}_3$, —$CHX^{18C}_2$, —$OCH_2X^{18C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{18C}_3$, —$OCHX^{18C}_2$, $R^{81C}$-substituted or unsubstituted alkyl (e.g., $C_1$-$C_8$, $C_1$-$C_6$, or $C_1$-$C_4$), $R^{81C}$-substituted or unsubstituted heteroalkyl (e.g., 2 to 8 membered, 2 to 6 membered, or 2 to 4 membered), $R^{81C}$-substituted or unsubstituted cycloalkyl (e.g., $C_3$-$C_8$, $C_3$-$C_6$, or $C_5$-$C_6$), $R^{81C}$-substituted or unsubstituted heterocycloalkyl (e.g., 3 to 8 membered, 3 to 6 membered, or 5 to 6 membered), $R^{81C}$-substituted or unsubstituted aryl (e.g., $C_6$-$C_{10}$, $C_{10}$, or phenyl), or $R^{81C}$-substituted or unsubstituted heteroaryl (e.g., 5 to 10 membered, 5 to 9 membered, or 5 to 6 membered). $X^{18C}$ is halogen. In embodiments, $X^{18C}$ is F.

$R^{81C}$ is independently oxo, halogen, —$CX^{81C}_3$, —$CHX^{81C}_2$, —$OCH_2X^{81C}$, —$OCHX^{81C}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{81C}_3$, —$OCHX^{81C}_2$, $R^{82C}$-substituted or unsubstituted alkyl (e.g., $C_1$-$C_8$, $C_1$-$C_6$, or $C_1$-$C_4$), $R^{82C}$-substituted or unsubstituted heteroalkyl (e.g., 2 to 8 membered, 2 to 6 membered, or 2 to 4 membered), $R^{82C}$-substituted or unsubstituted cycloalkyl (e.g., $C_3$-$C_8$, $C_3$-$C_6$, or $C_5$-$C_6$), $R^{82C}$-substituted or unsubstituted heterocycloalkyl (e.g., 3 to 8 membered, 3 to 6 membered, or 5 to 6 membered), $R^{82C}$-substituted or unsubstituted aryl (e.g., $C_6$-$C_{10}$, $C_{10}$, or phenyl), or $R^{82C}$-substituted or unsubstituted heteroaryl (e.g., 5 to 10 membered, 5 to 9 membered, or 5 to 6 membered). $X^{81C}$ is halogen. In embodiments, $X^{81C}$ is F.

$R^{82C}$ is independently oxo, halogen, —$CX^{82C}_3$, —$CHX^{82C}_2$, —$OCH_2X^{82C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{82C}_3$, —$OCHX^{82C}_2$, $R^{83C}$-substituted or unsubstituted alkyl (e.g., $C_1$-$C_8$, $C_1$-$C_6$, or $C_1$-$C_4$), $R^{83C}$-substituted or unsubstituted heteroalkyl (e.g., 2 to 8 membered, 2 to 6 membered, or 2 to 4 membered), $R^{83C}$-substituted or unsubstituted cycloalkyl (e.g., $C_3$-$C_8$, $C_3$-$C_6$, or $C_5$-$C_6$), $R^{83C}$-substituted or unsubstituted heterocycloalkyl (e.g., 3 to 8 membered, 3 to 6 membered, or 5 to 6 membered), $R^{83C}$-substituted or unsubstituted aryl (e.g., $C_6$-$C_{10}$, $C_{10}$, or phenyl), or $R^{83C}$-substituted or unsubstituted heteroaryl (e.g., 5 to 10 membered, 5 to 9 membered, or 5 to 6 membered). $X^{82C}$ is halogen. In embodiments, $X^{82C}$ is F.

In embodiments, $R^{19C}$ is independently hydrogen, oxo, halogen, —$CX^{19C}_3$, —$CHX^{19C}_2$, —$OCH_2X^{19C}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{19C}_3$, —OCHX$^{19C}_2$, R$^{84C}$-substituted or unsubstituted alkyl (e.g., C$_1$-C$_8$, C$_1$-C$_6$, or C$_1$-C$_4$), R$^{84C}$-substituted or unsubstituted heteroalkyl (e.g., 2 to 8 membered, 2 to 6 membered, or 2 to 4 membered), R$^{84C}$-substituted or unsubstituted cycloalkyl (e.g., C$_3$-C$_5$, C$_3$-C$_6$, or C$_5$-C$_6$), R$^{84C}$-substituted or unsubstituted heterocycloalkyl (e.g., 3 to 8 membered, 3 to 6 membered, or 5 to 6 membered), R$^{84C}$-substituted or unsubstituted aryl (e.g., C$_6$-C$_{10}$, C$_{10}$, or phenyl), or R$^{84C}$-substituted or unsubstituted heteroaryl (e.g., 5 to 10 membered, 5 to 9 membered, or 5 to 6 membered). X$^{19C}$ is halogen. In embodiments, X$^{19C}$ is F.

R$^{84C}$ is independently oxo, halogen, —CX$^{84C}_3$, —CHX$^{84C}_2$, —OCH$_2$X$^{84C}$, —OCHX$^{84C}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{84C}_3$, —OCHX$^{84C}_2$, R$^{85C}$-substituted or unsubstituted alkyl (e.g., C$_1$-C$_8$, C$_1$-C$_6$, or C$_1$-C$_4$), R$^{85C}$-substituted or unsubstituted heteroalkyl (e.g., 2 to 8 membered, 2 to 6 membered, or 2 to 4 membered), R$^{85C}$-substituted or unsubstituted cycloalkyl (e.g., C$_3$-C$_8$, C$_3$-C$_6$, or C$_5$-C$_6$), R$^{85C}$-substituted or unsubstituted heterocycloalkyl (e.g., 3 to 8 membered, 3 to 6 membered, or 5 to 6 membered), R$^{85C}$-substituted or unsubstituted aryl (e.g., C$_6$-C$_{10}$, C$_{10}$, or phenyl), or R$^{85C}$-substituted or unsubstituted heteroaryl (e.g., 5 to 10 membered, 5 to 9 membered, or 5 to 6 membered). X$^{84C}$ is halogen. In embodiments, X$^{84C}$ is F.

R$^{85C}$ is independently oxo, halogen, —CX$^{85C}_3$, —CHX$^{85C}_2$, —OCH$_2$X$^{85C}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{85C}_3$, —OCHX$^{85C}_2$, R$^{86C}$-substituted or unsubstituted alkyl (e.g., C$_1$-C$_8$, C$_1$-C$_6$, or C$_1$-C$_4$), R$^{86C}$-substituted or unsubstituted heteroalkyl (e.g., 2 to 8 membered, 2 to 6 membered, or 2 to 4 membered), R$^{86C}$-substituted or unsubstituted cycloalkyl (e.g., C$_3$-C$_8$, C$_3$-C$_6$, or C$_5$-C$_6$), R$^{86C}$-substituted or unsubstituted heterocycloalkyl (e.g., 3 to 8 membered, 3 to 6 membered, or 5 to 6 membered), R$^{86C}$-substituted or unsubstituted aryl (e.g., C$_6$-C$_{10}$, C$_{10}$, or phenyl), or R$^{86C}$-substituted or unsubstituted heteroaryl (e.g., 5 to 10 membered, 5 to 9 membered, or 5 to 6 membered). X$^{85C}$ is halogen. In embodiments, X$^{85C}$ is F.

In embodiments, R$^{16D}$ is independently hydrogen, oxo, halogen, —CX$^{16D}_3$, —CHX$^{16D}_2$, —OCH$_2$X$^{16D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{16D}_3$, —OCHX$^{16D}_2$, R$^{75D}$-substituted or unsubstituted alkyl (e.g., C$_1$-C$_8$, C$_1$-C$_6$, or C$_1$-C$_4$), R$^{75D}$-substituted or unsubstituted heteroalkyl (e.g., 2 to 8 membered, 2 to 6 membered, or 2 to 4 membered), R$^{77D}$-substituted or unsubstituted cycloalkyl (e.g., C$_3$-C$_8$, C$_3$-C$_6$, or C$_5$-C$_6$), R$^{75D}$-substituted or unsubstituted heterocycloalkyl (e.g., 3 to 8 membered, 3 to 6 membered, or 5 to 6 membered), R$^{75D}$-substituted or unsubstituted aryl (e.g., C$_6$-C$_{10}$, C$_{10}$, or phenyl), or R$^{75D}$-substituted or unsubstituted heteroaryl (e.g., 5 to 10 membered, 5 to 9 membered, or 5 to 6 membered). X$^{16D}$ is halogen. In embodiments, X$^{16D}$ is F.

R$^{75D}$ is independently oxo, halogen, —CX$^{75D}_3$, —CHX$^{75D}_2$, —OCH$_2$X$^{75D}$, —OCHX$^{75D}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{75D}$3, —OCHX$^{75D}_2$, R$^{76D}$-substituted or unsubstituted alkyl (e.g., C$_4$-C$_8$, C$_1$-C$_6$, or C$_1$-C$_4$), R$^{76D}$-substituted or unsubstituted heteroalkyl (e.g., 2 to 8 membered, 2 to 6 membered, or 2 to 4 membered), R$^{76D}$-substituted or unsubstituted cycloalkyl (e.g., C$_3$-C$_8$, C$_3$-C$_6$, or C$_5$-C$_6$), R$^{76D}$-substituted or unsubstituted heterocycloalkyl (e.g., 3 to 8 membered, 3 to 6 membered, or 5 to 6 membered), R$^{76D}$-substituted or unsubstituted aryl (e.g., C$_6$-C$_{10}$, C$_{10}$, or phenyl), or R$^{76D}$-substituted or unsubstituted heteroaryl (e.g., 5 to 10 membered, 5 to 9 membered, or 5 to 6 membered). X$^{75C}$ is halogen. In embodiments, X$^{75D}$ is F.

R$^{76D}$ is independently oxo, halogen, —CX$^{76D}_3$, —CHX$^{76D}_2$, —OCH$_2$X$^{76D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{76D}_3$, —OCHX$^{76D}_2$, R$^{77D}$-substituted or unsubstituted alkyl (e.g., C$_1$-C$_8$, C$_1$-C$_6$, or C$_1$-C$_4$), R$^{77D}$-substituted or unsubstituted heteroalkyl (e.g., 2 to 8 membered, 2 to 6 membered, or 2 to 4 membered), R$^{77D}$-substituted or unsubstituted cycloalkyl (e.g., C$_3$-C$_8$, C$_3$-C$_6$, or C$_5$-C$_6$), R$^{77D}$-substituted or unsubstituted heterocycloalkyl (e.g., 3 to 8 membered, 3 to 6 membered, or 5 to 6 membered), R$^{77D}$-substituted or unsubstituted aryl (e.g., C$_6$-C$_{10}$, Cm, or phenyl), or R$^{77D}$-substituted or unsubstituted heteroaryl (e.g., 5 to 10 membered, 5 to 9 membered, or 5 to 6 membered). X$^{76D}$ is halogen. In embodiments, X$^{76D}$ is F.

In embodiments, R$^{17D}$ is independently hydrogen, oxo, halogen, —CX$^{17D}_3$, —CHX$^{17D}_2$, —OCH$_2$X$^{17D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{17D}_3$, —OCHX$^{17D}_2$, R$^{78D}$-substituted or unsubstituted alkyl (e.g., C$_1$-C$_8$, C$_1$-C$_6$, or C$_1$-C$_4$), R$^{78D}$-substituted or unsubstituted heteroalkyl (e.g., 2 to 8 membered, 2 to 6 membered, or 2 to 4 membered), R$^{78D}$-substituted or unsubstituted cycloalkyl (e.g., C$_3$-C$_8$, C$_3$-C$_6$, or C$_5$-C$_6$), R$^{78D}$-substituted or unsubstituted heterocycloalkyl (e.g., 3 to 8 membered, 3 to 6 membered, or 5 to 6 membered), R$^{78D}$-substituted or unsubstituted aryl (e.g., C$_6$-C$_{10}$, C$_{10}$, or phenyl), or R$^{78D}$-substituted or unsubstituted heteroaryl (e.g., 5 to 10 membered, 5 to 9 membered, or 5 to 6 membered). X$^{17D}$ is halogen. In embodiments, X$^{17D}$ is F.

R$^{78D}$ is independently oxo, halogen, —CX$^{78D}_3$, —CHX$^{78D}_2$, —OCH$_2$X$^{78D}$, —OCHX$^{78D}_2$, —CN, —OH, —NH$_2$, —COOH, —CONH$_2$, —NO$_2$ 5, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^{78D}_3$, —OCHX$^{78D}_2$, R$^{79D}$-substituted or unsubstituted alkyl (e.g., C$_1$-C$_8$, C$_1$-C$_6$, or C$_1$-C$_4$), R$^{79D}$-substituted or unsubstituted heteroalkyl (e.g., 2 to 8 membered, 2 to 6 membered, or 2 to 4 membered), R$^{79D}$-substituted or unsubstituted cycloalkyl (e.g., C$_3$-C$_8$, C$_3$-C$_6$, or C$_5$-C$_6$), R$^{79D}$-substituted or unsubstituted heterocycloalkyl (e.g., 3 to 8 membered, 3 to 6 membered, or 5 to 6 membered), R$^{79D}$-substituted or unsubstituted aryl (e.g., C$_6$-C$_{10}$, C$_{10}$, or phenyl), or R$^{79D}$-substituted or unsubstituted heteroaryl (e.g., 5 to 10 membered, 5 to 9 membered, or 5 to 6 membered). X$^{78D}$ is halogen. In embodiments, X$^{78D}$ is F.

R$^{79D}$ is independently oxo, halogen, —CX$^{79D}_3$, —CHX$^{79D}_2$, —OCH$_2$X$^{79D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC=(O)NH$_2$, —NHSO$_2$H, —NHC=(O)H, —NHC(O)—OH, —NHOH, —OCX$^{79D}_3$, —OCHX$^{79D}_2$, R$^{80D}$-substituted or unsubstituted alkyl (e.g., C$_1$-C$_8$, C$_1$-C$_6$, or C$_1$-C$_4$), R$^{80D}$-substituted or unsubstituted heteroalkyl (e.g., 2 to 6 membered, 2 to 6 membered, or 2 to 4 membered), R$^{80D}$-substituted or unsubstituted cycloalkyl (e.g., C$_3$-C$_8$, C$_3$-C$_6$, or C$_5$-C$_6$), R$^{80D}$-substituted or unsubstituted heterocycloalkyl (e.g., 3 to 8 membered, 3 to 6 membered, or 5 to 6 membered), R$^{80D}$-substituted or unsubstituted aryl (e.g., C$_6$-C$_{10}$, C$_{10}$, or phenyl), or R$^{80D}$-substituted or unsubstituted heteroaryl (e.g., 5 to 10 membered, 5 to 9 membered, or 5 to 6 membered). X$^{79D}$ is halogen. In embodiments, X$^{79D}$ is F.

In embodiments, R$^{18D}$ is independently hydrogen, oxo, halogen, —CX$^{18D}_3$, —CHX$^{18D}_2$, —OCH$_2$X$^{18D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{18D}_3$, —OCHX$^{18D}_2$, R$^{81D}$-substituted or unsubstituted alkyl (e.g., C$_1$-C$_8$, C$_1$-C$_6$, or C$_1$-C$_4$), R$^{81D}$-substituted or unsubstituted heteroalkyl (e.g., 2 to 8 membered, 2 to 6 membered, or 2 to 4 membered), R$^{81D}$-substituted or unsubstituted cycloalkyl (e.g., C$_3$-C$_8$, C$_3$-C$_6$, or C$_5$-C$_6$), R$^{81D}$-substituted or unsubstituted heterocycloalkyl (e.g., 3 to 8 membered, 3 to 6 membered, or 5 to 6 membered), R$^{81D}$-substituted or unsubstituted aryl (e.g., C$_6$-C$_{10}$, C$_{10}$, or phenyl), or R$^{81D}$-substituted or unsubstituted heteroaryl (e.g., 5 to 10 membered, 5 to 9 membered, or 5 to 6 membered). X$^{18D}$ is halogen. In embodiments, X$^{18D}$ is F.

R$^{81D}$ is independently oxo, halogen, —CX$^{81D}_3$, —CHX$^{81D}_2$, —OCH$_2$X$^{81D}$, —OCHX$^{81D}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{81D}_3$, —OCHX$^{81D}_2$, R$^{82D}$-substituted or unsubstituted alkyl (e.g., C$_3$-C$_3$, C$_1$-C$_6$, or C$_1$-C$_4$), R$^{82D}$-substituted or unsubstituted heteroalkyl (e.g., 2 to 8 membered, 2 to 6 membered, or 2 to 4 membered), R$^{82D}$-substituted or unsubstituted cycloalkyl (e.g., C$_3$-C$_8$, C$_3$-C$_6$, or C$_5$-C$_6$), R$^{82D}$-substituted or unsubstituted heterocycloalkyl (e.g., 3 to 8 membered, 3 to 6 membered, or 5 to 6 membered), R$^{82D}$-substituted or unsubstituted aryl (e.g., C$_6$-C$_{10}$, C$_{10}$, or phenyl), or R$^{82D}$-substituted or unsubstituted heteroaryl (e.g., 5 to 10 membered, 5 to 9 membered, or 5 to 6 membered). X$^{81D}$ is halogen. In embodiments, X$^{81D}$ is F.

R$^{82D}$ is independently oxo, halogen, —CX$^{82D}_3$, —CHX$^{82D}_2$, —OCH$_2$X$^{82D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{82D}_3$, —OCHX$^{82D}_2$, R$^{83D}$-substituted or unsubstituted alkyl (e.g., C$_1$-C$_8$, C$_1$-C$_6$, or C$_1$-C$_4$), R$^{83D}$-substituted or unsubstituted heteroalkyl (e.g., 2 to 8 membered, 2 to 6 membered, or 2 to 4 membered), R$^{83D}$-substituted or unsubstituted cycloalkyl (e.g., C$_3$-C$_5$, C$_3$-C$_6$, or C$_5$-C$_6$), R$^{83D}$-substituted or unsubstituted heterocycloalkyl (e.g., 3 to 8 membered, 3 to 6 membered, or 5 to 6 membered), R$^{83D}$-substituted or unsubstituted aryl (e.g., C$_6$-C$_{10}$, C$_{10}$, or phenyl), or R$^{83D}$-substituted or unsubstituted heteroaryl (e.g., 5 to 10 membered, 5 to 9 membered, or 5 to 6 membered). X$^{82D}$ is halogen. In embodiments, X$^{82D}$ is F.

In embodiments, R$^{19D}$ is independently hydrogen, oxo, halogen, —CX$^{19D}_3$, —CHX$^{19D}_2$, —OCH$_2$X$^{19D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC(O)—OH, —NHOH, —OCX$^{19D}_3$, —OCHX$^{19D}_2$, R$^{84D}$-substituted or unsubstituted alkyl (e.g., C$_1$-C$_8$, C$_1$-C$_6$, or C$_1$-C$_4$), R$^{84D}$-substituted or unsubstituted heteroalkyl (e.g., 2 to 8 membered, 2 to 6 membered, or 2 to 4 membered), R$^{84D}$-substituted or unsubstituted cycloalkyl (e.g., C$_3$-C$_8$, C$_3$-C$_6$, or C$_5$-C$_6$), R$^{84D}$-substituted or unsubstituted heterocycloalkyl (e.g., 3 to 8 membered, 3 to 6 membered, or 5 to 6 membered), R$^{84D}$-substituted or unsubstituted aryl (e.g., C$_6$-C$_{10}$, C$_{10}$, or phenyl), or R$^{84D}$-substituted or unsubstituted heteroaryl (e.g., 5 to 10 membered, 5 to 9 membered, or 5 to 6 membered). X$^{19D}$ is halogen. In embodiments, X$^{19D}$ is F.

R$^{84D}$ is independently oxo, halogen, —CX$^{84D}_3$, —CHX$^{84D}_2$, —OCH$_2$X$^{84D}$, —OCHX$^{84D}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{84D}_3$, —OCHX$^{84D}_2$, R$^{85D}$-substituted or unsubstituted alkyl (e.g., C$_1$-C$_8$, C$_1$-C$_6$, or C$_1$-C$_4$), R$^{85D}$-substituted or unsubstituted heteroalkyl (e.g., 2 to 8 membered, 2 to 6 membered, or 2 to 4 membered), R$^{85D}$-substituted or unsubstituted cycloalkyl (e.g., C$_3$-C$_8$, C$_3$-C$_6$, or C$_5$-C$_6$), R$^{85D}$-substituted or unsubstituted heterocycloalkyl (e.g., 3 to 8 membered, 3 to 6 membered, or 5 to 6 membered), R$^{85D}$-substituted or unsubstituted aryl (e.g., C$_6$-C$_{10}$, C$_{10}$, or phenyl), or R$^{85D}$-substituted or unsubstituted heteroaryl (e.g., 5 to 10 membered, 5 to 9 membered, or 5 to 6 membered). X$^{84D}$ is halogen. In embodiments, X$^{84D}$ is F.

R$^{85D}$ is independently oxo, halogen, —CX$^{85D}_3$, —CHX$^{85D}_2$, —OCH$_2$X$^{85D}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{85D}_3$, —OCHX$^{85D}_2$, R$^{86D}$-substituted or unsubstituted alkyl (e.g., C$_1$-C$_8$, C$_1$-C$_6$, or C$_1$-C$_4$), R$^{86D}$-substituted or unsubstituted heteroalkyl (e.g., 2 to 8 membered, 2 to 6 membered, or 2 to 4 membered), R$^{86D}$-substituted or unsubstituted cycloalkyl (e.g., C$_3$-C$_5$, C$_3$-C$_6$, or C$_5$-C$_6$), R$^{86D}$-substituted or unsubstituted heterocycloalkyl (e.g., 3 to 8 membered, 3 to 6 membered, or 5 to 6 membered), R$^{86D}$-substituted or unsubstituted aryl (e.g., C$_6$-C$_{10}$, C$_{10}$, or phenyl), or R$^{86D}$-substituted or unsubstituted heteroaryl (e.g., 5 to 10 membered, 5 to 9 membered, or 5 to 6 membered). X$^{85D}$ is halogen. In embodiments, X$^{85D}$ is F.

In embodiments, R$^{20}$ is independently hydrogen, oxo, halogen, —CX$^{20}_3$, —CHX$^{20}_2$, —OCH$_2$X$^{20}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{20}_3$, —OCHX$^{20}_2$, R$^{87}$-substituted or unsubstituted alkyl (e.g., C$_1$-C$_8$, C$_1$-C$_6$, or C$_1$-C$_4$), R$^{87}$-substituted or unsubstituted heteroalkyl (e.g., 2 to 8 membered, 2 to 6 membered, or 2 to 4 membered), R$^{87}$-substituted or unsubstituted cycloalkyl (e.g., C$_3$-C$_5$, C$_3$-C$_6$, or C$_5$-C$_6$), R$^{87}$-substituted or unsubstituted heterocycloalkyl (e.g., 3 to 8 membered, 3 to 6 membered, or 5 to 6 membered), R$^{87}$-substituted or unsubstituted aryl (e.g., C$_6$-C$_{10}$, C$_{10}$, or phenyl), or R$^{87}$-substituted or unsubstituted heteroaryl (e.g., 5 to 10 membered, 5 to 9 membered, or 5 to 6 membered). X$^{20}$ is halogen. In embodiments, X$^{20}$ is F.

R$^{87}$ is independently oxo, halogen, —CX$^{87}_3$, —CHX$^{87}_2$, —OCH$_2$X$^{87}$, —OCHX$^{87}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{87}_3$, —OCHX$^{87}_2$, R$^{88}$-substituted or unsubstituted alkyl (e.g., C$_1$-C$_8$, C$_1$-C$_6$, or C$_1$-C$_4$), R$^{88}$-substituted or unsubstituted heteroalkyl (e.g., 2 to 8 membered, 2 to 6 membered, or 2 to 4 membered), R$^{88}$-substituted or unsubstituted cycloalkyl (e.g., C$_3$-C$_8$, C$_3$-C$_6$, or C$_5$-C$_6$), R$^{88}$-substituted or unsubstituted heterocycloalkyl (e.g., 3 to 8 membered, 3 to 6 membered, or 5 to 6 membered), R$^{88}$-substituted or unsubstituted aryl (e.g., C$_6$-C$_{10}$, C$_{10}$, or phenyl), or R$^{88}$-substituted or unsubstituted heteroaryl (e.g., 5 to 10 membered, 5 to 9 membered, or 5 to 6 membered). X$^{87}$ is halogen. In embodiments, X$^{87}$ is F.

R$^{88}$ is independently oxo, halogen, —CX$^{88}_3$, —CHX$^{88}_2$, —OCH$_2$X$^{88}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{88}_3$, —OCHX$^{88}_2$, R$^{89}$-substituted or unsubstituted alkyl (e.g., C$_1$-C$_8$, C$_1$-C$_6$, or C$_1$-C$_4$), R$^{89}$-substituted or unsubstituted heteroalkyl (e.g., 2 to 8 membered, 2 to 6 membered, or 2 to 4 membered), R$^{89}$-substituted or unsubstituted cycloalkyl (e.g., C$_3$-C$_8$, C$_3$-C$_6$, or C$_5$-C$_6$), R$^{89}$-substituted or unsubstituted heterocycloalkyl (e.g., 3 to 8 membered, 3 to 6 membered, or 5 to 6 membered), R$^{89}$-substituted or unsubstituted aryl (e.g., C$_6$-C$_{10}$, C$_{10}$, or phenyl), or R$^{89}$-substituted or unsubstituted heteroaryl (e.g., 5 to 10 membered, 5 to 9 membered, or 5 to 6 membered). X$^{88}$ is halogen. In embodiments, X$^{88}$ is F.

In embodiments, R$^{21}$ is independently hydrogen, oxo, halogen, —CX$^{21}_3$, —CHX$^{21}_2$, —OCH$_2$X$^{21}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{21}_3$, —OCHX$^{21}_2$, R$^{90}$-substituted or unsubstituted alkyl (e.g., C$_1$-C$_8$, C$_1$-C$_6$, or C$_1$-C$_4$), R$^{90}$-substituted or unsubstituted heteroalkyl (e.g., 2 to 8 membered, 2 to 6 membered, or 2 to 4 membered), R$^{90}$-substituted or unsubstituted cycloalkyl (e.g., C$_3$-C$_8$, C$_3$-C$_6$, or C$_5$-C$_6$), R$^{90}$-substituted or unsubstituted heterocycloalkyl (e.g., 3 to 8 membered, 3 to 6 membered, or 5 to 6 membered), R$^{90}$-substituted or unsubstituted aryl (e.g., C$_6$-C$_{10}$, C$_{10}$, or phenyl), or R$^{90}$-substituted or unsubstituted heteroaryl (e.g., 5 to 10 membered, 5 to 9 membered, or 5 to 6 membered). X$^{21}$ is halogen. In embodiments, X$^{21}$ is F.

R$^{90}$ is independently oxo, halogen, —CX$^{90}_3$, —CHX$^{90}_2$, —OCH$_2$X$^{90}$, —OCHX$^{90}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{90}_3$, —OCHX$^{90}_2$, R$^{91}$-substituted or unsubstituted alkyl (e.g., C$_1$-C$_8$, C$_1$-C$_6$, or C$_1$-C$_4$), R$^{91}$-substituted or unsubstituted heteroalkyl (e.g., 2 to 8 membered, 2 to 6 membered, or 2 to 4 membered), R$^{91}$-substituted or unsubstituted cycloalkyl (e.g., C$_3$-C$_8$, C$_3$-C$_6$, or C$_5$-C$_6$), R$^{91}$-substituted or unsubstituted heterocycloalkyl (e.g., 3 to 8 membered, 3 to 6 membered, or 5 to 6 membered), R$^{91}$-substituted or unsubstituted aryl (e.g., C$_6$-C$_{10}$, C$_{10}$, or phenyl), or R$^{91}$-substituted or unsubstituted heteroaryl (e.g., 5 to 10 membered, 5 to 9 membered, or 5 to 6 membered). X$^{90}$ is halogen. In embodiments, X$^{90}$ is F.

R$^{91}$ is independently oxo, halogen, —CX$^{91}_3$, —CHX$^{91}_2$, —OCH$_2$X$^{91}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{91}_3$, —OCHX$^{91}_2$, R$^{92}$-substituted or unsubstituted alkyl (e.g., C$_1$-C$_8$, C$_1$-C$_6$, or C$_1$-C$_4$), R$^{92}$-substituted or unsubstituted heteroalkyl (e.g., 2 to 8 membered, 2 to 6 membered, or 2 to 4 membered), R$^{92}$-substituted or unsubstituted cycloalkyl (e.g., C$_3$-C$_8$, C$_3$-C$_6$, or C$_5$-C$_6$), R$^{92}$-substituted or unsubstituted heterocycloalkyl (e.g., 3 to 8 membered, 3 to 6 membered, or 5 to 6 membered), R$^{92}$-substituted or unsubstituted aryl (e.g., C$_6$-C$_{10}$, C$_{10}$, or phenyl), or R$^{92}$-substituted or unsubstituted heteroaryl (e.g., 5 to 10 membered, 5 to 9 membered, or 5 to 6 membered). X$^{91}$ is halogen. In embodiments, X$^{91}$ is F.

In embodiments, R$^{22}$ is independently hydrogen, oxo, halogen, —CX$^{22}_3$, —CHX$^{22}_2$, —OCH$_2$X$^{22}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{22}_3$, —OCHX$^{22}_2$, R$^{93}$-substituted or unsubstituted alkyl (e.g., C$_1$-C$_8$, C$_1$-C$_6$, or C$_1$-C$_4$), R$^{93}$-substituted or unsubstituted heteroalkyl (e.g., 2 to 8 membered, 2 to 6 membered, or 2 to 4 membered), R$^{93}$-substituted or unsubstituted cycloalkyl (e.g., C$_3$-C$_5$, C$_3$-C$_6$, or C$_5$-C$_6$), R$^{93}$-substituted or unsubstituted heterocycloalkyl (e.g., 3 to 8 membered, 3 to 6 membered, or 5 to 6 membered), R$^{93}$-substituted or unsubstituted aryl (e.g., C$_6$-C$_{10}$, C$_{10}$, or phenyl), or R$^{93}$-substituted or unsubstituted heteroaryl (e.g., 5 to 10 membered, 5 to 9 membered, or 5 to 6 membered). X$^{22}$ is halogen. In embodiments, X$^{22}$ is F.

R$^{93}$ is independently oxo, halogen, —CX$^{93}_3$, —CHX$^{93}_2$, —OCH$_2$X$^{93}$, —OCHX$^{93}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{93}_3$, —OCHX$^{93}_2$, R$^{94}$-substituted or unsubstituted alkyl (e.g., C$_1$-C$_8$, C$_1$-C$_6$, or C$_1$-C$_4$), R$^{94}$-substituted or unsubstituted heteroalkyl (e.g., 2 to 8 membered, 2 to 6 membered, or 2 to 4 membered), R$^{94}$-substituted or unsubstituted cycloalkyl (e.g., C$_3$-C$_8$, C$_3$-C$_6$, or C$_5$-C$_6$), R$^{94}$-substituted or unsubstituted heterocycloalkyl (e.g., 3 to 8 membered, 3 to 6 membered, or 5 to 6 membered), R$^{94}$-substituted or unsubstituted aryl (e.g., C$_6$-C$_{10}$, C$_{10}$, or phenyl), or R$^{94}$-substituted or unsubstituted heteroaryl (e.g., 5 to 10 membered, 5 to 9 membered, or 5 to 6 membered). X$^{93}$ is halogen. In embodiments, X$^{93}$ is F.

R$^{94}$ is independently oxo, halogen, —CX$^{94}_3$, —CHX$^{94}_2$, —OCH$_2$X$^{94}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{94}_3$, —OCHX$^{94}_2$, R$^{95}$-substituted or unsubstituted alkyl (e.g., C$_1$-C$_8$, C$_3$-C$_6$, or C$_1$-C$_4$), R$^{95}$-substituted or unsubstituted heteroalkyl (e.g., 2 to 8 membered, 2 to 6 membered, or 2 to 4 membered), R$^{95}$-substituted or unsubstituted cycloalkyl (e.g., C$_3$-C$_8$, C$_3$-C$_6$, or C$_5$-C$_6$), R$^{95}$-substituted or unsubstituted heterocycloalkyl (e.g., 3 to 8 membered, 3 to 6 membered, or 5 to 6 membered), R$^{95}$-substituted or unsubstituted aryl (e.g., C$_6$-C$_{10}$, C$_{10}$, or phenyl), or R$^{95}$-substituted or unsubstituted heteroaryl (e.g., 5 to 10 membered, 5 to 9 membered, or 5 to 6 membered). X$^{94}$ is halogen. In embodiments, X$^{94}$ is F.

In embodiments, R$^{23}$ is independently hydrogen, oxo, halogen, —CX$^{23}_3$, —CHX$^{23}_2$, —OCH$_2$X$^{23}$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^{23}_3$, —OCHX$^{23}_2$, R$^{96}$-substituted or unsubstituted alkyl (e.g., C$_1$-C$_8$, C$_1$-C$_6$, or C$_1$-C$_4$), R$^{96}$-substituted or unsubstituted heteroalkyl (e.g., 2 to 8 membered, 2 to 6 membered, or 2 to 4 membered), $R^{96}$-substituted or unsubstituted cycloalkyl (e.g., $C_3$-$C_5$, $C_3$-$C_6$, or $C_5$-$C_6$), $R^{96}$-substituted or unsubstituted heterocycloalkyl (e.g., 3 to 8 membered, 3 to 6 membered, or 5 to 6 membered), $R^{96}$-substituted or unsubstituted aryl (e.g., $C_6$-$C_{10}$, $C_{10}$, or phenyl), or $R^{96}$-substituted or unsubstituted heteroaryl (e.g., 5 to 10 membered, 5 to 9 membered, or 5 to 6 membered). $X^{23}$ is halogen. In embodiments, $X^{23}$ is F.

$R^{96}$ is independently oxo, halogen, —$CX^{96}_3$, —$CHX^{96}_2$, —$OCH_2X^{96}$, —$OCHX^{96}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{96}_3$, —$OCHX^{96}_2$, $R^{97}$-substituted or unsubstituted alkyl (e.g., $C_1$-$C_8$, $C_1$-$C_6$, or $C_1$-$C_4$), $R^{97}$-substituted or unsubstituted heteroalkyl (e.g., 2 to 8 membered, 2 to 6 membered, or 2 to 4 membered), $R^{97}$-substituted or unsubstituted cycloalkyl (e.g., $C_3$-$C_8$, $C_3$-$C_6$, or $C_5$-$C_6$), $R^{97}$-substituted or unsubstituted heterocycloalkyl (e.g., 3 to 8 membered, 3 to 6 membered, or 5 to 6 membered), $R^{97}$-substituted or unsubstituted aryl (e.g., $C_6$-$C_{10}$, $C_{10}$, or phenyl), or $R^{97}$-substituted or unsubstituted heteroaryl (e.g., 5 to 10 membered, 5 to 9 membered, or 5 to 6 membered). $X^{96}$ is halogen. In embodiments, $X^{96}$ is F.

$R^{97}$ is independently oxo, halogen, —$CX^{97}_3$, —$CHX^{97}_2$, —$OCH_2X^{97}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{97}_3$, —$OCHX^{97}_2$, $R^{98}$-substituted or unsubstituted alkyl (e.g., $C_1$-$C_8$, $C_1$-$C_6$, or $C_1$-$C_4$), $R^{98}$-substituted or unsubstituted heteroalkyl (e.g., 2 to 8 membered, 2 to 6 membered, or 2 to 4 membered), $R^{98}$-substituted or unsubstituted cycloalkyl (e.g., $C_3$-$C_5$, $C_3$-$C_6$, or $C_5$-$C_6$), $R^{98}$-substituted or unsubstituted heterocycloalkyl (e.g., 3 to 8 membered, 3 to 6 membered, or 5 to 6 membered), $R^{98}$-substituted or unsubstituted aryl (e.g., $C_6$-$C_{10}$, $C_{10}$, or phenyl), or $R^{98}$-substituted or unsubstituted heteroaryl (e.g., 5 to 10 membered, 5 to 9 membered, or 5 to 6 membered). $X^{97}$ is halogen. In embodiments, $X^{97}$ is F.

In embodiments, $R^{24}$ is independently hydrogen, oxo, halogen, —$CX^{24}_3$, —$CHX^{24}_2$, —$OCH_2X^{24}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{24}_3$, —$OCHX^{24}_2$, $R^{99}$-substituted or unsubstituted alkyl (e.g., $C_1$-$C_8$, $C_1$-$C_6$, or $C_1$-$C_4$), $R^{99}$-substituted or unsubstituted heteroalkyl (e.g., 2 to 8 membered, 2 to 6 membered, or 2 to 4 membered), $R^{99}$-substituted or unsubstituted cycloalkyl (e.g., $C_3$-$C_5$, $C_3$-$C_6$, or $C_5$-$C_6$), $R^{99}$-substituted or unsubstituted heterocycloalkyl (e.g., 3 to 8 membered, 3 to 6 membered, or 5 to 6 membered), $R^{99}$-substituted or unsubstituted aryl (e.g., $C_6$-$C_{10}$, $C_{10}$, or phenyl), or $R^{99}$-substituted or unsubstituted heteroaryl (e.g., 5 to 10 membered, 5 to 9 membered, or 5 to 6 membered). $X^{24}$ is halogen. In embodiments, $X^{24}$ is F.

$R^{99}$ is independently oxo, halogen, —$CX^{99}_3$, —$CHX^{99}_2$, —$OCH_2X^{99}$, —$OCHX^{99}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{99}_3$, —$OCHX^{99}_2$, $R^{100}$-substituted or unsubstituted alkyl (e.g., $C_1$-$C_8$, $C_1$-$C_6$, or $C_1$-$C_4$), $R^{100}$-substituted or unsubstituted heteroalkyl (e.g., 2 to 8 membered, 2 to 6 membered, or 2 to 4 membered), $R^{100}$-substituted or unsubstituted cycloalkyl (e.g., $C_3$-$C_8$, $C_3$-$C_6$, or $C_5$-$C_6$), $R^{100}$-substituted or unsubstituted heterocycloalkyl (e.g., 3 to 8 membered, 3 to 6 membered, or 5 to 6 membered), $R^{100}$-substituted or unsubstituted aryl (e.g., $C_6$-$C_{10}$, $C_{10}$, or phenyl), or $R^{100}$-substituted or unsubstituted heteroaryl (e.g., 5 to 10 membered, 5 to 9 membered, or 5 to 6 membered). $X^{99}$ is halogen. In embodiments, $X^{99}$ is F.

$R^{100}$ is independently oxo, halogen, —$CX^{100}_3$, —$CHX^{100}_2$, —$OCH_2X^{100}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^{100}_3$, —$OCHX^{100}_2$, $R^{101}$-substituted or unsubstituted alkyl (e.g., $C_1$-$C_8$, $C_1$-$C_6$, or $C_1$-$C_4$), $R^{101}$-substituted or unsubstituted heteroalkyl (e.g., 2 to 8 membered, 2 to 6 membered, or 2 to 4 membered), $R^{101}$-substituted or unsubstituted cycloalkyl (e.g., $C_3$-$C_8$, $C_3$-$C_6$, or $C_5$-$C_6$), $R^{101}$-substituted or unsubstituted heterocycloalkyl (e.g., 3 to 8 membered, 3 to 6 membered, or 5 to 6 membered), $R^{101}$-substituted or unsubstituted aryl (e.g., $C_6$-$C_{10}$, $C_{10}$, or phenyl), or $R^{101}$-substituted or unsubstituted heteroaryl (e.g., 5 to 10 membered, 5 to 9 membered, or 5 to 6 membered). $X^{100}$ is halogen. In embodiments, $X^{100}$ is F.

$R^{32}$, $R^{35}$, $R^{38}$, $R^{41}$, $R^{44}$, $R^{47}$, $R^{50}$, $R^{53}$, $R^{56}$, $R^{59}$, $R^{50A}$, $R^{53A}$, $R^{56A}$, $R^{59A}$, $R^{50B}$, $R^{53B}$, $R^{56B}$, $R^{59B}$, $R^{62}$, $R^{65}$, $R^{71}$, $R^{74}$, $R^{77}$, $R^{80}$, $R^{83}$, $R^{86}$, $R^{77A}$, $R^{80A}$, $R^{83A}$, $R^{86A}$, $R^{77B}$, $R^{80B}$, $R^{83B}$, $R^{86B}$, $R^{77C}$, $R^{80C}$, $R^{83C}$, $R^{86C}$, $R^{77D}$, $R^{80D}$, $R^{83D}$, $R^{86D}$, $R^{89}$, $R^{92}$, $R^{95}$, $R^{98}$, and $R^{101}$ are independently hydrogen, oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered). $R^{32}$, $R^{35}$, $R^{38}$, $R^{41}$, $R^{44}$, $R^{47}$, $R^{50}$, $R^{53}$, $R^{56}$, $R^{59}$, $R^{50A}$, $R^{53A}$, $R^{56A}$, $R^{59A}$, $R^{50B}$, $R^{53B}$, $R^{56B}$, $R^{59B}$, $R^{62}$, $R^{65}$, $R^{68}$, $R^{71}$, $R^{74}$, $R^{77}$, $R^{80}$, $R^{83}$, $R^{86}$, $R^{77A}$, $R^{80A}$, $R^{83A}$, $R^{86A}$, $R^{77B}$, $R^{80B}$, $R^{83B}$, $R^{86B}$, $R^{77C}$, $R^{80C}$, $R^{83C}$, $R^{86C}$, $R^{77D}$, $R^{80D}$, $R^{83D}$, $R^{86D}$, $R^{89}$, $R^{92}$, $R^{95}$, $R^{98}$, and $R^{101}$ are independently oxo, halogen, —$CF_3$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCF_3$, —$OCHF_2$, unsubstituted alkyl (e.g., $C_1$-$C_8$, $C_1$-$C_6$, or $C_1$-$C_4$), unsubstituted heteroalkyl (e.g., 2 to 8 membered, 2 to 6 membered, or 2 to 4 membered), unsubstituted cycloalkyl (e.g., $C_3$-$C_8$, $C_3$-$C_6$, or $C_5$-$C_6$), unsubstituted heterocycloalkyl (e.g., 3 to 8 membered, 3 to 6 membered, or 5 to 6 membered), unsubstituted aryl (e.g., $C_6$-$C_{10}$, $C_{10}$, or phenyl), or unsubstituted heteroaryl (e.g., 5 to 10 membered, 5 to 9 membered, or 5 to 6 membered).

In embodiments, unless otherwise indicated, a compound described herein is a racemic mixture of all stereoisomers. In embodiments, unless otherwise indicated, a compound described herein is a racemic mixture of all enantiomers. In embodiments, unless otherwise indicated, a compound described herein is a racemic mixture of two opposite stereoisomers. In embodiments, unless otherwise indicated, a compound described herein is a racemic mixture of two opposite enantiomers. In embodiments, unless otherwise indicated, a compound described herein is a single stereoisomer. In embodiments, unless otherwise indicated, a compound described herein is a single enantiomer.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In some embodiments, the compound is any one of the compounds described herein (e.g., in an aspect, embodiment, claim, figure, table, or example).

In some embodiments, a compound as described herein may include multiple instances of $R^1$, $R^2$, $R^7$, $R^8$, $R^9$, $R^{10}$, X, $X^1$, $X^2$, m1, n1, v1, m2, n2, v2, and/or other variables. In such embodiments, each variable may optional be different and be appropriately labeled to distinguish each group for greater clarity. For example, where each $R^1$, $R^2$, $R^7$, $R^8$, $R^9$, $R^{10}$, X, $X^1$, $X^2$, m1, n1, v1, m2, n2, and/or v2, is different, they may be referred to, for example, as $R^{1.1}$, $R^{1.2}$, $R^{1.3}$, $R^{1.4}$, $R^{1.5}$, $R^{1.6}$, $R^{1.7}$, $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, $R^{7.1}$, $R^{7.2}$, $R^{7.3}$, $R^{7.4}$, $R^{7.5}$, $R^{7.6}$, $R^{7.7}$, $R^{8.1}$, $R^{8.2}$, $R^{8.3}$, $R^{8.4}$, $R^{8.5}$, $R^{8.6}$, $R^{8.7}$, $R^{9.1}$, $R^{9.2}$, $R^{9.3}$, $R^{9.4}$, $R^{9.5}$, $R^{9.6}$, $R^{9.7}$, $R^{10.4}$, $R^{10.2}$, $R^{10.3}$, $R^{10.4}$, $R^{10.5}$, $R^{10.6}$, $R^{10.7}$, $X^{0.1}$, $X^{0.2}$, $X^{0.3}$, $X^{0.4}$, $X^{0.5}$, $X^{0.6}$, $X^{0.7}$, $X^{1.1}$, $X^{1.2}$, $X^{1.3}$, $X^{1.4}$, $X^{1.5}$, $X^{1.6}$, $X^{2.1}$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, m1, m2, m3, m4, m5, m6, m7, n1, n2, n3, n4, n5, n6, n7, v1, v2, v3, v4, v5, v6, v7, m$1^1$, m$1^2$, m$1^3$, m$1^4$, m$1^5$, m$1^6$, n$1^1$, n$1^2$, n$1^3$, n$1^4$, n$1^5$, n$1^6$, v$1^1$, v$1^2$, v$1^3$, v$1^4$, v$1^5$, v$1^6$, respectively, wherein the definition of $R^1$ is assumed by $R^{1.1}$, $R^{1.2}$, $R^{1.3}$, $R^{1.4}$, $R^{1.5}$, $R^{1.6}$, $R^{1.7}$, the definition of $R^2$ is assumed by $R^{2.1}$, $R^{2.2}$, $R^{2.3}$, $R^{2.4}$, $R^{2.5}$, $R^{2.6}$, $R^{2.7}$, $R^{2.8}$, $R^{2.9}$, $R^{2.10}$, the definition of $R^7$ is assumed by $R^{7.1}$, $R^{7.2}$, $R^{7.3}$, $R^{7.4}$, $R^{7.5}$, $R^{7.6}$, $R^{7.7}$, the definition of $R^8$ is assumed by $R^{8.1}$, $R^{8.2}$, $R^{8.3}$, $R^{8.4}$, $R^{8.5}$, $R^{8.6}$, $R^{8.7}$, the definition of $R^9$ is assumed by $R^{9.1}$, $R^{9.2}$, $R^{9.3}$, $R^{9.4}$, $R^{9.5}$, $R^{9.6}$, $R^{9.7}$, the definition of $R^{10}$ is assumed by $R^{10.1}$, $R^{10.2}$, $R^{10.3}$, $R^{10.4}$, $R^{10.5}$, $R^{10.6}$, $R^{10.7}$, the definition of X is assumed by $X^{0.1}$, $X^{0.2}$, $X^{0.3}$, $X^{0.4}$, $X^{0.5}$, $X^{0.6}$, $X^{0.7}$, the definition of $X^1$ is assumed by $X^{1.1}$, $X^{1.2}$, $X^{1.3}$, $X^{1.4}$, $X^{1.5}$, $X^{1.6}$, the definition of $X^2$ is assumed by $X^{2.1}$, $X^{2.2}$, $X^{2.3}$, $X^{2.4}$, $X^{2.5}$, $X^{2.6}$, $X^{2.7}$, $X^{2.8}$, $X^{2.9}$, $X^{2.10}$, the definition of m is assumed by $m^1$, $m^2$, $m^3$, $m^4$, $m^5$, $m^6$, $m^7$, the definition of n is assumed by $n^1$, $n^2$, $n^3$, $n^4$, $n^5$, $n^6$, $n^7$, the definition of v is assumed by $v^1$, $v^2$, $v^3$, $v^4$, $v^5$, $v^6$, $v^7$, the definition of m1 is assumed by m$1^1$, m$1^2$, m$1^3$, m$1^4$, m$1^5$, m$1^6$, the definition of n1 is assumed by n$1^1$, n$1^2$, n$1^3$, n$1^4$, n$1^5$, n$1^6$, the definition of v1 is assumed by v$1^1$, v$1^2$, v$1^3$, v$1^4$, v$1^5$, v$1^6$, the definition of m2 is assumed by m$2^1$, m$2^2$, m$2^3$, m$2^4$, m$2^5$, m$2^6$, m$2^7$, m$2^8$, m$2^9$, m$2^{10}$, the definition of n2 is assumed by n$2^1$, n$2^2$, n$2^3$, n$2^4$, n$2^5$, n$2^6$, n$2^7$, n$2^8$, n$2^9$, n$2^{10}$, the definition of v2 is assumed by v$2^1$, v$2^2$, v$2^3$, v$2^4$, v$2^5$, v$2^6$, v$2^7$, v$2^8$, v$2^9$, v$2^{10}$.

The variables used within a definition of $R^1$, $R^2$, $R^7$, $R^8$, $R^9$, $R^{10}$, X, $X^1$, $X^2$, m1, n1, v1, m2, n2, v2, and/or other variables that appear at multiple instances and are different may similarly be appropriately labeled to distinguish each group for greater clarity.

In an aspect is provided a compound having the formula:

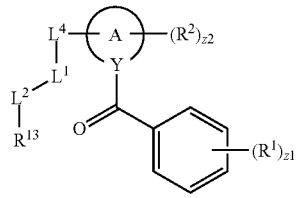

(IJ). Ring A, $R^1$, z1, $R^2$, z2, $L^1$, $L^2$, $L^4$, and $R^{13}$ are as described herein. In embodiments, $R^{13}$ is hydrogen. In embodiments, $R^{13}$ is unsubstituted methyl. In embodiments, the compound is LB9. In embodiments, the compound is DB9.

In an aspect is provided, a compound having the formula:

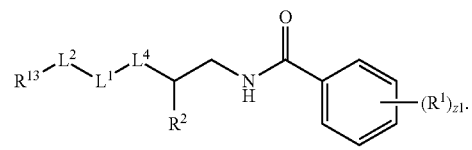

$R^1$, $R^2$, $L^1$, $L^2$, $L^4$, $R^{13}$, and z1 are as described herein. In embodiments, $R^{13}$ is hydrogen. In embodiments, $R^{13}$ is unsubstituted methyl.

In embodiments, the compound does not have the formula:

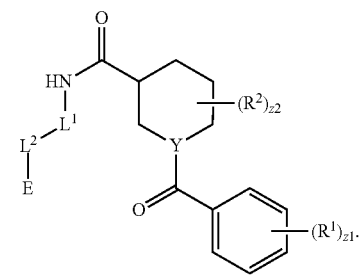

Y, $R^1$, z1, $R^2$, $L^2$, E, and z2 are as described herein. In embodiments, $R^1$ is halogen, —OH, —COOH, —OCF$_3$, $C_1$-$C_4$ unsubstituted alkyl, or 2 to 4 membered unsubstituted heteroalkyl. In embodiments, E is

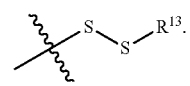

In embodiments, the compound does not have the formula:

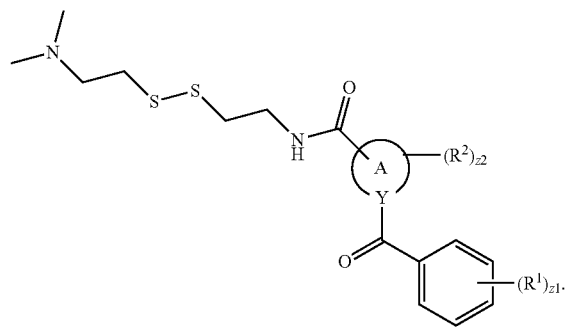

Ring A, Y, $R^1$, z1, $R^2$, and z2 are as described herein. In embodiments, $R^1$ is halogen, —OH, —COOH, —OCF$_3$, $C_1$-$C_4$ unsubstituted alkyl, or 2 to 4 membered unsubstituted heteroalkyl. In embodiments, $R^1$ is halogen.

In embodiments, the compound does not have the formula:

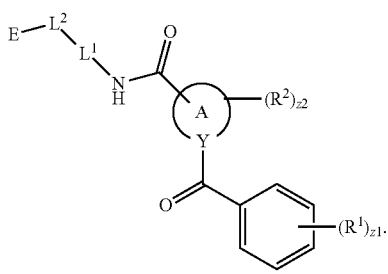

Ring A, Y, $R^1$, z1, $R^2$, z2, $L^1$, $L^2$, and E are as described herein. In embodiments, $R^1$ is halogen, —OH, —COOH, —OCF$_3$, C$_3$-C$_4$ unsubstituted alkyl, or 2 to 4 membered unsubstituted heteroalkyl. In embodiments, $R^1$ is halogen. In embodiments, E is

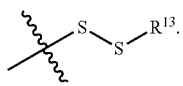

In embodiments, the compound does not have the formula:

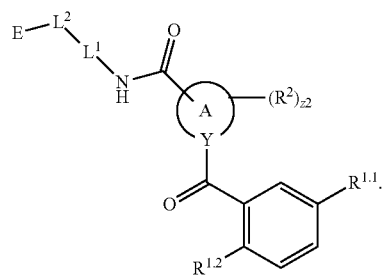

Ring A, Y, $R^{1.1}$, $R^{1.2}$, $R^2$, z2, $L^1$, $L^2$ and E are as described herein. In embodiments, $R^{1.1}$ is halogen, —OH, —COOH, —OCF$_3$, C$_1$-C$_4$ unsubstituted alkyl, or 2 to 4 membered unsubstituted heteroalkyl. In embodiments, $R^{1.2}$ is halogen, —OH, —COOH, —OCF$_3$, C$_1$-C$_4$ unsubstituted alkyl, or 2 to 4 membered unsubstituted heteroalkyl. In embodiments, $R^{1.1}$ is halogen. In embodiments, $R^{1.2}$ is halogen. In embodiments, E is

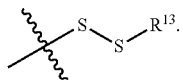

In embodiments, the compound does not have the formula:

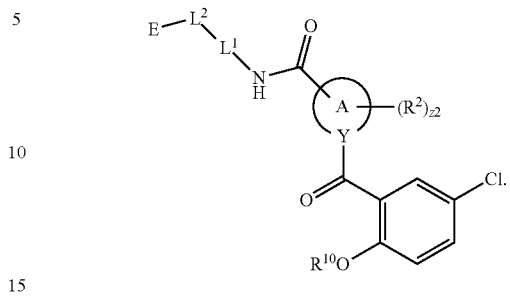

Ring A, Y, $R^2$, z2, $L^1$, $L^2$, E, and $R^{10}$ are as described herein. In embodiments, E is

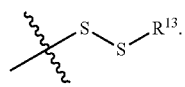

In embodiments, the compound does not have the formula:

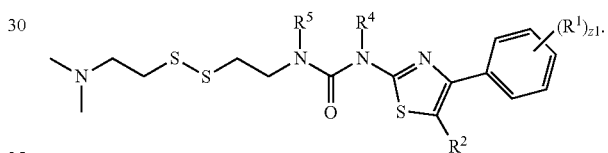

$R^1$, z1, $R^2$, $R^4$, and $R^5$ are as described herein. In embodiments, $R^1$ is halogen, —OH, —COOH, —OCF$_3$, C$_1$-C$_4$ unsubstituted alkyl, or 2 to 4 membered unsubstituted heteroalkyl.

In embodiments, the compound does not have the formula:

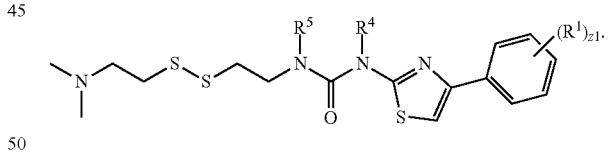

$R^1$, z1, $R^4$, and $R^5$ are as described herein. In embodiments, $R^1$ is halogen, —OH, —COOH, —OCF$_3$, C$_1$-C$_4$ unsubstituted alkyl, or 2 to 4 membered unsubstituted heteroalkyl.

In embodiments, the compound does not have the formula:

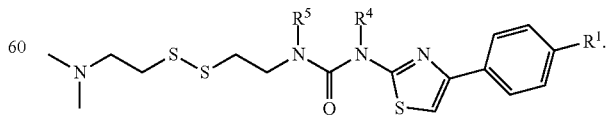

$R^1$, $R^4$, and $R^5$ are as described herein. In embodiments, $R^1$ is halogen, —OH, —COOH, —OCF$_3$, C$_1$-C$_4$ unsubstituted alkyl, or 2 to 4 membered unsubstituted heteroalkyl.

In embodiments, the compound does not have the formula:

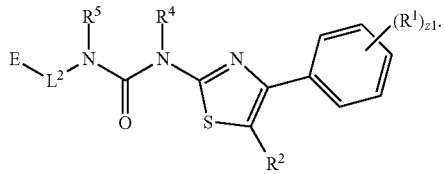

R$^1$, z1, L$^2$, E, R$^2$, R$^4$, and R$^5$ are as described herein. In embodiments, R$^1$ is halogen, —OH, —COOH, —OCF$_3$, C$_1$-C$_4$ unsubstituted alkyl, or 2 to 4 membered unsubstituted heteroalkyl. In embodiments, E is

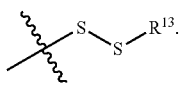

In embodiments, the compound does not have the formula:

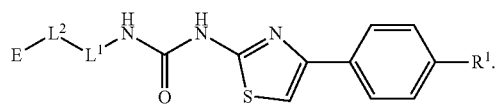

R$^1$, L$^1$, L$^2$, and E are as described herein. In embodiments, R$^1$ is halogen, —OH, —COOH, —OCF$_3$, C$_1$-C$_4$ unsubstituted alkyl, or 2 to 4 membered unsubstituted heteroalkyl. In embodiments, E is

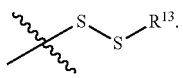

In embodiments, the compound does not have the formula:

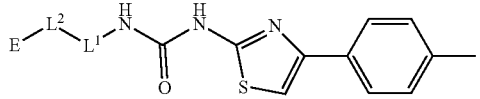

L$^1$, L$^2$, and E are as described herein. In embodiments, E is

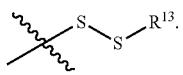

In embodiments, the compound does not have the formula:

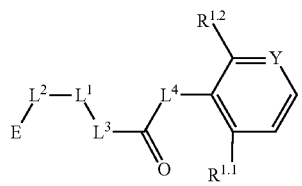

R$^{1.1}$, R$^{1.2}$, Y, L$^1$, L$^2$, L$^3$, L$^4$, and E are as described herein. In embodiments, R$^{1.1}$ is halogen, —OH, —COOH, —OCF$_3$, C$_1$-C$_4$ unsubstituted alkyl, or 2 to 4 membered unsubstituted heteroalkyl. In embodiments, R$^{1.2}$ is halogen, —OH, —COOH, —OCF$_3$, C$_1$-C$_4$ unsubstituted alkyl, or 2 to 4 membered unsubstituted heteroalkyl. In embodiments E is

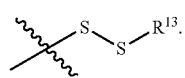

In embodiments, the compound does not have the formula:

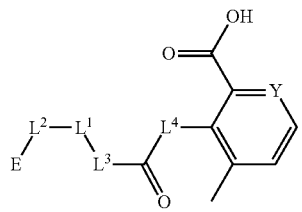

L$^1$, L$^2$, L$^3$, L$^4$, and E are as described herein. In embodiments, E is

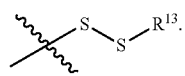

In embodiments, the compound does not have the formula:

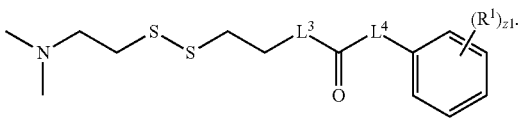

R$^1$, z1, L$^3$, and L$^4$ are as described herein. In embodiments, R$^1$ is halogen, —OH, —COOH, —OCF$_3$, C$_1$-C$_4$ unsubstituted alkyl, or 2 to 4 membered unsubstituted heteroalkyl.

In embodiments, the compound does not have the formula:

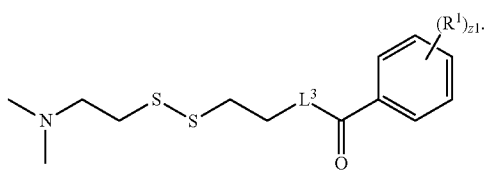

$R^1$, z1, and $L^3$ are as described herein. In embodiments, $R^1$ is halogen, —OH, —COOH, —OCF$_3$, $C_1$-$C_4$ unsubstituted alkyl, or 2 to 4 membered unsubstituted heteroalkyl.

In embodiments, the compound does not have the formula:

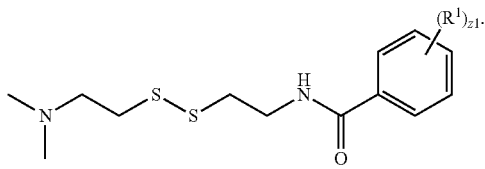

$R^1$ and z1, are as described herein. In embodiments, $R^1$ is halogen, —OH, —COOH, —OCF$_3$, $C_1$-$C_4$ unsubstituted alkyl, or 2 to 4 membered unsubstituted heteroalkyl.

In embodiments, the compound is not

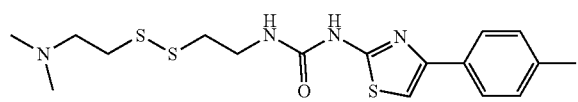

In embodiments, the compound is not

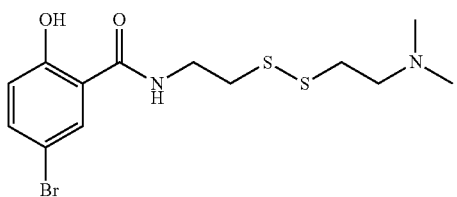 [SMILES: CN(C)CCSSCCNC(=O)c1cc(Br)ccc1O]

in embodiments, the compound is not

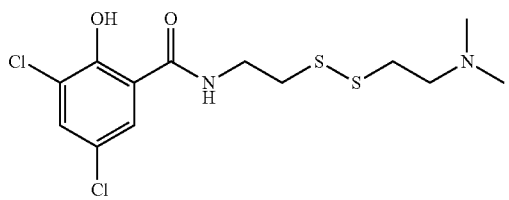

In embodiments, the compound is not

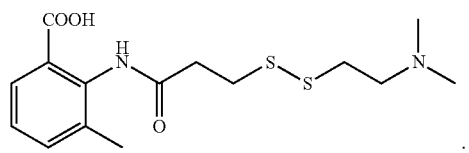 [SMILES: Cc1cccc(C(=O)O)c1NC(=O)CCSSCCN(C)C]

In embodiments, the compound is not

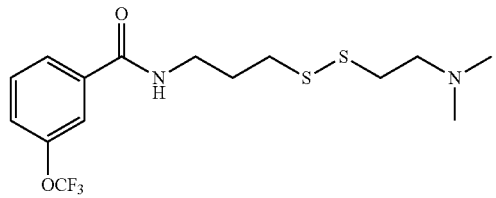

In embodiments, the compound is not

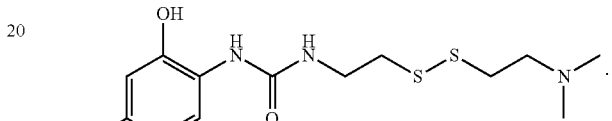

In embodiments, the compound is not

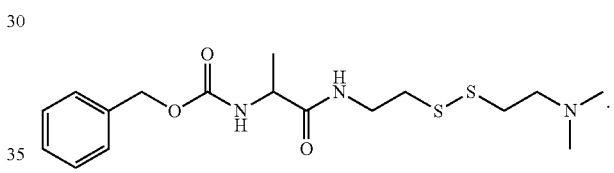

In embodiments, the compound is not

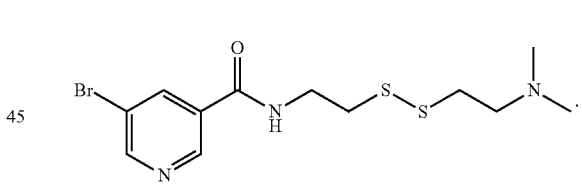

In embodiments, the compound is not

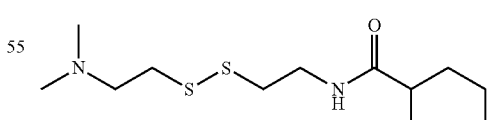

In embodiments, the compound is not

In embodiments, the compound is not

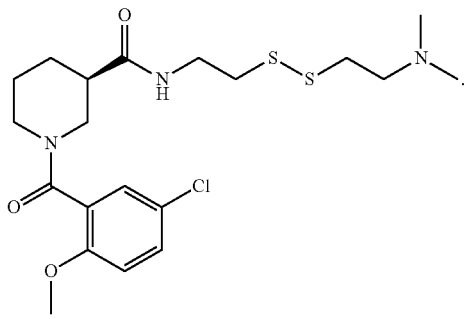 [SMILES: COc1ccc(Cl)cc1C(=O)N1CCC[C@@H](C(=O)NCCSSCCN(C)C)C1]

In embodiments, the compound is not

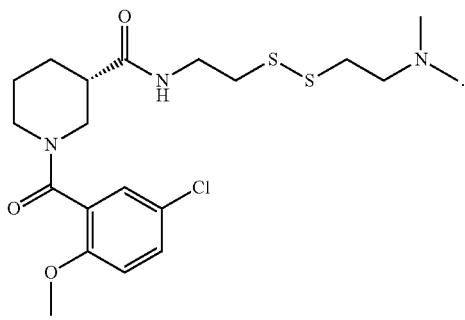 [SMILES: COc1ccc(Cl)cc1C(=O)N1CCC[C@H](C(=O)NCCSSCCN(C)C)C1]

In embodiments, the compound is not a compound described herein, including in an example, figures, or table. In embodiments, the compound does not include

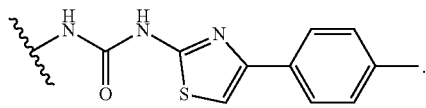 [SMILES: *NC(=O)Nc1nc(-c2ccc(C)cc2)cs1]

In embodiments, the compound does not include

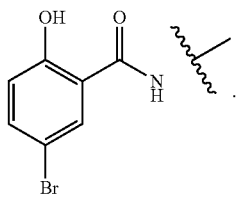

In embodiments, the compound does not include

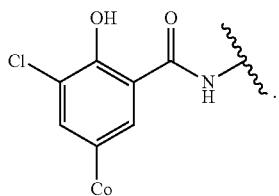

In embodiments, the compound does not include

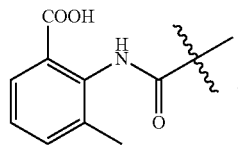

In embodiments, the compound does not include

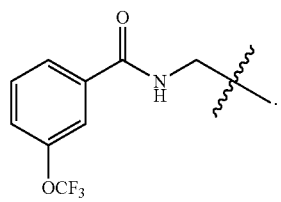 [SMILES: *CNC(=O)c1cccc(OC(F)(F)F)c1]

In embodiments, the compound does not include

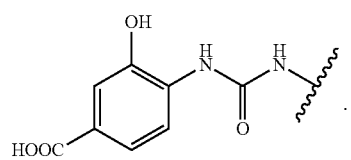 [SMILES: *NC(=O)Nc1ccc(C(=O)O)cc1O]

In embodiments, the compound does not include

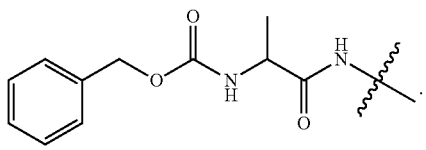 [SMILES: *NC(=O)C(C)NC(=O)OCc1ccccc1]

In embodiments, the compound does not include

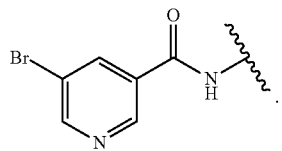 [SMILES: *NC(=O)c1cncc(Br)c1]

in embodiments, the compound does not include

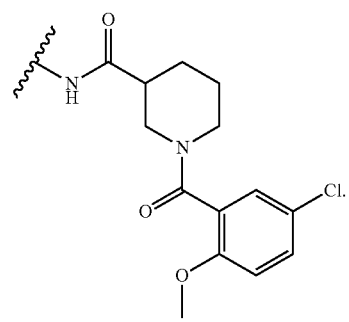 [SMILES: *NC(=O)C1CCCN(C(=O)c2cc(Cl)ccc2OC)C1]

In embodiments, the compound does not include

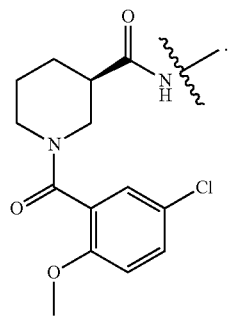

In embodiments, the compound does not include

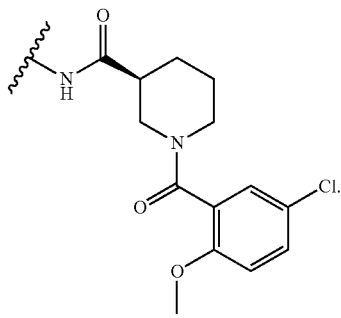 [SMILES: *NC(=O)[C@H]1CCCN(C(=O)c2cc(Cl)ccc2OC)C1]

In embodiments, the compound does not include

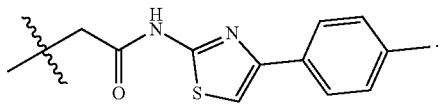 [SMILES: *CC(=O)Nc1nc(-c2ccc(C)cc2)cs1]

In embodiments, the compound does not include

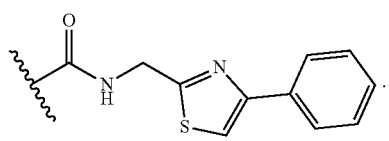 [SMILES: *C(=O)NCc1nc(-c2ccccc2)cs1]

In embodiments, the compound does not include

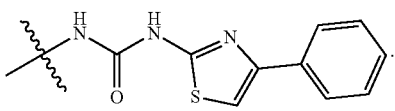 [SMILES: *NC(=O)Nc1nc(-c2ccccc2)cs1]

In embodiments, the compound does not include

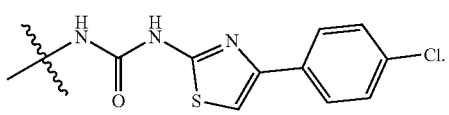 [SMILES: *NC(=O)Nc1nc(-c2ccc(Cl)cc2)cs1]

In embodiments, the compound does not include

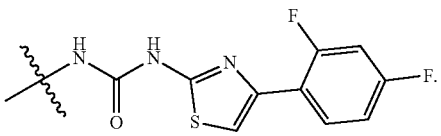 [SMILES: *NC(=O)Nc1nc(-c2ccc(F)cc2F)cs1]

In embodiments, the compound does not include

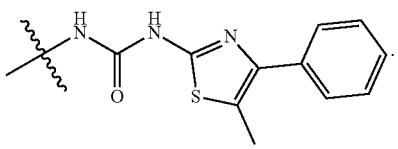 [SMILES: *NC(=O)Nc1nc(-c2ccccc2)c(C)s1]

In embodiments, the compound does not include

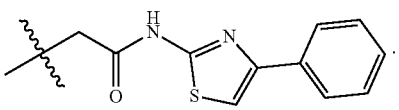 [SMILES: *CC(=O)Nc1nc(-c2ccccc2)cs1]

In embodiments, the compound does not include

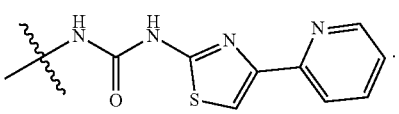 [SMILES: *NC(=O)Nc1nc(-c2ccccn2)cs1]

In embodiments, the compound does not include

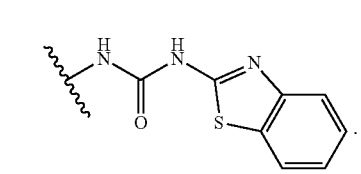 [SMILES: *NC(=O)Nc1nc2ccccc2s1]

III. PHARMACEUTICAL COMPOSITIONS

In an aspect is provided a pharmaceutical composition including a compound described herein and a pharmaceutically acceptable excipient.

In embodiments, the pharmaceutical composition includes an effective amount of the compound. In embodiments, the pharmaceutical composition includes a therapeutically effective amount of the compound. In embodiments, the pharmaceutical composition includes a second agent (e.g., an anti-cancer agent). In embodiments of the pharmaceutical compositions, the pharmaceutical composition includes a second agent in a therapeutically effective amount. In embodiments, the anti-cancer agent is an EGFR inhibitor (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, or BMS-599626). In embodiments, the anti-cancer agent is erlotinib. In embodiments, the anti-cancer agent is gefitinib. In embodiments, the anti-cancer agent is lapatinib. In embodiments, the anti-cancer agent is panitumumab. In embodiments, the anti-cancer agent is panitumumab.

The pharmaceutical compositions may include optical isomers, diastereomers, or pharmaceutically acceptable salts of the modulators disclosed herein. The compound included in the pharmaceutical composition may be covalently attached to a carrier moiety. Alternatively, the compound included in the pharmaceutical composition is not covalently linked to a carrier moiety.

IV. METHODS FOR TREATING DISEASES

In another aspect, a method of treating a disease in a subject in need of such treatment (patient) is provided. The method including administering a therapeutically effective amount of a compound described herein (including embodiments, examples, figures, tables) to the patient. In some embodiments, the disease is cancer. In some embodiments, the cancer is lung cancer, colorectal cancer, colon cancer, pancreatic cancer, breast cancer, or leukemia. In some embodiments, the cancer is lung cancer. In some embodiments, the cancer is non-small cell lung cancer. In some embodiments, the cancer is colon cancer. In some embodiments, the cancer is colorectal cancer. In some embodiments, the cancer is breast cancer. In some embodiments, the cancer is leukemia. In some embodiments, the cancer is pancreatic cancer. In some embodiments, the cancer is a cancer associated with aberrant K-Ras. In some embodiments, the cancer is a cancer associated with a mutant K-Ras. In some embodiments, the cancer is a cancer associated with K-Ras G12C. In some embodiments, the cancer is a cancer associated with K-Ras G12D. In some embodiments, the cancer is a cancer associated with K-Ras G12V. In some embodiments, the cancer is a cancer associated with K-Ras G12S. In some embodiments, the cancer is a cancer associated with K-Ras G13C. In some embodiments, the cancer is a cancer associated with K-Ras G13D.

In some embodiments, a method of treating a disorder in a subject in need thereof is provided, comprising a) determining the presence or absence of a mutation in a Ras protein (such as in a K-Ras, N-Ras, or H-Ras protein) in a malignant or neoplastic cell isolated from the subject and b) if the mutation is determined to be present in the subject, administering to the subject a therapeutically effective amount of a compound or pharmaceutically acceptable salt of the invention. In some embodiments, the disorder is cancer.

The compounds of the invention (i.e. compounds described herein, including in embodiments, examples, figures, tables) can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation or anti-cancer agents). In embodiments, the anti-cancer agent is an EGFR inhibitor (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/ PF299804, OSI-420/desmethyl erlotinib, AZD8931, AEE788, pelitinib/EKB-569, CUDC-101, WZ8040, WZ4002, WZ3146, AG-490, XL647, PD153035, or BMS-599626). In embodiments, the anti-cancer agent is erlotinib. In embodiments, the anti-cancer agent is gefitinib. In embodiments, the anti-cancer agent is lapatinib. In embodiments, the anti-cancer agent is panitumumab. In embodiments, the anti-cancer agent is panitumumab.

V. METHODS OF MODULATING ACTIVITY

In an aspect is provided a method of reducing the level of activity of a K-Ras protein (e.g., human K-Ras 4B), the method including contacting the K-Ras protein with a compound described herein (including in embodiments, examples, figures, and tables). In some embodiments, the activity of the K-Ras protein is it's GTPase activity, nucleotide exchange, differential GDP or GTP binding, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, K-Ras post-translational modifications, prenylation, or a GTP bound K-Ras signaling pathway. In some embodiments, the activity of the K-Ras protein is its GTPase activity, nucleotide exchange, effector protein binding, effector protein activation, guanine exchange factor (GEF) binding, GEF-facilitated nucleotide exchange, phosphate release, nucleotide release, nucleotide binding, or the activity of a GTP bound K-Ras signaling pathway. In some embodiments, the activity of the K-Ras protein is the activity of a signaling pathway activated by GTP bound K-Ras. In some embodiments, the modulating is increasing the activity of said K-Ras protein. In some embodiments, the modulating is reducing the activity of said K-Ras protein. In some embodiments, the K-Ras protein is a human K-Ras protein. In some embodiments, the human K-Ras protein contains a G12C mutation. In some embodiments, the human K-Ras protein contains a G12V mutation. In some embodiments, the human K-Ras protein contains a G12S mutation. In some embodiments, the human K-Ras protein contains a G12D mutation. In some embodiments, the human K-Ras protein contains a G13C mutation. In some embodiments, the human K-Ras protein contains a GOD mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism. In some embodiments of the method of modulating the activity of a K-Ras protein includes contacting the K-Ras protein with an effective amount of a compound described herein (including in embodiments, examples, figures, and tables), the compound is less effective at modulating the activity of an H-Ras protein (e.g., compared to the level of modulation of K-Ras). In some embodiments of the method, the compound modulates the activity of K-Ras at least two-fold more than it modulates the activity of H-Ras. In some embodiments of the method, the compound modulates the activity of K-Ras at least five-fold more than it modulates the activity of H-Ras. In some embodiments of the method, the compound modulates the activity of K-Ras at least ten-fold more than it modulates the activity of H-Ras. In some embodiments of the method, the compound modulates the activity of K-Ras at least fifty-fold more than it modulates the activity of H-Ras. In some embodiments of the method of modulating the activity of a K-Ras protein including contacting the K-Ras protein with an effective amount of a compound described herein (including embodiments, examples, figures, and tables), the compound is less effective at modulating the activity of an N-Ras protein. In some embodiments of the method, the compound modulates the activity of K-Ras at least two-fold more than it modulates the activity of N-Ras. In some embodiments of the method, the compound modulates the activity of K-Ras at least five-fold more than it modulates the activity of N-Ras. In some embodiments of the method, the compound modulates the activity of K-Ras at least ten-fold more than it modulates the activity of N-Ras. In some embodiments of the method, the compound modulates the activity of K-Ras at least fifty-fold more than it modulates the activity of N-Ras.

In another aspect, a method of modulating a K-Ras protein is provided. The method including contacting the K-Ras protein with an effective amount of a compound described herein (including in embodiments, examples, figures, and tables). In some embodiments, the K-Ras protein is modulated in K-Ras subcellular localization, K-Ras post-translational processing, K-Ras post-translational modifications, or a GTP bound K-Ras signaling pathway. In some embodiments, the modulating is increasing the post-translational processing or modifications of the K-Ras protein. In some embodiments, the modulating is reducing the post-translational processing or modifications of the K-Ras protein. In some embodiments, the K-Ras protein is a human K-Ras protein. In some embodiments, the human K-Ras protein contains a G12C mutation. In some embodiments, the human K-Ras protein contains a G12V mutation. In some embodiments, the human K-Ras protein contains a G12S mutation. In some embodiments, the human K-Ras protein contains a G12D mutation. In some embodiments, the human K-Ras protein contains a G13C mutation. In some embodiments, the human K-Ras protein contains a G13D mutation. In some embodiments, the K-Ras protein is a human K-Ras4A protein. In some embodiments, the K-Ras protein is a human K-Ras4B protein. In some embodiments, the K-Ras protein is a mutant K-Ras protein. In some embodiments, the K-Ras protein is an activated K-Ras protein. In some embodiments, the K-Ras protein is within a biological cell. In some embodiments, the biological cell forms part of an organism. In embodiments, compound (e.g., compound described herein) modulates the stability of the K-Ras protein. In embodiments, compound (e.g., compound described herein) reduces the stability of the K-Ras protein relative to the absence of the compound. In embodiments, compound (e.g., compound described herein) increases the rate of degradation of the K-Ras protein relative to the absence of the compound.

In embodiments, the compound (e.g., compound described herein) binds to the amino acid corresponding to His95 in K-Ras (e.g., K-Ras 4B). In embodiments, the compound (e.g., compound described herein) reacts with His95 in K-Ras (K-Ras 4B). In embodiments, the compound (e.g., compound described herein) covalently binds to the amino acid corresponding to His95 in K-Ras (e.g., K-Ras 4B). In embodiments, the compound (e.g., compound described herein) covalently reacts with His95 in K-Ras (K-Ras 4B). In embodiments, the compound (e.g., compound described herein) is capable of binding to the amino acid corresponding to His95 or Cys185 in K-Ras (e.g., K-Ras 4B). In embodiments, the compound (e.g., compound described herein) is capable of reacting with His95 or Cys185 in K-Ras (K-Ras 4B).

In embodiments, the compound (e.g., compound described herein) binds to the amino acid corresponding to His95 in K-Ras (e.g., K-Ras 4B) protein when the K-Ras (e.g., K-Ras 4B) protein Cys185 (or amino acid corresponding to Cys185 of K-Ras 4B) is covalently modified (e.g., prenylated, farnesylated). In embodiments, the compound (e.g., compound described herein) binds to the amino acid corresponding to Cys185 in K-Ras (e.g., K-Ras 4B) protein when the K-Ras (e.g., K-Ras 4B) protein Cys185 (or amino acid corresponding to Cys185 of K-Ras 4B) is not covalently modified (e.g., prenylated, farnesylated). In embodiments, the compound (e.g., compound described herein) binds to the amino acid corresponding to Cys185 in K-Ras (e.g., K-Ras 4B) protein following protein synthesis, when the K-Ras (e.g., K-Ras 4B) protein Cys185 (or amino acid corresponding to Cys185 of K-Ras 4B) has not yet been covalently modified (e.g., prenylated, farnesylated).

In embodiments, the compound prevents productive folding of K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound increases misfolding of K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound increases unfolding of K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound increases degradation of K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound reduces GTP binding to K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound decreases GDP release by K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound decreases interactions of a second protein (e.g., pathway component, effector) with K-Ras protein (e.g., by binding to K-Ras protein, by binding to the amino acid corresponding to His95 of K-Ras, by binding to the amino acid corresponding to Cys185 of K-Ras) relative to the absence of the compound. In embodiments, the compound decreases prenylation (e.g., farnesylation, geranylgeranylation) of K-Ras protein (e.g., by binding to K-Ras protein, by binding to the amino acid corresponding to His95 of K-Ras, by binding to the amino acid corresponding to Cys185 of K-Ras) relative to the absence of the compound.

In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than about 1 hour (e.g., less than about 1, 2, 3, 4, 5, 6, 7, 8, 9, 10, 20, 30, 40, or 50 minutes). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than 1 hour (e.g., less than 1, 2, 3, 4, 5, 6, 7, 8, 9, 10, 20, 30, 40, or 50 minutes). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than about 1 day (e.g., less than about 1, 2, 3, 4, 5, 6, 7, 8, 9, 10, 11, 12, 13, 14, 15, 16, 17, 18, 19, 20, 21, 22, or 23 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than 1 day (e.g., less than 1, 2, 3, 4, 5, 6, 7, 8, 9, 10, 11, 12, 13, 14, 15, 16, 17, 18, 19, 20, 21, 22, or 23 hours). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than about 1 month (e.g., less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). In embodiments, the compound decreases (e.g., by at least 1, 2, 3, 4, 5, 6, 7, 8, 9, 10, 20, 30, 40, 50, 60, 70, 80, 90, 91, 92, 93, 94, 95, 96, 97, 98, or 99%) the level of K-Ras function in a cell (e.g., by binding to K-Ras protein, by binding to the amino acid corresponding to His95 of K-Ras, by binding to the amino acid corresponding to Cys185 of K-Ras) relative to the absence of the compound, in less than 1 month (e.g., less than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days). In embodiments, the compound binds to K-Ras (e.g., only K-Ras 4B, only K-Ras 4A, or both K-Ras 4A and K-Ras 4B).

VI. COMPOSITIONS

In another aspect is provided, a K-Ras protein covalently (e.g., reversibly or irreversibly) bonded to a compound, for example a compound as described herein (including modulators, inhibitors, embodiments, examples, in figures, and in tables). In embodiments, the compound is a compound described herein. In embodiments, the compound is covalently bonded to a cysteine residue of the protein. In embodiments, the compound is irreversibly covalently bonded to a cysteine residue of the protein. In embodiments, the compound is covalently bonded to the residue corresponding to C185 of human K-Ras 4B. In embodiments, the compound is covalently bonded to a histidine residue of the protein. In embodiments, the compound is irreversibly covalently bonded to a histidine residue of the protein. In embodiments, the compound is covalently bonded to the residue corresponding to H95 of human K-Ras 4B.

In embodiments, the covalently modified K-Ras protein has a modulated activity relative to a control, wherein the activity is selected from GTPase activity, nucleotide exchange, effector protein binding, effector protein activation, guanine exchange factor (GEF) binding, GEF-facilitated nucleotide exchange, phosphate release, nucleotide release, nucleotide binding, K-Ras subcellular localization, K-Ras post-translational processing, and K-Ras post-translational modifications. In some embodiments, the covalently modified K-Ras protein is modulated in K-Ras subcellular localization, K-Ras post-translational processing, or K-Ras post-translational modifications. In some embodiments, the covalently modified K-Ras protein contains a G12C mutation. In some embodiments, the covalently modified K-Ras protein contains a G12V mutation. In some embodiments, the covalently modified K-Ras protein contains a G12S mutation. In some embodiments, the compound is covalently bonded to cysteine residue 185. In some embodiments, the compound is covalently bonded to histidine residue 95 (e.g., corresponding to H95 of K-Ras). In some embodiments, the covalently modified K-Ras protein contains a G13C mutation. In some embodiments, the K-Ras protein is bonded to a K-Ras inhibitor, a mutant K-Ras inhibitor, K-Ras H95 inhibitor, or a K-Ras C185 inhibitor. In some embodiments, the K-Ras protein is bonded to a K-Ras modulator, a mutant K-Ras modulator, K-Ras H95 inhibitor, or a K-Ras C185 modulator.

In an aspect is provided a K-Ras protein covalently bonded to a compound having the formula:

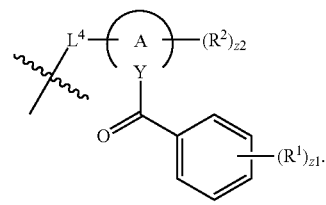

$R^1$, $R^2$, Ring A, Y, $L^4$, z1, and z2 are as described herein.

In an aspect is provided a K-Ras protein covalently bonded to a compound having the formula:

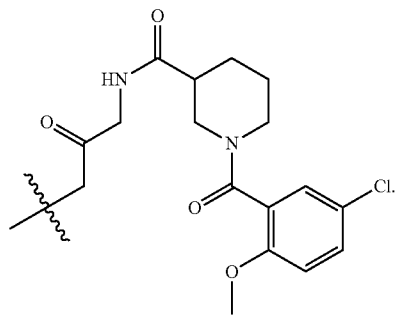 [SMILES: *CC(=O)CNC(=O)C1CCCN(C(=O)c2cc(Cl)ccc2OC)C1]

In an embodiment, the K-Ras protein is covalently bonded to a compound having the formula:

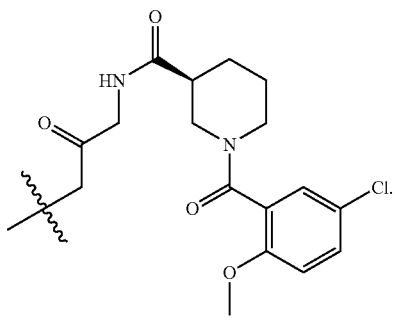 [SMILES: *CC(=O)CNC(=O)[C@H]1CCCN(C(=O)c2cc(Cl)ccc2OC)C1]

In an aspect is provided a K-Ras protein covalently bonded to a compound having the formula:

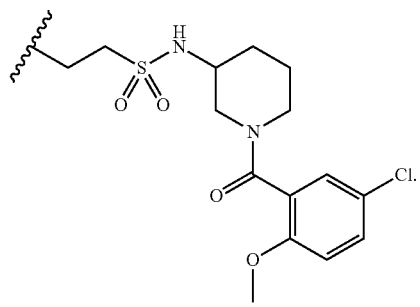 [SMILES: *CCS(=O)(=O)NC1CCCN(C(=O)c2cc(Cl)ccc2OC)C1]

In an embodiment, the K-Ras protein is covalently bonded to a compound having the formula:

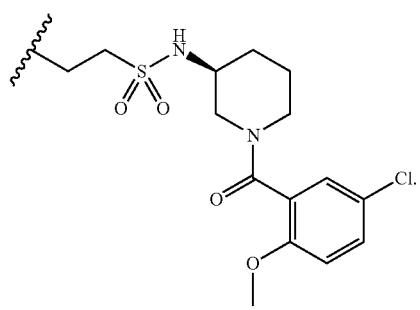 [SMILES: *CCS(=O)(=O)N[C@H]1CCCN(C(=O)c2cc(Cl)ccc2OC)C1]

In an embodiment, the K-Ras protein is covalently bonded to a compound having the formula:

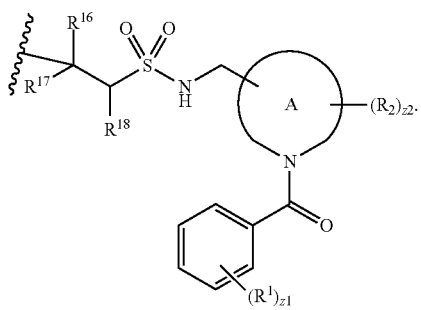

In an embodiment, the K-Ras protein is covalently bonded to a compound having the formula:

In an embodiment, the K-Ras protein is covalently bonded to a compound having the formula:

E, $R^1$, $R^2$, $R^3$, $R^4$, $R^5$, Ring A, Y, $L^1$, $L^2$, $L^3$, $L^4$, z1, and z2 are as described herein.

In embodiments, the compound is covalently bonded to a cysteine residue of the protein. In embodiments, the compound is covalently bonded to a cysteine residue of the protein corresponding to C185 of human K-Ras-4B. In embodiments, the compound is irreversibly covalently bonded to a cysteine (e.g., corresponding to C185 of human K-Ras-4B) of the protein. In embodiments, the compound is covalently bonded to a histidine residue of the protein. In embodiments, the compound is covalently bonded to a histidine residue of the protein corresponding to H95 of human K-Ras-4B. In embodiments, the compound is irreversibly covalently bonded to a histidine (e.g., corresponding to H95 of human K-Ras-4B) of the protein.

In another aspect, a Ras protein (e.g. K-Ras, N-Ras, H-Ras, or another Ras protein described herein) covalently bonded (e.g. reversibly or irreversibly) to a compound, for example a compound as described herein (including modulators, inhibitors, embodiments, figures, examples, and tables), is provided. In some embodiments, the compound is a modulator. In some embodiments, the compound is a modulator such as an inhibitor. In some embodiments, the compound is a Ras modulator. In some embodiments, the compound is a Ras inhibitor.

In embodiments, the compound binds Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) at the CAAX box. In embodiments, the compound binds Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to the residue corresponding to C185 of human K-Ras 4B. In embodiments, the compound binds Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to the residue corresponding to H95 of human K-Ras 4B.

In embodiments, the compound modulates the conformation of the protein. In embodiments, the compound modulates the conformation of the CAAX box. In embodiments, the compound modulates (e.g., reduces or inhibits) the prenylation of the protein at the CAAX box (e.g., residue corresponding to C185 of human K-Ras 4B). In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000, 9000, 10000 fold or more) Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) activity relative to the absence of the compound. In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, or 100%) Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) activity relative to the absence of the compound. In embodiments, the compound inhibits (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, or 100%) Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) prenylation relative to the absence of the compound. In embodiments, the compound reduces (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, or 100%) the amount of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) protein (e.g., in a cell) relative to the absence of the compound. In embodiments, the compound reduces (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, or 100%) production of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) protein (e.g., in a cell) relative to the absence of the compound. In embodiments, the compound increases (e.g. by about 0.1, 0.2, 0.3, 0.4, 0.5, 0.6, 0.7, 0.8, 0.9, 1.0, 2.0, 3.0, 4.0, 5.0, 6.0, 7.0, 8.0, 9.0, 10, 11, 12, 13, 14, 15, 16, 17, 18, 19, 20, 25, 30, 35, 40, 45, 50, 55, 60, 65, 70, 75, 80, 85, 90, 95, or 100%) the degradation of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) protein (e.g., in a cell) relative to the absence of the compound. In embodiments, the compound inhibits protein association with a membrane relative to the absence of the compound.

In embodiments, the compound inhibits proliferation of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under nutrient deficient conditions relative to the absence of the compound. In embodiments, the compound inhibits growth of cancer cells under serum deprivation conditions relative to the absence of the compound. In embodiments, the compound inhibits proliferation of cancer cells under serum deprivation conditions relative to the absence of the compound. In embodiments, the compound inhibits growth of cancer cells under conditions (e.g. local cell environment in a patient) mimicking serum deprivation relative to the absence of the compound. In embodiments, the compound inhibits proliferation of cancer cells under conditions (e.g. local cell environment in a patient) mimicking serum deprivation relative to the absence of the compound.

In embodiments, the compound increases the flexibility of the CAAX box (amino acid sequence at the C terminus of a protein wherein C is a cysteine that may be prenylated, A is an aliphatic amino acid, and X is an amino acid with variable sequence depending on the protein (e.g., M, S, Q, A, or C; L or E)) relative to the absence of the compound. In embodiments, the compound increases the disorder of the CAAX box relative to the absence of the compound. In embodiments, the compound inhibits the binding of Ras ((e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to another protein. In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to another protein, wherein the binding is dependent on Ras prenylation. In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to another protein, wherein the binding is dependent on Ras membrane association.

In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to Raf (e.g. Raf1). In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to SOS. In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to a GEF. In embodiments, the compound inhibits the binding of Ras (e.g. K-Ras, K-Ras 4B, human K-Ras 4B, H-Ras, N-Ras, mutant Ras, K-Ras G12C, K-Ras G12V, K-Ras G12S, K-Ras G13C, K-Ras G12D, K-Ras G13D) to PI3K.

VII. SELECTED EMBODIMENTS

Embodiment P1. A compound having the formula:

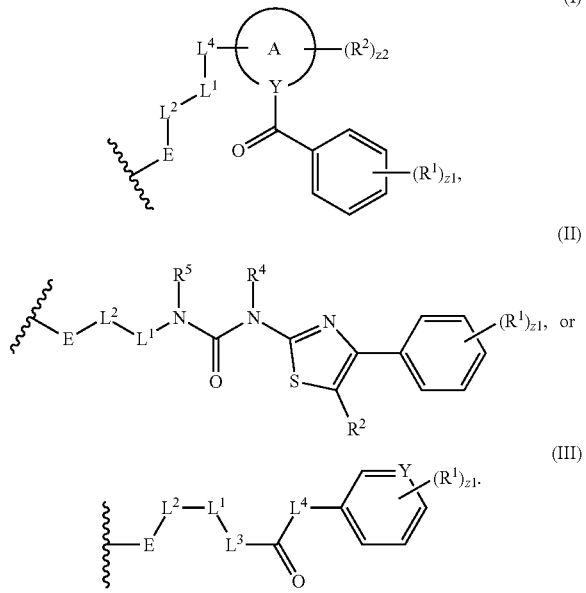

wherein, Y is N or CH; Ring A is a C5-C$_7$ cycloalkyl or 5 to 7 membered heterocycloalkyl; R$^1$ is independently halogen, CX$^1_3$, —CHX$^1_2$, —CH$_2$X$^1$, —CN, —SO$_2$Cl, —SO$_{n1}$R$^{10}$, —SO$_{v1}$NR$^7$R$^8$, —NHNR$^7$R$^8$, —ONR$^7$R$^8$, —NHC=(O)NHNR$^7$R$^8$, —NHC(O)NR$^7$R$^8$, —N(O)$_{m1}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C(O)R$^9$, —NR$^7$C(O)OR$^9$, —NR$^7$OR$^9$, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl; L$^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; L$^2$ is a bond, —O—, —C(O)—, —S—, —SO—, —S(O)$_2$—, —NR$^{7B}$—, —NR$^{7B}$C(O)—, —C(O)NR$^{7B}$—, —SO$_2$NR$^{7B}$—, —NR$^{7B}$SO$_2$—, —OC(O)NR$^{7B}$—, —NR$^{7B}$C(O)O—, —CR$^{9B}$=NO—, —ON=CR$^{9B}$—, —NR$^{8B}$C(O)NR$^{7B}$—, —NR$^{8B}$C(=NR$^{10B}$)NR$^{7B}$—, —NR$^{8B}$C(=NR$^{10B}$)—, —C(=NR$^{10B}$)NR$^{7B}$—, —OC(=NR$^{10B}$)—, —C(=NR$^{10B}$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; L$^3$ is a bond, —O—, —C(O)—, —S—, —SO—, —S(O)$_2$—, —NR$^5$—, —NR$^5$C(O)—, —C(O)NR$^5$—, —SO$_2$NR$^5$—, —NR$^5$SO$_2$—, —OC(O)NR$^5$—, —NR$^5$C(O)O—, substituted or unsubstituted C$_3$-C$_6$ alkylene, substituted or unsubstituted 2 to 6 membered heteroalkylene; L$^4$ is a bond, —O—, —C(O)—, —S—, —SO—, —S(O)$_2$—, —NR$^4$—, —NR$^4$C(O)—, —C(O)NR$^4$—, —SO$_2$NR$^4$—, —NR$^4$SO$_2$—, —NR$^4$SO$_2$—, —OC(O)NR$^4$—, —NR$^4$C(O)O—, substituted or unsubstituted C$_1$-C$_3$ alkylene, substituted or unsubstituted 2 to 3 membered heteroalkylene; E is a covalent cysteine modifier moiety; R$^2$ is independently oxo, halogen, CX$^2_3$, —CHX$^2_2$, —CH$_2$X$^2$, —CN, —SO$_2$Cl, —SO$_{n2}$R$^{14}$, —SO$_{v2}$NR$^{11}$R$^{12}$, —NHNR$^{11}$R$^{12}$, —ONR$^{11}$R$^{12}$, —NHC=(O)NHNR$^{11}$R$^{12}$, —NHC(O)NR$^{11}$R$^{12}$, —N(O)$_{m2}$, —NR$^{11}$R$^{12}$, —C(O)R$^{14}$, —C(O)—OR$^{14}$, —C(O)NR$^{11}$R$^{12}$, —OR$^{15}$, —NR$^{11}$SO$_2$R$^{15}$, —NR$^{11}$C(O)R$^{14}$, —NR$^{11}$C(O)OR$^{14}$, —NR$^{11}$OR$^{14}$, —OCX$^2_3$, —OCHX$^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent R$^2$ substituents or two R$^2$ substituents bonded to the same atom may optionally be joined to form a substituted or unsubstituted cycloalkyl or substituted or unsubstituted heterocycloalkyl; R$^4$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^5$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; R$^7$, R$^8$, R$^9$, R$^{10}$, R$^{7B}$, R$^{8B}$, R$^{9B}$, R$^{10B}$, R$^{11}$, R$^{12}$, R$^{14}$, and R$^{15}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl; each X, X$^1$, and X$^2$ is independently —F, —Cl, —Br, or —I; n1, n2, v1, and v2 are independently an integer from 0 to 4; m1 and m2 are independently an integer between 1 and 2; z1 is independently an integer from 0 to 5; and z2 is independently an integer from 0 to 10.

Embodiment P2. The compound of embodiment P1 having the formula:

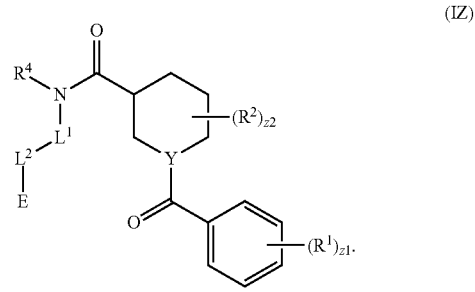

Embodiment P3. The compound of embodiment P1 having the formula:

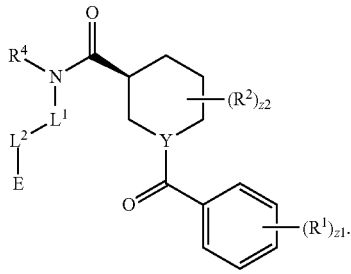
(IA)

Embodiment P4. The compound of embodiment P1 having the formula:

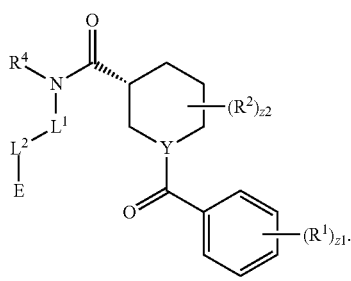
(IB)

Embodiment P5. The compound of embodiment P1 having the formula:

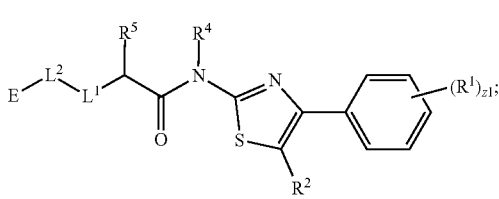
(II)

wherein
$R^2$, $R^4$ and $R^5$ are hydrogen.

Embodiment P6. The compound of embodiment P5 having the formula:

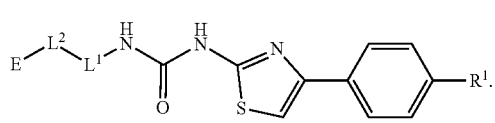
(IIA)

Embodiment P7. The compound of embodiment P5 having the formula:

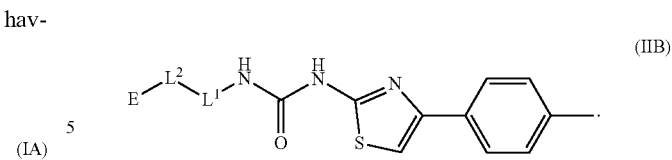
(IIB)

Embodiment P8. The compound of embodiment P1 having the formula:

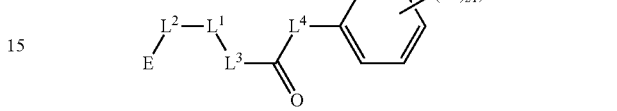
(III)

wherein $L^3$ is a bond, —O—, —C(O)—, —S—, —SO—, —S(O)$_2$—, —NH—, —NHC(CH$_3$)C(O)NH—, or unsubstituted $C_1$-$C_3$ alkylene; and $L^4$ is a bond, —CH$_2$O—, —C(O)—, —NH—, or —O—.

Embodiment P9. The compound of one of embodiments P1 to P8, wherein Y is CH.

Embodiment P10. The compound of one of embodiments P1 to P8, wherein Y is N.

Embodiment P11. The compound of one of embodiments P1 to P10, wherein $R^1$ is independently halogen, —CX$^1_3$, —CHX$^1_2$, —CH$_2$X$^1$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^1_3$, —OCHX$^1_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl.

Embodiment P12. The compound of one of embodiments P1 to P10, wherein $R^1$ is independently halogen, —CX$^1_3$, —CHX$^1_2$, —CH$_2$X$^1$, —OH, —SH, —COOH, —OCX$^1_3$, —OCHX$^1_2$, —CH$_3$, —CH$_2$CH$_3$, —OCH$_3$, —OCH$_2$CH$_3$, —SCH$_3$, or —SCH$_2$CH$_3$.

Embodiment P13. The compound of one of embodiments P1 to P12, wherein z1 is 2.

Embodiment P14. The compound of one of embodiments P1 to P12, wherein z1 is 3.

Embodiment P15. The compound of one of embodiments P1 to P14, wherein $R^2$ is independently oxo, halogen, CX$^2_3$, —CHX$^2_2$, —CH$_2$X$^2$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$^2_3$, —OCHX$^2_2$, substituted or unsubstituted $C_1$-$C_6$ alkyl, substituted or unsubstituted 2 to 6 membered heteroalkyl, substituted or unsubstituted $C_3$-$C_3$ cycloalkyl, substituted or unsubstituted 3 to 8 membered heterocycloalkyl, substituted or unsubstituted $C_6$ aryl, or substituted or unsubstituted 5 to 6 membered heteroaryl.

Embodiment P16. The compound of one of embodiments P1 to P14, wherein $R^2$ is independently oxo, halogen, —CX$^2_3$, —CHX$^2_2$, —CH$_2$X$^2$, —OH, —SH, —OCX$^2_3$, —OCHX$^2_2$, —CH$_3$, —CH$_2$CH$_3$, —OCH$_3$, —OCH$_2$CH$_3$, —SCH$_3$, or —SCH$_2$CH$_3$.

Embodiment P17. The compound of one of embodiments P1 to P16, wherein z2 is 0.

Embodiment P18. The compound of one of embodiments P1 to P17, wherein $R^4$ is hydrogen.

Embodiment P19. The compound of one of embodiments P1 to P18, wherein $R^5$ is hydrogen.

Embodiment P20. The compound of one of embodiments P1 to P19, wherein $L^1$ is a bond, substituted or unsubstituted alkylene, or substituted or unsubstituted heteroalkylene.

Embodiment P21. The compound of one of embodiments P1 to P19, wherein $L^1$ is a bond, unsubstituted $C_1$-$C_4$ alkylene, or unsubstituted 2 to 4 membered heteroalkylene.

Embodiment P22. The compound of one of embodiments P1 to P19, wherein $L^1$ is a bond.

Embodiment P23. The compound of one of embodiments P1 to P22, wherein $L^2$ is a bond, —O—, —C(O)—, —S—, —SO—, —S(O)$_2$—, —NH—, —NHC(O)—, —C(O)NH—, —SO$_2$NH—, —NHSO$_2$—, —OC(O)NH—, —NHC(O)O—, —NHC(O)NH—, substituted or unsubstituted alkylene, or substituted or unsubstituted heteroalkylene.

Embodiment P24. The compound of one of embodiments P1 to P22, wherein $L^2$ is a bond, —O—, —C(O)—, —S—, —NH—, —NHC(O)—, —C(O)NH—, unsubstituted $C_1$-$C_4$ alkylene, or unsubstituted 2 to 4 membered heteroalkylene.

Embodiment P25. The compound of one of embodiments P1 to P22, wherein $L^2$ is a bond.

Embodiment P26. The compound of one of embodiments P1 to P25, wherein E is

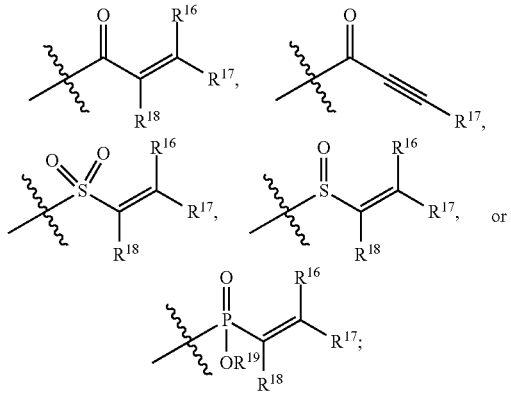

wherein $R^{16}$ is independently hydrogen, halogen, $CX^{16}_3$, —CHX$^{16}_2$, —CH$_2$X$^{16}$, —CN, —SO$_2$Cl, —SO$_{n16}$R$^{16D}$, —SO$_{v16}$NR$^{16A}$R$^{16B}$, —NHNR$^{16A}$R$^{16B}$, —ONR$^{16A}$R$^{16B}$, —NHC=(O)NHNR$^{16A}$R$^{16B}$, —NHC(O)NR$^{16A}$R$^{16B}$, —N(O)$_{m16}$, —NR$^{16A}$R$^{16B}$, —C(O)R$^{16C}$, —C(O)—OR$^{16C}$, —C(O)NR$^{16A}$R$^{16B}$, —OR$^{16D}$, —NR$^{16A}$SO$_2$R$^{16D}$, —NR$^{16A}$C(O)R$^{16C}$, —NR$^{16A}$C(O)OR$^{16C}$, —NR$^{16A}$OR$^{16C}$, —OCX$^{16}_3$, —OCHX$^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $CX^{17}_3$, —CHX$^{17}_2$, —CH$_2$X$^{17}$, —CN, —SO$_2$Cl, —SO$_{n17}$R$^{17D}$, —SO$_{v17}$NR$^{17A}$R$^{17B}$, —NHNR$^{17A}$R$^{17B}$, —ONR$^{17A}$R$^{17B}$, —NHC=(O)NHNR$^{17A}$R$^{17B}$, —NHC(O)NR$^{17A}$R$^{17B}$, —N(O)$_{m17}$, —NR$^{17A}$R$^{17B}$, —C(O)R$^{17C}$, —C(O)—OR$^{17C}$, —C(O)NR$^{17A}$R$^{17B}$, —OR$^{17D}$, —NR$^{17A}$SO$_2$R$^{17D}$, —NR$^{17A}$C(O)R$^{17C}$, —NR$^{17A}$C(O)OR$^{17C}$, —NR$^{17A}$OR$^{17C}$, —OCX$^{17}_3$, —OCHX$^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, halogen, $CX^{18}_3$, —CHX$^{18}_2$, —CH$_2$X$^{18}$, —CN, —SO$_2$Cl, —SO$_{n18}$R$^{18D}$, —SO$_{v18}$NR$^{18A}$R$^{18B}$, —NHNR$^{18A}$R$^{18B}$, —ONR$^{18A}$R$^{18B}$, —NHC=(O)NHNR$^{18A}$R$^{18B}$, —NHC(O)NR$^{18A}$R$^{18B}$, —N(O)$_{m18}$, —NR$^{18A}$R$^{18B}$, —C(O)R$^{18C}$, —C(O)—OR$^{18C}$, —C(O)NR$^{18A}$R$^{18B}$, —OR$^{18D}$, —NR$^{18A}$SO$_2$R$^{18D}$, —NR$^{18A}$C(O)R$^{18C}$, —NR$^{18A}$C(O)OR$^{18C}$, —NR$^{18A}$OR$^{18C}$, —OCX$^{18}_3$, —OCHX$^{18}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{19}$ is independently hydrogen, halogen, $CX^{19}_3$, —CHX$^{19}_2$, —CH$_2$X$^{19}$, —CN, —SO$_2$Cl, —SO$_{n19}$R$^{19D}$, —SO$_{v19}$NR$^{19A}$R$^{19B}$, —NHNR$^{19A}$R$^{19B}$, —ONR$^{19A}$R$^{19B}$, —NHC=(O)NHNR$^{19A}$R$^{19B}$, —NHC(O)NR$^{19A}$R$^{19B}$, —N(O)$_{m19}$, —NR$^{19A}$R$^{19B}$, —C(O)R$^{19C}$, —C(O)—OR$^{19C}$, —C(O)NR$^{19A}$R$^{19B}$, —OR$^{19D}$, —NR$^{19A}$SO$_2$R$^{19D}$, —NR$^{19A}$C(O)R$^{19C}$, —NR$^{19A}$C(O)OR$^{19C}$, —NR$^{19A}$OR$^{19C}$, —OCX$^{19}_3$, —OCHX$^{19}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$, $R^{19D}$, are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; R and R substituents bonded to the same nitrogen atom may optionally be joined to form a substituted or unsubstituted heterocycloalkyl or substituted or unsubstituted heteroaryl; R and R substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; each X, $X^{16}$, $X^{17}$, $X^{18}$ and $X^{19}$ is independently —F, —Cl, —Br, or —I; n16, n17, n18, n19, v16, v17, v18, and v19 are independently an integer from 0 to 4; and m16, m17, m18, and m19 are independently an integer from 1 to 2.

Embodiment P27. The compound of one of embodiments P1 to P25, wherein E is

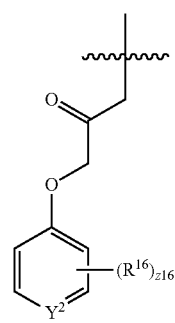

wherein $R^{16}$ is independently halogen, $CX^{16}_3$, —$CHX^{16}_2$, —$CH_2X^{16}$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCX^{16}_3$, —$OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $Y^2$ is N or CH; z16 is an integer between 0 and 4; and each $X^{16}$ is independently —F, —Cl, —Br, or —I.

Embodiment P28. The compound of embodiment P27 wherein $R^{16}$ is independently halogen.

Embodiment P29. The compound of embodiment P27 wherein $R^{16}$ is independently —F.

Embodiment P30. The compound of one of embodiments P27 to P29, wherein z16 is 4.

Embodiment P31. The compound of one of embodiments P27 to P29, wherein z1b is 2.

Embodiment P32. The compound of embodiment P31 wherein E is

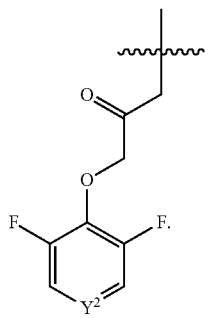

Embodiment P33. The compound of one of embodiments P27 to P32, wherein $Y^2$ is CH.

Embodiment P34. The compound of one of embodiments P27 to P32, wherein $Y^2$ is N.

Embodiment P35. The compound of one of embodiments P1 to P25, wherein E comprises a substituted or unsubstituted vinyl sulfone moiety, substituted or unsubstituted vinyl sulfonamide moiety, substituted or unsubstituted fluoro($C_1$-$C_4$)alkylketone moiety, substituted or unsubstituted chloro ($C_1$-$C_4$)alkylketone moiety, substituted or unsubstituted acrylamide moiety, substituted or unsubstituted disulfide moiety, substituted or unsubstituted thiol moiety, substituted or unsubstituted phosphonate moiety, substituted or unsubstituted aldehyde moiety, substituted or unsubstituted enone moiety, substituted or unsubstituted diazomethylketone moiety, substituted or unsubstituted diazomethylamide moiety, substituted or unsubstituted cyanocyclopropyl carboxamide moiety, substituted or unsubstituted epoxide moiety, substituted or unsubstituted epoxyketone moiety, substituted or unsubstituted epoxyamide moiety, substituted or unsubstituted aryl aldehyde moiety, substituted or unsubstituted aryl dialdehyde moiety, substituted or unsubstituted dialdehyde moiety, substituted or unsubstituted nitrogen mustard moiety, substituted or unsubstituted propargyl moiety, substituted or unsubstituted propargylamide moiety,

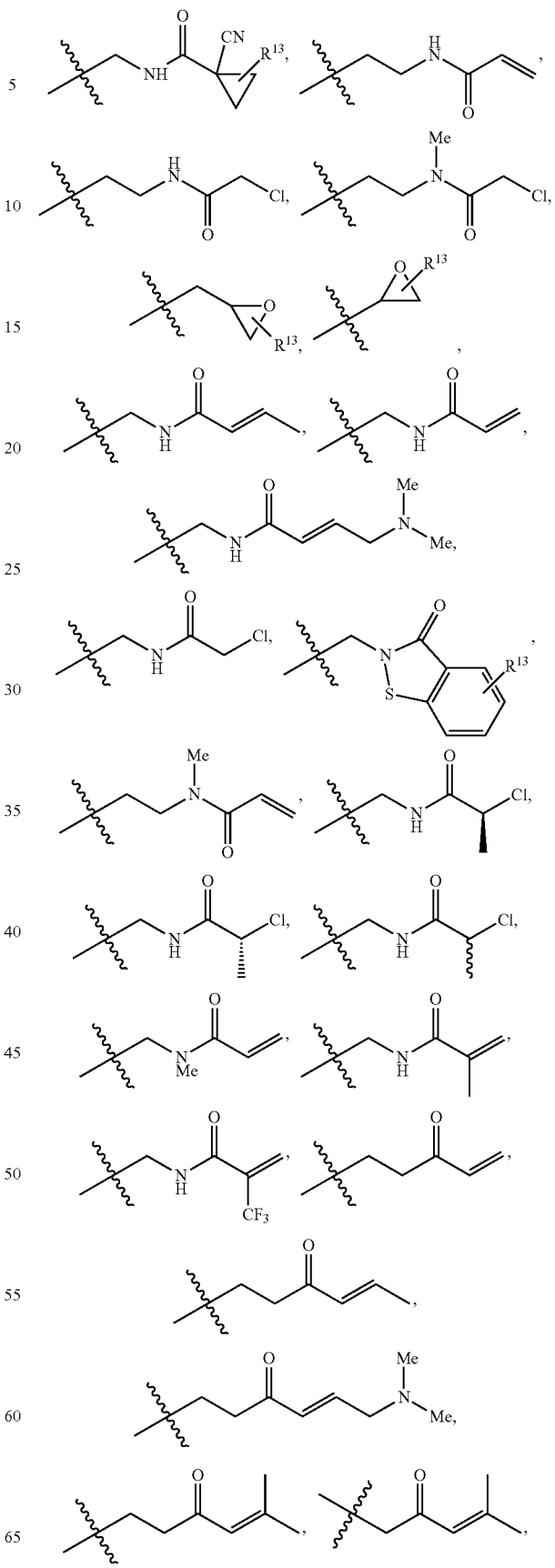

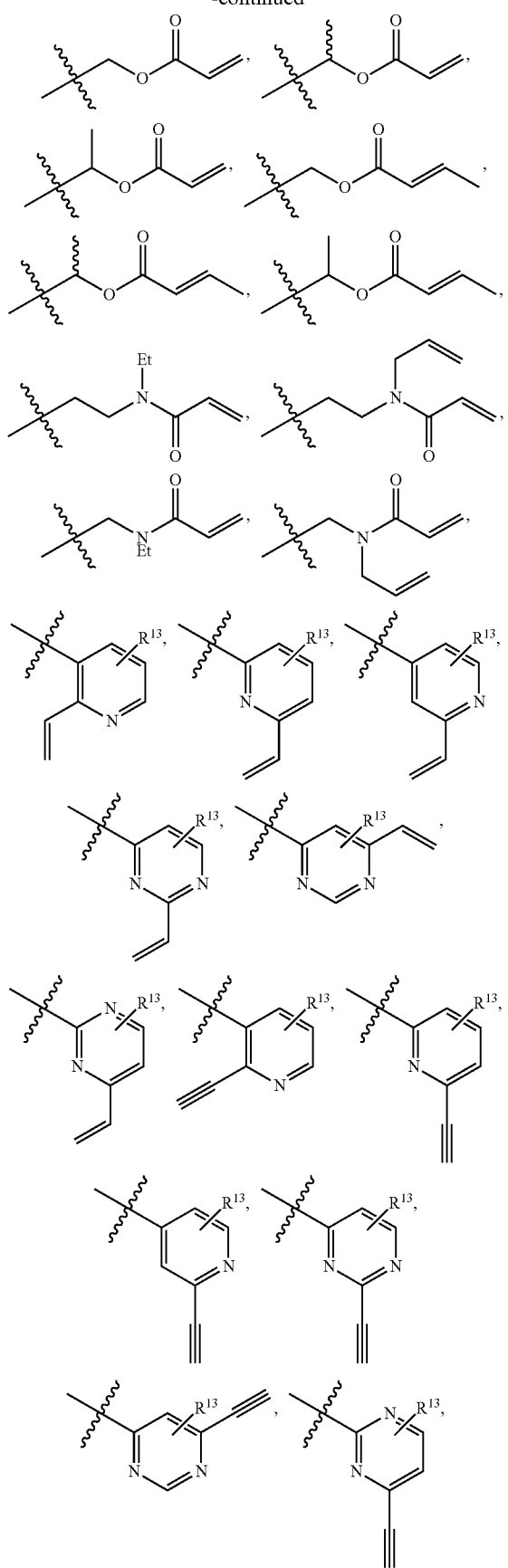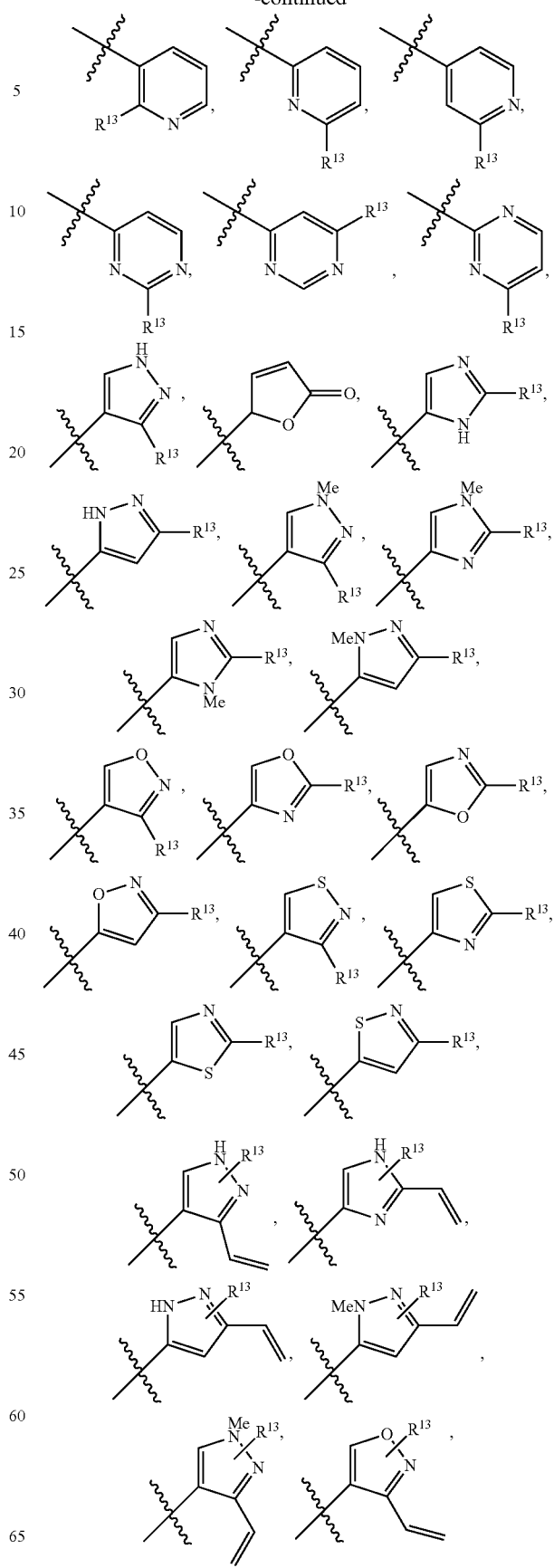

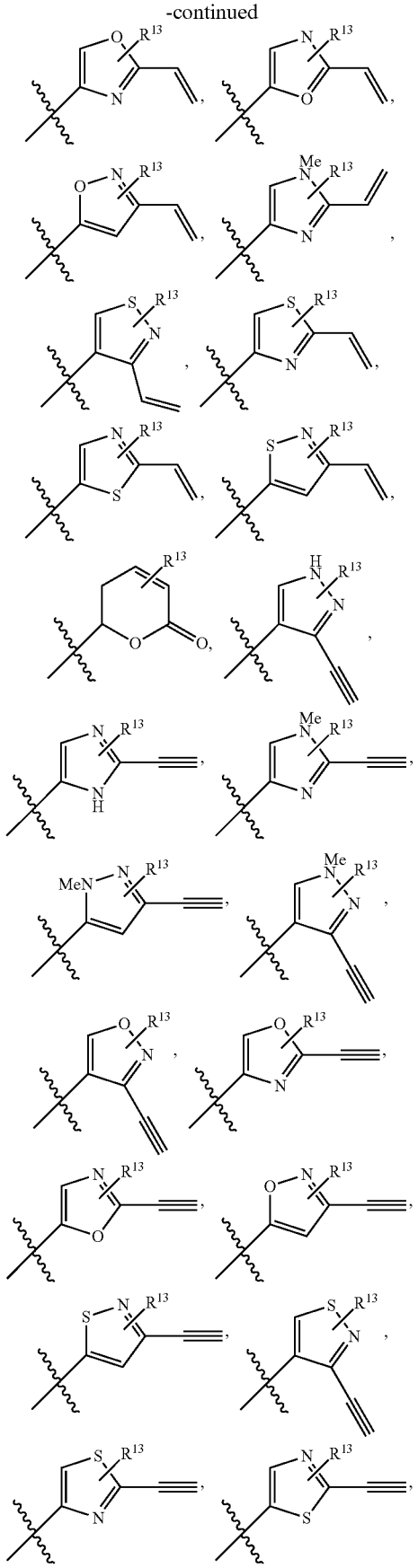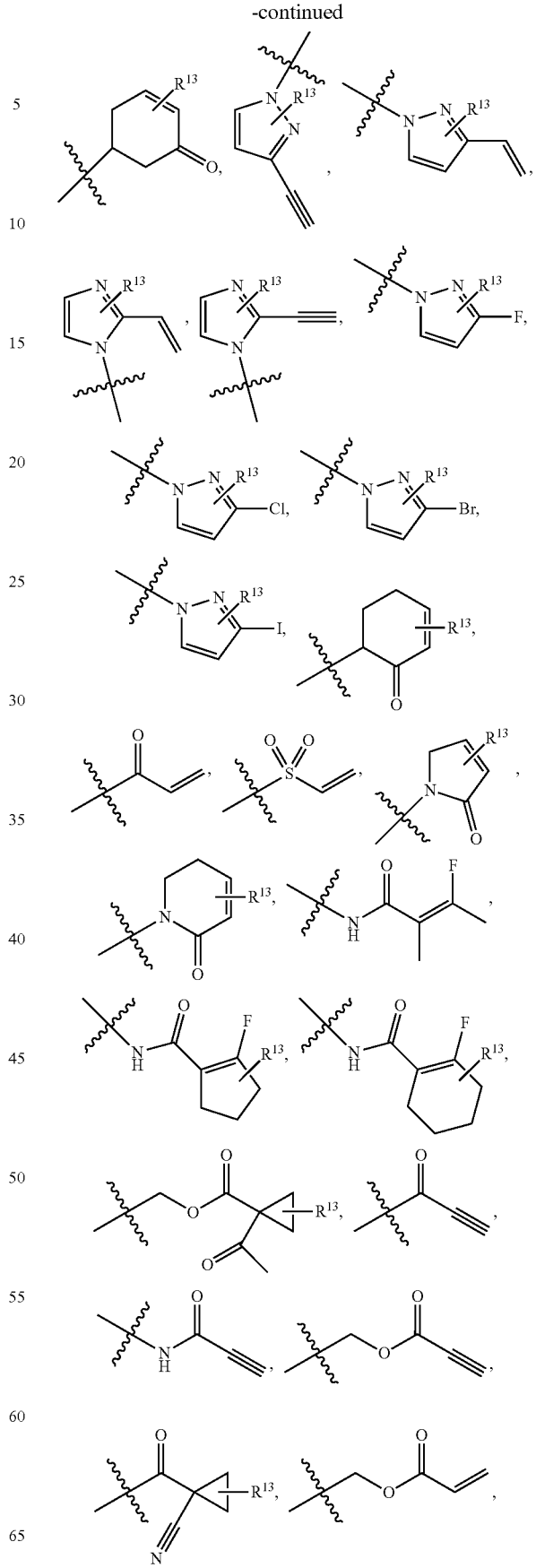

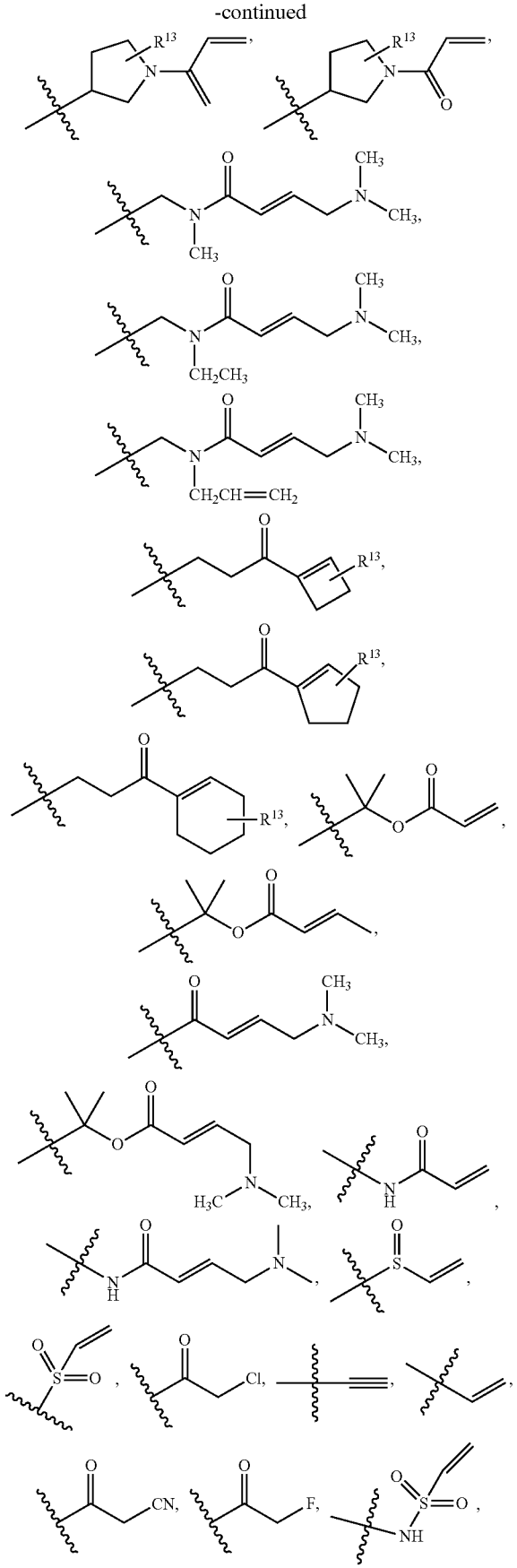
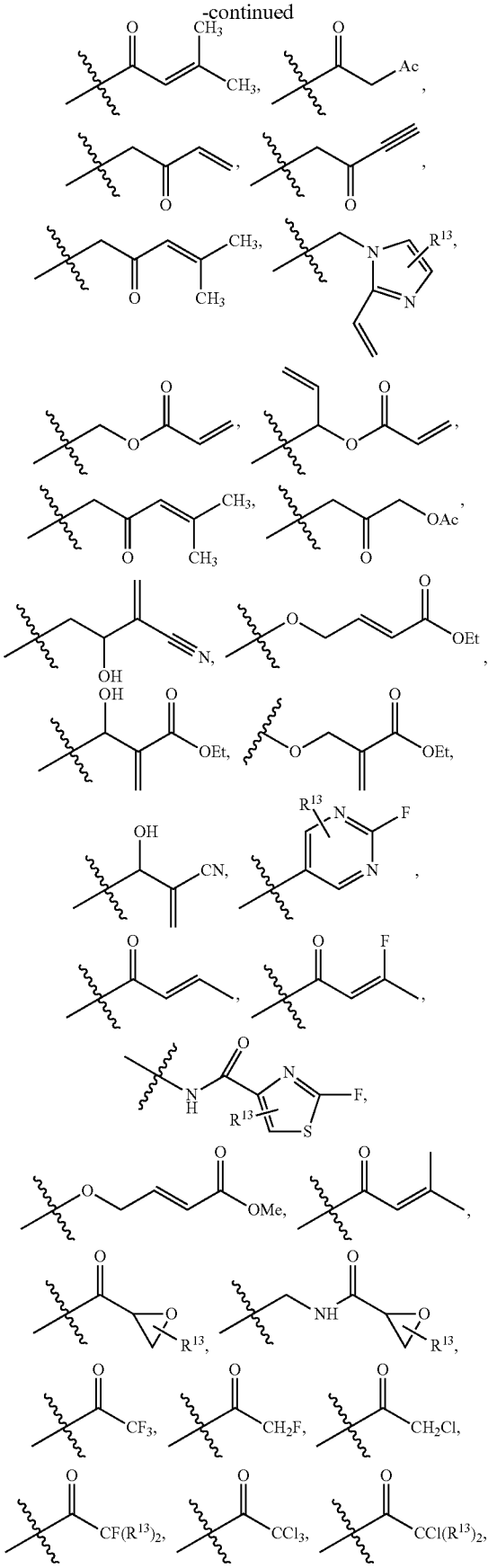

-continued

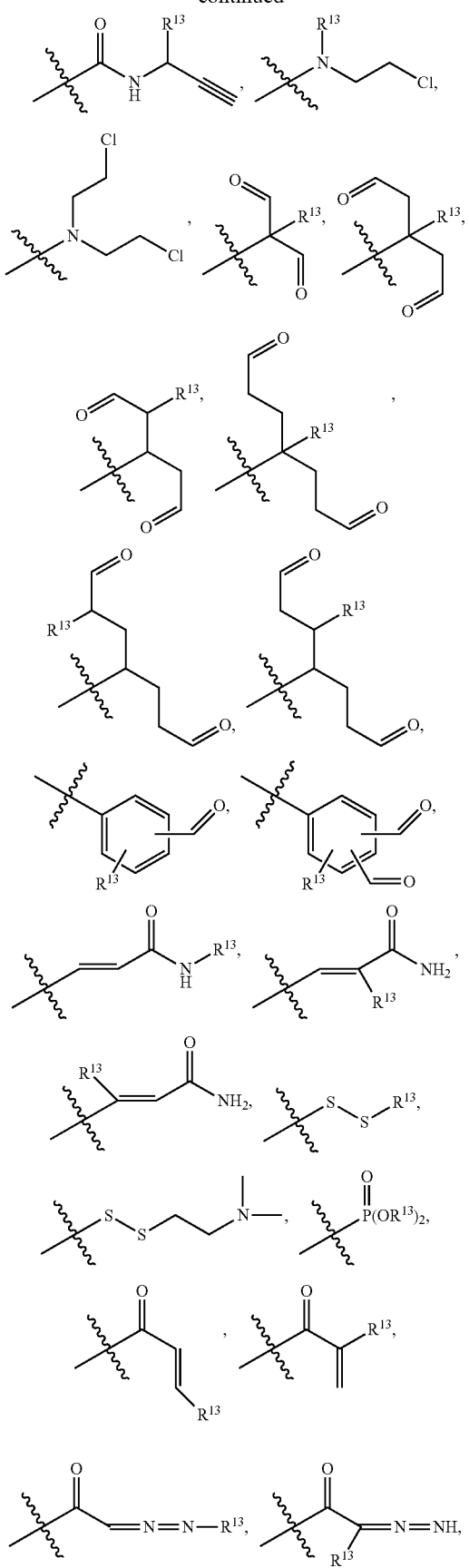

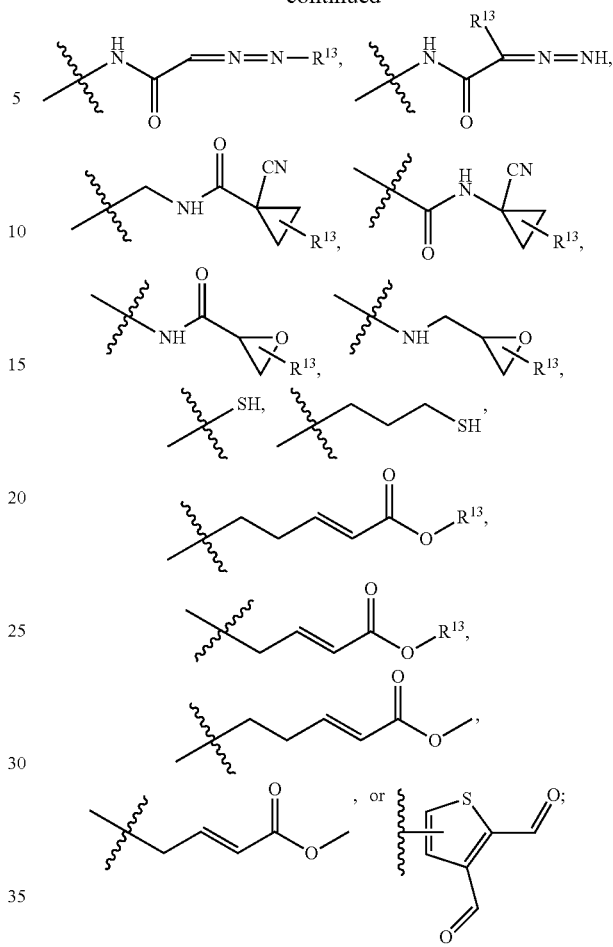

R[13] is independently hydrogen, oxo, halogen, $CX^{13}_3$, —$CHX^{13}_2$, —$CH_2X^{13}$, —CN, —$SO_2Cl$, —$SO_{n13}R^{22}$, —$SO_{v13}NR^{20}R^{21}$, —$NHNR^{20}R^{21}$, —$ONR^{20}R^{21}$, —NHC=(O)$NHNR^{20}R^{21}$, —NHC(O)$NR^{20}R^{21}$, —N(O)$_{m13}$, —$NR^{20}R^{21}$, —C(O)$R^{22}$, —C(O)—$OR^{22}$, —C(O)$NR^{20}R^{21}$, —$OR^{23}$, —$NR^{20}SO_2R^{23}$, —$NR^{20}C(O)R^{22}$, —$NR^{20}C(O)OR^{22}$, —$NR^{20}OR^{22}$, —$OCX^{13}_3$, —$OCHX^{13}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents or two $R^2$ substituents bonded to the same atom may optionally be joined to form a substituted or unsubstituted cycloalkyl or substituted or unsubstituted heterocycloalkyl; $R^{20}$, $R^{21}$, $R^{22}$, and $R^{23}$ are independently hydrogen, halogen, —$CX^A_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCX^A_3$, —$OCHX^A_2$, —$CHX^A_2$, —$CH_2X^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{20}$ and $R^{21}$ substituents bonded to the same nitrogen atom may optionally be joined to form a substituted or unsubstituted heterocycloalkyl or substituted or unsubstituted heteroaryl; each $X^A$ and $X^{13}$ is independently —F, —Cl, —Br, or —I; n13 and v13 are independently an integer from 0 to 4; and m13 is independently an integer from 1 to 2.

Embodiment P36. A compound having the formula:

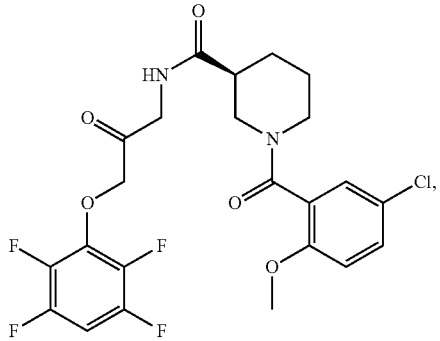

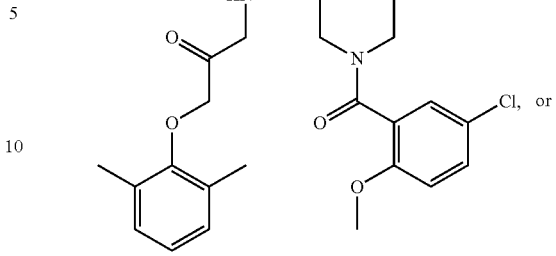

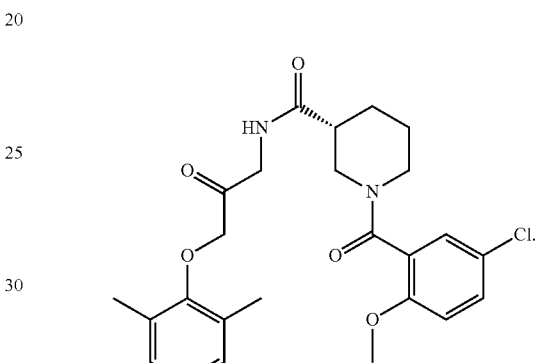

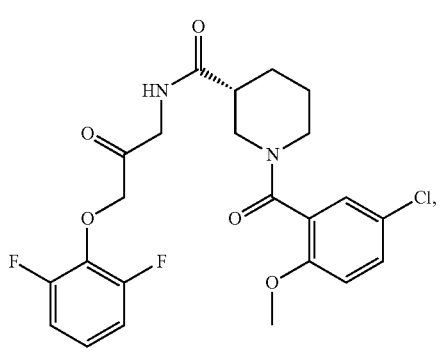

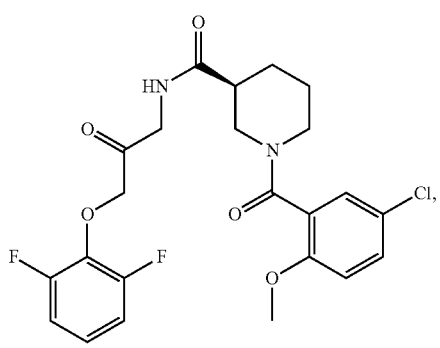

Embodiment P37. A pharmaceutical composition comprising the compound of any one of embodiments P1 to P36 and a pharmaceutically acceptable excipient.

Embodiment P38. A method of reducing the level of activity of a K-Ras protein, said method comprising contacting the K-Ras protein with a compound of one of embodiments P1 to P36.

Embodiment P39. A method of reducing the level of activity of a K-Ras-4B protein, said method comprising contacting the K-Ras-4B protein with a compound of one of embodiments P1 to P36.

Embodiment P40. A method for treating cancer, said method comprising administering to a subject in need thereof a therapeutically effective amount of a compound of one of embodiments P1 to P36.

Embodiment P41. The method of embodiment P40, wherein said cancer is pancreatic cancer, lung cancer, or colorectal cancer.

Embodiment P42. A K-Ras protein covalently bonded to a compound of one of embodiments P1 to P36.

Embodiment P43. The K-Ras protein of embodiment P42, wherein the compound is covalently bonded to a cysteine residue of the protein.

Embodiment P44. The K-Ras protein of embodiment P42, wherein the compound is irreversibly covalently bonded to a cysteine residue of the protein.

Embodiment P45. A K-Ras protein covalently bonded to a compound having the formula:

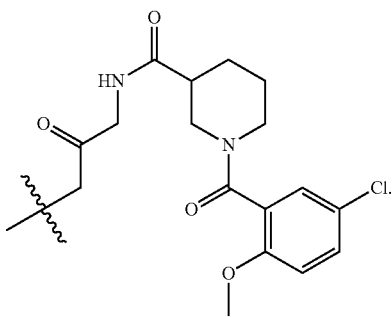 [SMILES: *CC(=O)CNC(=O)C1CCCN(C(=O)c2cc(Cl)ccc2OC)C1]

Embodiment P46. The K-Ras protein of embodiment P45, wherein the compound is covalently bonded to a cysteine residue of the protein.

Embodiment P47. The K-Ras protein of embodiment P45, wherein the compound is covalently bonded to a cysteine residue of the protein corresponding to C185 of human K-Ras-4B.

VIII. ADDITIONAL EMBODIMENTS

Embodiment 1. A compound having the formula:

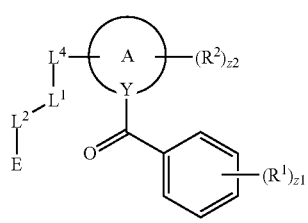

(I)

wherein, Y is N or CH; Ring A is a $C_3$-$C_7$ cycloalkyl or 3 to 7 membered heterocycloalkyl; $R^1$ is independently halogen, $CX^1_3$, —$CHX^1_2$, —$CH_2X^1$, —CN, —$SO_2Cl$, —$SO_{n1}R^{10}$, —$SO_{v1}NR^7R^8$, —$NHNR^7R^8$, —$ONR^7R^8$, —NHC=(O)NHNR$^7$R$^8$, —NHC(O)NR$^7$R$^8$, —N(O)$_{m1}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C(O)R$^9$, —NR$^7$C(O)OR$^9$, —NR$^7$OR$^9$, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $L^1$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $L^2$ is a bond, —O—, —C(O)—, —S—, —SO—, —S(O)$_2$—, —NR$^{7B}$—, —NR$^{7B}$C(O)—, —C(O)NR$^{7B}$—, —SO$_2$NR$^{7B}$—, —NR$^{7B}$SO$_2$—, —OC(O)NR$^{7B}$—, —NR$^{7B}$C(O)O—, —CR$^{9B}$=NO—, —ON=CR$^{9B}$—, —NR$^{8B}$C(O)NR$^{7B}$—, —NR$^{8B}$C(=NR$^{10B}$)NR$^{7B}$—, —NR$^{8B}$C(=NR$^{10B}$)—, —C(=NR$^{10B}$)NR$^{7B}$—, —OC(=NR$^{10B}$)—, —C(=NR$^{10B}$)O—, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene; $L^4$ is a bond, —O—, —C(O)—, —S—, —SO—, —S(O)$_2$—, —NR$^4$—, —NR$^4$C(O)—, —C(O)NR$^4$—, —SO$_2$NR$^4$—, —NR$^4$SO$_2$—, —NR$^4$SO$_2$—, —OC(O)NR$^4$—, —NR$^4$C(O)O—, substituted or unsubstituted $C_3$-$C_3$ alkylene, substituted or unsubstituted 2 to 3 membered heteroalkylene; E is an electrophilic moiety; $R^2$ is independently oxo, halogen, $CX^2_3$, —$CHX^2_2$, —$CH_2X^2$, —CN, —$SO_2Cl$, —$SO_{n2}R^{14}$, —$SO_{v2}NR^{11}R^{12}$, —$NHNR^{11}R^{12}$, —ONR$^{11}$R$^{12}$, —NHC=(O)NHNR$^{11}$R$^{12}$, —NHC(O)NR$^{11}$R$^{12}$, —N(O)$_{m2}$, —NR$^{11}$R$^{12}$, —C(O)R$^{14}$, —C(O)—OR$^{14}$, —C(O)NR$^{11}$R$^{12}$, —OR$^{15}$, —NR$^{11}$SO$_2$R$^{15}$, —NR$^{11}$C(O)R$^{14}$, —NR$^{11}$C(O)OR$^{14}$, —NR$^{11}$OR$^{14}$, —OCX$^2_3$, —OCHX$^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; two adjacent $R^2$ substituents or two $R^2$ substituents bonded to the same atom may optionally be joined to form a substituted or unsubstituted cycloalkyl or substituted or unsubstituted heterocycloalkyl; $R^4$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^7$, $R^8$, $R^9$, $R^{10}$, $R^{7B}$, $R^{8B}$, $R^{9B}$, $R^{10B}$, $R^{11}$, $R^{12}$, $R^{14}$, and $R^{15}$ are independently hydrogen, halogen, —CX$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCX$_3$, —OCHX$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{1.1}$ and $R^{1.2}$ substituents bonded to the same nitrogen atom may optionally be joined to form a substituted or unsubstituted heterocycloalkyl or substituted or unsubstituted heteroaryl; each X, $X^1$, and $X^2$ is independently —F, —Cl, —Br, or —I; n1, n2, v1, and v2 are independently an integer from 0 to 4; m1 and m2 are independently an integer from 1 to 2; z1 is independently an integer from 0 to 5; and z2 is independently an integer from 0 to 10.

Embodiment 2. The compound of embodiment 1, having the formula:

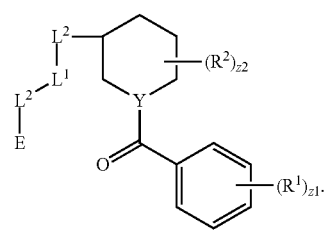

Embodiment 3. The compound of embodiment 1, having the formula:

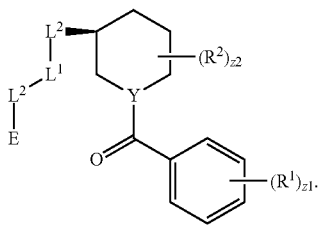

Embodiment 4. The compound of one of embodiments 1 to 3, wherein Y is CH.

Embodiment 5. The compound of one of embodiments 1 to 3, wherein Y is N.

Embodiment 6. The compound of one of embodiments 1 to 5, wherein $R^1$ is independently halogen, $-CX^1_3$, $-CHX^1_2$, $-CH_2X^1$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^1_3$, $-OCHX^1_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl.

Embodiment 7. The compound of one of embodiments 1 to 5, wherein $R^1$ is independently halogen, $-CX^1_3$, $-CHX^1_2$, $-CH_2X^1$, $-OH$, $-SH$, $-COOH$, $-OCX^1_3$, $-OCHX^1_2$, $-CH_3$, $-CH_2CH_3$, $-OCH_3$, $-OCH_2CH_3$, $-SCH_3$, or $-SCH_2CH_3$.

Embodiment 8. The compound of one of embodiments 1 to 5, wherein $R^1$ is independently halogen or $-OCH_3$.

Embodiment 9. The compound of one of embodiments 1 to 8, wherein z1 is 2.

Embodiment 10. The compound of one of embodiments 1 to 8, wherein z1 is 3.

Embodiment 11. The compound of one of embodiments 1 to 10, wherein $R^2$ is independently oxo, halogen, $-CX^2_3$, $-CHX^2_2$, $-CH_2X^2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^2_3$, $-OCHX^2_2$, substituted or unsubstituted $C_1$-$C_6$ alkyl, substituted or unsubstituted 2 to 6 membered heteroalkyl, substituted or unsubstituted $C_3$-$C_8$ cycloalkyl, substituted or unsubstituted 3 to 8 membered heterocycloalkyl, substituted or unsubstituted $C_6$ aryl, or substituted or unsubstituted 5 to 6 membered heteroaryl.

Embodiment 12. The compound of one of embodiments 1 to 10, wherein $R^2$ is independently oxo, halogen, $-CX^2_3$, $-CHX^2_2$, $-CH_2X^2$, $-OH$, $-SH$, $-OCX^2_3$, $-OCHX^2_2$, $-CH_3$, $-CH_2CH_3$, $-OCH_3$, $-OCH_2CH_3$, $-SCH_3$, or $-SCH_2CH_3$.

Embodiment 13. The compound of one of embodiments 1 to 12, wherein z2 is 0.

Embodiment 14. The compound of one of embodiments 1 to 13, wherein $L^1$ is a bond, substituted or unsubstituted alkylene, or substituted or unsubstituted heteroalkylene.

Embodiment 15. The compound of one of embodiments 1 to 13, wherein $L^1$ is a bond, unsubstituted $C_1$-$C_4$ alkylene, or unsubstituted 2 to 4 membered heteroalkylene.

Embodiment 16. The compound of one of embodiments 1 to 13, wherein $L^1$ is a bond.

Embodiment 17. The compound of one of embodiments 1 to 16, wherein $L^2$ is a bond, $-O-$, $-C(O)-$, $-S-$, $-SO-$, $-S(O)_2-$, $-NH-$, $-NHC(O)-$, $-C(O)NH-$, $-SO_2NH-$, $-NHSO_2-$, $-OC(O)NH-$, $-NHC(O)O-$, $-NHC(O)NH-$, substituted or unsubstituted alkylene, or substituted or unsubstituted heteroalkylene.

Embodiment 18. The compound of one of embodiments 1 to 16, wherein $L^2$ is a bond, $-O-$, $-C(O)-$, $-S-$, $-NH-$, $-NHC(O)-$, $-C(O)NH-$, unsubstituted $C_1$-$C_4$ alkylene, or unsubstituted 2 to 4 membered heteroalkylene.

Embodiment 19. The compound of one of embodiments 1 to 16, wherein $L^2$ is $-NH-$.

Embodiment 20. The compound of one of embodiments 1 to 16, wherein $L^2$ is a bond.

Embodiment 21. The compound of one of embodiments 1 to 20, wherein E is

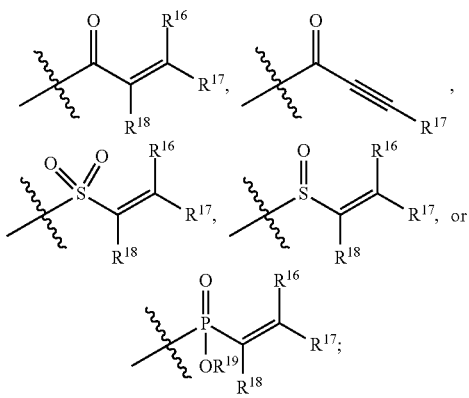

wherein $R^{16}$ is independently hydrogen, halogen, $CX^{16}_3$, $-CHX^{16}_2$, $-CH_2X^{16}$, $-CN$, $-SO_{n16}R^{16D}$, $-SO_{v16}NR^{16A}R^{16B}$, $-NHNR^{16A}R^{16B}$, $-ONR^{16A}R^{16B}$, $-NHC=(O)NHNR^{16A}R^{16B}$, $-NHC(O)NR^{16A}R^{16B}$, $-N(O)_{m16}$, $-NR^{16A}R^{16B}$, $-C(O)R^{16C}$, $-C(O)-OR^{16C}$, $-C(O)NR^{16A}R^{16B}$, $-OR^{16D}$, $-NR^{16A}SO_2R^{16D}$, $-NR^{16A}C(O)R^{16C}$, $-NR^{16A}C(O)OR^{16C}$, $-NR^{16A}OR^{16C}$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{17}$ is independently hydrogen, halogen, $CX^{17}_3$, $-CHX^{17}_2$, $-CH_2X^{17}$, $-CN$, $-SO_{n17}R^{17D}$, $-SO_{v17}NR^{17A}R^{17B}$, $-NHNR^{17A}R^{17B}$, $-ONR^{17A}R^{17B}$, $-NHC=(O)NHNR^{17A}R^{17B}$, $-NHC(O)NR^{17A}R^{17B}$, $-N(O)_{m17}$, $-NR^{17A}R^{17B}$, $-C(O)R^{17C}$, $-C(O)-OR^{17C}$, $-C(O)NR^{17A}R^{17B}$, $-OR^{17D}$, $-NR^{17A}SO_2R^{17D}$, $-NR^{17A}C(O)R^{17C}$, $-NR^{17A}C(O)OR^{17C}$, $-NR^{17A}OR^{17C}$, $-OCX^{17}_3$, $-OCHX^{17}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{18}$ is independently hydrogen, halogen, $CX^{18}_3$, $-CHX^{18}_2$, $-CH_2X^{18}$, $-CN$, $-SO_{n18}R^{18D}$, $-SO_{v18}NR^{18A}R^{18B}$, $-NHNR^{18A}R^{18B}$, $-ONR^{18A}R^{18B}$, $-NHC=(O)NHNR^{18A}R^{18B}$, $-NHC(O)NR^{18A}R^{18B}$, $-N(O)_{m18}$, $-NR^{18A}R^{18B}$, $-C(O)R^{18C}$, $-C(O)-OR^{18C}$, $-C(O)NR^{18A}R^{18B}$, $-OR^{18D}$, $-NR^{18A}SO_2R^{18D}$, $-NR^{18A}C(O)R^{18C}$, $-NR^{18A}C(O)OR^{18C}$, $-NR^{18A}OR^{18C}$, $-OCX^{18}_3$, $-OCHX^{18}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{19}$ is independently hydrogen, halogen, $CX^{19}_3$, $-CHX^{19}_2$, $-CH_2X^{19}$, $-CN$, $-SO_{n19}R^{19D}$, $-SO_{v19}NR^{19A}R^{19B}$, $-NHNR^{19A}R^{19B}$, $-ONR^{19A}R^{19B}$, $-NHC=(O)NHNR^{19A}R^{19B}$, $-NHC(O)NR^{19A}R^{19D}$, $-N(O)_{m19}$, $-NR^{19A}R^{19B}$, $-C(O)R^{19C}$, $-C(O)-OR^{19C}$, $-C(O)NR^{19A}R^{19B}$, $-OR^{19D}$, $-NR^{19A}SO_2R^{19D}$, $-NR^{19A}C(O)R^{19C}$, $-NR^{19A}C(O)OR^{19C}$, $-NR^{19A}OR^{19C}$, $-OCX^{19}_3$, $-OCHX^{19}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $R^{16A}$, $R^{16B}$, $R^{16C}$, $R^{16D}$, $R^{17A}$, $R^{17B}$, $R^{17C}$, $R^{17D}$, $R^{18A}$, $R^{18B}$, $R^{18C}$, $R^{18D}$, $R^{19A}$, $R^{19B}$, $R^{19C}$, $R^{19D}$, are independently hydrogen, halogen, $-CX_3$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX_3$, $-OCHX_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; each X, $X^{16}$, $X^{17}$, $X^{18}$ and $X^{19}$ is independently $-F$, $-Cl$, $-Br$, or $-I$; n16, n17, n18, n19, v16, v17, v18, and v19 are independently an integer from 0 to 4; and m16, m17, m18, and m19 are independently an integer from 1 to 2.

Embodiment 22. The compound of embodiment 21, wherein E is

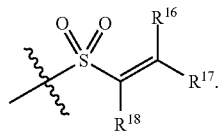

Embodiment 23. The compound of embodiment 21, wherein E is

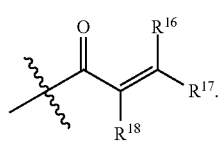

Embodiment 24. The compound of one of embodiments 21 to 23, wherein $R^{16}$, $R^{17}$, and $R^{18}$ are independently hydrogen, $-CH_2NH_2$, $-CH_2CH_2NH_2$, $-CH_2N(CH_3)_2$, or $-CH_2CH_2N(CH_3)_2$.

Embodiment 25. The compound of one of embodiments 21 to 24, wherein $L^4$ is a bond or $-CH_2-$.

Embodiment 26. The compound of one of embodiments 21, 22, 24, or 25, having the formula:

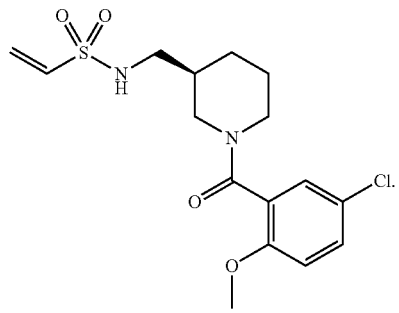 [SMILES: C=CS(=O)(=O)NC[C@H]1CCCN(C(=O)c2cc(Cl)ccc2OC)C1]

Embodiment 27. The compound of one of embodiments 1 to 20, wherein E is

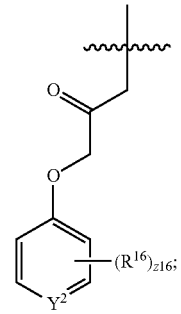

wherein $R^{16}$ is independently halogen, $CX^{16}_3$, $-CHX^{16}_2$, $-CH_2X^{16}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; $Y^2$ is N or CH; z16 is an integer from 0 to 4; and each $X^{16}$ is independently $-F$, $-Cl$, $-Br$, or $-I$.

Embodiment 28. The compound of embodiment 27 wherein $R^{16}$ is independently halogen.

Embodiment 29. The compound of embodiment 27 wherein $R^{16}$ is independently $-F$.

Embodiment 30. The compound of one of embodiments 27 to 29, wherein z16 is 4.

Embodiment 31. The compound of one of embodiments 27 to 29, wherein z16 is 2.

Embodiment 32. The compound of embodiment 31 wherein E is

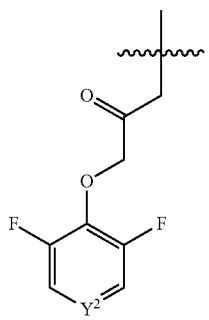

Embodiment 33. The compound of one of embodiments 27 to 32, wherein $Y^2$ is CH.

Embodiment 34. The compound of one of embodiments 27 to 32, wherein $Y^2$ is N.

Embodiment 35. The compound of one of embodiments 27 to 34, wherein $L^4$ is —N($R^4$)C(O)—.

Embodiment 36. The compound of one of embodiments 27 to 35, wherein $R^4$ is hydrogen.

Embodiment 37. The compound of one of embodiments 27 to 36, having the formula:

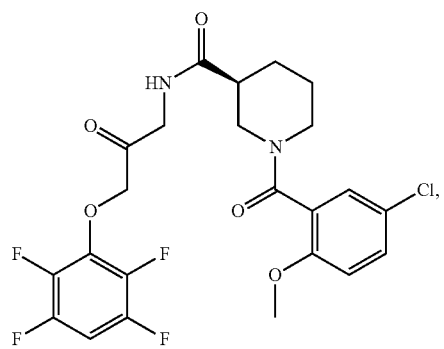

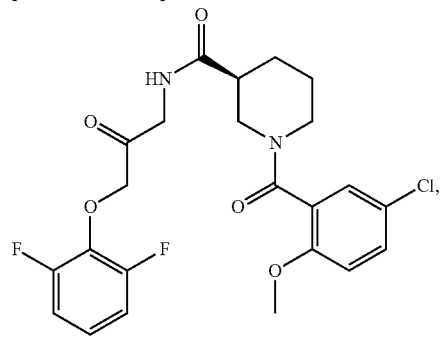

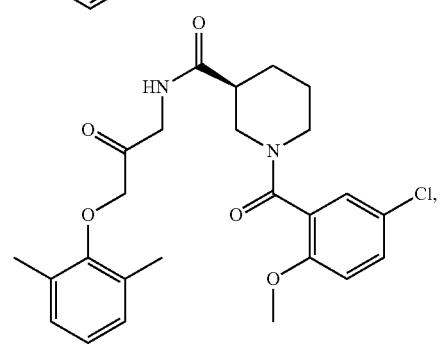

-continued

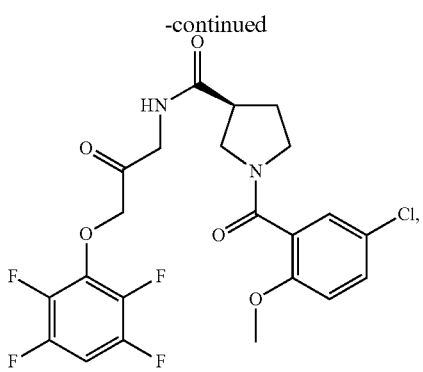

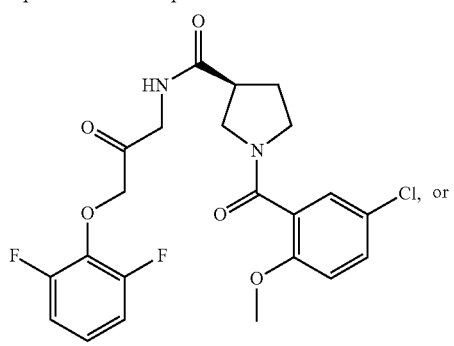

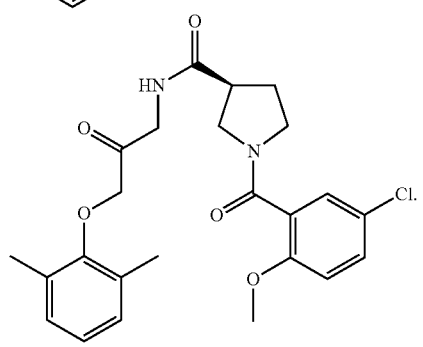

Embodiment 38. A pharmaceutical composition comprising the compound of any one of embodiments 1 to 37 and a pharmaceutically acceptable excipient.

Embodiment 39. A method of reducing the level of activity of a K-Ras protein, said method comprising contacting the K-Ras protein with a compound of one of embodiments 1 to 37.

Embodiment 40. A method of reducing the level of activity of a K-Ras-4B protein, said method comprising contacting the K-Ras-4B protein with a compound of one of embodiments 1 to 37.

Embodiment 41. A method for treating cancer, said method comprising administering to a subject in need thereof a therapeutically effective amount of a compound of one of embodiments 1 to 37.

Embodiment 42. The method of embodiment 41, wherein said cancer is pancreatic cancer, lung cancer, or colorectal cancer.

Embodiment 43. A K-Ras protein covalently bonded to a compound of one of embodiments 1 to 37.

Embodiment 44. The K-Ras protein of embodiment 43, wherein the compound is covalently bonded to a cysteine residue of the protein.

Embodiment 45. The K-Ras protein of embodiment 43, wherein the compound is irreversibly covalently bonded to a cysteine residue of the protein.

Embodiment 46. The K-Ras protein of embodiment 43, wherein the compound is covalently bonded to a histidine residue of the protein.

Embodiment 47. The K-Ras protein of embodiment 43, wherein the compound is irreversibly covalently bonded to a histidine residue of the protein.

Embodiment 48. A K-Ras protein covalently bonded to a compound having the formula:

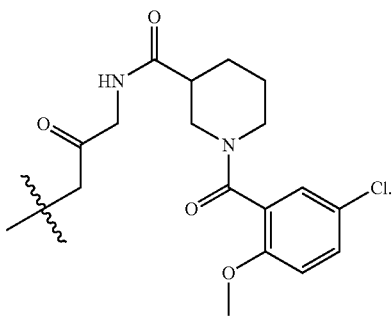 [SMILES: *CC(=O)CNC(=O)C1CCCN(C(=O)c2cc(Cl)ccc2OC)C1]

Embodiment 49. A K-Ras protein covalently bonded to a compound having the formula:

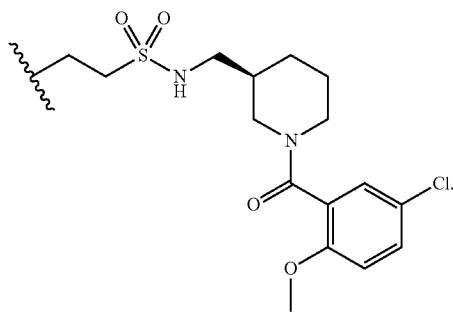 [SMILES: *CCS(=O)(=O)NC[C@H]1CCCN(C(=O)c2cc(Cl)ccc2OC)C1]

Embodiment 50. The K-Ras protein of one of embodiments 48 to 49, wherein the compound is covalently bonded to a cysteine residue of the protein.

Embodiment 51. The K-Ras protein of embodiment 48, wherein the compound is covalently bonded to a cysteine residue of the protein corresponding to C185 of human K-Ras-4B.

Embodiment 52. The K-Ras protein of one of embodiments 48 to 49, wherein the compound is covalently bonded to a histidine residue of the protein.

Embodiment 53. The K-Ras protein of embodiment 48, wherein the compound is covalently bonded to a histidine residue of the protein corresponding to H95 of human K-Ras-4B.

IX. EXAMPLES

Example 1. Covalent Modification of H95 Residue in Kras Using Tethering Small Molecule Compounds K-Ras is the most frequently mutated oncogene, with activating mutations in this small GTPase found in 30% of human cancers. Mutations in K-Ras are associated with resistance to chemotherapy or radiation. Patients whose tumors harbor these mutations are often excluded from targeted therapies, and tend to have poor overall survival. Despite decades of research effort, there are no effective treatments for cancers with mutant K-Ras.

The development of small-molecule inhibitors that directly target Ras is highly desirable but has proven to be a major challenge. The isoforms of the Ras protein (H-Ras, N-Ras and K-Ras) play essential roles in normal cells. Therefore, the ideal Ras-targeting drug would specifically target the oncogenic form of the protein. However, targeting K-Ras (i.e. without distinguishing between wildtype and mutant protein) could be an effective approach, since all isoforms are redundant in normal tissues, and eliminating one is expected to be tolerable.

Considerable effort has been directed towards inhibiting Ras posttranslational processing. Inhibitors of farnesyl transferases (FTIs) have been investigated for their potential to attenuate C-terminal lipid modification of Ras required for correct plasma membrane localization and subsequent signaling. This approach is challenging since K-Ras was found to undergo alternative prenylation and remain oncogenically active.

The covalent modification of the CAAX-box cysteine of K-Ras may block prenylation at that site and inhibit the subsequent translocation/attachment of the K-Ras protein to the membrane that is necessary for its activity. This could be achieved with small molecule inhibitors designed for binding to the CAAX-box cysteine of K-Ras. The complication of alternative prenylation, inherent in alternative methods of inhibiting Ras prenylation, would be bypassed. Tethering compounds are composed of a fragment group that confers a non-covalent interaction with a potential pocket on the protein. Additionally, there is a disulfide moiety that interacts covalently with the CAAX-box cysteine under reducing conditions in a reversible fashion by disulfide exchange. The screen of recombinant His-tagged K-Ras G12D protein against the library of 1600 tethering compounds, followed by SAR, led to development of the FB9, depicted below:

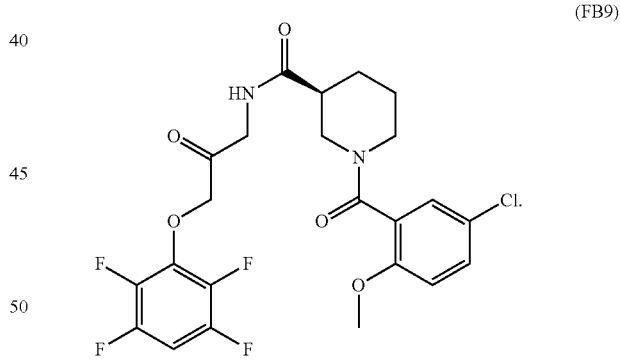

(FB9)

In embodiments, compounds described herein (e.g., FB9) covalently labeled C185 in the full-length recombinant K-Ras4B. However, if FB9 is reacted with recombinant FME-Kras4B protein (farnesylated-carboxymethylated), where C185 is modified/blocked by farnesyl (as it is in the native, fully post-translationally processed K-Ras 4B in vivo), FB9 is not able to displace the farnesyl from C185; instead, it covalently modifies other residues in the K-Ras4B protein.

Herein we show that in embodiments the recombinant FME-Kras4B, FB9 covalently modifies histidine 95 residue (H95), that is unique for Kras (Q in H-Ras or L in N-Ras). This residue is nucleophilic, making it vulnerable to electrophilic attack. This modification not only was observed with recombinant FME-Kras4B protein; it was also detected in Kras4B G12V that was purified from cells treated with the compound.

Chemical modification of unprocessed KRAS-4b at His-95 (protein G-Hs.KRAS4b(1-188), mass (average) 21481.59 Da.

KRAS4b (FIG. 43) was modified by FB9 in vitro (using 8.8-fold molar excess of FB9 for 1 h at 37° C., followed by 16 h at room temperature, 22° C.). MALDI-TOF MS analysis revealed that chemical modification of the protein was close to complete. Molecular species with 1 and 2 and 3 modification groups were present (FIG. 44).

To identify the modified amino acid residues, the protein preparation was digested by protease Glu-C. Analysis of the digest by MALDI-TOF MS revealed the presence of peptides with m/z 2324 and 2674 with 2324 corresponding to unmodified peptide KMSKDGKKKKKKSKTKCVIM (SEQ ID NO:4) (170-189) and 2674 to the same peptide modified by FB9 at Cys-186 (FIG. 45) (confirmed by fragmentation). Peptide with m/z 1735 corresponds to sequence GKKKKKKSKTKCVIM (SEQ ID NO: 3) (174-189) and m/z 2085 corresponds to the same peptide modified by FB9 at Cys-186 (confirmed by fragmentation).

To identify other potential residues modified by FB9, peptides obtained after digestion by Glu-C were further digested by trypsin (FIG. 46A). Fragmentation spectrum of a peptide with m/z 1320.614 revealed major fragment of 969, which is close to m/z of peptide DIHHYRE (SEQ ID NO:2) (expected m/z 969.4537, 93-99), suggesting that m/z 1320 corresponds to peptide DIHHYRE (SEQ ID NO:2) modified by FB9 (FIG. 45). Indeed, comparison of fragmentation spectra of peptides 969.485 and 1320.614 demonstrated their relationship. Common fragments are indicated in FIG. 46B.

Modification of processed (farnesylated and carboxylmethylated KRAS4b). Protein prep GG-HsKRAS-4b, RP1151105092454 FmeKRAS4b (FIG. 47A) was modified by FB9 with 7.6-fold molar excess of FB9 for 1 h at 37° C., followed by 16 h at room temperature (22° C.). MALDI-TOF MS analysis of chemical modification to the protein revealed that major form represented species with 1 added modification group, less protein had 2 modification groups, and a little with 3 modification groups, some protein was left un-modified (FIG. 47B). To identify the modified amino acid residues protein preparation was digested by trypsin.

MALDI-TOF MS demonstrated that K-RAS tryptic peptides with m/z 1203 (SFEDIHHYR, SEQ ID NO:6), 1702 (SFEDIHHYREQIK, SEQ ID NO:8), 1858 (SFEDIHHYREQIKR, SEQ ID NO:7) are present also in modified form +(350-351) Da. During fragmentation, these modified peptides yielded intensive fragment corresponding to unmodified peptide and fragments of peptide (mostly without modification).

These peptides were modified on His residues. To identify which His was modified (i.e. 95 or 96 in the sequence of used recombinant KRAS) fragmentation spectra were analyzed in BioTools when FB9 modification (C17H20Cl1N2O4, 350/351) was set on one of these His residues in Sequence Editor.

Analysis of fragmentation of m/z 1203.660 and 1554.856 observed in reflector mode (low intensity in reflector mode but well detected in linear mode as 1554.7) allowed to conclude that in peptide SFEDIHHYR (SEQ ID NO:6) His7 (i.e. H95 in the native protein) is modified. In fragmentation spectrum of 1554 a fragment 825.409 was present but not in a spectrum of 1203. When FB9 modification was on His-7 this fragment was assigned by BioTools as modified y-3. Manual examination of the spectrum confirmed this conclusion.

Modification of H95 in Kras4B G12V in cells.

Figure 1A:
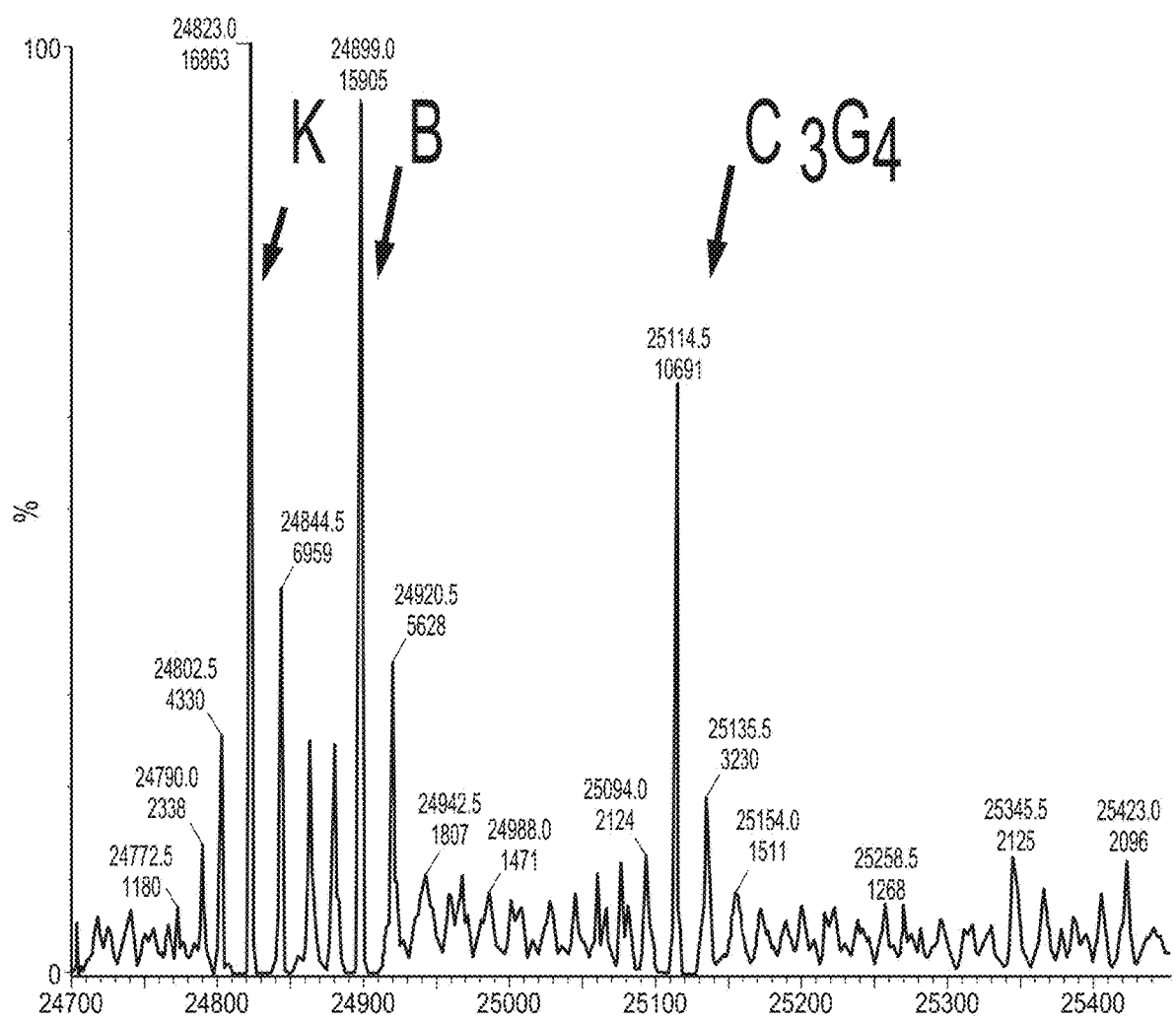
FIGS. 1A-1C. LC-MS data from screen with His-K-Ras 4B (G12V) and (G12V/C185S). K refers to His-K-Ras 4B (G12V) (24823 Da) not bound to compound. B refers to His-K-Ras 4B (G12V) (24899 Da) bound to βMe. C: His-K-Ras 4B (G12V) (25114.5 Da for 3G4 vs. 25178 Da for 6B9) bound to tethering compound. Kmut refers to His-K-Ras 4B (G12V/C185S) (24808 Da) not bound to compound.
Figure 1B:
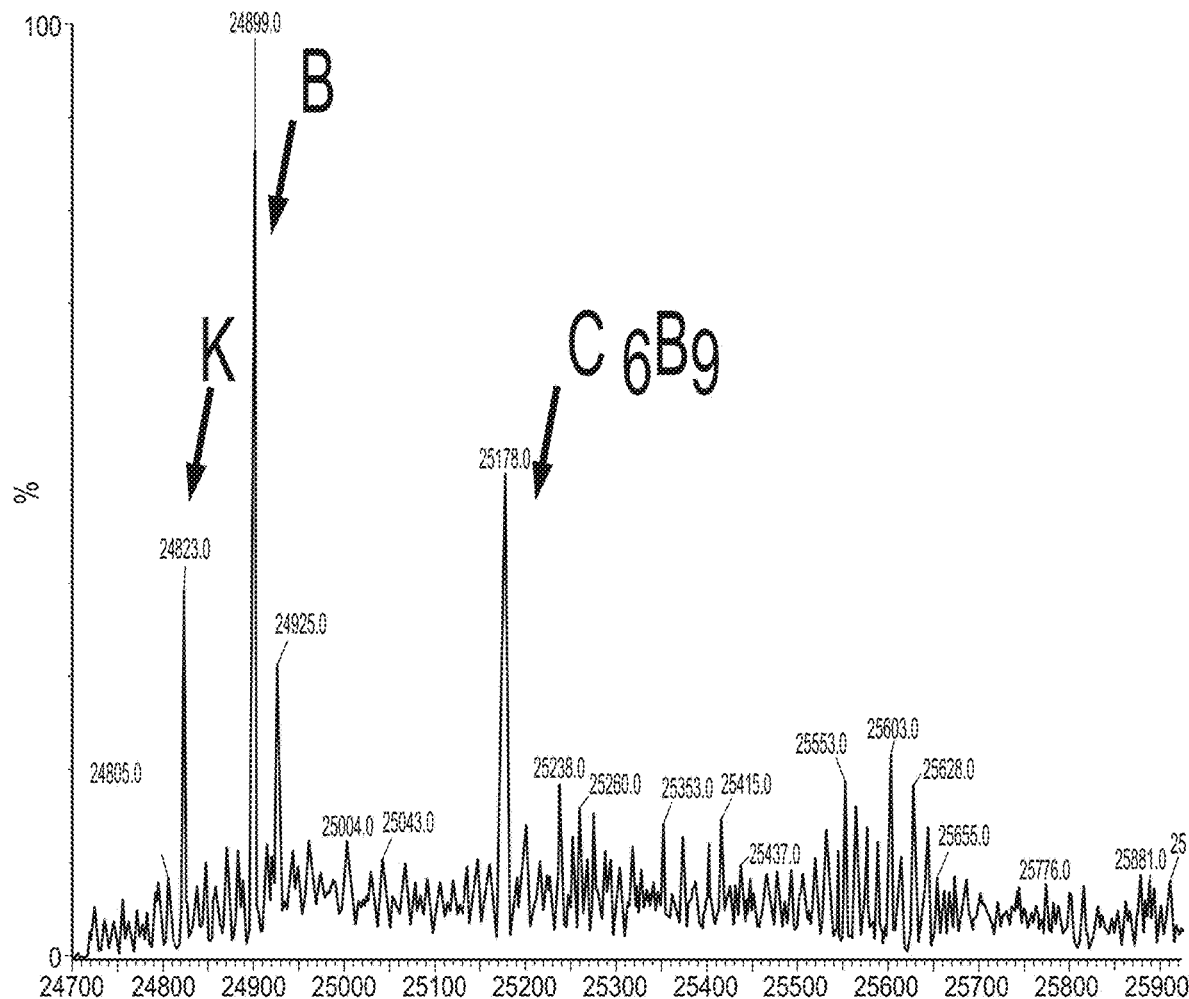
Figure 1C:
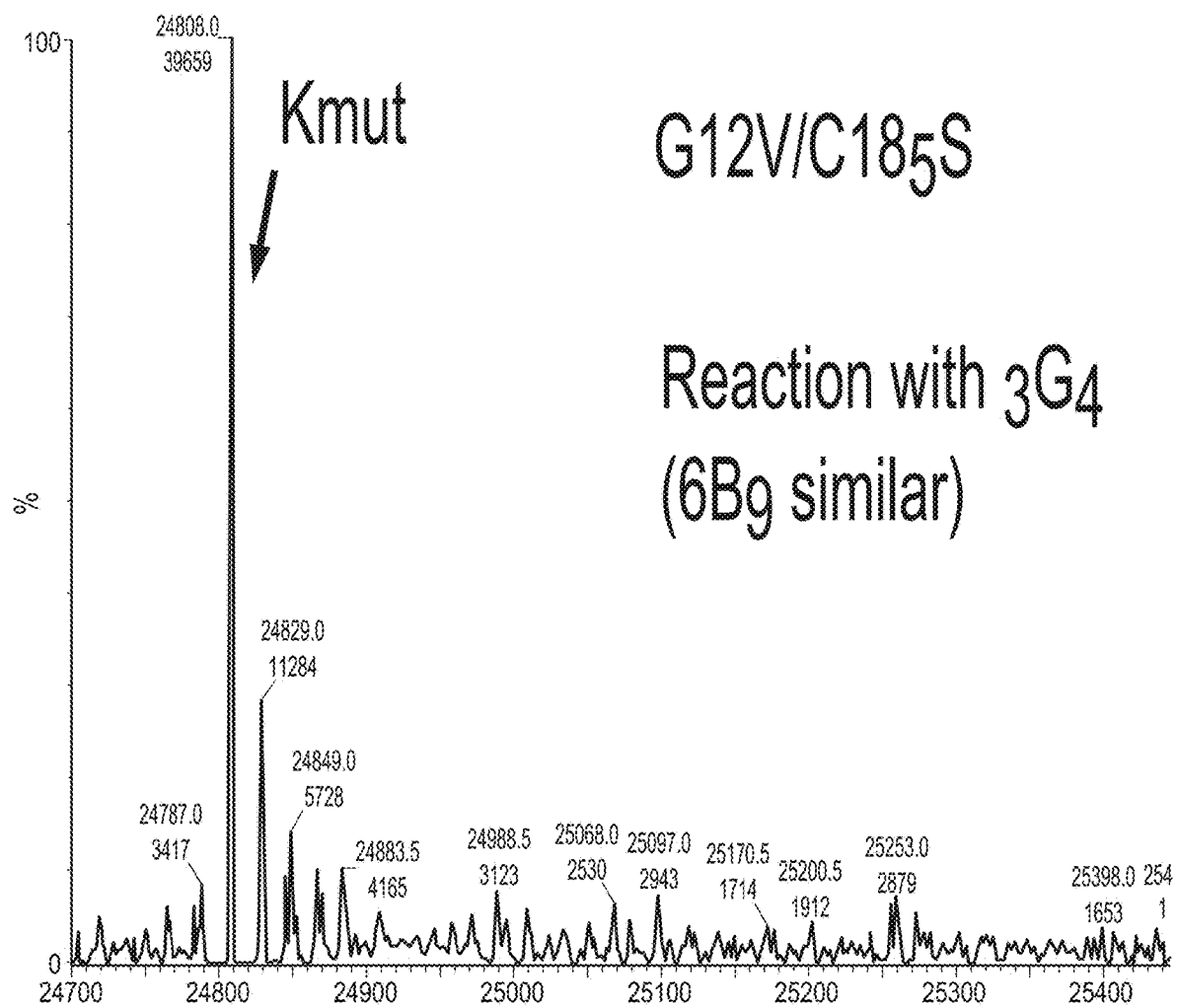
Figure 2A:
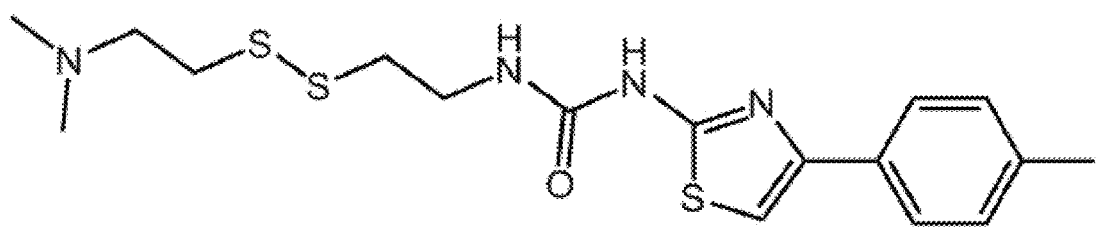
FIGS. 2A-2D. Exemplary compounds from screen and derivatives thereof, 3G4 (phenyl thiazole containing compound) and derivatives wherein disulfide of 3G4 replaced with alternative electrophilic moieties.
Figure 2B:
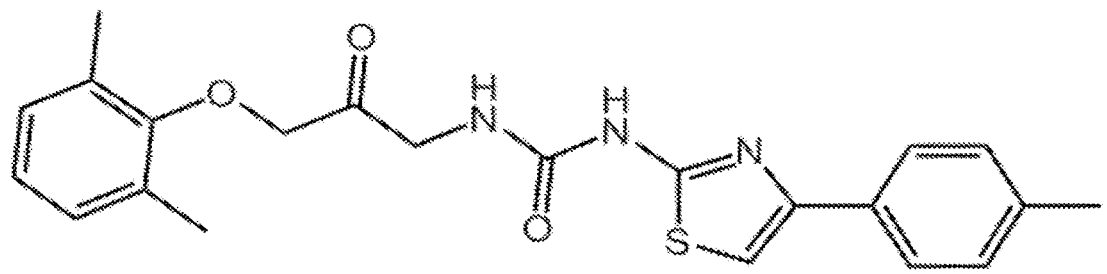
Figure 2C:
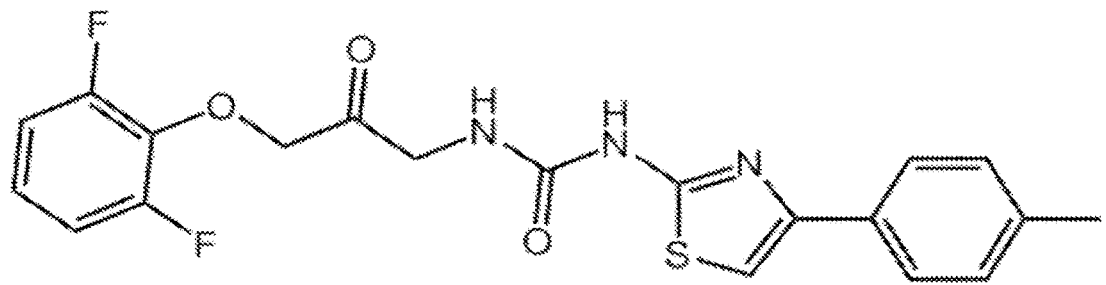
Figure 2D:
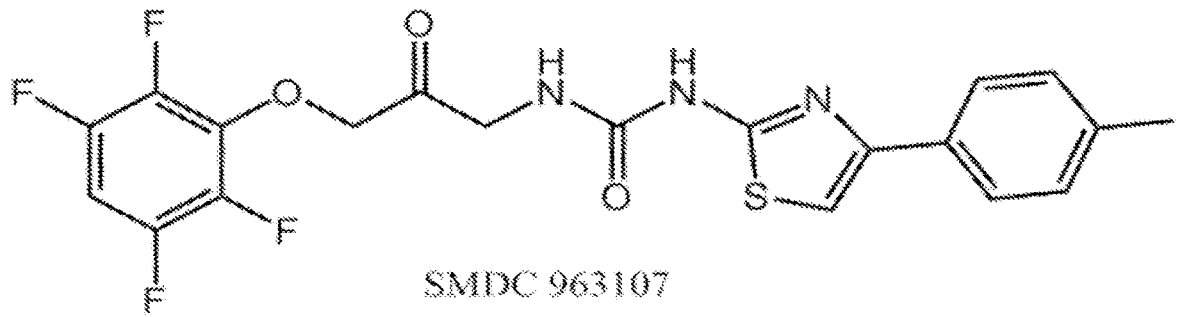
Figure 3A:
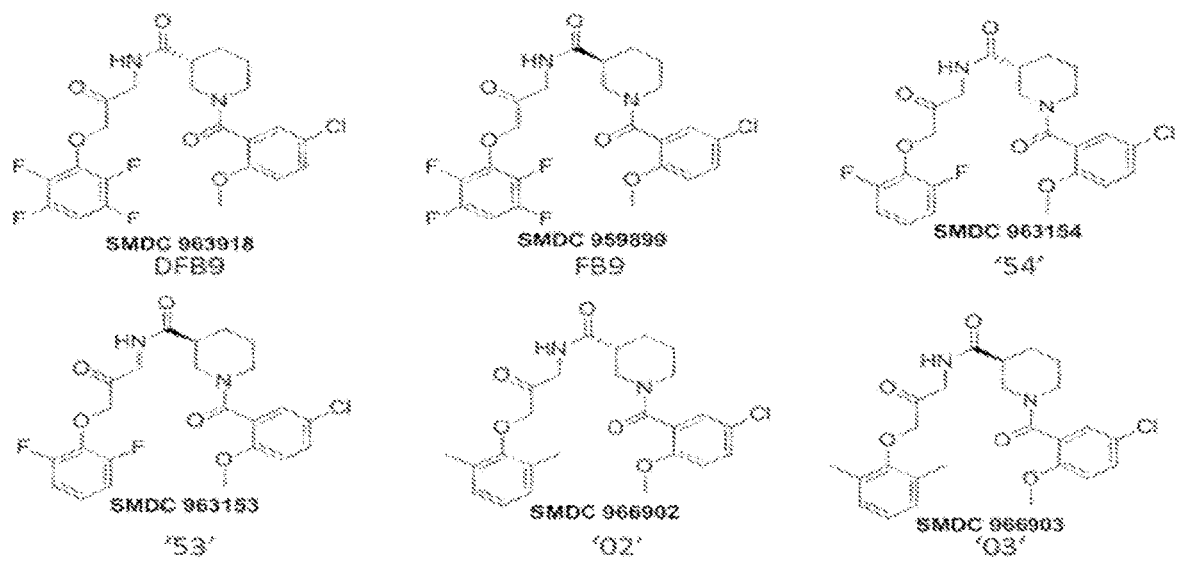
FIGS. 3A-3C. Exemplary compounds from screen and derivatives thereof, including 6B9 (nipecotic acid derivative), 3G4 (phenyl thiazole containing compound); disulfide moiety of 6B9 was replaced with other electrophilic moieties, including tetrafluoro-phenoxy (FB9, also referred to herein as SMDC 959899) or difluoro-phenoxy (53, also referred to herein as SMDC 963153); disulfide of 3G4 replaced with alternative electrophilic moieties.
Figure 3B:
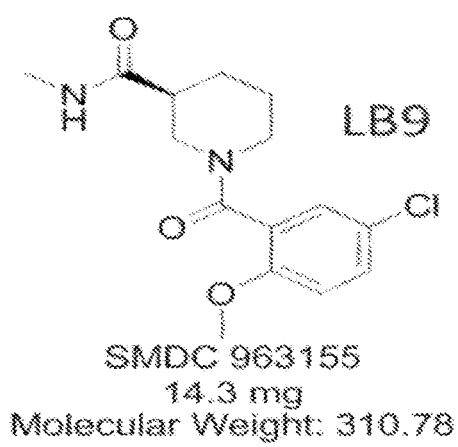
Figure 3C:
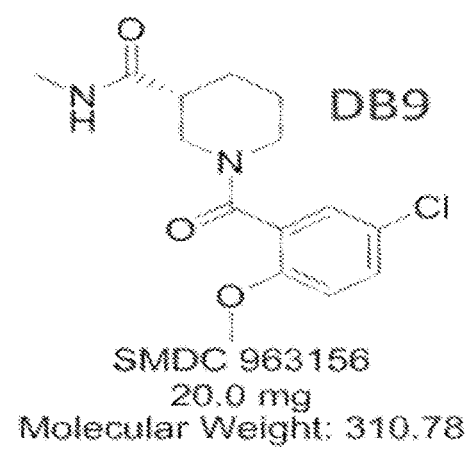
Figure 4A:
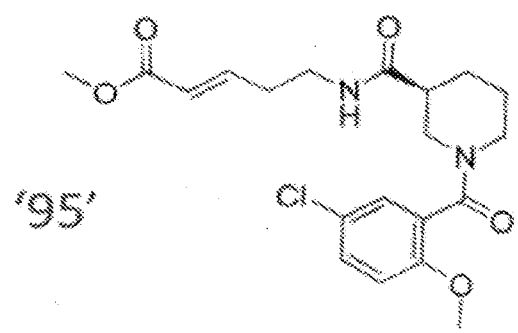
FIGS. 4A-4D Exemplary compounds from screen and derivatives thereof, including 6B9 (nipecotic acid derivative and derivatives wherein the disulfide moiety of 6B9 was replaced with other electrophilic moieties, including tetrafluoro-phenoxy (FB9) or difluoro-phenoxy (53). Derivatives of 6B9 with other electrophilic moieties.
Figure 4B:
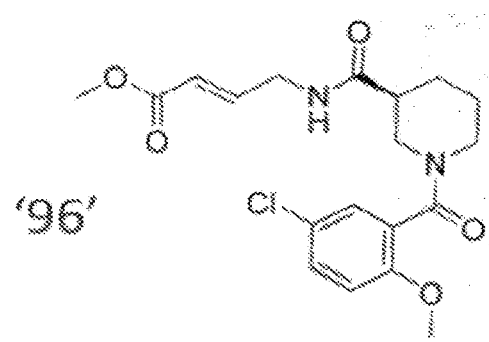
Figure 4C:
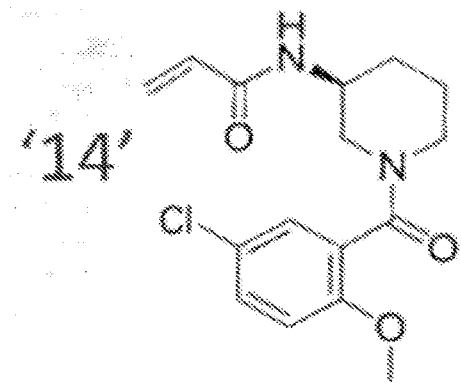
Figure 4D:
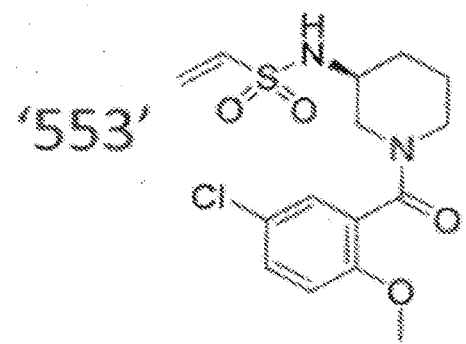
Figure 5A:
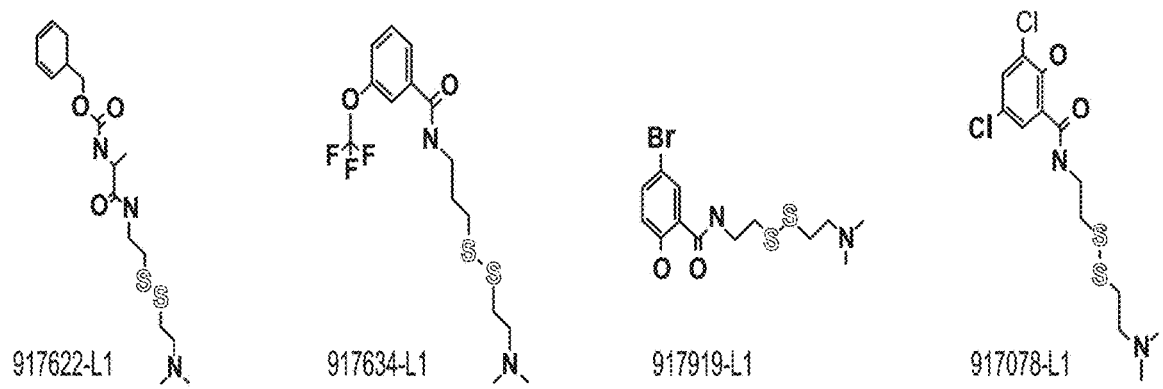
FIGS. 5A-5B. Exemplary compounds capable of binding to K-Ras.
Figure 5B:
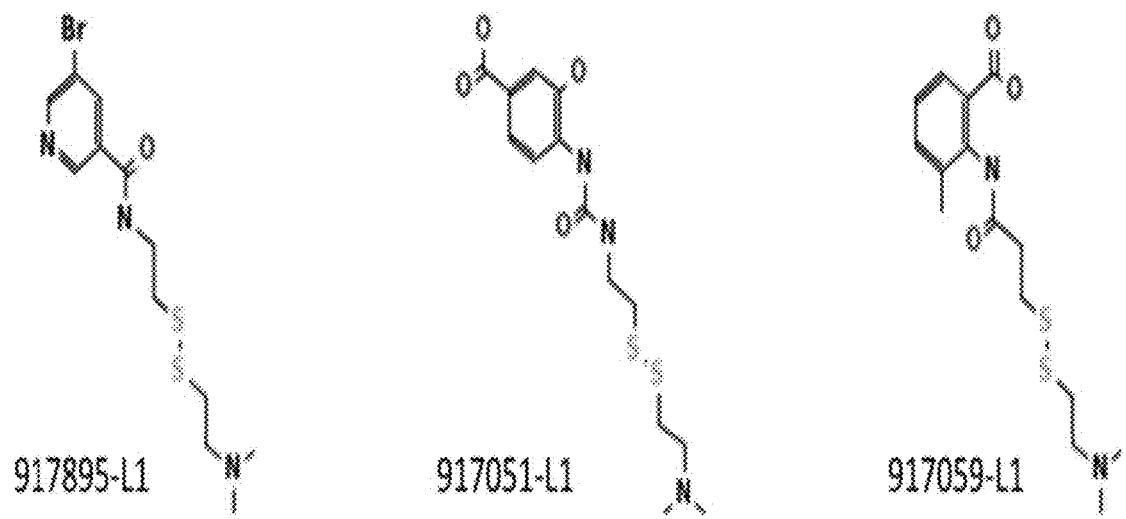
Figure 6A:
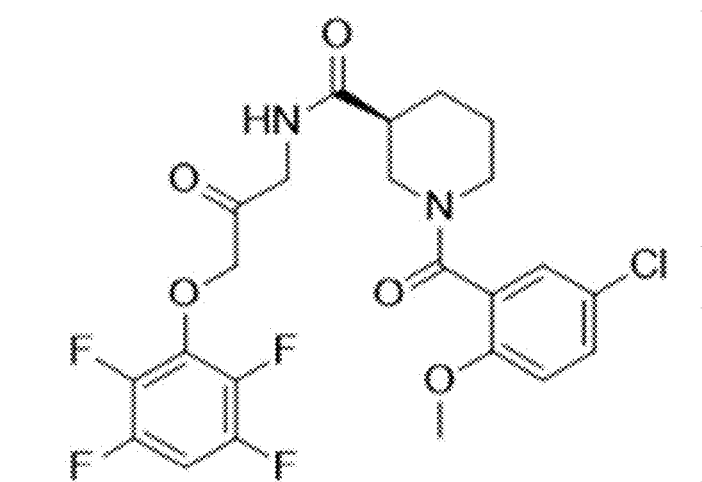
Figure 7B:
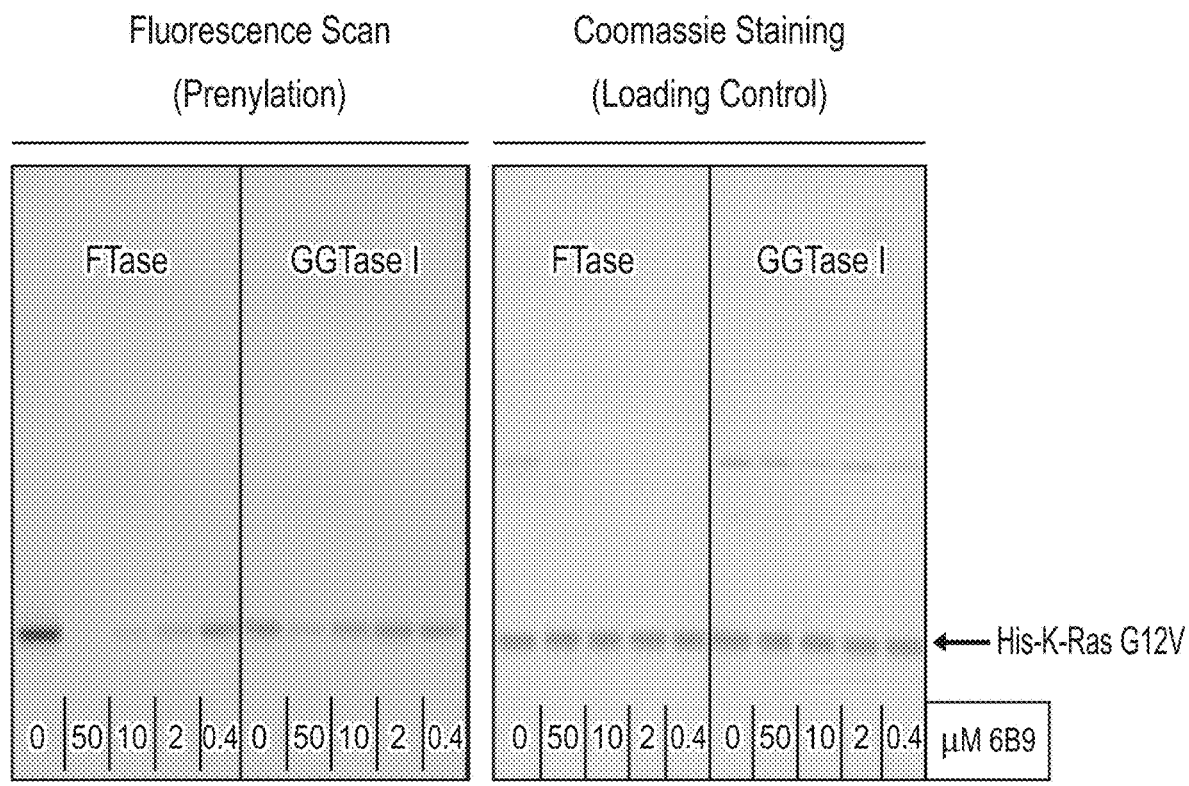
Figures 8A, 8B:
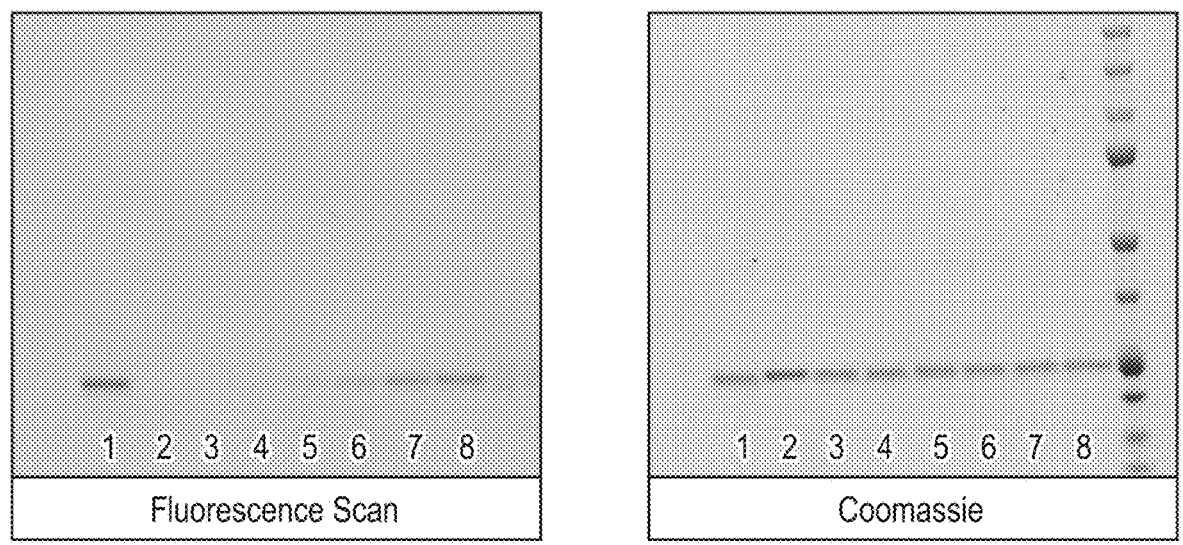
FIGS. 8A-8B. In vitro prenylation with 6B9 tethering compound.
Figure 9:
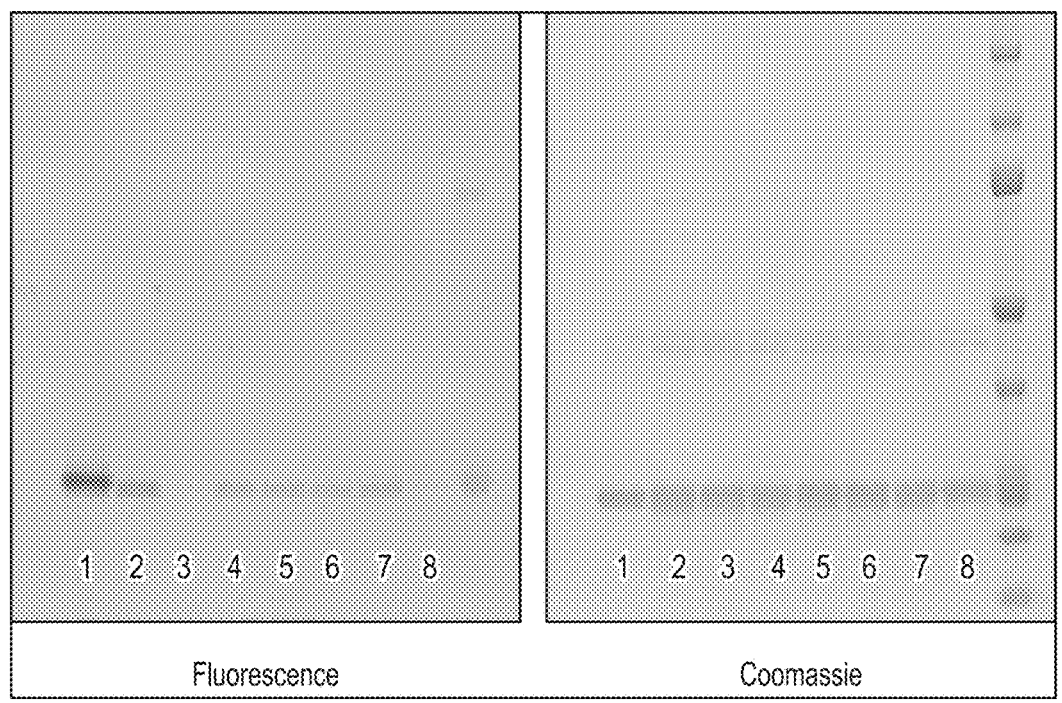
FIG. 9. In vitro prenylation comparing N-Ras with different compounds; 1. KRAS4B wt CT; 2. KRAS4B mut CT; 3.50 μM 6B9; 4.20 μM 6B9; 5.8 μM 6B9; 6. 3.2 μM 6B9; 7. 1.3 μM 6B9; and 8. 0.5 μM 6B9. A fluorescent substrate for farnesyl transferase, 3,7-dimethyl-8-(7-nitro-benzo[1,2, 5]oxadiazol-4-ylamino)-octa-2,6-diene-1-pyrophosphate (NBD-GPP), has similar kinetics as the natural substrate for farnesyl pyrophosphate.
Figure 10:
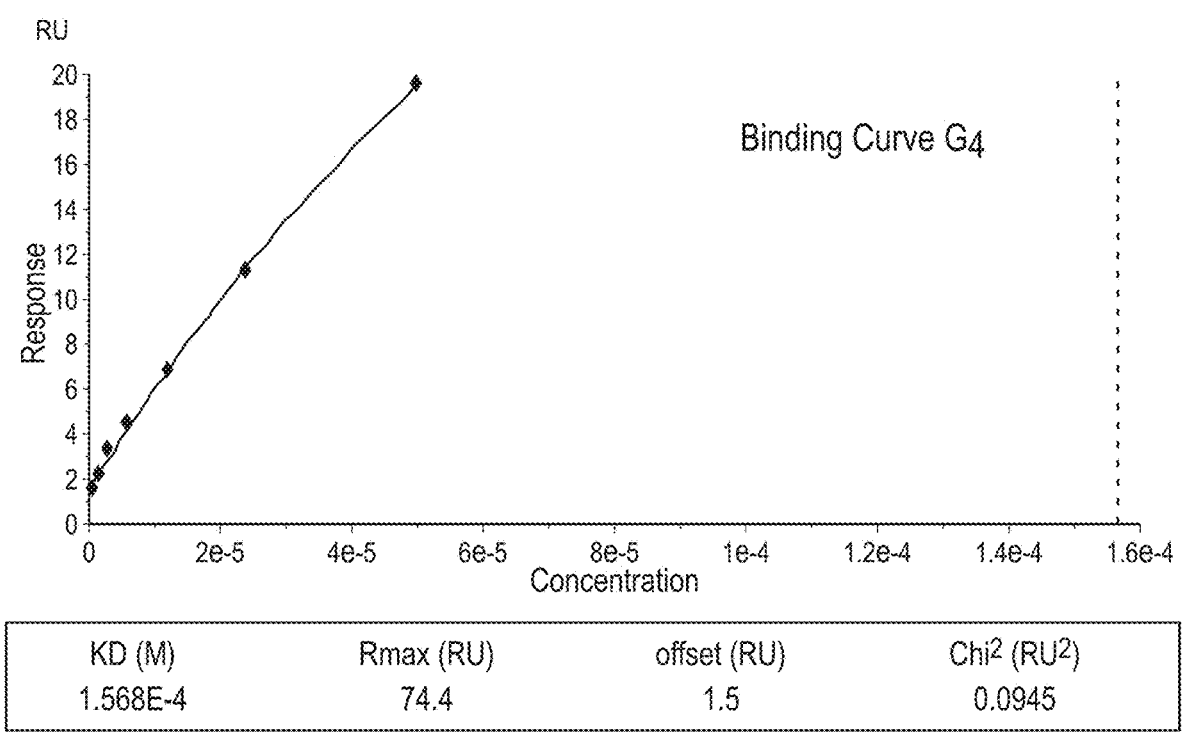
FIG. 10. BIACore Experiment with 3G4 on K-Ras 4B; Surface Plasmon Resonance (SPR) and ForteBio/Octet Experiment showing whether 3G4 and 6B9 Fragment (LB9) had a secondary non-covalent interaction site in K-Ras 4B; experiment should show whether compounds interact with K-Ras 4B at 2 sites (e.g., the covalent site which is the CAAX-box cysteine and a non-covalent site); SPR experiments with K-Ras 4B G12V/C185S so that only possible non-covalent interaction; binding curve of 3G4 with K-Ras 4B G12V/C185S; Binding Curve of Compound 3G4 with K-Ras C186S, demonstrating potential non-covalent interaction.
Figure 11A:
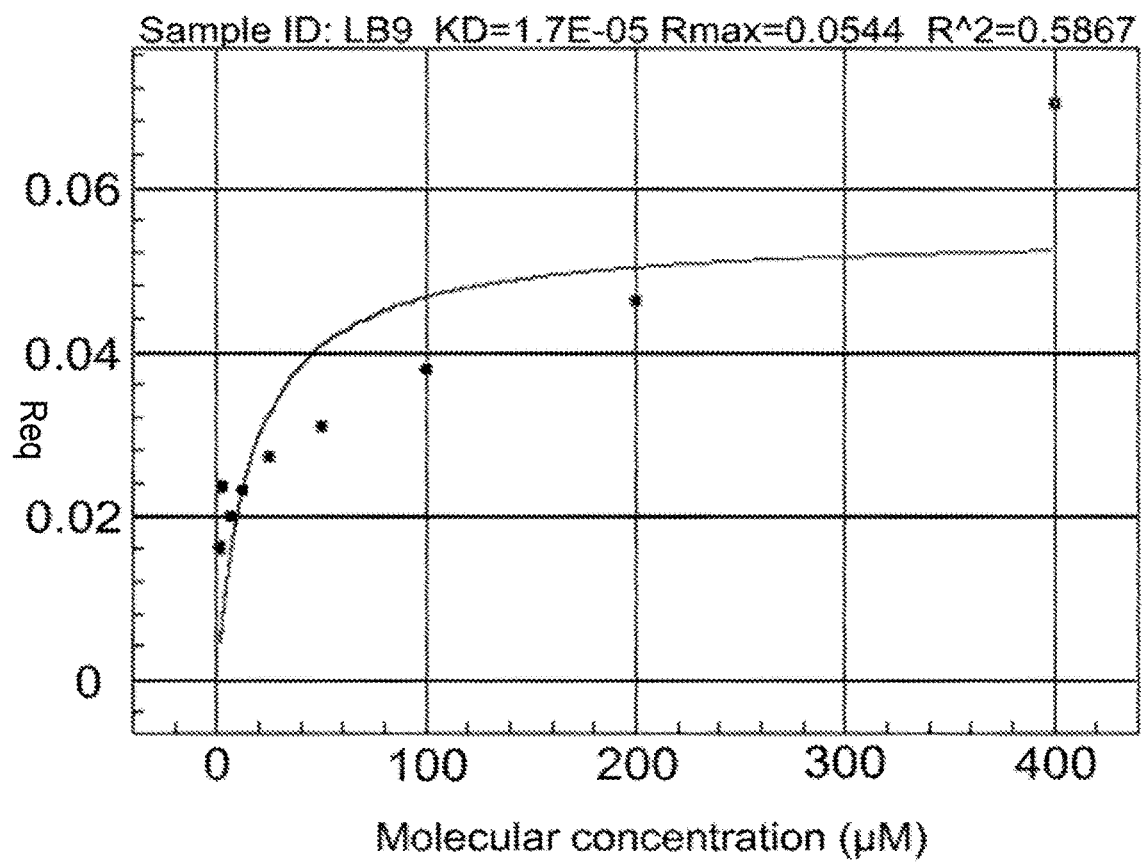
FIGS. 11A-11B. ForteBio/Octet Assays; Measures compound binding to protein: association versus dissociation, steady state; Tested Avi-tagged Kras G12D with Fragments of FB9 and FB9D (parts of FB9/FB9D that make non-covalent interactions); LB9: =fragment of FB9; DB9: =fragment of FB9D; Avi-tagged K-Ras G12D was loaded with GTPyS/Mg; Curve with LB9 better than with DB9; Kd for LB9 around 17 μM.
Figure 11B:
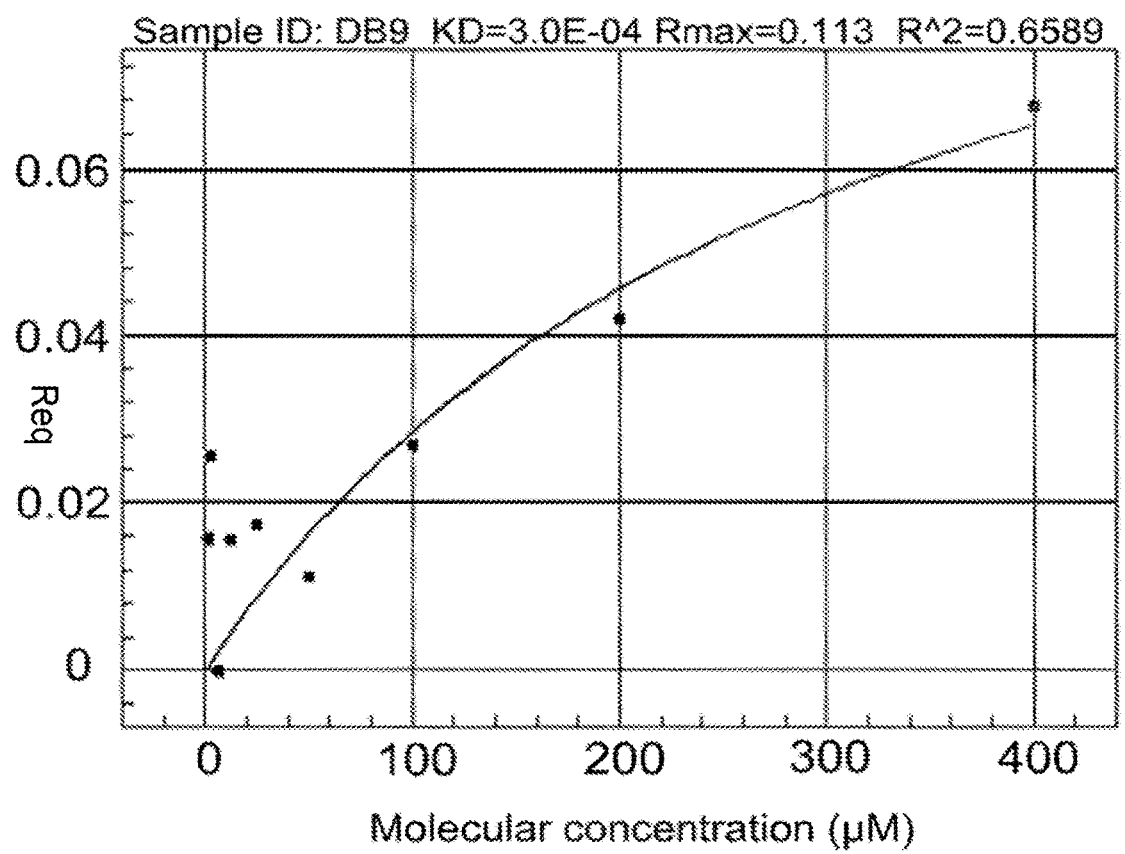
Figure 12A:
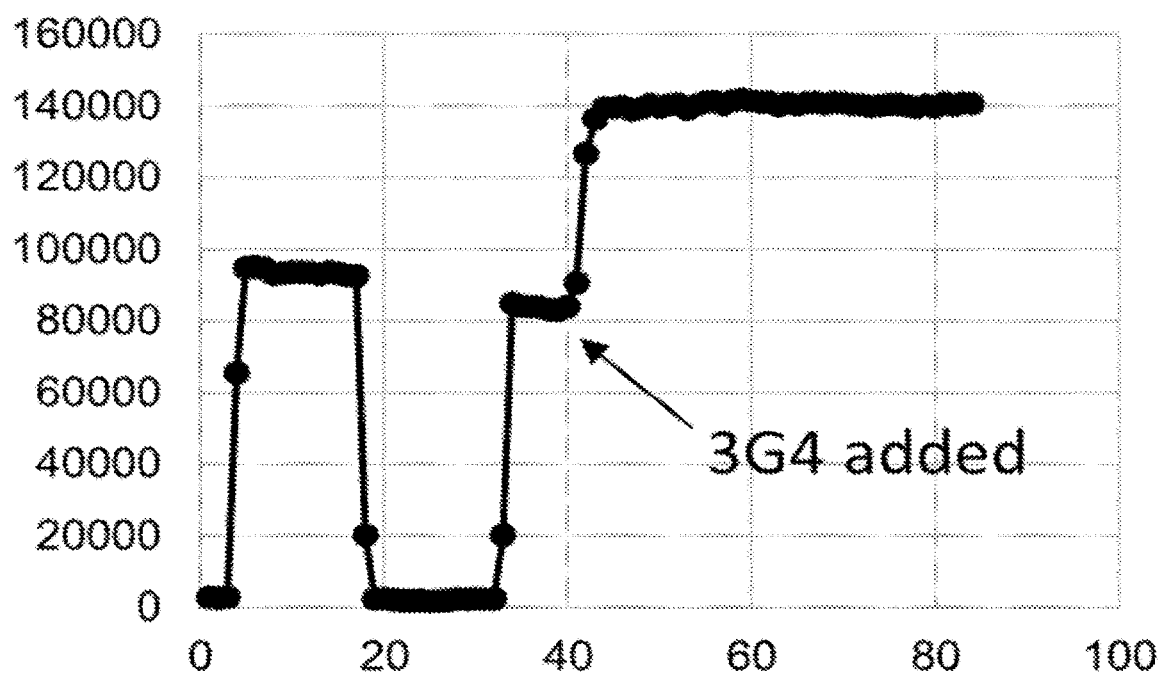
FIGS. 12A-12B. Measuring Conformational Changes Induced by Adding 3G4; Second Harmonic Generation (SHG) Experiments; SHG experiments were designed in order to see whether compound 3G4 induces any conformational change in K-Ras 4B; FPLC purified K-Ras was labelled either with EDA-GTP-ATTO 390, a fluorescent GTP analog, or PyMPO-Maleimide, a fluorescent dye that labels cysteines, or PyMPO-SE, another fluorescent dye that labels amines; Labeled K-Ras 4B was immobilized via His-tag on the surface of a chip and the experiments were performed in the presence of DMSO or 3G4 compound; 2 experiments with K-Ras 4B G12V/C185S labelled either with EDA-GTP-ATTO 390 or PyMPO-Maleimide. Fluorescent dyes, EDA-GTP-ATTO 390 and PyMPO-Maleimide, that have second harmonic generation activity were used.
Figure 12B:
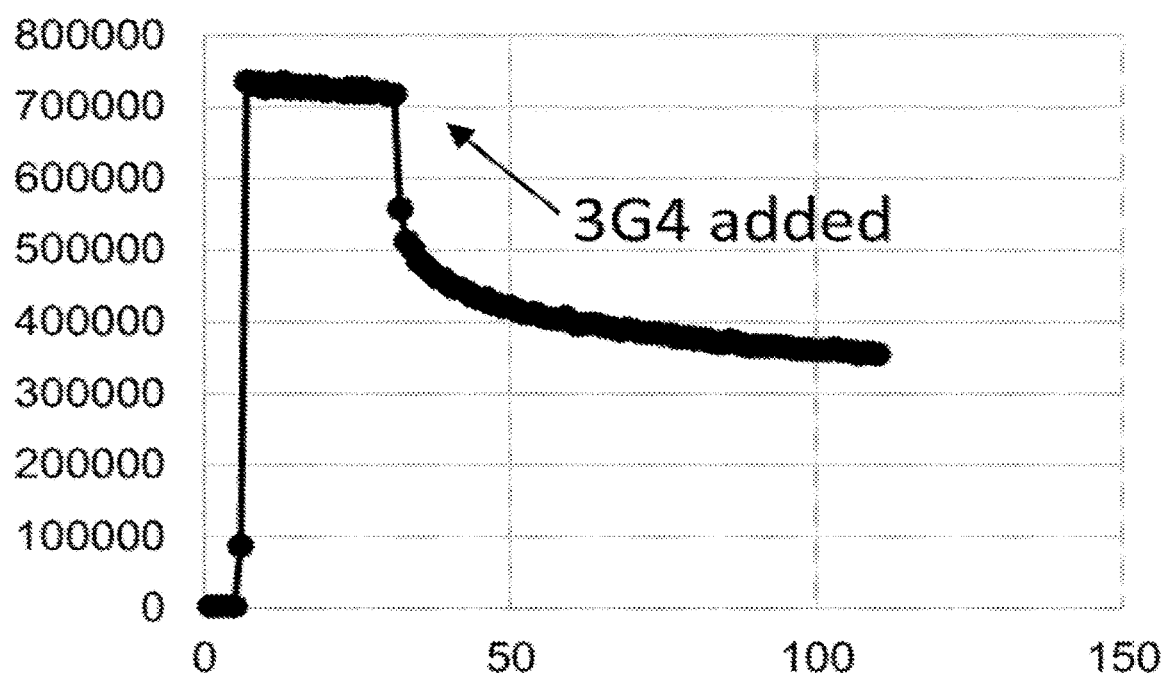
Figure 13A:
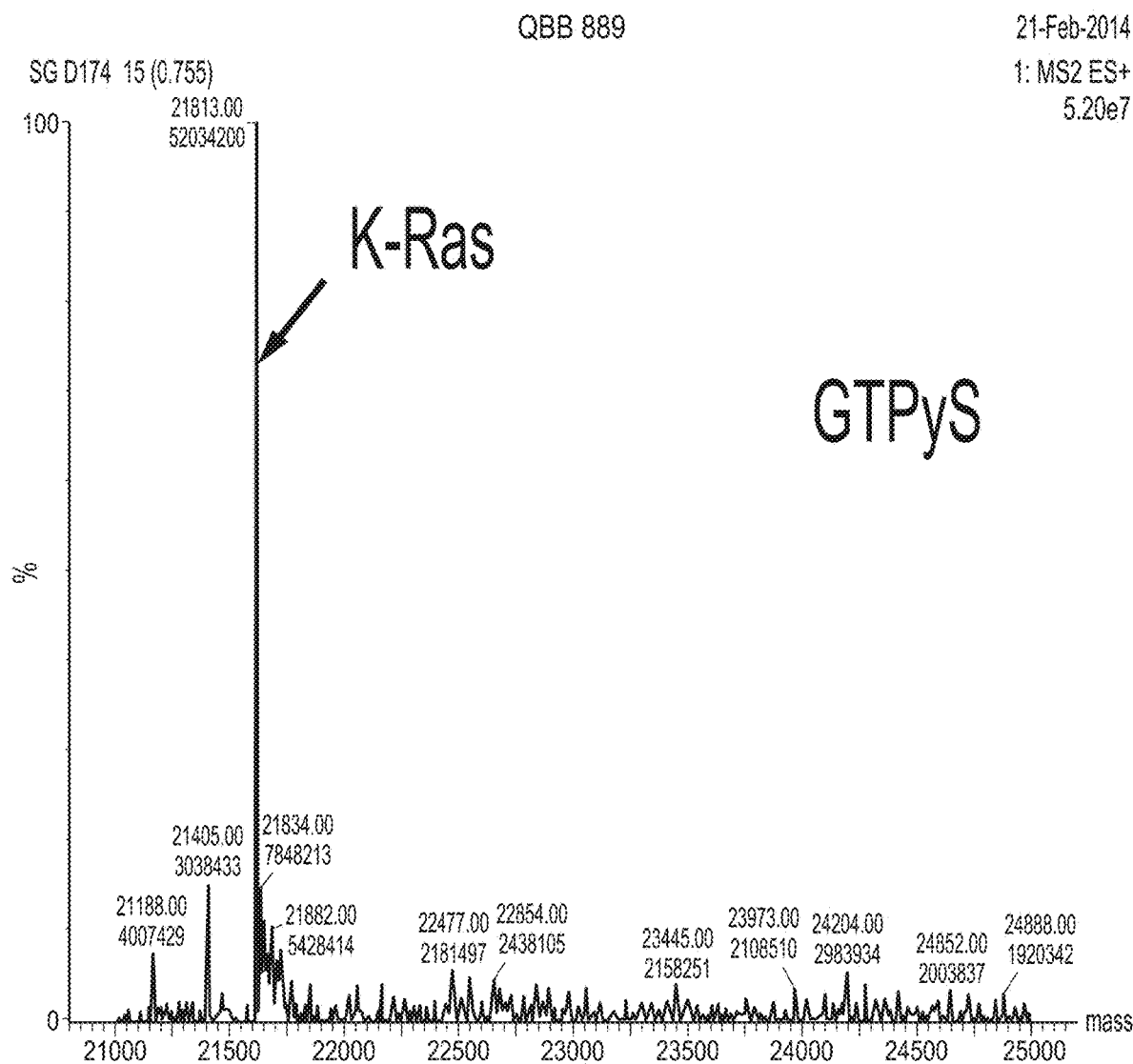
FIGS. 13A-13E. Binding Assay of FB9 to either GTPyS or GDP bound K-Ras G12D; Binding of FB9 to His-tagged K-Ras wt, G12D, G12V and His-tagged K-Ras G12V/C185S was compared; Proteins were loaded with GTPyS/Mg; Binding reaction with FB9 was done at RT for 4 hours; Rec full length G12D became loaded with either GDP or GTPyS and Mg2+; ~10 µM protein was bound to 100 µM electrophile compound at RT and time points were taken after 5 and 23 hours; Compound 6B9 had a tetrafluorophenoxy electrophile modification (FB9); Compound bound better when K-Ras was in complex with GTPyS/Mg2+; In the case of K-Ras/GDP/Mg2+ the protein got significantly labelled at a second site after 5 h.
Figure 13B:
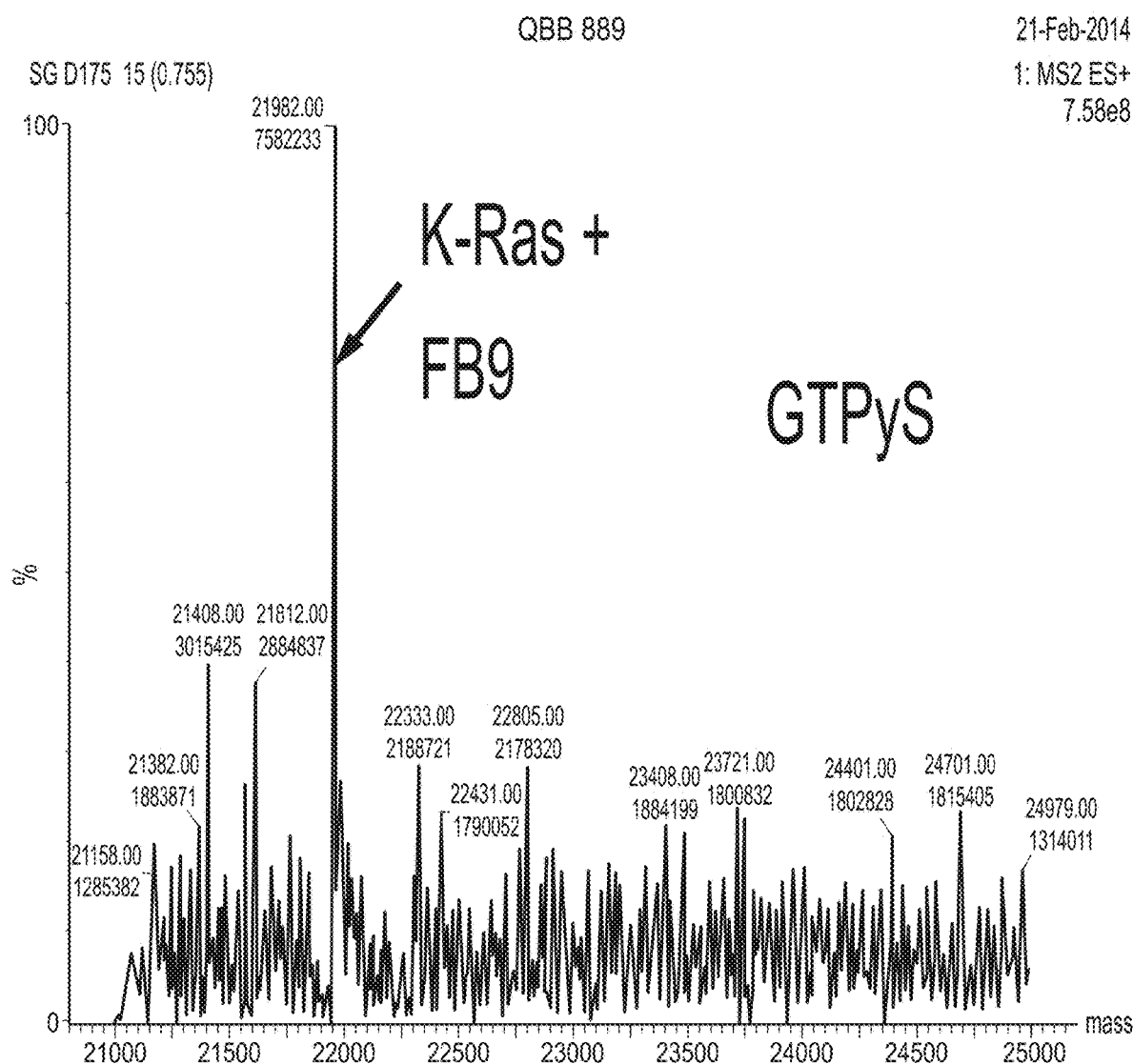
Figure 13C:
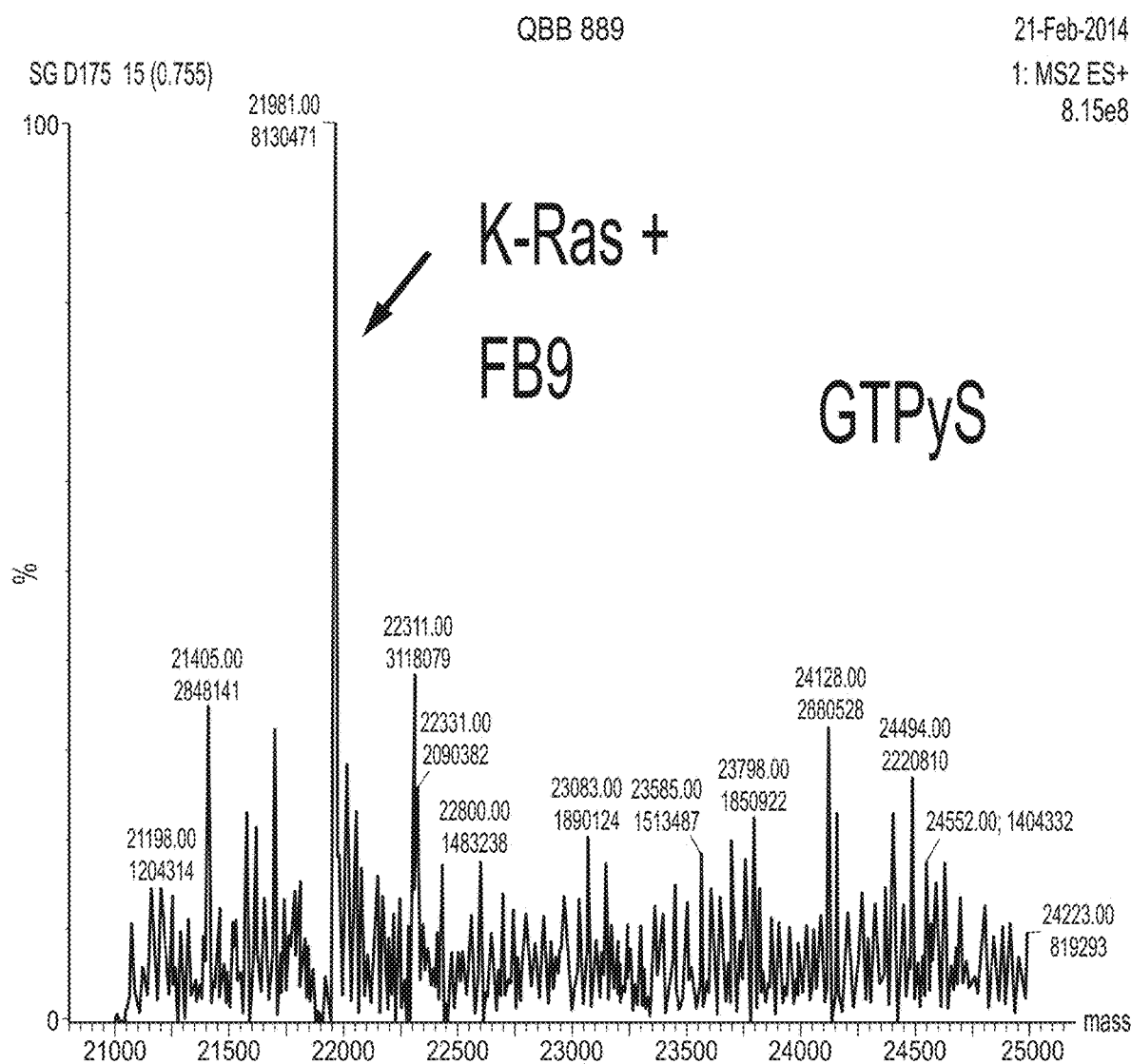
Figure 13D:
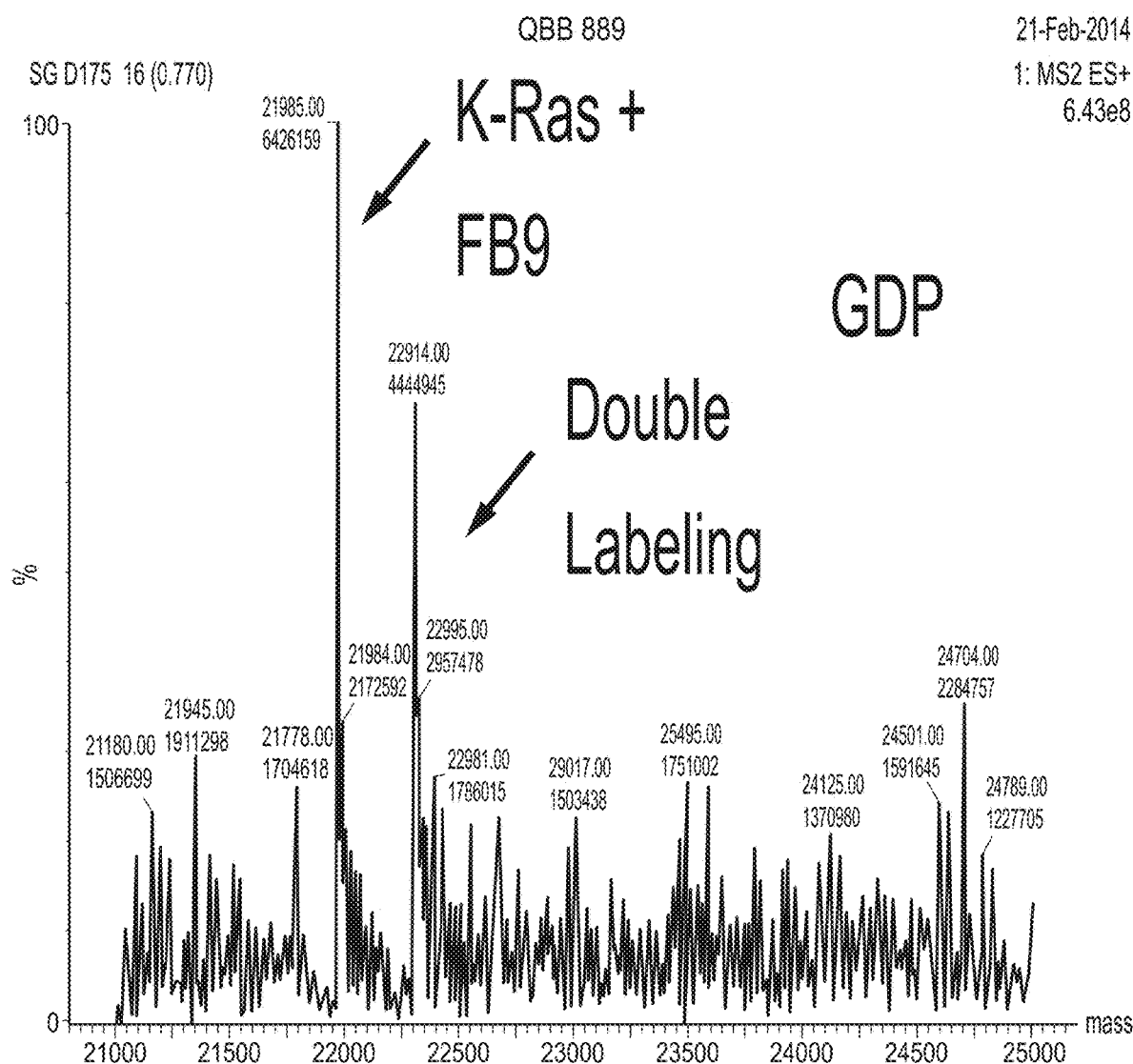
Figure 13E:
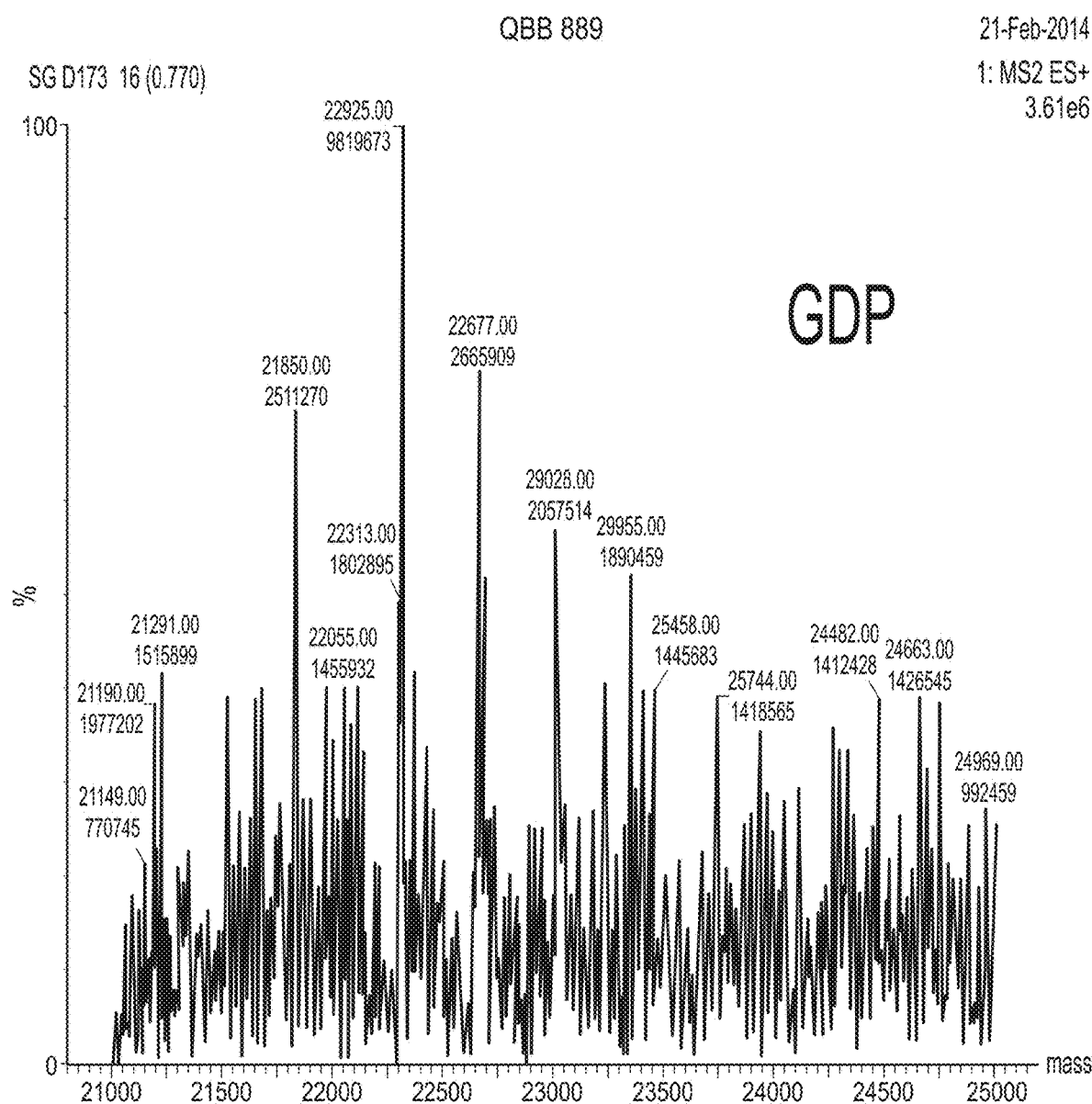
Figure 14A:
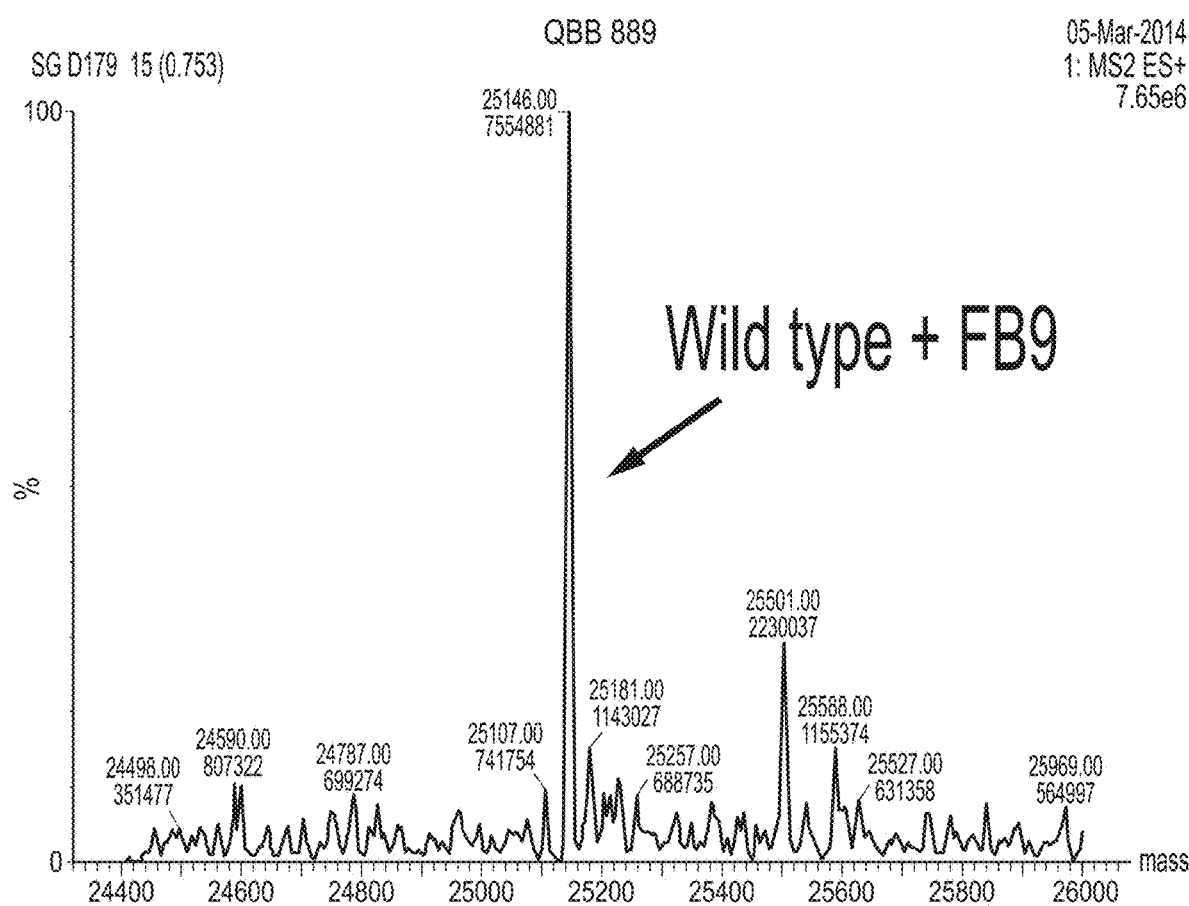
FIG. 14A-14D. Binding of Electrophilic 6B9 Derivative (FB9) to Different Oncogenic His-K-Ras 4B.
Figure 14B:
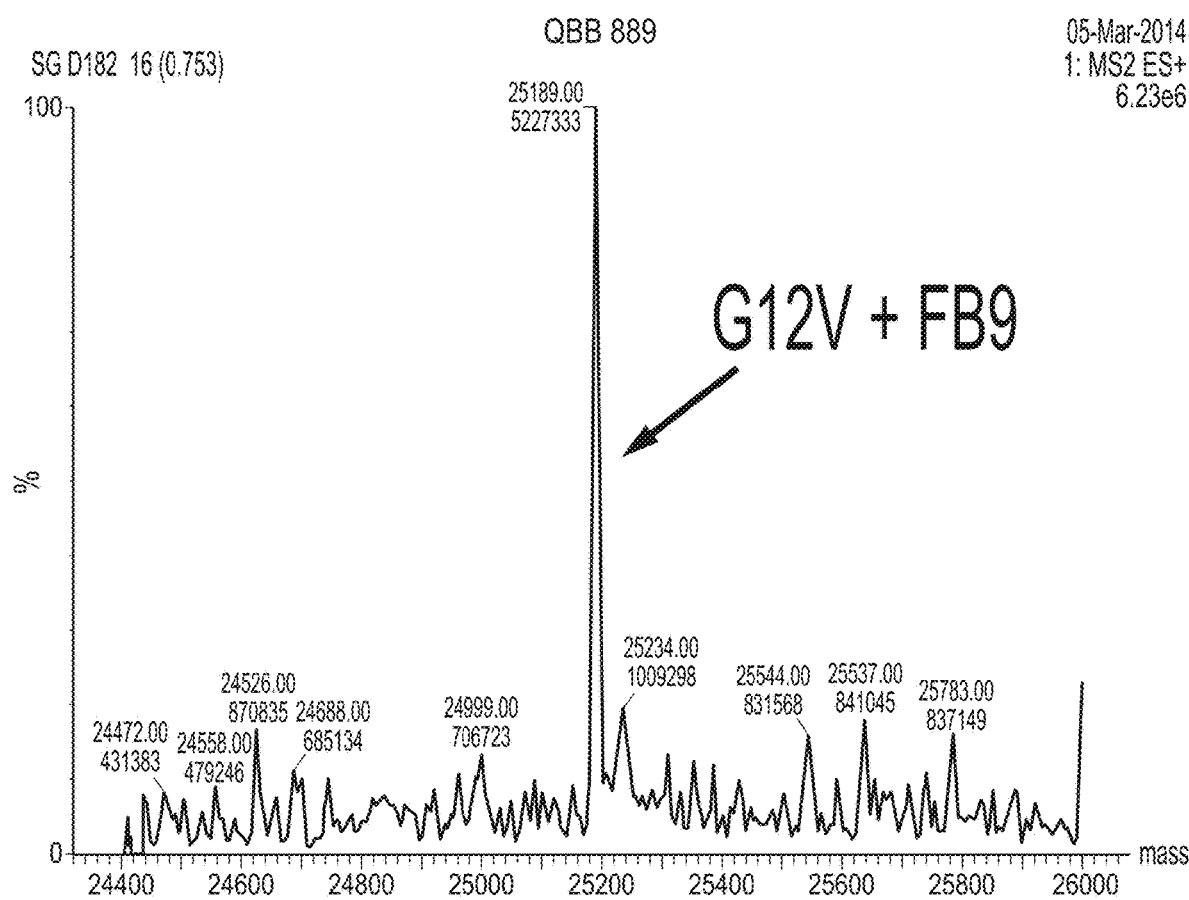
Figure 14C:
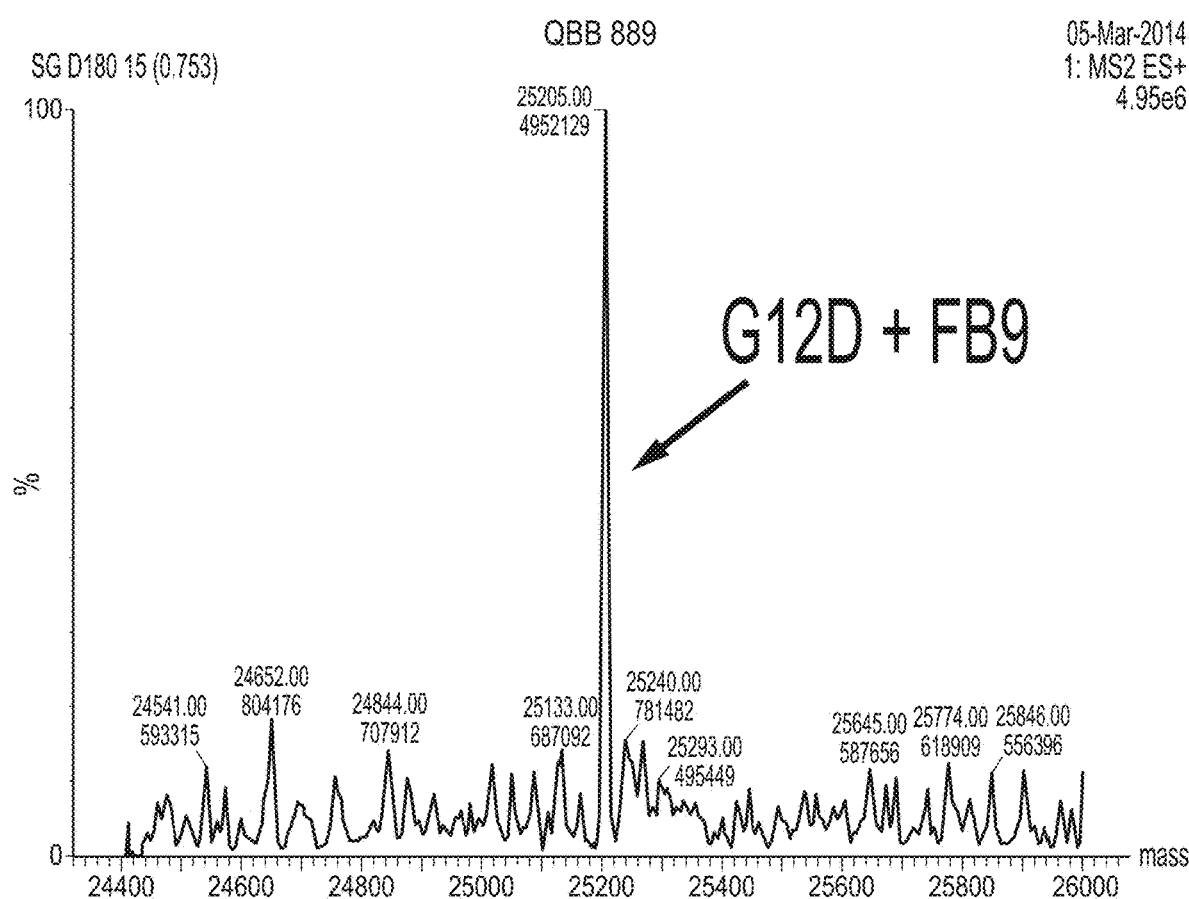
Figure 14D:
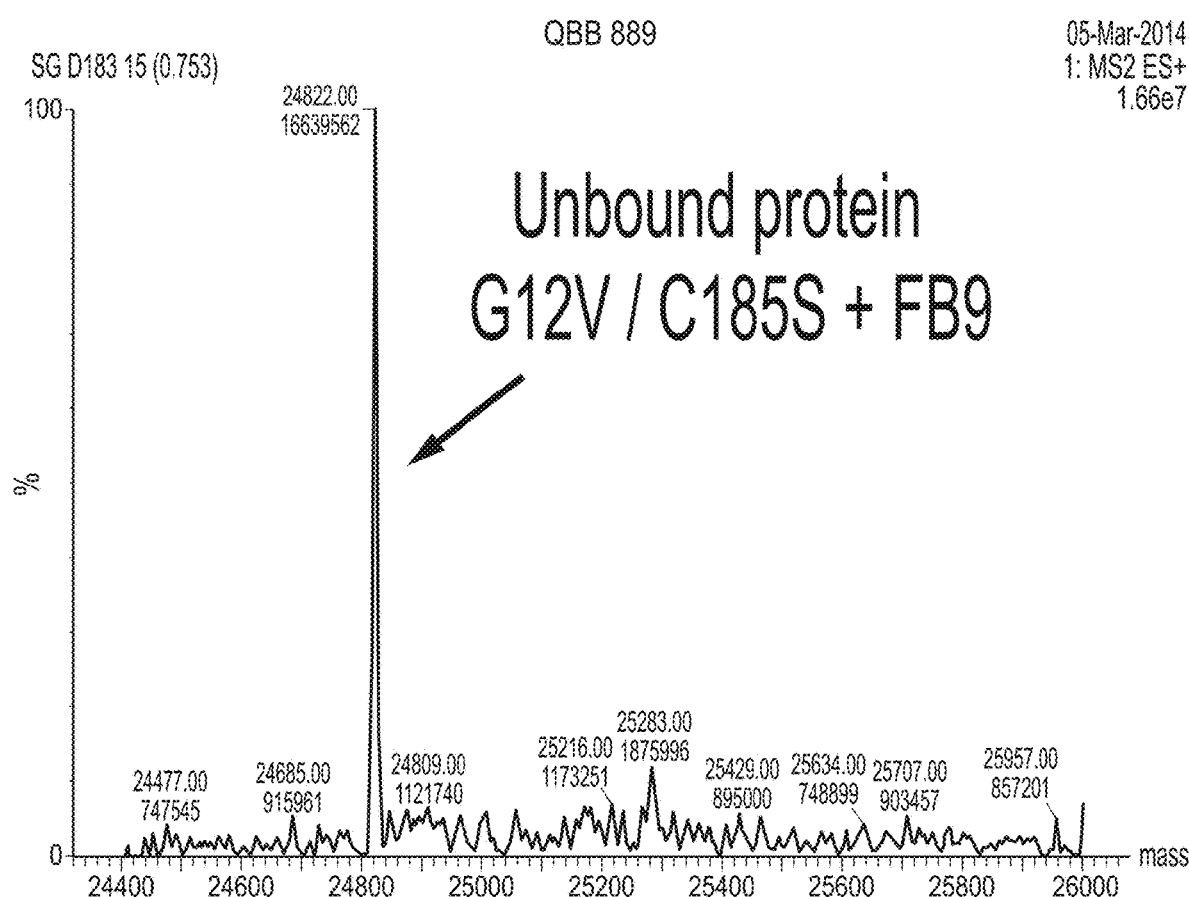
Figure 15A:
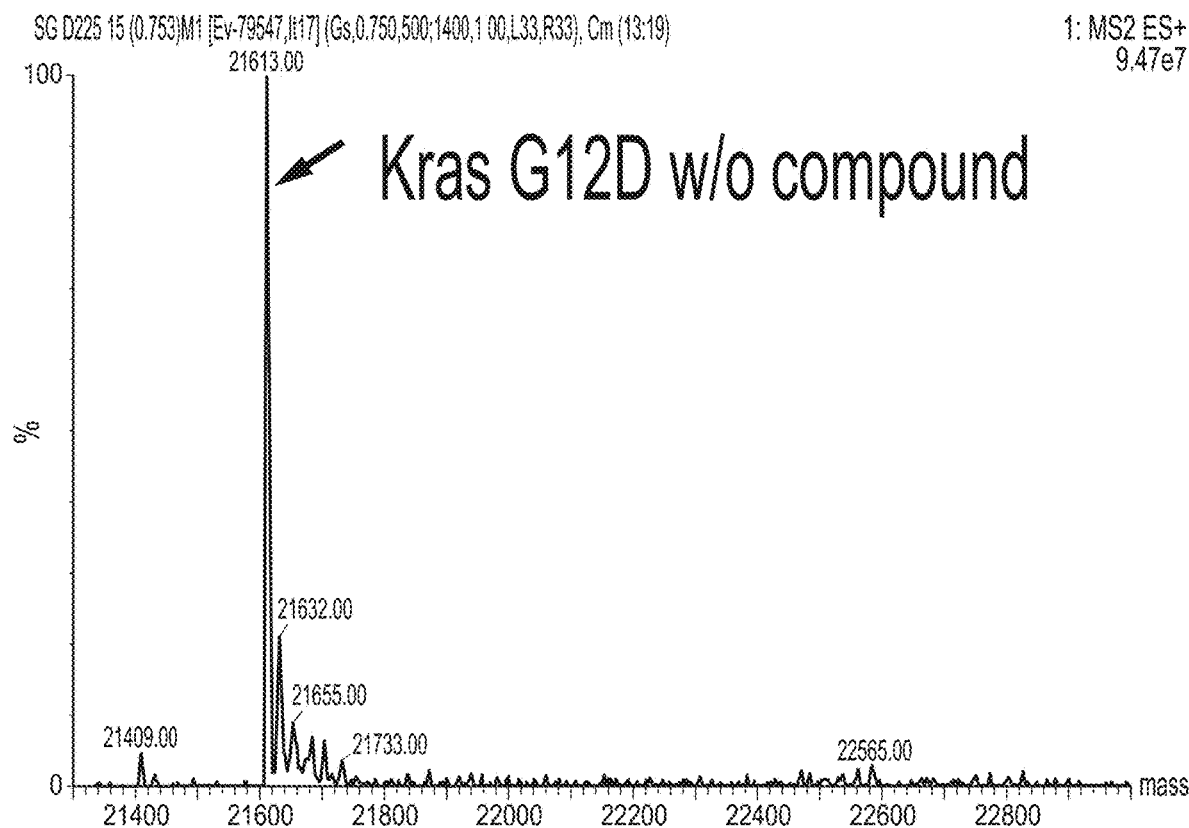
FIGS. 15A-15D. Experiments with Stereoisomers of Difluorophenoxy-6B9; Kras G12D/GTPyS/Mg2+, DMSO control, 2 h incubation at RT; The binding of FB9 to Kras G12D was compared with the stereoisomers of Difluorophenoxy-6B9 (53, 54); FB9 bound 100% after 2 h incubation; Difluorophenoxy-6B9 (compound '53') bound to about 62% compared to FB9 under the same condition; The stereoisomer ('54') of compound '53' bound to roughly 35% compared to FB9 which is roughly 50% of compound '53'; Partial stereospecific interaction.
Figure 15B:
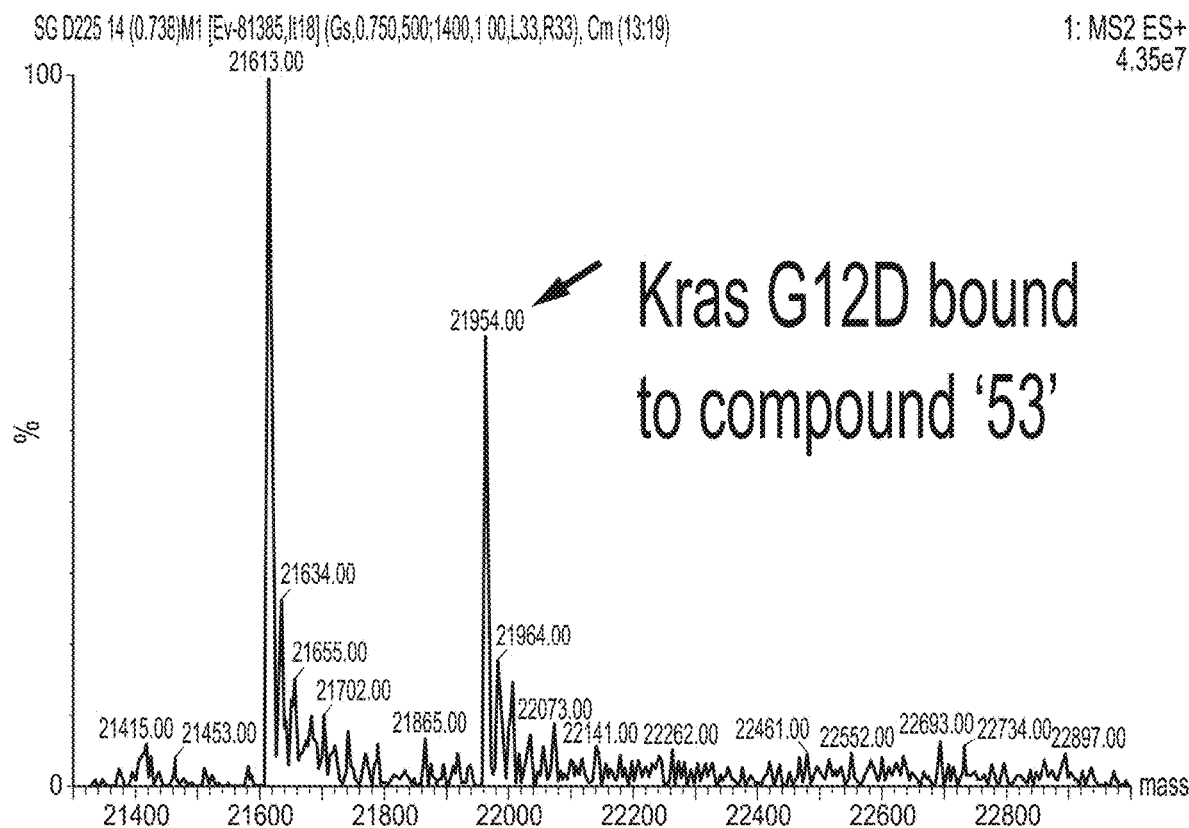
Figure 15C:
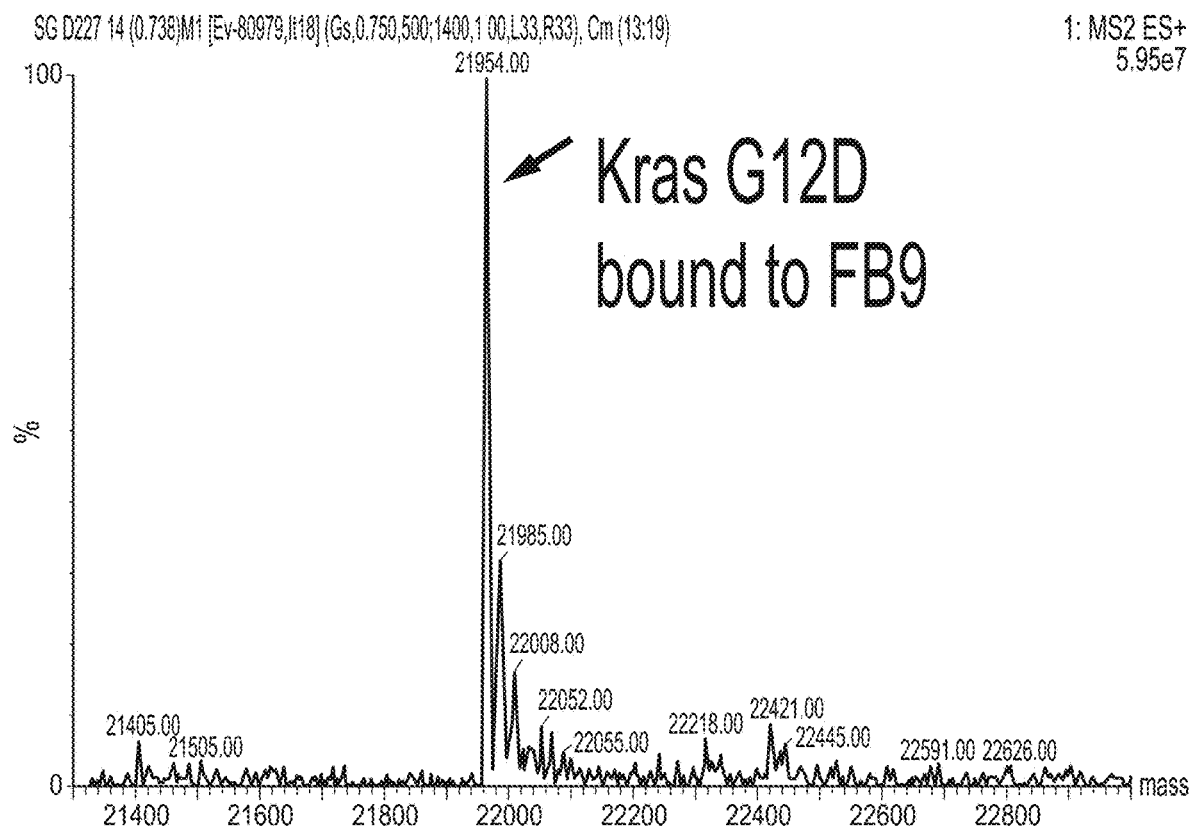
Figure 15D:
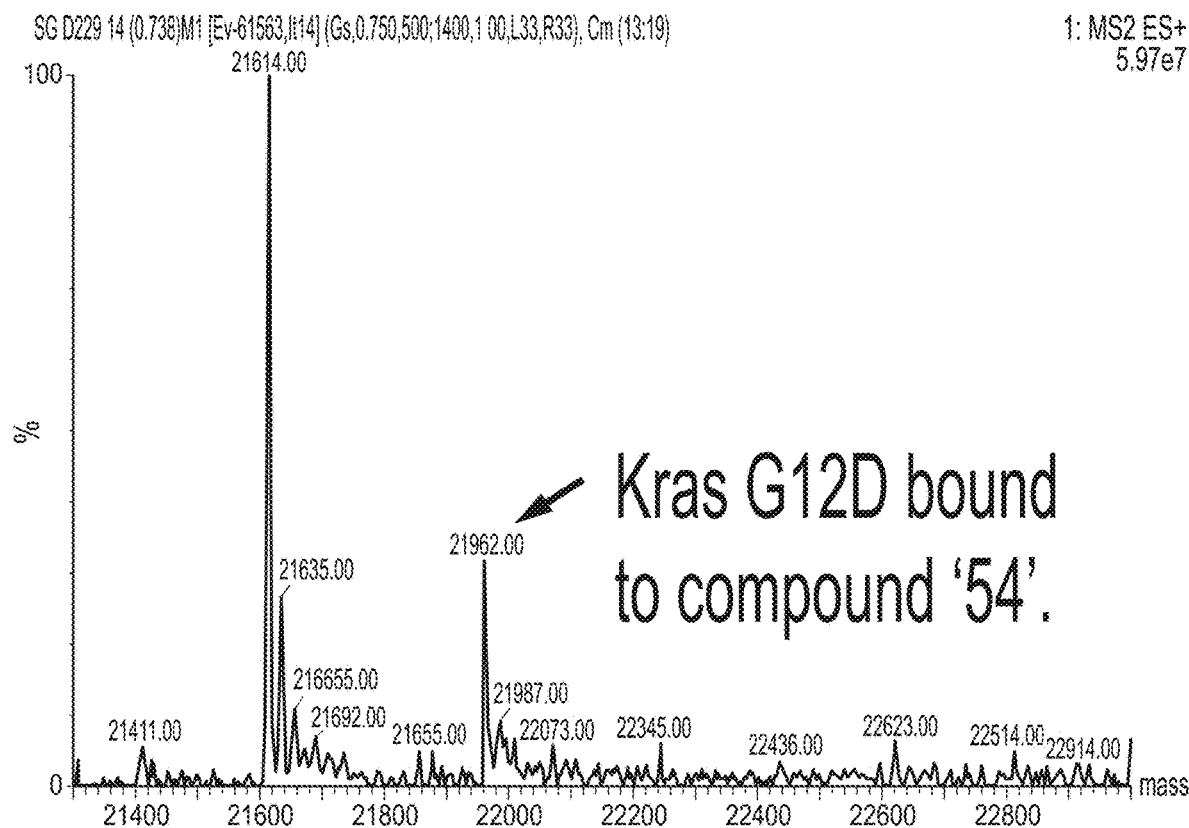
Figure 16A:
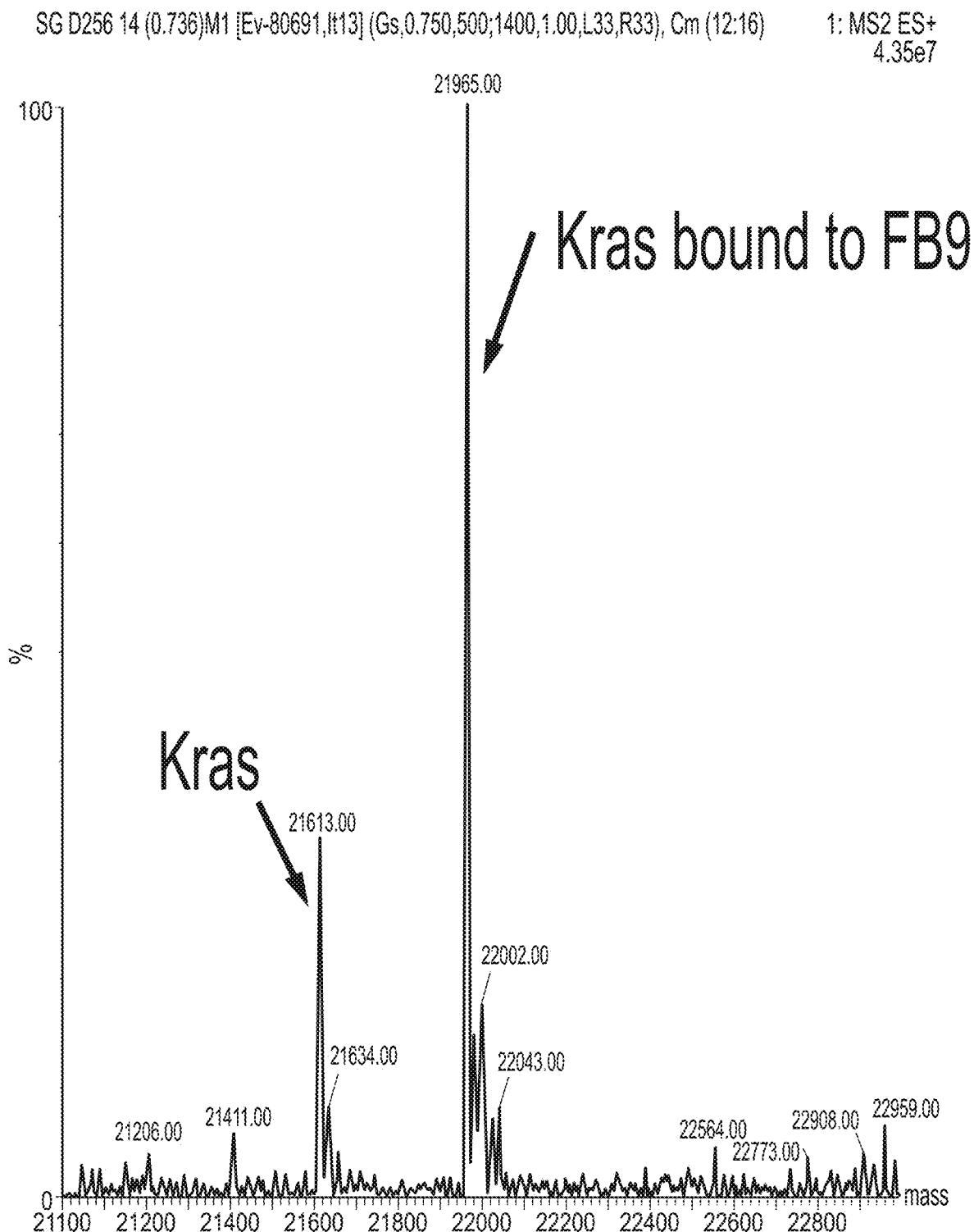
FIGS. 16A-16B. Binding Comparison of FB9 and FB9D to K-Ras (G12D), GTPyS/Mg; Original compound (FB9): 50 µM for 2.5 h at RT; The binding of FB9 with its enantiomer FB9D was also compared; FB9 bound about 25-30% better than FB9D, shows partial stereoselectivity.
Figure 16B:
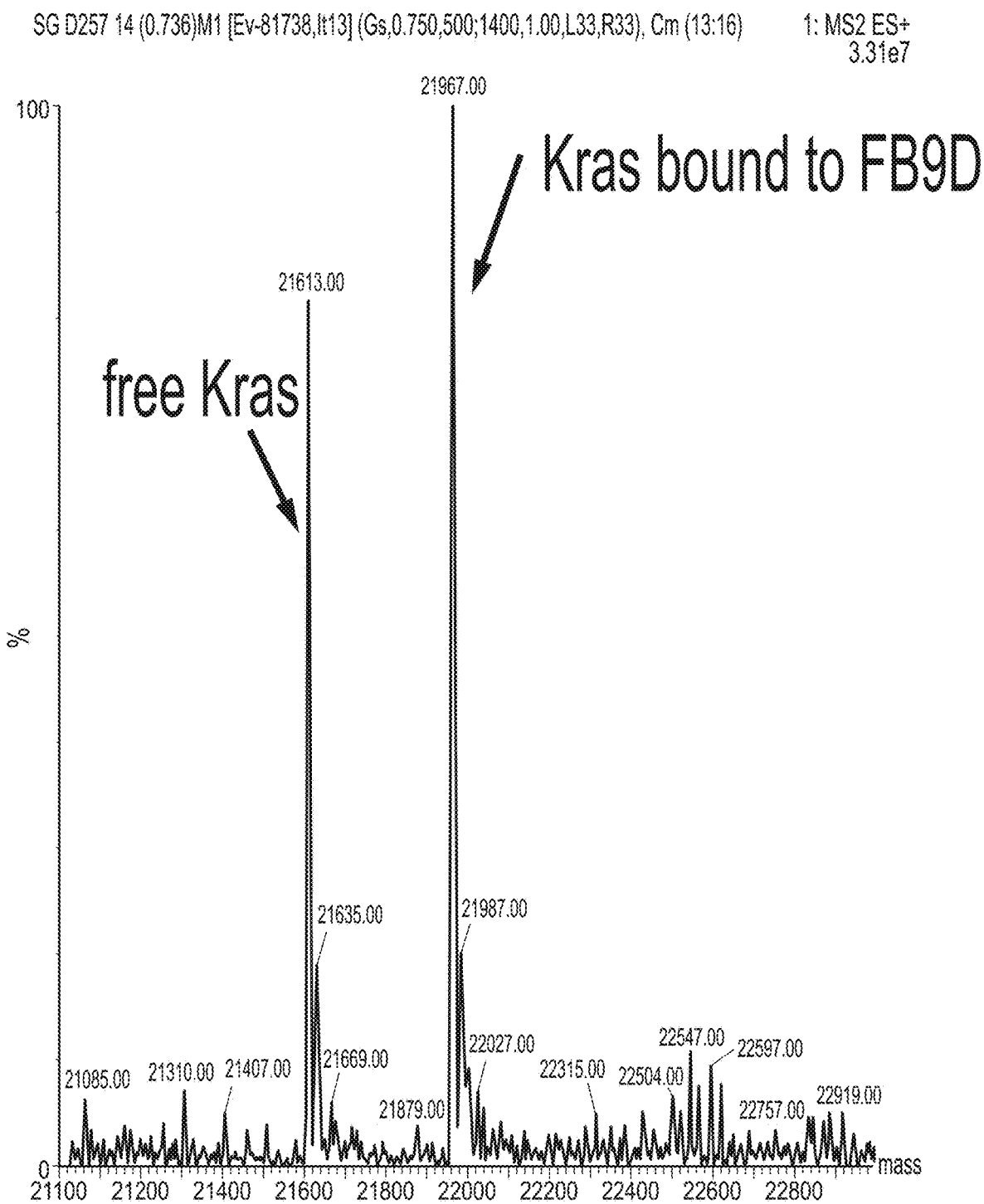
Figure 17A:
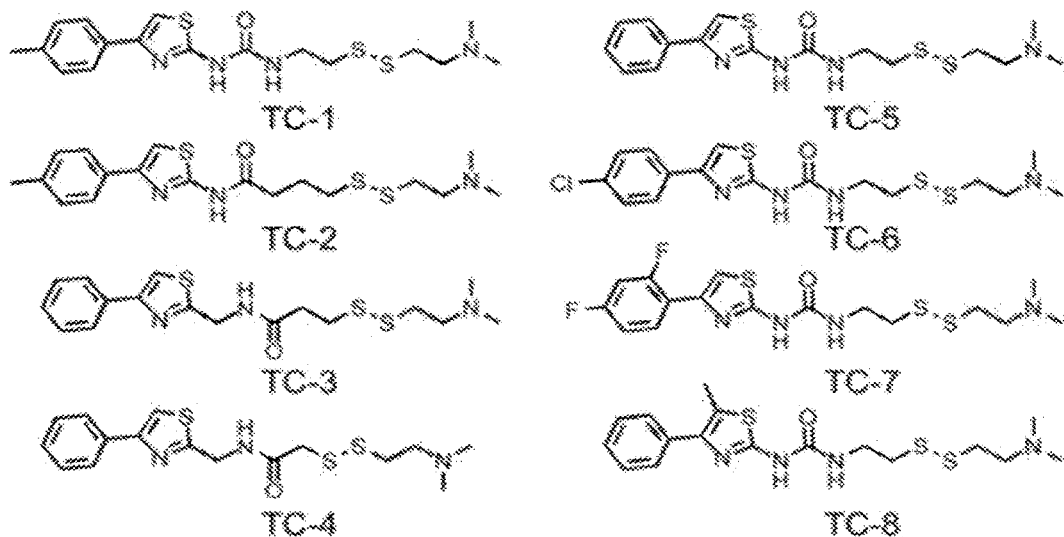
FIGS. 17A-17B. Modifications of 3G4 (phenyl thiazole) and relative binding as determined by mass spectrometry.
Figure 17B:
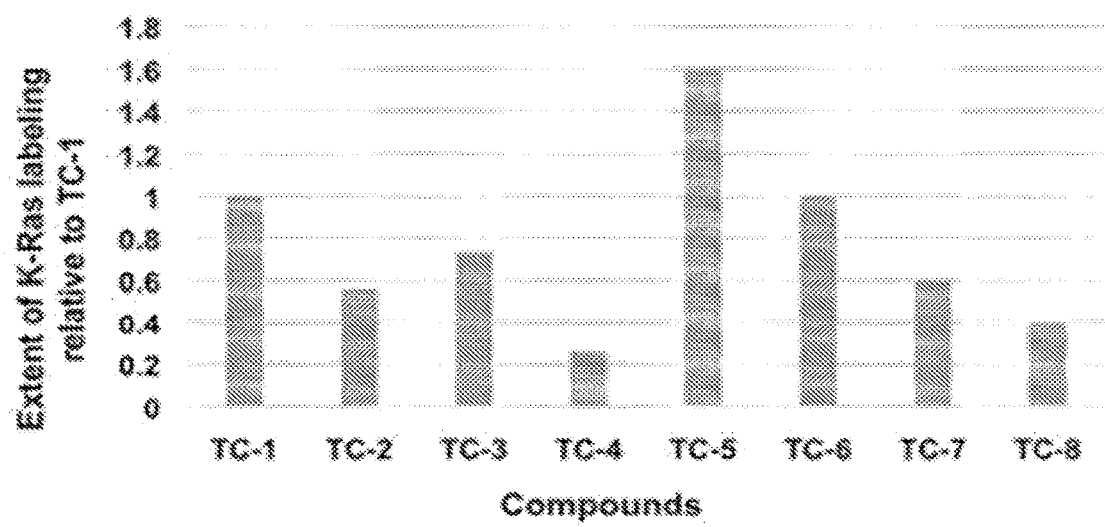
Figure 18A:
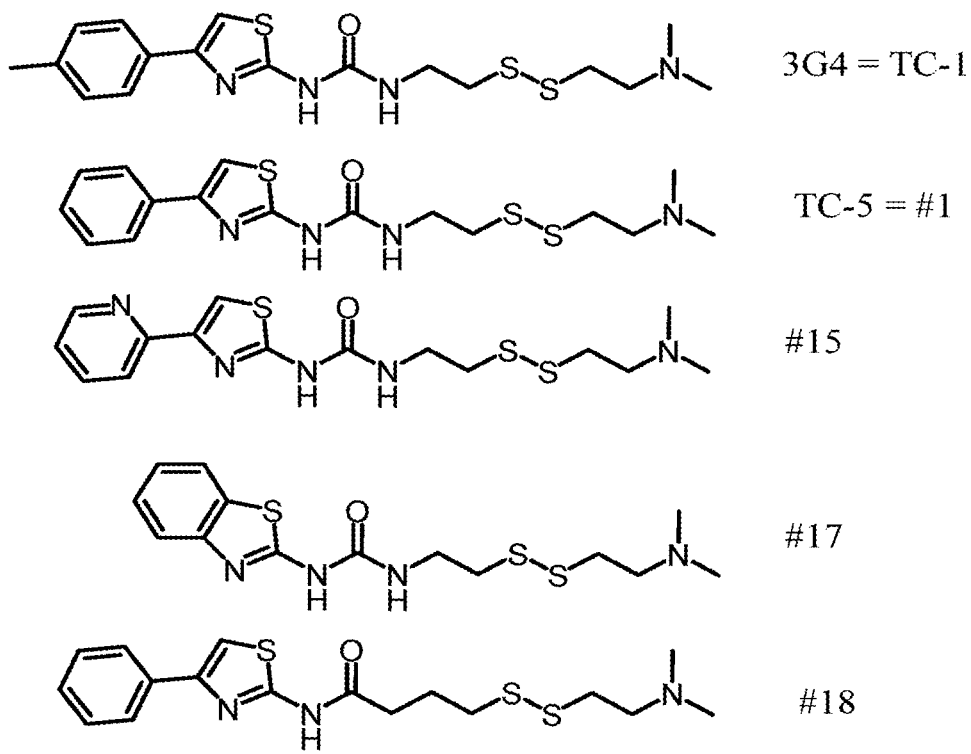
FIGS. 18A-18B. Additional Modifications of 3G4 and mass spectrometry binding assays.
Figure 18B:
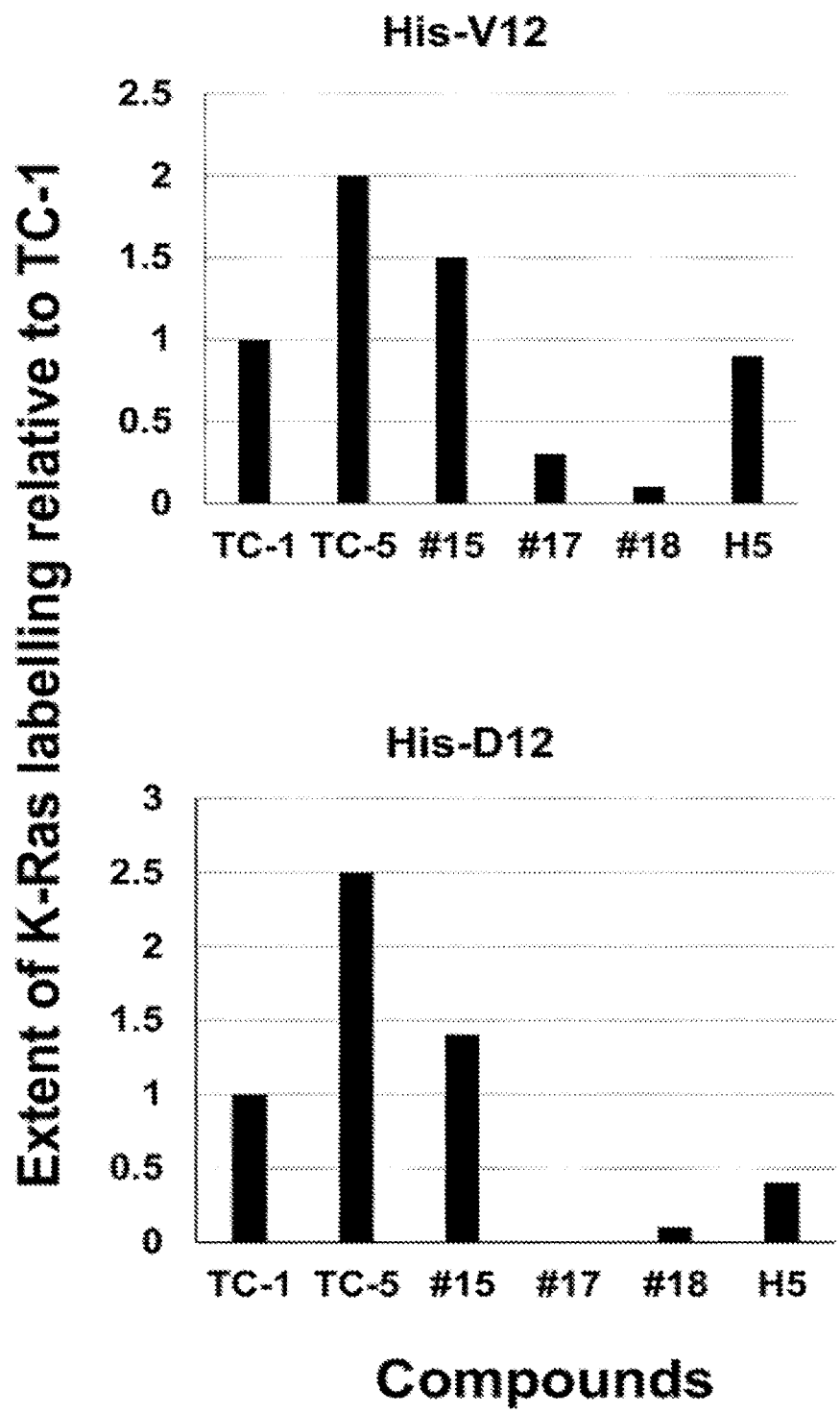
Figure 19A:
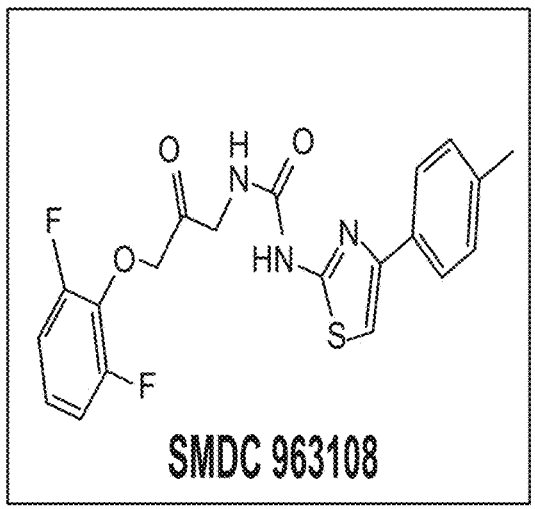
FIGS. 19A-19C. Different Electrophiles of Compound 3G4 (Tetrafluoro-phenoxy-3G4, Difluoro-phenoxy-3G4, Fimethyl-phenoxy-3G4); certain electrophilic modifications resulted in reduced binding in the present assay; 3G4 may find different pocket than 6B9 (e.g., makes different contacts or interactions).
Figure 19B:
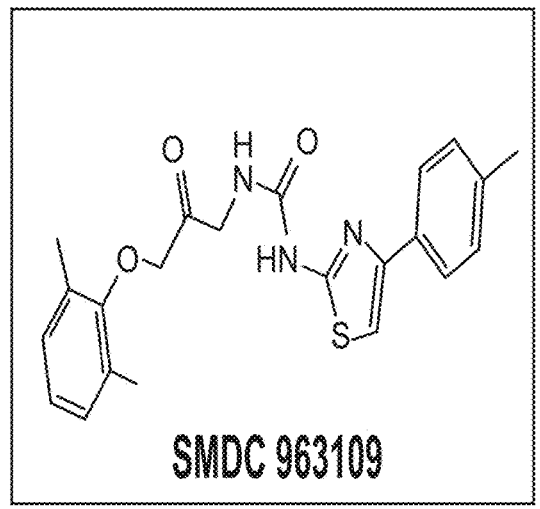
Figure 19C:
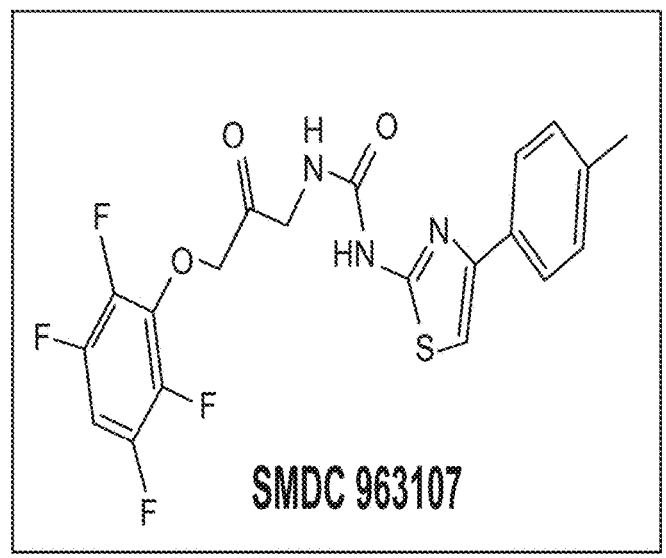
Figure 20A:
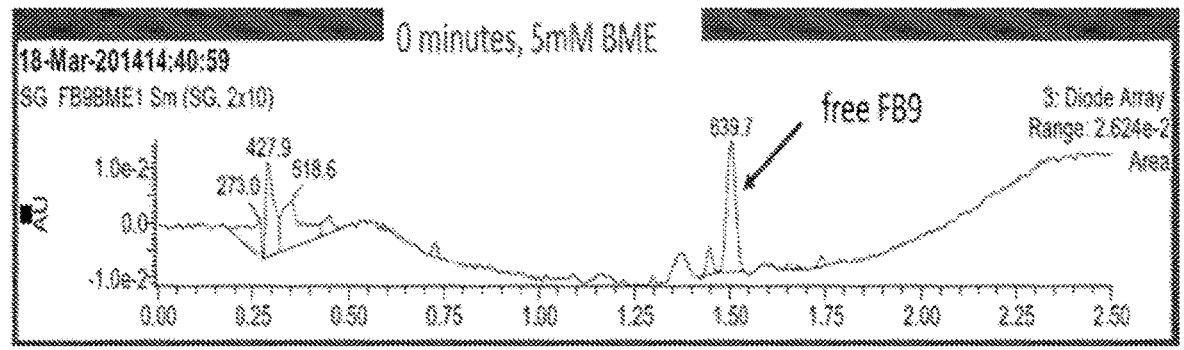
FIGS. 20A-20C. Reactivity of Tetrafluorophenoxy-6B9 (FB9) with BME; experiment was done with 1 mM FB9 and minus or plus 5 mM BME at 37° C. Time points were taken at 0, 18, and 55 minutes; graphs show the area under curve vs time; analysis of the reduction of the free compound peak shows about 25% product coming up after 55 minutes.
Figure 20B:
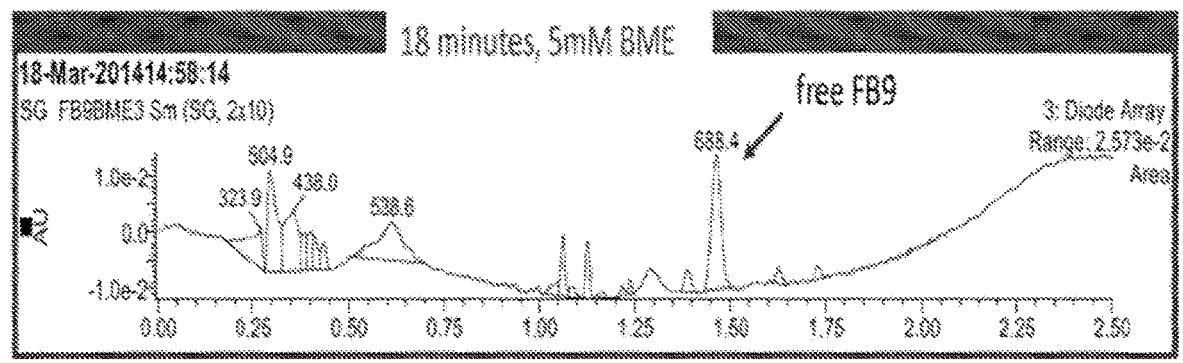
Figure 20C:
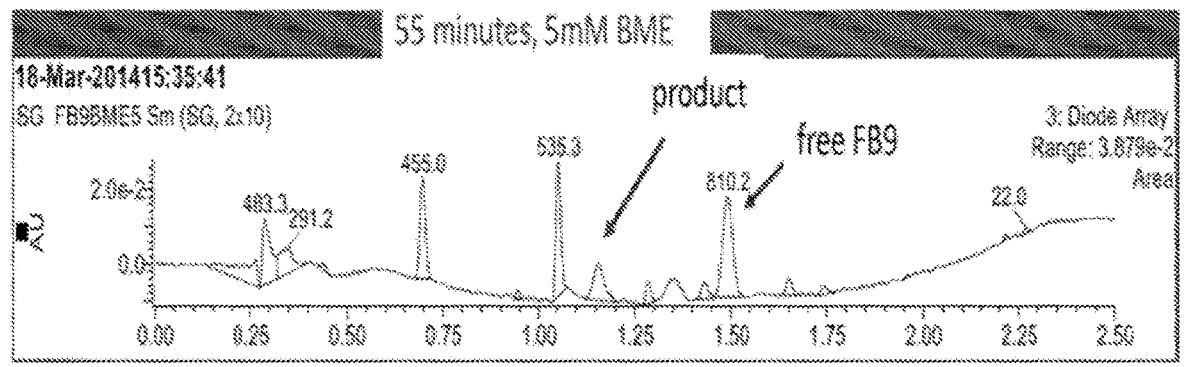
Figure 21A:
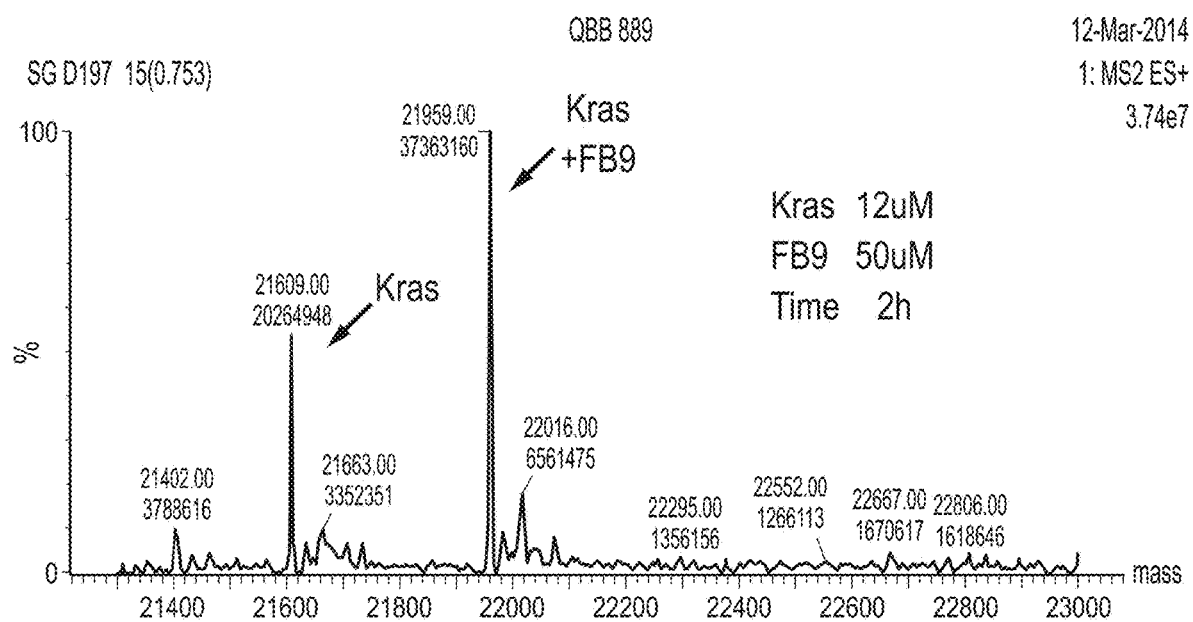
FIGS. 21A-21C. Interaction of FB9 with Kras in the absence or presence of BME; at RT for the indicated times; titrating in BME results in reactivity of the compound being reduced; BME itself did not react with the protein.
Figure 21B:
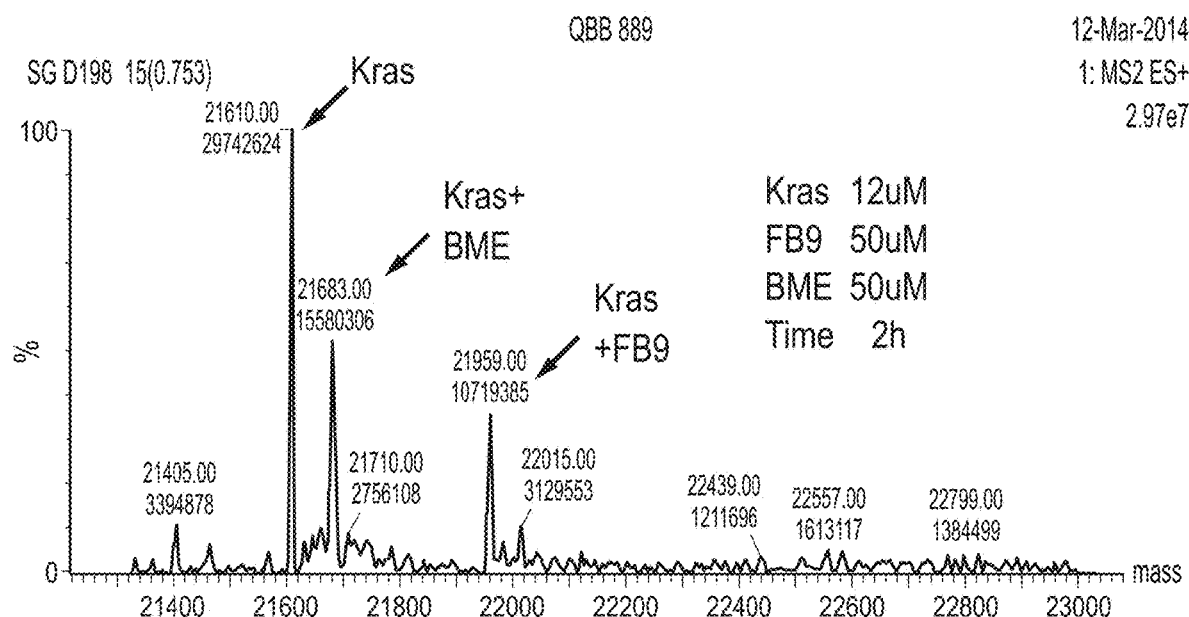
Figure 21C:
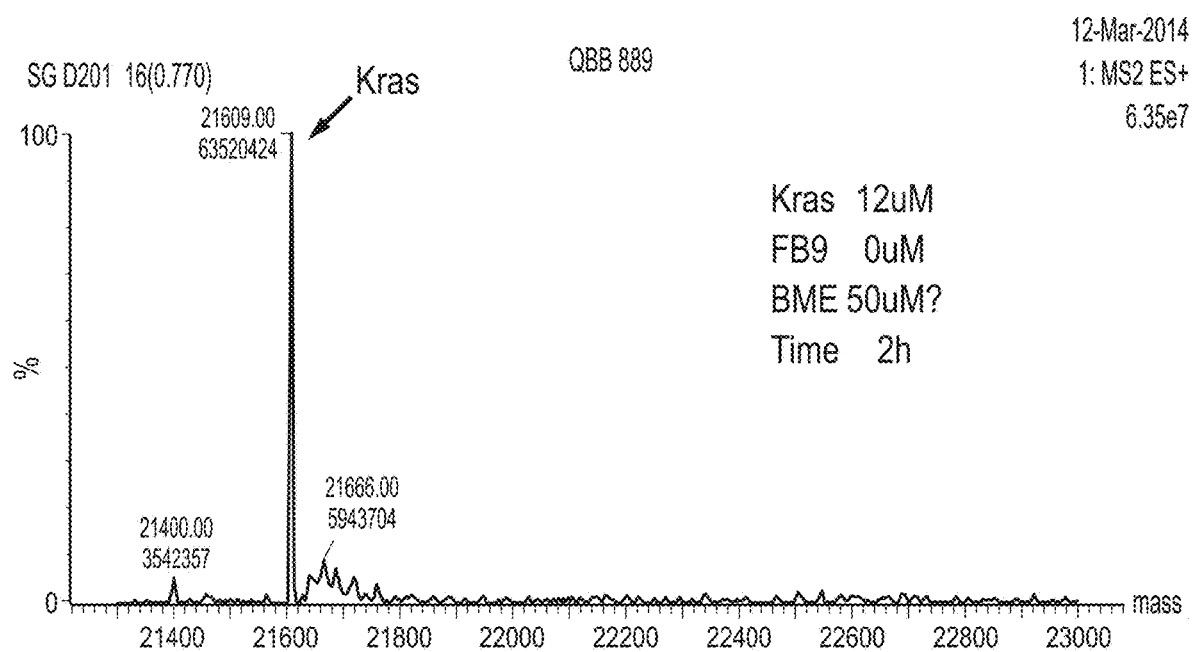
Figure 22:
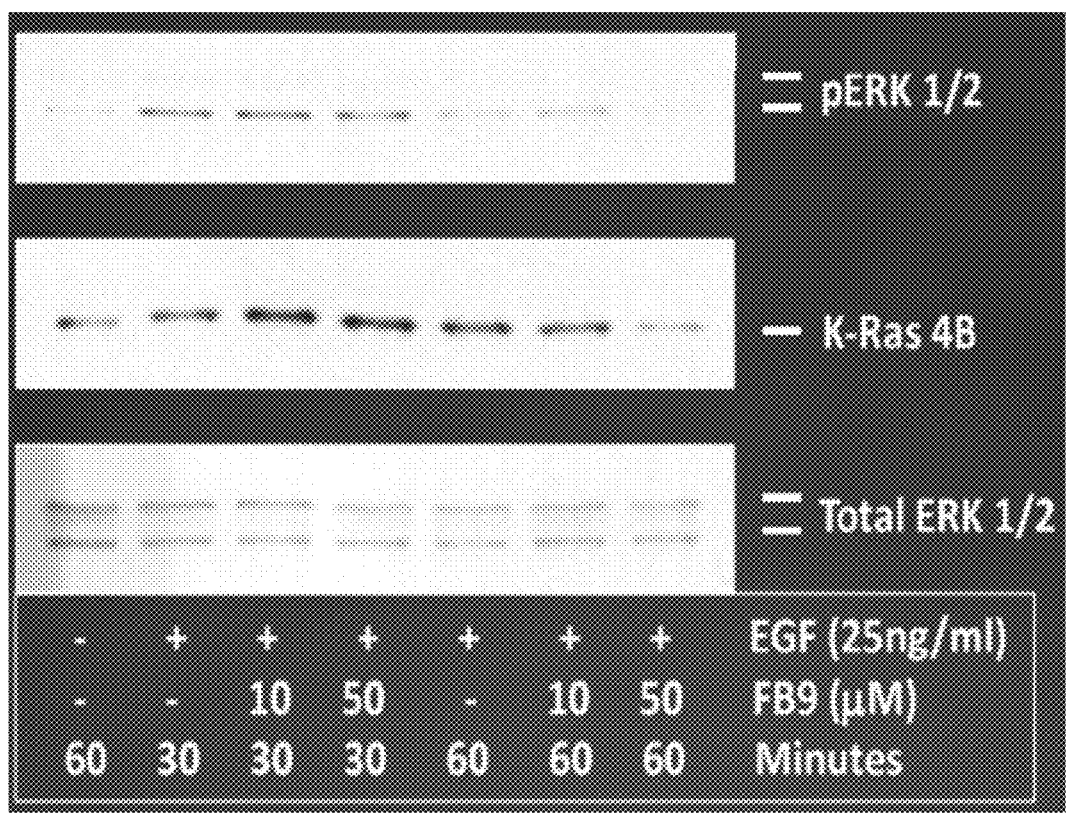
FIG. 22. Cell Based Assays with G12D expressing RAS-less MEFS; Ras-less cells exogenously expressing K-Ras G12D were stimulated with EGF for 30 and 60 minutes. Concomitantly FB9 was added at various concentrations. Similar experiments were done with pancreatic cell lines expressing various oncogenic mutations. Changes at K-Ras protein levels are visible. Growth curves were also performed.
Figure 23:
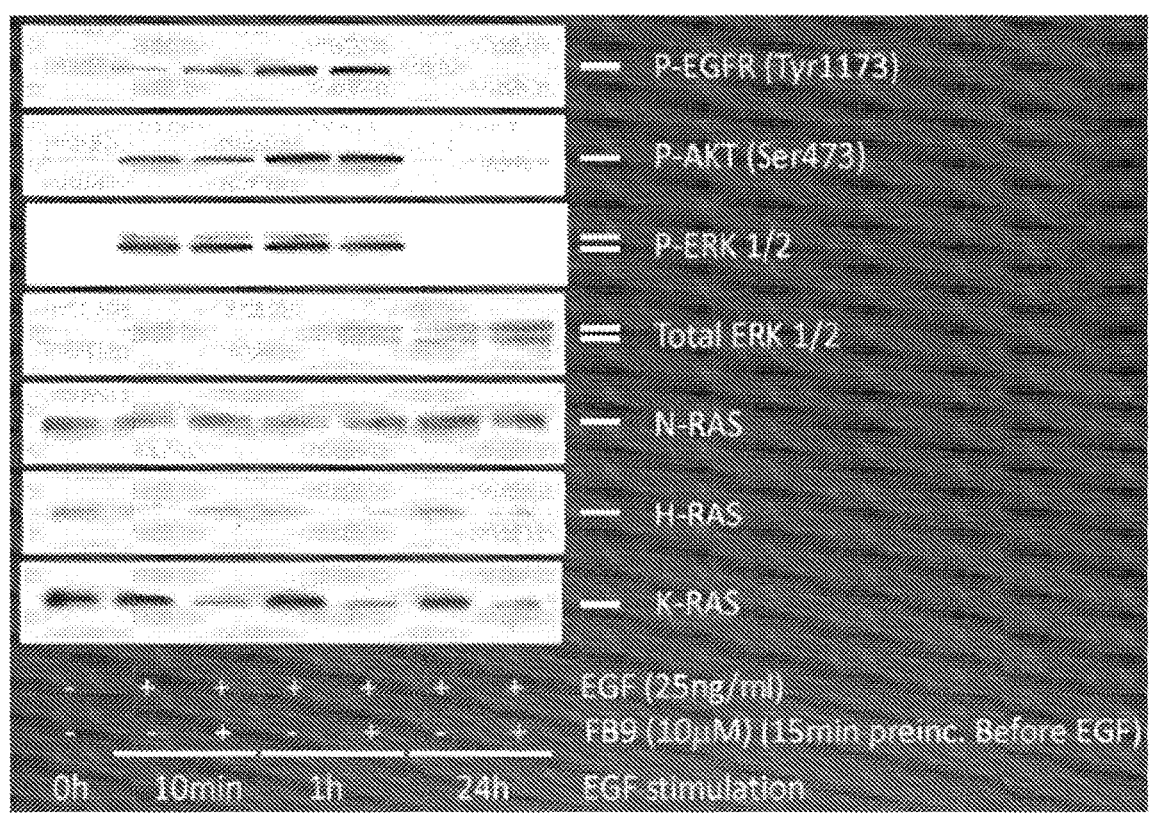
FIG. 23. Time course EGF stimulation in combination with FB9 treatment (L3.6pl G12D).
Figure 24:
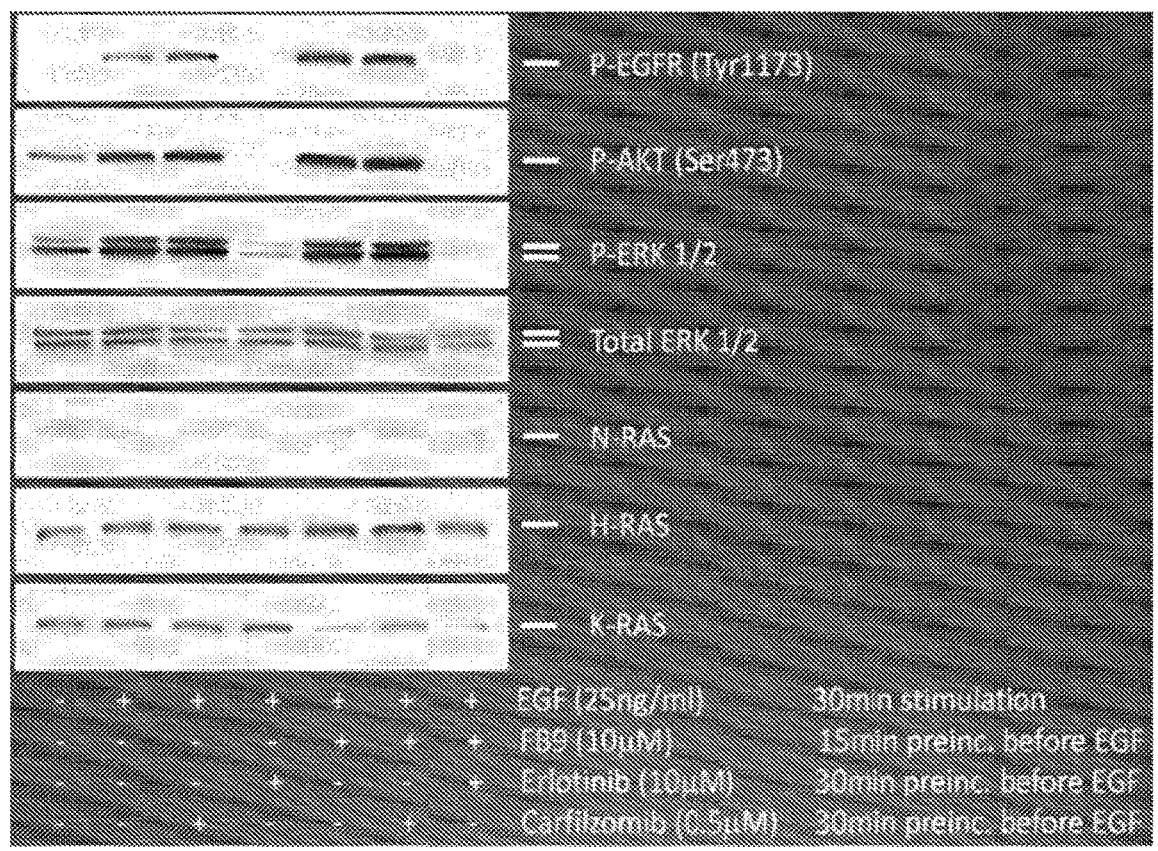
FIG. 24. Stimulation with EGF in combination with FB9, Erlotinib, Carfilzomib treatment (L3.6pl G12D).
Figure 25A:
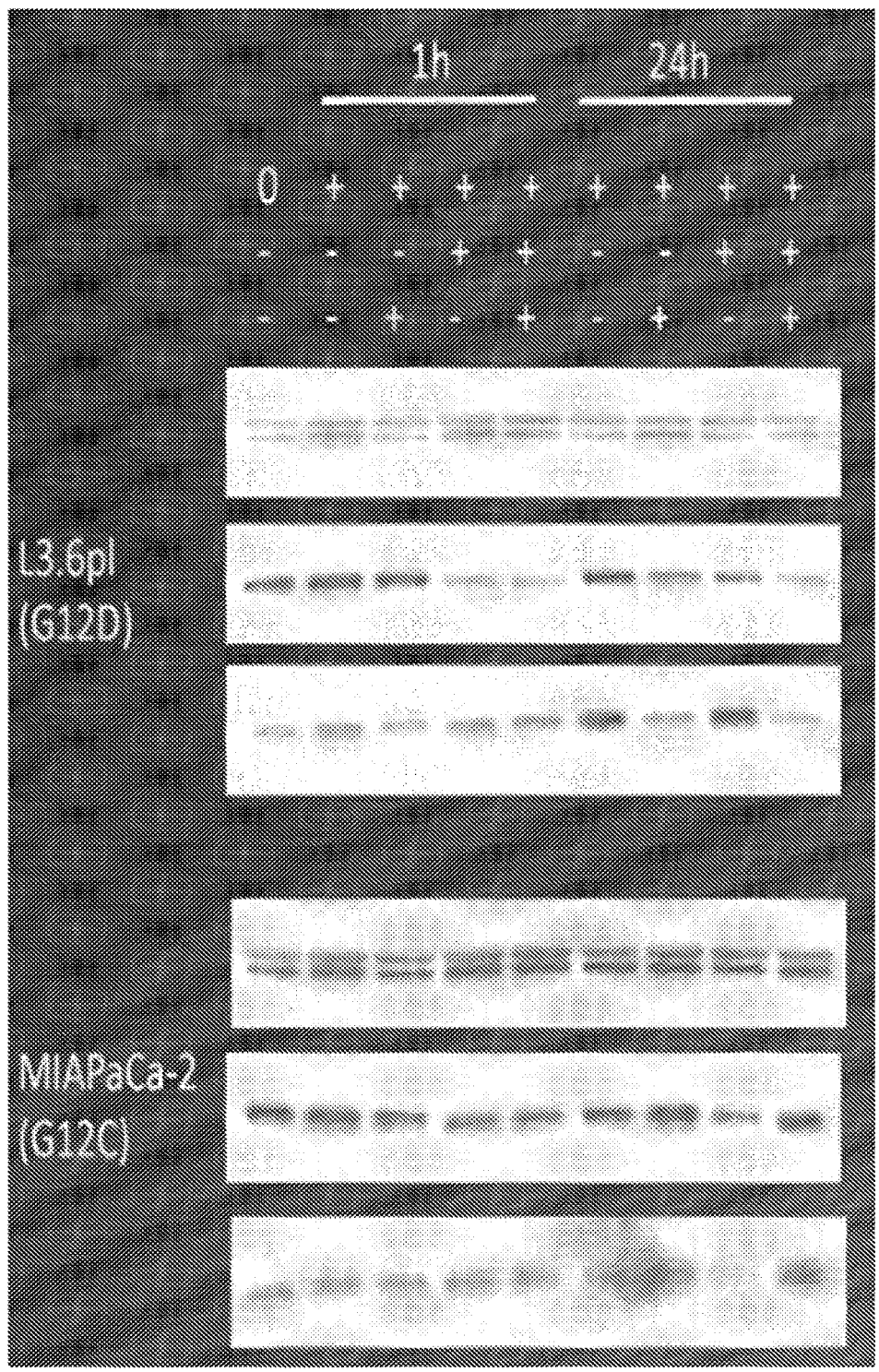
FIGS. 25A-25B. Time course EGF stimulation in combination with FB9 treatment (L3.6pl G12D).
Figure 25B:
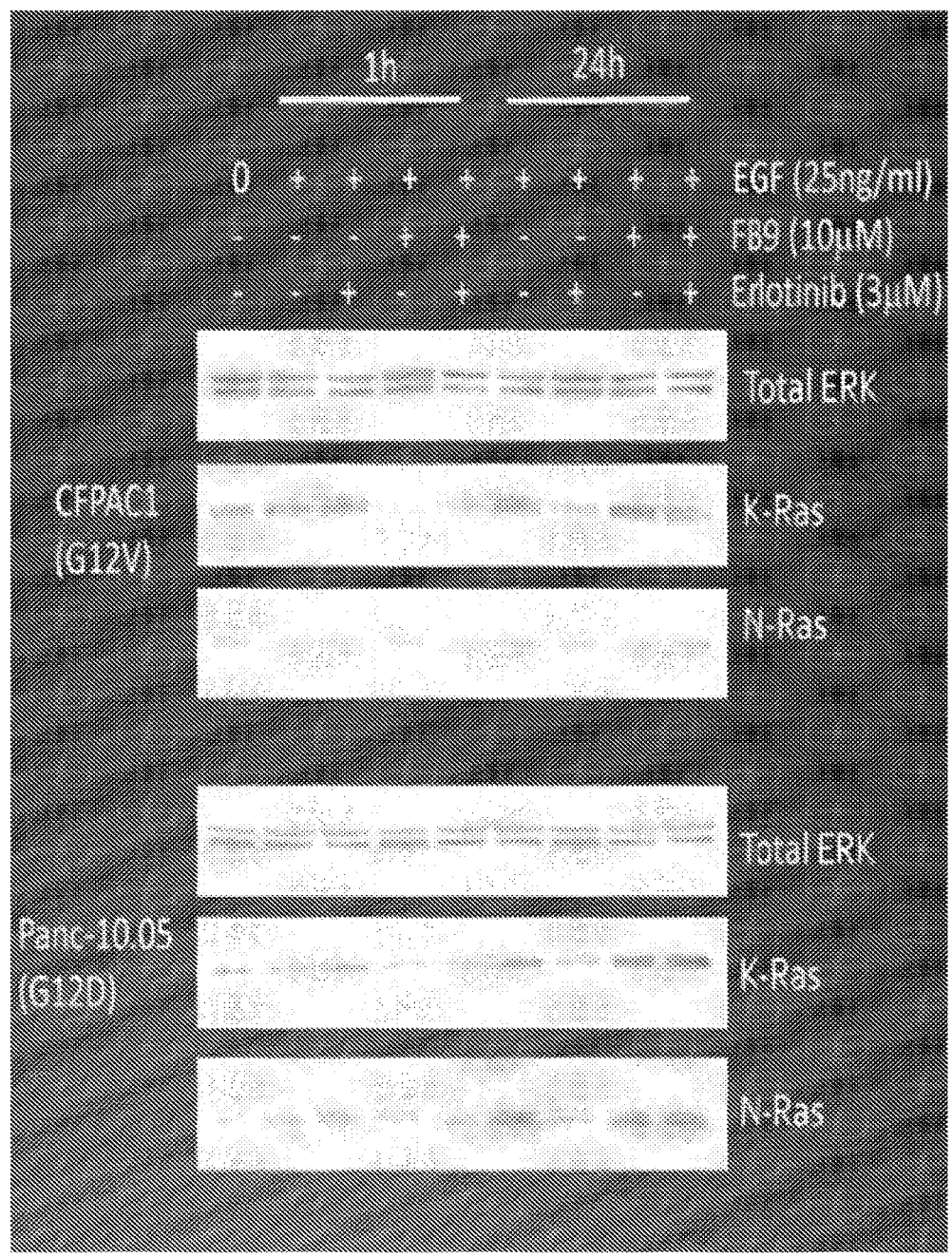
Figure 26:
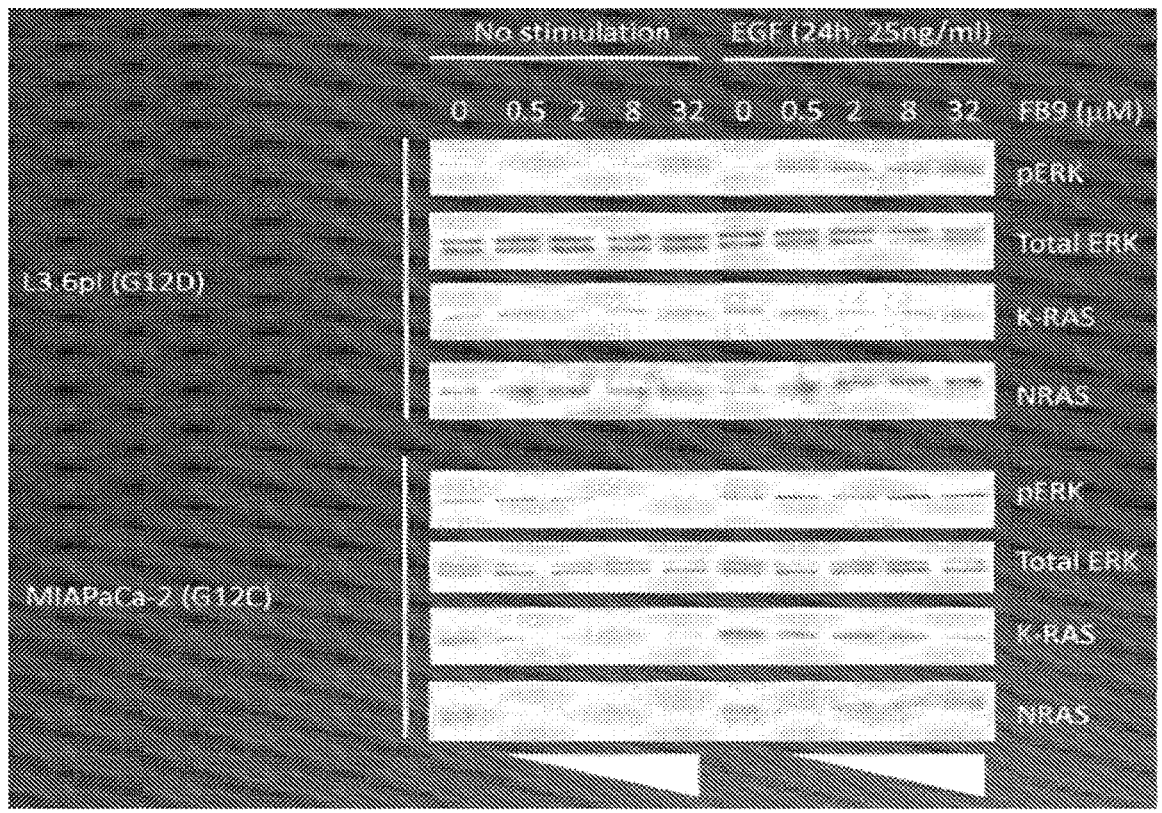
FIG. 26. Time course EGF stimulation in combination with FB9 treatment (L3.6pl G12D).
Figure 27:
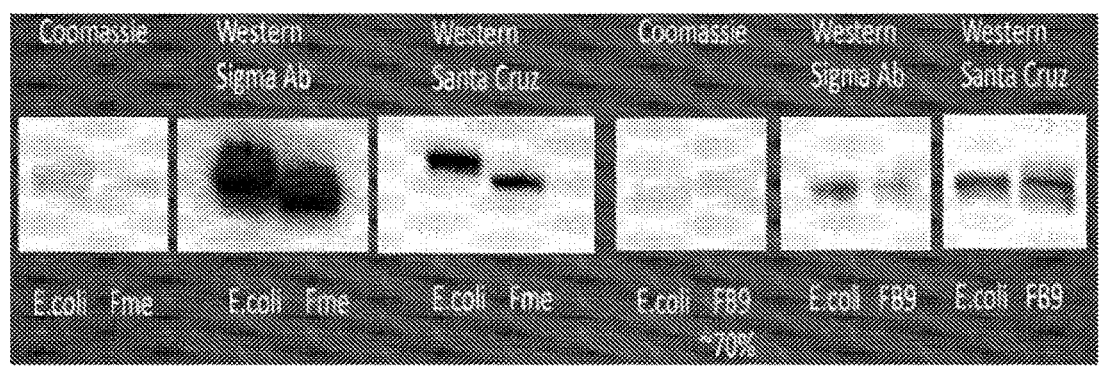
FIG. 27. Comparing Gel Mobility and Antibody Reactivity of Different Purified K-Ras 4B Forms. E. Coli: unprocessed K-ras 4B purified from E. coli. Fme: processed K-ras 4B purified from SF9 cells. FB9: unprocessed K-ras 4B labeled with FB9 to about 70%.
Figure 28:
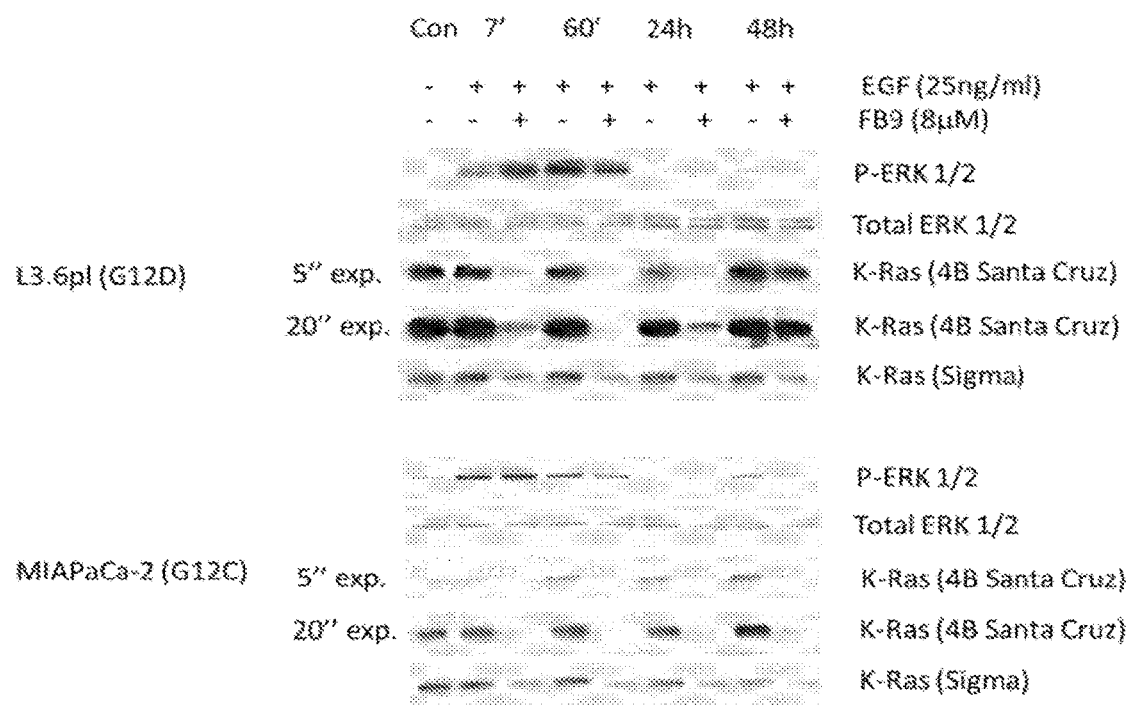
FIG. 28. Time Course: Short and Long.
Figure 29:
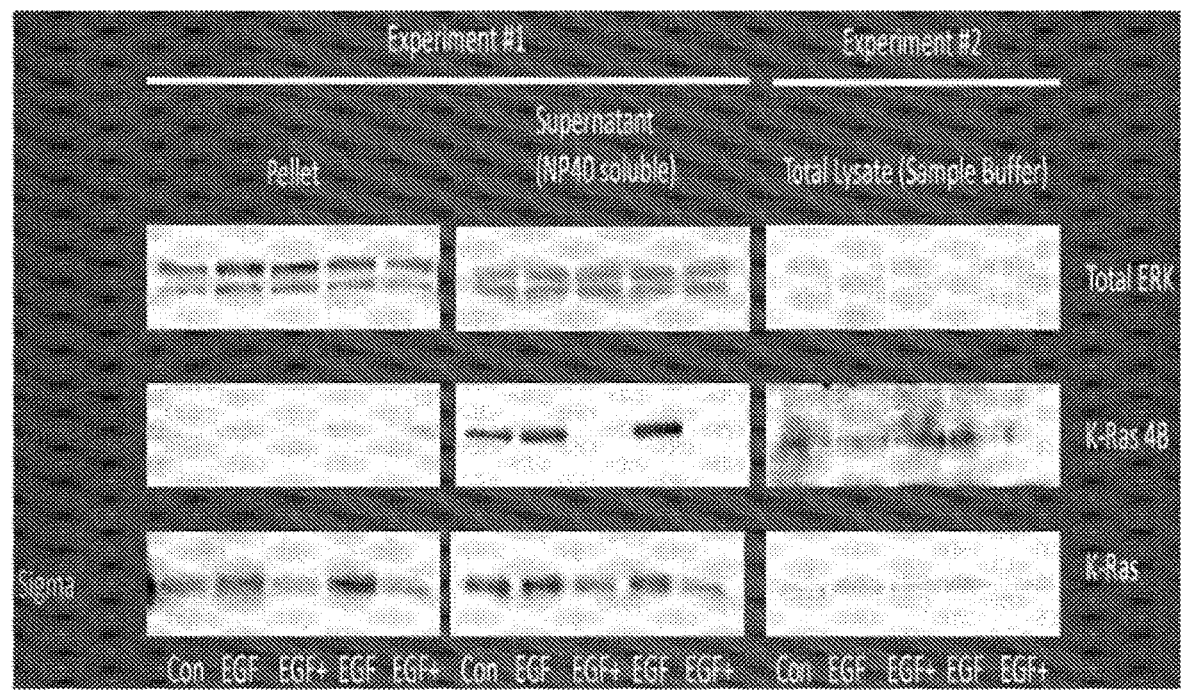
FIG. 29. Different Extraction Techniques and Antibody Comparison. Experiment #1 and #2 were performed at the same time, and in the same media solutions and cells (L3.6pl (G12D)); pellet fraction did not completely go into solution. The pellet fraction recognized by the Santa Cruz antibody shows two bands. The upper band is K-Ras.
Figure 30:
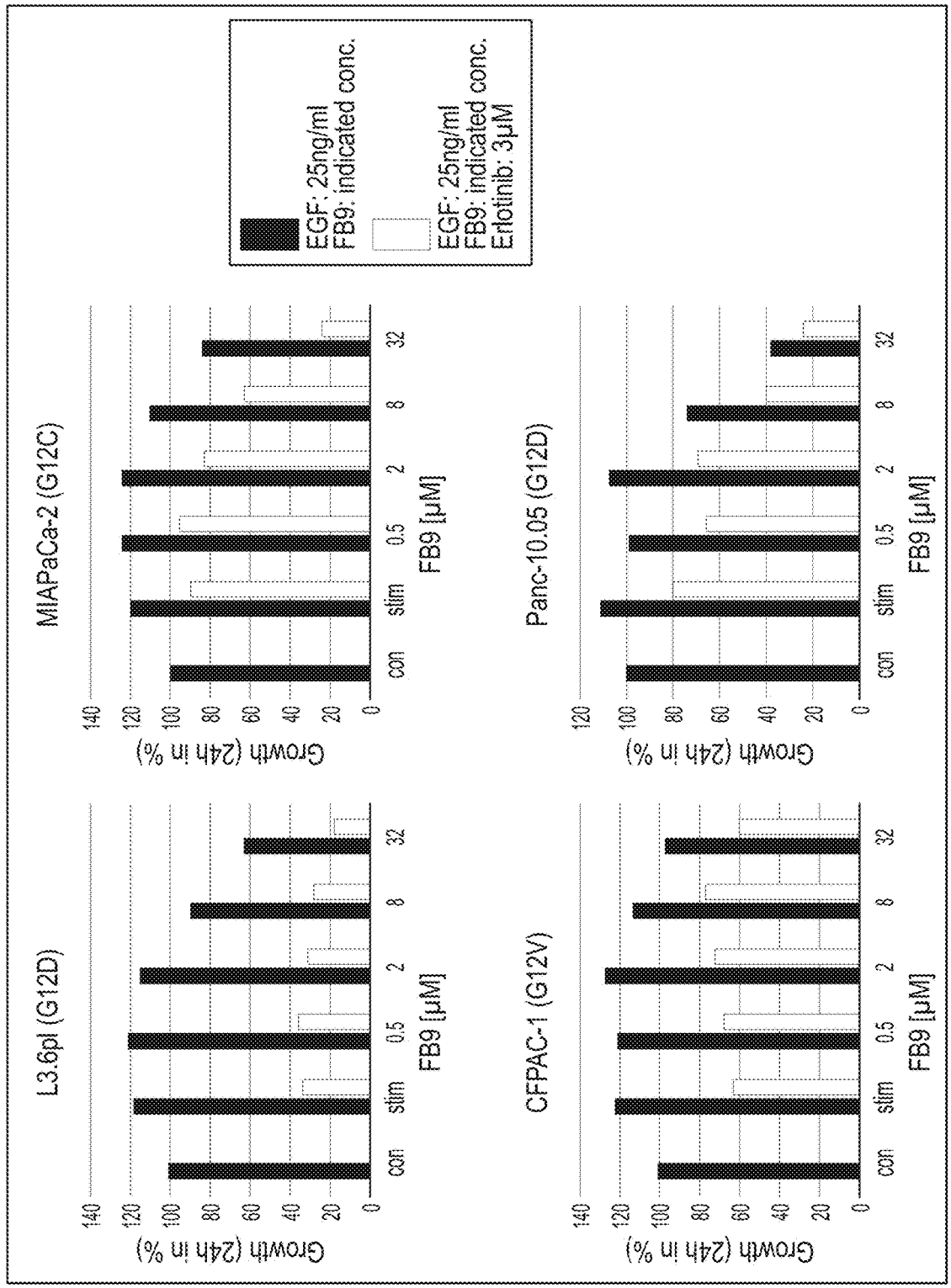
FIG. 30. Growth Curves with human pancreatic cancer cell lines over 24 hours:EGF plus FB9, or EGF plus FB9 plus Erlotinib.
Figure 31:
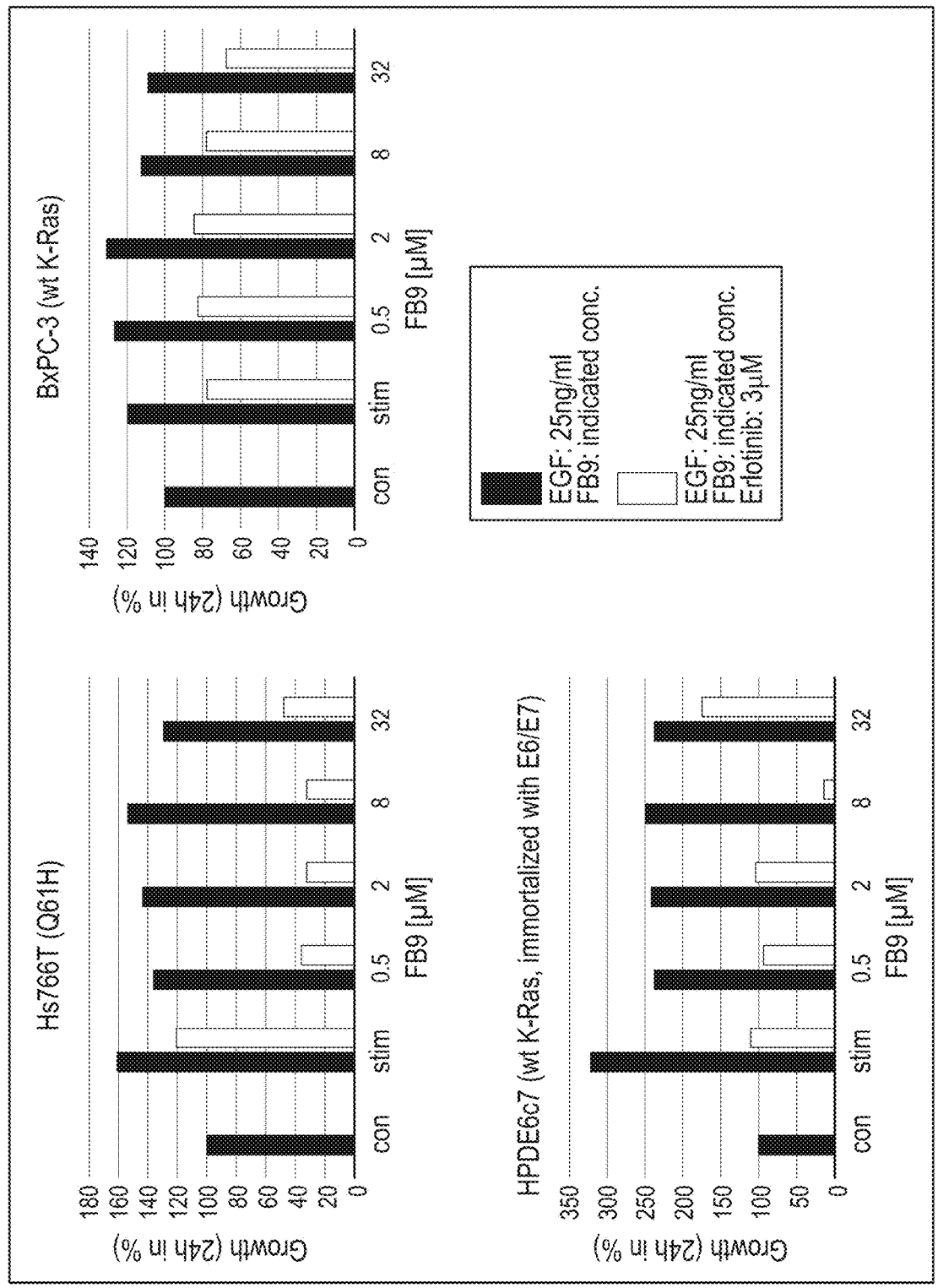
FIG. 31. Growth Curves with human pancreatic cancer cell lines over 24 hours:EGF plus FB9, or EGF plus FB9 plus Erlotinib.
Figure 33:
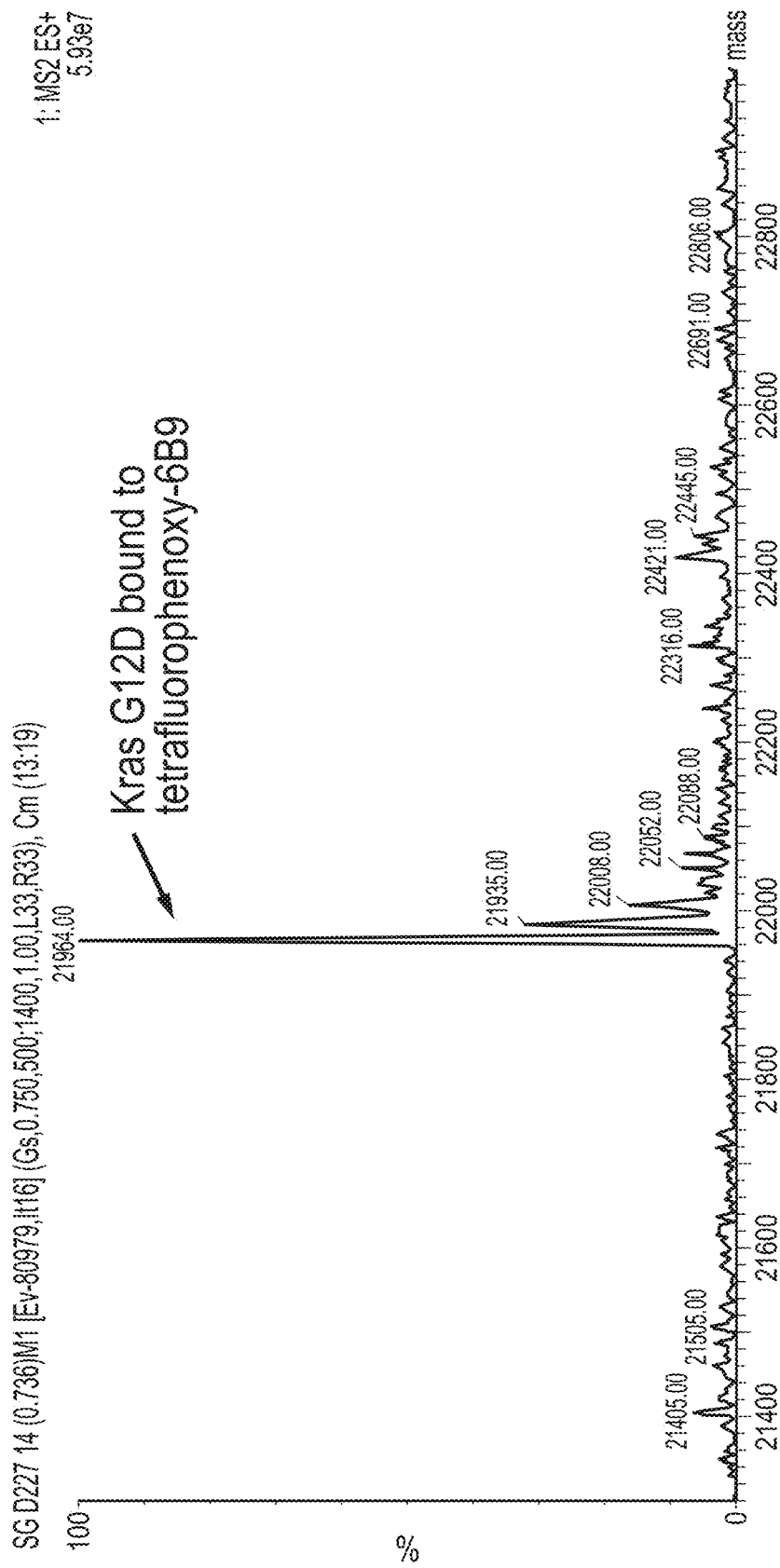
FIG. 33. Identification of Kras G12D bound to tetrafluorophenoxy-6B9.
Figure 34:
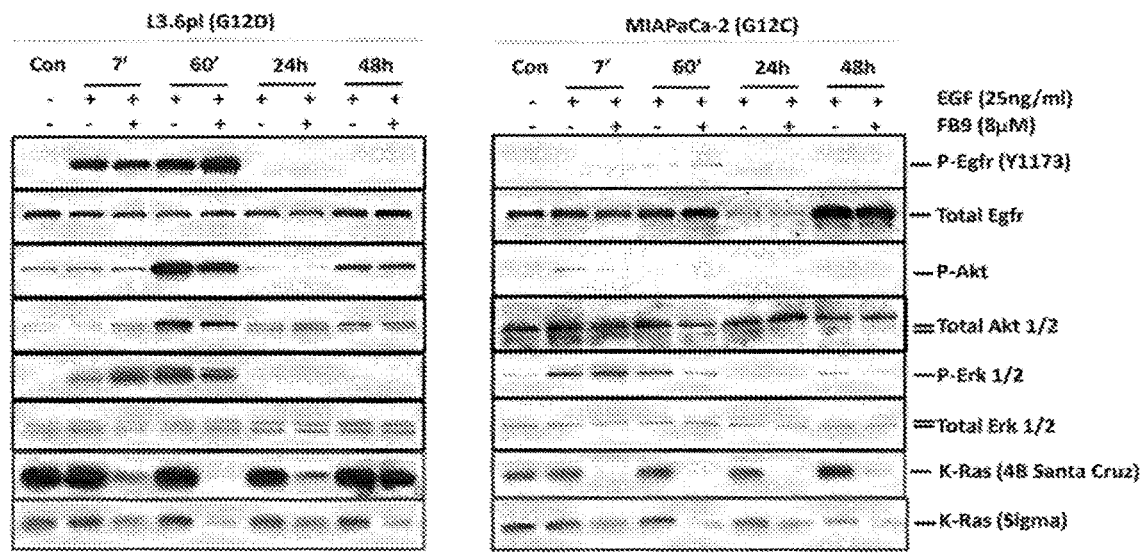
FIG. 34. Time Course: Short and Long.
Figure 35:
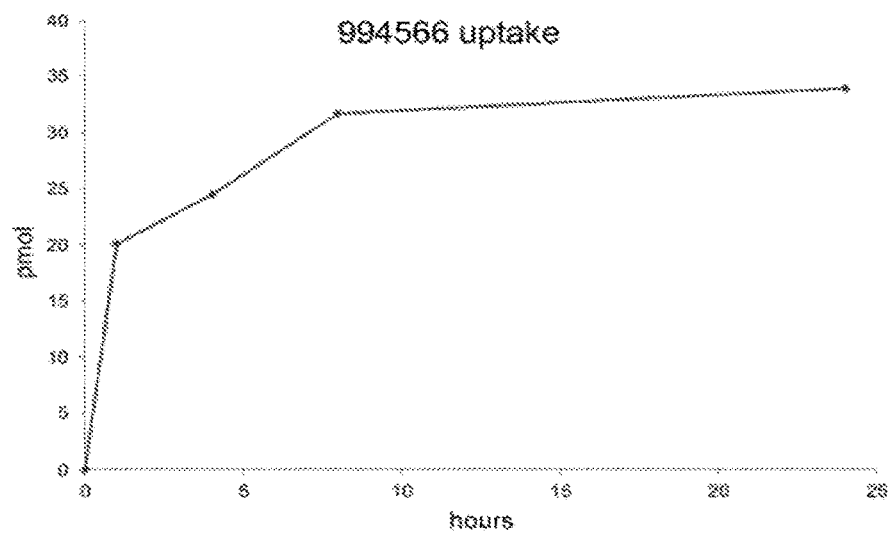
FIG. 35. Cell uptake experiment showing stability of 994566 in MiaPaCa-2 cells within 24-h. Cells plated 1×10$^6$ on Petri dishes were treated, with 994566 in complete medium). Cells were collected into 200 µl acetonitrile, lysate was centrifuged 15,000 g×15 min, filtered into HPLC vials and analyzed by LC/MS for the presence of the parent compound.
Figure 36:
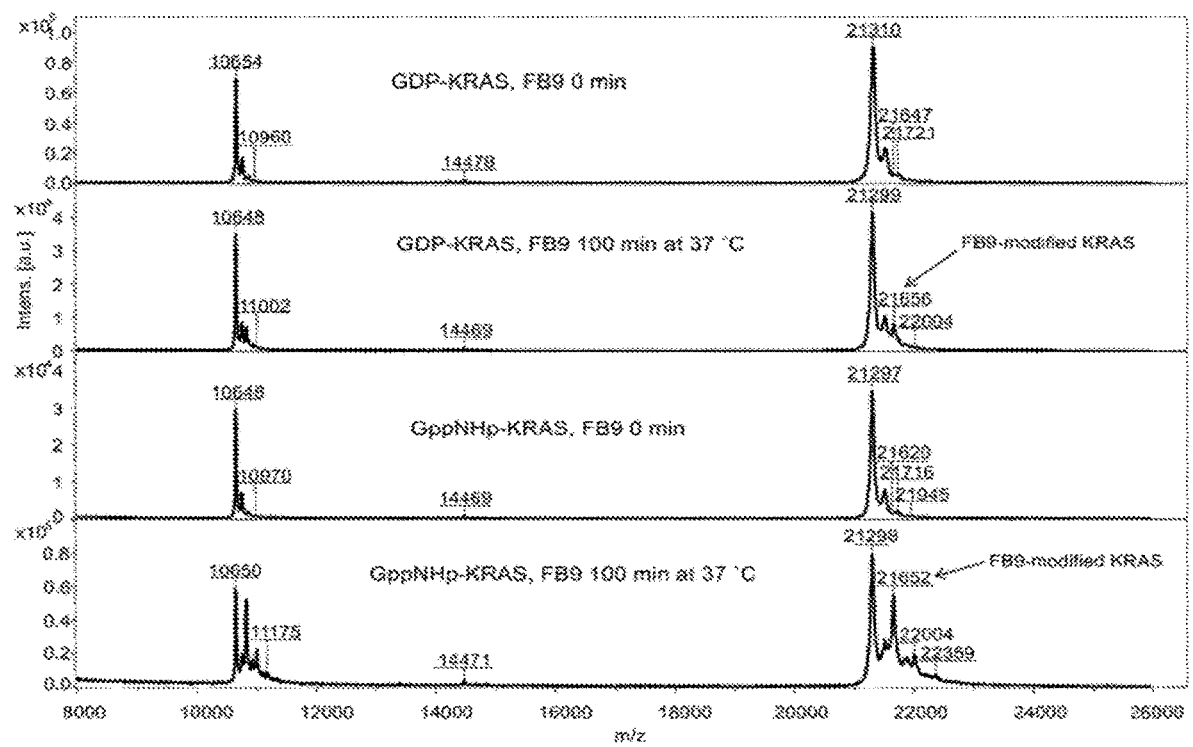
FIG. 36. Modification of fmeKRAS4b by FB9. Recombinant fmeKRAS4b was loaded with GDP or GppNHp (a nonhydrolyzable analogue of GTP), then reacted with FB9 at 37° C. for 100 min. The MALDI-TOF analysis revealed that covalent modification of the protein by FB9 (350 Da mass addition) was more pronounced when GTP analogue was present.
Figure 37:
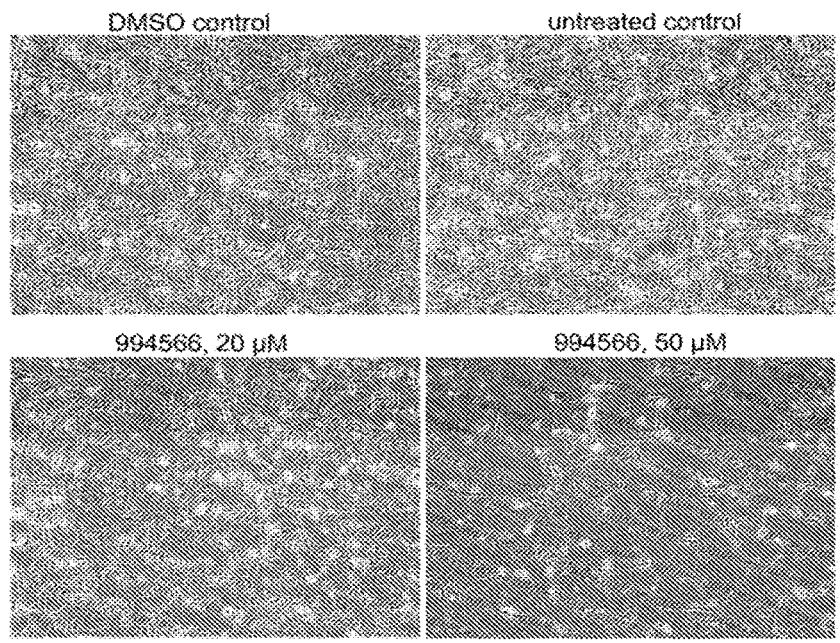
FIG. 37. Vinyl sulfonamide analogue of FB9, compound 994566, inhibited proliferation of mouse embryonic fibroblasts (MEF) expressing Kras4B G12D. Cells were serum-starved overnight, followed by treatment with 994566 and EGF (30 ng/ml). Medium was changed to complete (10% FBS) after 8 h, then compound was added again. Images were taken after 72 h in culture.
Figure 38A:
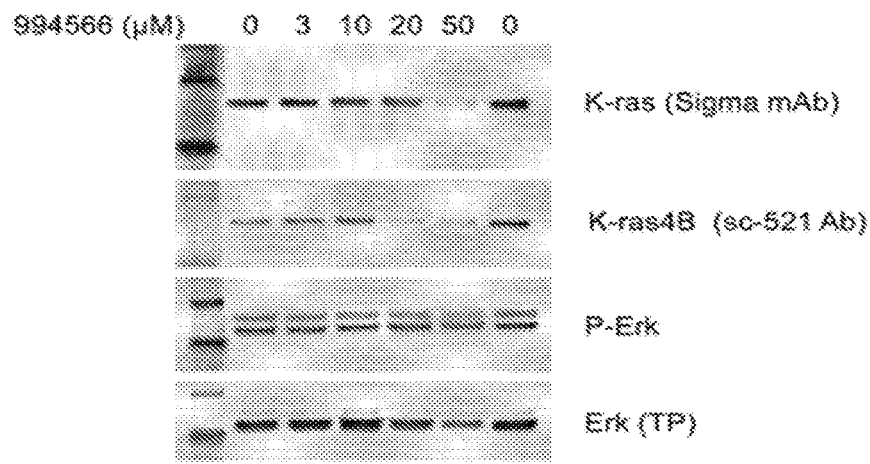
FIGS. 38A-38B.
Figure 38B:
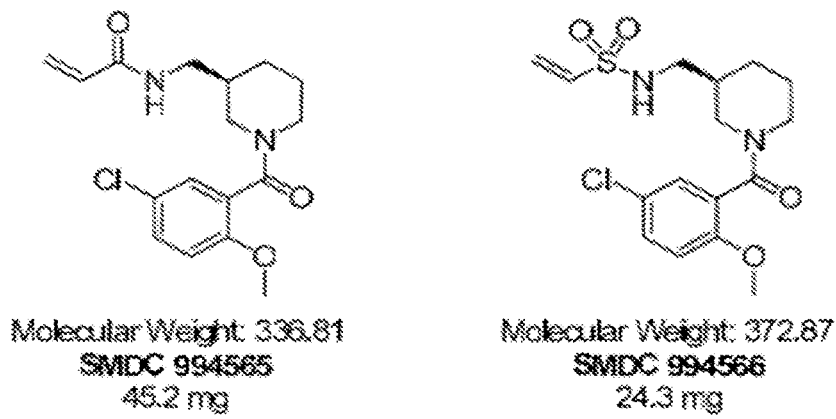
Figure 39:
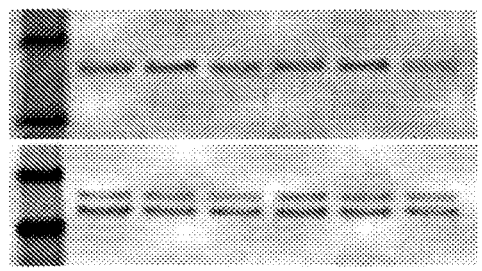
FIG. 39. Vinyl sulfonamide analogue of FB9, compound 994566, decreased Kras protein expression in mouse embryonic fibroblasts (MEF) expressing Kras4B G12D after 24-h treatment. Cells were serum-starved overnight, followed by treatment with 994566 or 994565, followed immediately by EGF (30 ng/ml). Cells harvested after 24 h were processed for Western blot analysis.
Figure 40:
FIG. 40. Conformations of the protein showing H95 is on the surface and exposed as drug-accessible.
Figure 41:
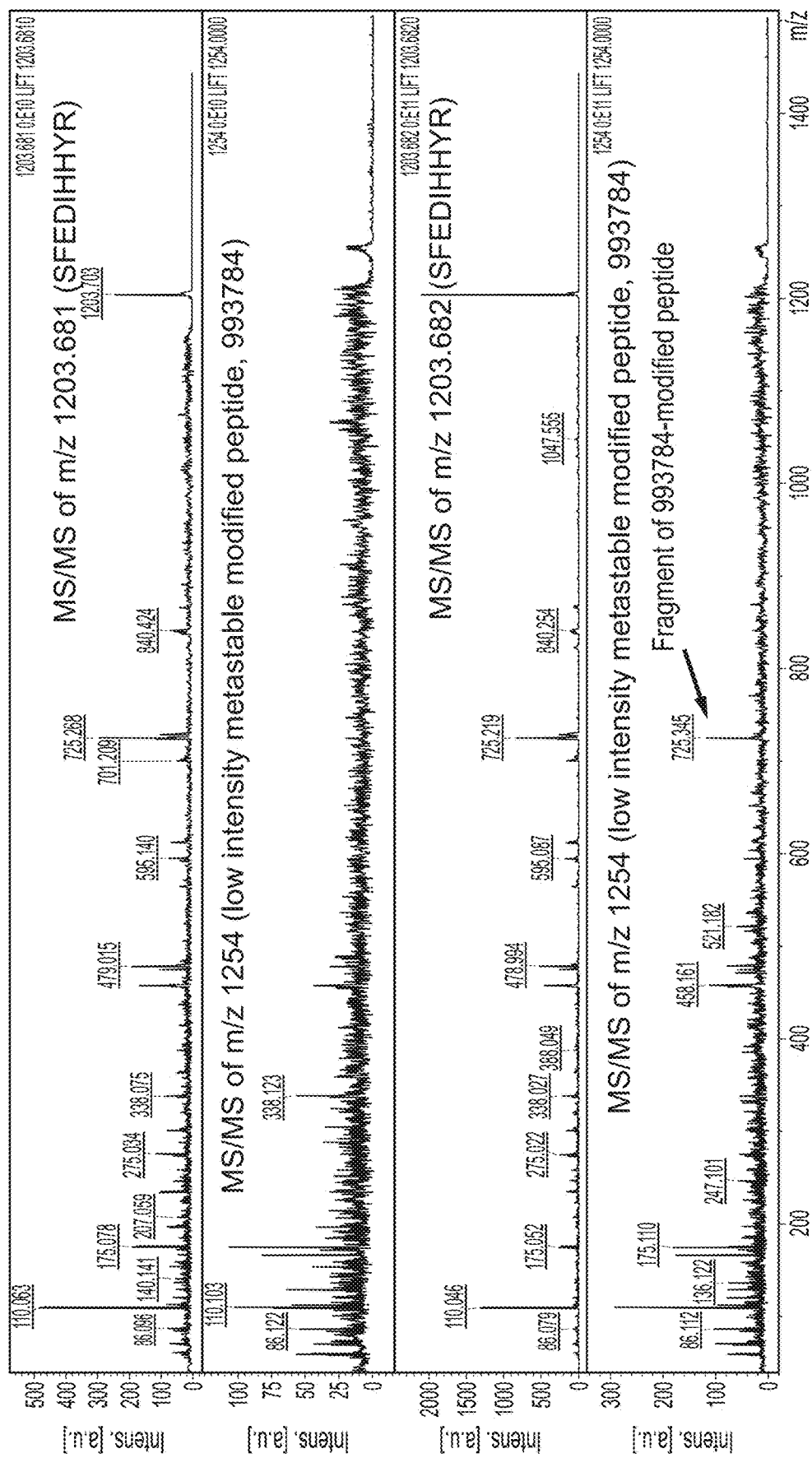
FIG. 41. Control sample. Mouse lung epithelial cell line stably transduced with HA-tagged Kras4B G12V was used in this experiment. HA-Kras4BG12V expression was induced with doxycycline for 48 h, then cells were treated with a close analogue of FB9, compound 993784. Kras protein was purified from cell lysate using immunoaffinity chromatography followed by SDS-PAGE, then subjected to MALDI-TOF analysis of modification to Kras protein. Characteristic fragment of peptide modified with the compound was detected (bottom panel). This fragment was not present in the control sample (second panel from the top).

Mouse lung type II epithelial cell line E10 was transduced with HA-tagged KRas4B G12V, in a tetracycline-inducible retroviral expression vector. Individual clones were developed. Expression of the KRas4B transgene was induced with 500 ng/ml doxycycline for 48 h, then cells were treated with 20 μM of a close analogue of FB9, compound SMDC 993784, for 30 min. Cells homogenates were cleared by centrifugation, and Kras4B G12V was purified from lysates using HA-agarose immunoaffinity chromatography, resolved by SDS-PAGE, and subjected to MALDI-TOF analysis of modification to Kras4B G12V. FIG. 42 shows the fragment of Kras4b peptide containing H95 modified with the compound. This fragment is not present in the control sample (FIG. 41), obtained from cells that were not subjected to the drug treatment.

Example 2. Synthetic Schemes

Scheme 1. Synthesis of covalent analogues of 6B9.

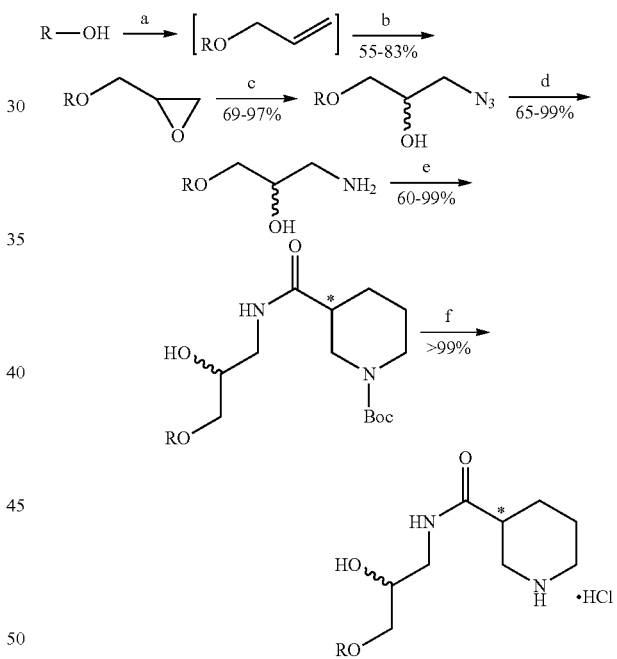

Conditions: (a) allyl bromide, K₂CO₃, DMF, RT, 24 h; (b) mCPBA, DCM, RT, 24 h; (c) NaN₃, NH₄Cl, MeOH/H₂O (8:1), RT, 72 h; (d) 10% Pd/C, H₂, MeOH, RT, 18 h; (e) (R)-Boc-nipecotic acid or (S)-Boc-nipecotic acid, HATU, DIPEA, DMF, RT, 18 h; (f) 4N dioxane HCl, RT, 3 h.

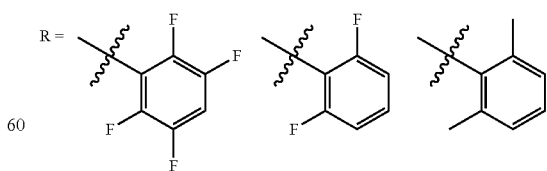

A six-step enantioselective synthesis of the electrophilic precursor group was devised starting from the appropriate phenol (scheme 1). Each step occurred in an acceptable yield and was well suited for performance on a gram scale.

Scheme 2. Synthesis of covalent analogues of 6B9 (continued)

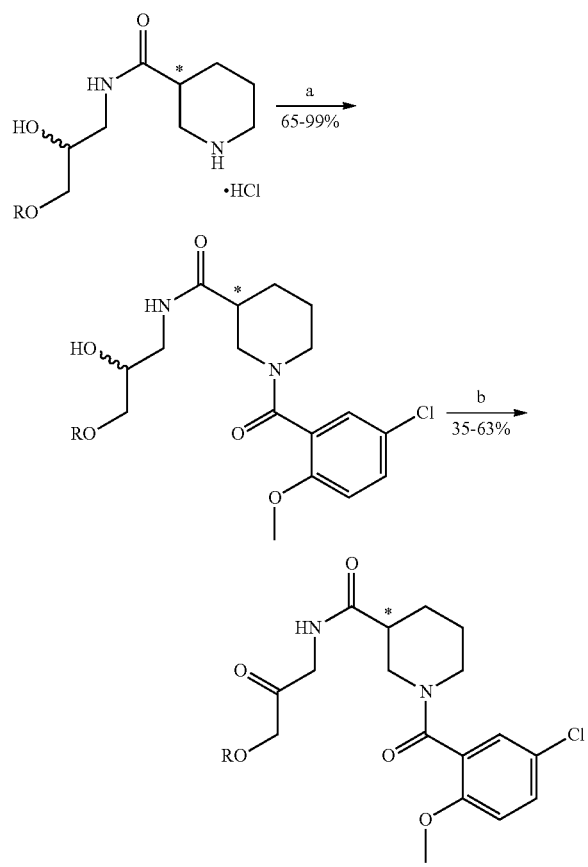

Conditions: (a) HATU, DIPEA, DMF, RT, 18 h; (b) Dess-Martin periodinane, DCM, 0° C.-RT, 72 h.

The electrophilic precursor group was attached to the acid fragment in good yield using peptide coupling conditions (scheme 2a). In the final step of the reaction scheme the alcohol functionality was oxidized to the ketone using Dess-Martin periodinane, which formed the reactive covalent species. By varying the acid fragment in this synthetic route (scheme 2a) it was be possible to prepare a small library of 6B9 analogues for use in future SAR studies.

Scheme 3. Synthesis of covalent analogues of 3G4

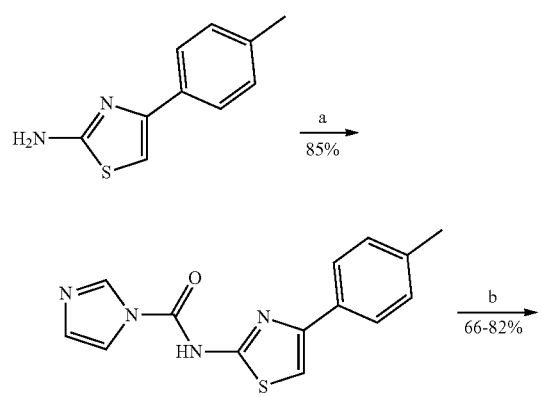

1 (X = F, Y = F)
2 (X = F, Y = H)
3 (X = CH$_3$, Y = H)

Conditions: (a) CDI, THF, RT, 18 h; (b) 1, 2, or 3, THF, RT, 18 h; (c) Dess-Martin periodinane, DCM, 0° C.-RT, 72 h.

Electrophilic derivatives of 3G4 were synthesized over three-steps following scheme 3. In contrast to the first two steps, which were high yielding, a modest yield (15-35%) was obtained for the final reaction (scheme 3c), which was attributed to formation of multiple unidentified side products.

Scheme 4. Synthesis of non-covalent analogues of 6B9 for SPR studies

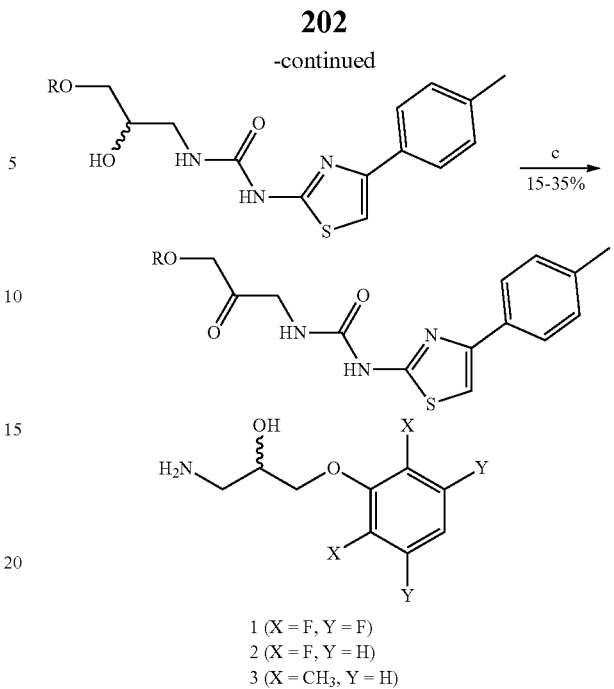

Conditions: (a) MeNH$_2$•HCl, EDC•HCl, HOBt, Et$_3$N, THF/DCM (1:3), RT, 18 h; (b) 4N dioxane HCl, RT, 3 h; (c) HATU, DIPEA, DMF, RT, 18 h.

Non-tethering analogues of 6B9 were prepared in satisfactory yield over three-steps following scheme 4. Boc-protected (R) or (S)-nipecotic acid was chosen as the starting material and allowed for enantioselective synthesis of the target molecule. This synthetic approach would likely be appropriate for future non-tethering derivatives, including the N-ethylamide and N-propylamide analogues of 6B9.

Scheme 5. Synthesis of 34G urea analogues

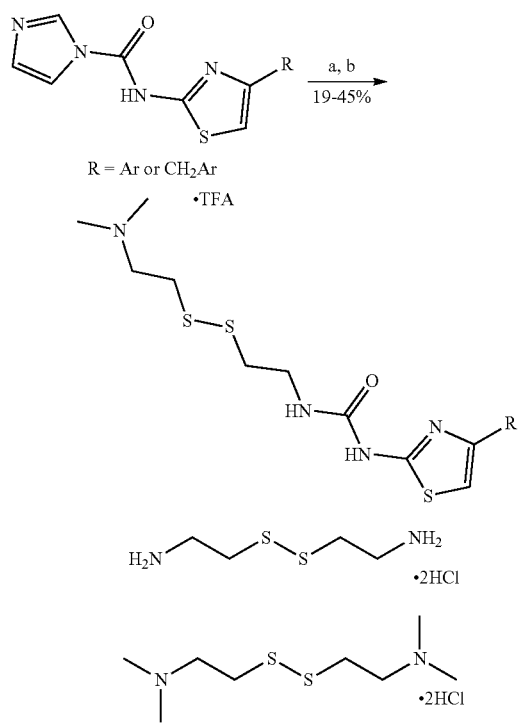

Conditions: (a) 4, Et₃N, water/DMF (1:2); (b) 5, TCEP (0.1 equiv.), Et₃N, water/DMF.

A simple two-step one-pot approach allowed the preparation of a small library of urea based analogues of 6B9 from their respective CDI adducts. Solubility issues of the urea product made purification problematic, which likely accounts of the modest yield.

Scheme 6. Synthesis of 6B9 propylamide analogues

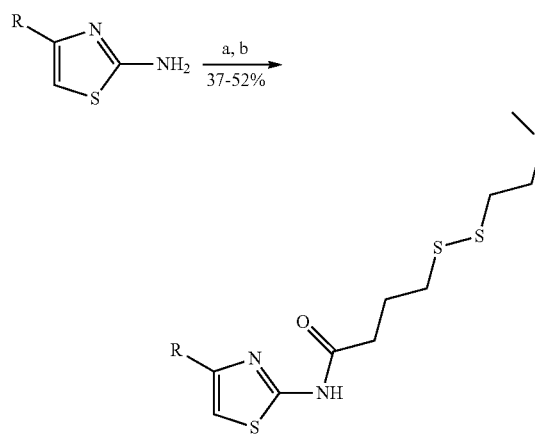

-continued

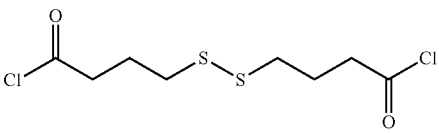

R = Ar or CH₂Ar
Conditions: (a) 6 (0.5 equiv.), DIPEA, DCM, RT, 3 h; (b) 5, TCEP (0.1 equiv.), Et₃N, water/DMF, RT, 18 h.

A small library of propylamides were prepared via the reaction of 2-aminothiazoles with acid chloride 6 followed by disulfide exchange with dimethyl crystamine 5 in the presence of TCEP.

Scheme 7. Synthesis of disulfide tethering agent 6B9

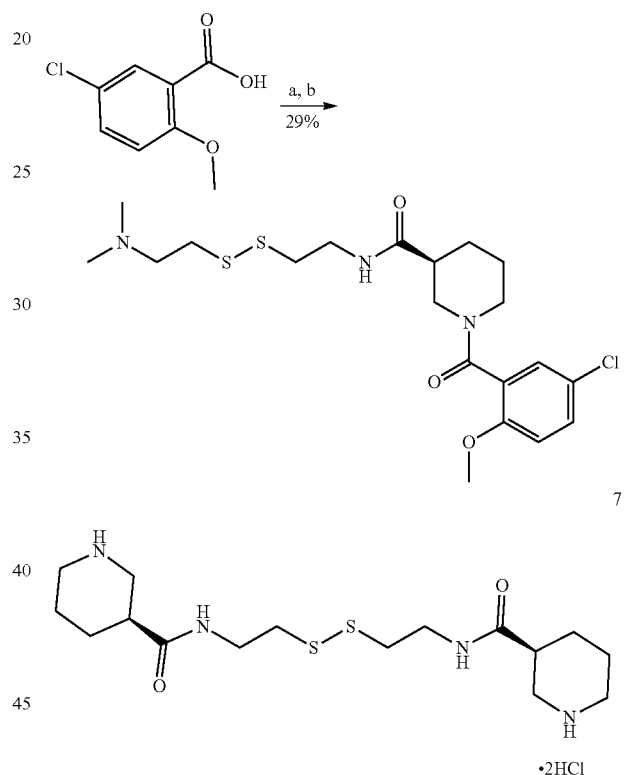

Conditions: (a) 7 (0.5 equiv.), EDC·HCl, HOBt, Et₃N, DMF, RT, 18 h; (b) 5, TCEP (0.1 equiv.), Et₃N, water/DMF, RT, 18 h 5-Chloro-2-methoxybenzoic acid was coupled with amine 7 followed by disulfide exchange with crystamine 5 in the presence of TCEP using a method developed in-house for the preparation of disulfide fragment libraries.

QC. Validation

¹H-NMR and LC-MS analysis was performed upon all intermediates and target molecules to allow structural determination. Compounds submitted for biological evaluation were deemed to be in excess of 95% purity and were stored at −80° C. to prevent decomposition.

Equipment

¹H-NMR spectra were obtained from samples dissolved in deuterated chloroform (CDCl₃) using a Bruker Avance III 300 MHz Spectrometer. Chemical shift values (δ) are reported in parts per million (ppm) with splitting patterns abbreviated to: s (singlet), br. s (broad singlet), d (doublet), t (triplet) and m (multiplet). The coupling constant (J) is given in Hz and was calculated using the software package ACD Labs™ 12.0. Chemical shift values (δ) are reported in parts per million (ppm) with splitting patterns abbreviated to: s (singlet), br. s (broad singlet), d (doublet), t (triplet) and m (multiplet). The coupling constant (J) is given in Hz and was calculated using the software package ACD Labs™ 12.0.

LC-MS analysis was performed using a Waters Micromass ZQ mass spectrometer with a Waters 2795 chromatography separations module, Waters 2996 photodiode array detector and Waters 2424 evaporative light scattering detector (ELSD) system controlled by MassLynx 4.1 software. The HPLC column used was a Waters XTerra MS C18 5 μm 4.6×50 mm column with a mobile phase of water (0.01% formic acid)/MeOH (0.01% formic acid).

1,2,4,5-Tetrafluoro-3-(prop-2-en-1-yloxy)benzene

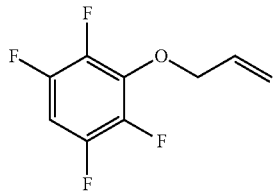

To a solution of 2,3,5,6-tetrafluorophenol (1.00 g, 6.02 mmol) in DMF (15 mL) was added K2CO3 (1.66 g, 0.12 mol) followed by the dropwise addition of allyl bromide (547 uL, 6.32 mmol). The reaction mixture was stirred (RT, 3 h), after which no starting material remained (observed by silica TLC, 1:9 EtOAc/Hexane). The reaction mixture was diluted with water (100 mL) then extracted with DCM (150 mL). The aqueous layer was removed and the remaining organic layer was washed with water (4×100 mL) and then dried (Na2SO4). The volume of solvent was reduced by half in-vacuo and the resulting DCM solution was used directly in the next reaction without further purification.

Rf=0.75 (1:9 EtOAc/Hexane).

2-(2,3,5,6-Tetrafluorophenoxymethyl)oxirane

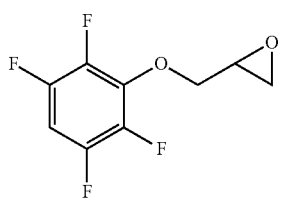 [SMILES: Fc1cc(F)c(F)c(OCC2CO2)c1F]

To a solution of 1,2,4,5-tetrafluoro-3-(prop-2-en-1-yloxy) benzene (1.24 g, 6.02 mmol) at 0° C. in DCM (50 mL) (prepared previously) was added 3-Chloroperbenzoic acid (2.7 g, 12.0 mmol). The reaction was stirred at 0° C. then warmed to room temperature for an additional 3 days. The resulting solution was poured into a saturated aqueous solution of sodium thiosulfate (50 mL) and was allowed to stir for 30 minutes. The organic layer was removed then washed sequentially with saturated NaHCO3 (50 mL), water (50 mL), and brine (50 mL), dried (Na2SO4), and purified by MPLC on silica (0-50% EtOAc/Hexane) to give 2-(2,3,5,6-tetrafluorophenoxymethyl)oxirane (735 mg, 3.31 mmol, 55%) as a colorless oil.

Rf=0.28 (1:9 EtOAc/Hexane); 1H NMR (300 MHz, CDCl3) δ 6.70-6.93 (m, 1H), 4.49 (dd, J=2.92, 11.59 Hz, 1H), 4.12-4.25 (m, 1H), 3.30-3.50 (m, 1H), 2.89 (dd, J=3.70, 4.90 Hz, 1H), 2.73 (dd, J=2.64, 4.90 Hz, 1H).

1-Azido-3-(2,3,5,6-tetrafluorophenoxy)propan-2-ol

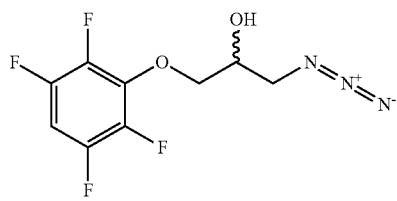 [SMILES: [N-]=[N+]=NCC(O)COc1c(F)c(F)cc(F)c1F]

A solution of 2-(2,3,5,6-tetrafluorophenoxymethyl)oxirane (1.89 g, 8.5 mmol) in MeOH (30 mL) was added to a suspension of sodium azide (5.11 g, 78.6 mmol) in water (3.8 mL). Ammonium chloride (915 mg, 210 mmol) was added and reaction was stirred at room temperature for 24 hours. The reaction mixture was diluted with brine (100 mL) then extracted with EtOAc (2×50 mL). The combined organic layers were washed with brine (2×100 mL), dried (Na2SO4) and the solvent was removed in-vacuo. The crude product was purified by MPLC on silica (1:9 EtOAc: Hexane) to give the title compound (1.92 g, 7.3 mmol, 85%) as a colorless oil.

Rf=0.14 (1:9 EtOAc/Hexane); 1H NMR (300 MHz, CDCl3) δ 6.72-6.93 (m, 1H), 4.22-4.36 (m, 2H), 4.07-4.22 (m, 1H), 3.45-3.65 (m, 2H), 2.56 (br. s., 1H).

1-Amino-3-(2,3,5,6-tetrafluorophenoxy)propan-2-ol

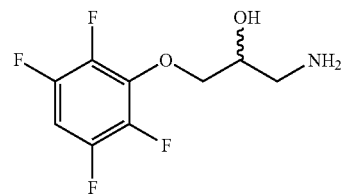 [SMILES: NCC(O)COc1c(F)c(F)cc(F)c1F]

To a solution of 1-azido-3-(2,3,5,6-tetrafluorophenoxy) propan-2-ol (1.9 g, 7.3 mmol) in MeOH (15 ml) was added 10% palladium on carbon (386 mg, 3.6 mmol). The reaction vessel was placed under an atmosphere of hydrogen and stirred overnight (RT, 18 h). The resulting mixture was filtered through Celite and the solvent was removed to give 1-amino-3-(2,3,5,6-tetrafluorophenoxy)propan-2-ol (1.2 g, 5.0 mmol, 69%) as a white solid.

1H NMR (300 MHz, MeOD) δ 7.01-7.21 (m, 1H), 4.22 (d, J=5.09 Hz, 2H), 3.85-3.99 (m, 1H), 2.90 (dd, J=3.96, 12.81 Hz, 1H), 2.77 (dd, J=7.70, 13.00 Hz, 1H); LRMS (ES+) m/z=239.9 [M+H]+.

tert-Butyl (3S)-3-{[2-hydroxy-3-(2,3,5,6-tetrafluorophenoxy)propyl]carbamoyl}piperidine-1-carboxylate

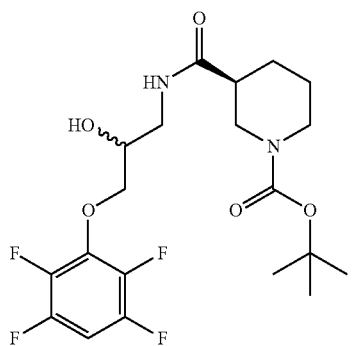 [SMILES: CC(C)(C)OC(=O)N1CCC[C@H](C(=O)NCC(O)COc2c(F)c(F)cc(F)c2F)C1]

To a solution of 1-amino-3-(2,3,5,6-tetrafluorophenoxy)propan-2-ol (1.1 g, 4.6 mmol) in DMF (26 ml) was added hydroxybenzotriazole (HOBt) (59 mg, 0.4 mmol), l-ethyl-3-(3-dimethylaminopropyl) carbodiimide hydrochloride (EDC.HCl) (1.84 g, 11.9 mmol) and water (4.1 ml). Triethylamine (608 µl, 4.4 mmol) was added and the resulting mixture was stirred (RT, 3 h) resulting in consumption of the starting material (observed by TLC). The reaction was added to a saturated brine solution (100 mL) then extracted with EtOAc (150 mL). The organic layer was removed then washed sequentially with saturated aqueous NaHCO3 (100 mL) and brine (100 mL) then dried (MgSO4) and the solvent was removed in-vacuo. The crude product was purified by MPLC on silica (0-10% MeOH/DCM) to give the title compound (1.94 g, 4.3 mmol, 99%) as a colorless oil.

Rf=0.45 (1:9 MeOH/DCM); 1H NMR (300 MHz, CDCl3) δ 6.73-6.93 (m, 1H), 4.01-4.30 (m, 3H), 3.55-4.00 (m, 3H), 3.24-3.54 (m, 2H), 3.12 (m, 1H), 2.84-3.01 (m, 1H), 2.29-2.50 (m, 1H), 1.77-2.05 (m, 2H), 1.57-1.77 (m, 1H), 1.47 (s, 9H); LRMS (ES+) m/z=451.1 [M+H]+.

(3S)—N-[2-Hydroxy-3-(2,3,5,6-tetrafluorophenoxy)propyl]piperidine-3-carboxamide hydrochloride

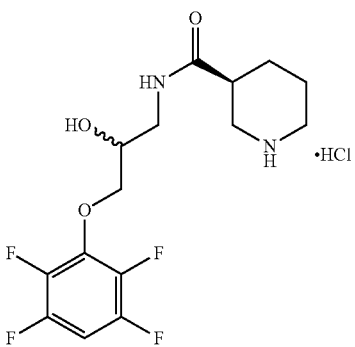 [SMILES: O=C(NCC(O)COc1c(F)c(F)cc(F)c1F)[C@H]1CCCNC1 ; Cl]

To a flask containing tert-butyl (3S)-3-{[2-hydroxy-3-(2,3,5,6-tetrafluorophenoxy)propyl]carbamoyl} piperidine-1-carboxylate (50 mg, 0.1 mmol) was added 4N Hydrochloric acid in dioxane (500 µl, 2.0 mmol). The resulting solution was stirred at room temperature for 30 minutes then the solvent was removed in-vacuo to give the title compound (41 mg, 0.1 mmol, 96%) as a colorless oil.

1H NMR (300 MHz, CDCl3) δ 8.95 (br. s., 2H), 7.75-8.43 (m, 1H), 6.77 (br. s., 1H), 4.02-4.68 (m, 3H), 2.65-3.97 (m, 9H), 1.55-2.32 (m, 3H); LRMS (ES+) m/z=351.1 [M+H]+.

(3S)-1-[(5-Chloro-2-methoxyphenyl)carbonyl]-N-[2-hydroxy-3-(2,3,5,6-tetrafluorophenoxy) propyl]piperidine-3-carboxamide

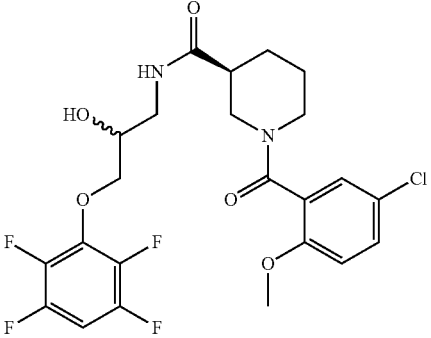 [SMILES: COc1ccc(Cl)cc1C(=O)N1CCC[C@H](C(=O)NCC(O)COc2c(F)c(F)cc(F)c2F)C1]

To a solution of (3S)—N-[2-hydroxy-3-(2,3,5,6-tetrafluorophenoxy)propyl]piperidine-3-carboxamide hydrochloride (155 mg, 0.40 mmol), (l-[bis(dimethylamino)methylene]-1H-1,2,3-triazolo[4,5-b]pyridinium 3-oxid hexafluorophosphate) (HATU) (168 mg, 0.44 mmol) and N,N-diisopropylethylamine (243 µl, 1.4 mmol) in DMF (2.3 ml) was added 5-chloro-2-methoxybenzoic acid (75 mg, 0.40 mmol). The reaction mixture was stirred overnight (RT, 18 h) then added to saturated brine solution (25 mL). The aqueous mixture was extracted with EtOAc (2×25 mL) and the organic layers were combined, washed with brine (25 mL), dried (Na2SO4), and the solvent was removed in-vacuo. The crude product was purified by MPLC on silica (0-80% Hexane/EtOAc) to give the title product (206 mg, 0.40 mmol) as a colorless oil.

Rf=0.40 (10% MeOH/DCM); 1H NMR (300 MHz, CDCl3) δ 7.32 (dd, J=2.45, 8.85 Hz, 1H), 7.13-7.21 (m, 1H), 6.86 (d, J=8.85 Hz, 1H), 6.68-6.79 (m, 1H), 4.16-4.30 (m, 1H), 3.99-4.16 (m, 2H), 3.80-3.87 (s, 3H), 3.66-3.76 (m, 1H), 3.43-3.65 (m, 1H), 3.07-3.43 (m, 3H), 2.67-2.78 (m, 1H), 2.55 (m, 1H), 1.96-2.31 (m, 1H), 1.71-1.95 (m, 1H), 1.41-1.69 (m, 2H); LRMS (ES+) m/z=519.1 [M+H]+.

(3S)-1-[(5-Chloro-2-methoxyphenyl)carbonyl]-N-[2-oxo-3-(2,3,5,6-tetrafluorophenoxy)propyl]piperidine-3-carboxamide ('FB9')

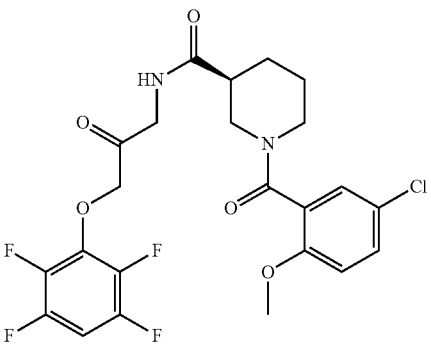 [SMILES: COc1ccc(Cl)cc1C(=O)N1CCC[C@H](C(=O)NCC(=O)COc2c(F)c(F)cc(F)c2F)C1]

To a solution of (3S)-1-[(5-chloro-2-methoxyphenyl)carbonyl]-N-[2-hydroxy-3-(2,3,5,6-tetrafluoro phenoxy)propyl]piperidine-3-carboxamide (17 mg, 3.4×10-2 mmol) in DCM (500 µL, 7.8 mmol) at 0° C. was added Dess-Martin periodinane (28 mg, 6.8×10-2 mmol). The reaction mixture was stirred at 0° C. for 1 hour and was then allowed to warm to room temperature for an additional 72 hours. The crude product was diluted with DCM (2 mL) then added to a saturated solution of sodium thiosulfate in aqueous NaHCO3 (3 mL). The resulting mixture was stirred rapidly for 1 hour at which point the aqueous layer was removed. The remaining organic layer was washed sequentially with NaHCO3 (3 mL) and brine (3 mL) then dried (Na2SO4) and the solved was removed in-vacuo. The crude product was purified by MPLC on silica (0-10% MeOH/DCM) to give the title compound (12 mg, 2.3×10-2 mmol, 69%) as a colorless oil.

Rf=0.43 (1:9 MeOH/DCM); 1H NMR (300 MHz, CDCl3) δ 7.31 (dd, J=2.64, 8.85 Hz, 1H), 7.16-7.25 (m, 1H), 6.75-6.92 (m, 2H), 4.80-4.97 (m, 2H), 4.17-4.59 (m, 2H), 3.75-3.95 (m, 3H), 3.51-3.74 (m, 1H), 3.11-3.38 (m, 2H), 2.52-2.72 (m, 2H), 2.00-2.22 (m, 1H), 1.89 (d, J=11.87 Hz, 1H), 1.35-1.80 (m, 2H); 19F NMR (282 MHz, CDCl3) δ −138.0, −156.7; LRMS (ES+) m/z=517.1 [M+H]+.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

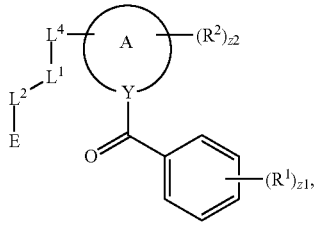

(I)

or a pharmaceutically acceptable salt thereof, wherein:
Y is N;
Ring A is a 5 to 6 membered heterocycloalkyl;
E is

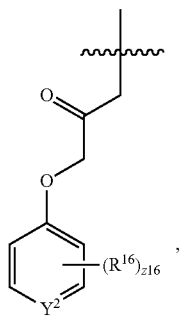

$Y^2$ is N or CH;
$L^1$ is a bond;

$L^2$ is a bond, —C(O)—, —NR$^{7B}$—, —NR$^{7B}$C(O)—, —C(O)NR$^{7B}$—, wherein R$^{7B}$ is hydrogen;

$L^4$ is a bond, —C(O)—, —NR$^4$—, —NR$^4$C(O)—, —C(O)NR$^4$—, substituted or unsubstituted $C_1$-$C_3$ alkylene, or substituted or unsubstituted 2 to 3 membered heteroalkylene;

$R^1$ is independently halogen, —CX$^1_3$, —CHX$^1_2$, —CH$_2$X$^1$, —CN, —SO$_2$Cl, —SO$_{n1}$R$^{10}$, —SO$_{v1}$NR$^7$R$^8$, —NHNR$^7$R$^8$, —ONR$^7$R$^8$, —NHC=(O)NHNR$^7$R$^8$, —NHC(O)NR$^7$R$^8$, —N(O)$_{m1}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C(O)R$^9$, —NR$^7$C(O)OR$^9$, —NR$^7$OR$^9$, —OCX$^1_3$, —OCHX$^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and two adjacent R$^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently oxo, halogen, —CX$^2_3$, —CHX$^2_2$, —CH$_2$X$^2$, —CN, —SO$_2$Cl, —SO$_{n2}$R$^{14}$, SO$_{v2}$NR$^{11}$R$^{12}$, —NHNR$^{11}$R$^{12}$, —ONR$^{11}$R$^{12}$, —NHC=(O)NHNR$^{11}$R$^{12}$, —NHC(O)NR$^{11}$R$^{12}$, —N(O)$_{m2}$, —NR$^{11}$R$^{12}$, —C(O)R$^{14}$, —C(O)—OR$^{14}$, —C(O)NR$^{11}$R$^{12}$, —OR$^{15}$, —NR$^{11}$SO$_2$R$^{15}$, —NR$^{11}$C(O)R$^{14}$, —NR$^{11}$C(O)OR$^{14}$, —NR$^{11}$OR$^{14}$, —OCX$^2_3$, —OCHX$^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and two adjacent R$^2$ substituents or two R$^2$ substituents bonded to the same atom may optionally be joined to form a substituted or unsubstituted cycloalkyl or substituted or unsubstituted heterocycloalkyl;

$R^4$ is independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^{16}$ is independently halogen, $CX^{16}_3$, $-CHX^{16}_2$, $-CH_2X^{16}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX^{16}_3$, $-OCHX^{16}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$, $R^8$, $R^9$, $R^{10}$, $R^{11}$, $R^{12}$, $R^{14}$, and $R^{15}$ are independently hydrogen, halogen, $-CX_3$, $-CN$, $-OH$, $-NH_2$, $-COOH$, $-CONH_2$, $-NO_2$, $-SH$, $-SO_2Cl$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCX_3$, $-OCHX_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl;

each X $X^1$, $X^2$, and $X^{16}$ is independently $-F$, $-Cl$, $-Br$, or $-I$;

n1, n2, v1, and v2 are independently an integer from 0 to 4;

m1 and m2 are independently 1 or 2;

z1 is independently an integer from 0 to 5;

z2 is independently an integer from 0 to 10; and z16 is an integer from 0 to 4.

2. The compound of claim 1, having the formula:

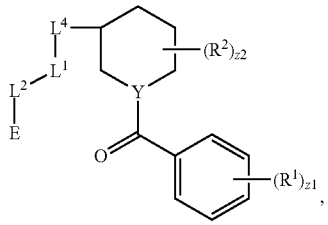

or a pharmaceutically acceptable salt thereof.

3. The compound of claim 2, having the formula:

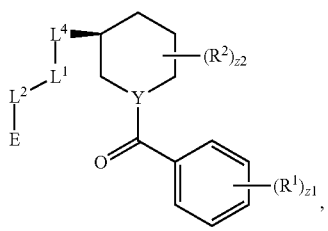

or a pharmaceutically acceptable salt thereof.

4. The compound of claim 1, wherein $R^1$ is independently halogen, $-CX^1_3$, $-CHX^1_2$, $-CH_2X^1$, $-OH$, $-SH$, $-COOH$, $-OCX^1_3$, $-OCHX^1_2$, $-CH_3-CH_2CH_3$, $-OCH_3$, $-OCH_2CH_3$, $-SCH_3$, or $-SCH_2CH_3$.

5. The compound of claim 4, wherein $R^1$ is independently halogen or $-OCH_3$.

6. The compound of claim 1, wherein z1 is 2 or 3.

7. The compound of claim 1, wherein $R^2$ is independently oxo, halogen, $-CX^2_3$, $-CHX^2_2$, $-CH_2X^2$, $-OH$, $-SH$, $-OCX^2_3$, $-OCHX^2_2$, $-CH_3$, $-CH_2CH_3$, $-OCH_3$, $-OCH_2CH_3$, $-SCH_3$, or $-SCH_2CH_3$.

8. The compound of claim 1, wherein z2 is 0.

9. The compound of claim 1, wherein $L^2$ is a bond or $-NH-$.

10. The compound of claim 1 wherein $R^{16}$ is halogen.

11. The compound of claim 10 wherein $R^{16}$ is $-F$.

12. The compound of claim 1, wherein z16 is 2 or 4.

13. The compound of claim 1, wherein E is

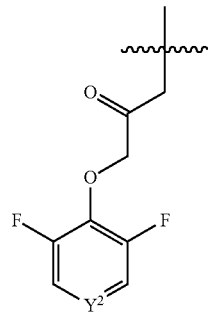

14. The compound of claim 13, wherein $Y^2$ is CH.

15. The compound of claim 1, wherein $L^4$ is $-N(R^4)C(O)-$ and wherein $R^4$ is hydrogen.

16. The compound of claim 1, having the formula:

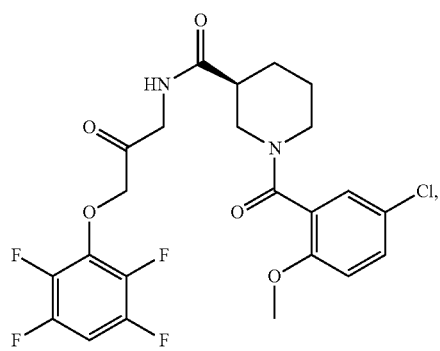 [SMILES: COc1ccc(Cl)cc1C(=O)N1CCC[C@H](C(=O)NCC(=O)COc2c(F)c(F)cc(F)c2F)C1]

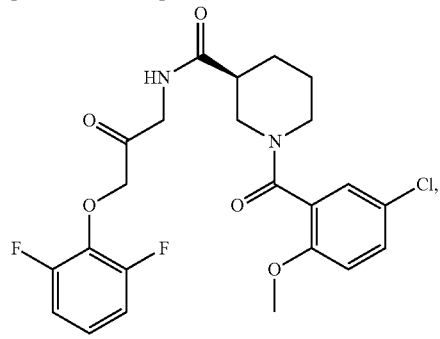

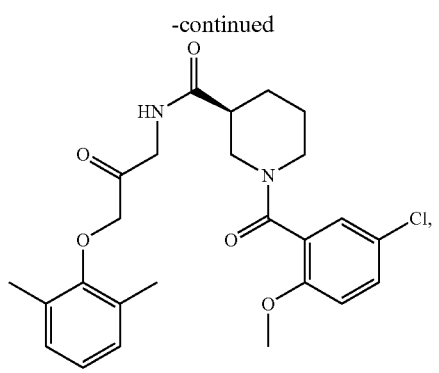

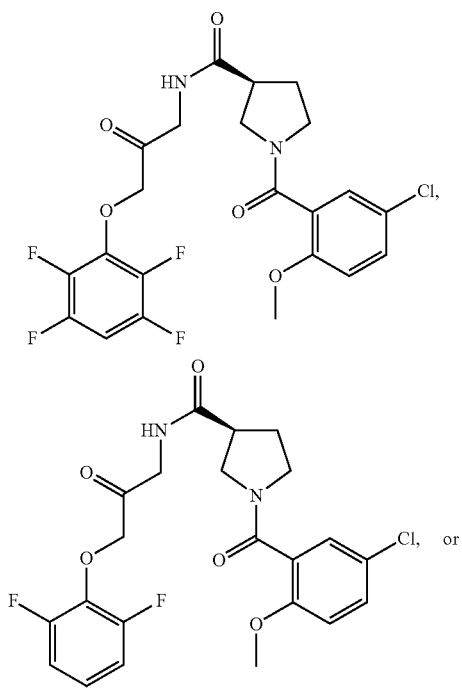

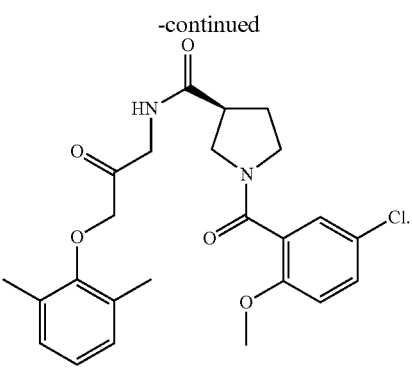

17. The compound of claim 16 of the formula:

18. A pharmaceutical composition comprising the compound of claim 1, or a pharmaceutically acceptable salt thereof, and a pharmaceutically acceptable excipient.

19. A method for treating cancer, said method comprising administering to a subject in need thereof a therapeutically effective amount of a compound of claim 1, wherein the cancer is pancreatic cancer, lung cancer, or colorectal cancer.

* * * * *